(12) United States Patent
Kim et al.

(10) Patent No.: US 11,997,925 B2
(45) Date of Patent: May 28, 2024

(54) CYCLIC COMPOUND AND ORGANIC LIGHT EMITTING DEVICE COMPRISING SAME

(71) Applicant: LG CHEM, LTD., Seoul (KR)

(72) Inventors: Young Seok Kim, Daejeon (KR); Kongkyeom Kim, Daejeon (KR); Ki Dong Koo, Daejeon (KR); Min Woo Lee, Daejeon (KR); Jung Min Yoon, Daejeon (KR)

(73) Assignee: LG CHEM, LTD., Seoul (KR)

( * ) Notice: Subject to any disclaimer, the term of this patent is extended or adjusted under 35 U.S.C. 154(b) by 290 days.

(21) Appl. No.: 17/269,190

(22) PCT Filed: Aug. 30, 2019

(86) PCT No.: PCT/KR2019/011168
§ 371 (c)(1),
(2) Date: Feb. 17, 2021

(87) PCT Pub. No.: WO2020/046049
PCT Pub. Date: Mar. 5, 2020

(65) Prior Publication Data
US 2022/0352472 A1    Nov. 3, 2022

(30) Foreign Application Priority Data

Aug. 31, 2018  (KR) .................. 10-2018-0103626
Aug. 28, 2019  (KR) .................. 10-2019-0105960

(51) Int. Cl.
*H01L 51/00*    (2006.01)
*C07D 239/74*   (2006.01)
(Continued)

(52) U.S. Cl.
CPC ......... *H10K 85/654* (2023.02); *C07D 239/74* (2013.01); *C07D 251/24* (2013.01);
(Continued)

(58) Field of Classification Search
None
See application file for complete search history.

(56) References Cited

U.S. PATENT DOCUMENTS 7,274,141 B2   9/2007  Leo et al.
9,722,189 B2   8/2017  Tada
(Continued)

FOREIGN PATENT DOCUMENTS

CN   103503188 A   1/2014
CN   103946215 A   7/2014
(Continued)

OTHER PUBLICATIONS

Chen, C-H. et al., "Synthesis and characterization of spiro(adamantane-2,9'-fluorene)-based triaryldiamines: thermally stable hole-transporting materials", Synthetic Metals, 2004, vol. 143, pp. 215-220.
(Continued)

*Primary Examiner* — Jay Yang
(74) *Attorney, Agent, or Firm* — BRYAN CAVE LEIGHTON PAISNER LLP

(57) ABSTRACT

A cyclic compound represented by Chemical Formula 1, and an organic light emitting device comprising the same, and the compound used as a material of an organic material layer in the organic light emitting device and providing improved
(Continued)

efficiency, low driving voltage and improved lifetime characteristics of the organic light emitting device.

[Chemical Formula 1]

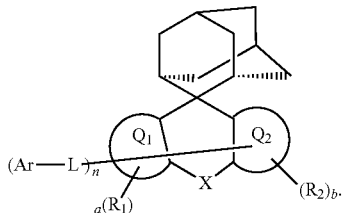

14 Claims, 1 Drawing Sheet

(51) Int. Cl.
    C07D 251/24      (2006.01)
    C07D 401/04      (2006.01)
    C07D 401/10      (2006.01)
    C07D 405/04      (2006.01)
    C07D 405/10      (2006.01)
    C07D 405/14      (2006.01)
    C07D 409/04      (2006.01)
    C07D 409/10      (2006.01)
    C07D 413/10      (2006.01)
    C07D 413/14      (2006.01)
    C07D 471/04      (2006.01)
    C09K 11/06       (2006.01)
    H10K 85/60       (2023.01)
    H10K 50/16       (2023.01)

(52) U.S. Cl.
    CPC ......... C07D 401/04 (2013.01); C07D 401/10
           (2013.01); C07D 405/04 (2013.01); C07D
           405/10 (2013.01); C07D 405/14 (2013.01);
              C07D 409/04 (2013.01); C07D 409/10
           (2013.01); C07D 413/10 (2013.01); C07D
              413/14 (2013.01); C07D 471/04 (2013.01);
                  C09K 11/06 (2013.01); H10K 85/622
             (2023.02); H10K 85/624 (2023.02); H10K
           85/626 (2023.02); H10K 85/6565 (2023.02);
                H10K 85/657 (2023.02); H10K 85/6572
             (2023.02); H10K 85/6574 (2023.02); H10K
                    85/6576 (2023.02); C09K 2211/1018
                       (2013.01); H10K 50/16 (2023.02)

(56)           References Cited
           U.S. PATENT DOCUMENTS

2004/0251816 A1    12/2004  Leo et al.
    2014/0061548 A1     3/2014  Montenegro et al.
    2014/0070146 A1     3/2014  Parham et al.
    2014/0316134 A1    10/2014  Stoessel et al.
    2016/0072064 A1     3/2016  Tada
    2017/0098777 A1     4/2017  Huh et al.
    2019/0016666 A1     1/2019  Jeong et al.
    2020/0251660 A1     8/2020  Parham et al.

FOREIGN PATENT DOCUMENTS

CN        104529870 A      4/2015
    CN        106164056 A     11/2016
    CN        106459018 A      2/2017
    CN        107459466 A     12/2017
    EP         1 184 379 A1    3/2002
    JP         2002-275103 A   9/2002
    JP         2004-171986 A   6/2004
    JP         2005-220080 A   8/2005
    JP         2013-108015 A   6/2013
    KR      10-2000-0051826 A  8/2000
    KR      10-2014-0026552 A  3/2014
    KR      10-2014-0096372 A  8/2014
    KR      10-2015-0139969 A 12/2015
    KR      10-2016-0050827 A  5/2016
    KR         10-1708176 B1   2/2017
    KR      10-2017-0116944 A 10/2017
    KR      10-2017-0136980 A 12/2017
    KR      10-2018-0065246 A  6/2018
    TW           201339201 A * 10/2013
    WO         2003-012890 A   2/2003
    WO         2014-168138 A  10/2014

OTHER PUBLICATIONS

Lee et al., "Red Fluorescent DCM Derivatives with the Bulky-substituents on Pyran and Julolidine Moieties for Organic Light-Emitting Diodes (OLEDs)", Bull. Korean Chem. Soc. 2012, vol. 33, No. 10, pp. 3433-3436.
Krajcovic et al., "Adamantyl side groups boosting the efficiency and thermal stability of organic solid-state fluorescent dyes", Journal of Luminescence (2016), 175, 94-99.
Gu et al., "Tetrasubstituted adamantane derivatives with arylamine groups Solution-processable hole-transporting and host materials with high triplet energy and good thermal stability for organic light-emitting devices", Organic Electronics (2015), 25, 193-199.
Li et al., "Reduction of chain interactions in a class of blue fluorene copolymers with adamantane units", Thin Solid Films (2006), 515(4), 2686-2691.
Lee et al., "Synthesis and Electro-Optical Properties of Adamantane-Based Host and Hole-Transporting Material for Thermal Stable Blue Phosphorescent OLEDs"—abstract only, Journal of Nanoscience and Nanotechnology (2017), 17 (10), 7292-7296.
Mathur et al., "Synthesis and characterisation of [Fe2M3(μ4-E)(μ3-E')(CO)17] and [Os3(μ3-E)(μ3-E')(CO)9] (M=Os or Ru; E=S, Se, Te; E'=Se, Te)", Journal of Macromolecular Science, Part A: Pure and Applied Chemistry (2018), 55(2), 176-182.
Gu et al., "Adamantane-Based Wide-Bandgap Host Material Blue Electrophosphorescence with High Efficiency and Very High Brightness", Chemistry—A European Journal (2015), 21(22), 8250-8256.
Wen Y. Huang and S.Y.Huang, "Sterically Encumbered Fluorene-Based Poly(arylene ether)s Containing Spiro-Annulated Substituents on the Main Chain", Macromolecules 2010, 43, pp. 10355-10365.
Wen Y. Huang et al., "Sterically encumbered poly(arylene ether)s containing spiro-annulated substituents: synthesis and thermal properties"Journal of Polymer Science, Part A: Polymer Chemistry (2010), 48(24), pp. 5872-5884.

* cited by examiner

[FIG. 1]
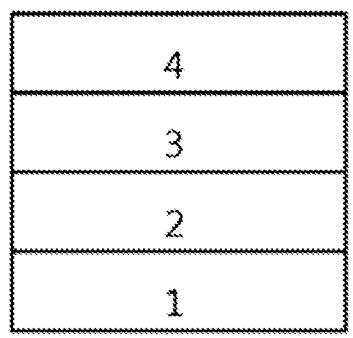
[FIG. 2]
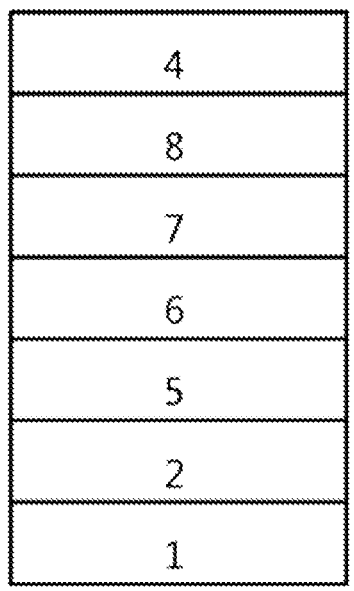

CYCLIC COMPOUND AND ORGANIC LIGHT EMITTING DEVICE COMPRISING SAME

CROSS-REFERENCE TO RELATED APPLICATION(S)

This application is a National Stage Application of International Application No. PCT/KR2019/011168 filed on Aug. 30, 2019, which claims the benefit of Korean Patent Application No. 10-2018-0103626 filed on Aug. 31, 2018 and Korean Patent Application No. 10-2019-0105960 filed on Aug. 28, 2019 with the Korean Intellectual Property Office, each of which is incorporated herein by reference in its entirety.

TECHNICAL FIELD

The present disclosure relates to a novel compound and an organic light emitting device comprising the same.

BACKGROUND

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently has a multilayered structure that comprises different materials in order to enhance efficiency and stability of the organic light emitting device, and for example, the organic material layer may be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

There is a continuing need for the development of new materials for the organic materials used in the organic light emitting devices as described above.

RELATED ARTS (Patent Literature 0001) Korean Patent Application Laid-Open Publication No. 10-2000-0051826

SUMMARY

Technical Problem

It is an object of the present disclosure to provide a novel compound and an organic light emitting device comprising the same.

Technical Solution

According to one embodiment of the present disclosure, there is provided a compound represented by the following Chemical Formula 1:

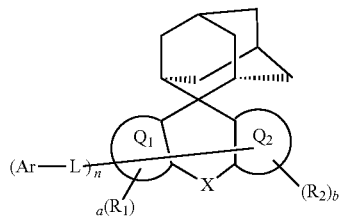

[Chemical Formula 1]

in Chemical Formula 1,
$Q_1$ and $Q_2$ are each independently a $C_{6-30}$ aromatic ring;
n is an integer of 1 to 3,
a and b are each independently an integer of 0 to 3,
X is a single bond; $CR_3R_4$; $SiR_5R_6$; $NR_7$; O; S; $SO_2$; or a substituent represented by the following Chemical Formula 2,

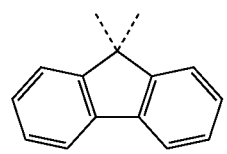

[Chemical Formula 2]

$R_1$ to $R_7$ are each independently hydrogen; deuterium; a substituted or unsubstituted $C_{1-60}$ alkyl; a substituted or unsubstituted $C_{1-60}$ alkoxy; a substituted or unsubstituted $C_{6-60}$ aryl; or a substituted or unsubstituted $C_{5-60}$ heteroaryl containing at least one heteroatom selected from the group consisting of N, O and S, or adjacent groups of $R_1$ to $R_7$ are bonded to each other to form a ring, L is a single bond; a substituted or unsubstituted $C_{6-60}$ arylene; or a substituted or unsubstituted $C_{2-60}$ heteroarylene containing at least one heteroatom selected from the group consisting of N, O and S, and Ar is a substituted or unsubstituted $C_{6-60}$ aryl; or a substituted or unsubstituted $C_{2-60}$ heteroaryl containing at least one heteroatom selected from the group consisting of N, O and S, or a di($C_{6-60}$ aryl)phosphine oxide group.

According to another aspect of the present disclosure, there is provided an organic light emitting device comprising: a first electrode; a second electrode that is provided to face the first electrode; and one or more organic material layers that are provided between the first electrode and the second electrode, wherein one or more layers of the organic material layers include a compound represented by Chemical Formula 1.

Advantageous Effects

The above-mentioned compound represented by Chemical Formula 1 can be used as a material of an organic material layer of an organic light emitting device, and can improve the efficiency, achieve low driving voltage and/or improve lifetime characteristics in the organic light emitting device. In particular, the compound represented by the Chemical Formula 1 may be used as a hole injection material, hole transport material, hole injection and transport material, light emitting material, electron transport material, or electron injection material.

BRIEF DESCRIPTION OF THE DRAWINGS

FIG. 1 shows an example of an organic light emitting device comprising a substrate 1, an anode 2, a light emitting layer 3, and a cathode 4.

FIG. 2 shows an example of an organic light emitting device comprising a substrate 1, an anode 2, a hole injection layer 5, a hole transport layer 6, a light emitting layer 7, an electron transport layer 8, and a cathode 4.

DETAILED DESCRIPTION

Hereinafter, embodiments of the present disclosure will be described in more detail to facilitate understanding of the invention.

The present disclosure provides the compound represented by Chemical Formula 1.

As used herein, the notation

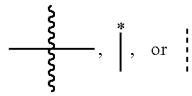

means a bond linked to another substituent group.

As used herein, the term "substituted or unsubstituted" means being unsubstituted or substituted with one or more substituents selected from the group consisting of deuterium; a halogen group; a cyano group; a nitro group; a hydroxy group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a heterocyclic group containing at least one of N, O and S atoms; or being unsubstituted or substituted with a substituent in which two or more substituents of the above-exemplified substituents are connected. For example, "a substituent in which two or more substituents are connected" may be a biphenyl group. Namely, a biphenyl group may be an aryl group, or it may also be interpreted as a substituent in which two phenyl groups are connected.

In the present disclosure, the carbon number of a carbonyl group is not particularly limited, but is preferably 1 to 40. Specifically, the carbonyl group may be a compound having the following structural formulas, but is not limited thereto.

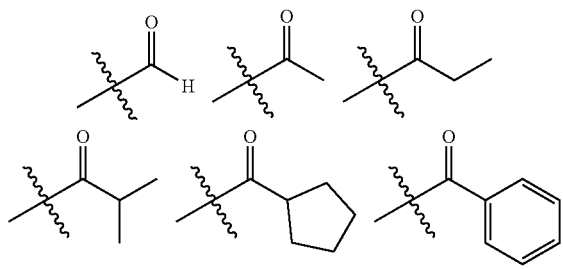

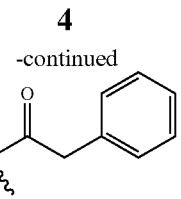

In the present disclosure, an ester group may have a structure in which oxygen of the ester group may be substituted by a straight-chain, branched-chain, or cyclic alkyl group having 1 to 25 carbon atoms, or an aryl group having 6 to 25 carbon atoms. Specifically, the ester group may be a compound having the following structural formulas, but is not limited thereto.

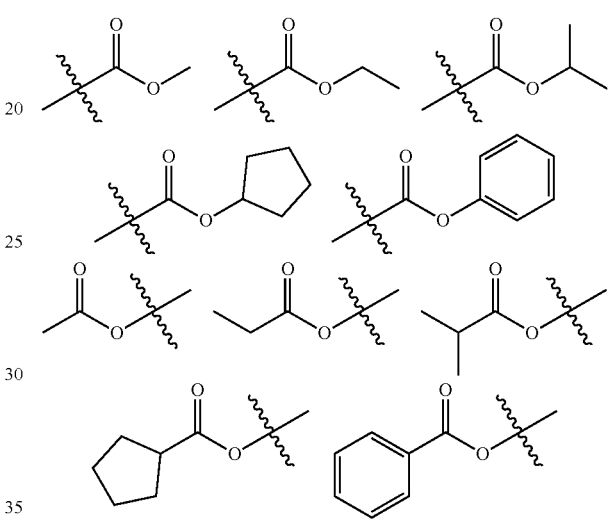

In the present disclosure, the carbon number of an imide group is not particularly limited, but is preferably 1 to 25. Specifically, the imide group may be a compound having the following structural formulas, but is not limited thereto.

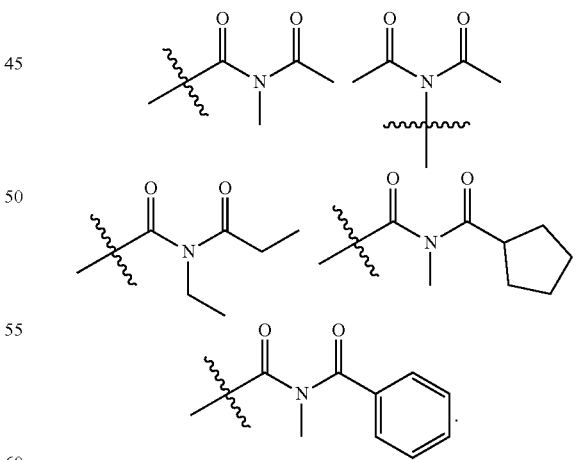

In the present disclosure, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but is not limited thereto.

In the present disclosure, a boron group specifically includes a trimethylboron group, a triethylboron group, a t-butyldimethylboron group, a triphenylboron group, and a phenylboron group, but is not limited thereto.

In the present disclosure, examples of a halogen group include fluorine, chlorine, bromine, or iodine.

In the present disclosure, the alkyl group may be straight-chain or branched-chain, and the carbon number thereof is not particularly limited, but is preferably 1 to 40. According to one embodiment, the carbon number of the alkyl group is 1 to 20. According to another embodiment, the carbon number of the alkyl group is 1 to 10. According to another embodiment, the carbon number of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cycloheptylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present disclosure, the alkenyl group may be straight-chain or branched-chain, and the carbon number thereof is not particularly limited, but is preferably 2 to 40. According to one embodiment, the carbon number of the alkenyl group is 2 to 20. According to another embodiment, the carbon number of the alkenyl group is 2 to 10. According to still another embodiment, the carbon number of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present disclosure, a cycloalkyl group is not particularly limited, but the carbon number thereof is preferably 3 to 60. According to one embodiment, the carbon number of cycloalkyl group is 3 to 30. According to another embodiment, the carbon number of the cycloalkyl group is 3 to 20. According to still another embodiment, the carbon number of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present disclosure, an aryl group is not particularly limited, but the carbon number thereof is preferably 6 to 60, and it may be a monocyclic aryl group or a polycyclic aryl group. According to one embodiment, the carbon number of the aryl group is 6 to 30. According to one embodiment, the carbon number of the aryl group is 6 to 20. The aryl group may be a phenyl group, a biphenyl group, a terphenyl group or the like as the monocyclic aryl group, but is not limited thereto. The polycyclic aryl group includes a naphthyl group, an anthracenyl group, a phenanthryl group, a pyrenyl group, a perylenyl group, a chrysenyl group, or the like, but is not limited thereto.

In the present disclosure, the fluorenyl group may be substituted, and two substituents may be linked with each other to form a spiro structure. In the case where the fluorenyl group is substituted,

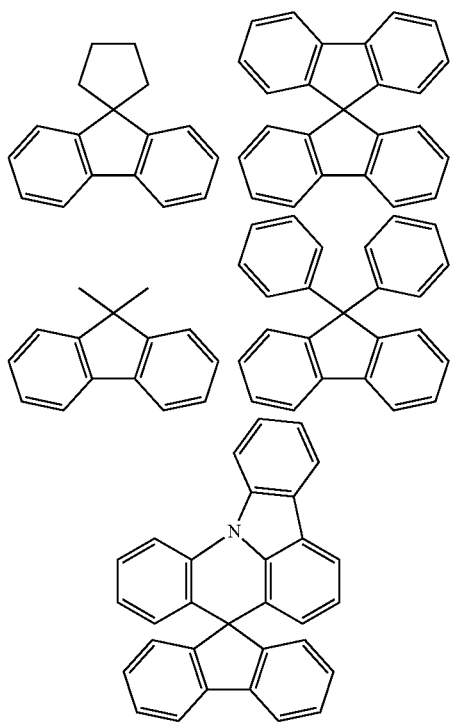

and the like can be formed. However, the structure is not limited thereto.

In the present disclosure, a heterocyclic group is a heterocyclic group containing one or more of O, N, P, Si and S as a heteroatom, and the carbon number thereof is not particularly limited, but is preferably 2 to 60. Examples of the heterocyclic group include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzoimidazole group, a benzothiazol group, a benzocarbazole group, a benzothiophene group, a dibenzothiophene group, a benzofuranyl group, a phenanthroline group, an isoxazolyl group, a thiadiazolyl group, a phenothiazinyl group, a dibenzofuranyl group, and the like, but are not limited thereto.

In the present disclosure, the aryl group in the aralkyl group, the aralkenyl group, the alkylaryl group, the arylamine group and the arylsily group is the same as the aforementioned examples of the aryl group. In the present disclosure, the alkyl group in the aralkyl group, the alkylaryl group and the alkylamine group is the same as the aforementioned examples of the alkyl group. In the present disclosure, the heterocyclic group in the heteroarylamine can be applied to the aforementioned description of the heteroaryl group. In the present disclosure, the alkenyl group in the aralkenyl group is the same as the aforementioned examples of the alkenyl group. In the present disclosure, the aforementioned description of the aryl group may be applied except that the arylene is a divalent group. In the present disclosure, the aforementioned description of the heterocyclic group can be applied except that the heteroarylene is a divalent group. In the present disclosure, the aforementioned description of the aryl group or cycloalkyl group can be applied except that the hydrocarbon ring is not a monovalent group but formed by combining two substituent groups. In the present disclosure, the aforementioned description of the heterocyclic group can be applied, except that the heterocyclic group is not a monovalent group but formed by combining two substituent groups.

In Chemical Formula 1, preferably, $Q_1$ and $Q_2$ may be each independently a benzene or naphthalene ring, and more preferably, both $Q_1$ and $Q_2$ may be a benzene ring.

In Chemical Formula 1, preferably, X may be a single bond; $C(CH_3)_2$; $C(phenyl)_2$; $N(phenyl)$; O; S; $SO_2$; or a substituent represented by the following Chemical Formula 2:

[Chemical Formula 2]

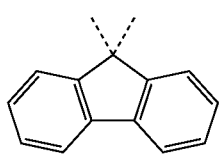

For example, the Chemical Formulas 1 may be the following Chemical Formulas 1-1 to 1-7:

[Chemical Formula 1-1]

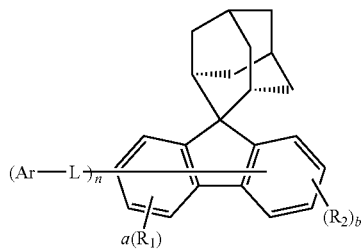

[Chemical Formula 1-2]

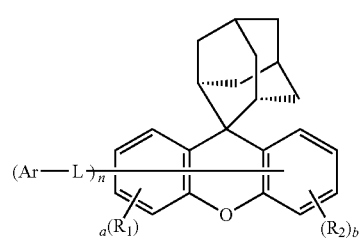

[Chemical Formula 1-3]

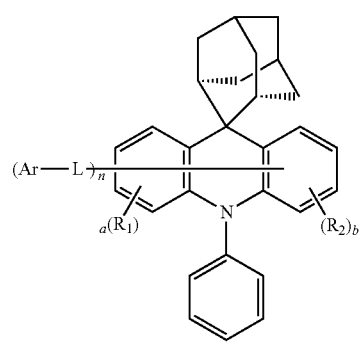

[Chemical Formula 1-4]

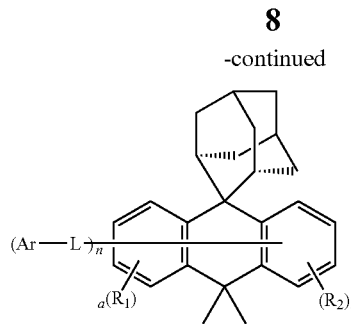

[Chemical Formula 1-5]

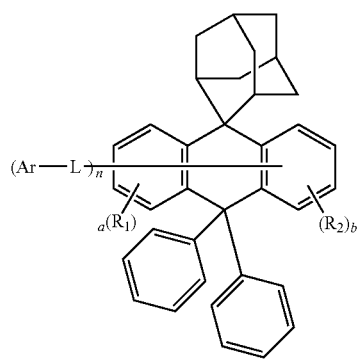

[Chemical Formula 1-6]

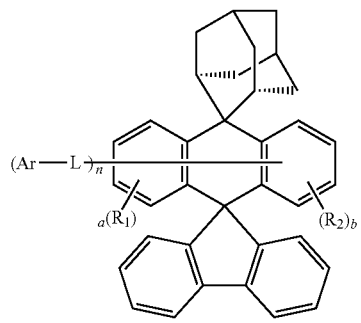

[Chemical Formula 1-7]

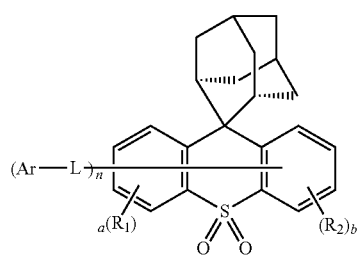

in Chemical Formulas 1-1 to 1-7
$R_1$, $R_2$, L, Ar, n, a and b are the same as defined above.
In Chemical Formula 1, preferably n may be 1.
In general, the electron mobility of a compound depends on the orientation in the three-dimensional structure of a molecule, and when it a more horizontal structure, the electron mobility is enhanced. Therefore, when n is 1, the horizontal structural propensity of the molecule is strong, and thus, the electron mobility can be higher.

In Chemical Formula 1, preferably, both a and b may be 0.

Preferably L may be a single bond; phenylene; biphenyldiyl; naphthalenediyl; furandiyl; thiophenediyl; or pyridindiyl. More preferably, L may be a single bond; phenylene; biphenyldiyl; or naphthalenediyl.

Preferably, Ar may be a phenyl substituted with cyano; —P(O)(phenyl)$_2$; or any one selected from the group consisting of the following:

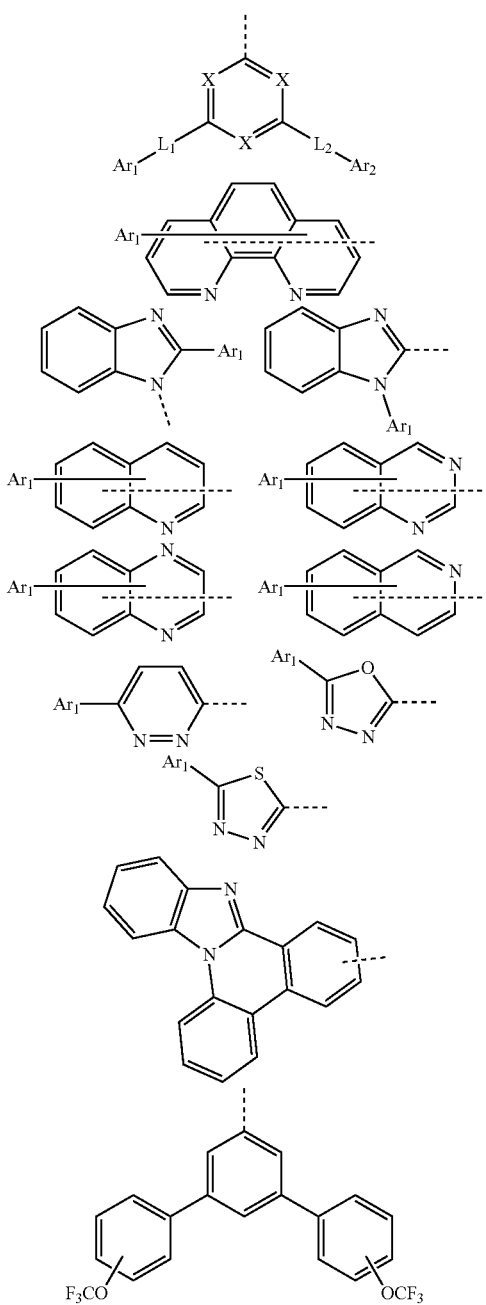

wherein,

L₁ and L₂ are each independently a single bond; a substituted or unsubstituted $C_{6-60}$ arylene; or a substituted or unsubstituted $C_{2-60}$ heteroarylene containing at least one heteroatom selected from the group consisting of N, O, and S, X is each independently N or C(R₈), provided that at least one of X is N, Ar₁ and Ar₂ are each independently hydrogen; a substituted or unsubstituted $C_{6-60}$ aryl; or a substituted or unsubstituted $C_{2-60}$ heteroaryl containing at least one heteroatom selected from the group consisting of N, O, and S, and R₈ is hydrogen; deuterium; a substituted or unsubstituted $C_{1-60}$ alkyl; a substituted or unsubstituted $C_{1-60}$ alkoxy; a substituted or unsubstituted $C_{6-60}$ aryl; a substituted or unsubstituted $C_{5-60}$ heteroaryl containing at least one heteroatom selected from the group consisting of N, O and S.

Preferably, L₁ and L₂ are each independently a single bond; phenylene; biphenyldiyl; or naphthalenediyl.

Preferably, Ar₁ and Ar₂ may be each independently hydrogen; phenyl; phenyl substituted with cyano; biphenylene; terphenylene; naphthyl; phenanthrenyl; 9,10-dimethylphenanthrenyl; triphenylenyl; pyridinyl; dimethylfluorenyl; dibenzofuranyl; dibenzothiophenyl; carbazolyl; benzocarbazolyl; phenalenyl; quinolinyl; fluoranthenyl; phenoxazinyl; phenothiazinyl; 10-phenylphenazinyl; or 9,9-dimethylacridinyl.

Preferably Ar may be any one selected from the group consisting of the following:

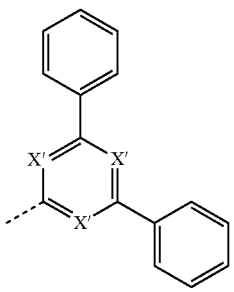

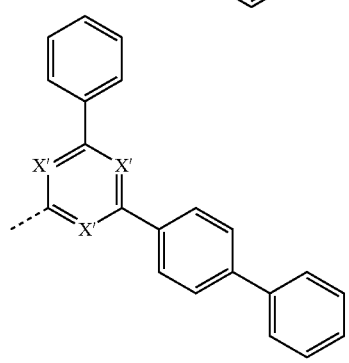

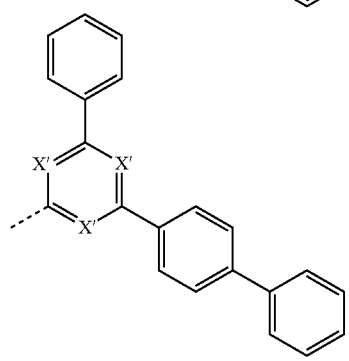

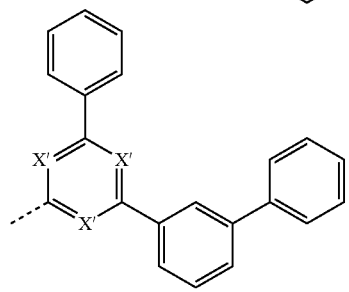

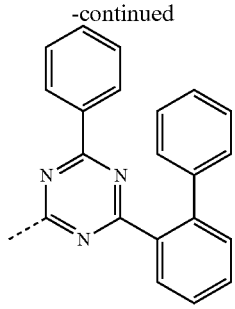
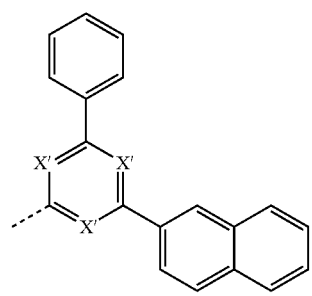
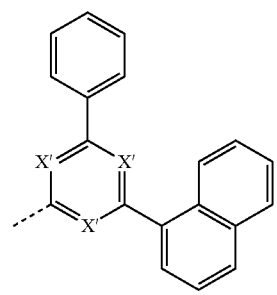
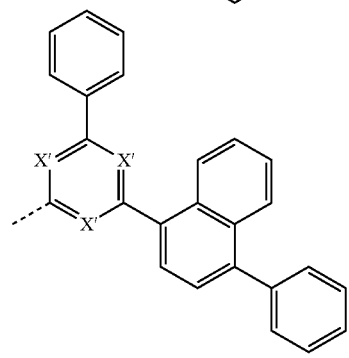
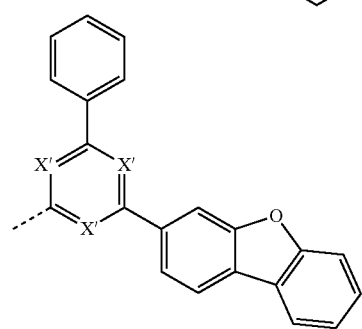
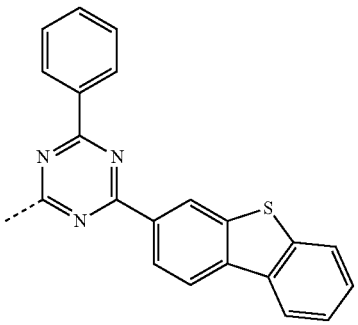
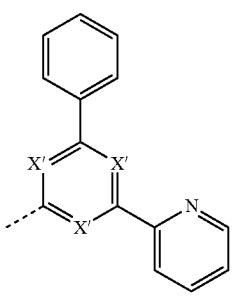
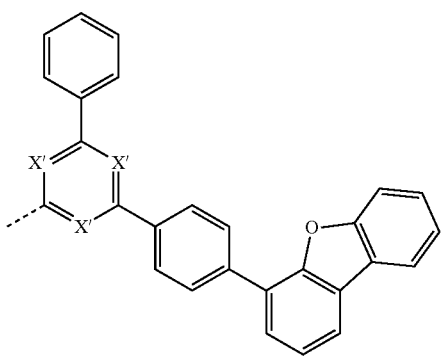
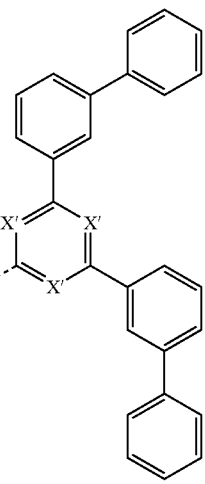

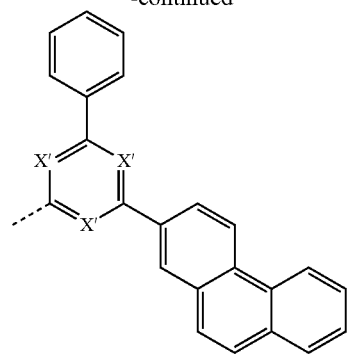
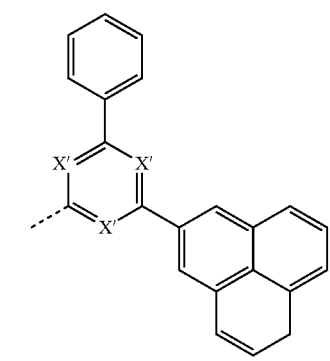
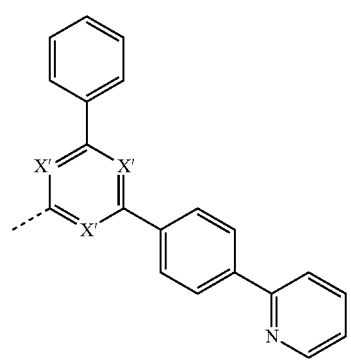
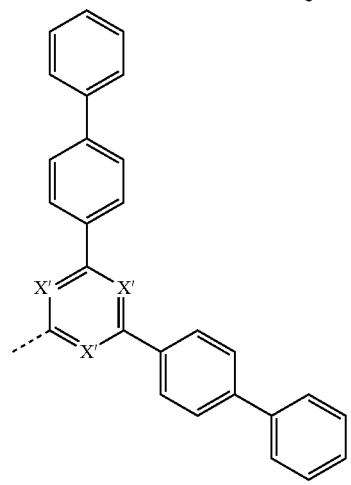
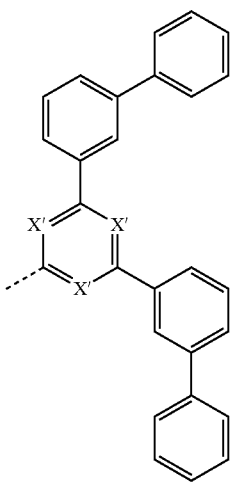
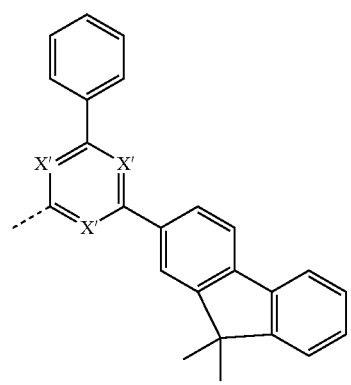
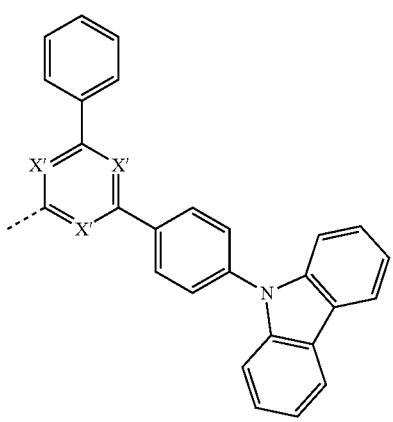

-continued
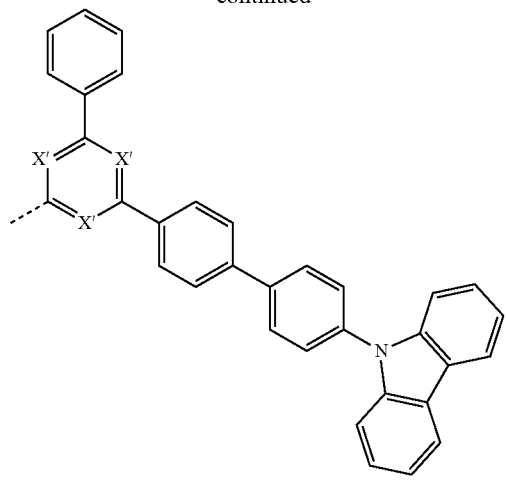
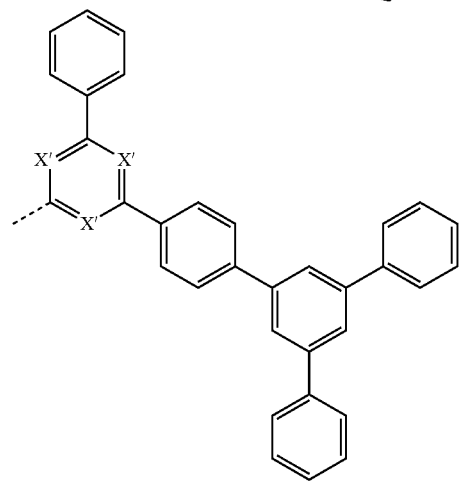
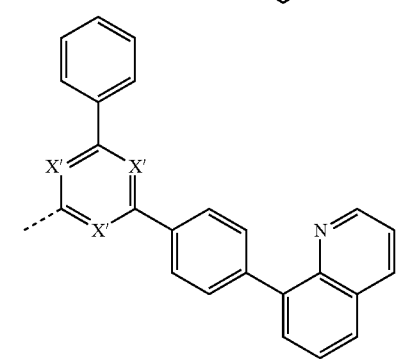
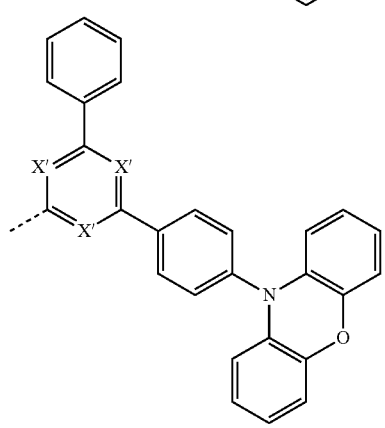
-continued
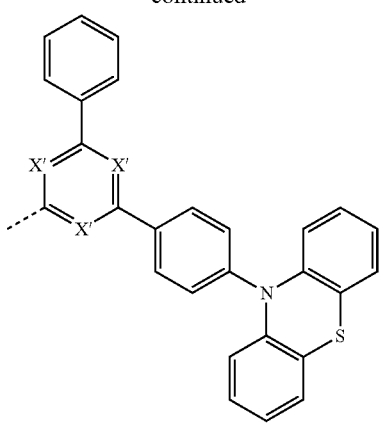
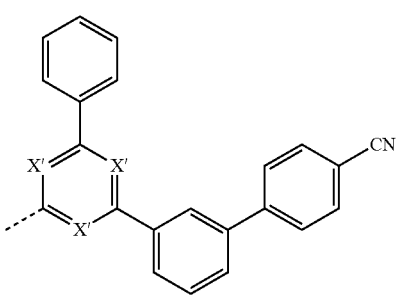
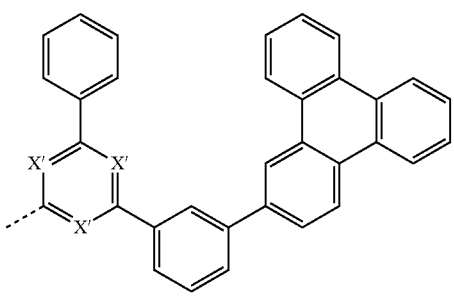
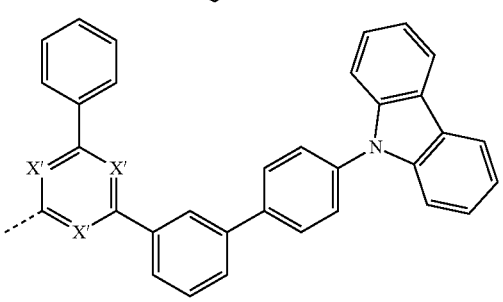
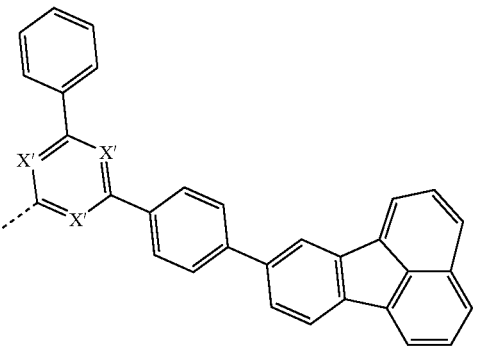

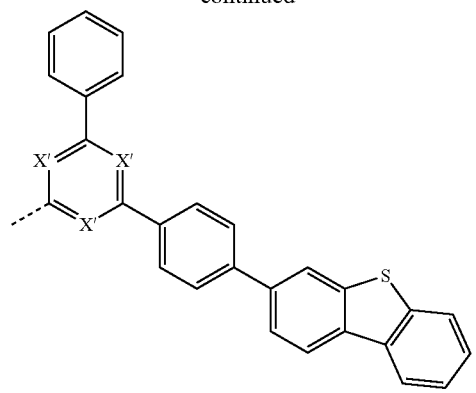
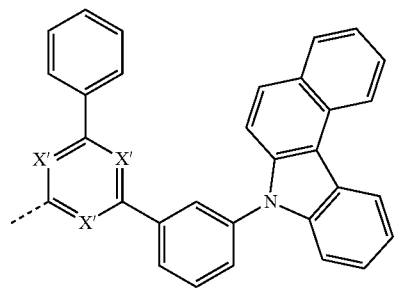
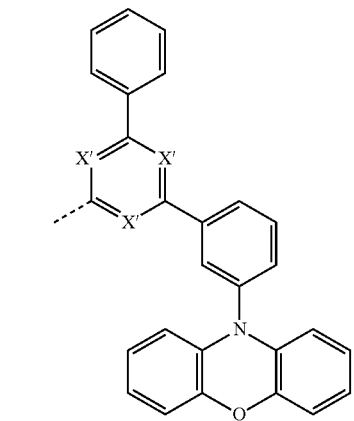
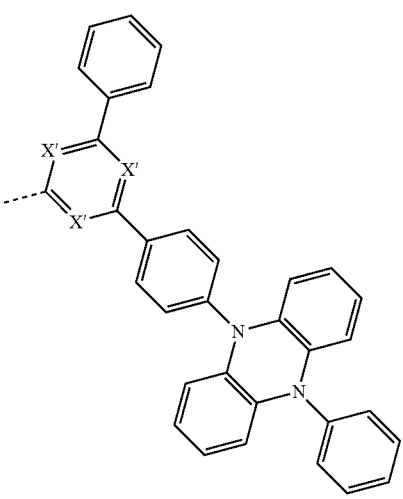
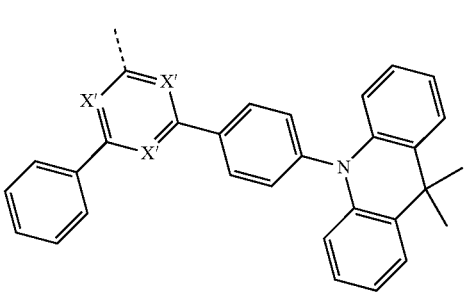
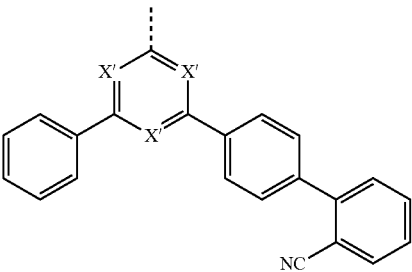
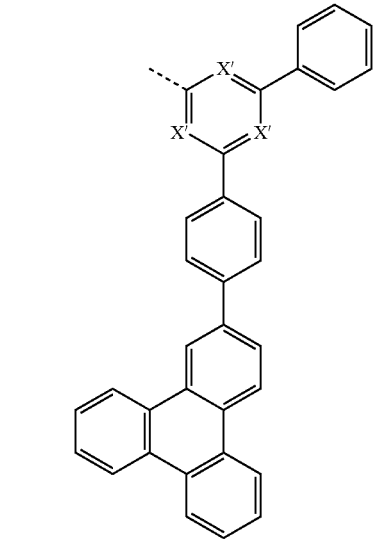

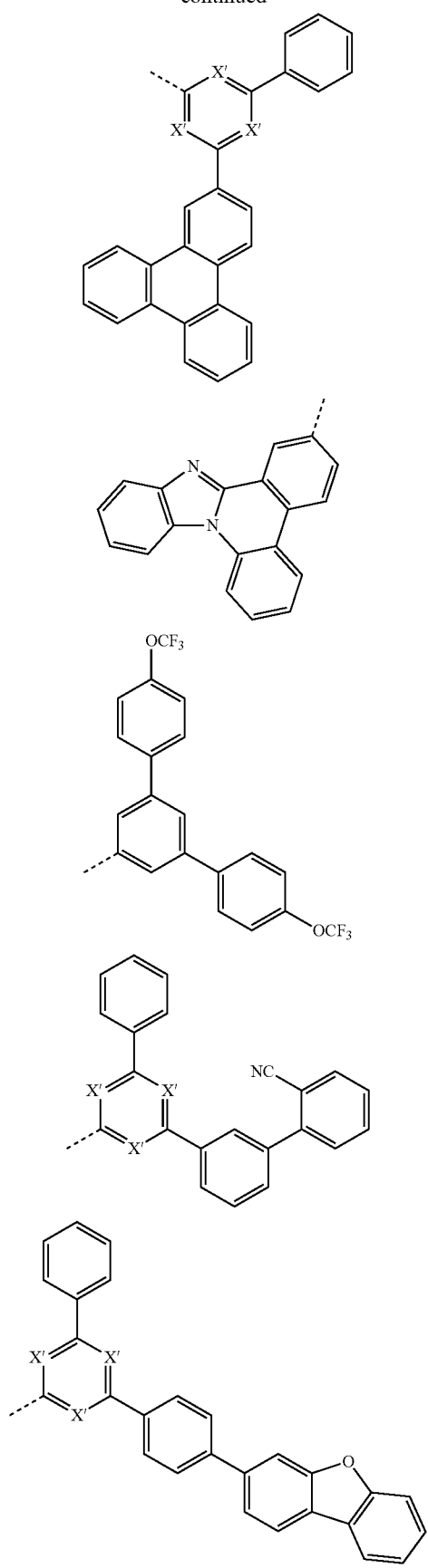
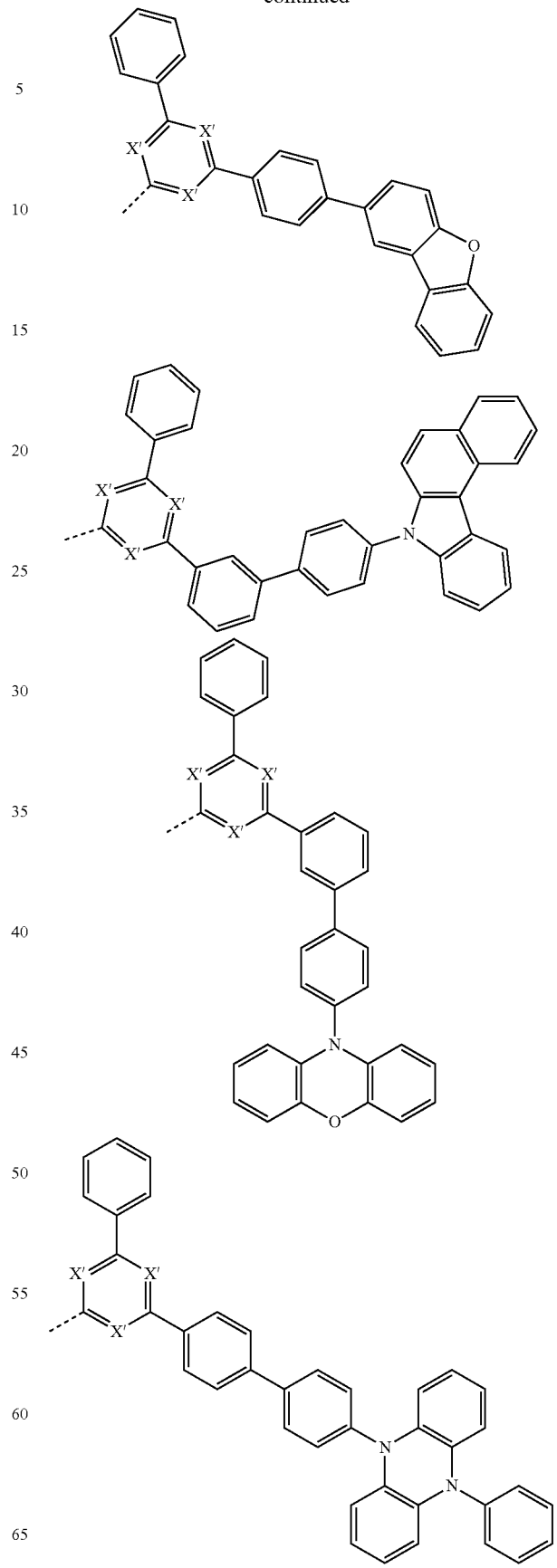

-continued
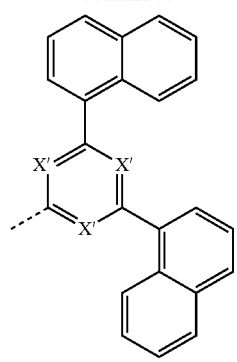
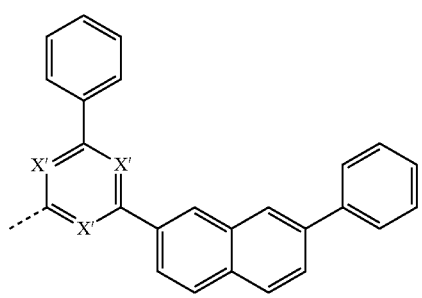
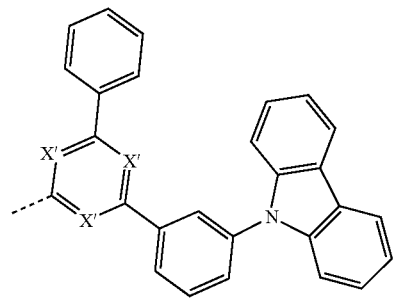
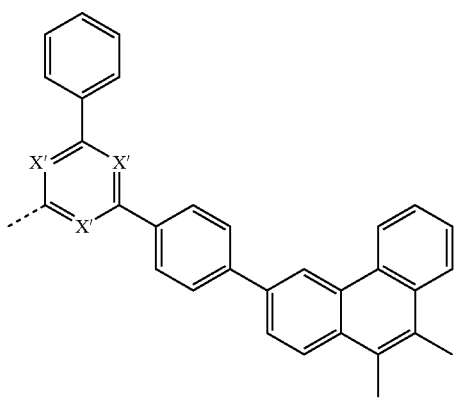
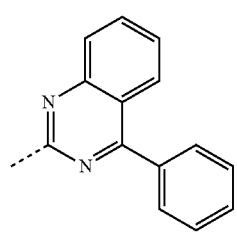
-continued
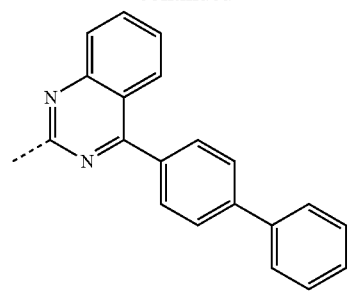
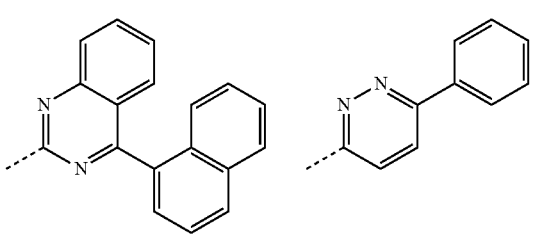
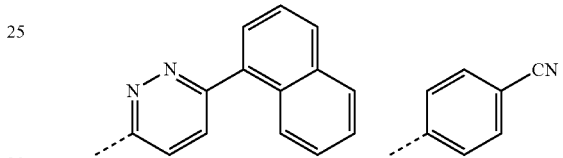
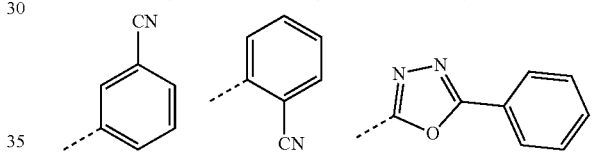
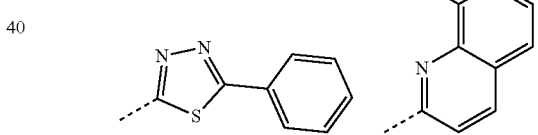
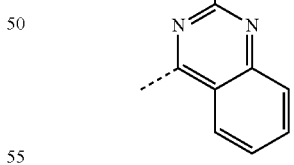
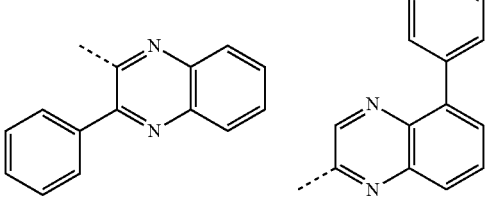

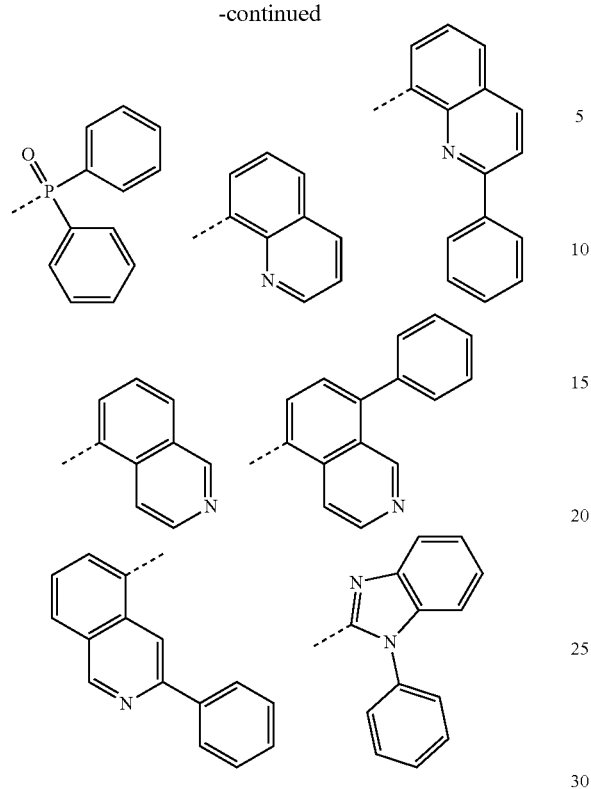
wherein, X' is N or CH, provided that at least one of X' is N.
For example, the compound may be selected from the group consisting of the following compounds.
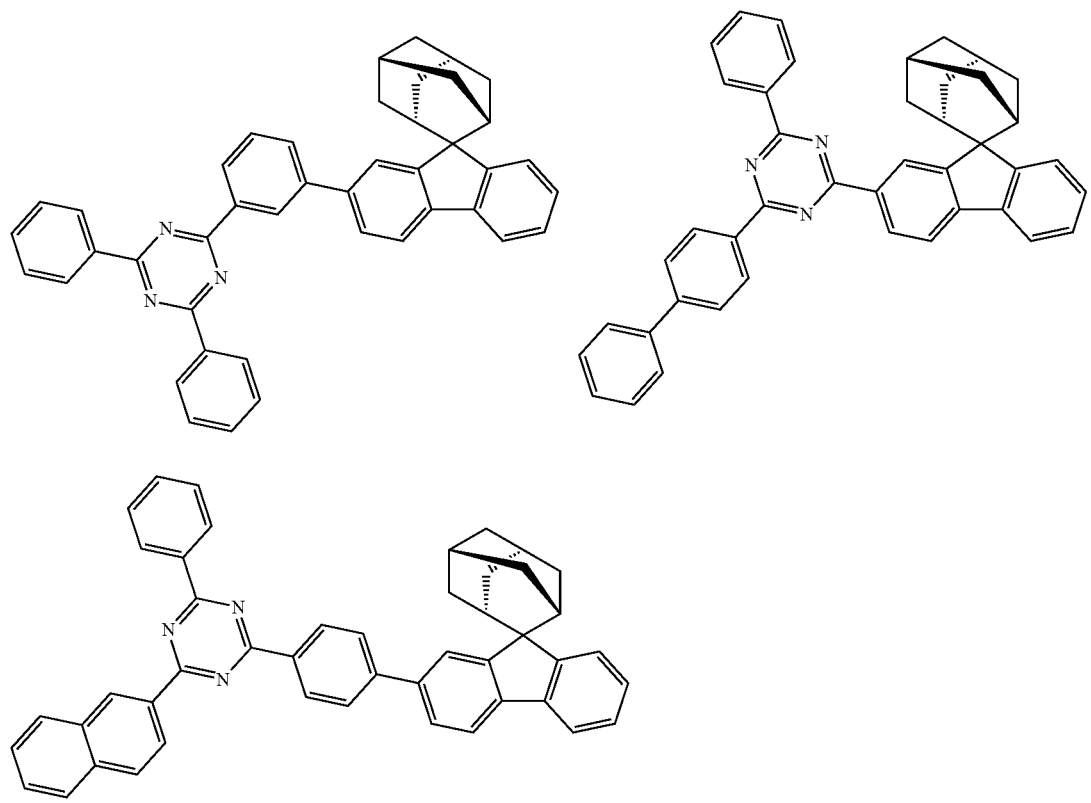

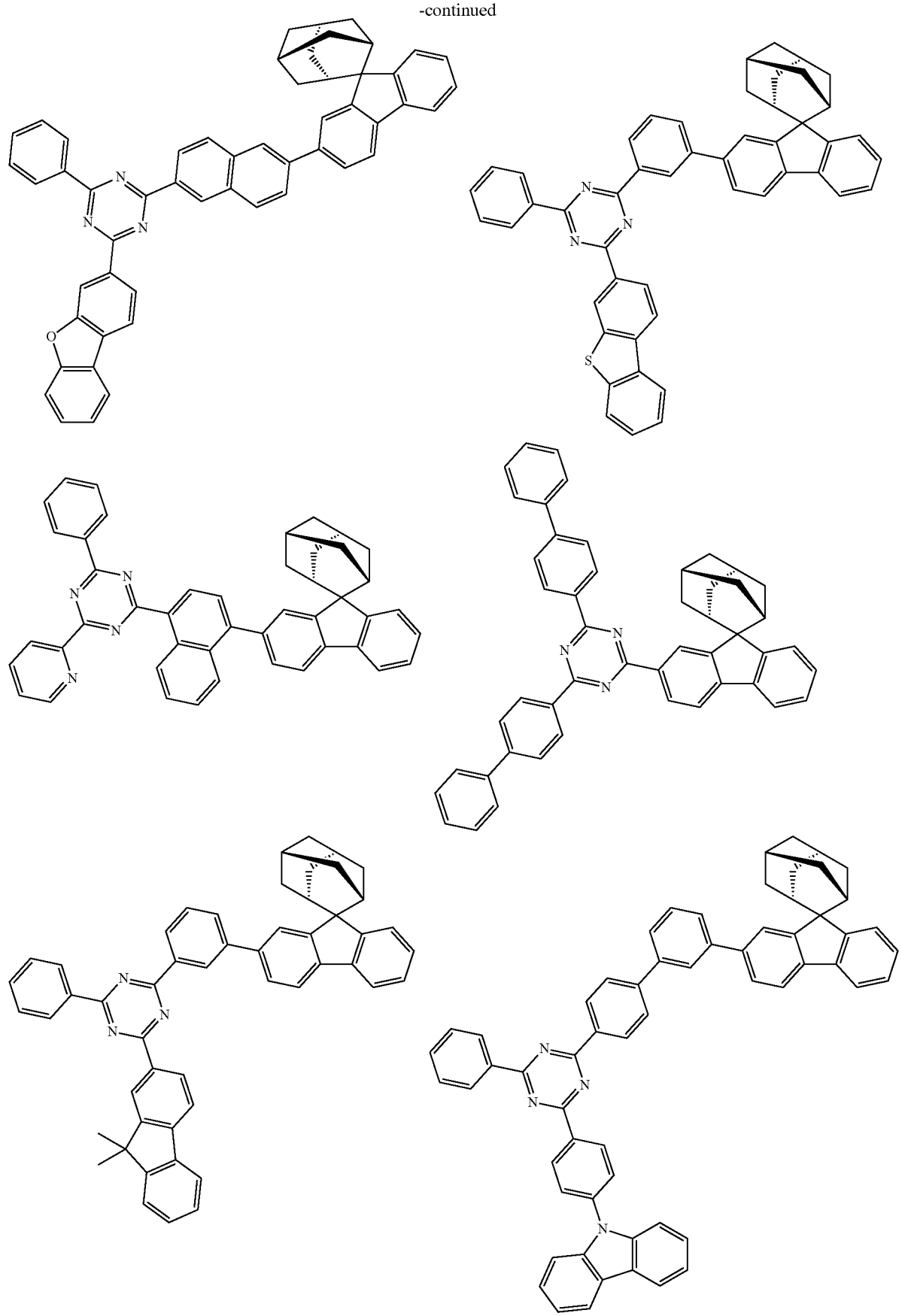

-continued
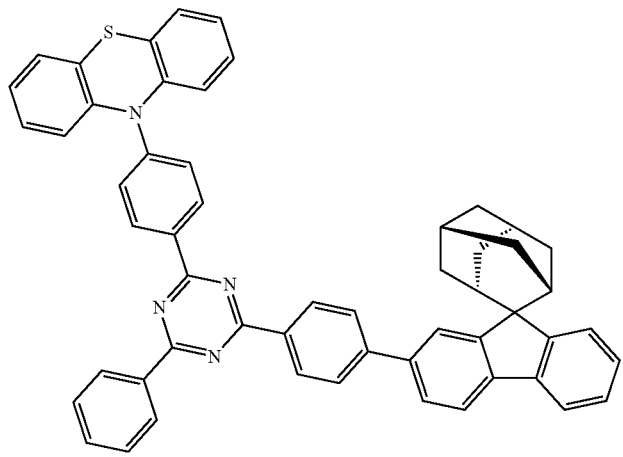
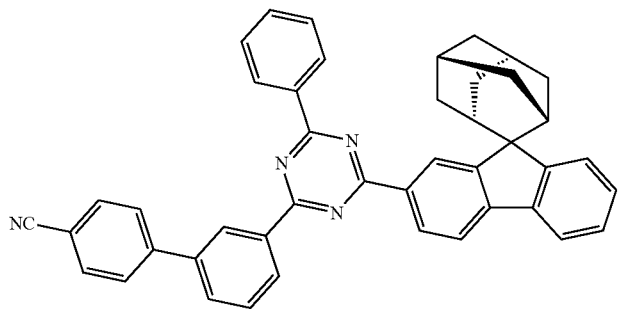
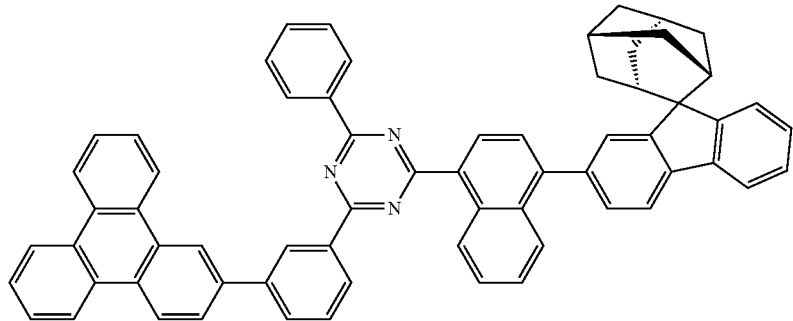
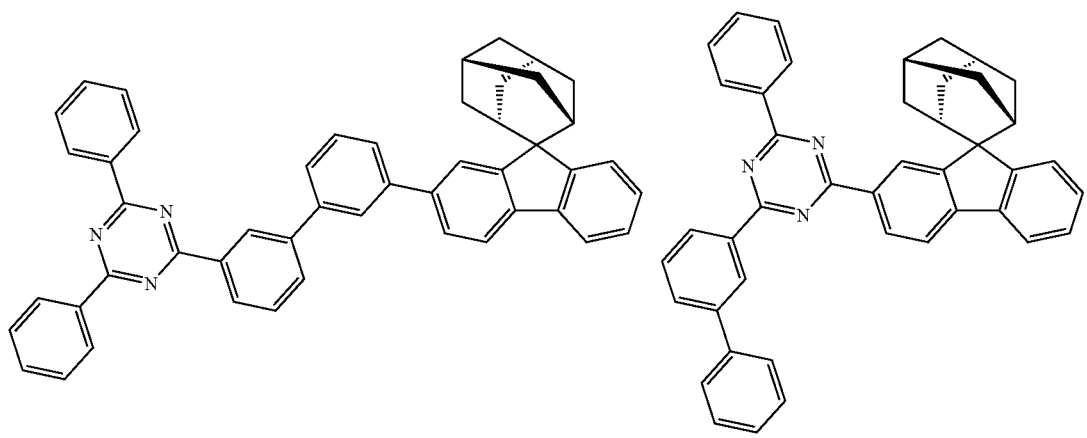

-continued
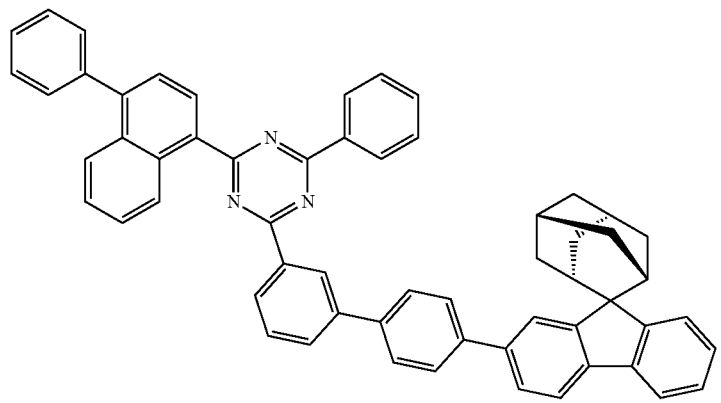
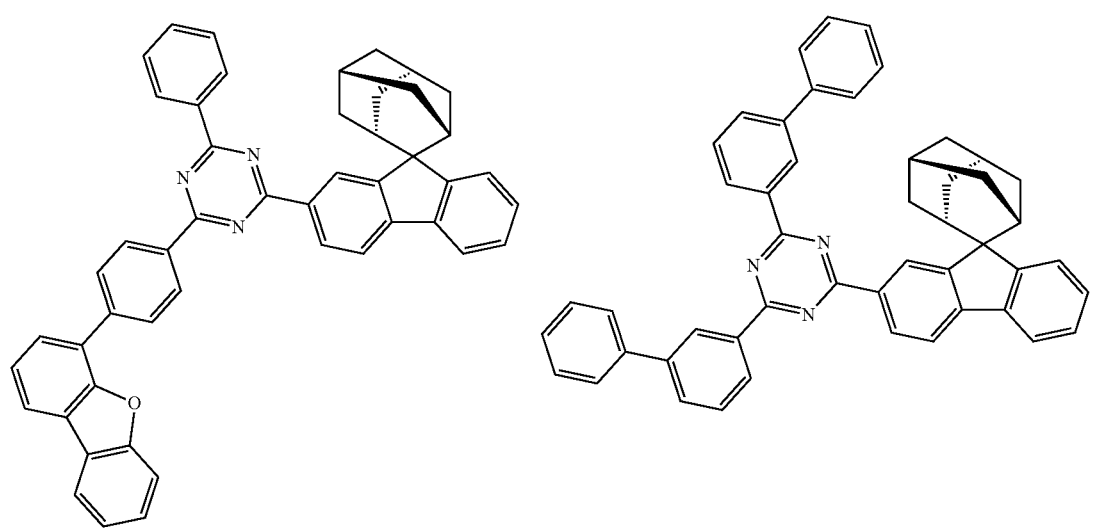
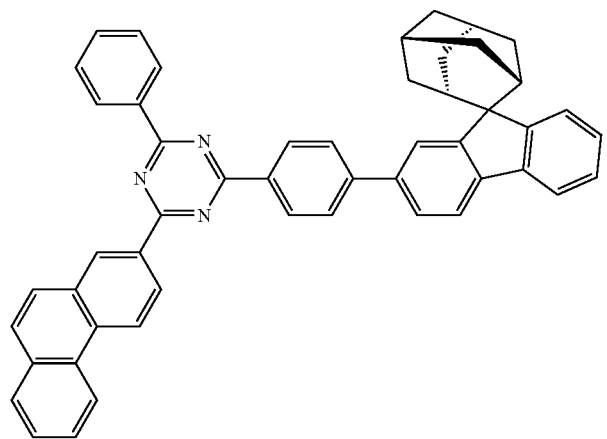

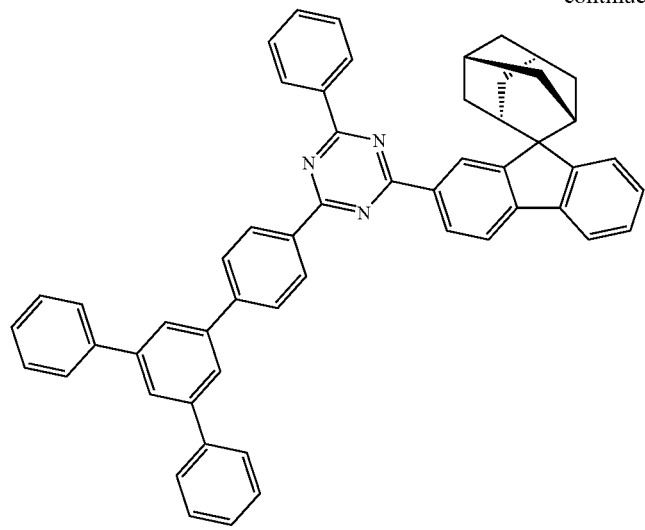
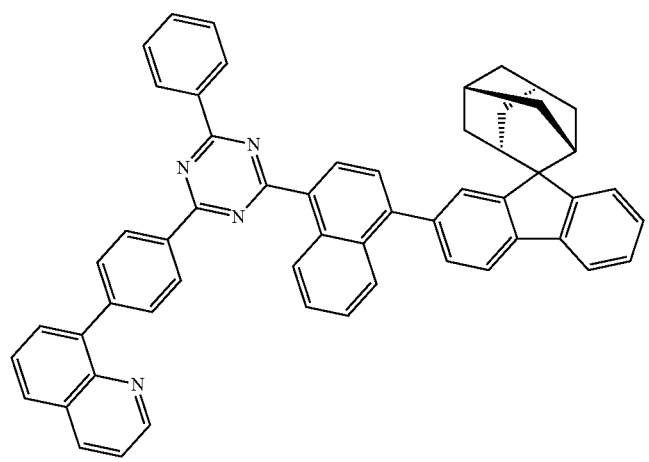
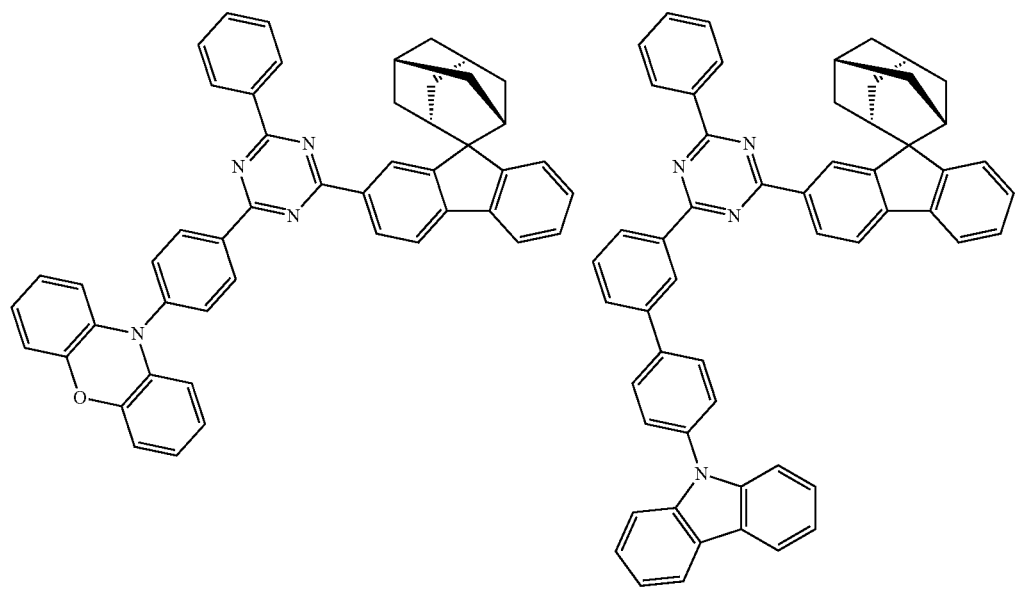

-continued
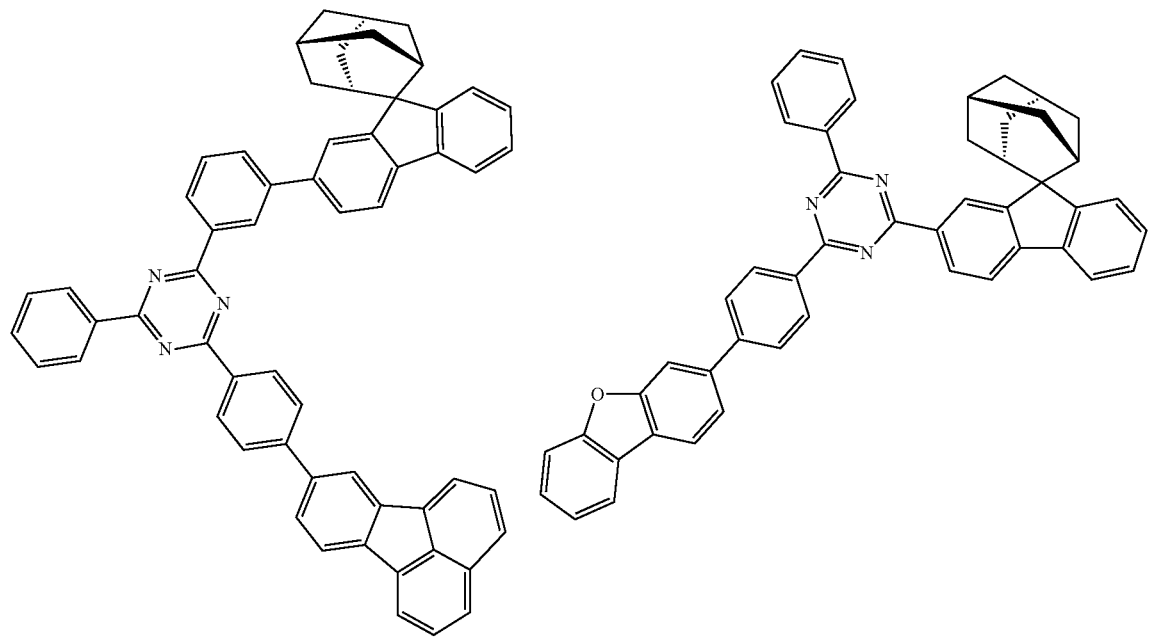
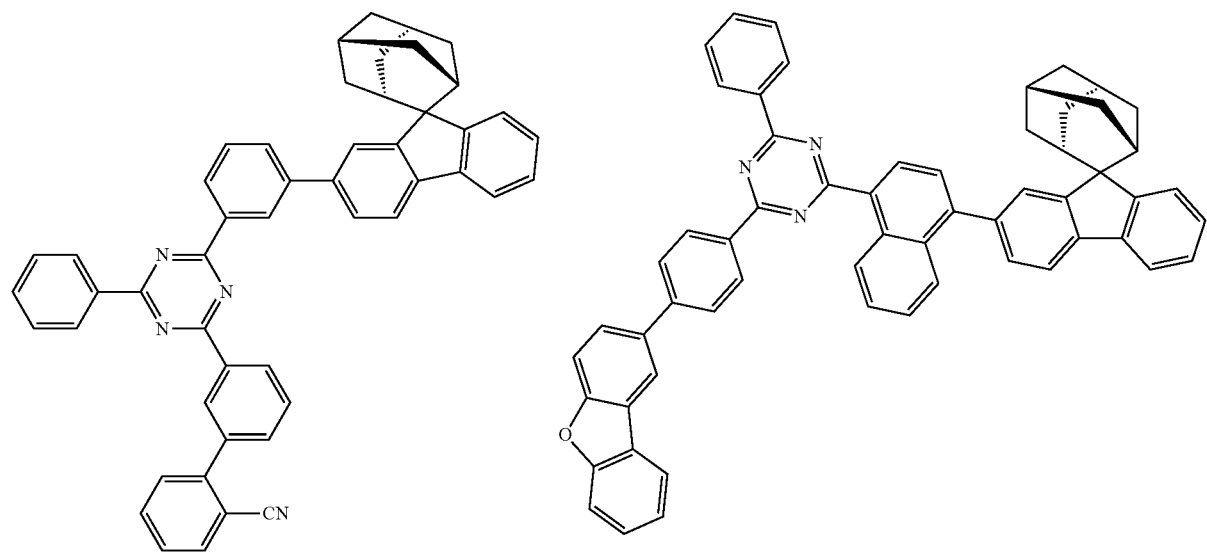

-continued
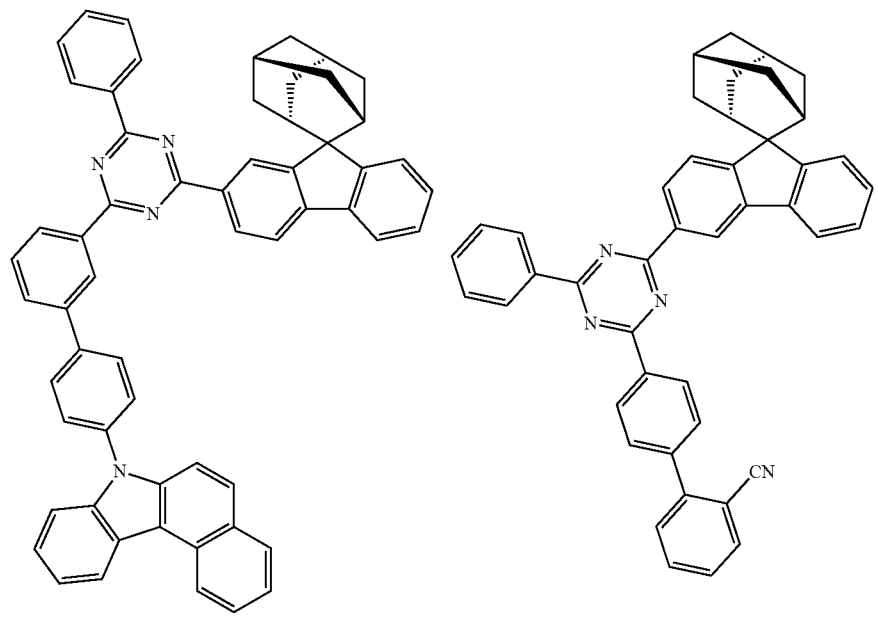
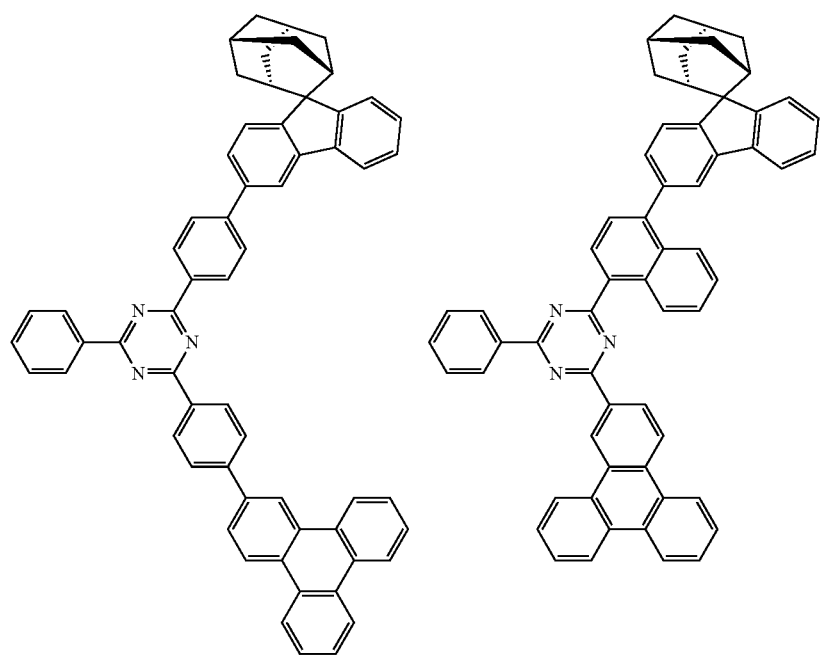

-continued
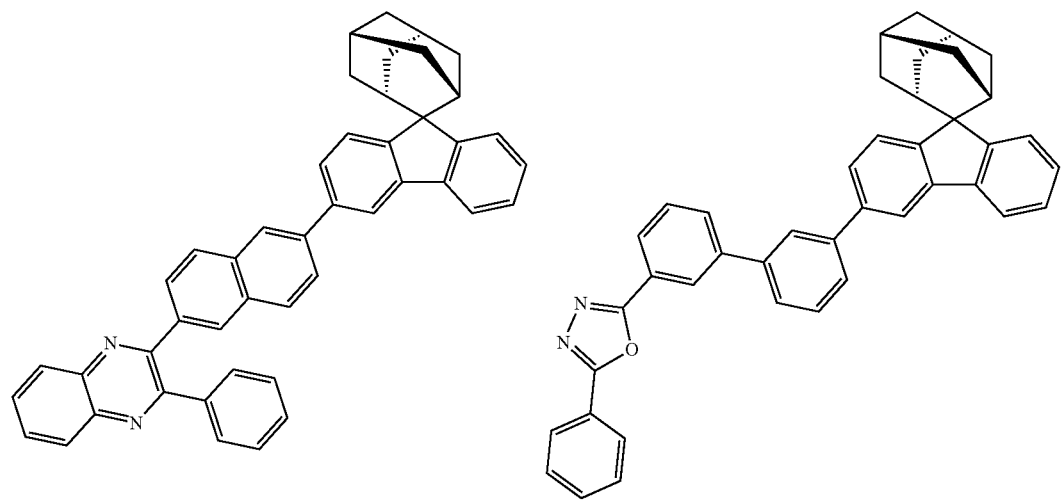
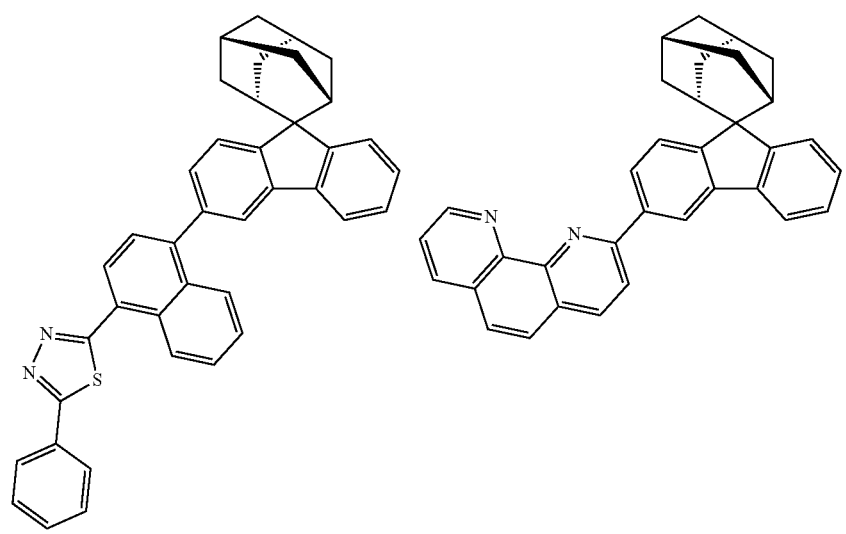
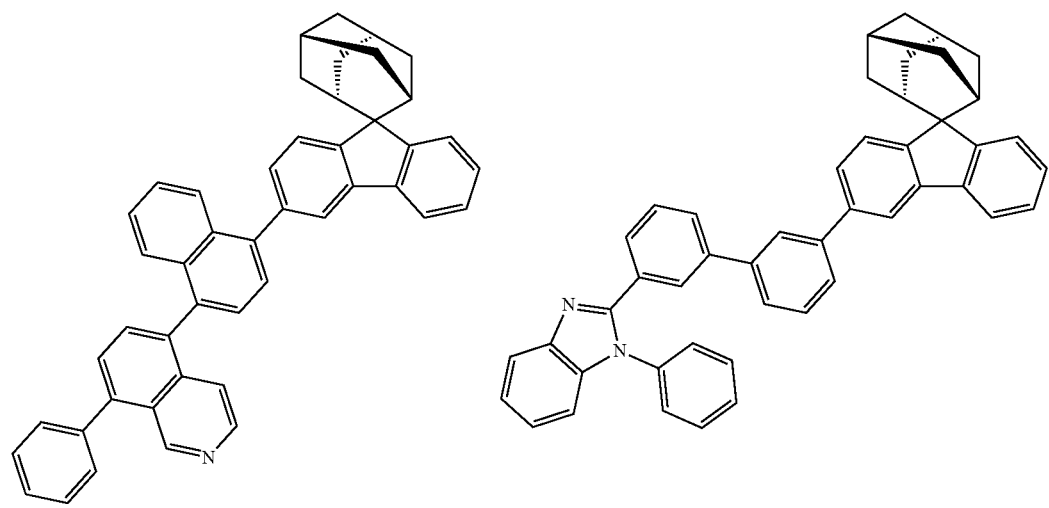

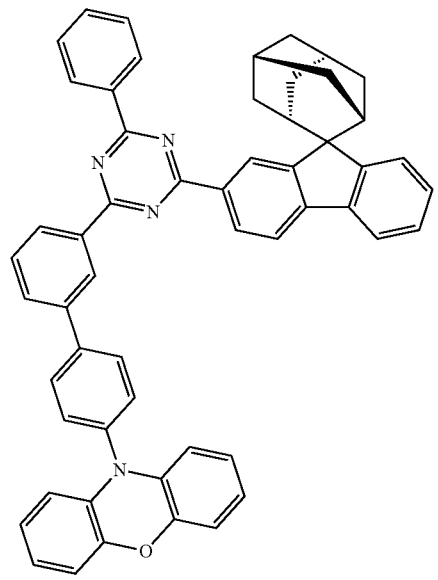
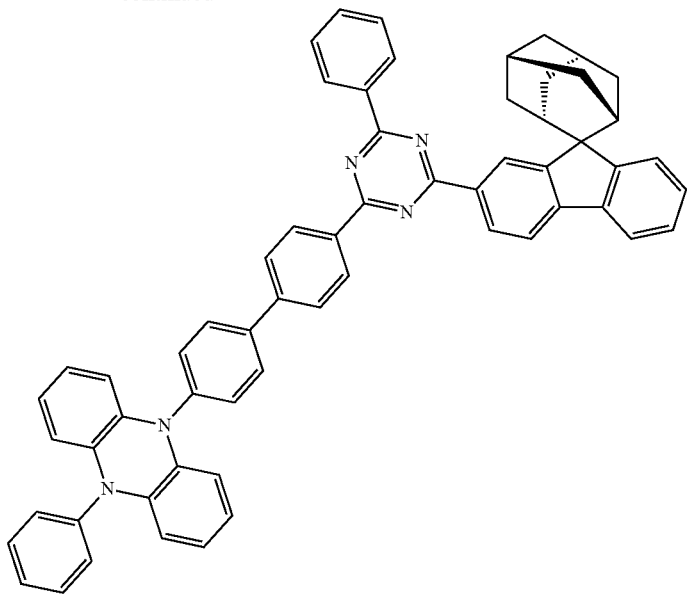
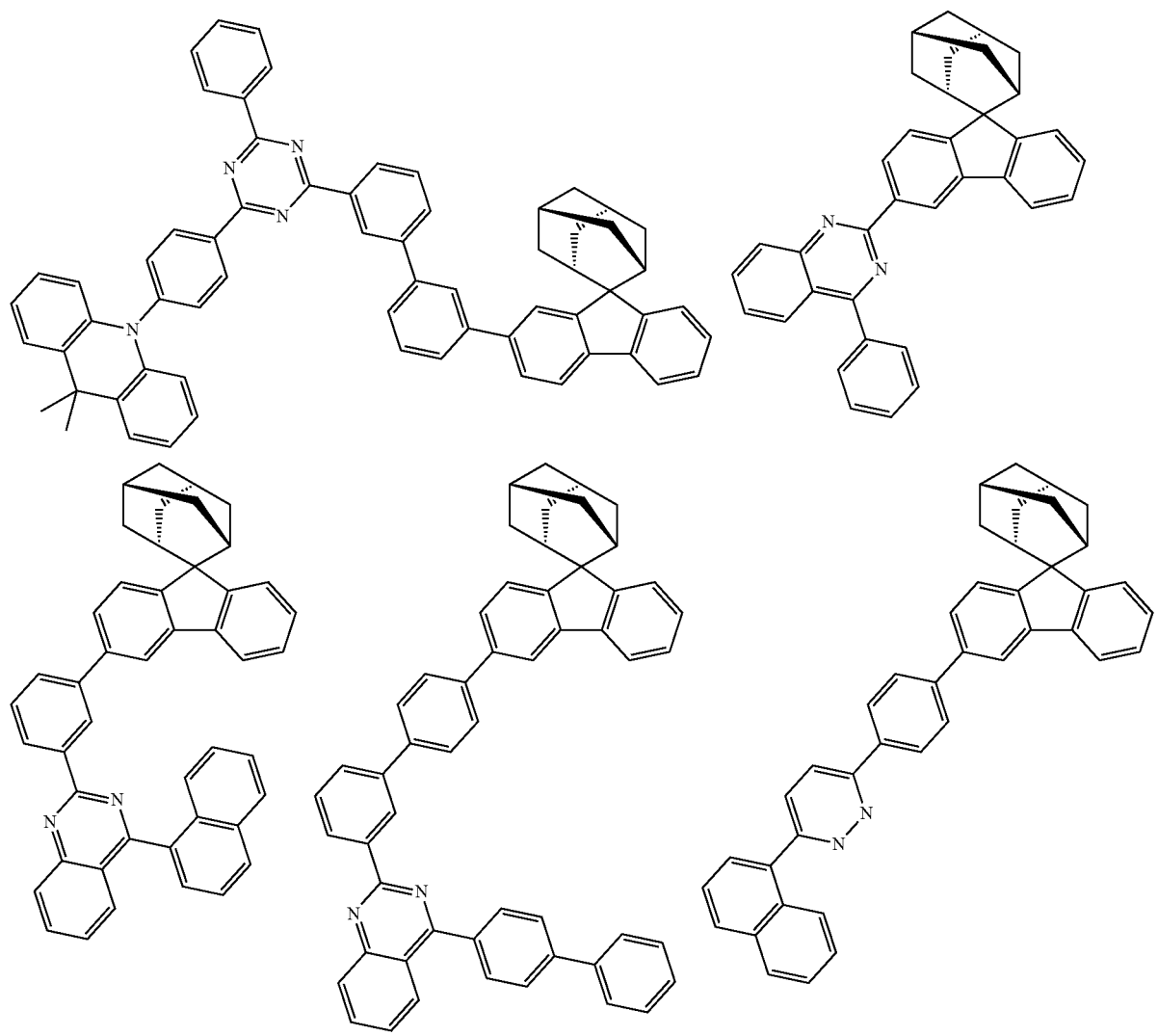

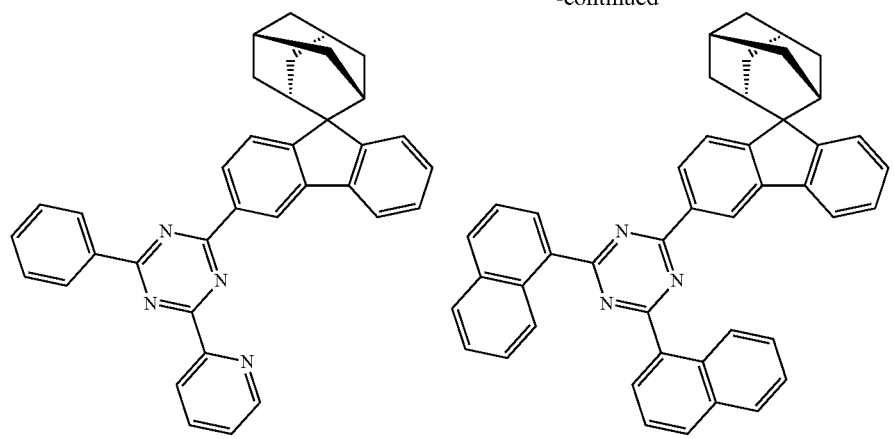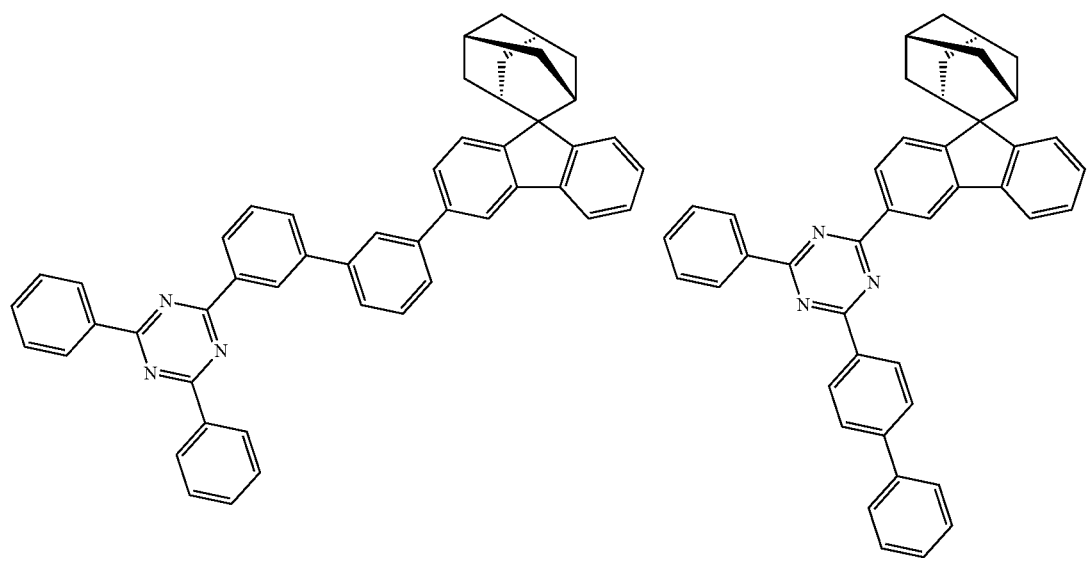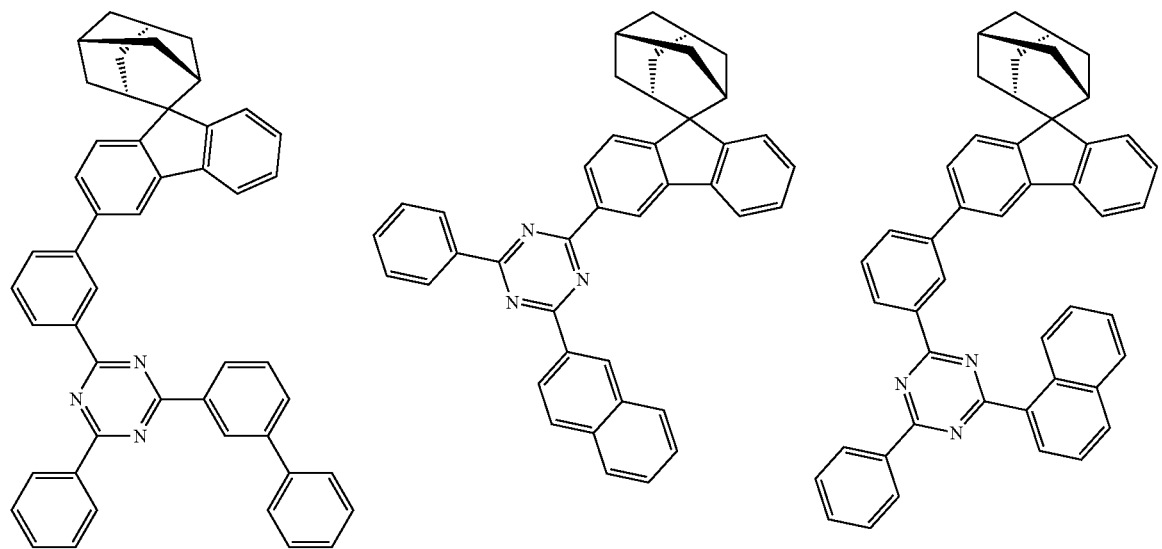

43
44
-continued
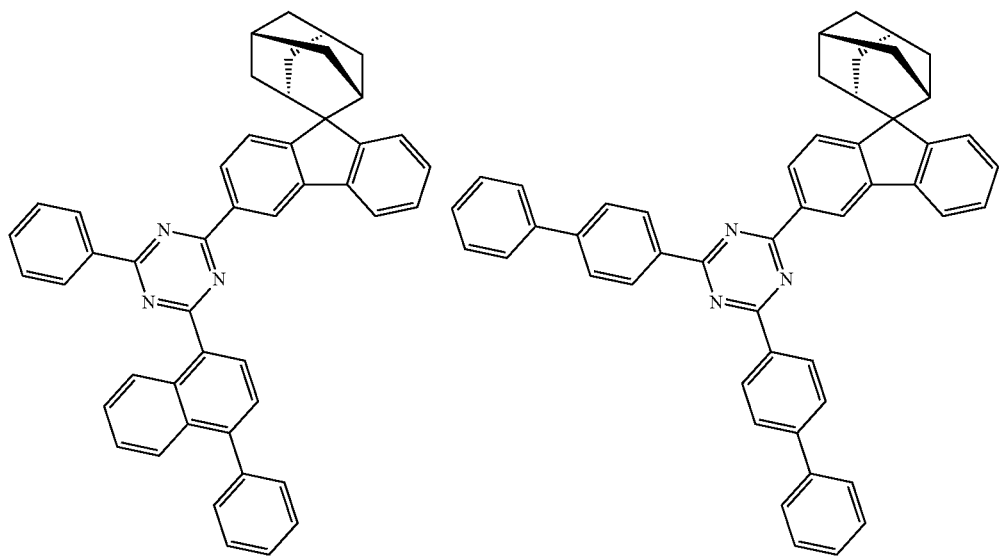
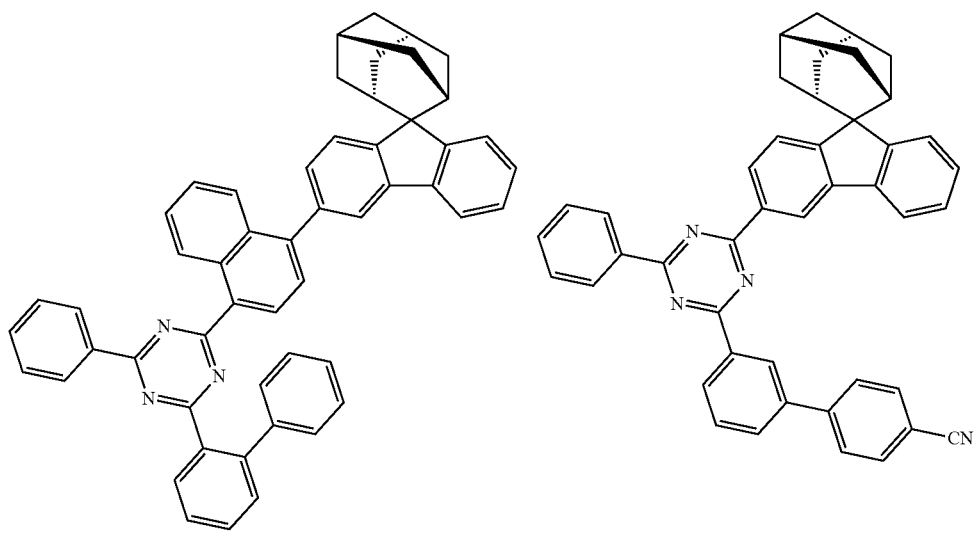
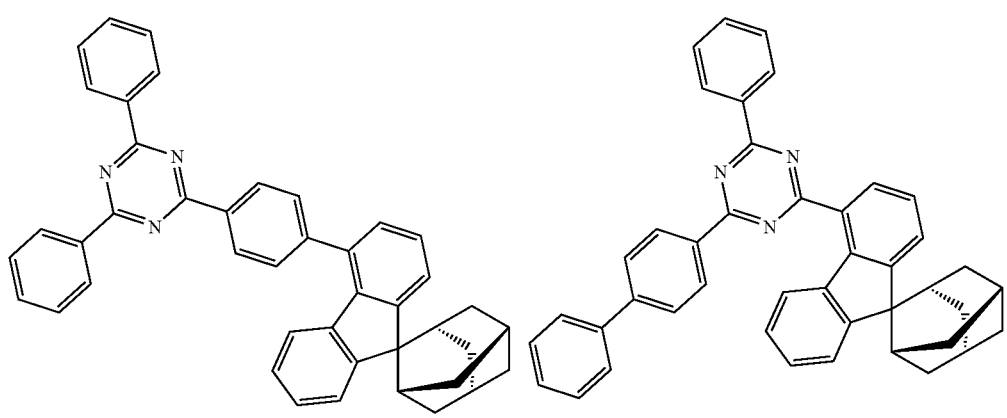

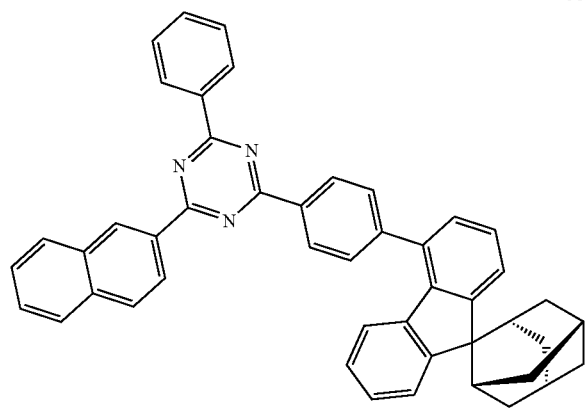
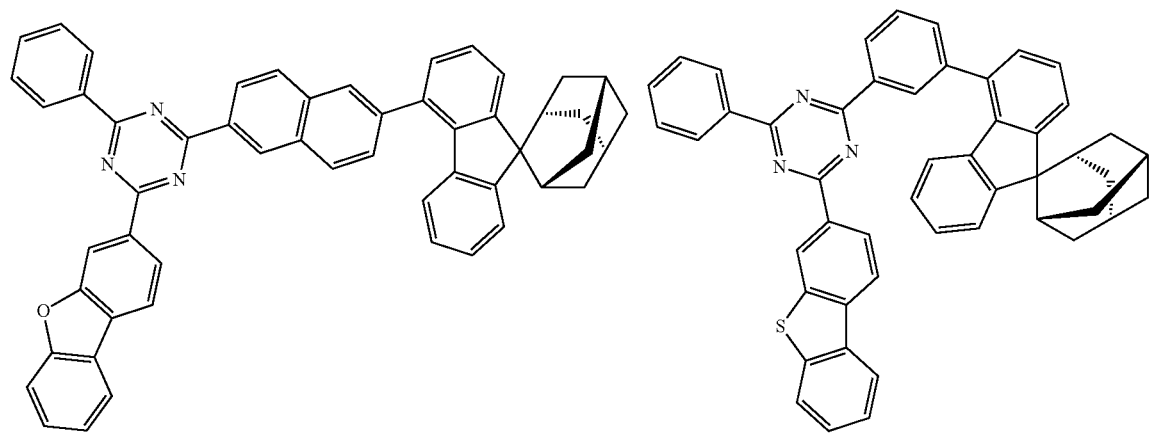
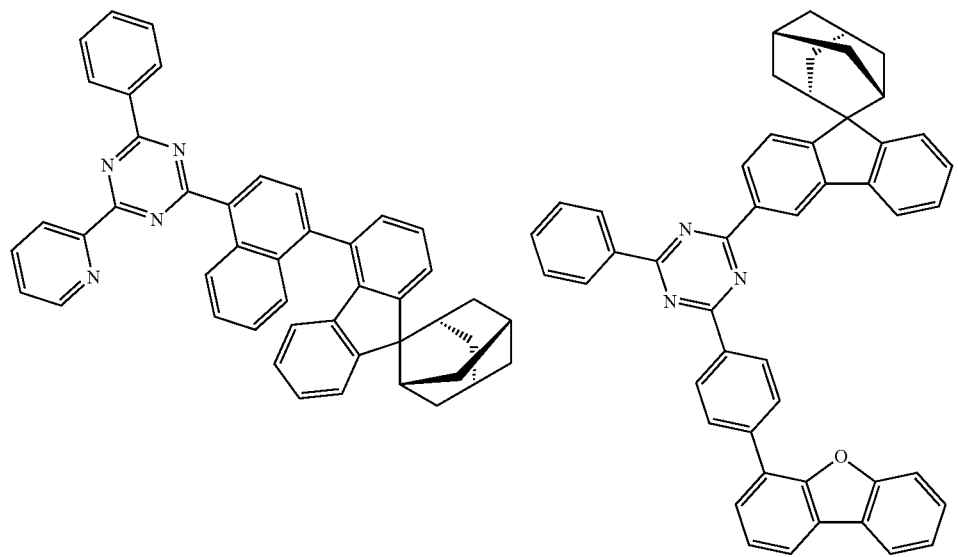

-continued
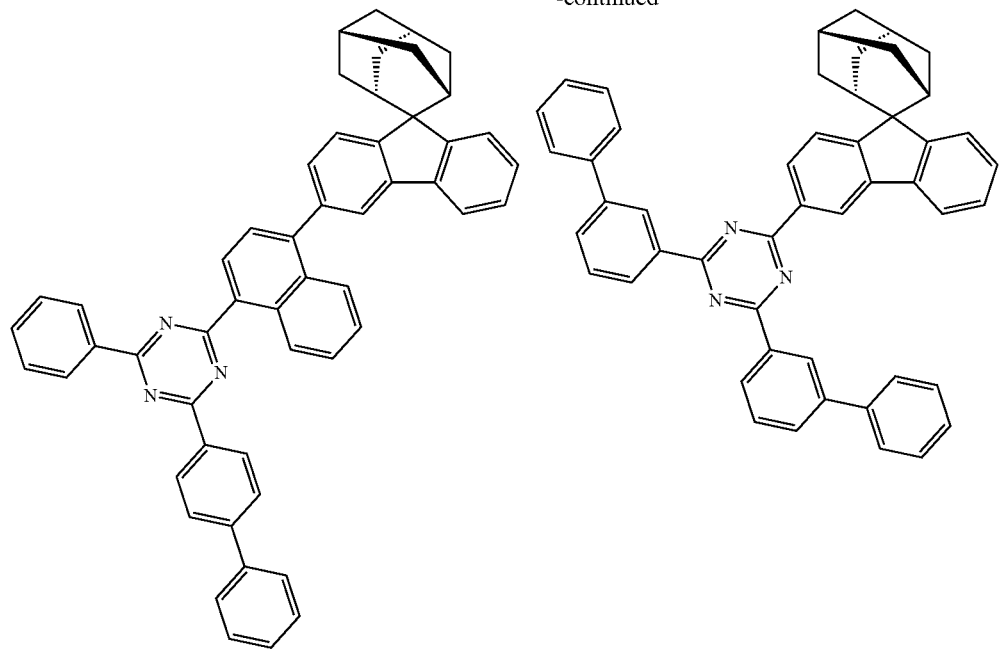
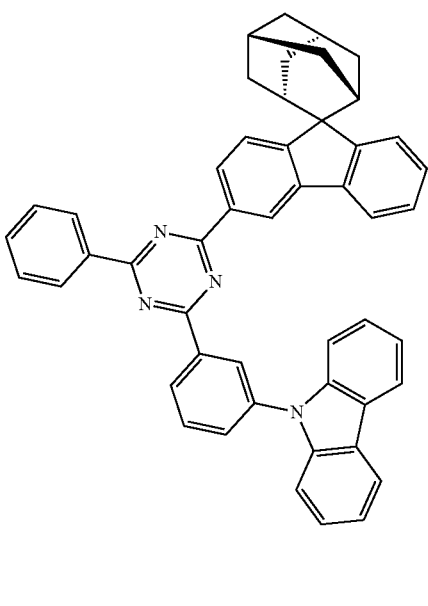

-continued
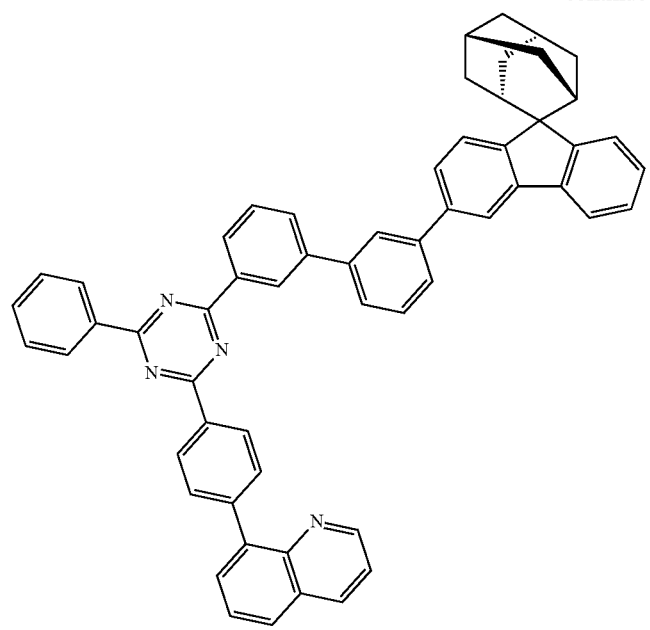
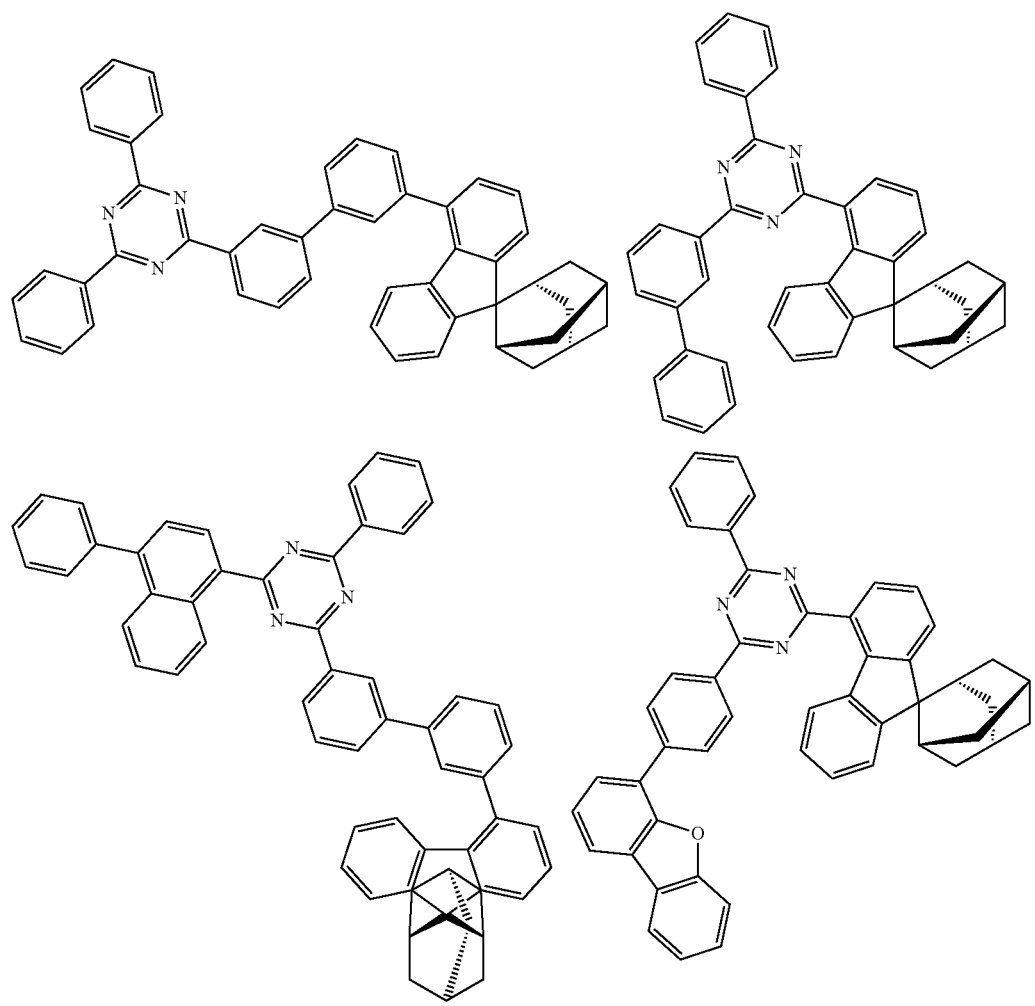

-continued
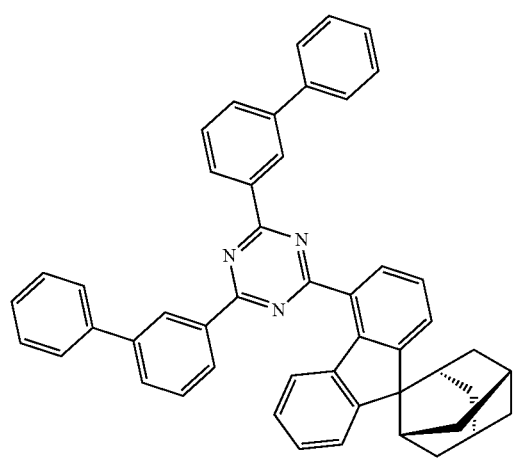
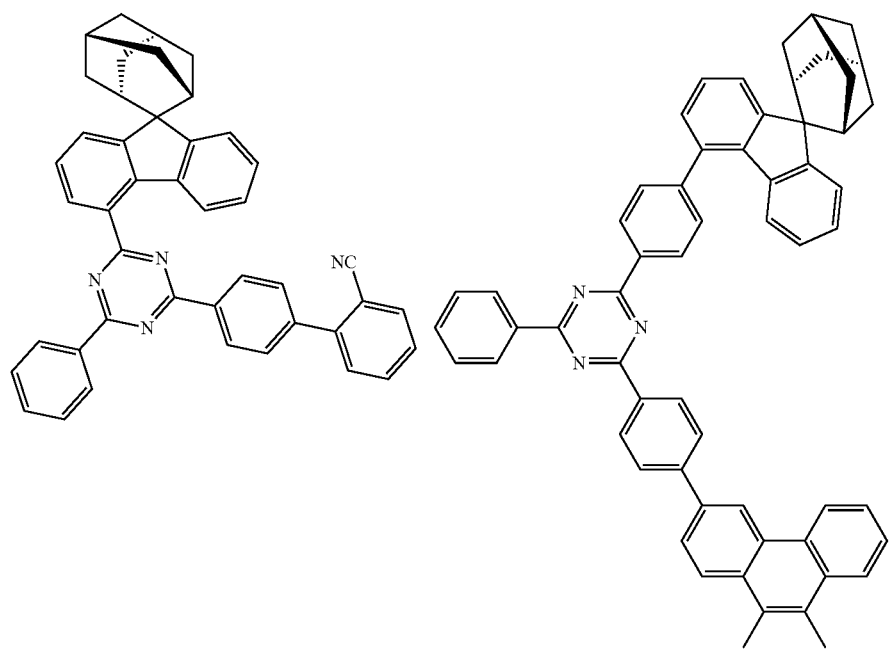
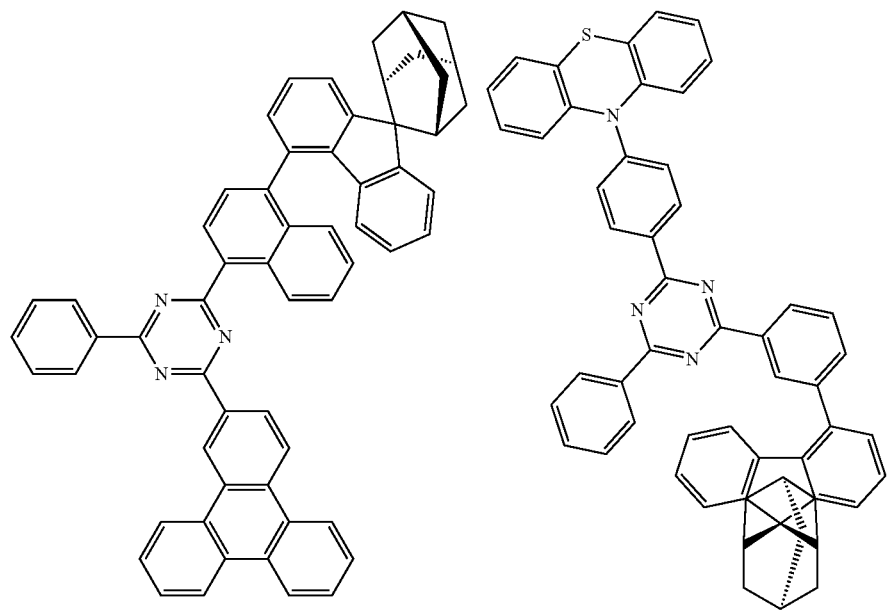

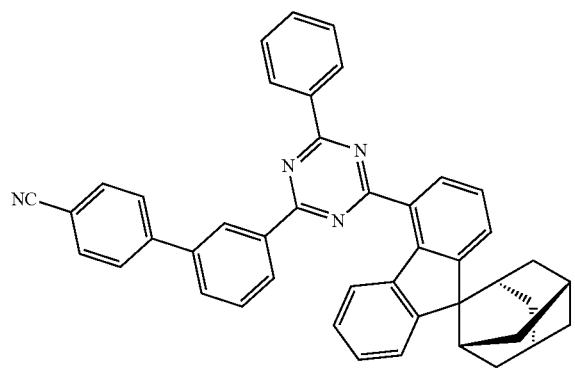
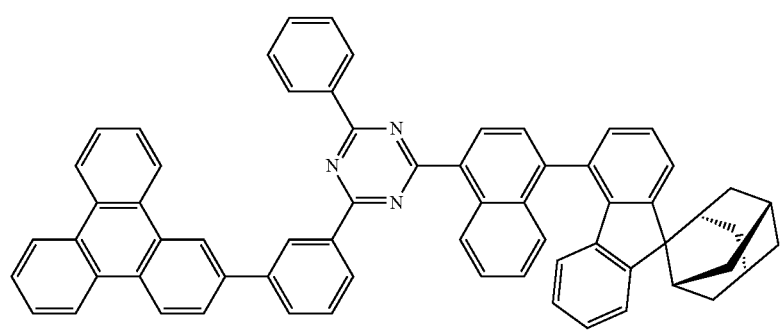
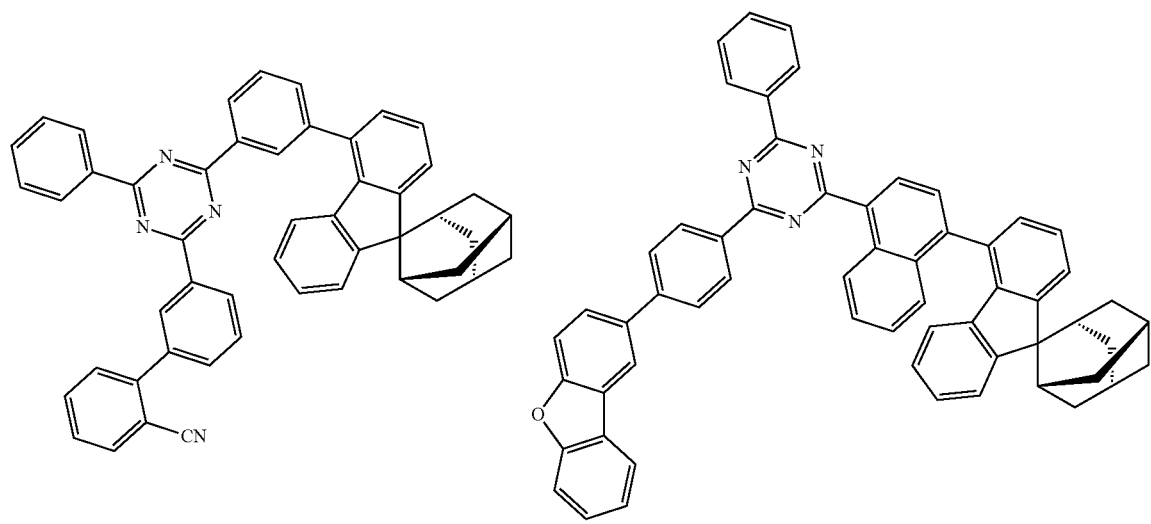

-continued
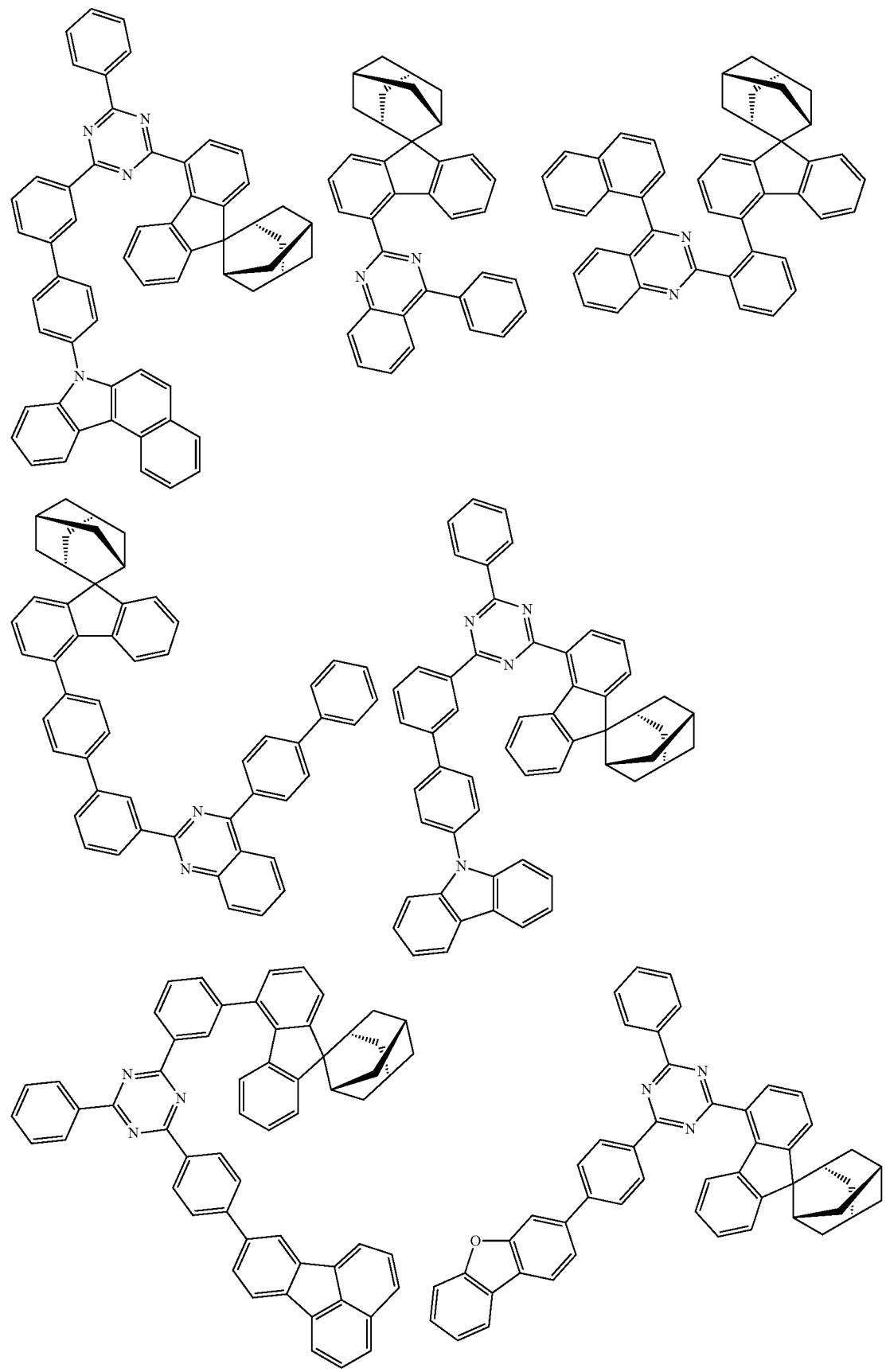

-continued
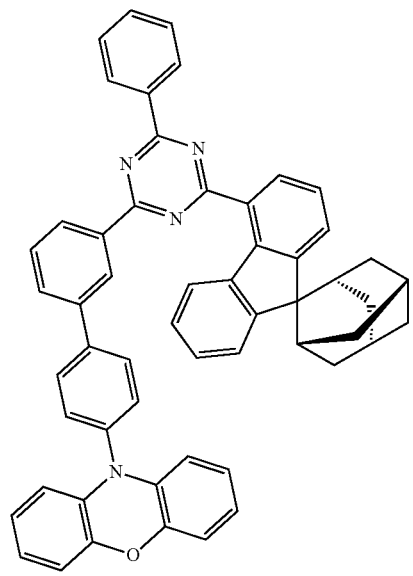
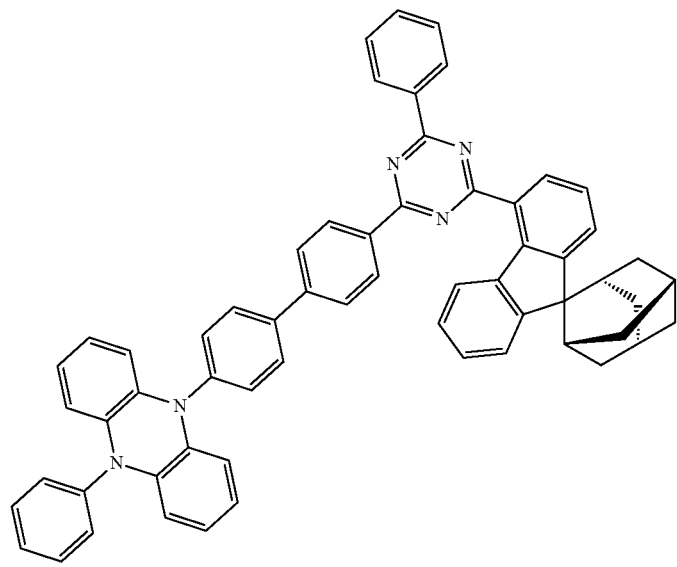
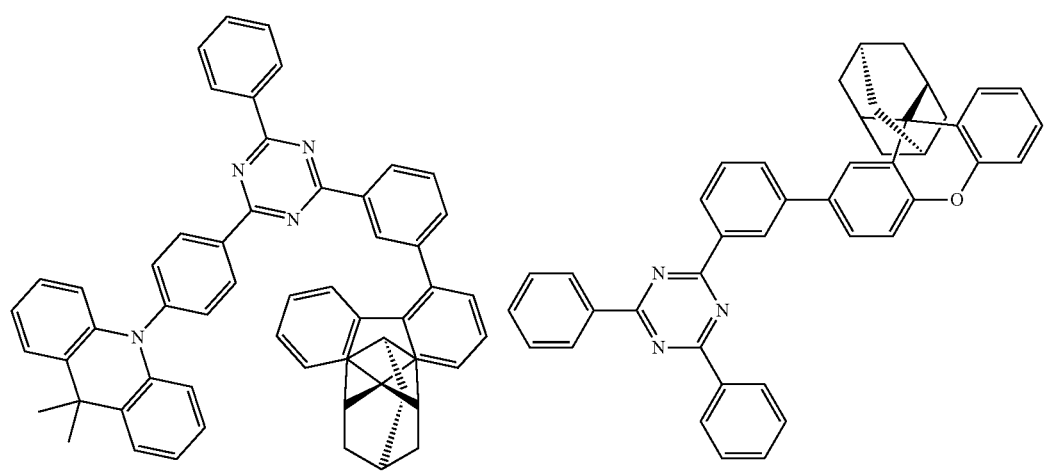
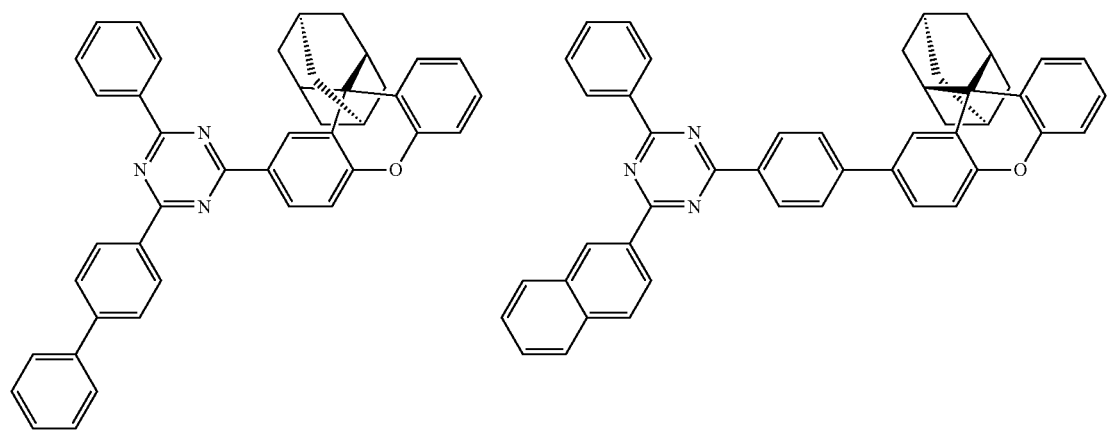

-continued
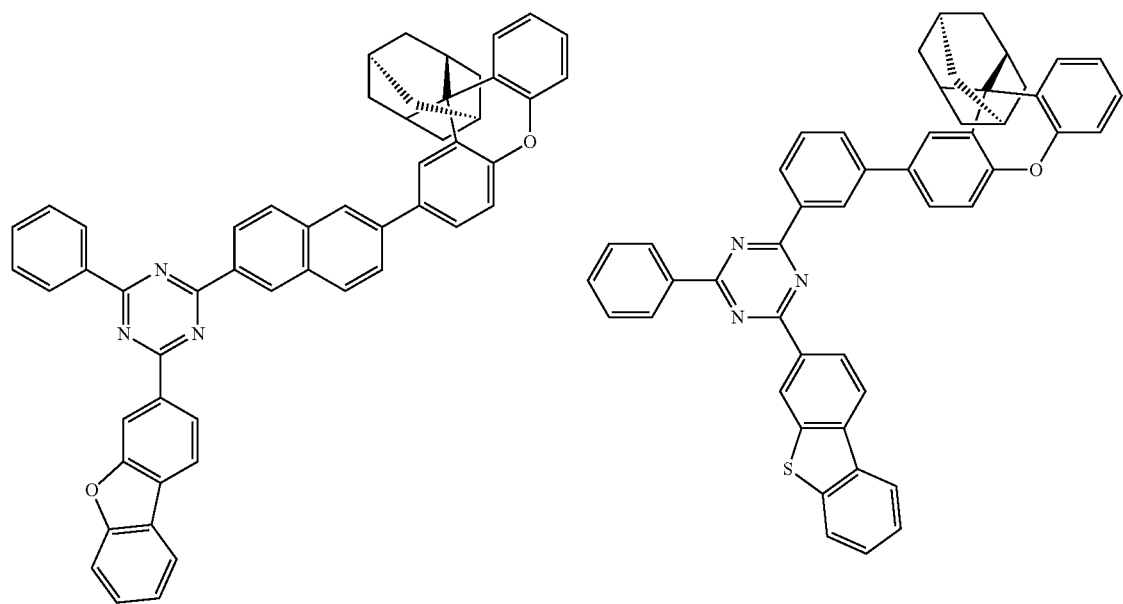
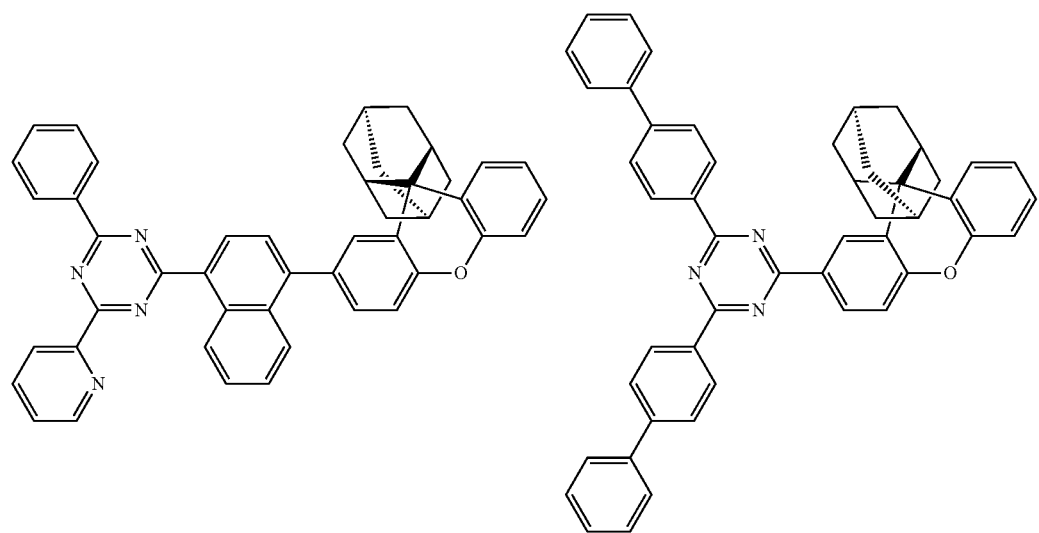

-continued
61
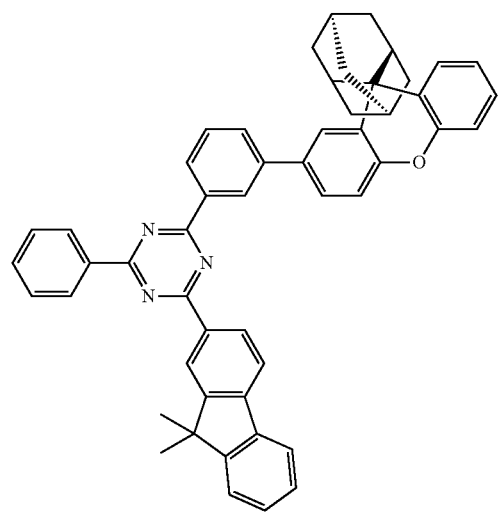
62
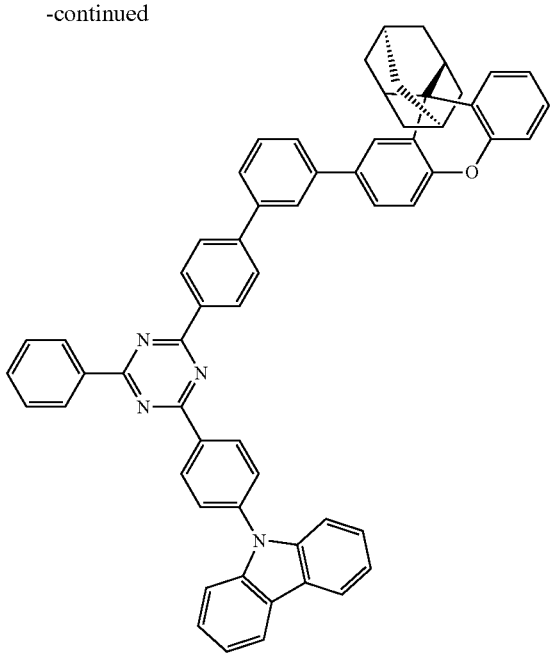
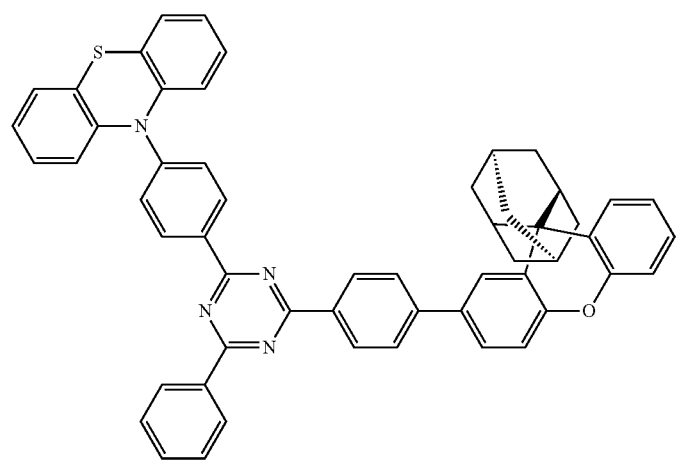
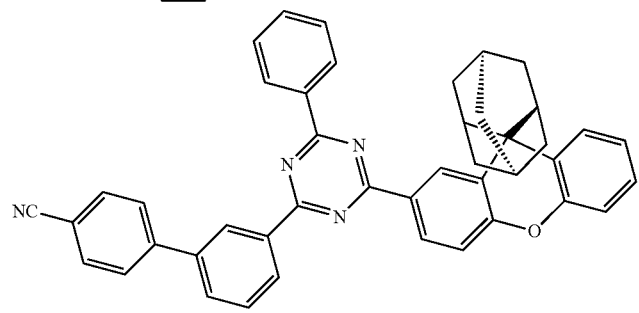
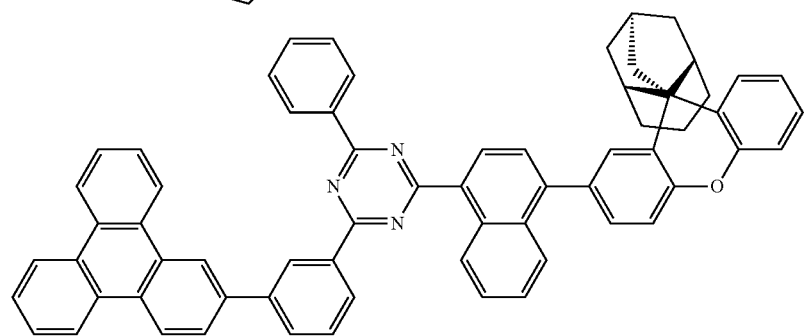

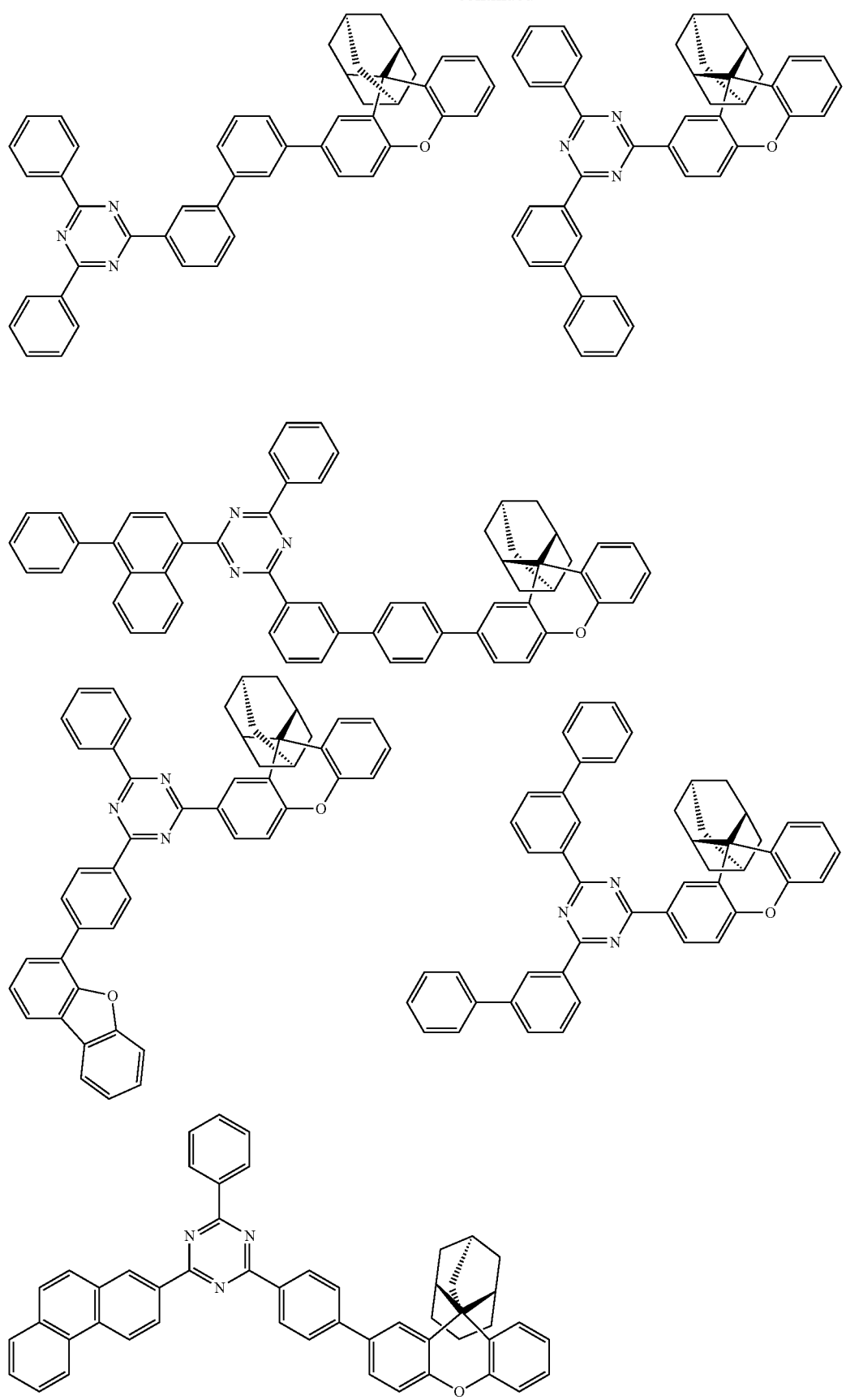

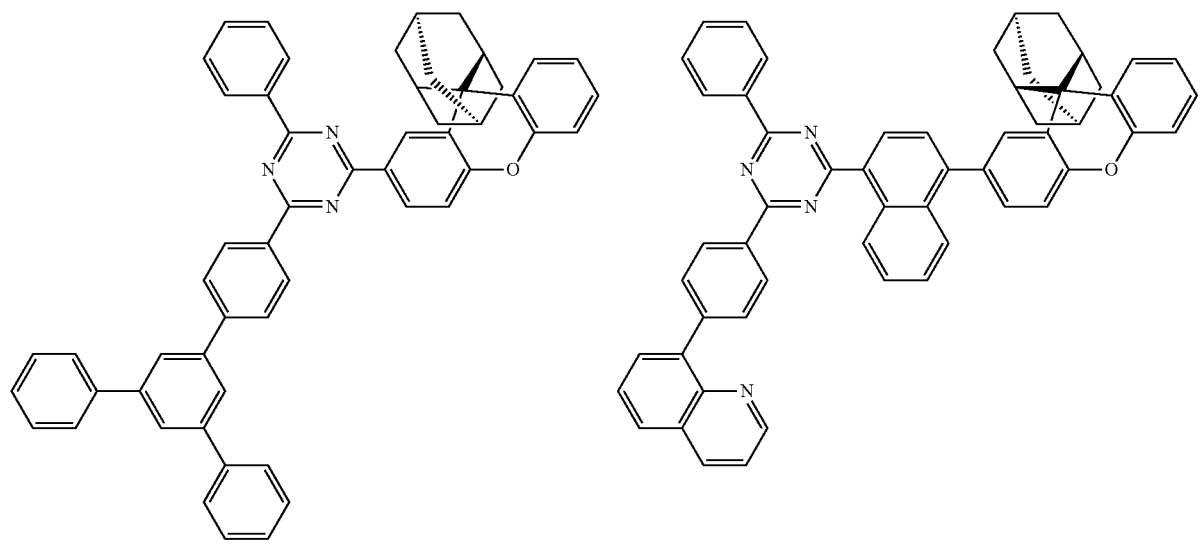
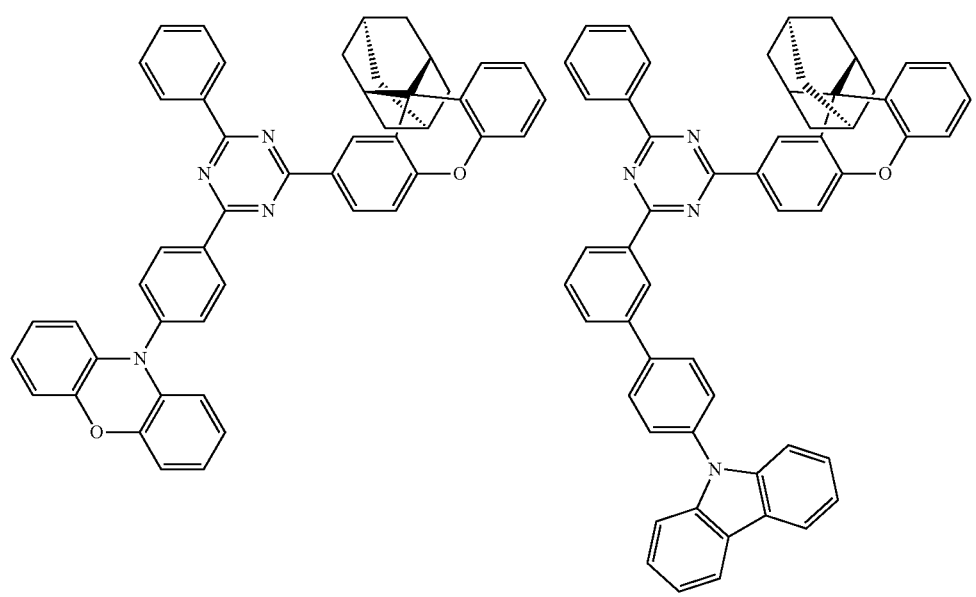

67
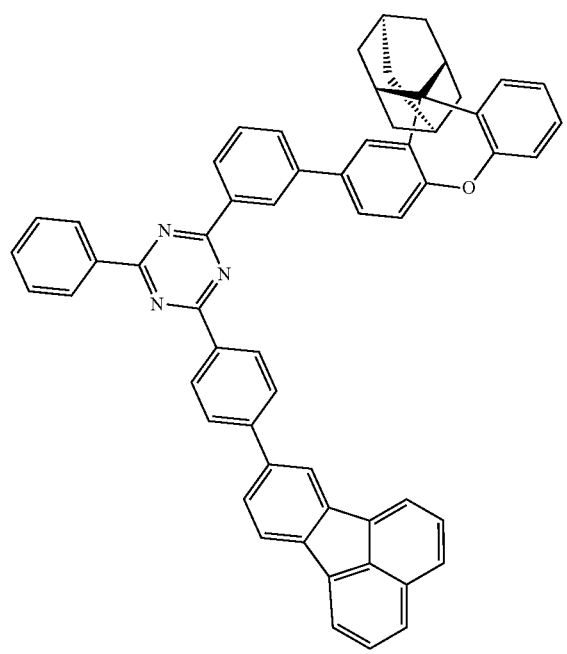
68
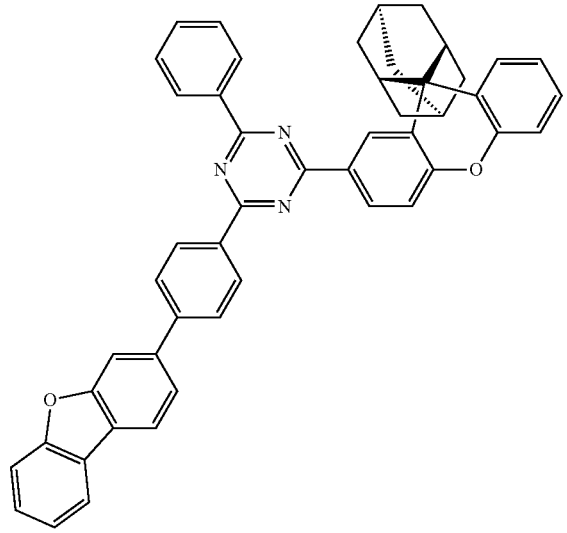
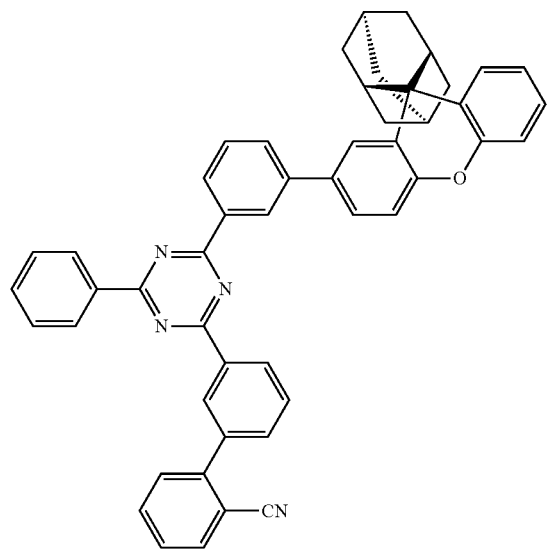
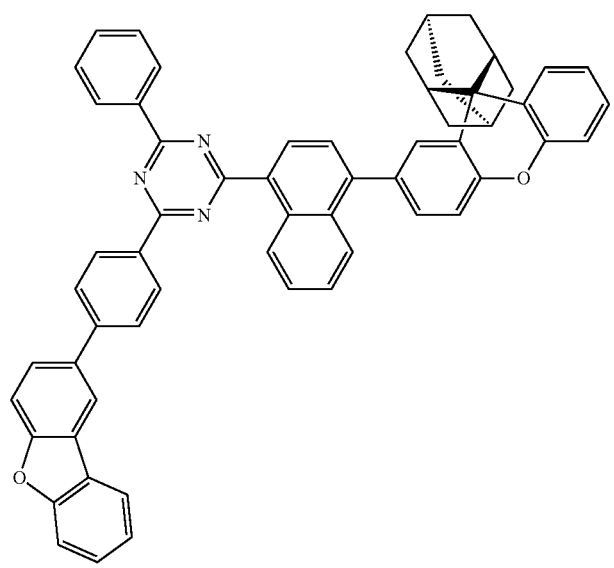

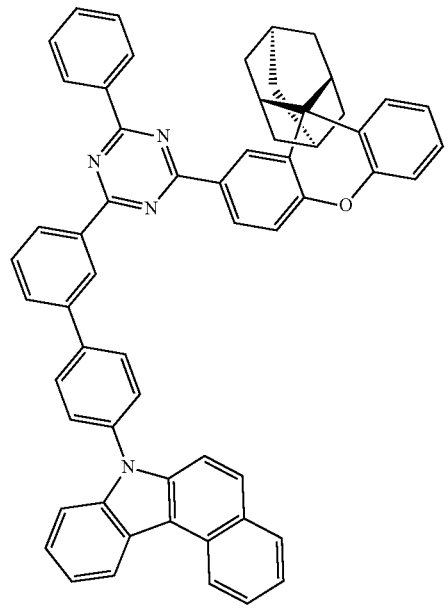
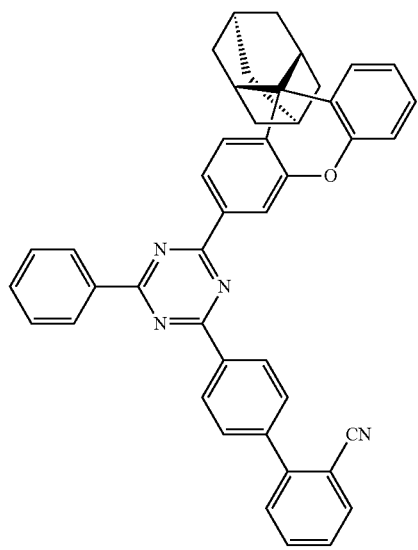
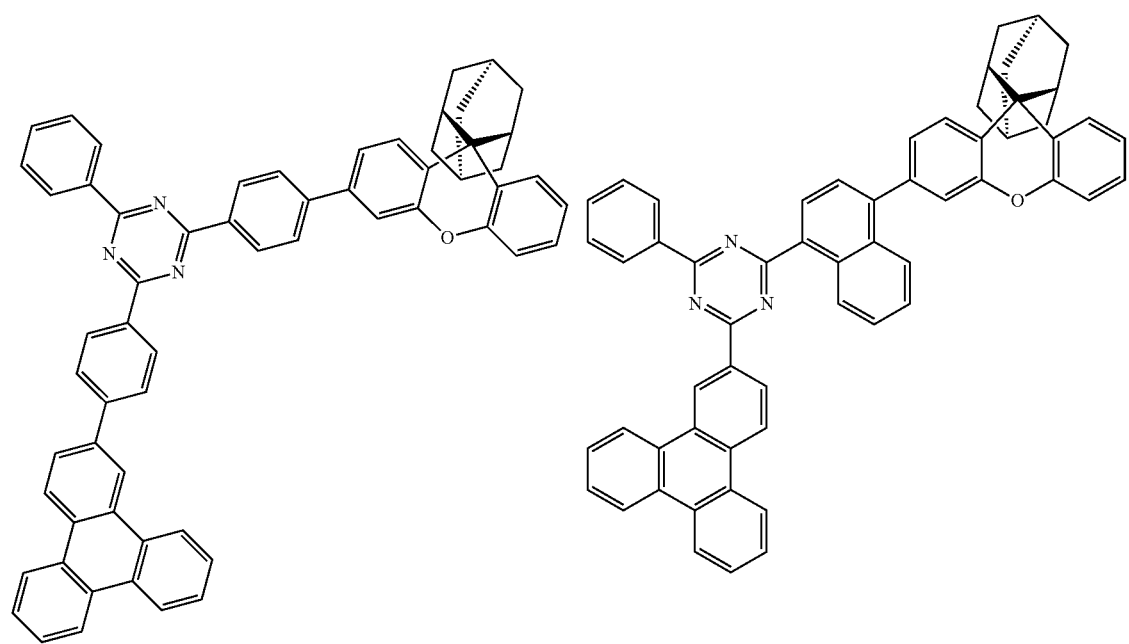

71
72
-continued
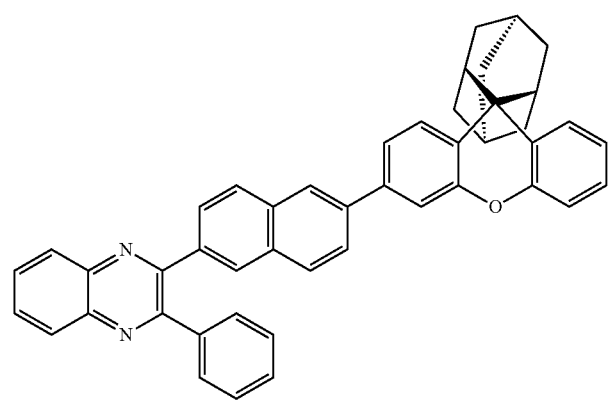
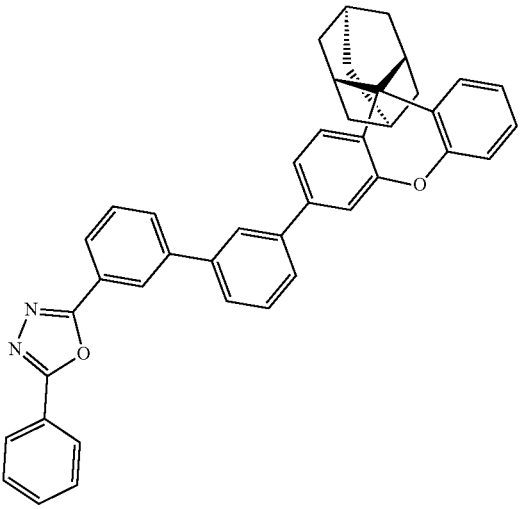
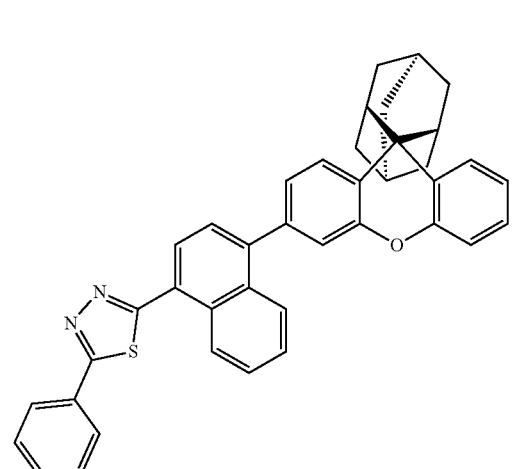
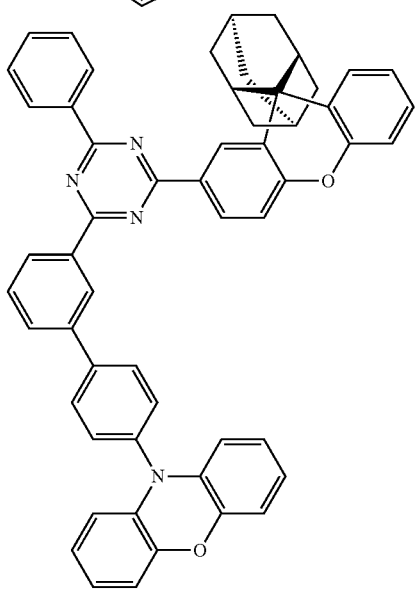
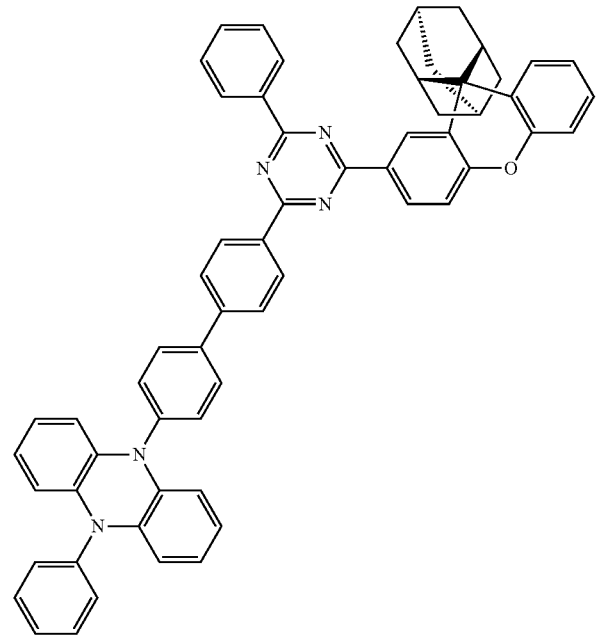

73 74
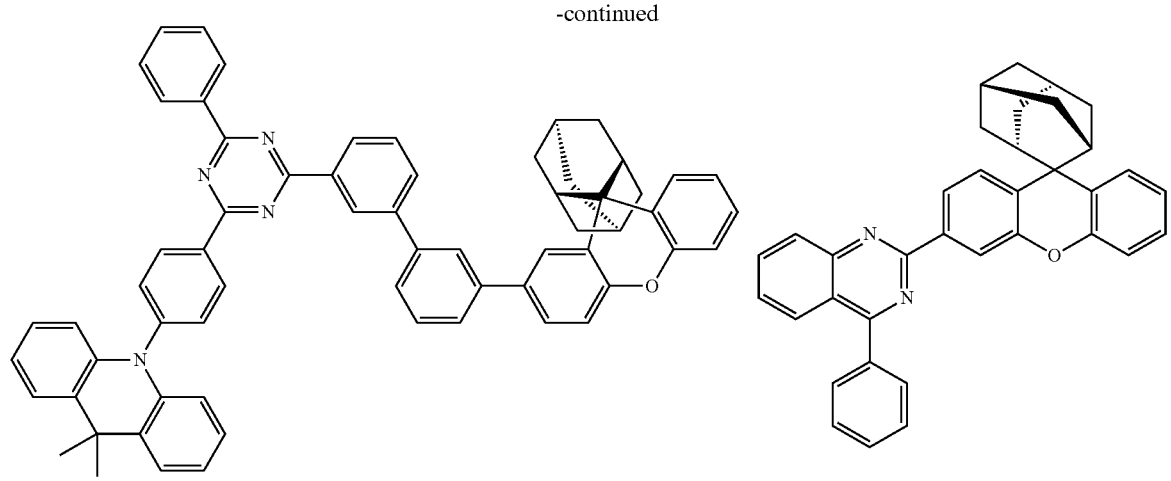
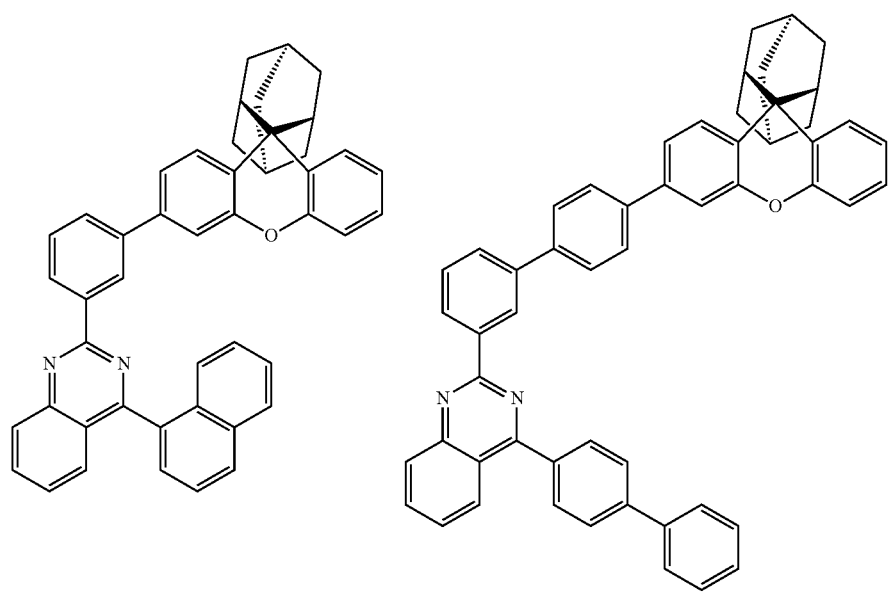
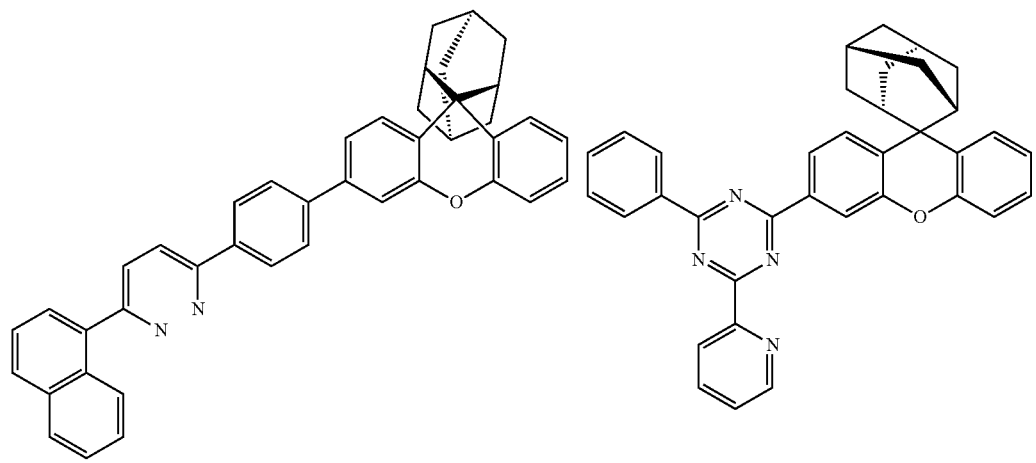

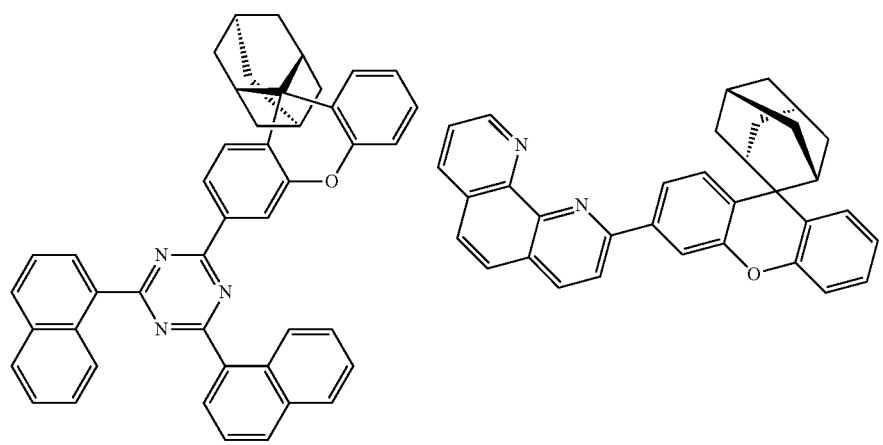
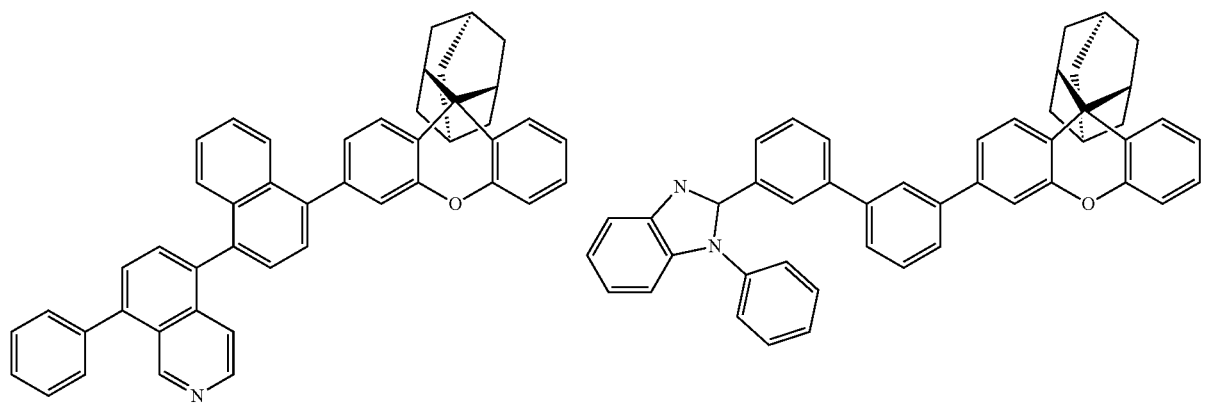
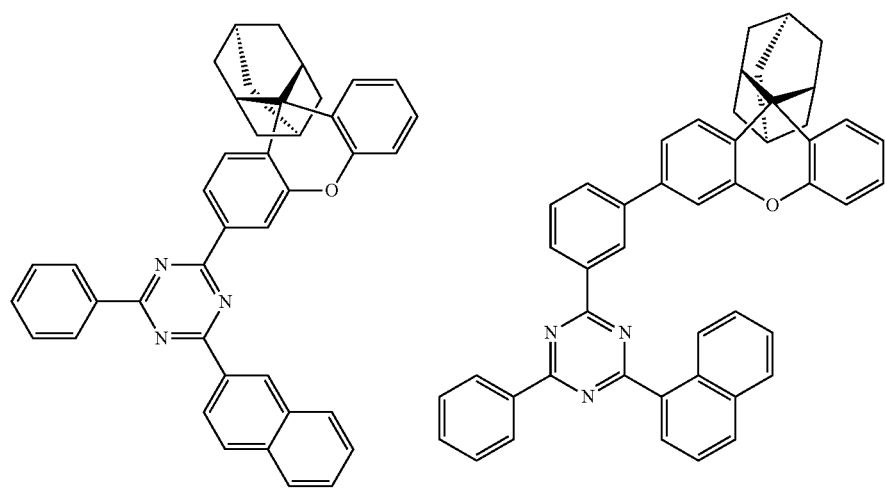

-continued
| 77 | 78 |
|---|---|
| 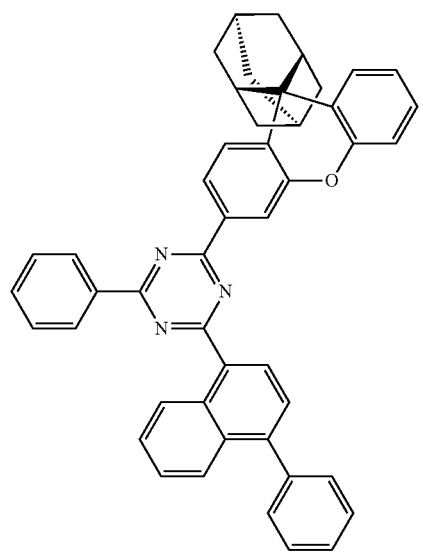 | 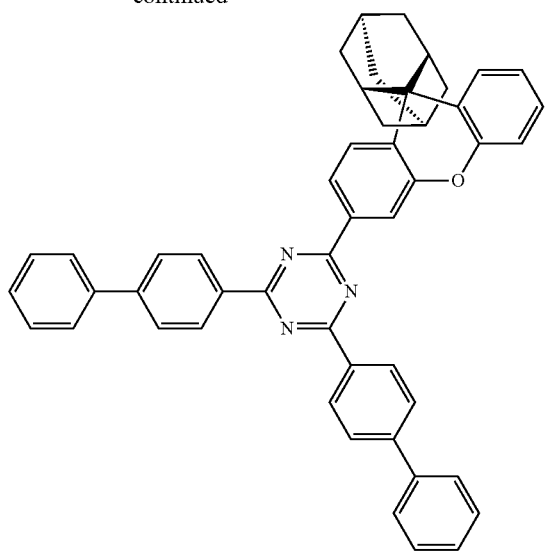 |
| 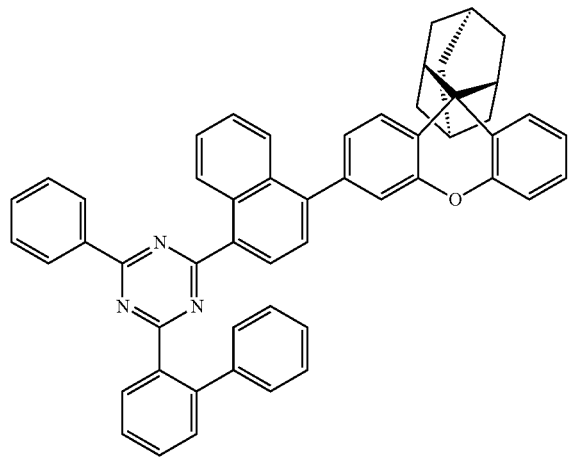 | 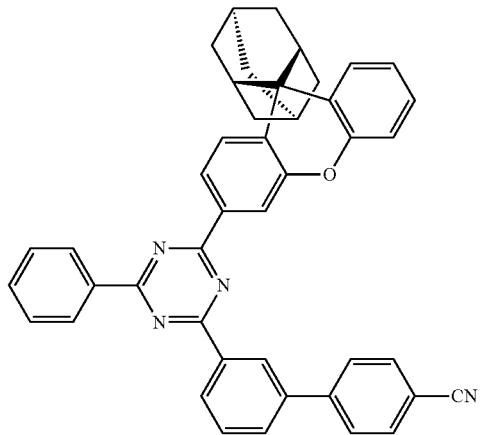 |
| 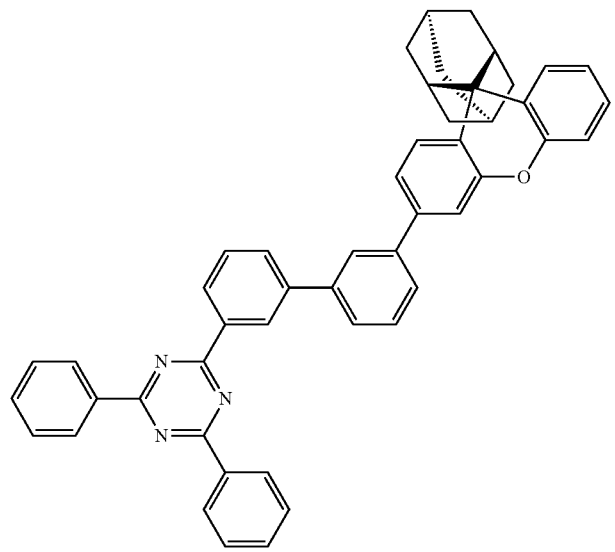 | 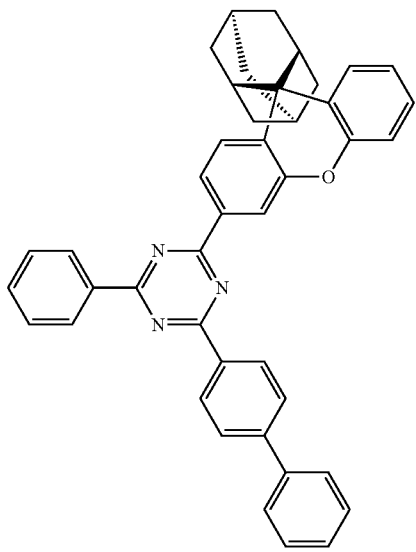 |

-continued
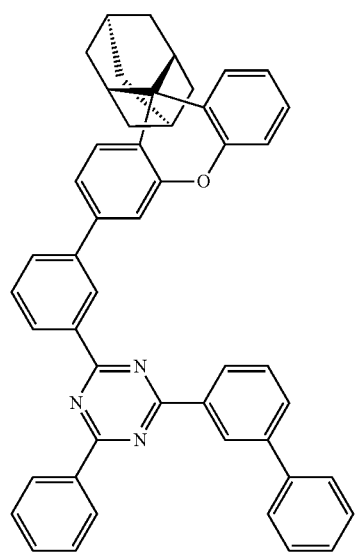
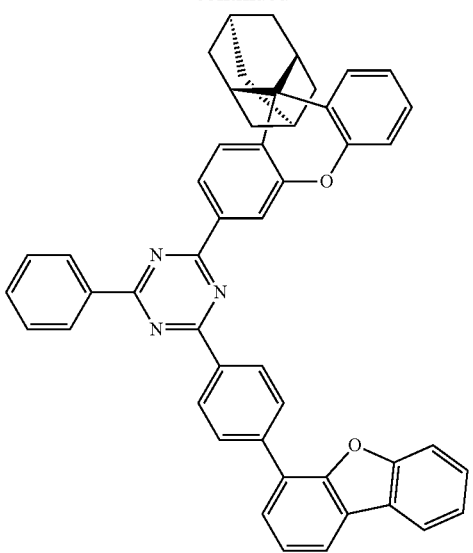
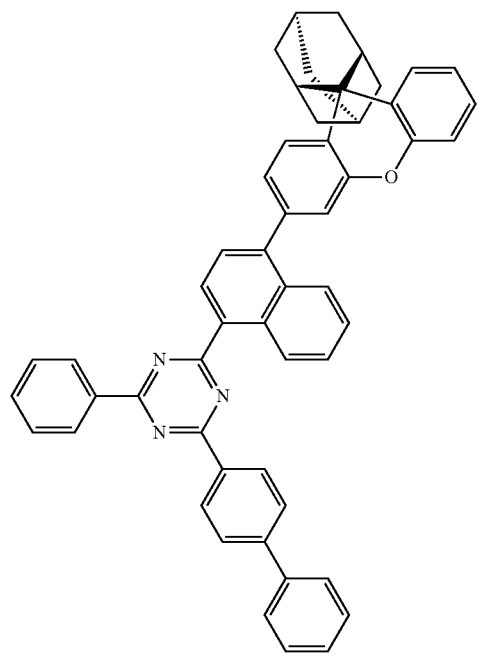
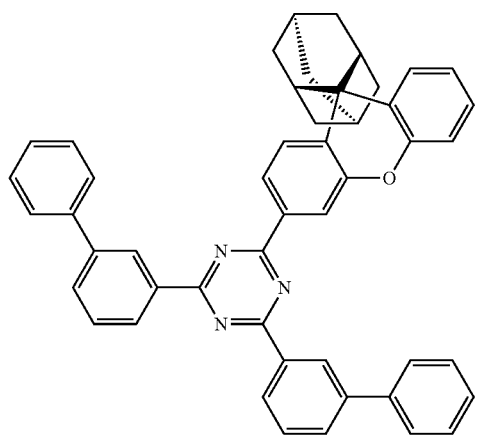

-continued
81
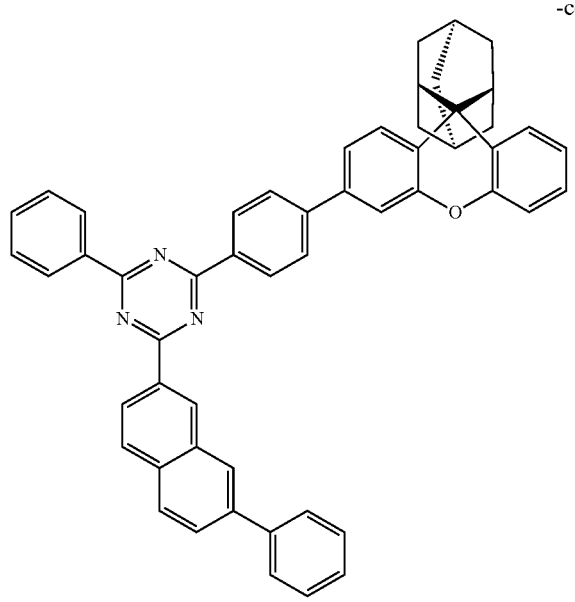
82
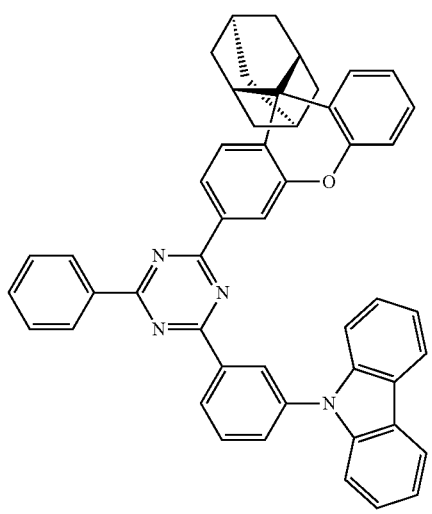
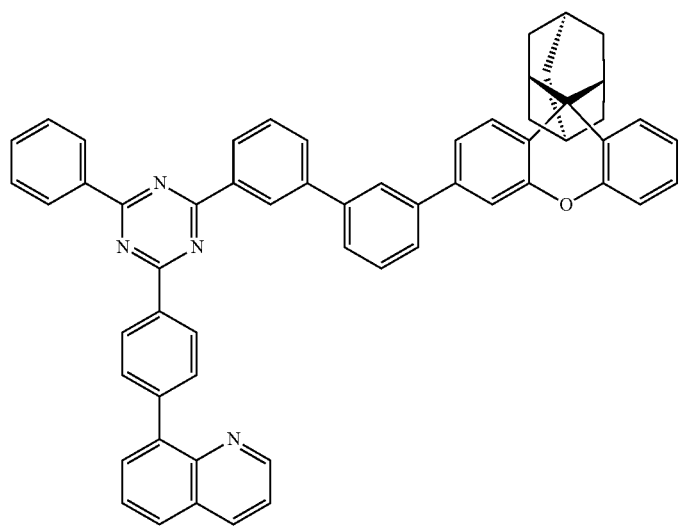
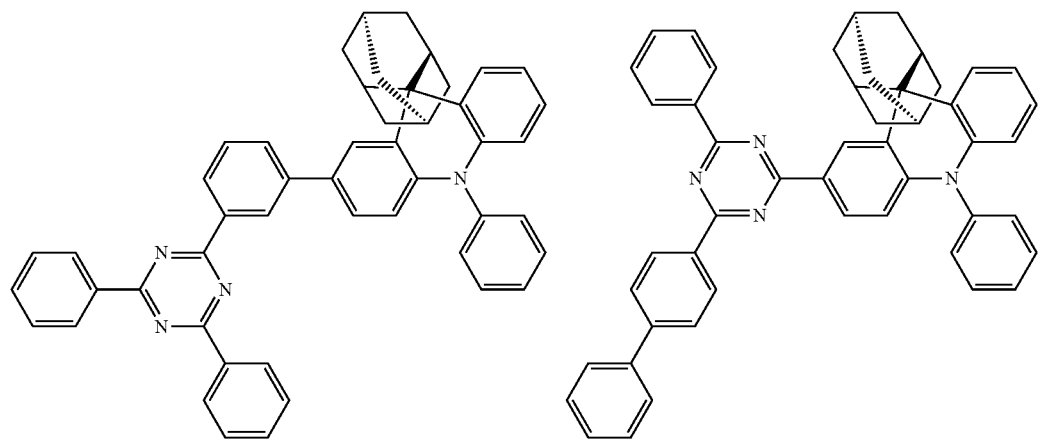

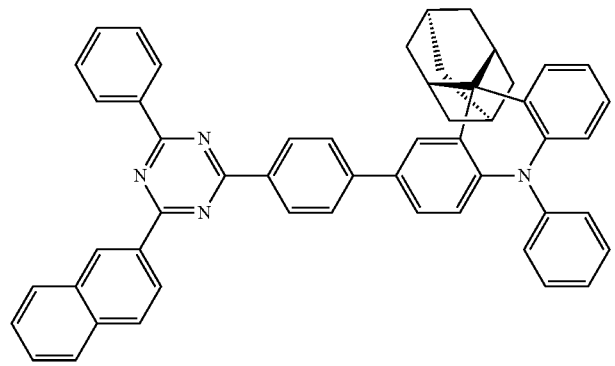
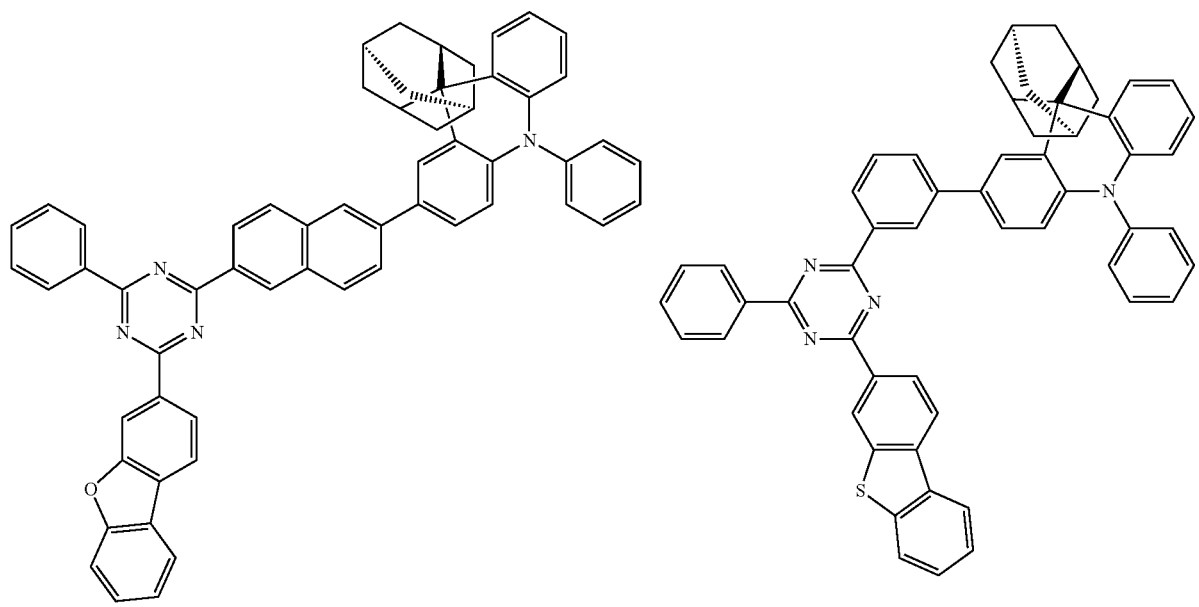
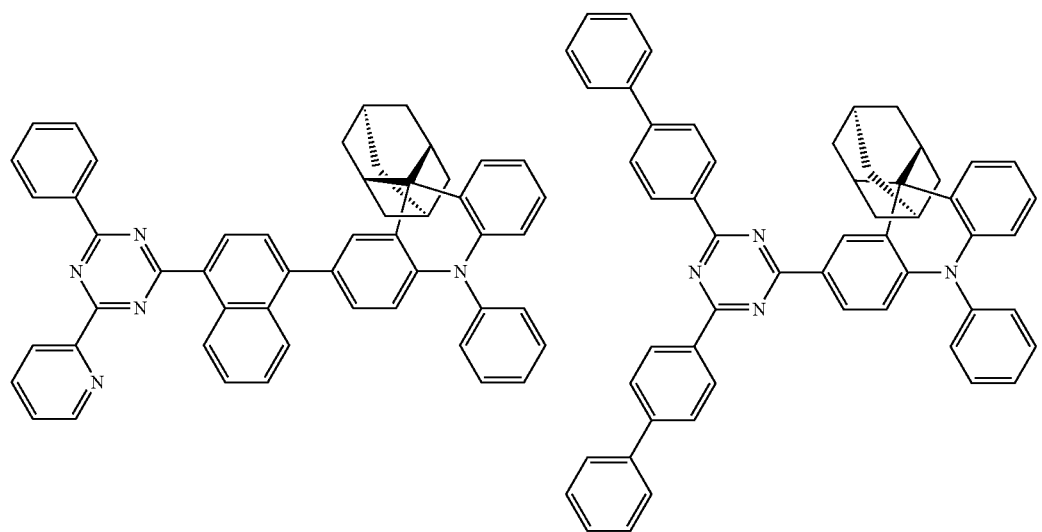

85
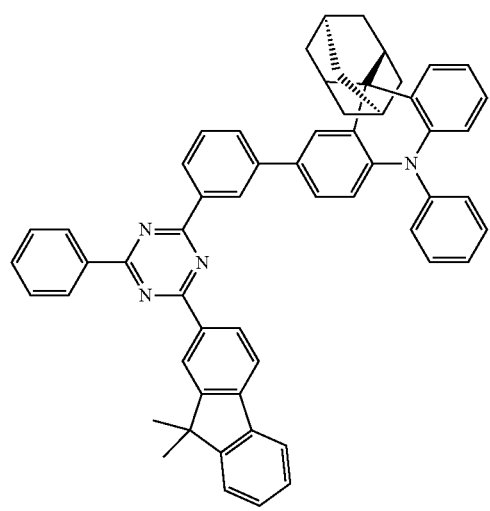
86
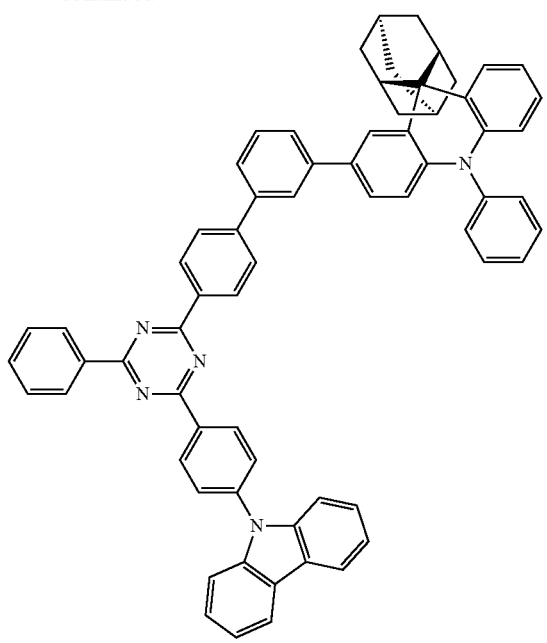
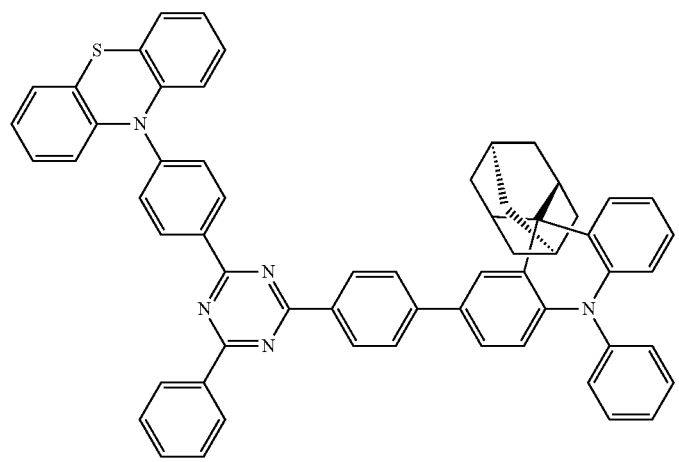
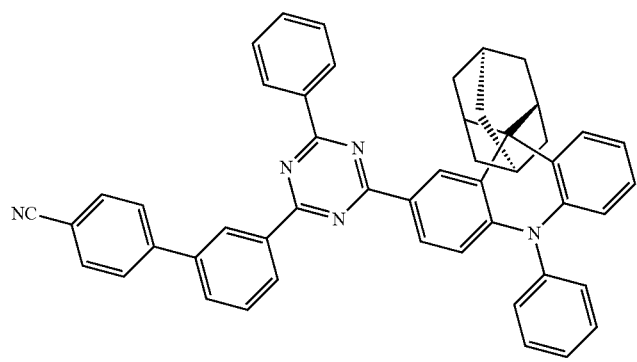

-continued
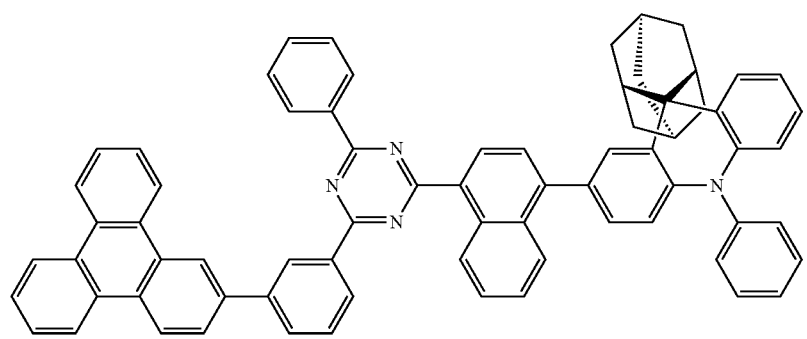
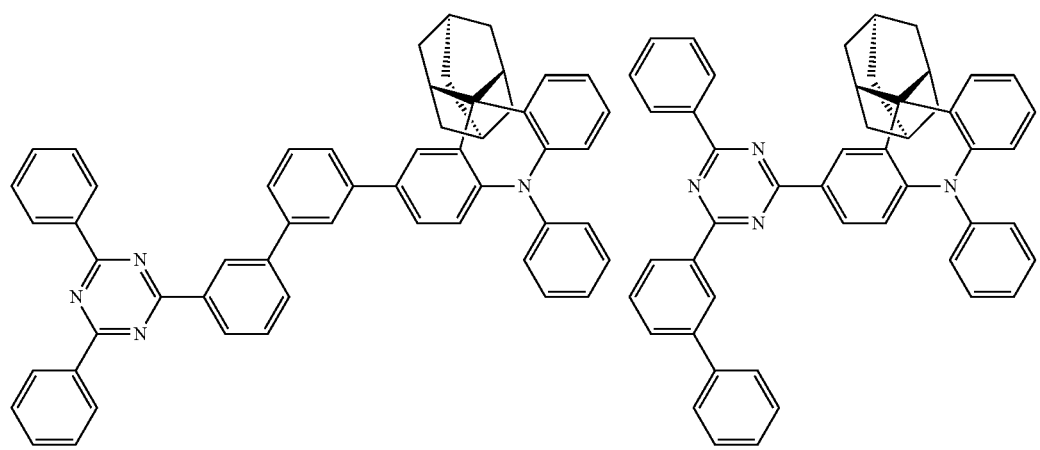
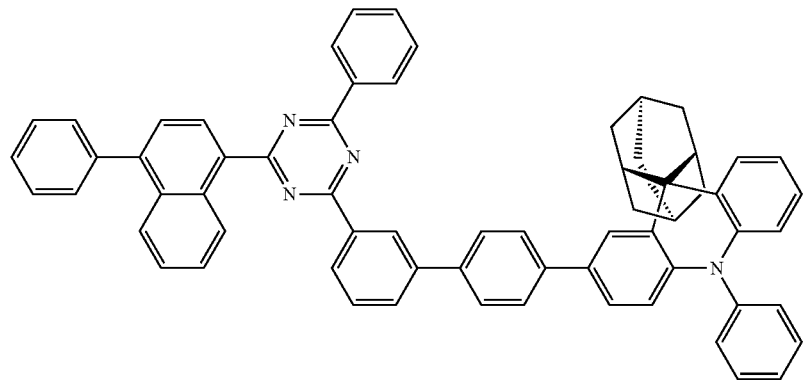

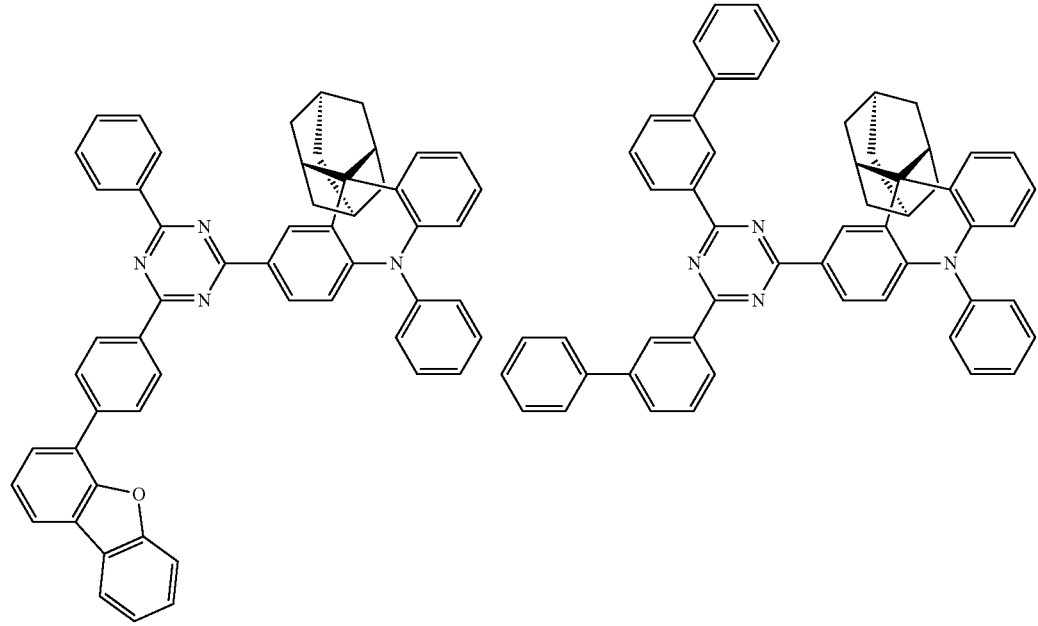
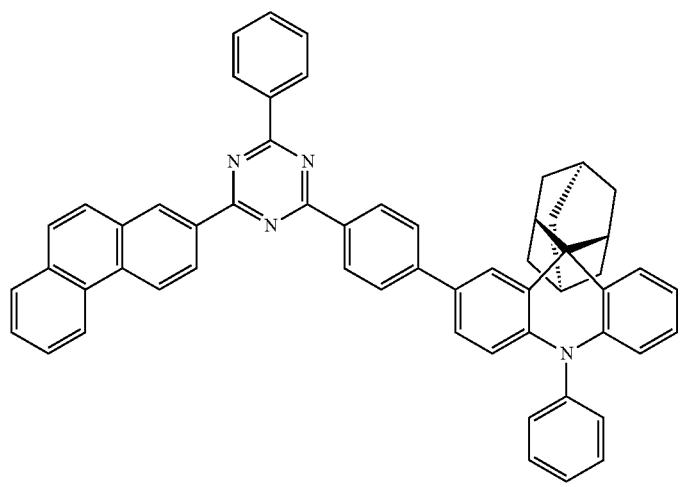
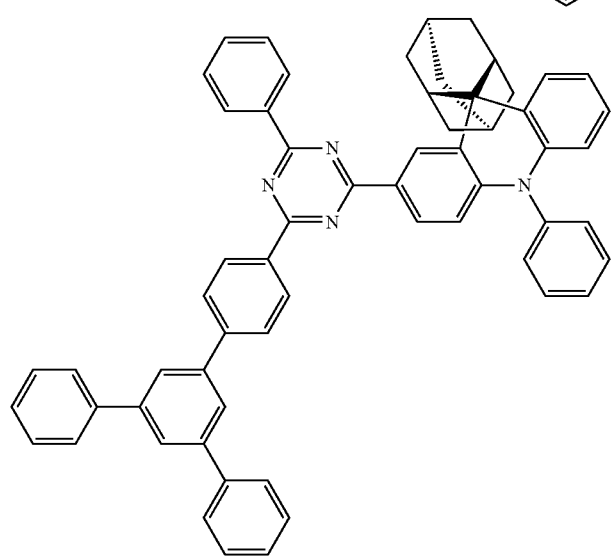

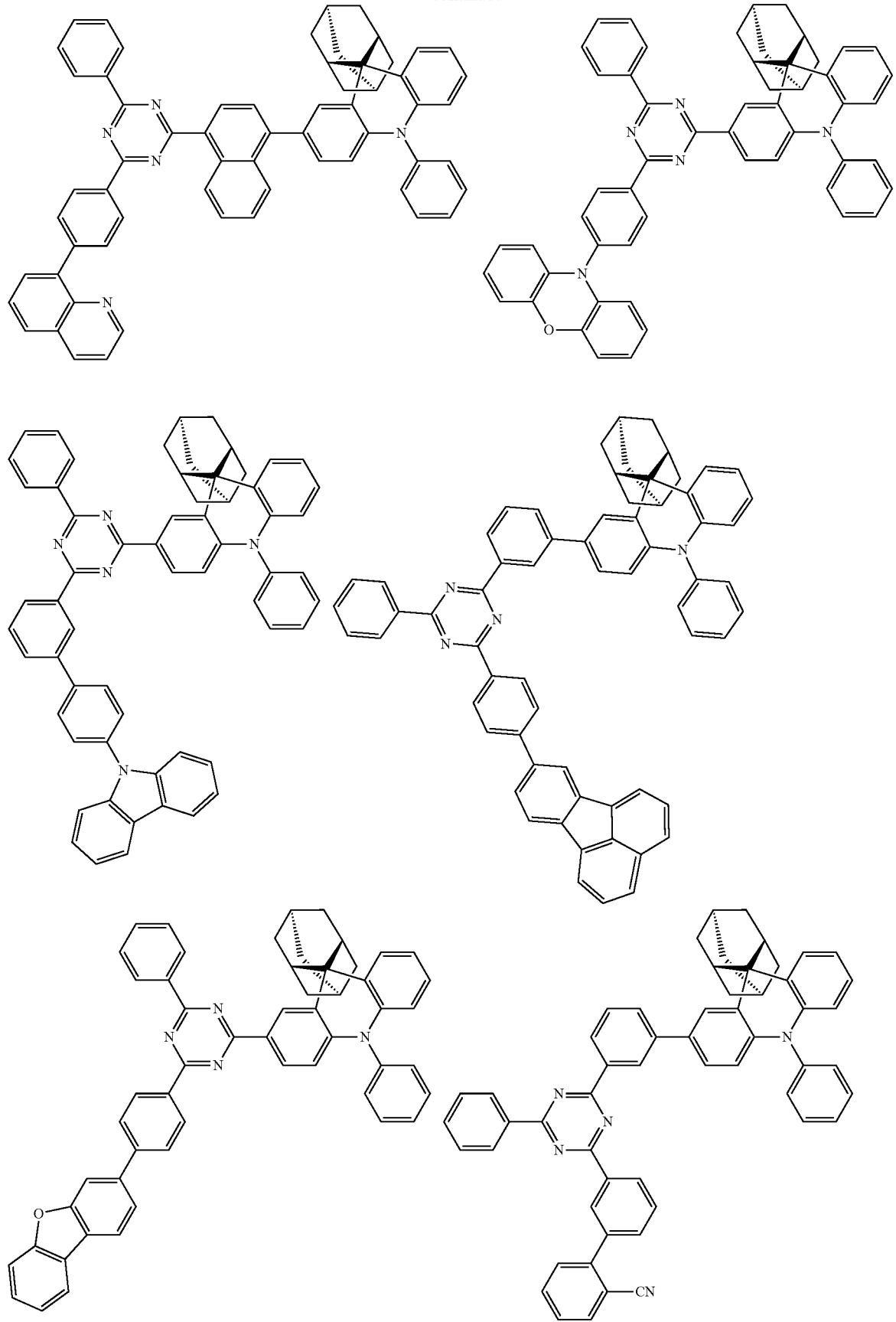

93 94
-continued
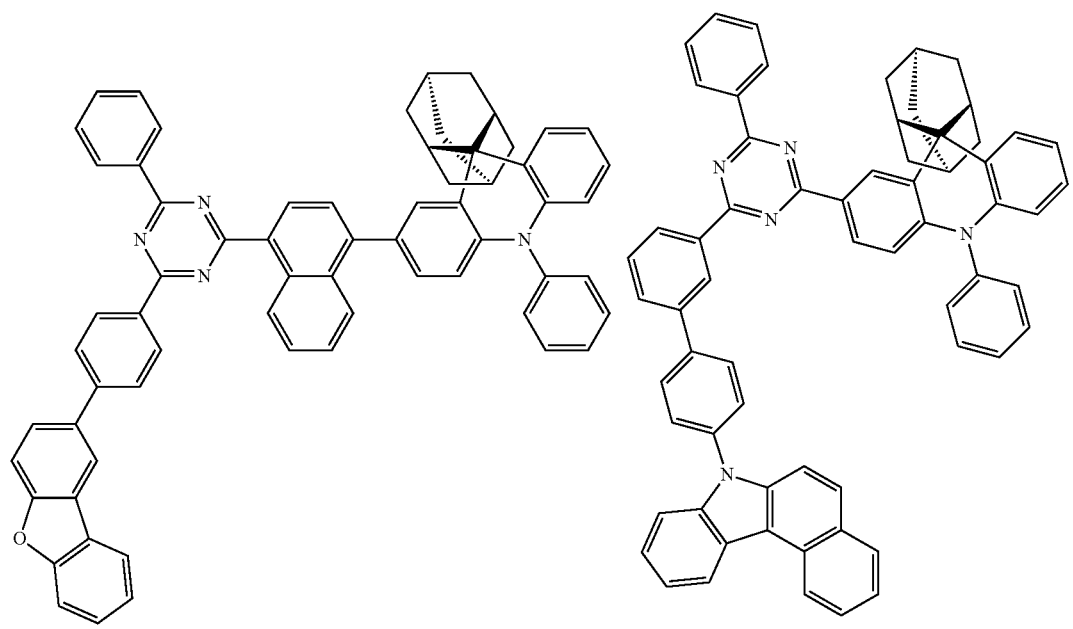
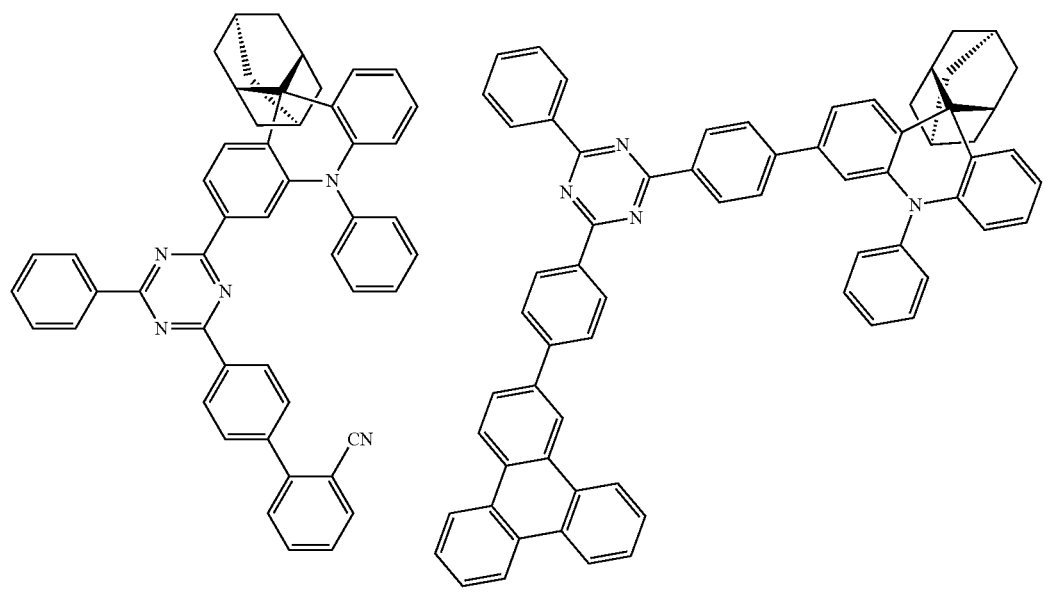

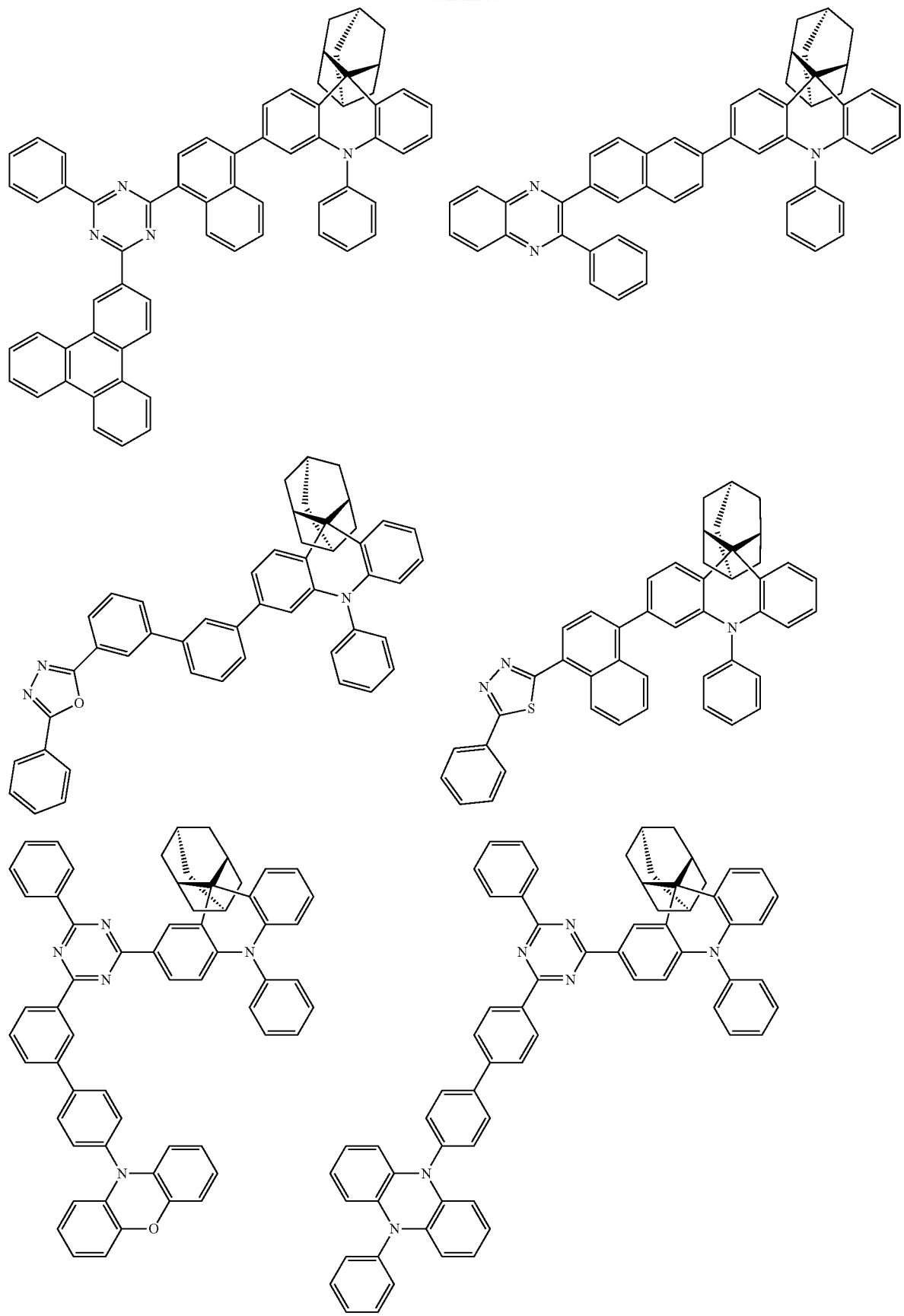

97 98
-continued
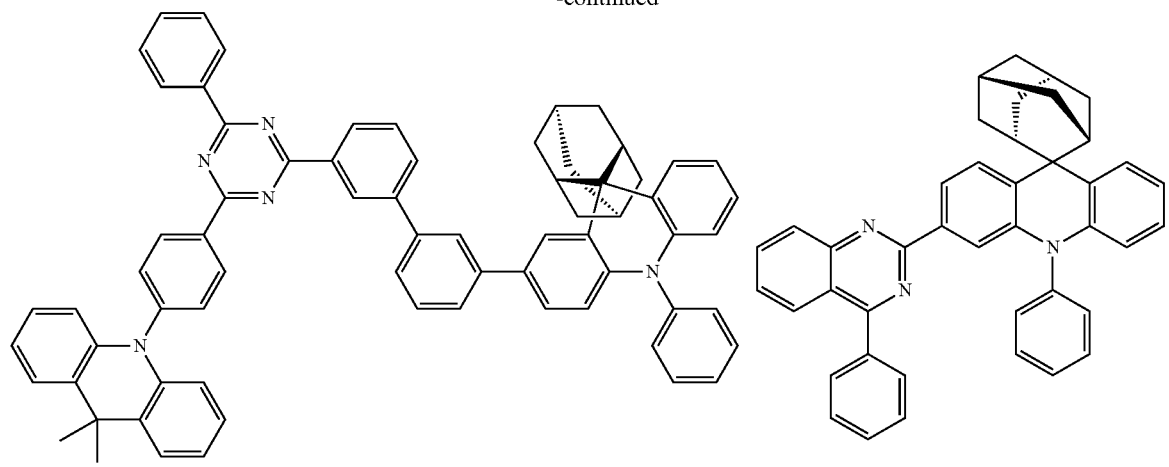
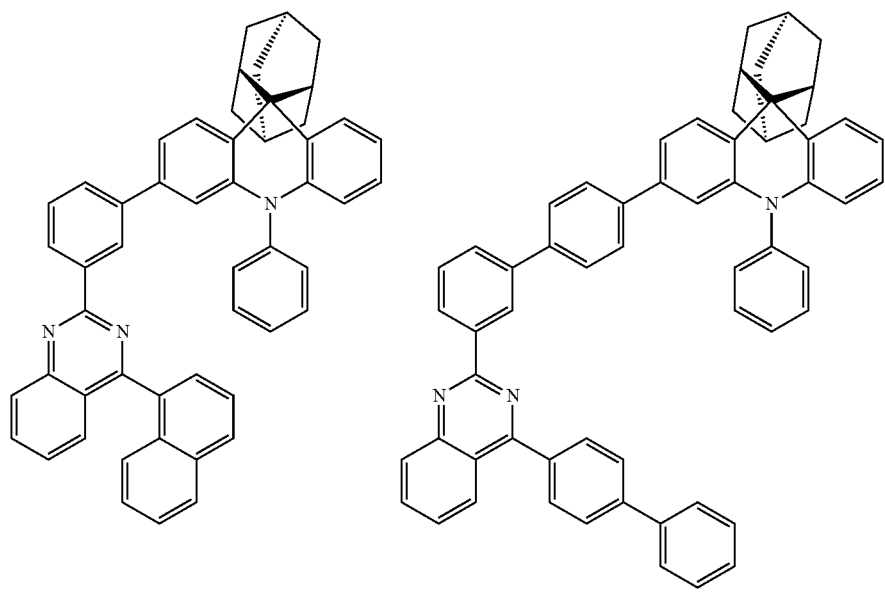
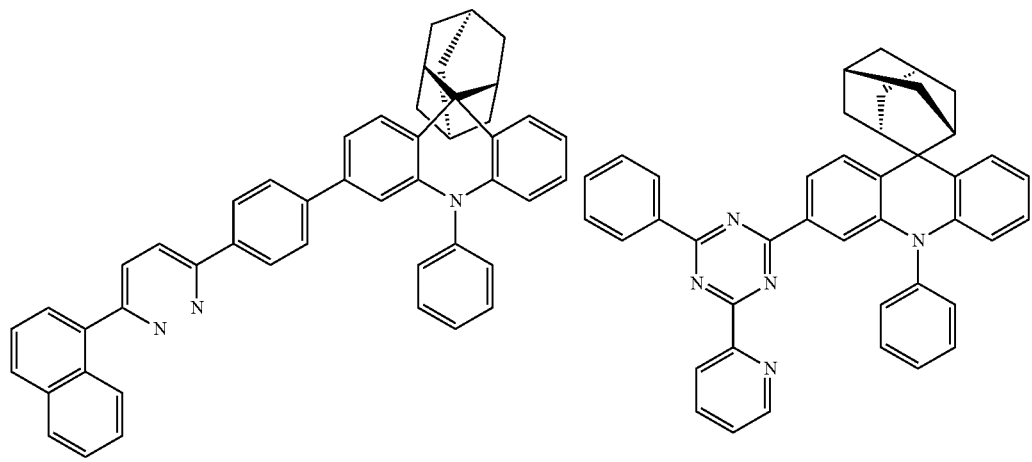

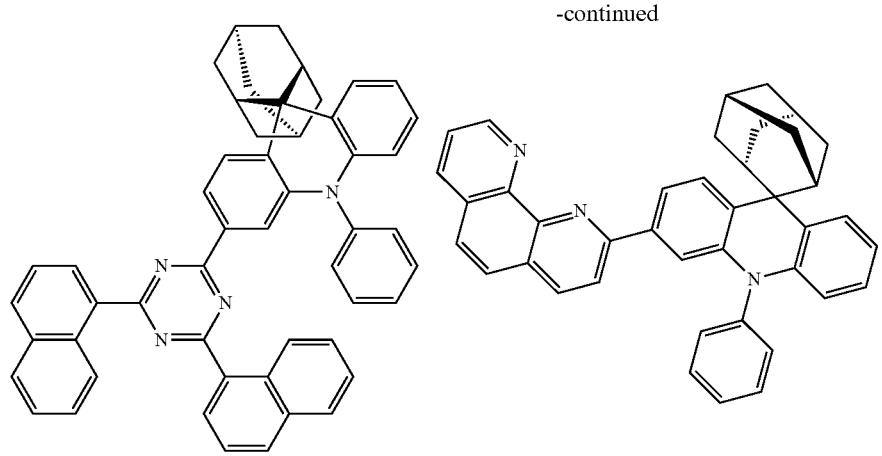
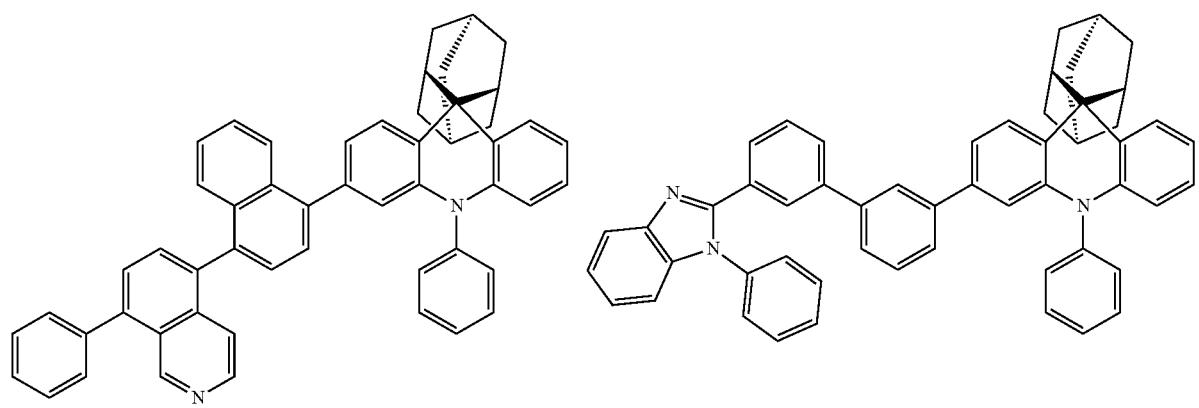
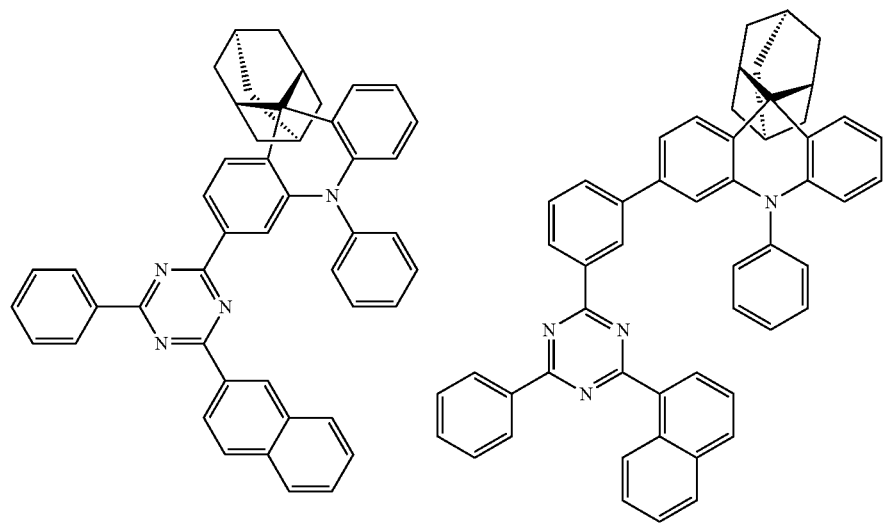

101 102
-continued
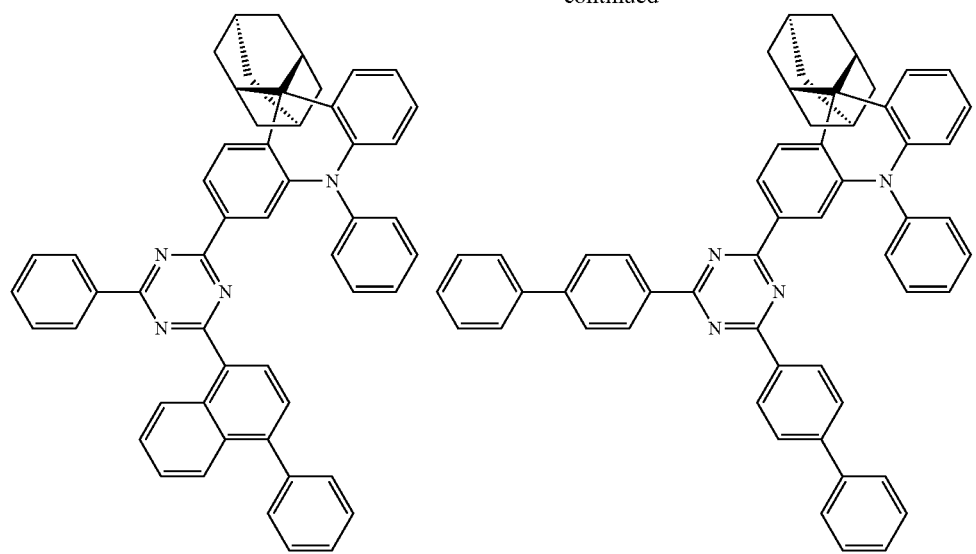
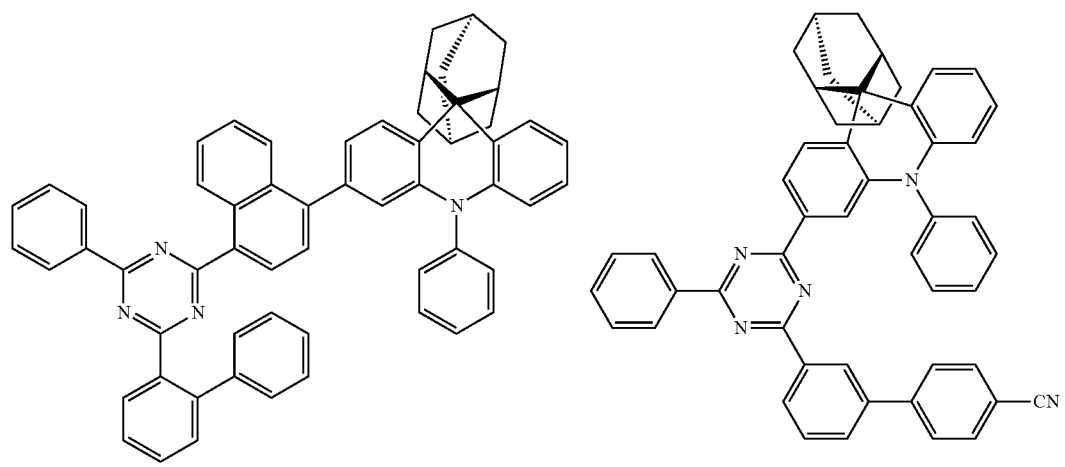
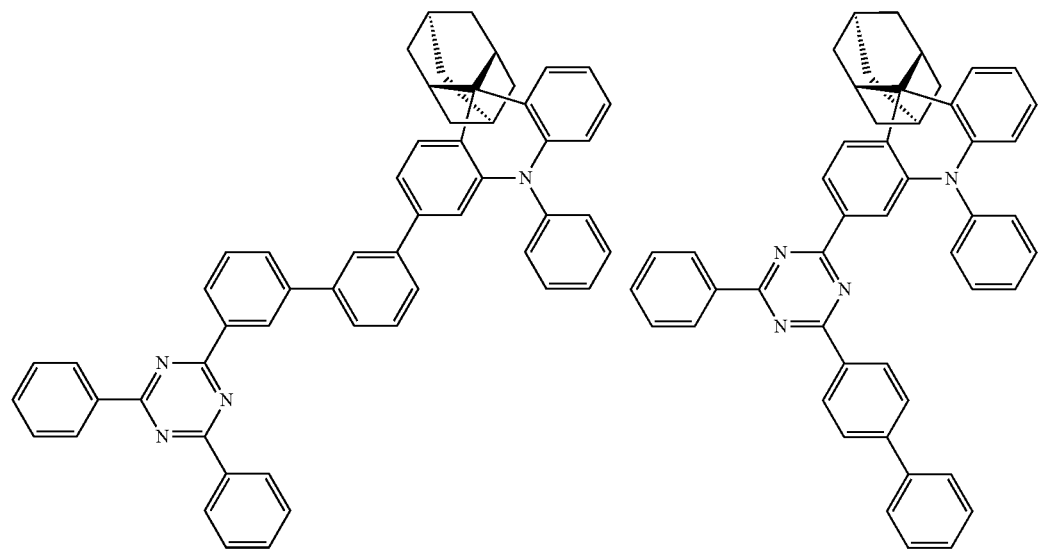

| 103 | 104 |
|---|---|
| 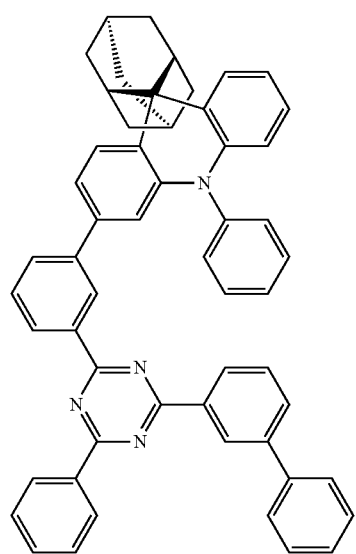 | 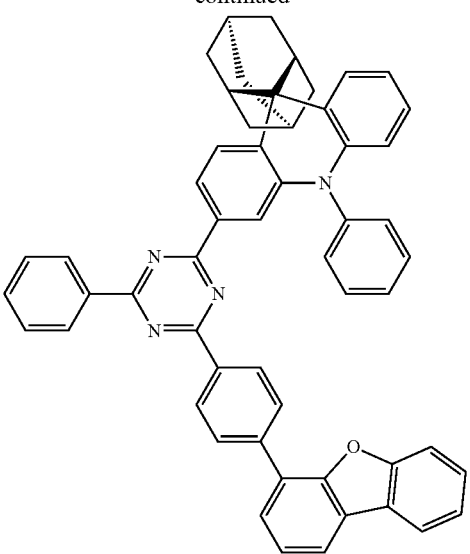 |
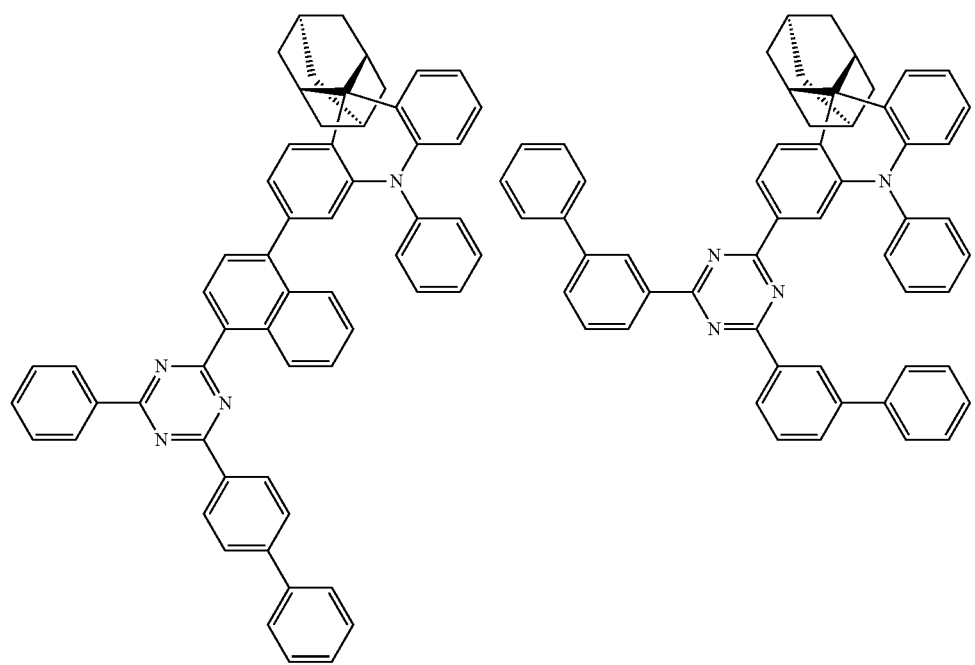

105
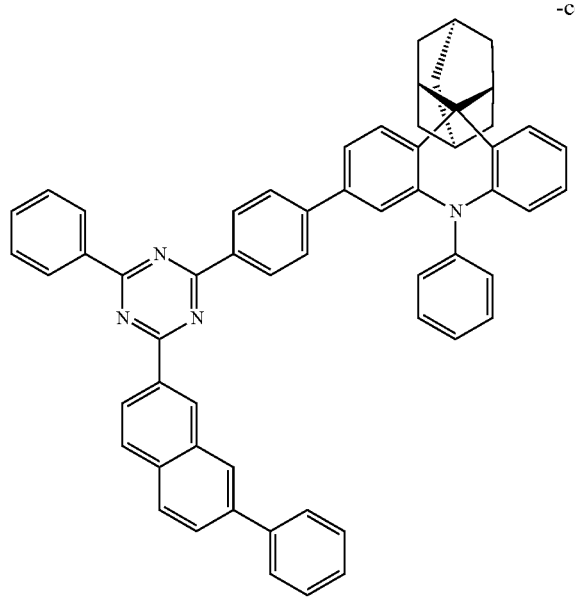
106
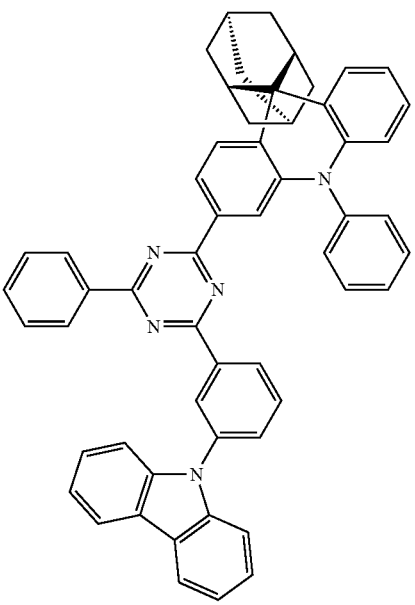
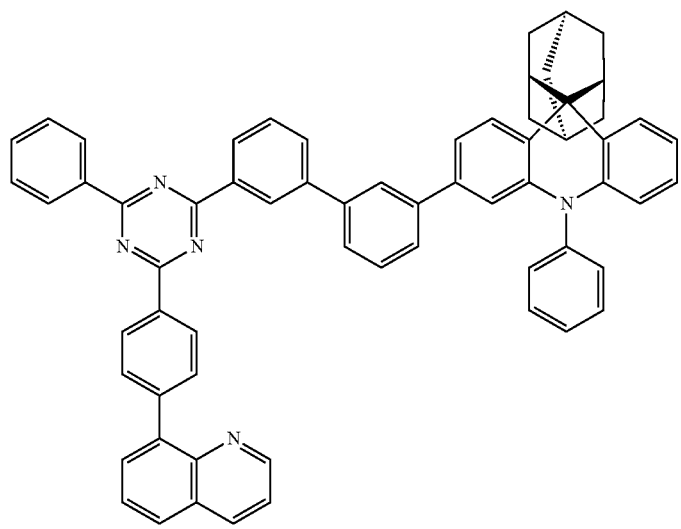
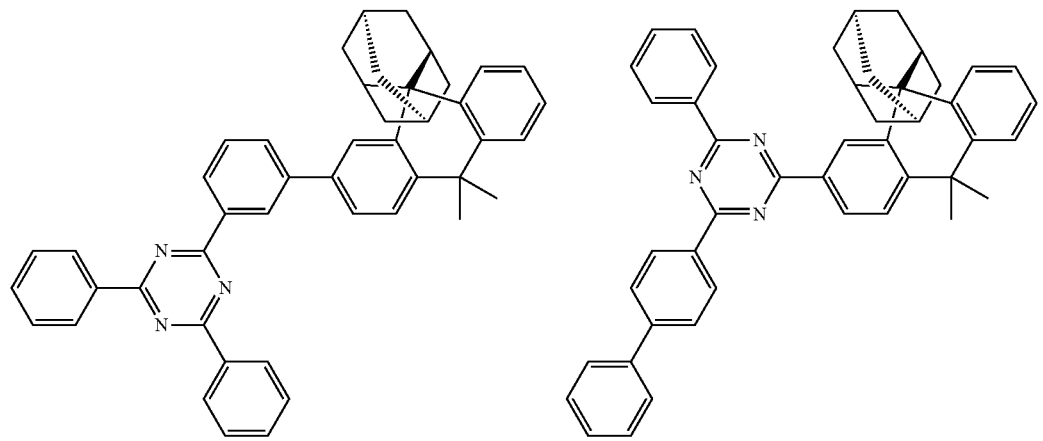

107 108
-continued
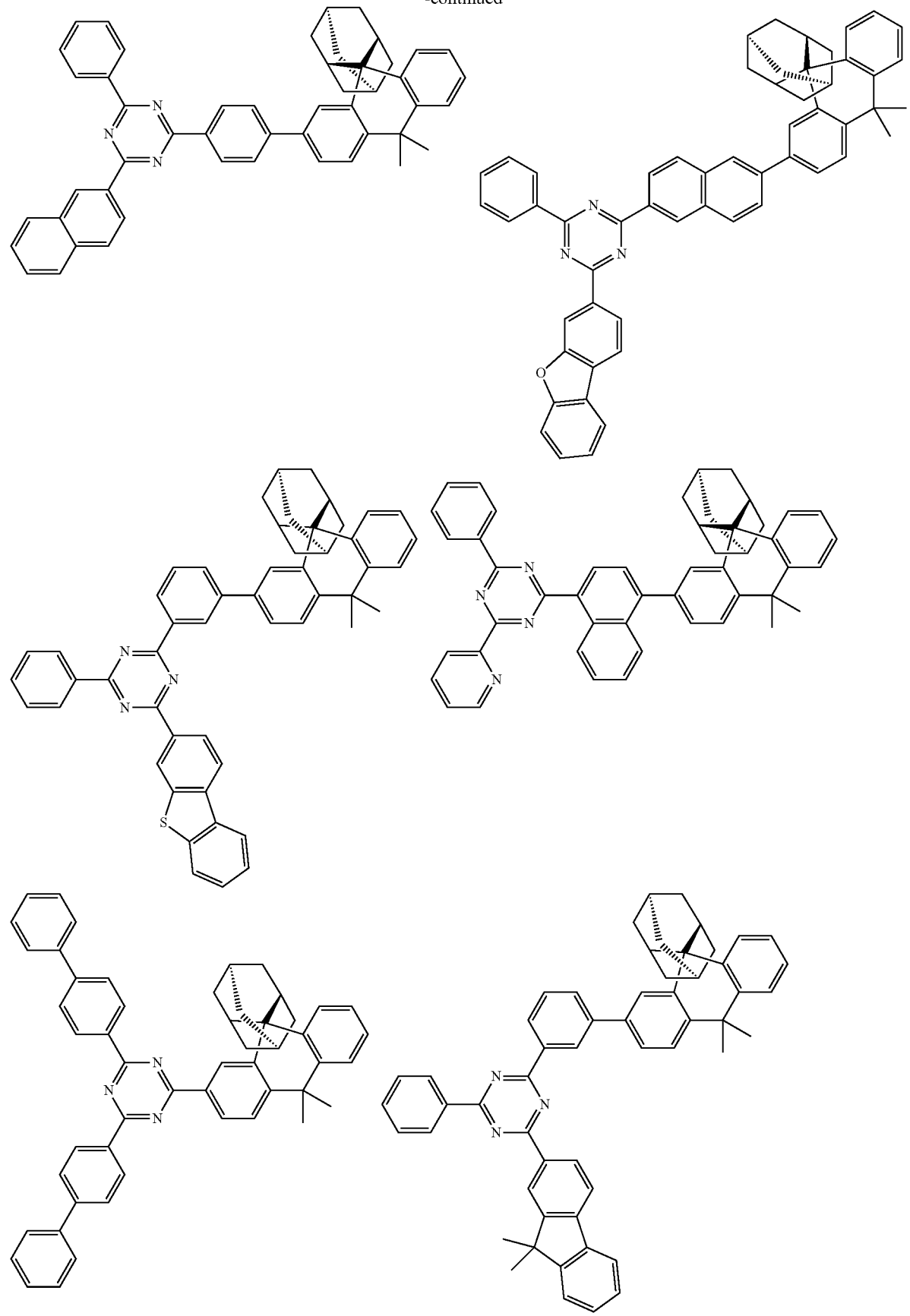

-continued
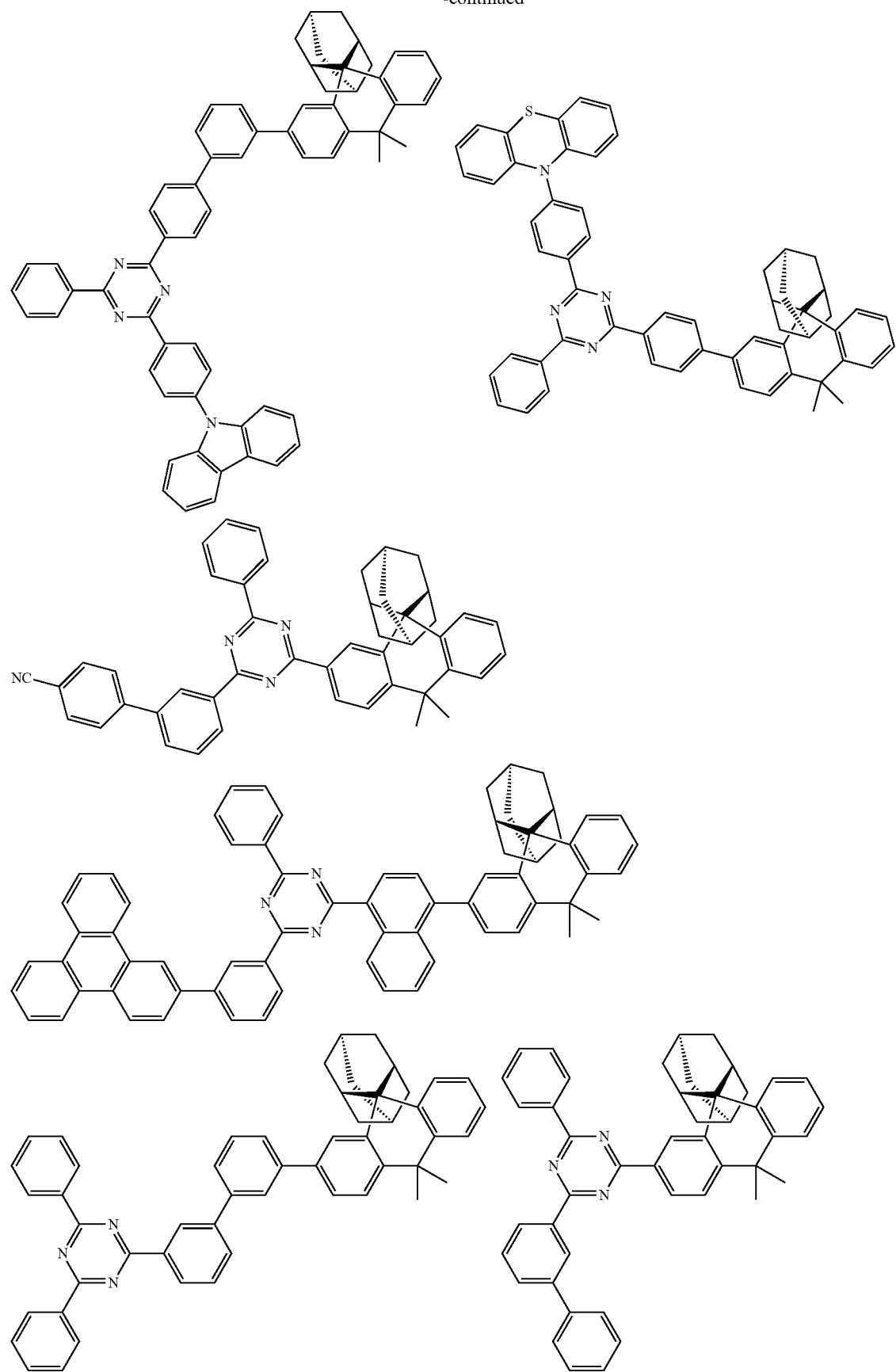

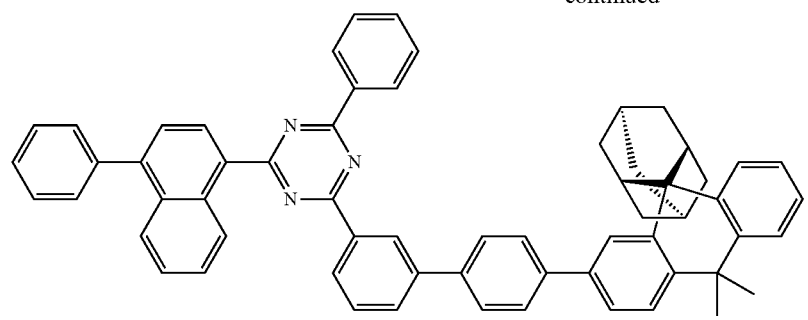
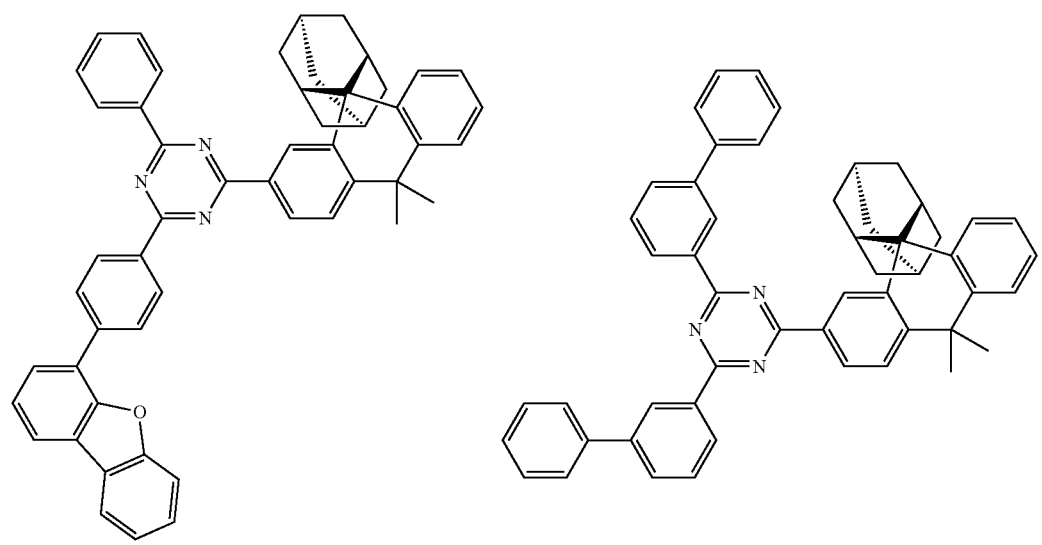
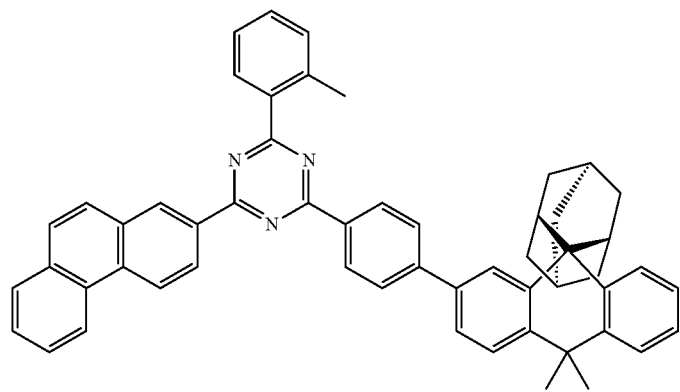

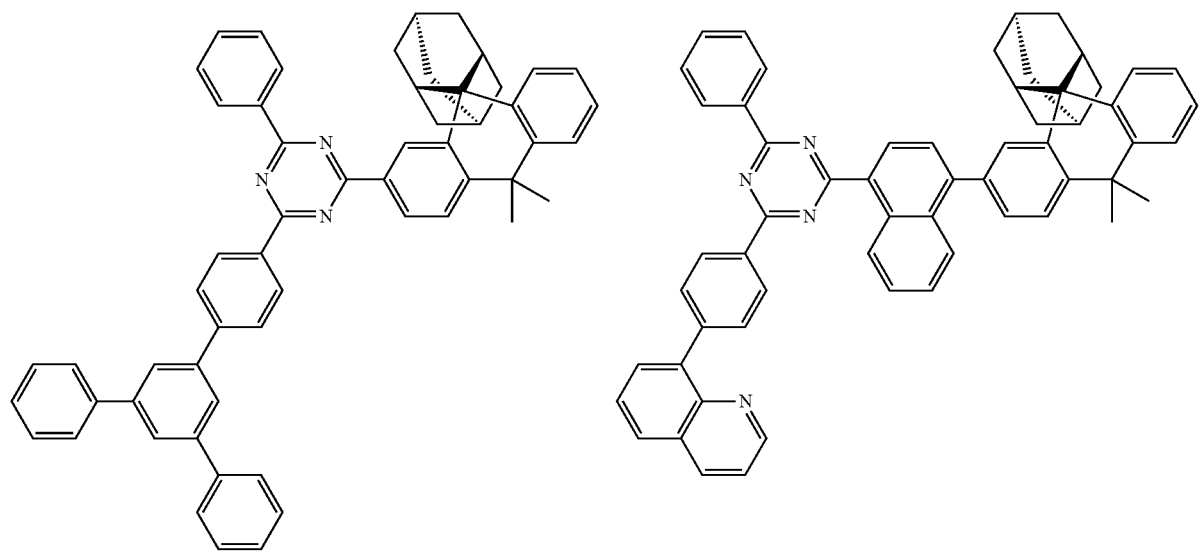
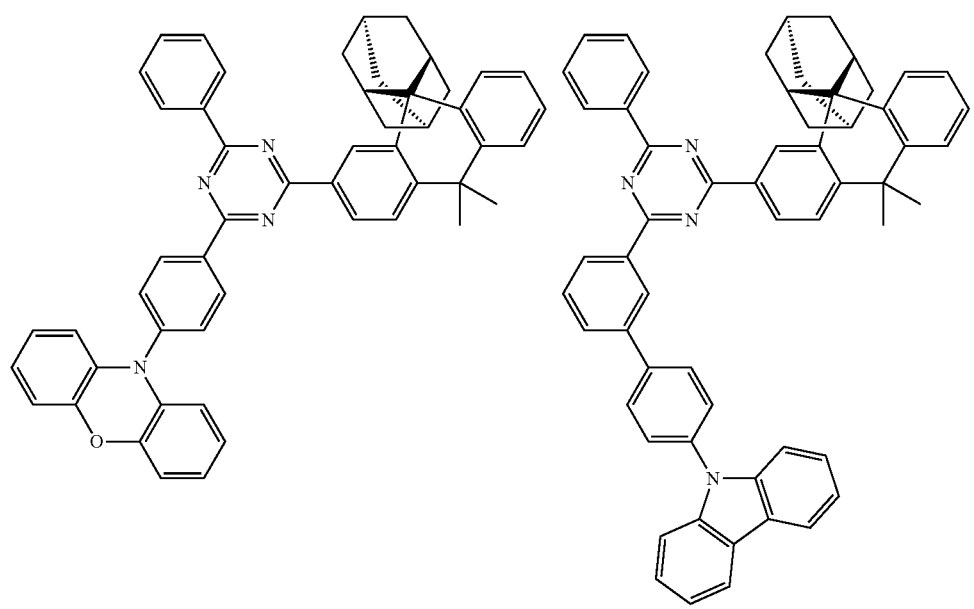

-continued
115
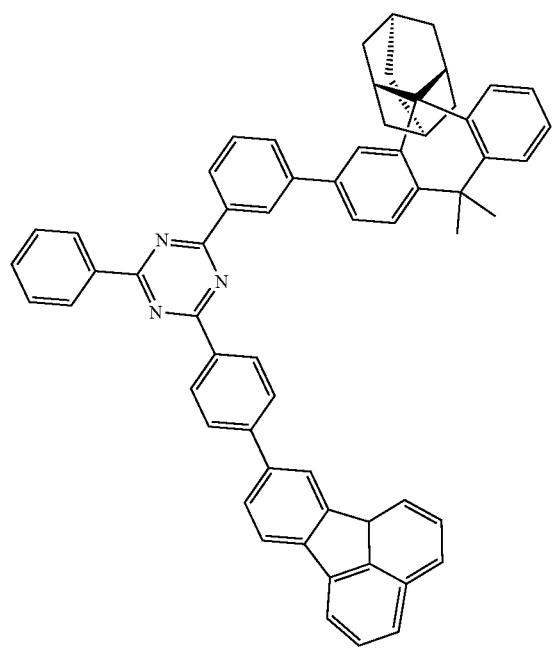
116
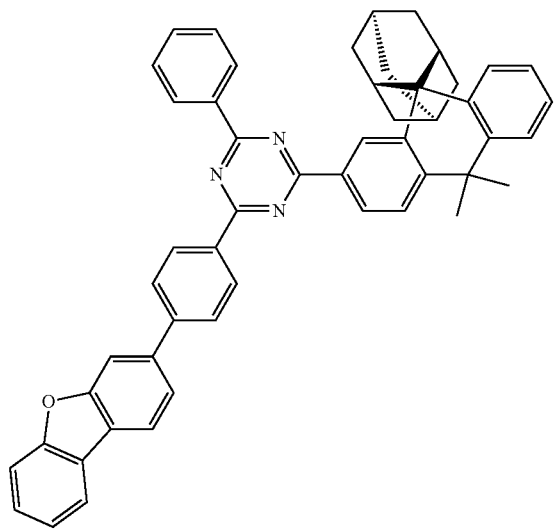
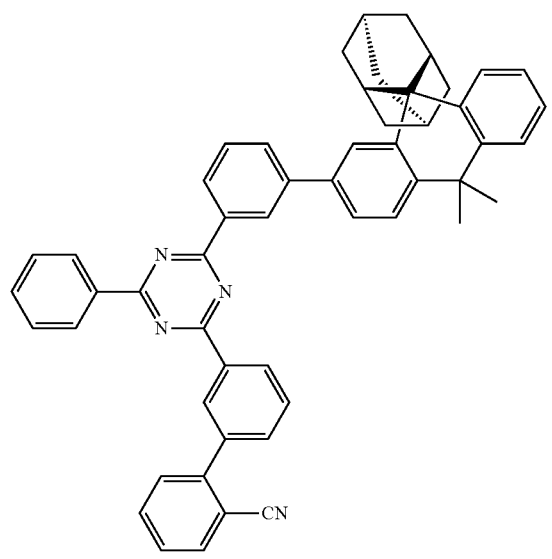
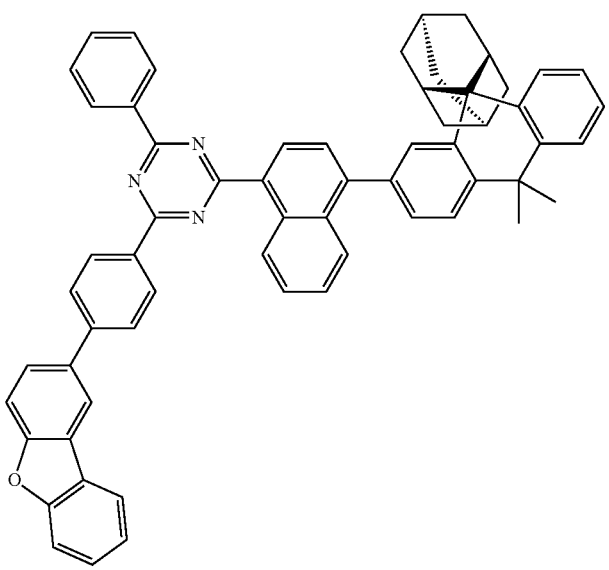

117
118
-continued
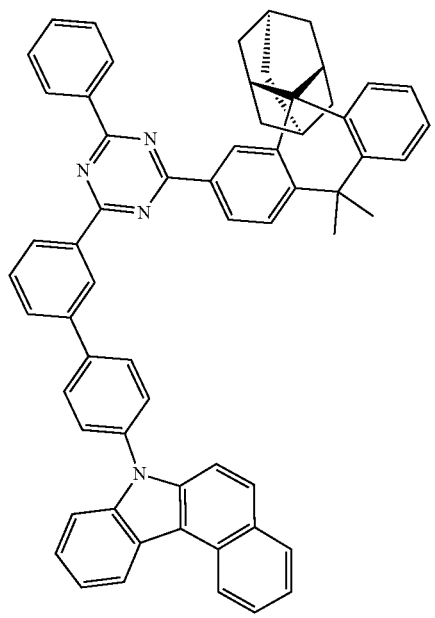
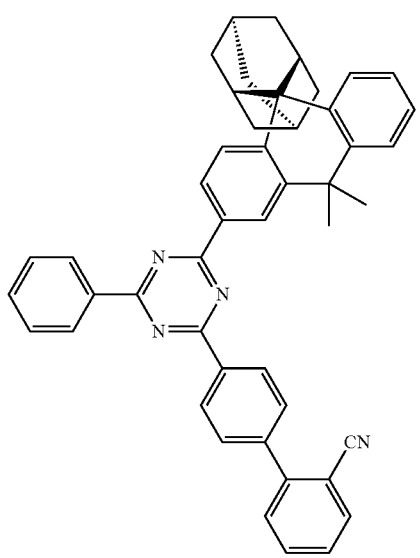
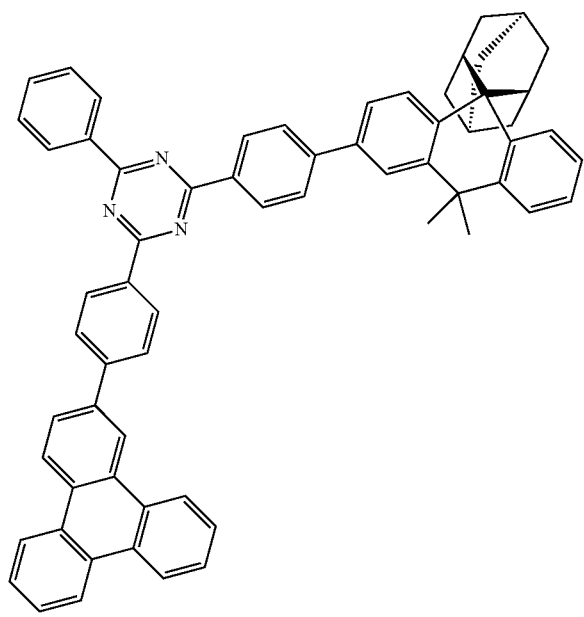
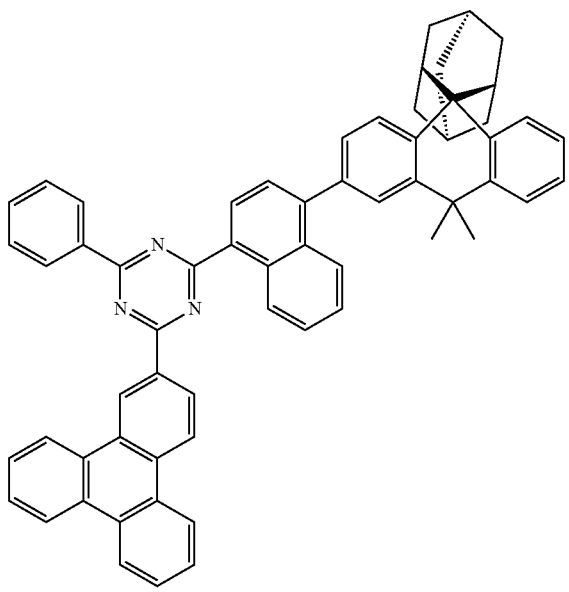
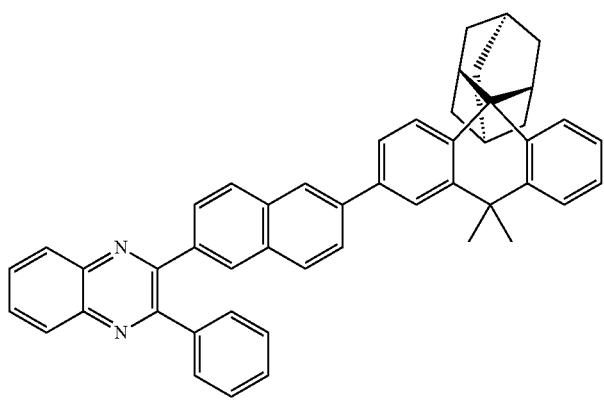
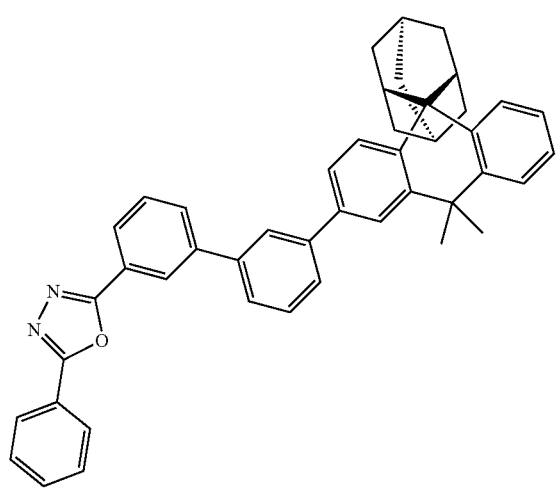

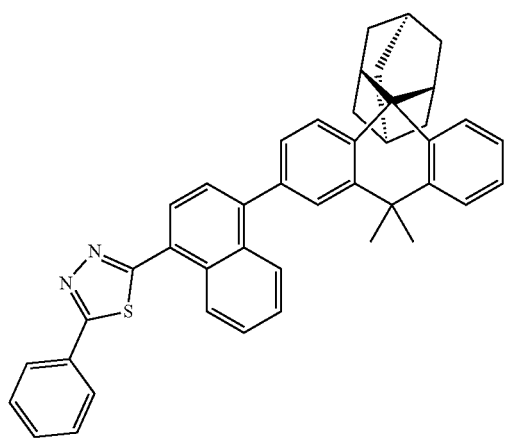
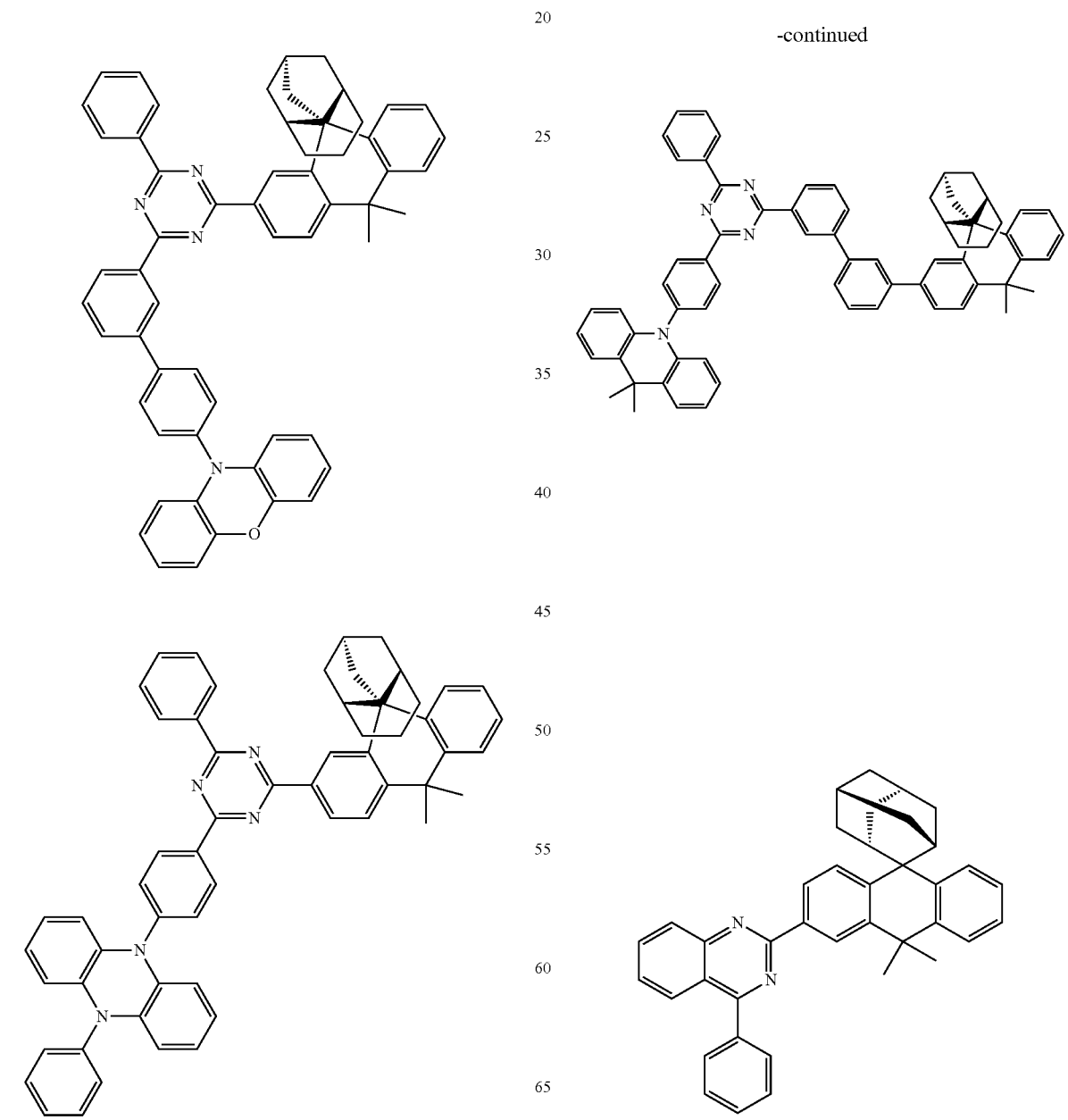

121
-continued
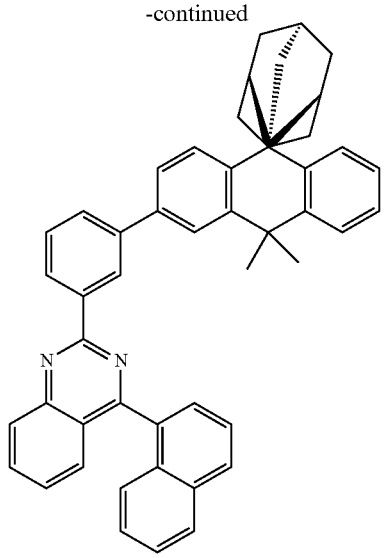
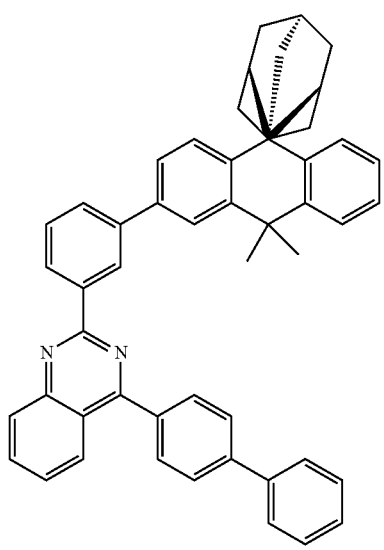
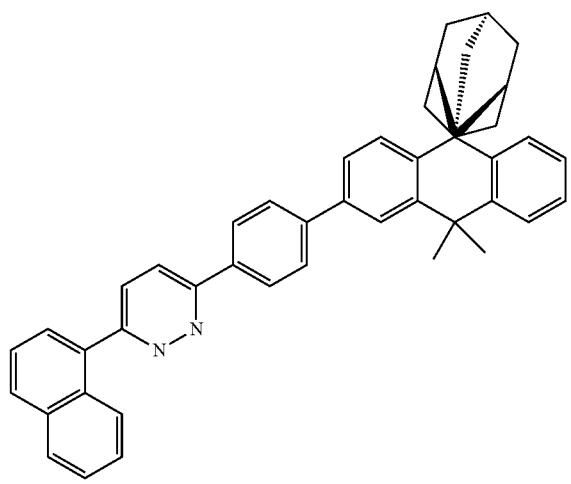
122
-continued
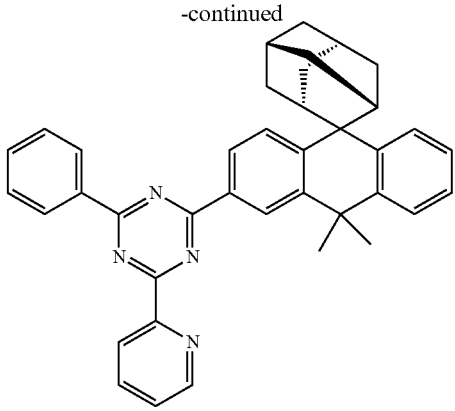
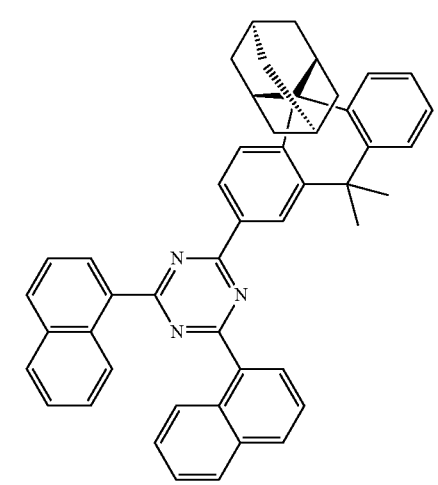
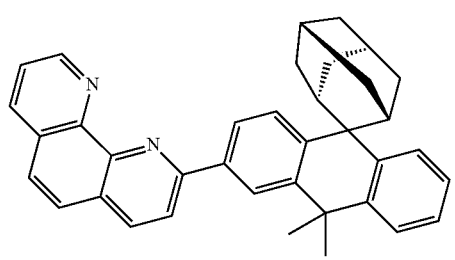
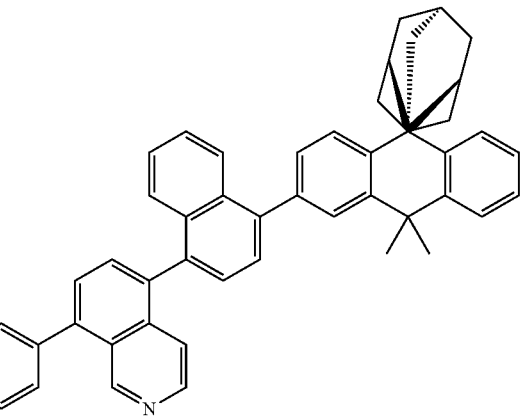

123
-continued
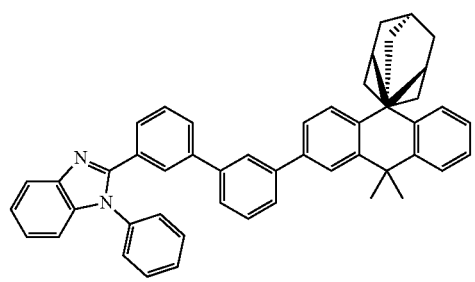
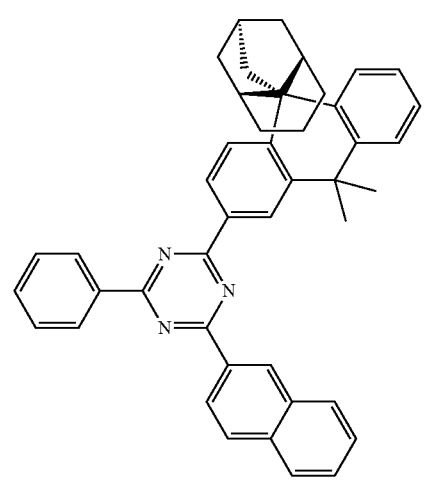
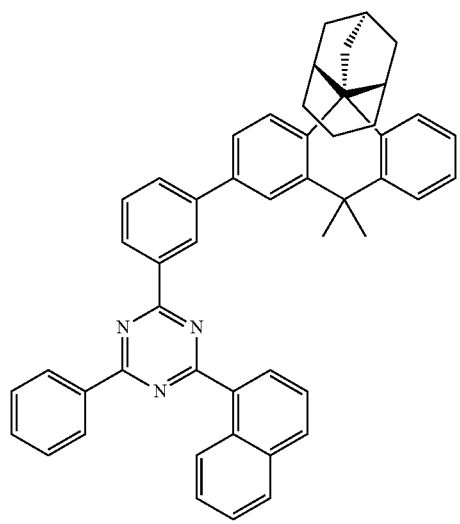
124
-continued
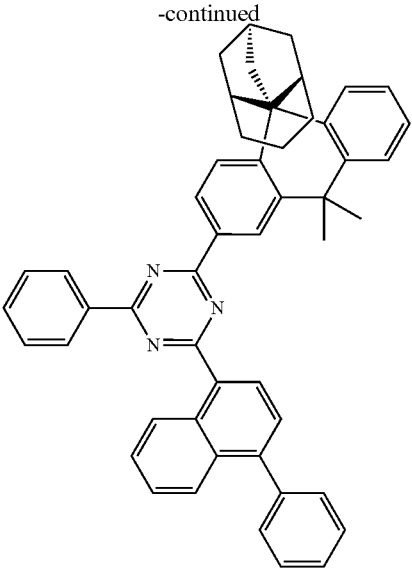
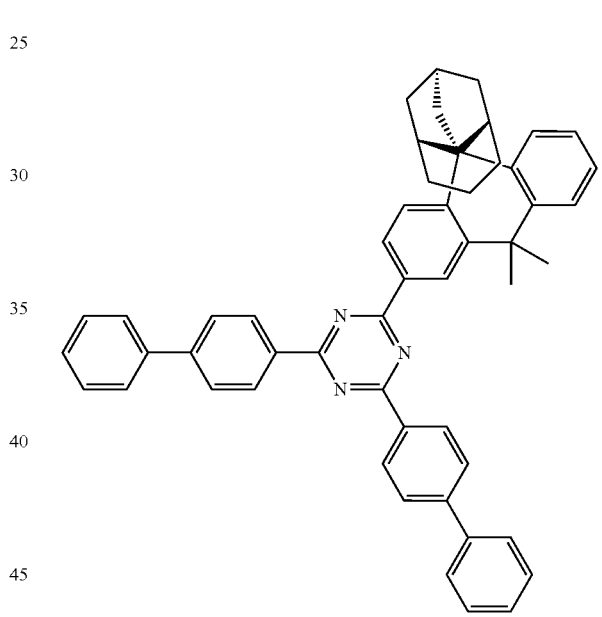
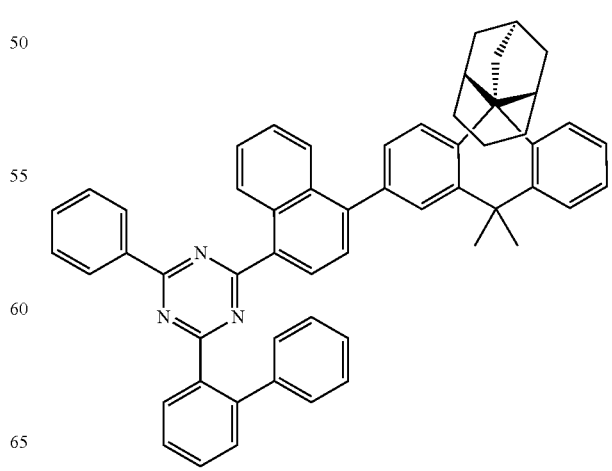

125
-continued
126
-continued
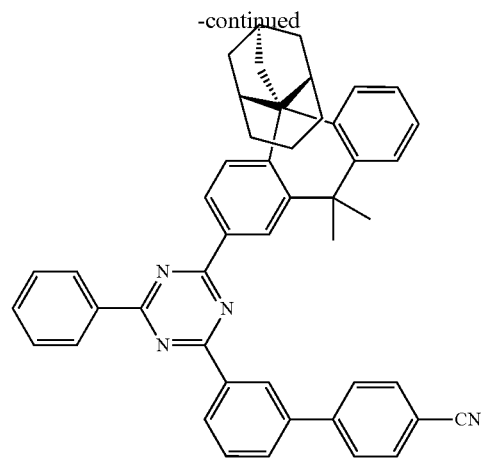
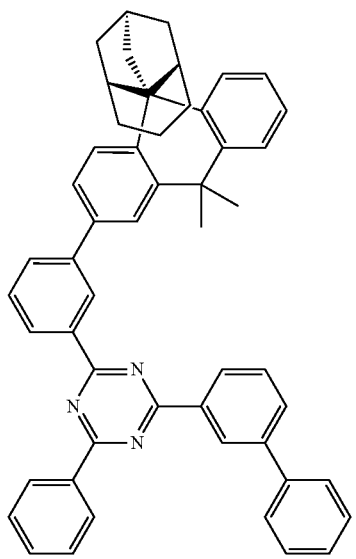
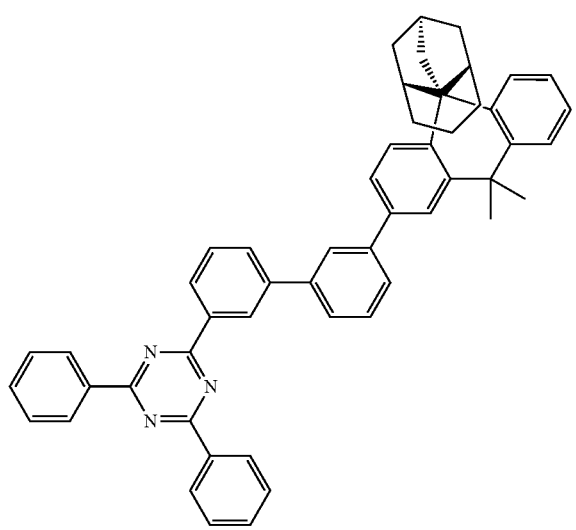
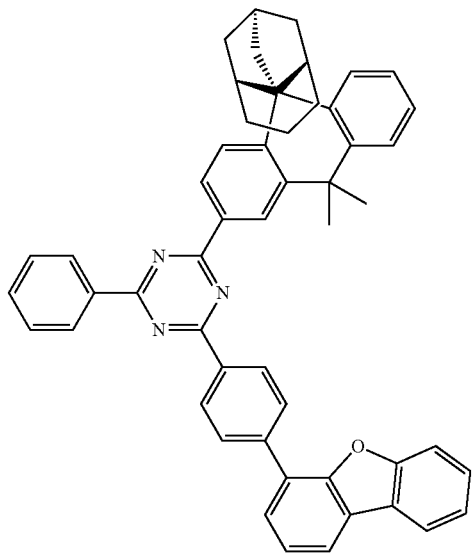

127
-continued
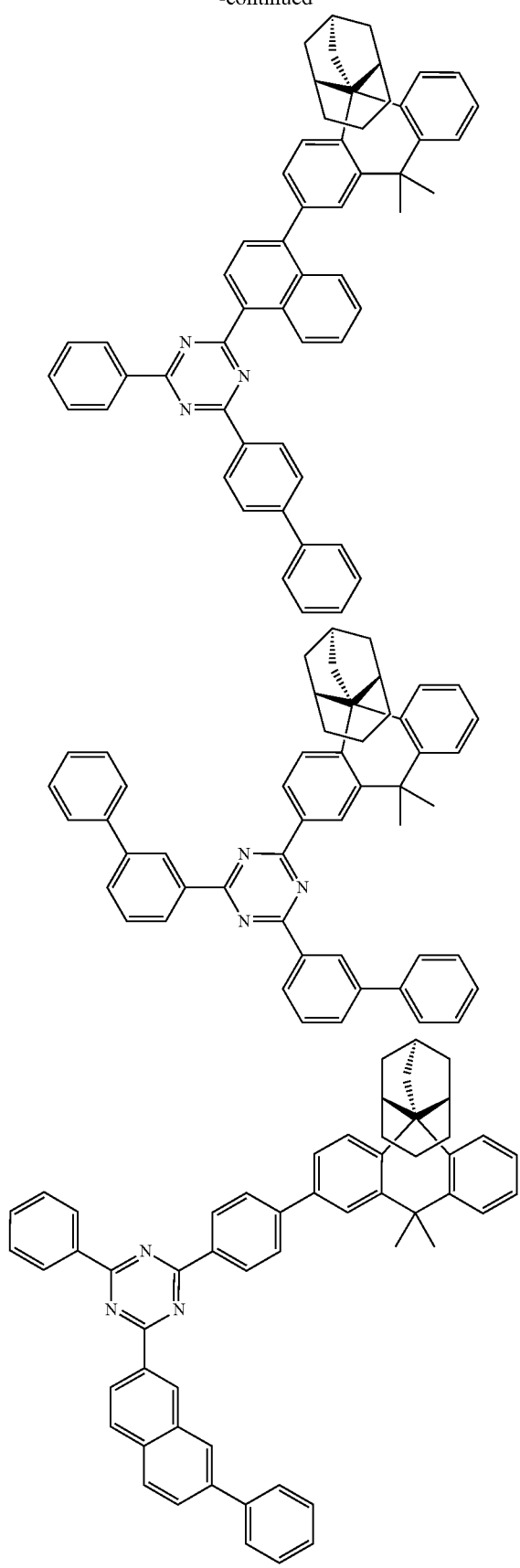
128
-continued
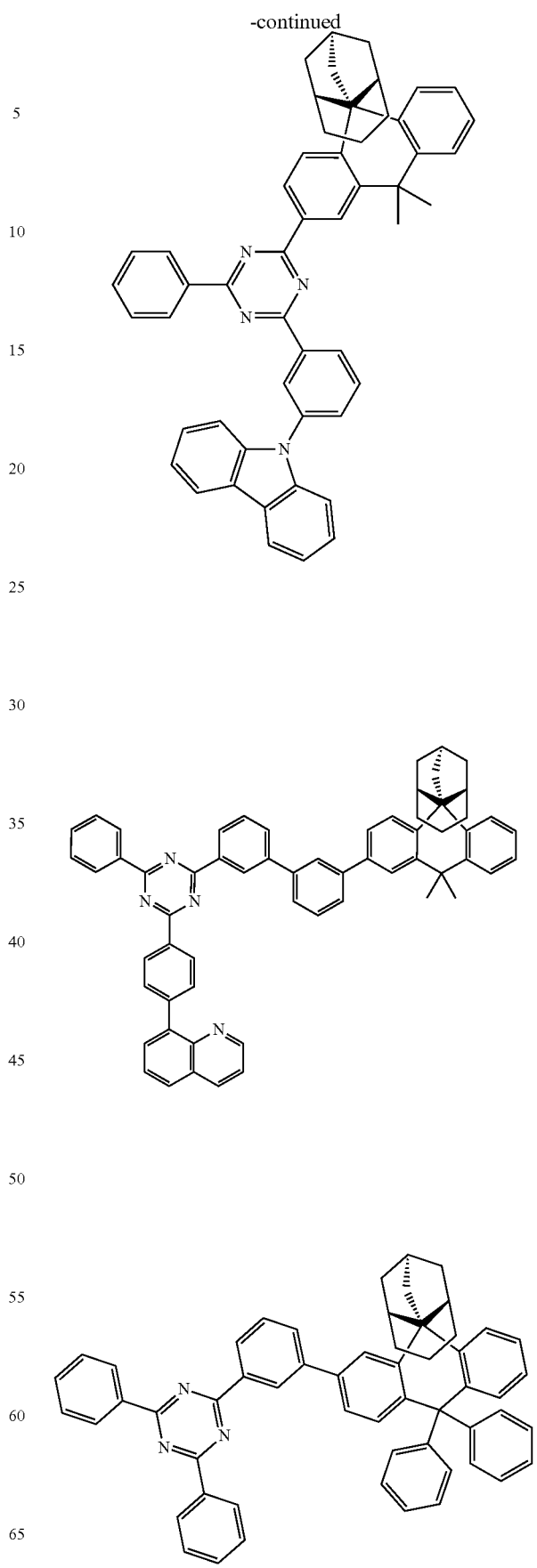

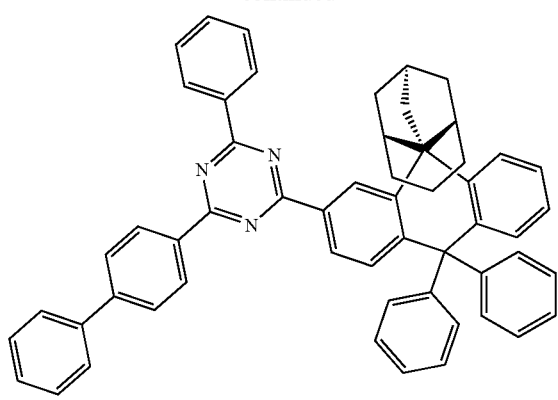
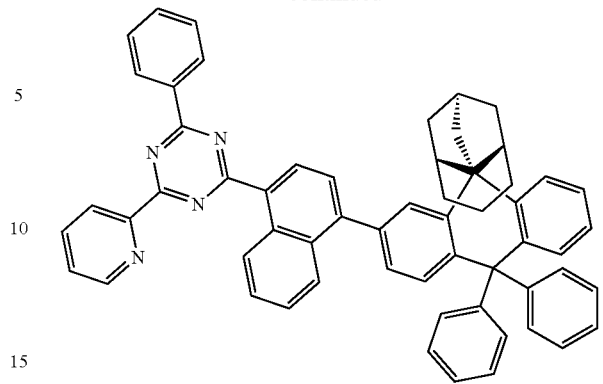
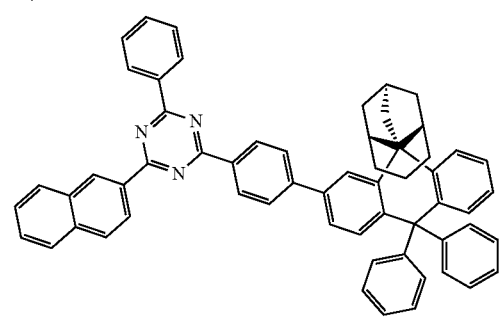
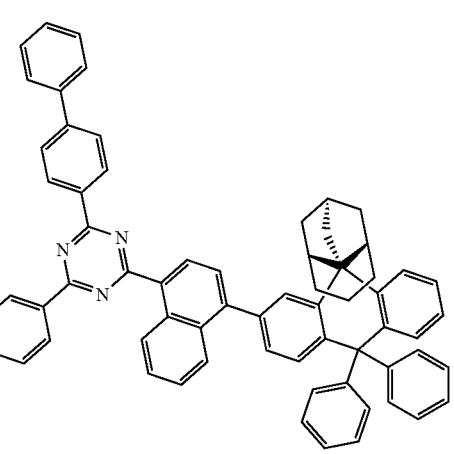
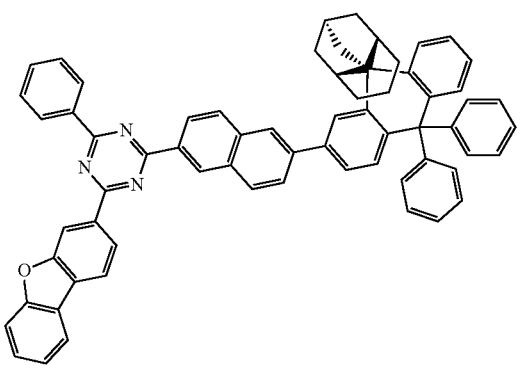
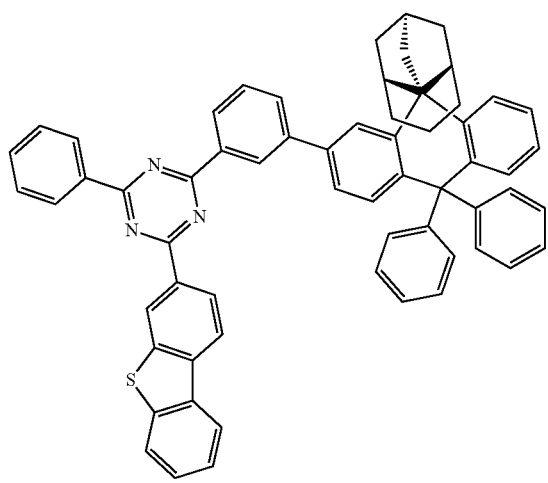
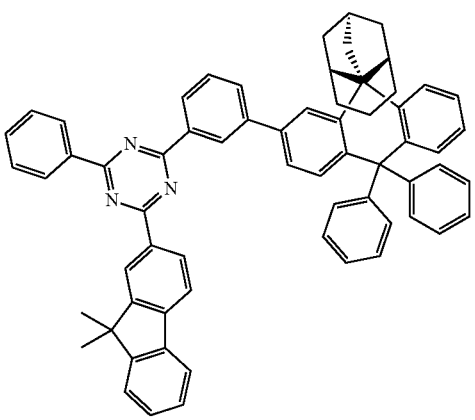

131
-continued
132
-continued
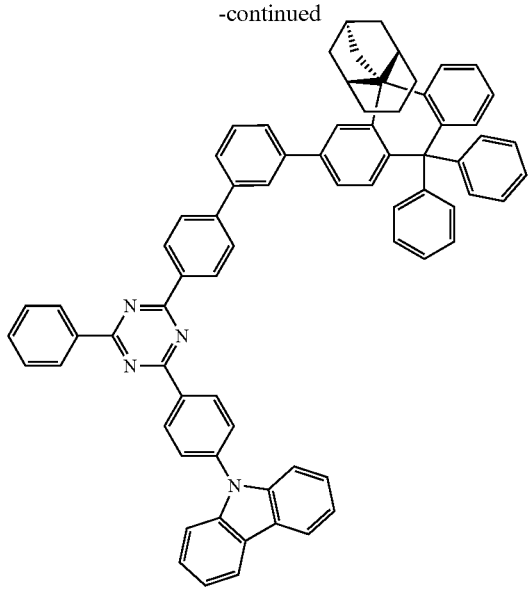
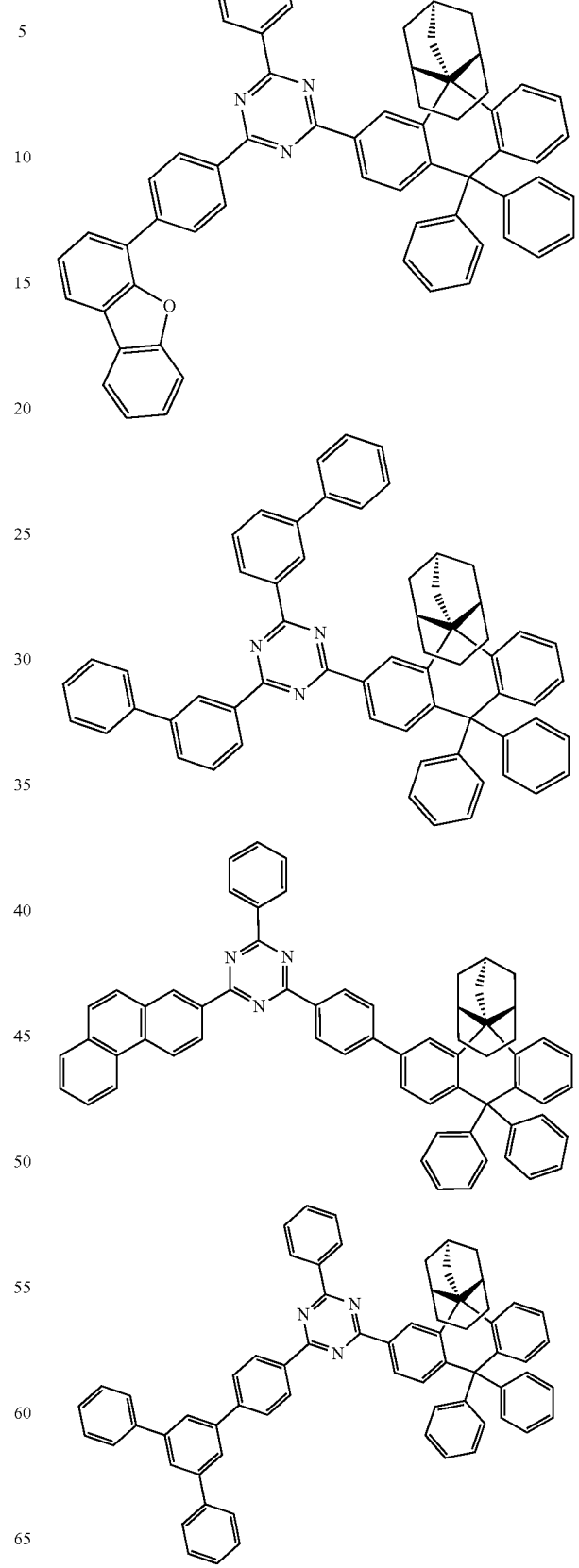

133
-continued
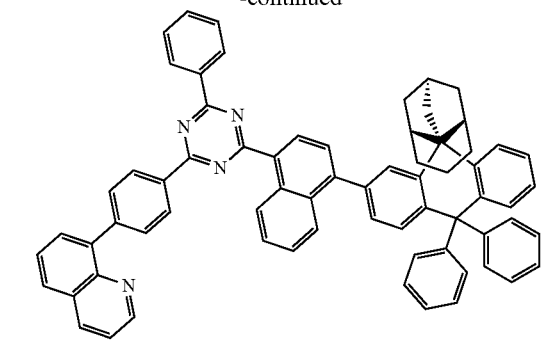
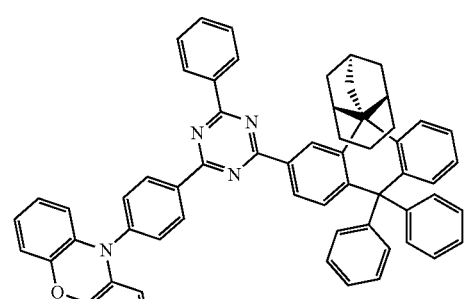
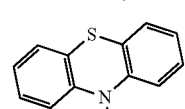
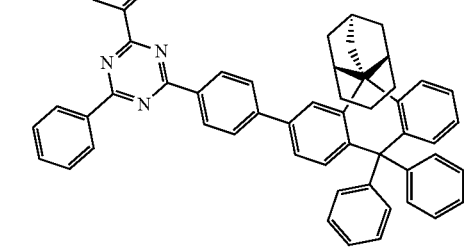
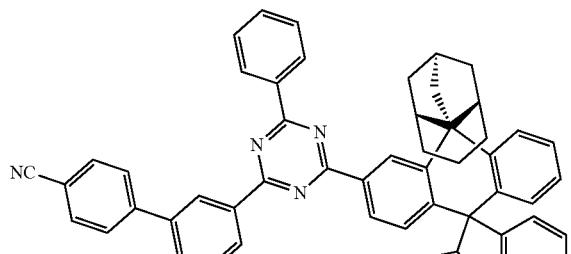
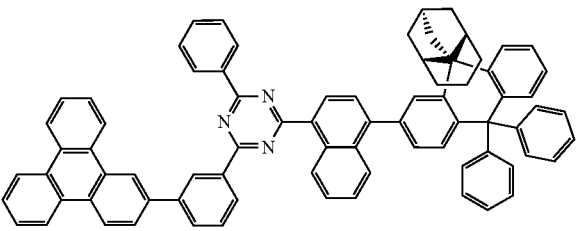
134
-continued
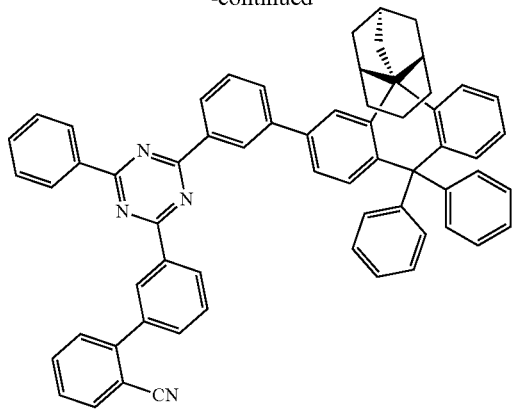
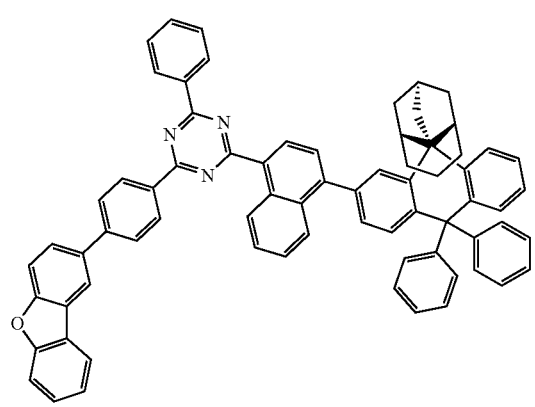
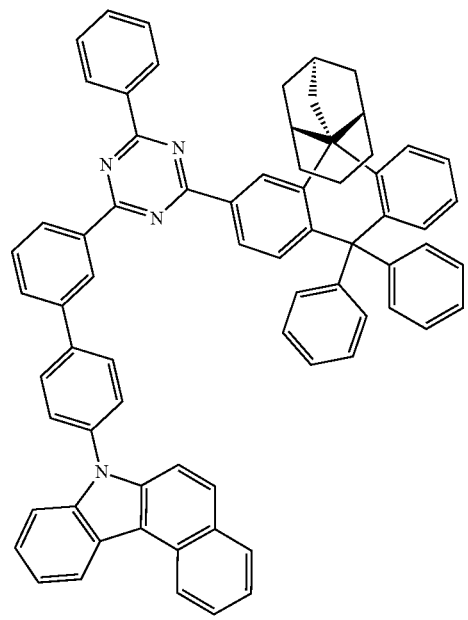

135
-continued
136
-continued
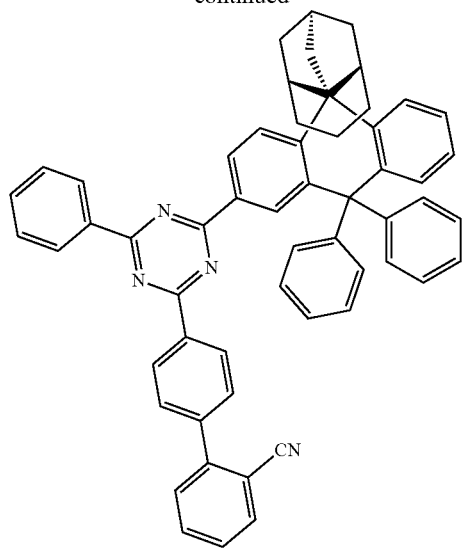
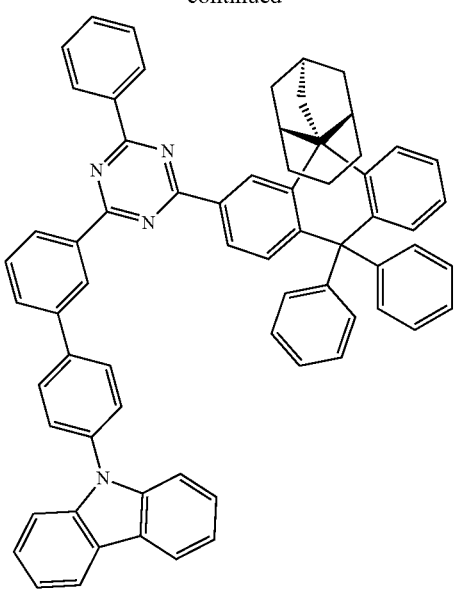
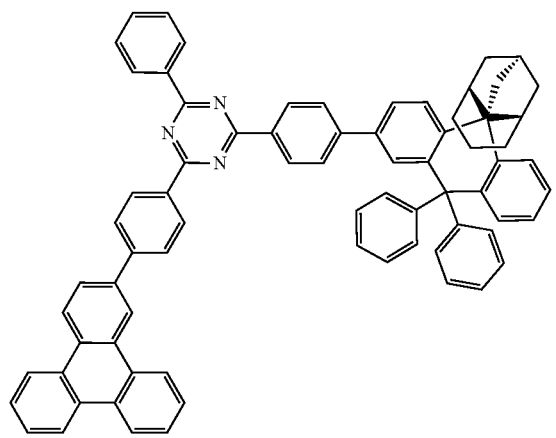
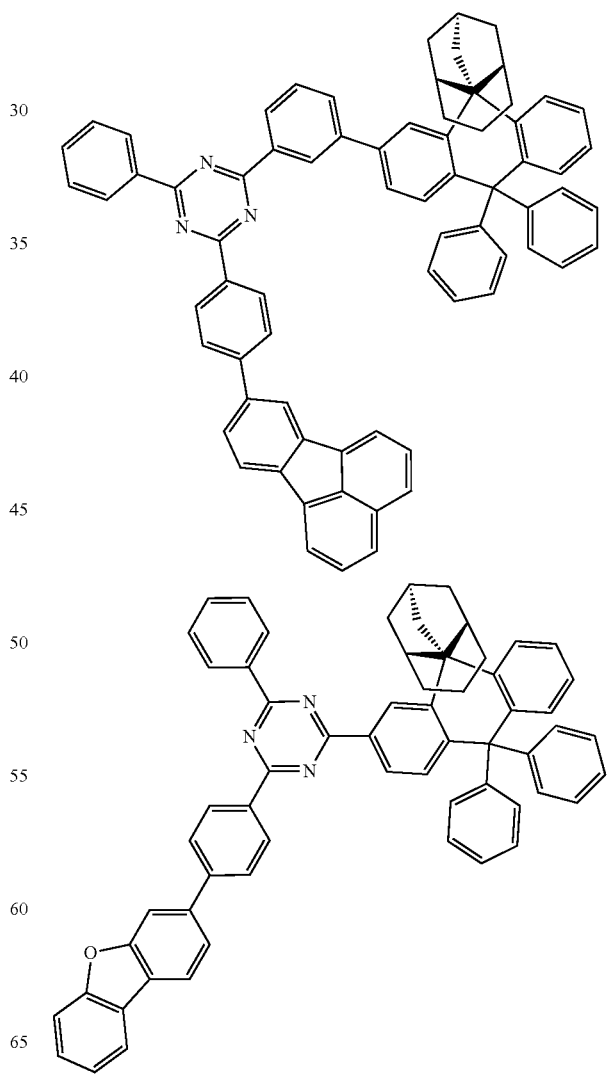
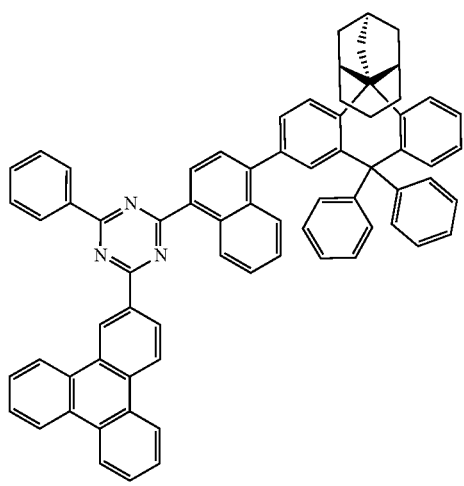

137
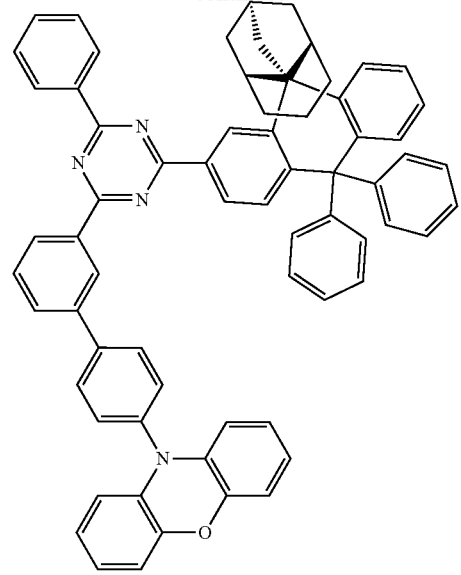
138
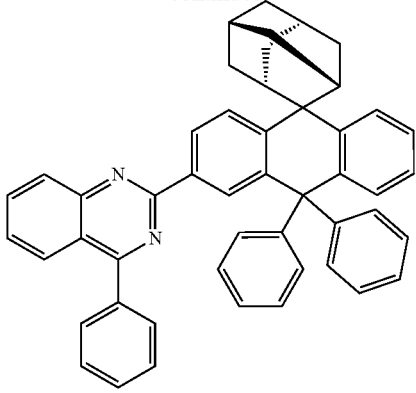
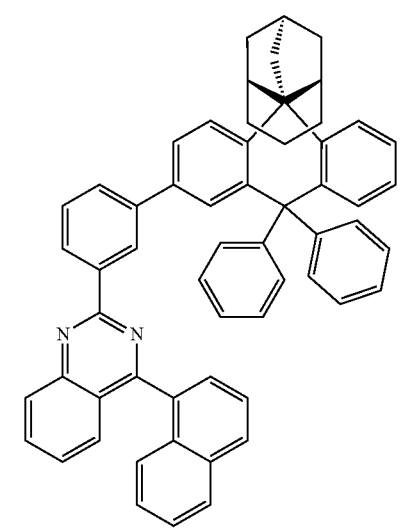
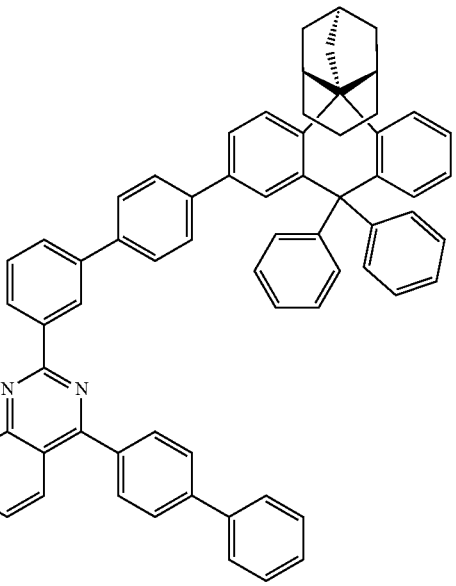

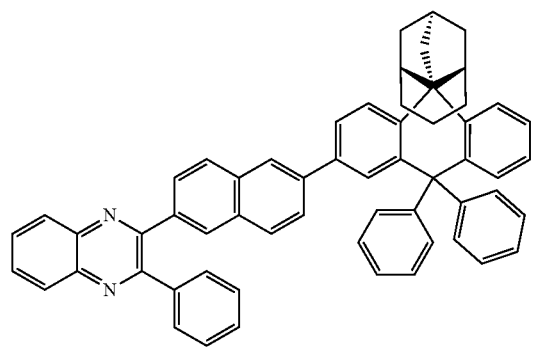
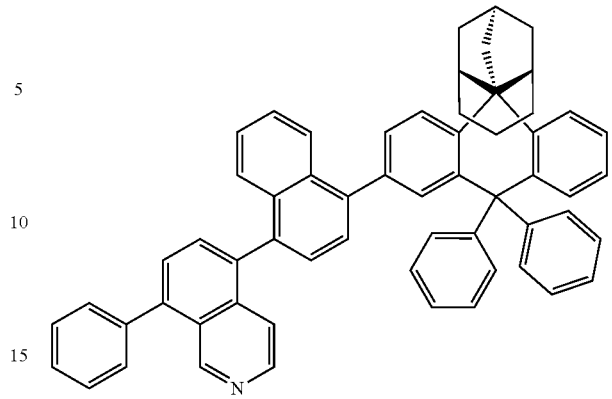
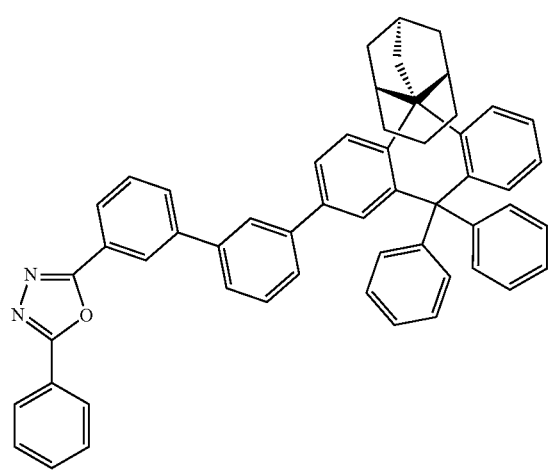
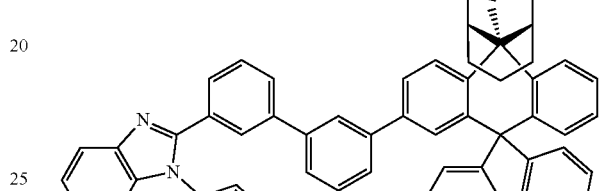
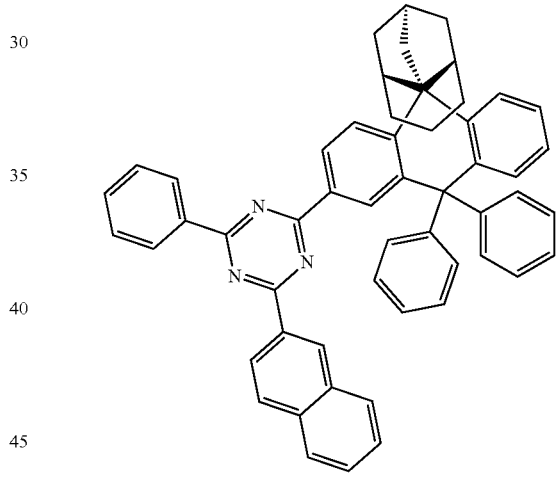
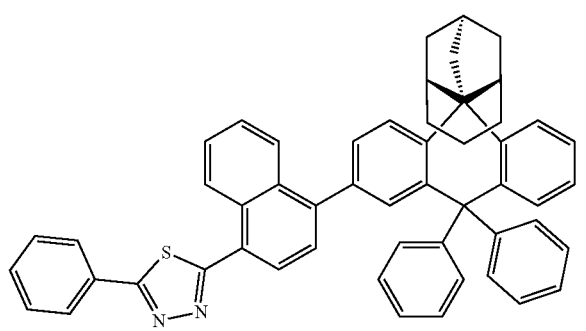
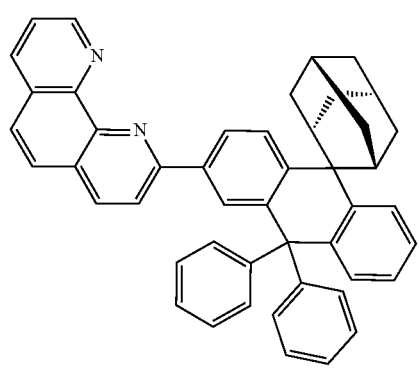
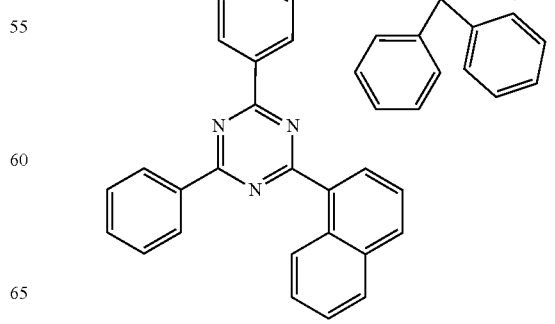

-continued
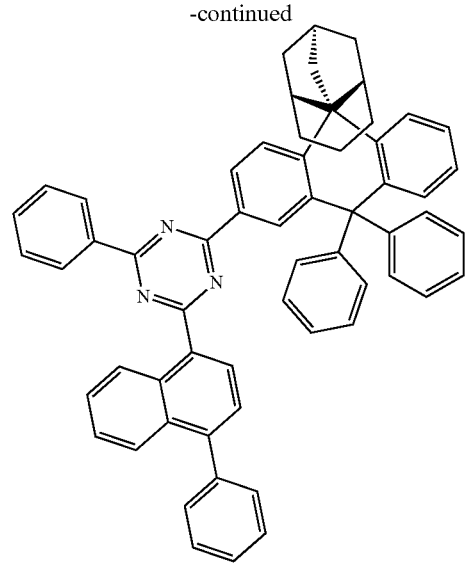
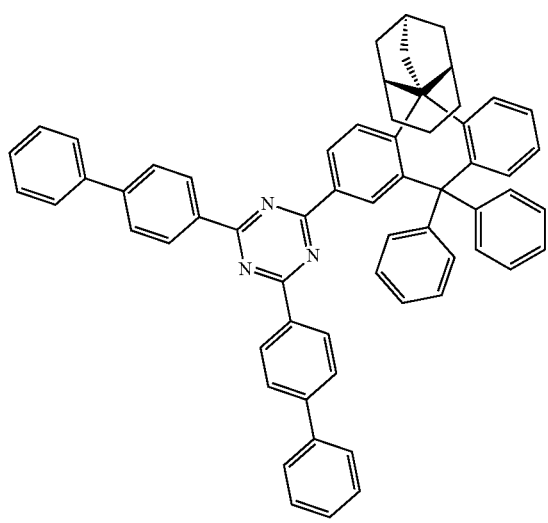
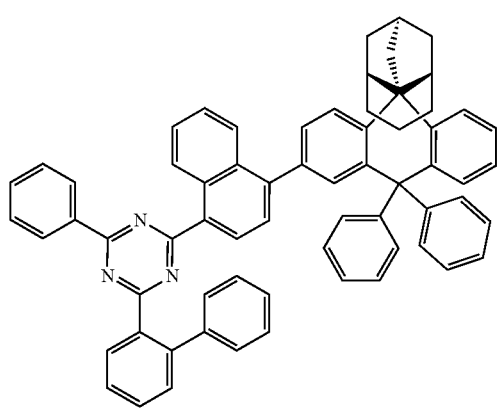
-continued
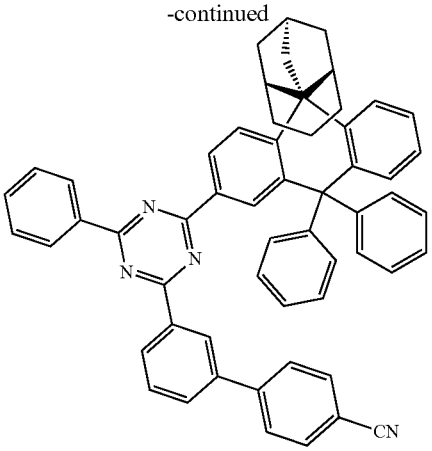
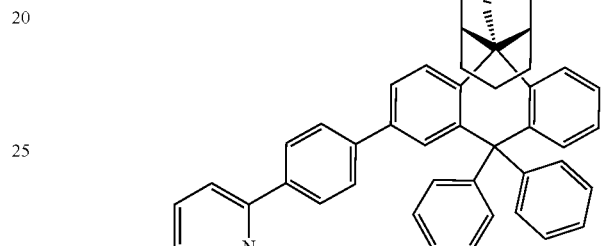
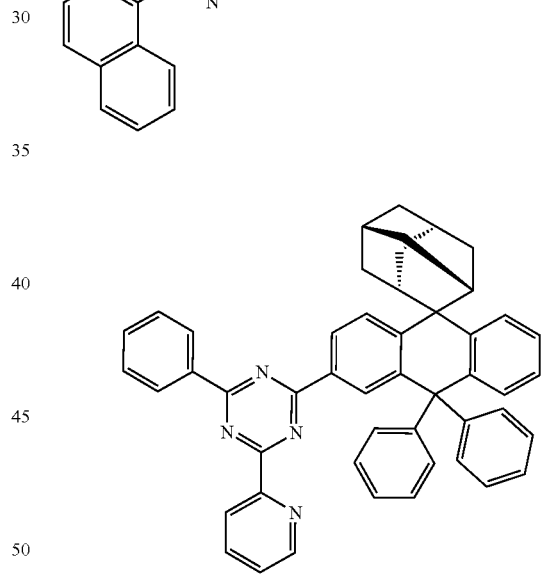
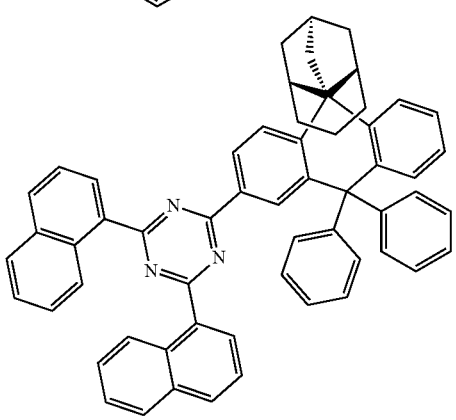

143
-continued
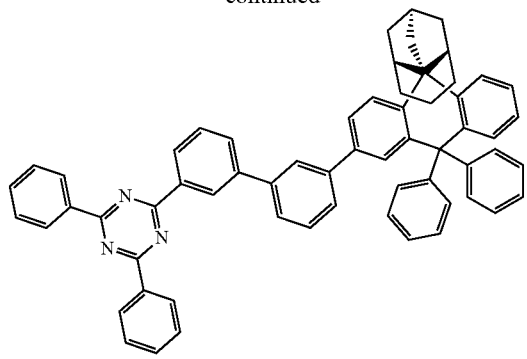
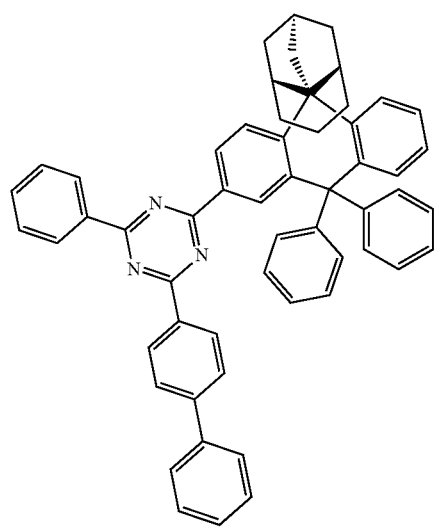
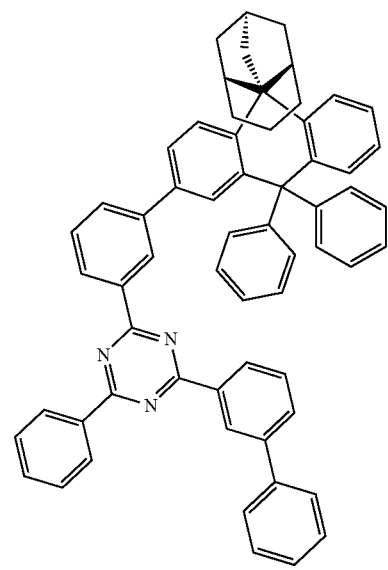
144
-continued
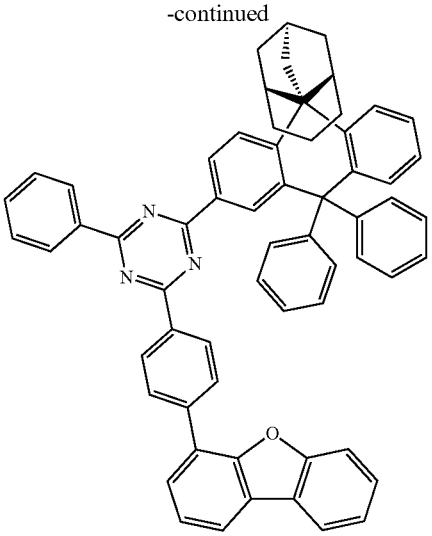
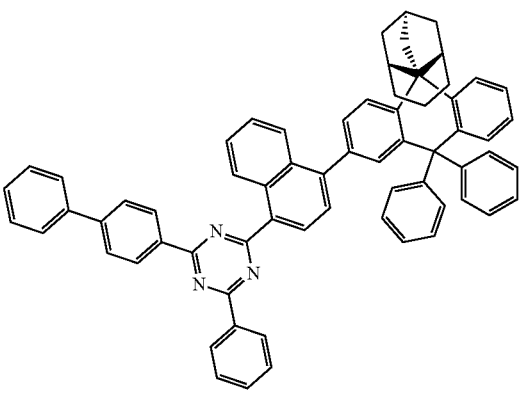
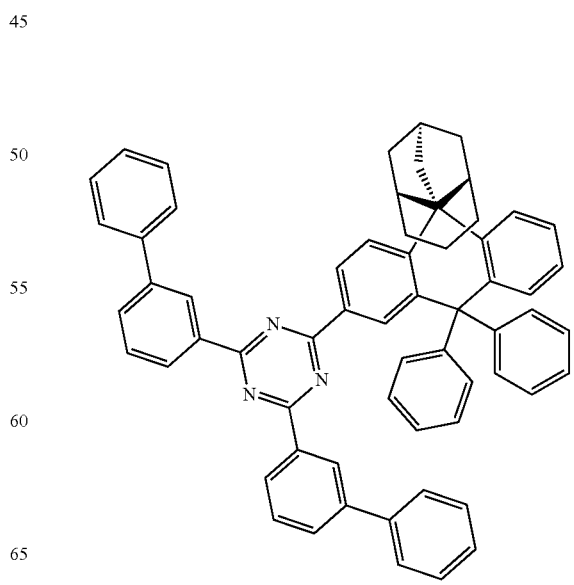

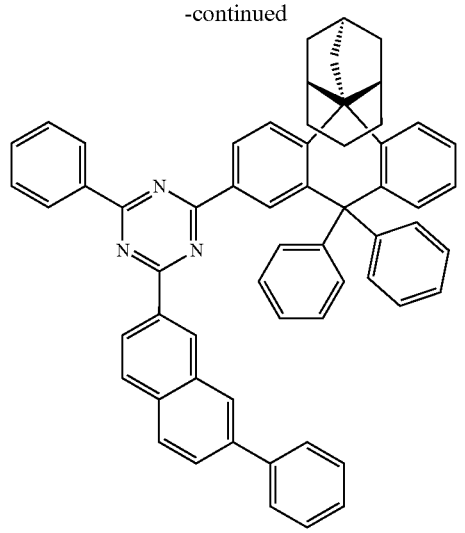
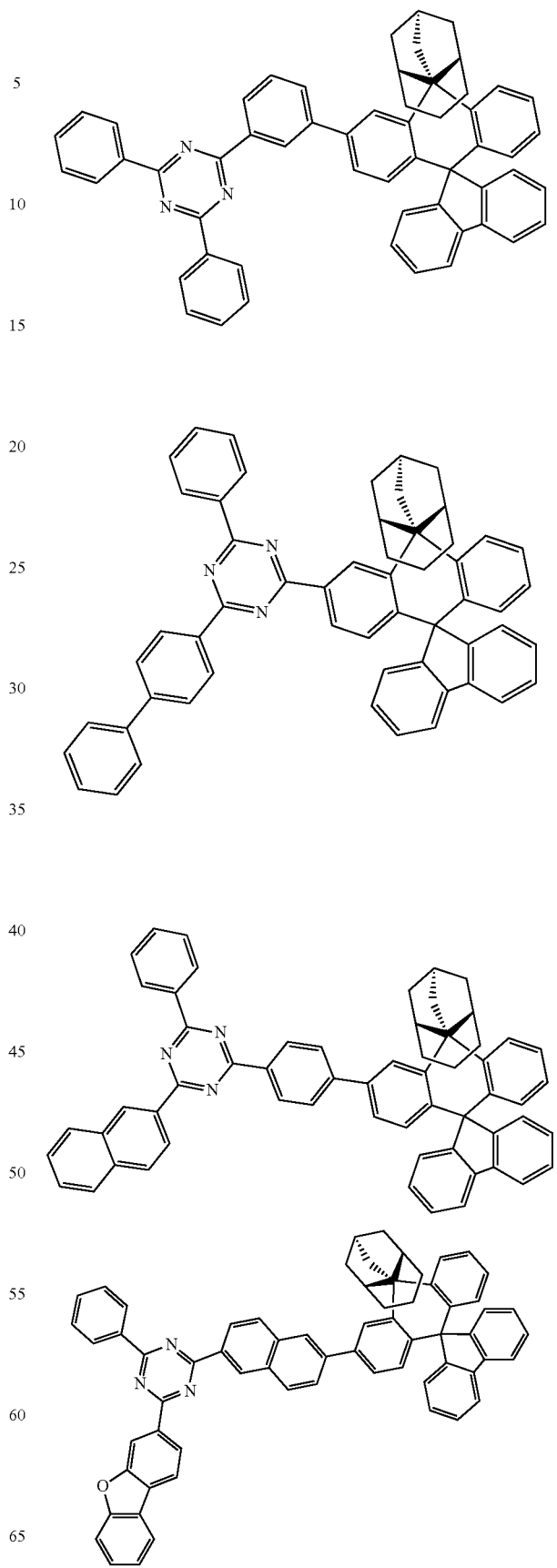

147
-continued
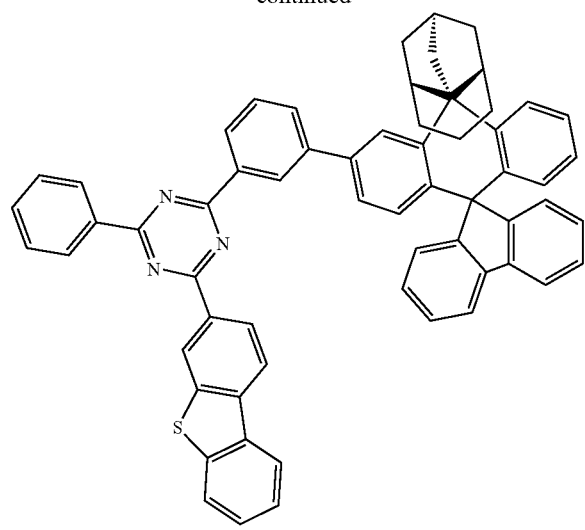
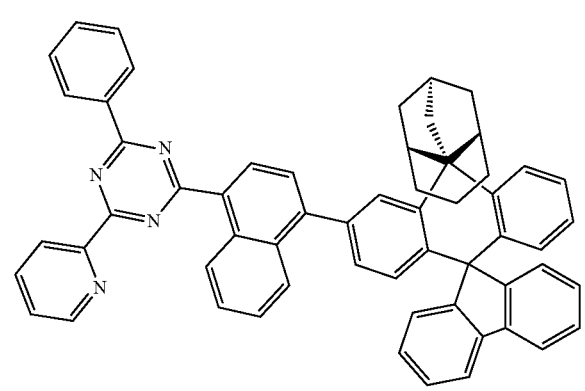
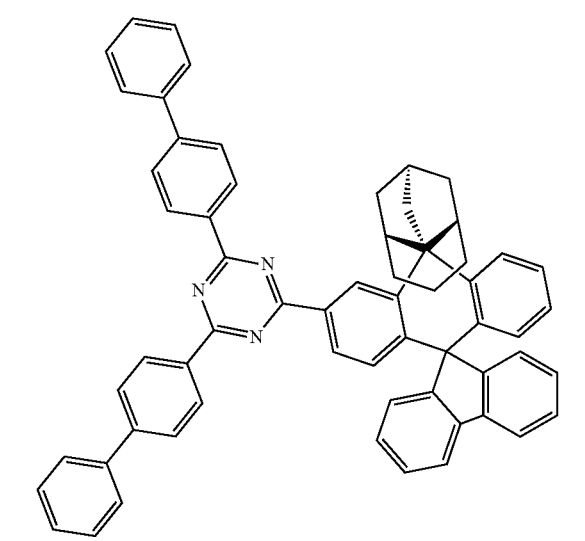
148
-continued
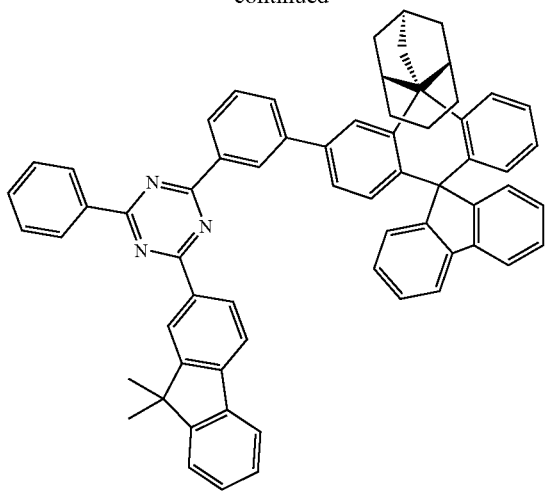
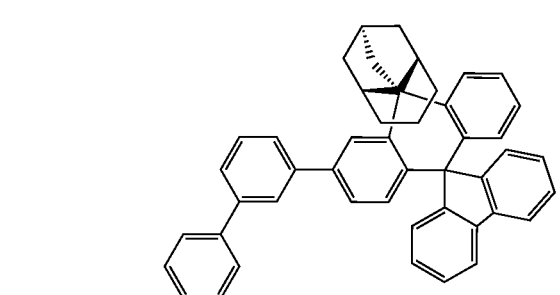
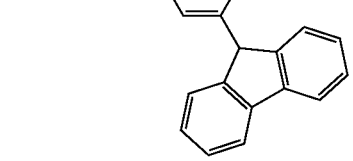
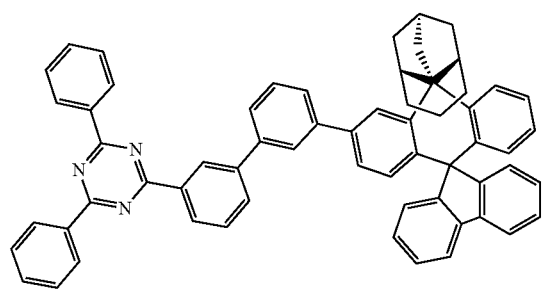

149
-continued
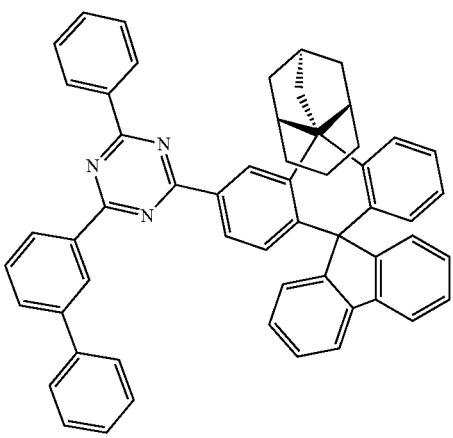
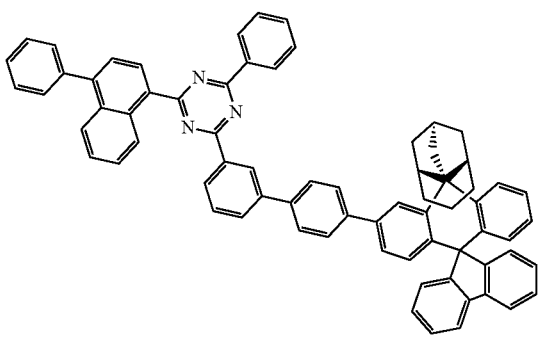
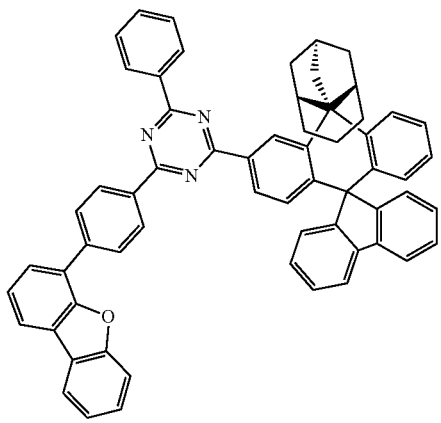
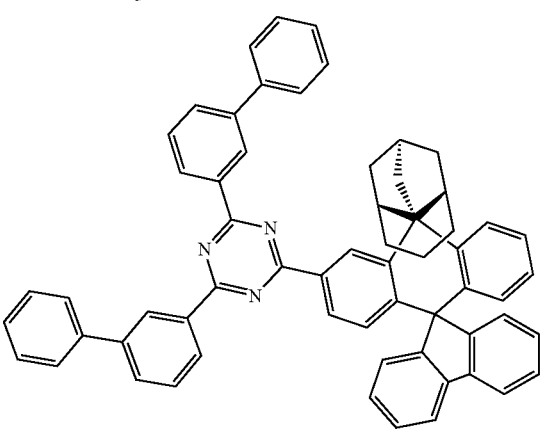
150
-continued
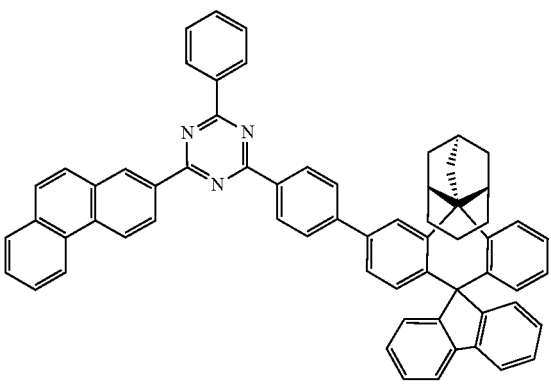
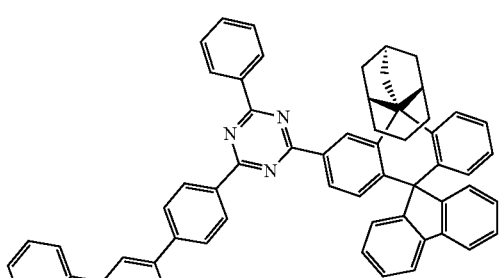
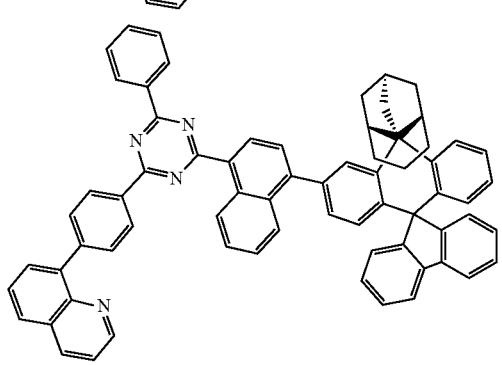
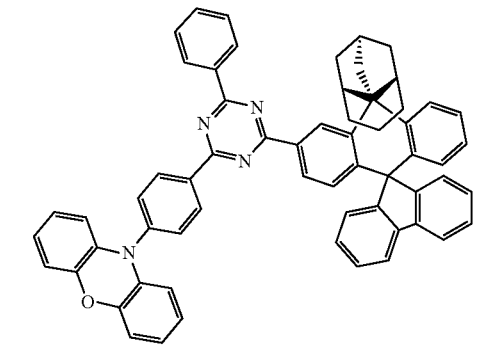

151
-continued
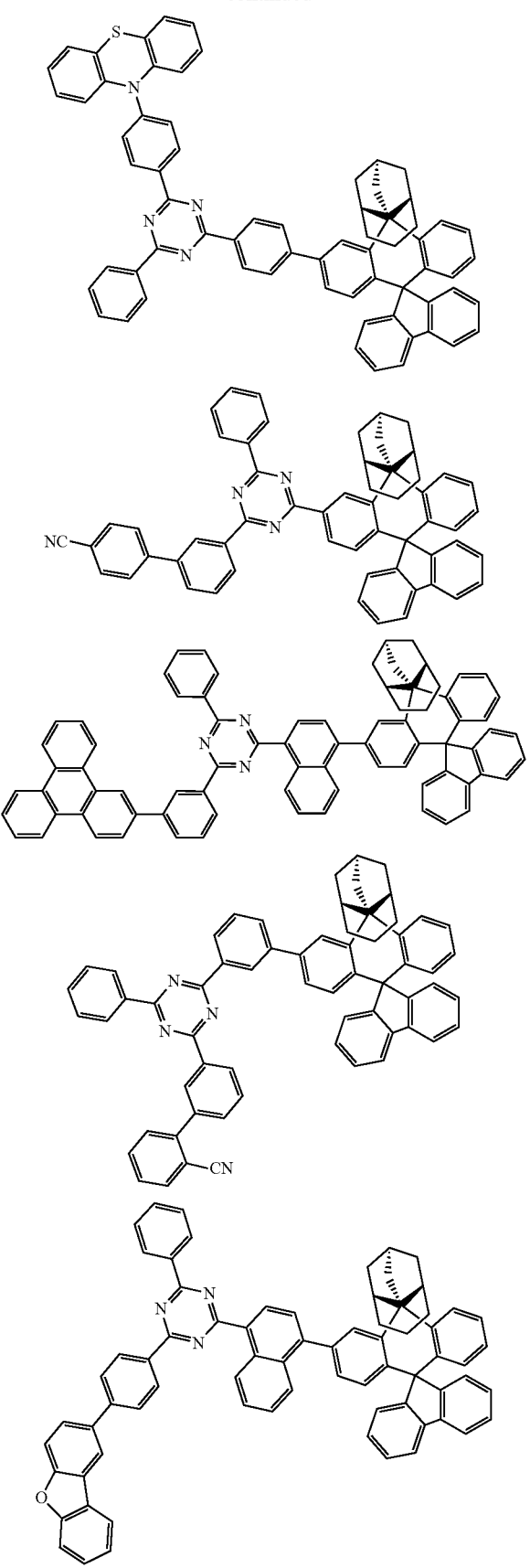
152
-continued
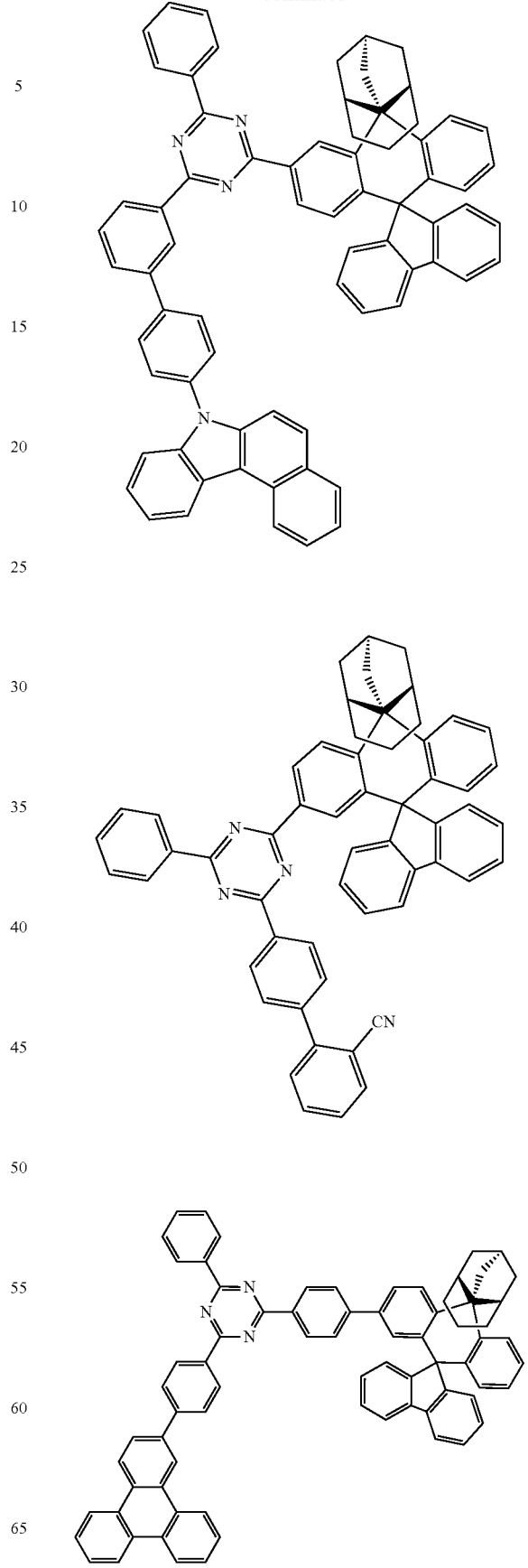

153
-continued
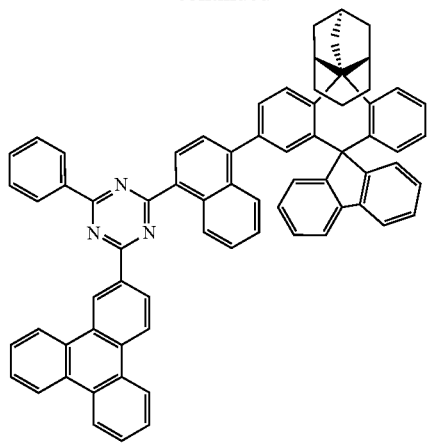
154
-continued
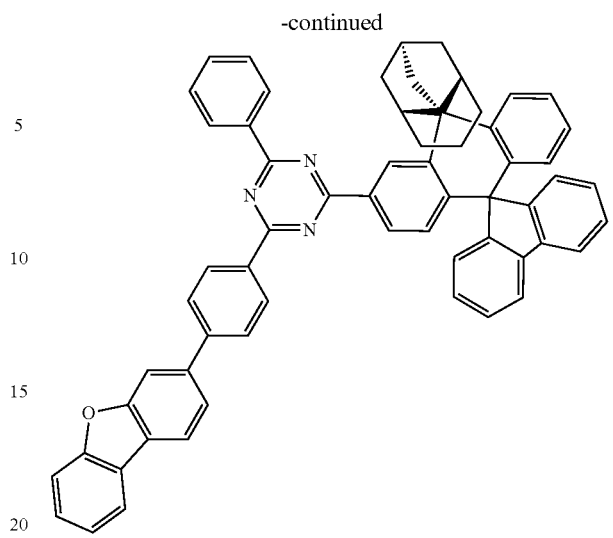
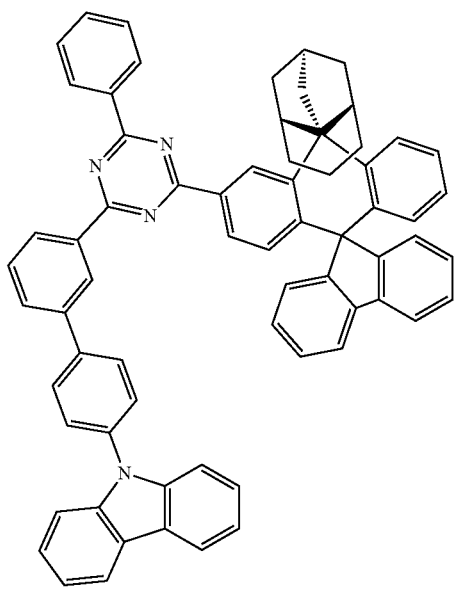
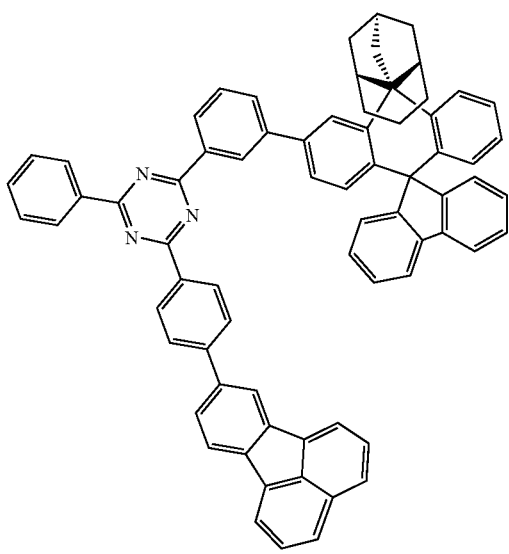

155
-continued
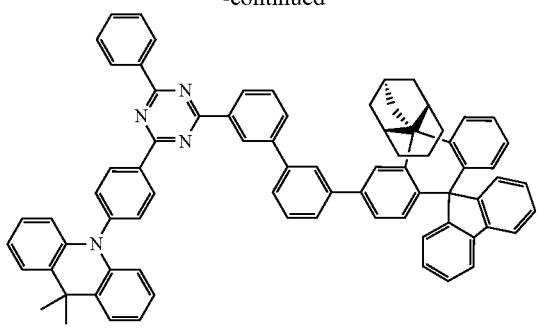
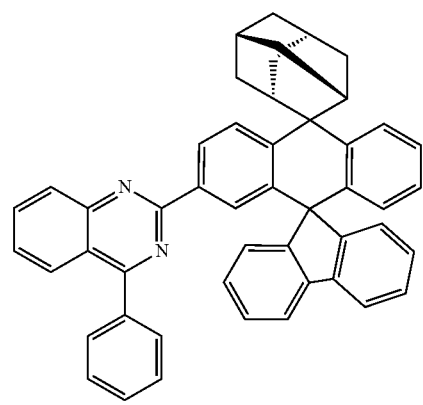
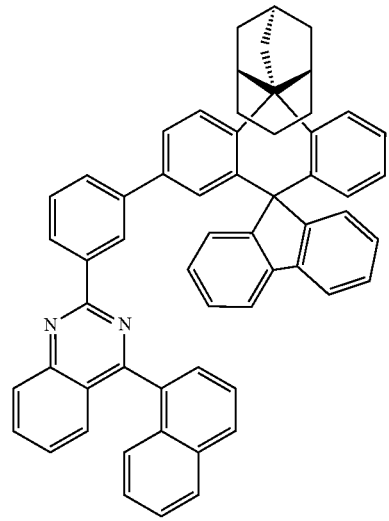
156
-continued
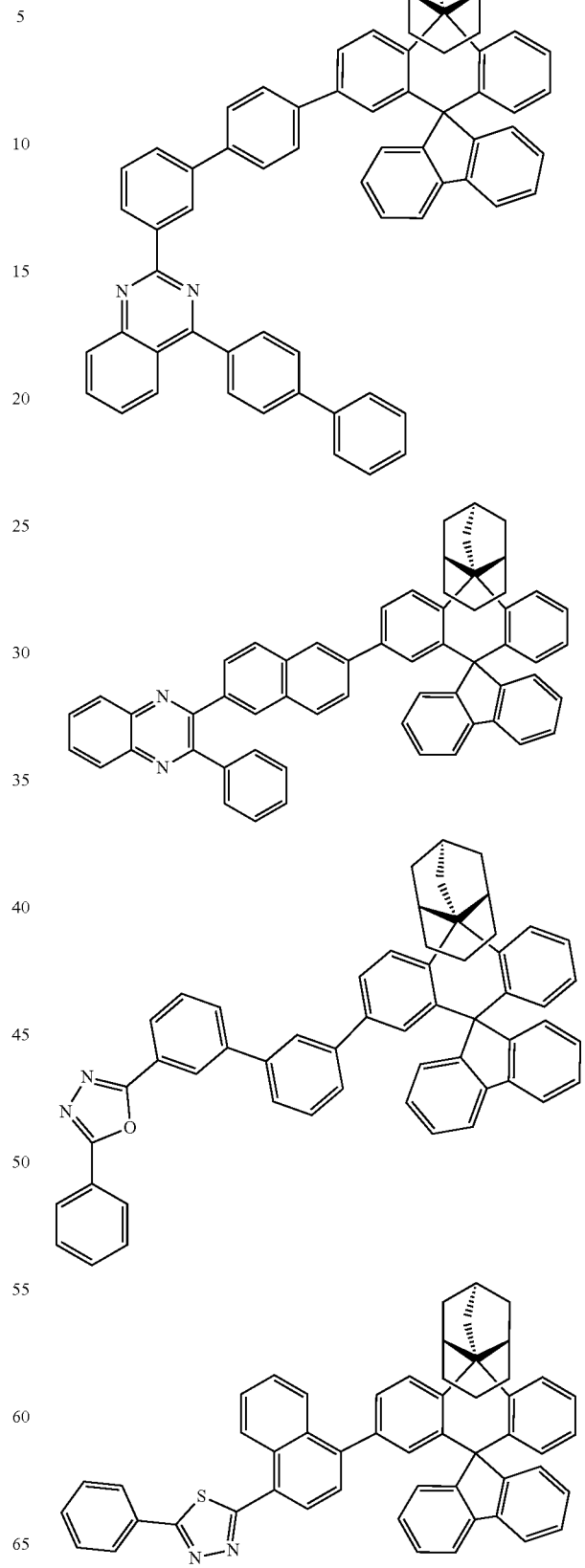

157
-continued
158
-continued
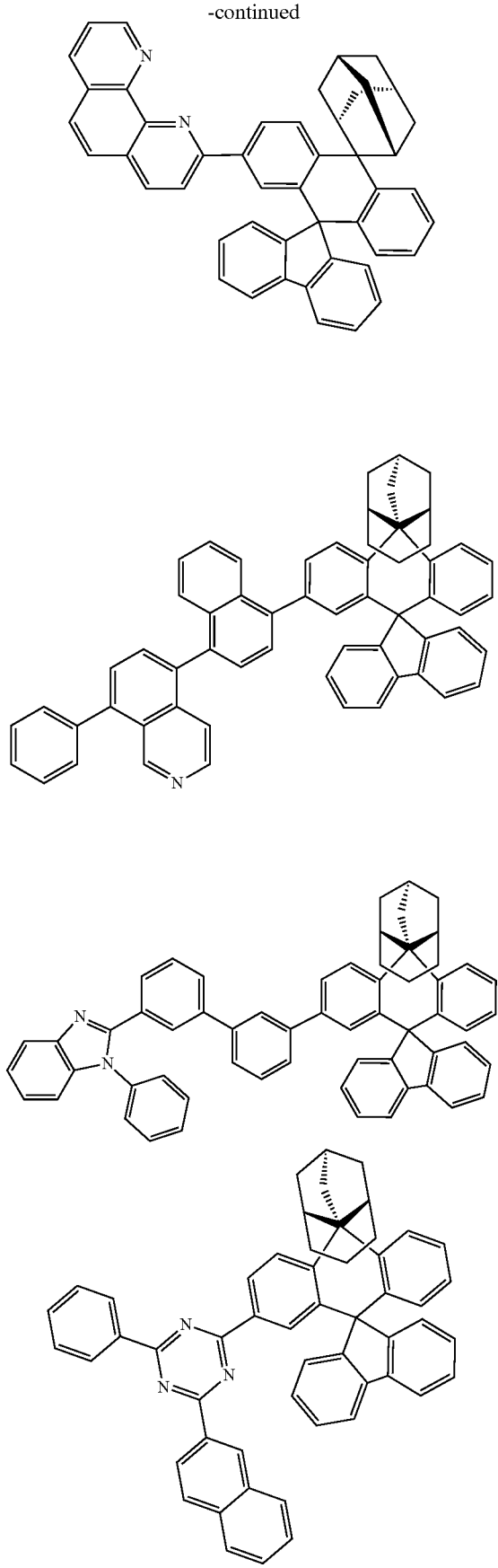
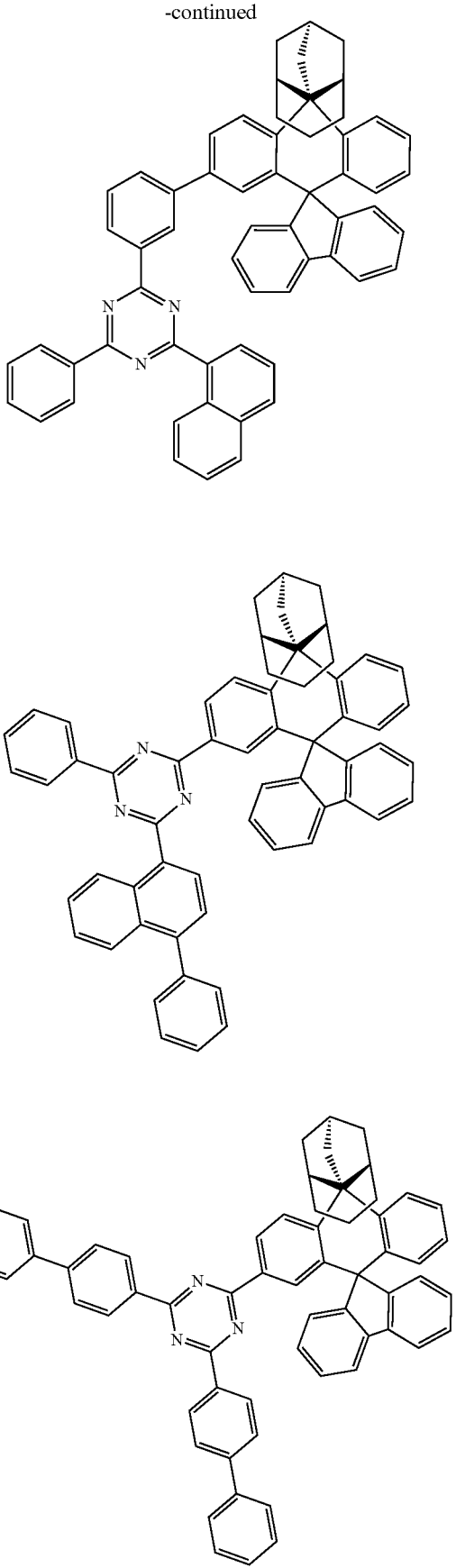

159
-continued
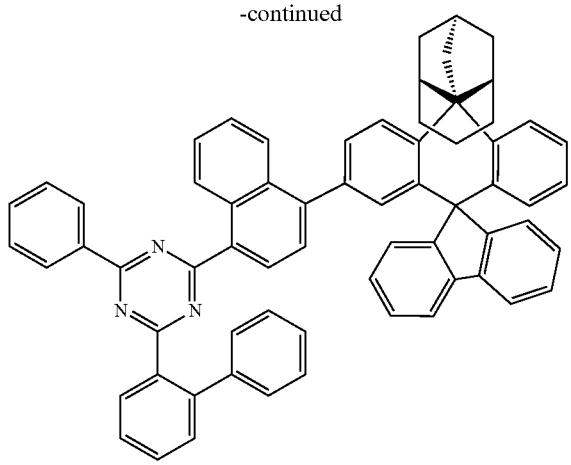
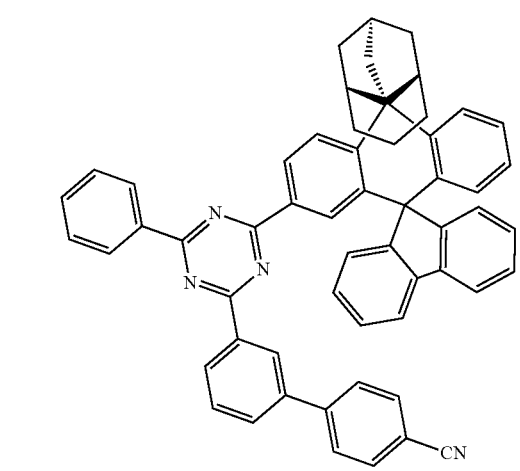
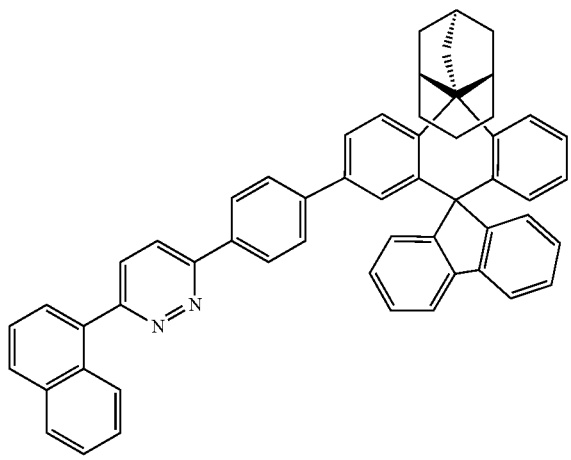
160
-continued
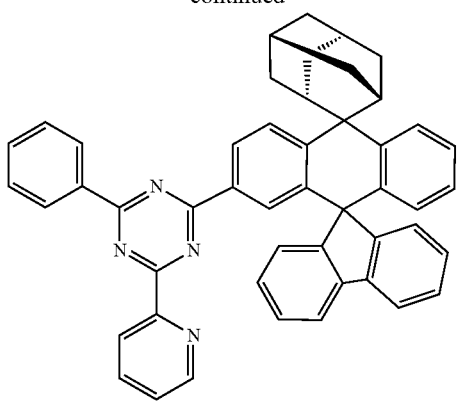
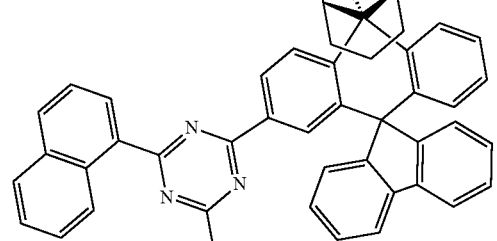
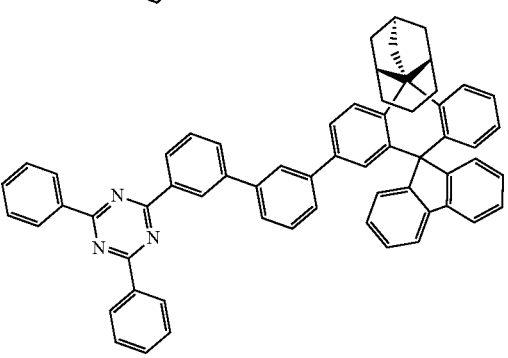
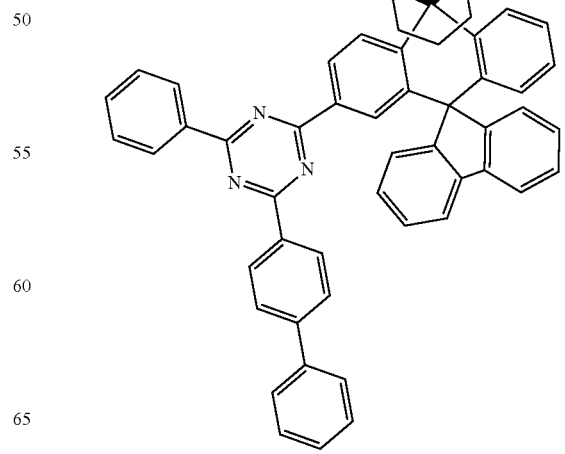

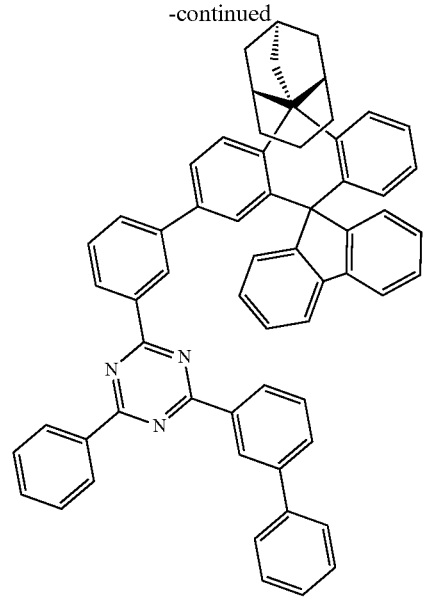
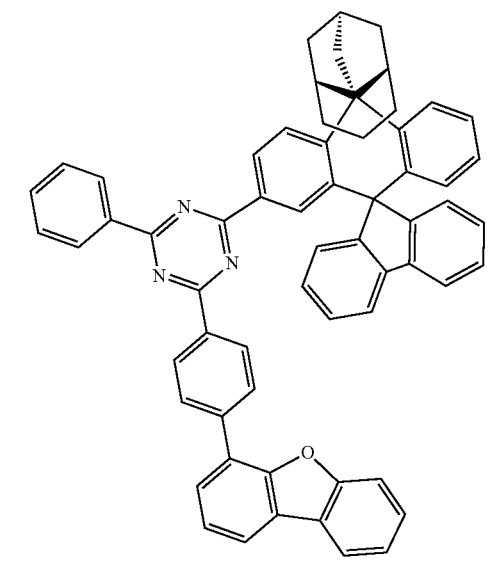
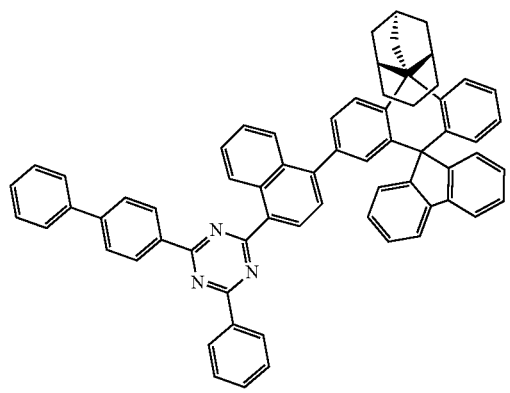
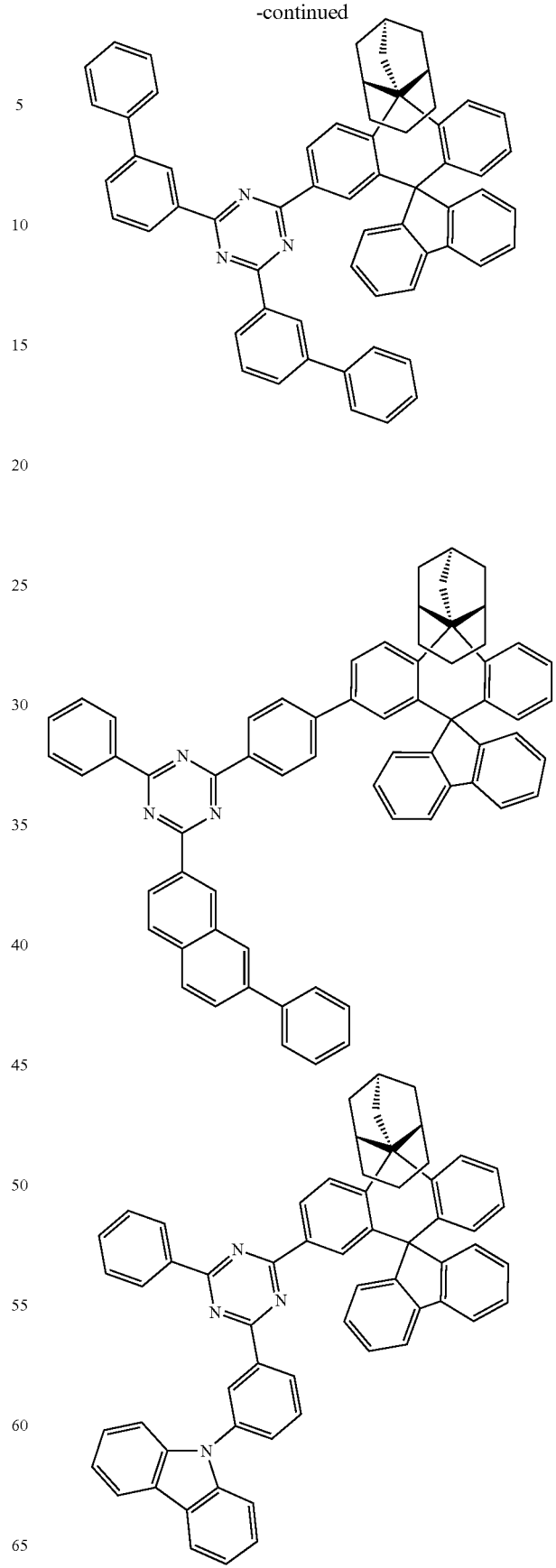

163
-continued
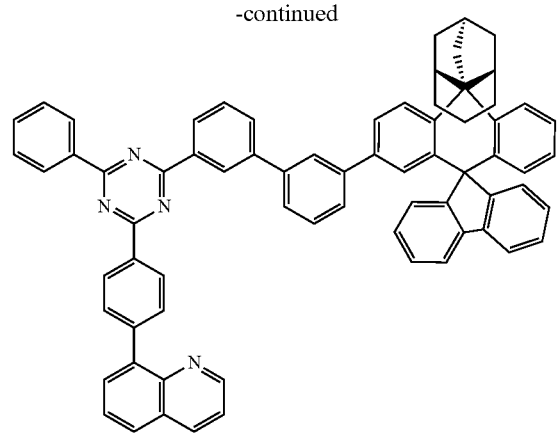
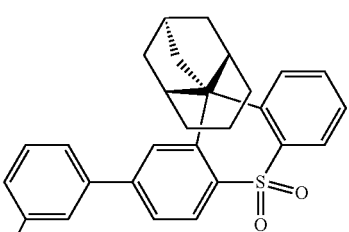
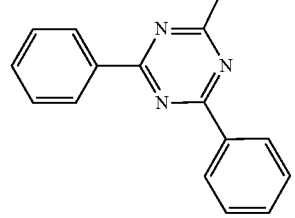
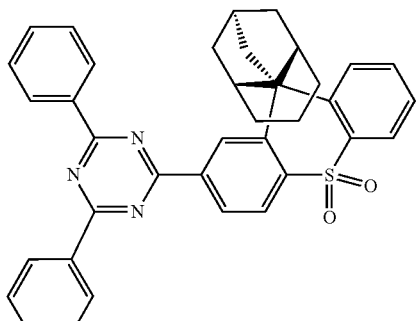
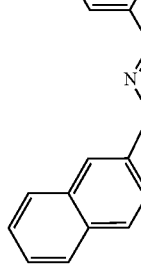
164
-continued
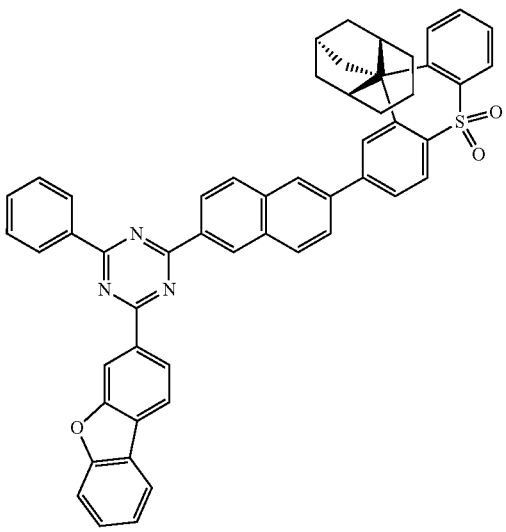
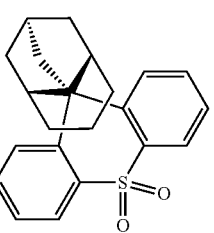
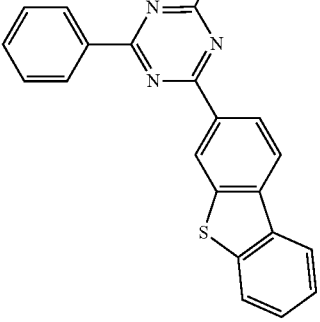
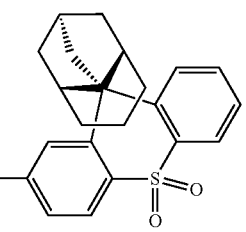
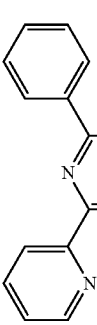

165
-continued
166
-continued
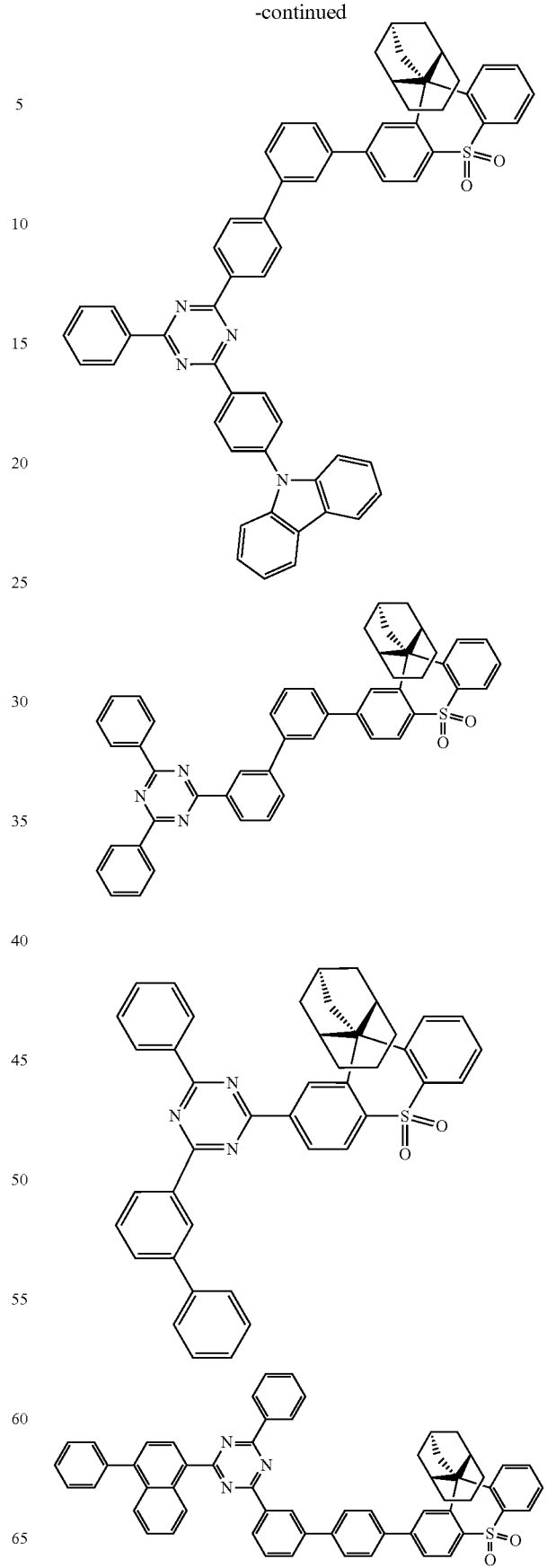

167
-continued
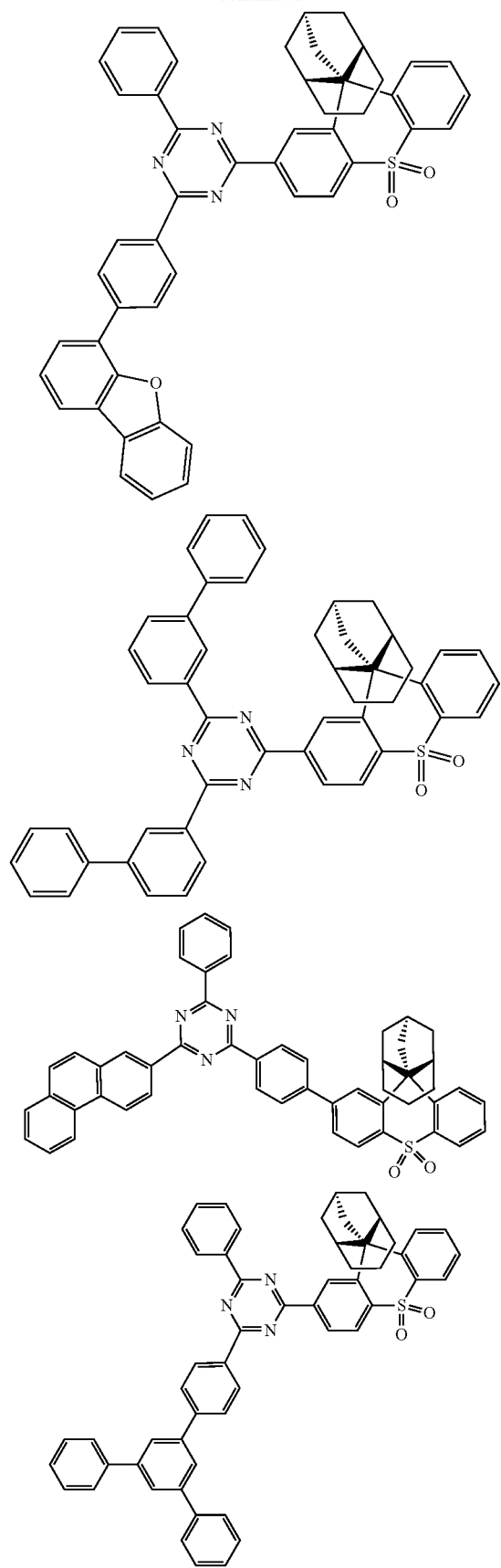
168
-continued
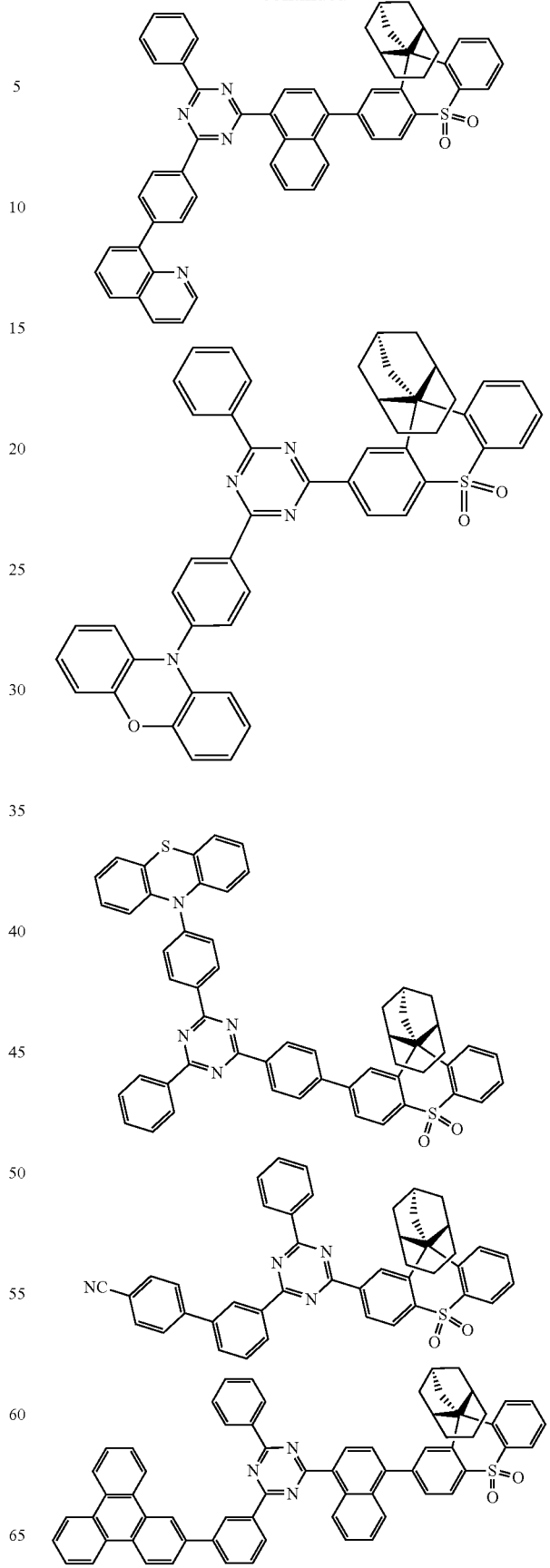

169
-continued
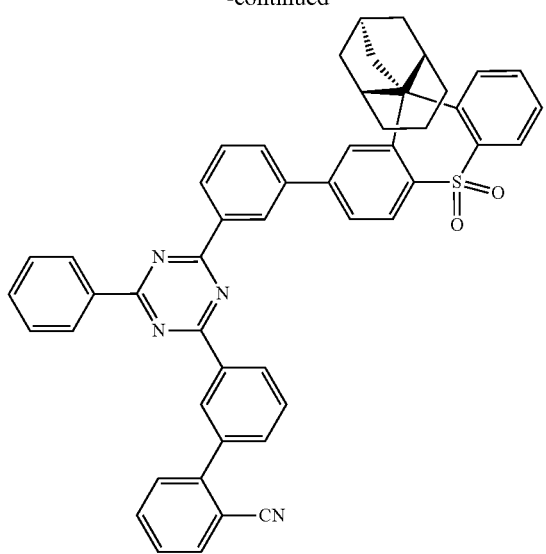
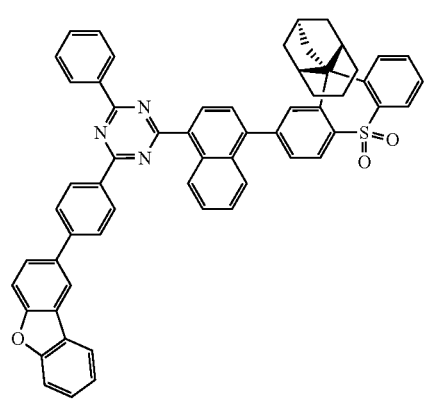
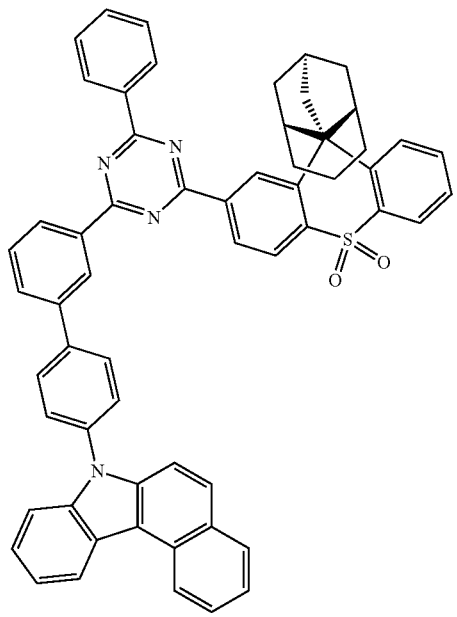
170
-continued
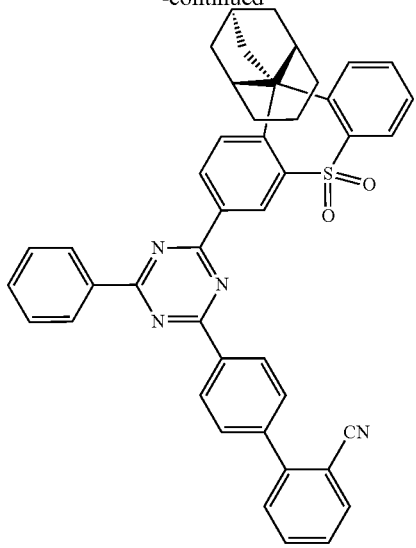
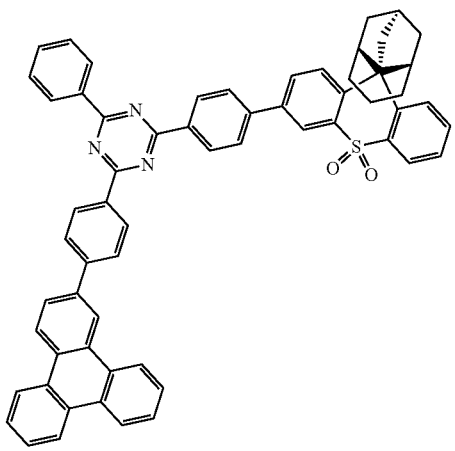
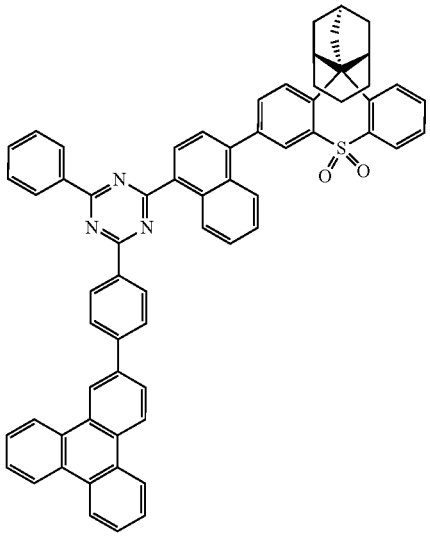

171
-continued
172
-continued
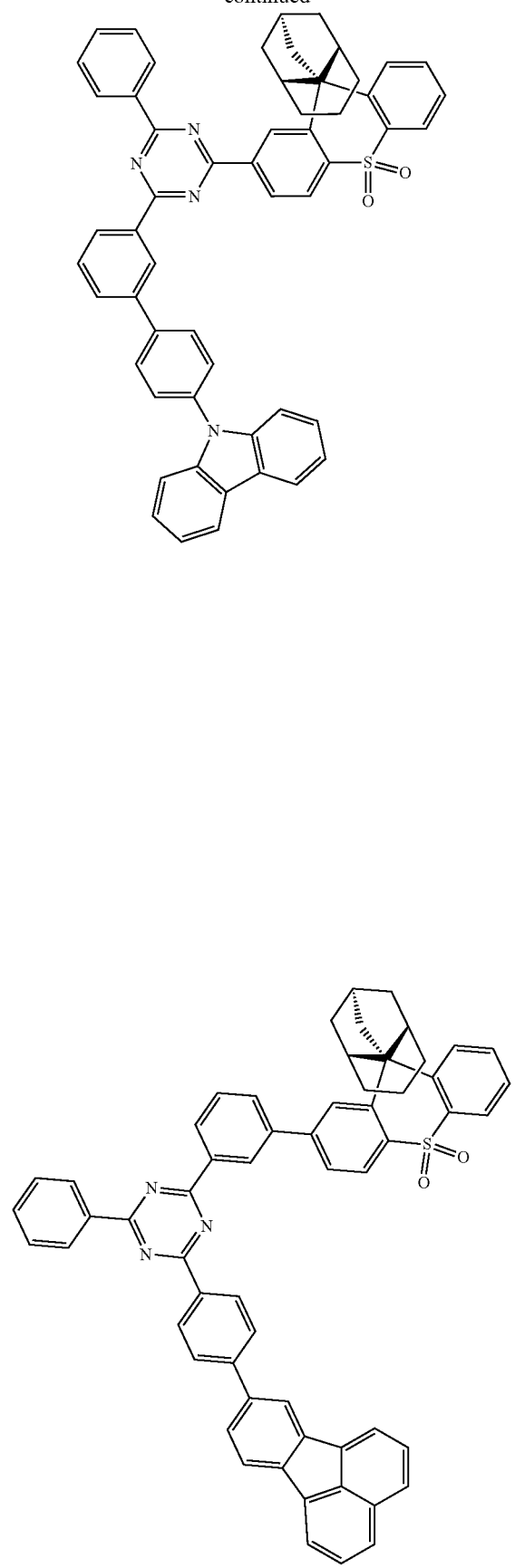
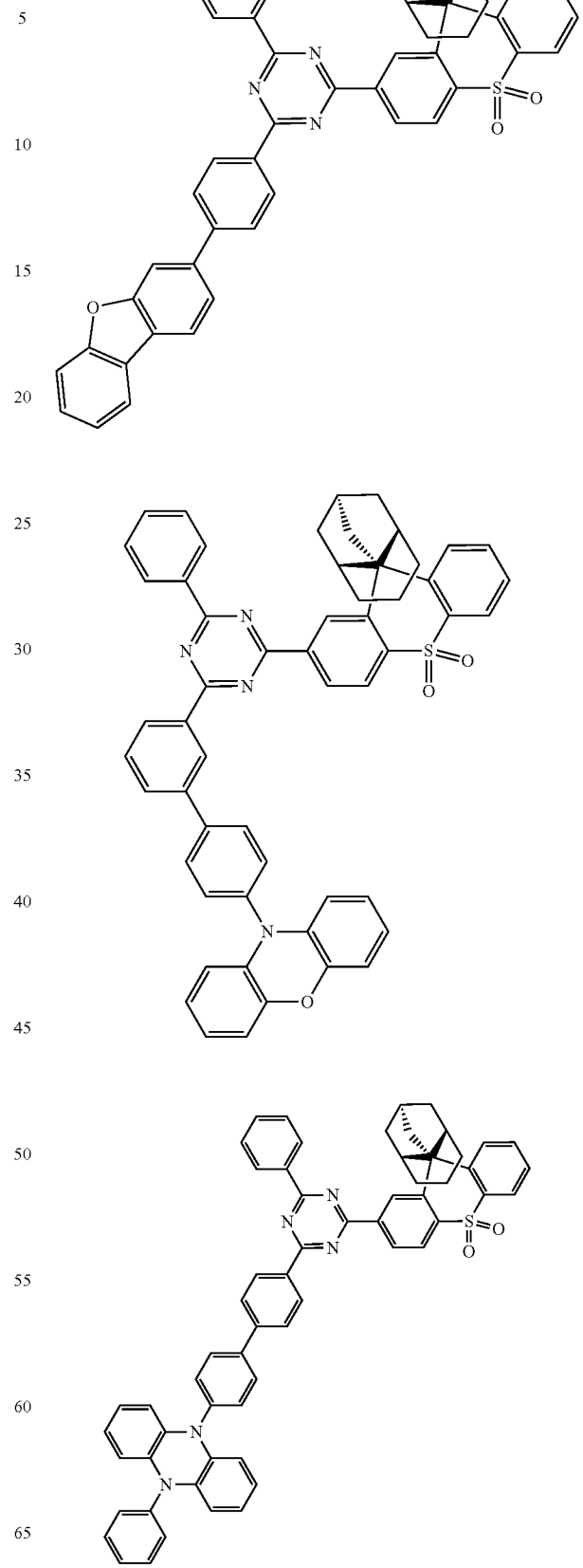

-continued
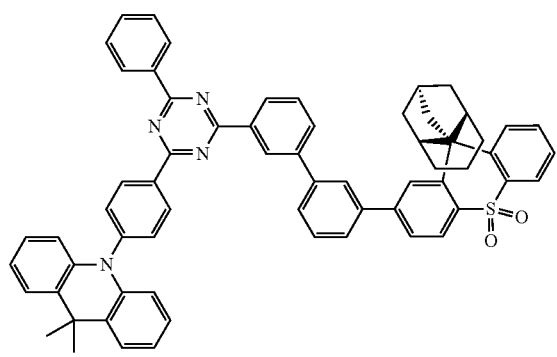
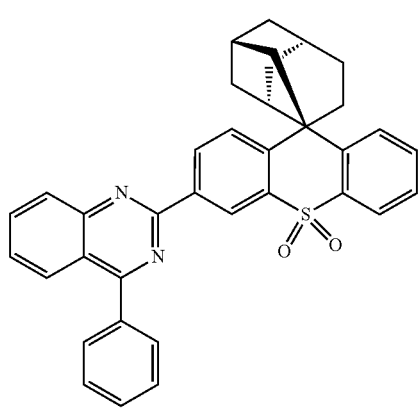
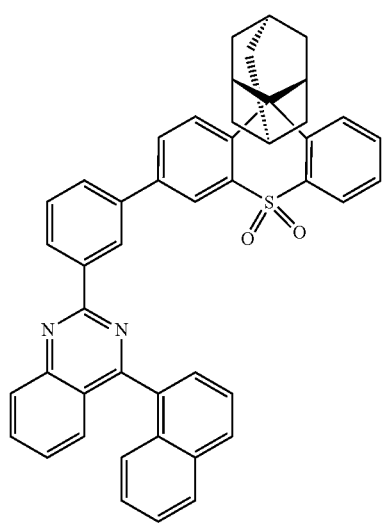
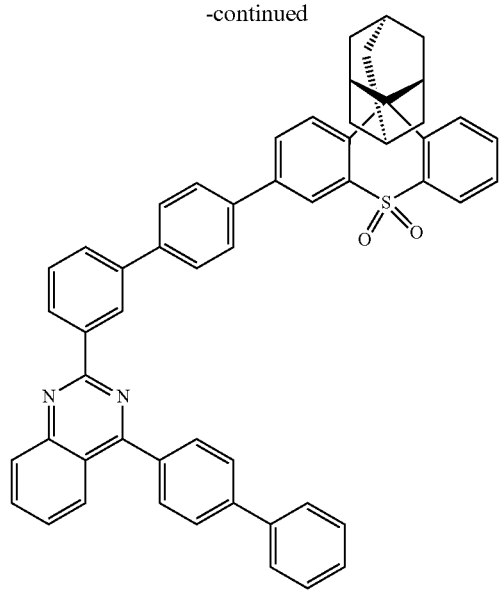
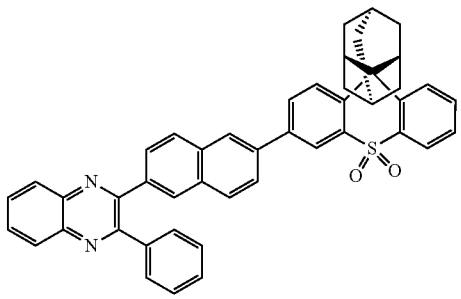
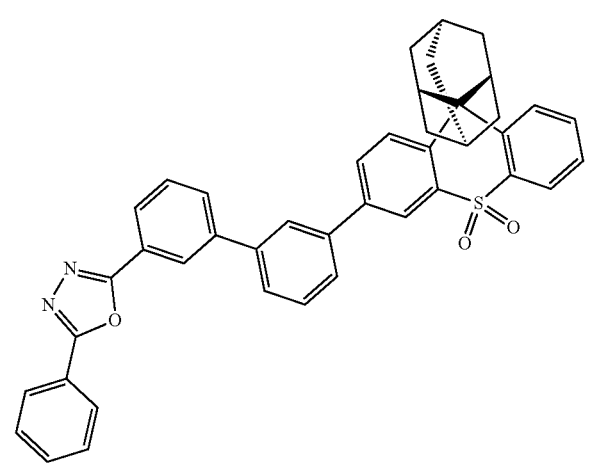

175
-continued
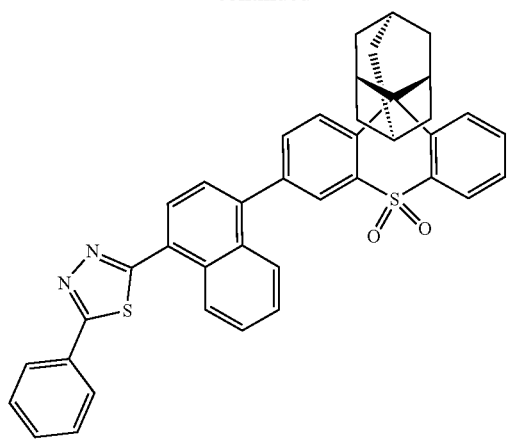
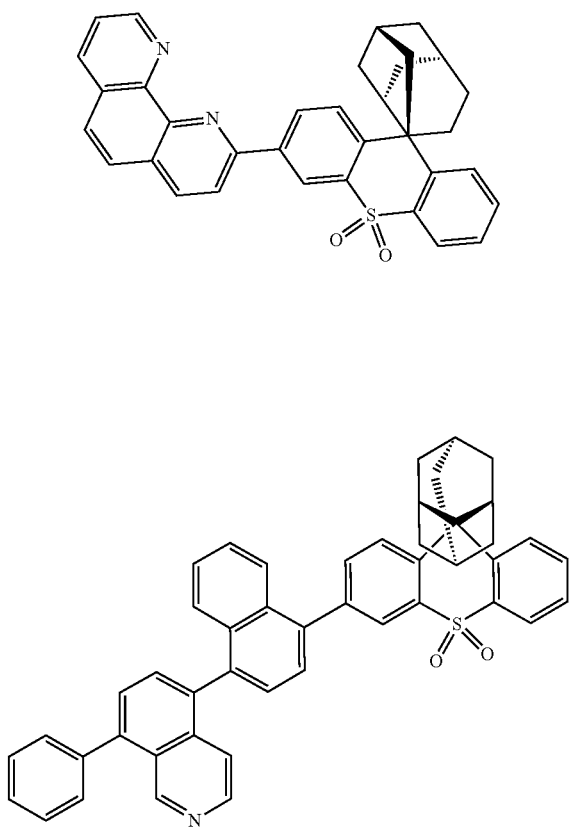
176
-continued
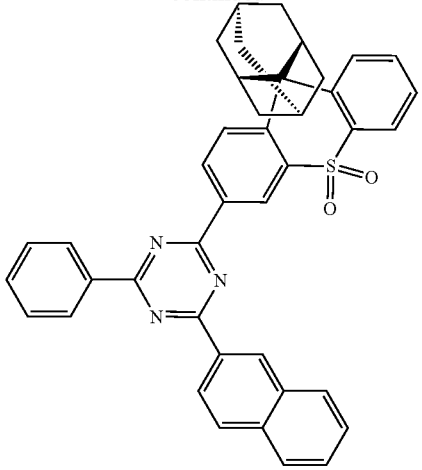
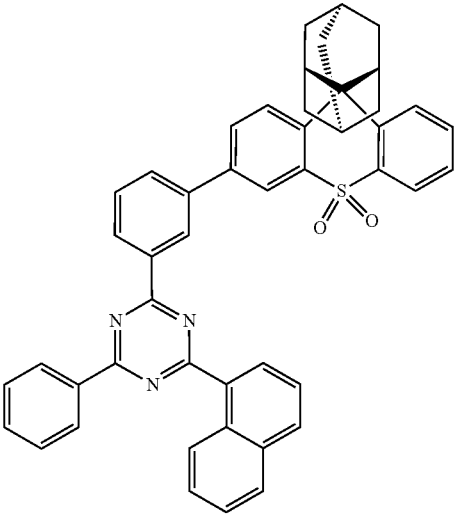
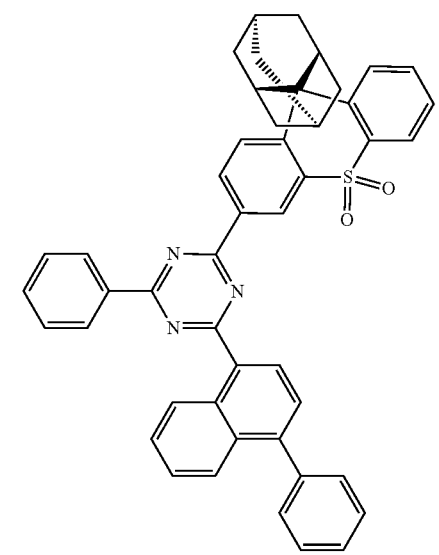

177
-continued
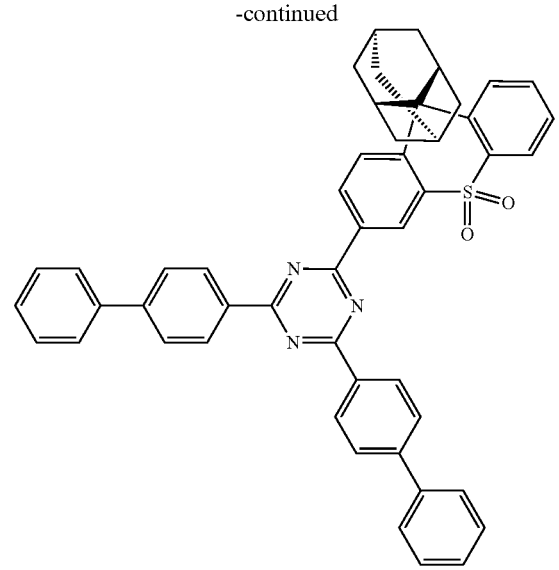
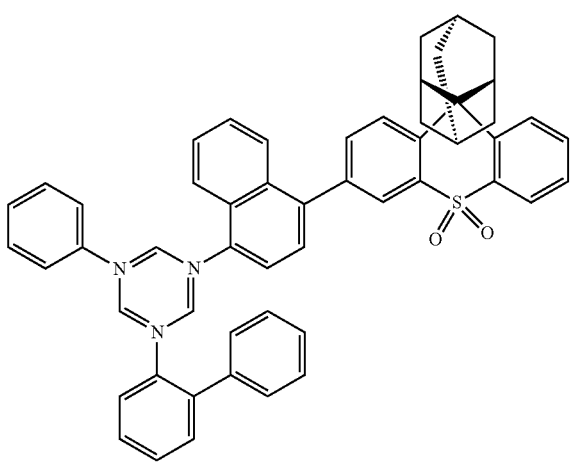
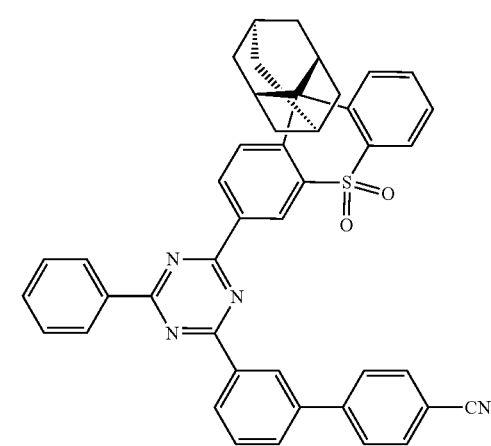
178
-continued
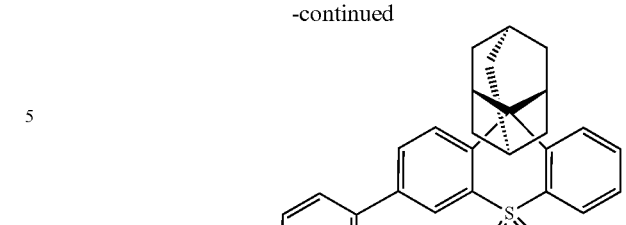
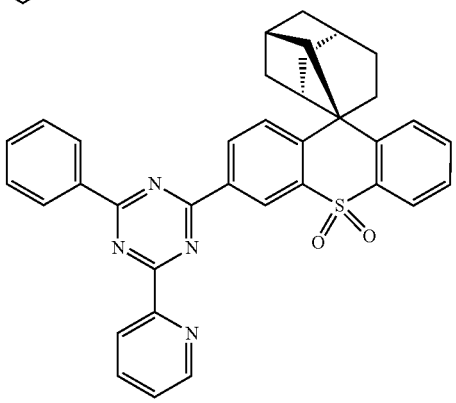
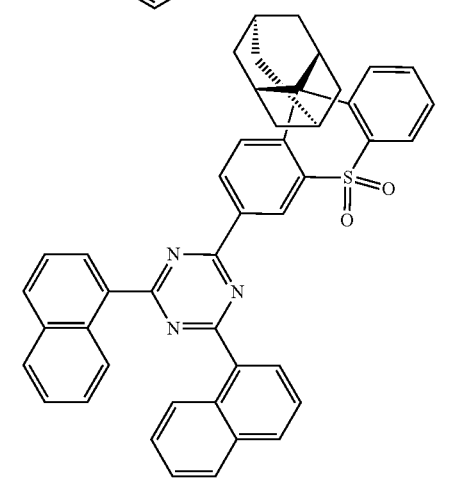
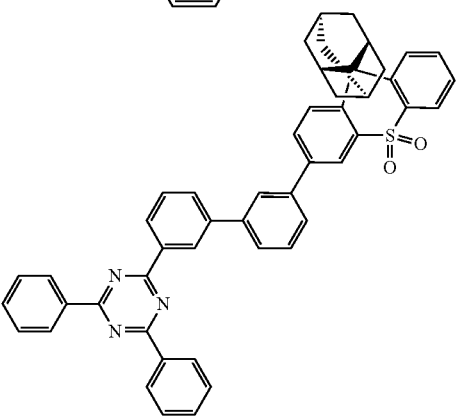

-continued
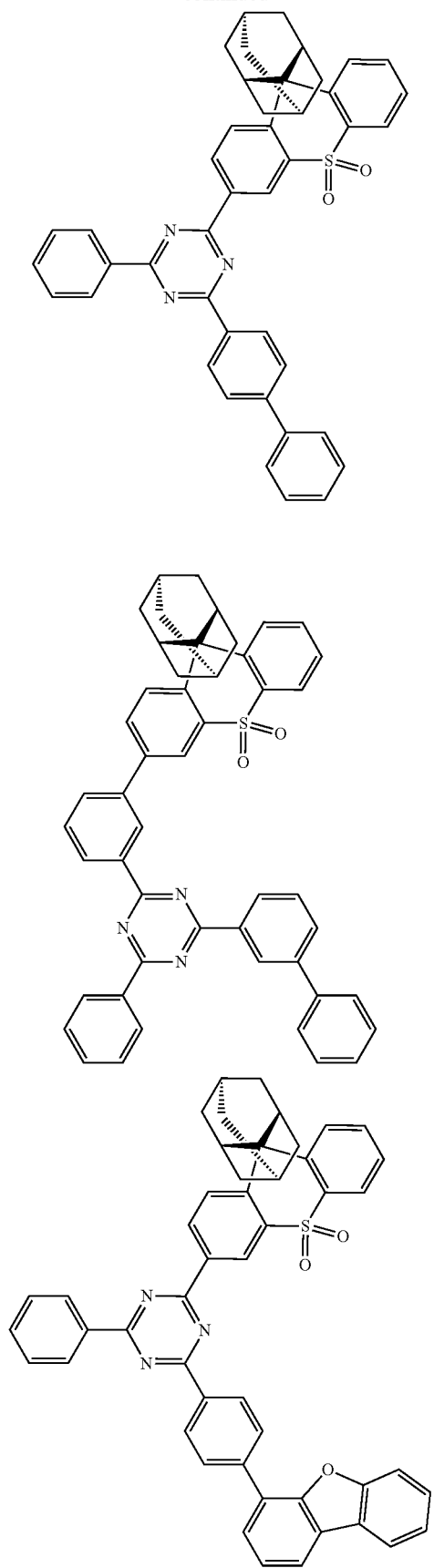
-continued
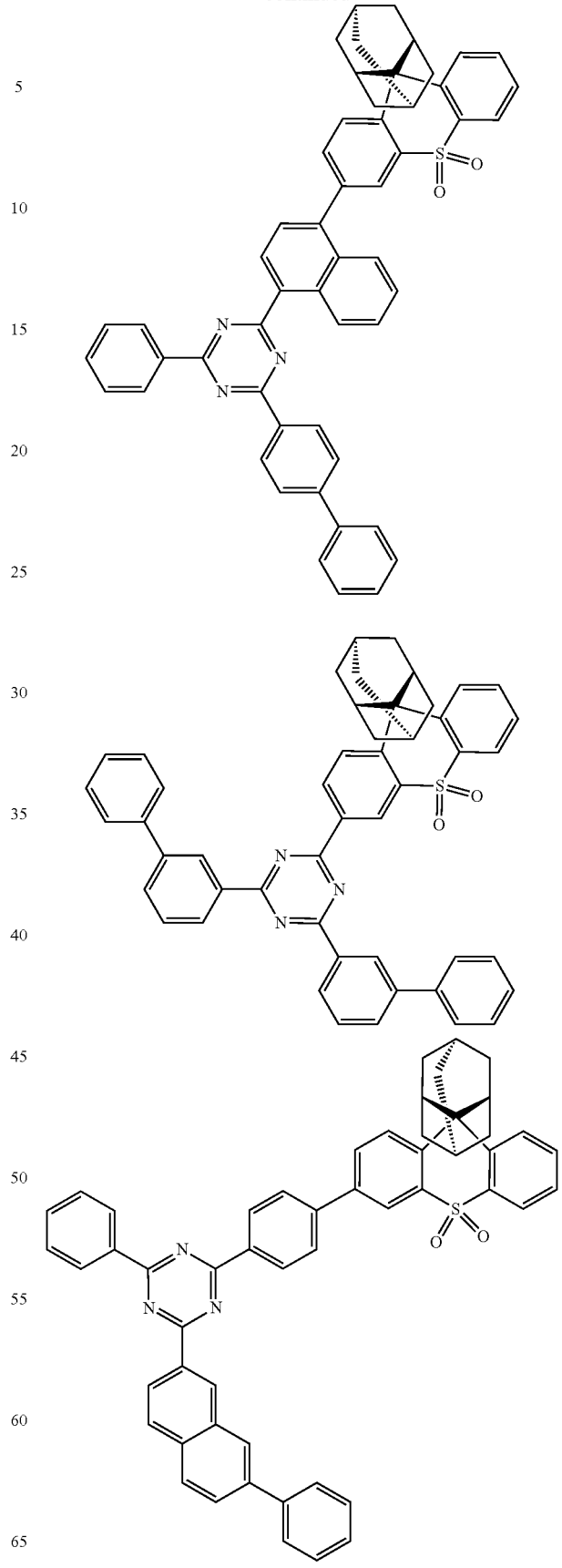

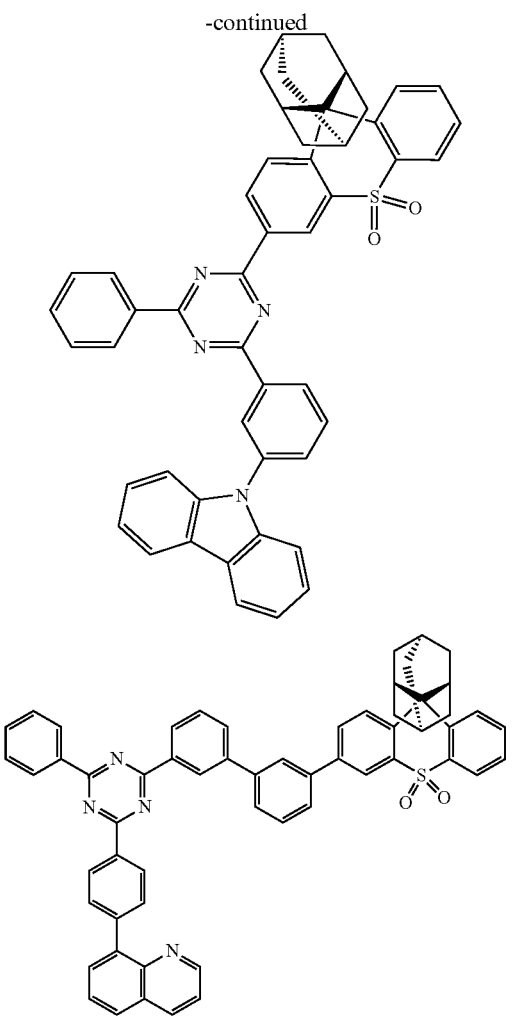

Meanwhile, the compound represented by Chemical Formula 1 can be prepared by the preparation method as shown in the following Reaction Scheme 1.

[Reaction Scheme 1]

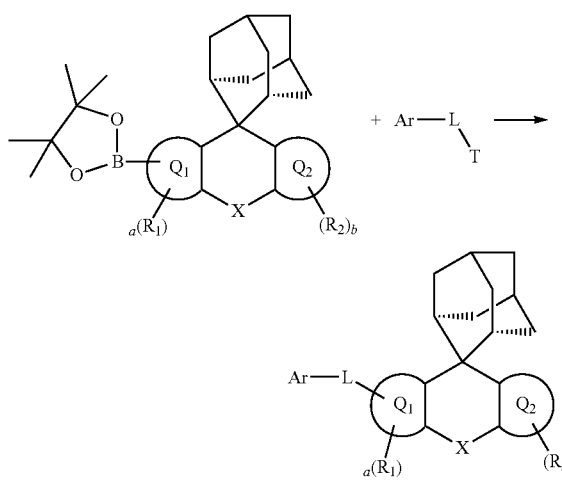

In Reaction Scheme 1, T is halogen, preferably bromo or chloro, and the definitions of other substituents are the same as described above.

Specifically, the compound represented by Chemical Formula 1 is prepared by coupling starting materials through a Suzuki coupling reaction. Such a Suzuki coupling reaction is preferably carried out in the presence of a palladium catalyst and a base, and a reactive group for the Suzuki coupling reaction can be modified as known in the art. The above preparation method may be further embodied in Preparation Examples described hereinafter.

In addition, the present disclosure provides an organic light emitting device comprising the compound represented by Chemical Formula 1. In one example, the present disclosure provides an organic light emitting device comprising: a first electrode; a second electrode that is provided to face the first electrode; and one or more organic material layers that are provided between the first electrode and the second electrode, wherein one or more layers of the organic material layers include the compound represented by Chemical Formula 1.

In general, in the case of adamantane, due to its three-dimensional size and rigidity, it has excellent sublimation properties and chemical structural stability, so it exhibits excellent thermal stability. Consequently, the compound represented by Chemical Formula 1 has excellent sublimation property and chemical structural stability through introduction of the bulky and rigid structure of adamantane, and thus has excellent thermal stability. Therefore, the efficiency and lifetime may be improved when an organic light emitting device including the compound represented by Chemical Formula 1 is produced.

The organic material layer of the organic light emitting device of the present disclosure may have a single-layer structure, or it may have a multilayered structure in which two or more organic material layers are stacked. For example, the organic light emitting device of the present disclosure may have a structure comprising a hole injection layer, a hole transport layer, a light emitting layer, an electron transport layer, an electron injection layer and the like as the organic material layer. However, the structure of the organic light emitting device is not limited thereto, and it may include a smaller number of organic material layers.

Further, the organic material layer may include a hole injection layer, a hole transport layer, a layer for simultaneously performing hole injection and transport, wherein the hole injection layer, the hole transport layer, the layer for simultaneously performing hole injection and transport may include the compound represented by Chemical Formula 1.

Further, the organic material layer may include a light emitting layer, wherein the light emitting layer may include the compound represented by Chemical Formula 1.

Further, the organic material layer may include an electron transport layer, or an electron injection layer, wherein the electron transport layer, or the electron injection layer includes the compound represented by Chemical Formula 1.

Further, the electron transport layer, the electron injection layer, or a layer for simultaneously performing electron transport and electron injection may include the compound represented by Chemical Formula 1.

Further, the organic material layer may include a light emitting layer and an electron transport layer, wherein the electron transport layer may include the compound represented by Chemical Formula 1.

Further, the organic light emitting device according to the present disclosure may be a normal type organic light emitting device in which an anode, one or more organic material layers, and a cathode are sequentially stacked on a substrate. Further, the organic light emitting device according to the present disclosure may be an inverted type organic light emitting device in which a cathode, one or more organic material layers, and an anode are sequentially stacked on a substrate.

FIG. 1 shows an example of an organic light emitting device comprising a substrate 1, an anode 2, a light emitting layer 3, and a cathode 4. In such a structure, the compound represented by Chemical Formula 1 may be included in the light emitting layer.

FIG. 2 shows an example of an organic light emitting device comprising a substrate 1, an anode 2, a hole injection layer 5, a hole transport layer 6, a light emitting layer 7, an electron transport layer 8, and a cathode 4. In such a structure, the compound represented by Chemical Formula 1 may be included in at least one of the hole injection layer, the hole transport layer, the light emitting layer and the electron transport layer.

The organic light emitting device according to the present disclosure may be manufactured by materials and methods known in the art, except that at least one of the organic material layers includes the compound represented by Chemical Formula 1. Further, when the organic light emitting device includes a plurality of organic material layers, the organic material layers may be formed of the same material or different materials.

For example, the organic light emitting device according to the present disclosure can be manufactured by sequentially stacking a first electrode, an organic material layer and a second electrode on a substrate. In this case, the organic light emitting device may be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer and the electron transport layer thereon, and then depositing a material that can be used as the cathode thereon. In addition to such a method, the organic light emitting device may be manufactured by sequentially depositing a cathode material, an organic material layer and an anode material on a substrate.

Further, the compound represented by Chemical Formula 1 may be formed into an organic layer by a solution coating method as well as a vacuum deposition method at the time of manufacturing an organic light emitting device. Herein, the solution coating method means a spin coating, a dip coating, a doctor blading, an inkjet printing, a screen printing, a spray method, a roll coating, or the like, but is not limited thereto.

In addition to such a method, the organic light emitting device may be manufactured by sequentially depositing a cathode material, an organic material layer and an anode material on a substrate (International Publication WO2003/012890). However, the manufacturing method is not limited thereto.

As an example, the first electrode is an anode, and the second electrode is a cathode, or alternatively, the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SnO_2$:Sb, conductive compounds such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection layer is a layer for injecting holes from the electrode, and the hole injection material is preferably a compound which has a capability of transporting the holes, thus has a hole injecting effect in the anode and an excellent hole injecting effect to the light emitting layer or the light emitting material, prevents excitons produced in the light emitting layer from moving to a hole injection layer or the electron injection material, and further is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive polymer, and the like, but are not limited thereto.

The hole transport layer is a layer that receives holes from a hole injection layer and transports the holes to the light emitting layer. The hole transport layer is suitably a material having large mobility to the holes, which may receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The light emitting material is preferably a material which may receive holes and electrons transported from a hole transport layer and an electron transport layer, respectively, and combine the holes and the electrons to emit light in a visible ray region, and has good quantum efficiency to fluorescence or phosphorescence. Specific examples of the light emitting material include an 8-hydroxy-quinoline aluminum complex ($Alq_3$), a carbazole-based compound; a dimerized styryl compound; BAlq; a 10-hydroxybenzoquinoline-metal compound; a benzoxazole, benzthiazole and benzimidazole-based compound; a poly(p-phenylenevinylene)(PPV)-based polymer; a spiro compound; polyfluorene, lubrene, and the like, but are not limited thereto.

The light emitting layer may include a host material and a dopant material. The host material may be a fused aromatic ring derivative, a heterocycle-containing compound or the like. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, and the like, but are not limited thereto.

Examples of the dopant material include an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene and the like, which have an arylamino group. The styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto.

The electron transport layer is a layer which receives electrons from an electron injection layer and transports the electrons to a light emitting layer, and an electron transport material is suitably a material which may receive electrons well from a cathode and transfer the electrons to a light emitting layer, and has a large mobility for electrons. Specific examples of the electron transport material include: an Al complex of 8-hydroxyquinoline; a complex including $Alq_3$; an organic radical compound; a hydroxyflavone-metal complex, and the like, but are not limited thereto. The electron transport layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples of the electron injection layer include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The organic light emitting device according to the present disclosure may be a front side emission type, a back side emission type, or a double side emission type according to the used material.

In addition, the compound represented by Chemical Formula 1 may be included in an organic solar cell or an organic transistor in addition to an organic light emitting device.

The preparation of the compound represented by Chemical Formula 1 and the organic light emitting device containing the same will be described in detail in the following examples. However, these examples are presented for illustrative purposes only, and are not intended to limit the scope of the present disclosure.

Preparation Example

Preparation Example 1: Preparation of Compound 1

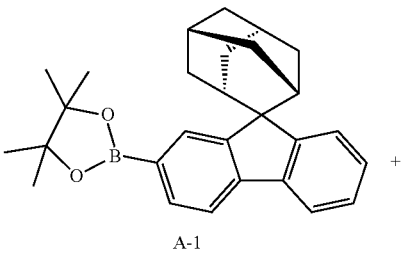

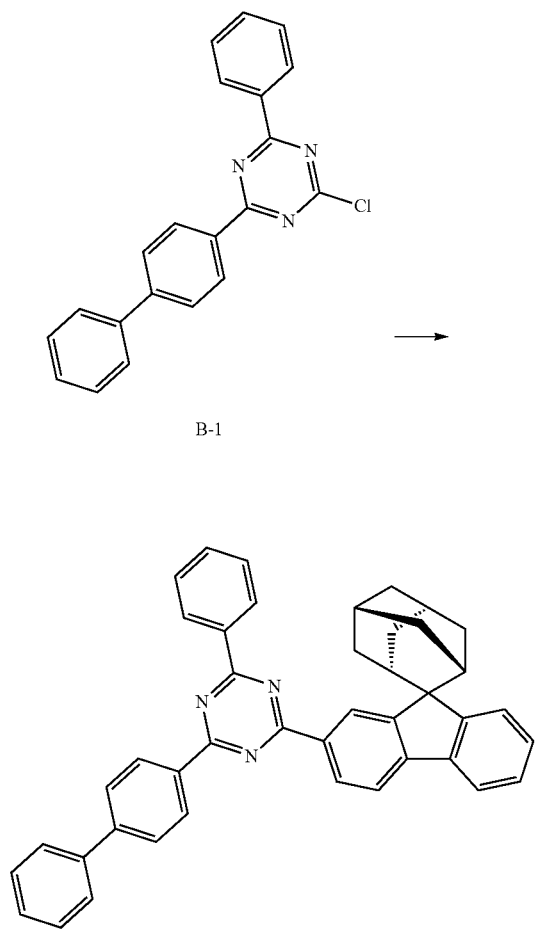

10 g (1 eq.) of Compound A-1 and 8.3 g (1 eq.) of Compound B-1 were added to tetrahydrofuran (150 mL). 2M potassium carbonate aqueous solution (100 mL) and tetrakistriphenyl-phosphinopalladium (0.56 g, 0.02 eq.) were added thereto, and the mixture was stirred and refluxed for 5 hours. After the reaction temperature was lowered to room temperature and the reaction was completed, the potassium carbonate solution was removed to filter the white solid. The filtered solid was washed with tetrahydrofuran and ethyl acetate twice, respectively, to give Compound 1 (11.1 g, yield: 77%).

MS: [M+H]⁺=594

Preparation Example 2: Preparation of Compound 2

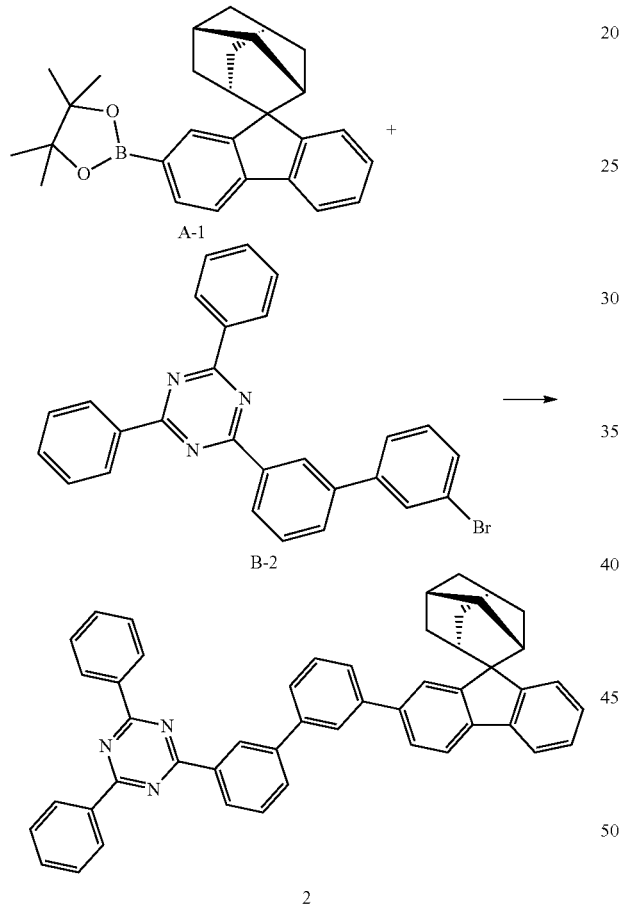

Preparation Example 3: Preparation of Compound 3

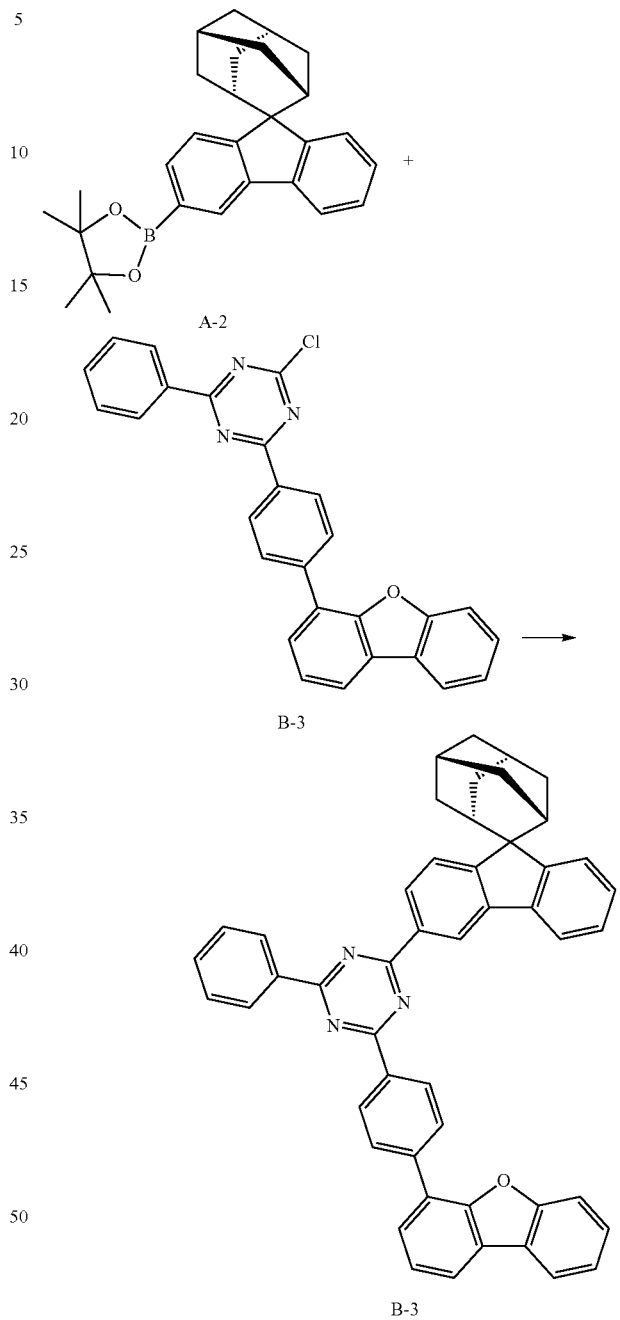

10 g (1 eq.) of Compound A-1 and 11.3 g (1 eq.) of Compound B-2 were added to tetrahydrofuran (150 mL). 2M potassium carbonate aqueous solution (100 mL) and tetrakistriphenyl-phosphinopalladium (0.56 g, 0.02 eq.) were added thereto, and the mixture was stirred and refluxed for 5 hours. After the reaction temperature was lowered to room temperature and the reaction was completed, the potassium carbonate solution was removed to filter the white solid. The filtered solid was washed with tetrahydrofuran and ethyl acetate twice, respectively, to give Compound 2 (13.8 g, yield: 85%).

MS: [M+H]⁺=670

10 g (1 eq.) of Compound A-2 and 10.5 g (1 eq.) of Compound B-3 were added to tetrahydrofuran (150 mL). 2M potassium carbonate aqueous solution (100 mL) and tetrakistriphenyl-phosphinopalladium (0.56 g, 0.02 eq.) were added thereto, and the mixture was stirred and refluxed for 5 hours. After the reaction temperature was lowered to room temperature and the reaction was completed, the potassium carbonate solution was removed to filter the white solid. The filtered solid was washed with tetrahydrofuran and ethyl acetate twice, respectively, to give Compound 3 (11.4 g, yield: 69%).

MS: [M+H]⁺=684

Preparation Example 4: Preparation of Compound 4

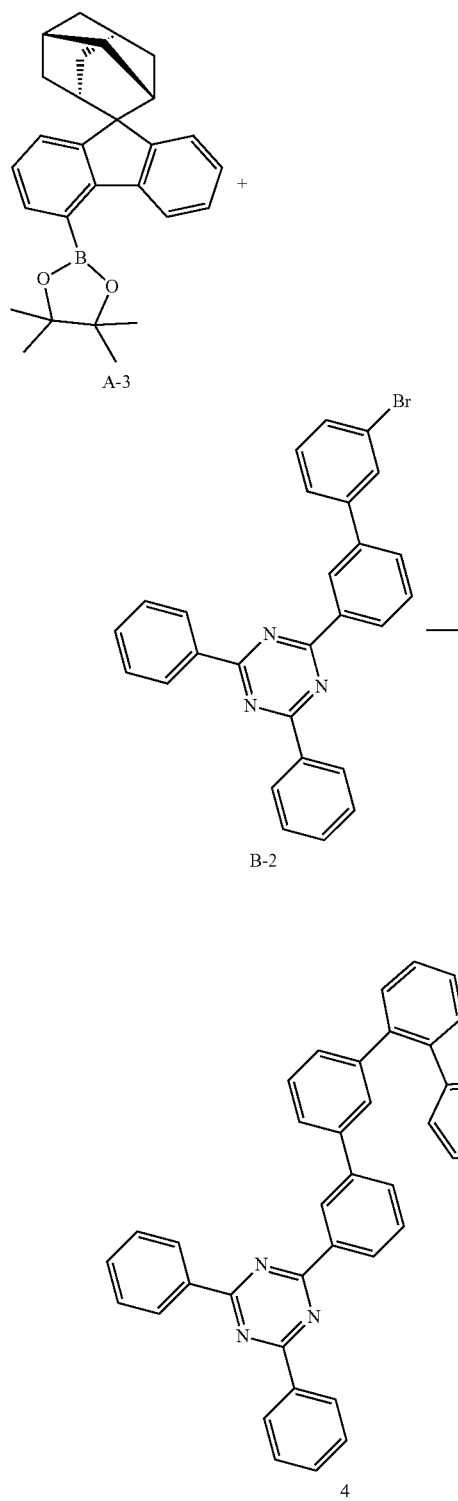

10 g (1 eq.) of Compound A-3 and 11.3 g (1 eq.) of Compound B-2 were added to tetrahydrofuran (150 mL). 2M potassium carbonate aqueous solution (100 mL) and tetrakistriphenyl-phosphinopalladium (0.56 g, 0.02 eq.) were added thereto, and the mixture was stirred and refluxed for 5 hours. After the reaction temperature was lowered to room temperature and the reaction was completed, the potassium carbonate solution was removed to filter the white solid. The filtered solid was washed with tetrahydrofuran and ethyl acetate twice, respectively, to give Compound 4 (10.1 g, yield: 62%).

MS: $[M+H]^+=670$

Preparation Example 5: Preparation of Compound 5

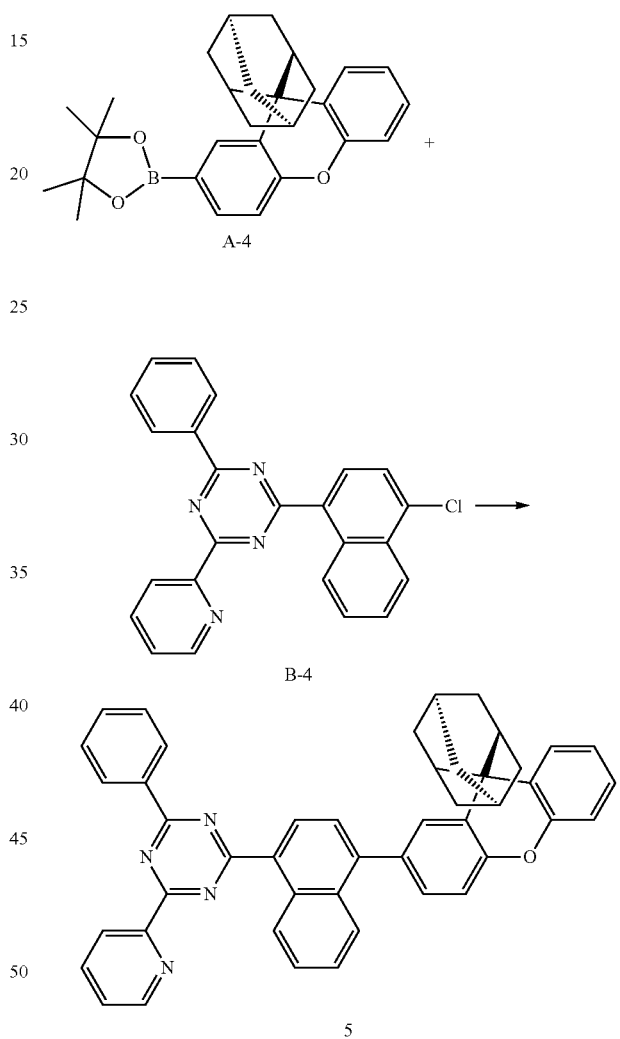

10 g (1 eq.) of Compound A-4 and 9.2 g (1 eq.) of Compound B-4 were added to tetrahydrofuran (150 mL). 2M potassium carbonate aqueous solution (100 mL) and tetrakistriphenyl-phosphinopalladium (0.54 g, 0.02 eq.) were added thereto, and the mixture was stirred and refluxed for 5 hours. After the reaction temperature was lowered to room temperature and the reaction was completed, the potassium carbonate solution was removed to filter the white solid. The filtered solid was washed with tetrahydrofuran and ethyl acetate twice, respectively, to give Compound 5 (11.1 g, yield: 72%).

MS: $[M+H]^+=661$

Preparation Example 6: Preparation of Compound 6

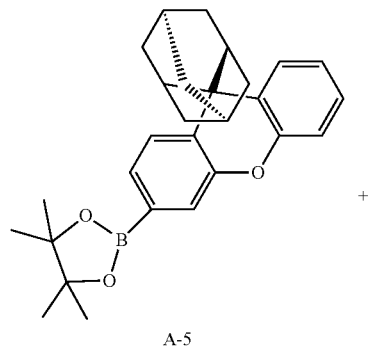

A-5

+

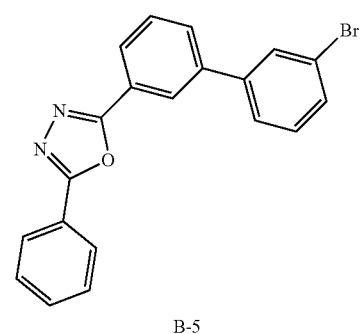

B-5

→

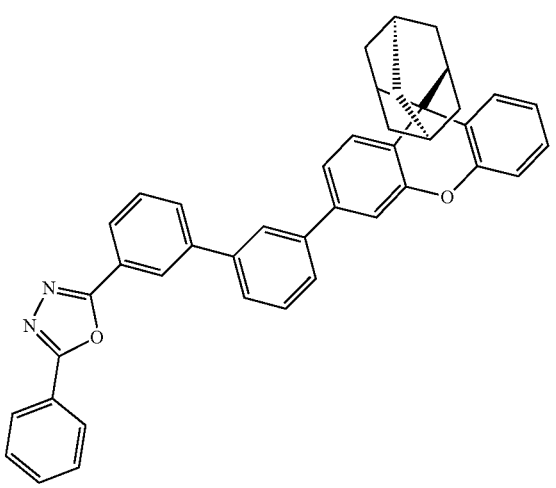

6

10 g (1 eq.) of Compound A-5 and 8.8 g (1 eq.) of Compound B-5 were added to tetrahydrofuran (150 mL). 2M potassium carbonate aqueous solution (100 mL) and tetrakistriphenyl-phosphinopalladium (0.54 g, 0.02 eq.) were added thereto, and the mixture was stirred and refluxed for 5 hours. After the reaction temperature was lowered to room temperature and the reaction was completed, the potassium carbonate solution was removed to filter the white solid. The filtered solid was washed with tetrahydrofuran and ethyl acetate twice, respectively, to give Compound 6 (11.3 g, yield: 81%).

MS: $[M+H]^+$=599

Preparation Example 7: Preparation of Compound 7

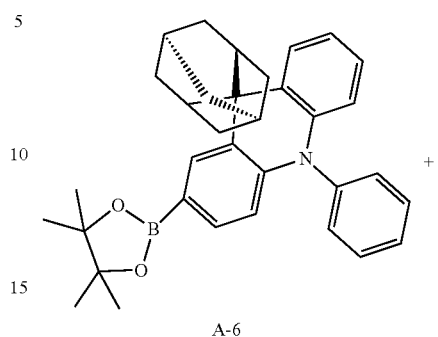

A-6

+

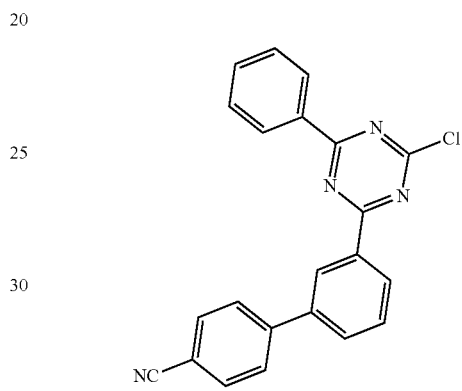

B-6

→

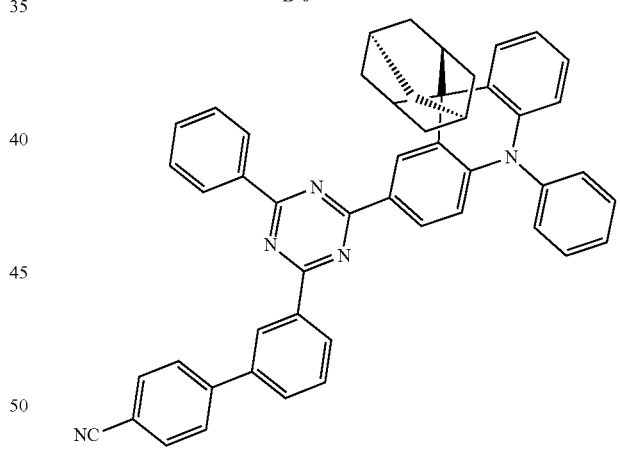

7

10 g (1 eq.) of Compound A-6 and 7.3 g (1 eq.) of Compound B-6 were added to tetrahydrofuran (150 mL). 2M potassium carbonate aqueous solution (100 mL) and tetrakistriphenyl-phosphinopalladium (0.46 g, 0.02 eq.) were added thereto, and the mixture was stirred and refluxed for 5 hours. After the reaction temperature was lowered to room temperature and the reaction was completed, the potassium carbonate solution was removed to filter the white solid. The filtered solid was washed with tetrahydrofuran and ethyl acetate twice, respectively, to give Compound 7 (12.0 g, yield: 85%).

MS: $[M+H]^+$=710

Preparation Example 8: Preparation of Compound 8

Preparation Example 9: Preparation of Compound 9

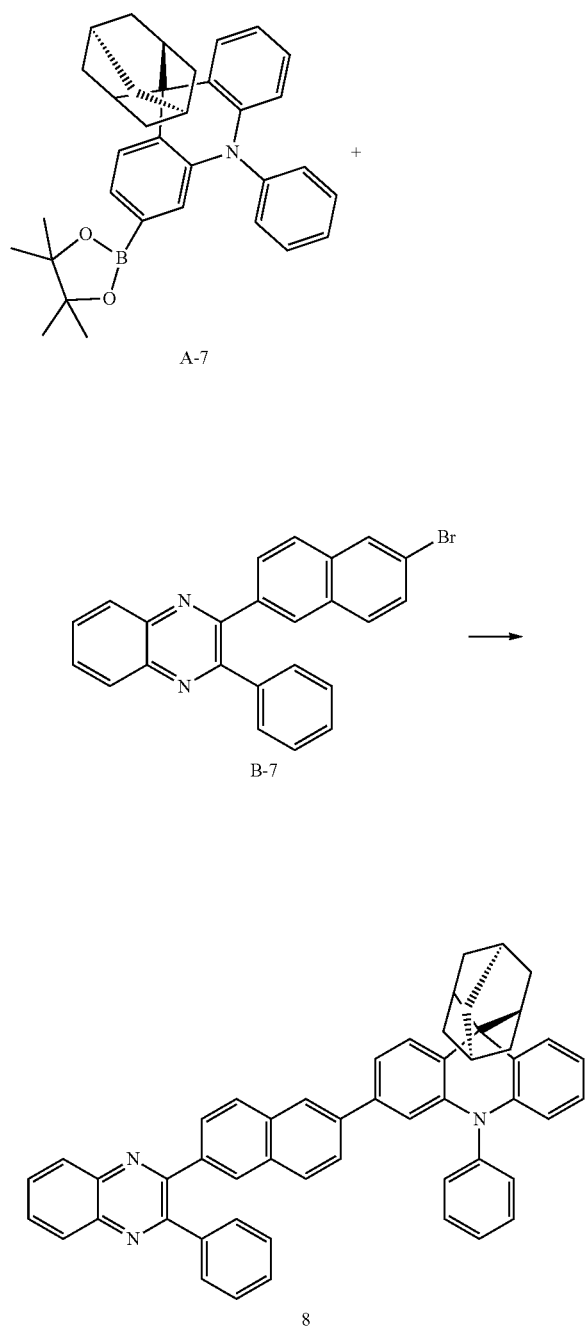

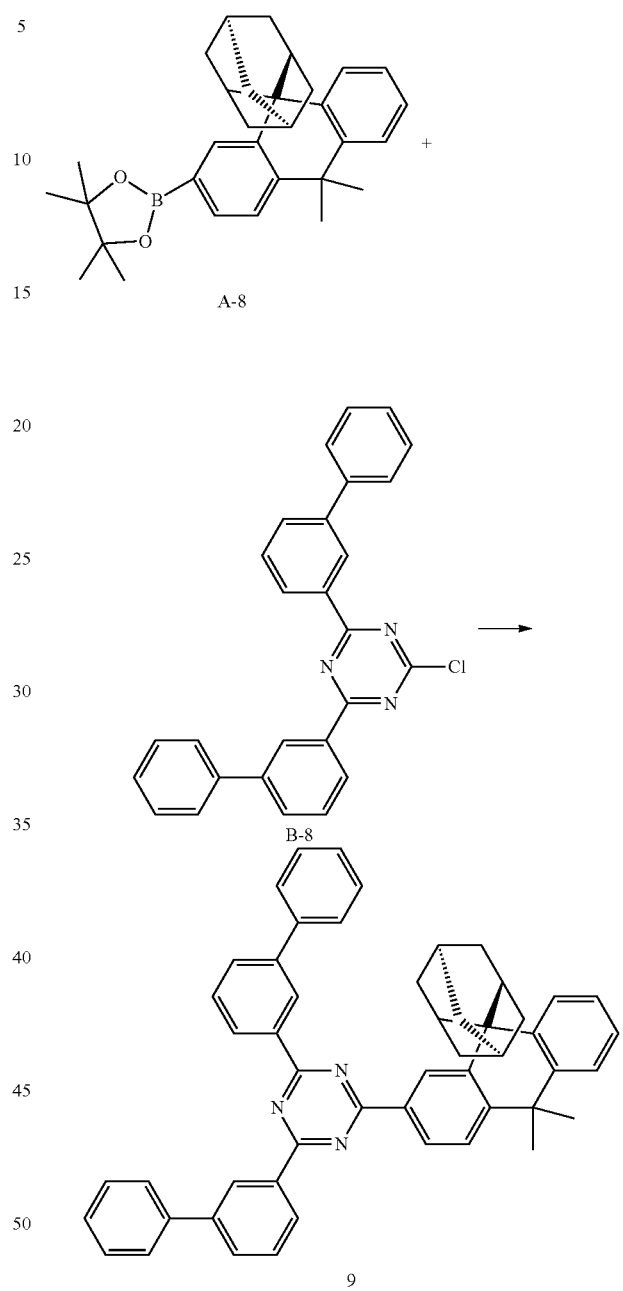

10 g (1 eq.) of Compound A-7 and 8.2 g (1 eq.) of Compound B-7 were added to tetrahydrofuran (150 mL). 2M potassium carbonate aqueous solution (100 mL) and tetrakistriphenyl-phosphinopalladium (0.46 g, 0.02 eq.) were added thereto, and the mixture was stirred and refluxed for 5 hours. After the reaction temperature was lowered to room temperature and the reaction was completed, the potassium carbonate solution was removed to filter the white solid. The filtered solid was washed with tetrahydrofuran and ethyl acetate twice, respectively, to give Compound 8 (11.4 g, yield: 73%).

MS: [M+H]$^+$=708

10 g (1 eq.) of Compound A-8 and 9.2 g (1 eq.) of Compound B-8 were added to tetrahydrofuran (150 mL). 2M potassium carbonate aqueous solution (100 mL) and tetrakistriphenyl-phosphinopalladium (0.51 g, 0.02 eq.) were added thereto, and the mixture was stirred and refluxed for 5 hours. After the reaction temperature was lowered to room temperature and the reaction was completed, the potassium carbonate solution was removed to filter the white solid. The filtered solid was washed with tetrahydrofuran and ethyl acetate twice, respectively, to give Compound 9 (10.5 g, yield: 67%).

MS: [M+H]$^+$=712

Preparation Example 10: Preparation of Compound 10

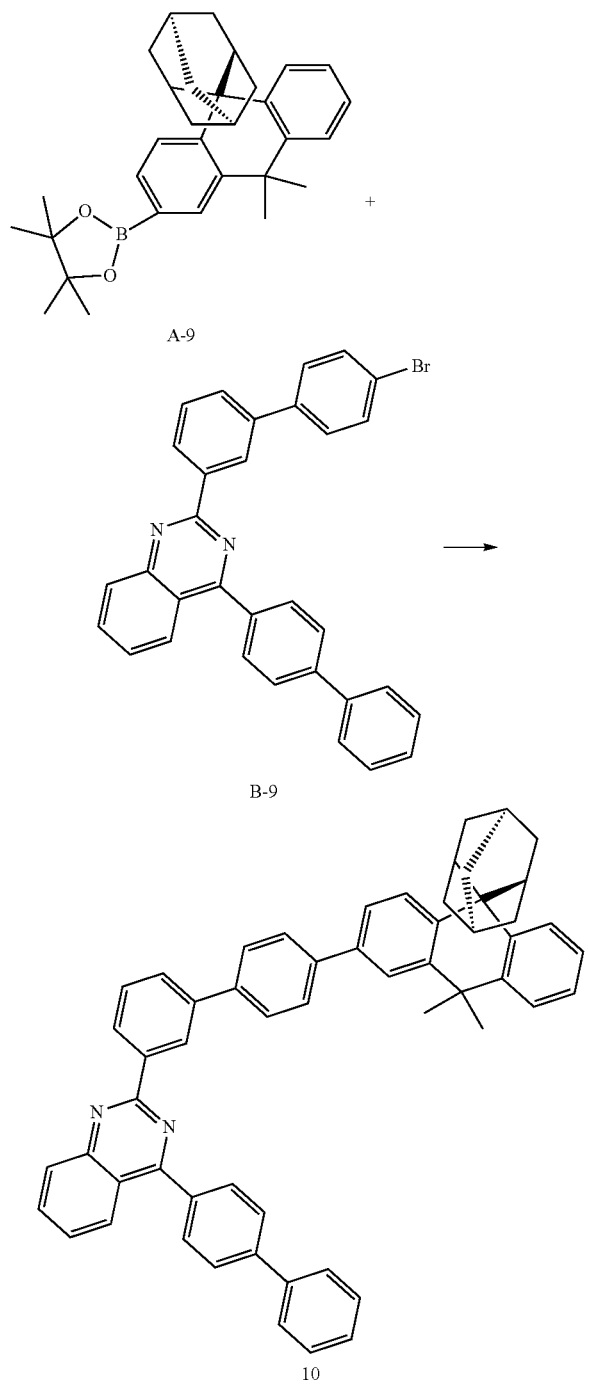

10 g (1 eq.) of Compound A-9 and 11.3 g (1 eq.) of Compound B-9 were added to tetrahydrofuran (150 mL). 2M potassium carbonate aqueous solution (100 mL) and tetrakistriphenyl-phosphinopalladium (0.51 g, 0.02 eq.) were added thereto, and the mixture was stirred and refluxed for 5 hours. After the reaction temperature was lowered to room temperature and the reaction was completed, the potassium carbonate solution was removed to filter the white solid. The filtered solid was washed with tetrahydrofuran and ethyl acetate twice, respectively, to give Compound 10 (12.4 g, yield: 74%).
MS: [M+H]$^+$=762

Preparation Example 11: Preparation of Compound 11

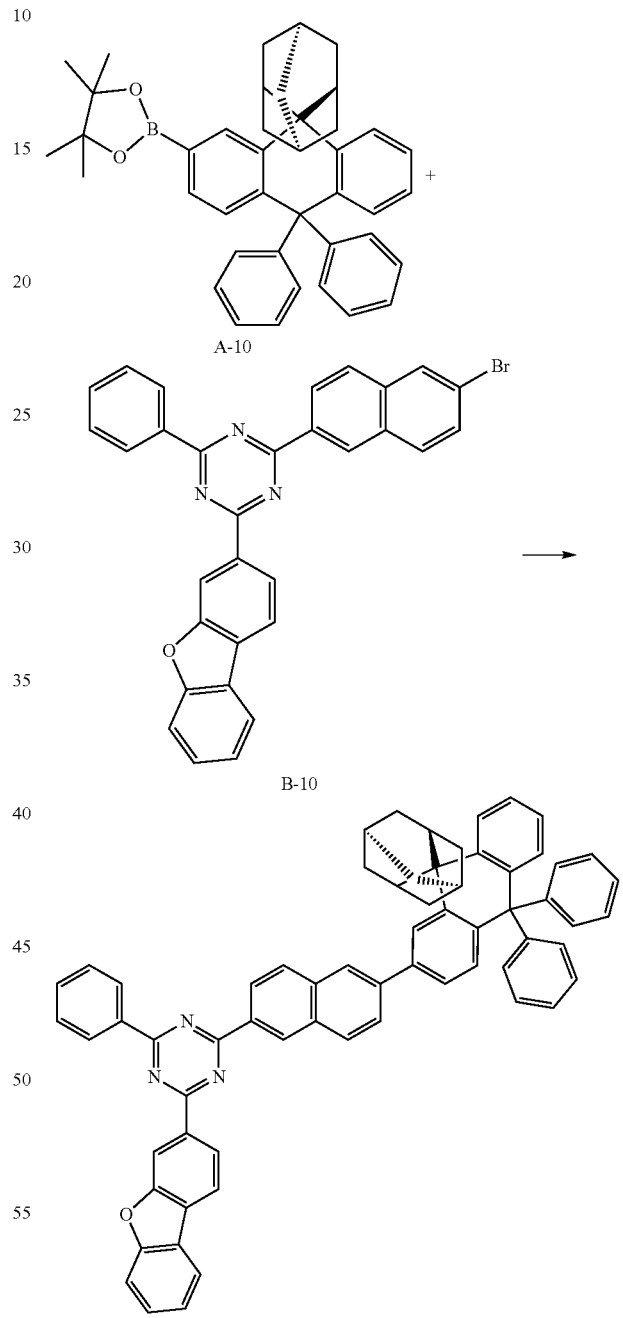

10 g (1 eq.) of Compound A-10 and 9.1 g (1 eq.) of Compound B-10 were added to tetrahydrofuran (150 mL). 2M potassium carbonate aqueous solution (100 mL) and tetrakistriphenyl-phosphinopalladium (0.40 g, 0.02 eq.) were added thereto, and the mixture was stirred and refluxed for 5 hours. After the reaction temperature was lowered to room temperature and the reaction was completed, the potassium carbonate solution was removed to filter the white solid. The filtered solid was washed with tetrahydrofuran and ethyl acetate twice, respectively, to give Compound 11 (10.9 g, yield: 70%).

MS: $[M+H]^+=901$

Preparation Example 12: Preparation of Compound 12

10 g (1 eq.) of Compound A-11 and 9.4 g (1 eq.) of Compound B-11 were added to tetrahydrofuran (150 mL). 2M potassium carbonate aqueous solution (100 mL) and tetrakistriphenyl-phosphinopalladium (0.40 g, 0.02 eq.) were added thereto, and the mixture was stirred and refluxed for 5 hours. After the reaction temperature was lowered to room temperature and the reaction was completed, the potassium carbonate solution was removed to filter the white solid. The filtered solid was washed with tetrahydrofuran and ethyl acetate twice, respectively, to give Compound 12 (13.1 g, yield: 79%).

MS: $[M+H]^+=961$

Preparation Example 13: Preparation of Compound 13

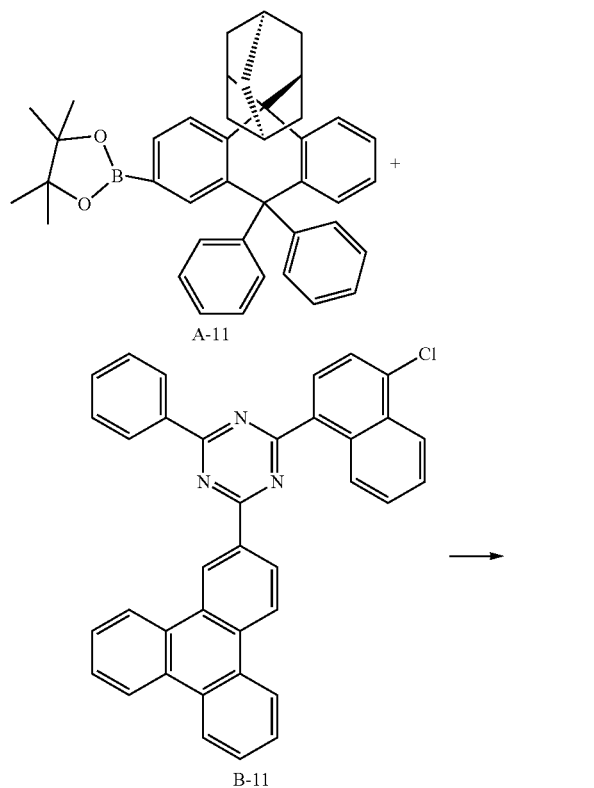

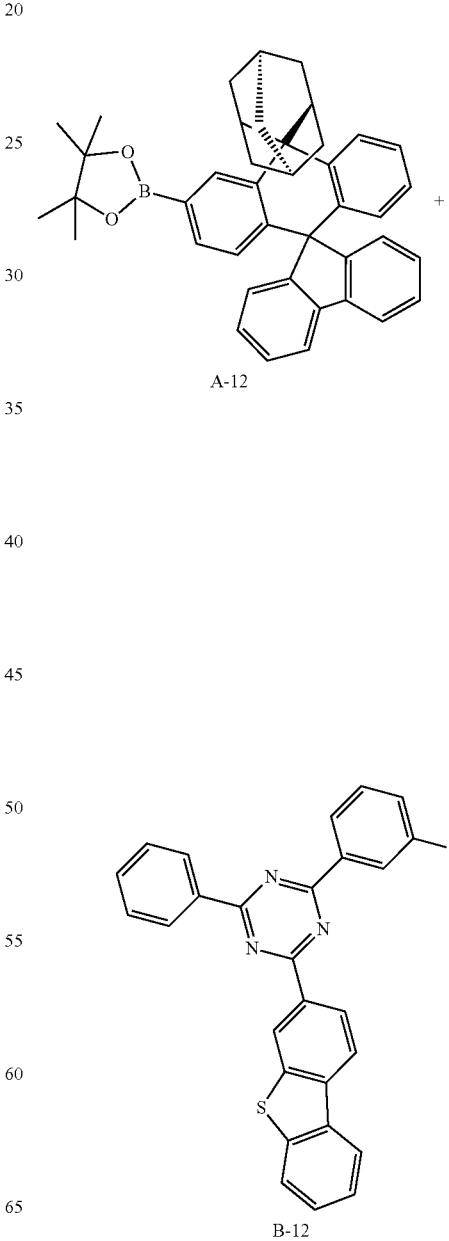

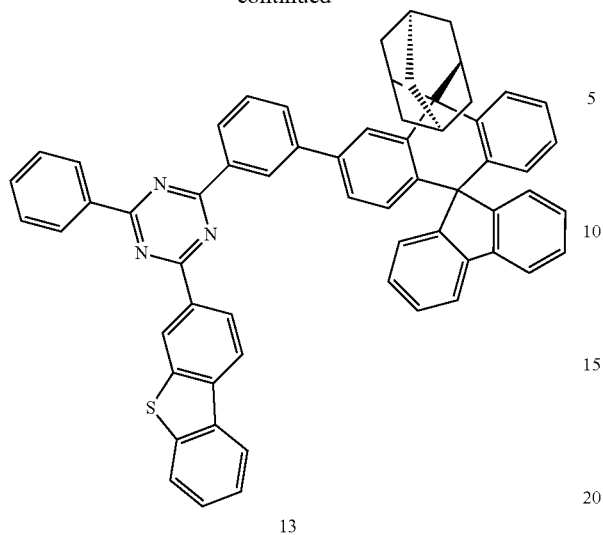

13

10 g (1 eq.) of Compound A-12 and 7.8 g (1 eq.) of Compound B-12 were added to tetrahydrofuran (150 mL). 2M potassium carbonate aqueous solution (100 mL) and tetrakistriphenyl-phosphinopalladium (0.40 g, 0.02 eq.) were added thereto, and the mixture was stirred and refluxed for 5 hours. After the reaction temperature was lowered to room temperature and the reaction was completed, the potassium carbonate solution was removed to filter the white solid. The filtered solid was washed with tetrahydrofuran and ethyl acetate twice, respectively, to give Compound 13 (10.6 g, yield: 71%).

MS: [M+H]$^+$=865

Preparation Example 14: Preparation of Compound 14

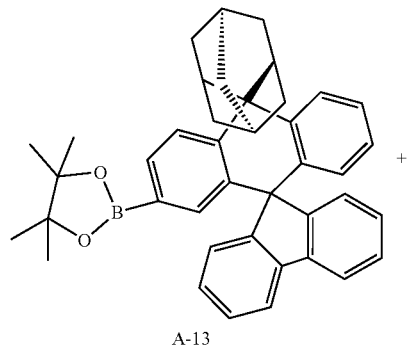

A-13

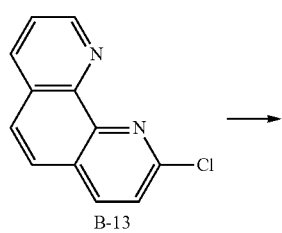

B-13

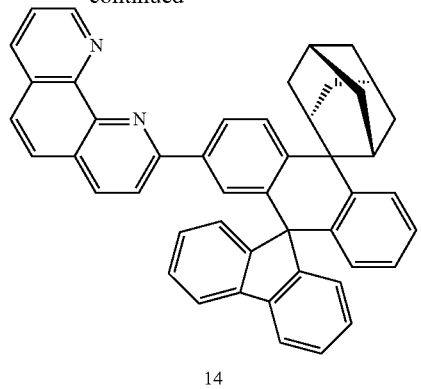

14

10 g (1 eq.) of Compound A-13 and 3.7 g (1 eq.) of Compound B-13 were added to tetrahydrofuran (150 mL). 2M potassium carbonate aqueous solution (100 mL) and tetrakistriphenyl-phosphinopalladium (0.40 g, 0.02 eq.) were added thereto, and the mixture was stirred and refluxed for 5 hours. After the reaction temperature was lowered to room temperature and the reaction was completed, the potassium carbonate solution was removed to filter the white solid. The filtered solid was washed with tetrahydrofuran and ethyl acetate twice, respectively, to give Compound 14 (9.2 g, yield: 84%).

MS: [M+H]$^+$=629

Preparation Example 15: Preparation of Compound 15

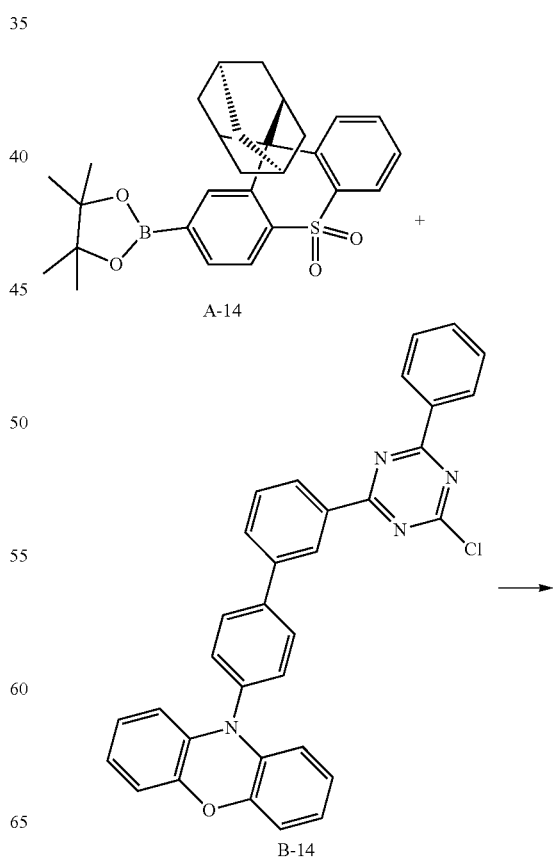

A-14

B-14

-continued

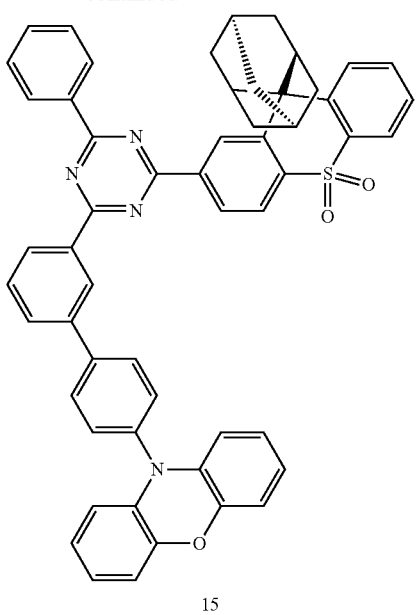

15

10 g (1 eq.) of Compound A-14 and 11.0 g (1 eq.) of Compound B-14 were added to tetrahydrofuran (150 mL). 2M potassium carbonate aqueous solution (100 mL) and tetrakistriphenyl-phosphinopalladium (0.49 g, 0.02 eq.) were added thereto, and the mixture was stirred and refluxed for 5 hours. After the reaction temperature was lowered to room temperature and the reaction was completed, the potassium carbonate solution was removed to filter the white solid. The filtered solid was washed with tetrahydrofuran and ethyl acetate twice, respectively, to give Compound 15 (14.3 g, yield: 81%).

MS: [M+H]$^+$=840

Preparation Example 16: Preparation of Compound 16

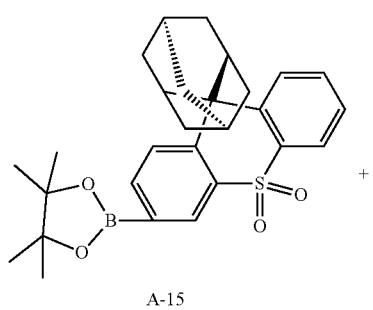

A-15

+

-continued

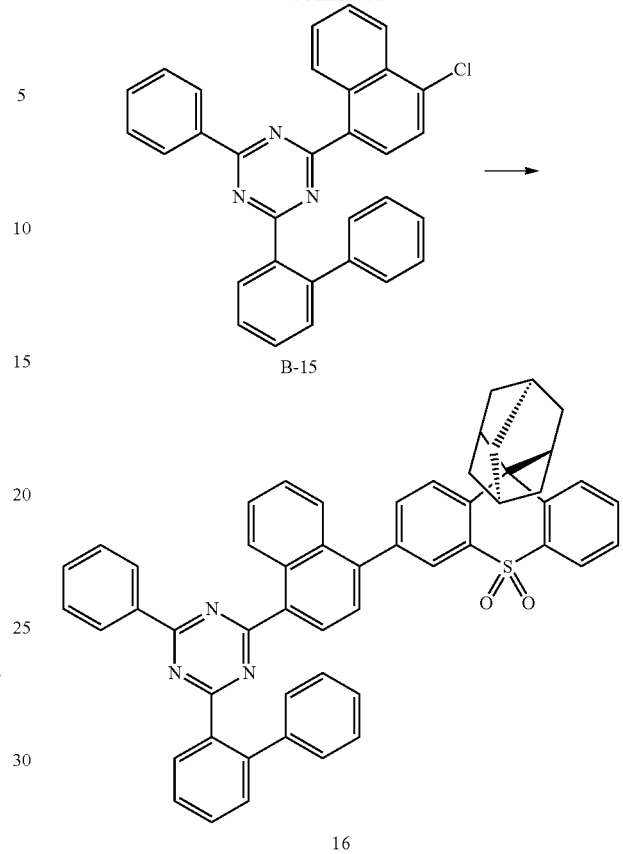

10 g (1 eq.) of Compound A-15 and 9.9 g (1 eq.) of Compound B-15 were added to tetrahydrofuran (150 mL). 2M potassium carbonate aqueous solution (100 mL) and tetrakistriphenyl-phosphinopalladium (0.49 g, 0.02 eq.) were added thereto, and the mixture was stirred and refluxed for 5 hours. After the reaction temperature was lowered to room temperature and the reaction was completed, the potassium carbonate solution was removed to filter the white solid. The filtered solid was washed with tetrahydrofuran and ethyl acetate twice, respectively, to give Compound 16 (13.0 g, yield: 79%).

MS: [M+H]$^+$=785

Experimental Example

Example 1

A glass substrate on which ITO (indium tin oxide) was coated as a thin film to a thickness of 1,000 Å was put into distilled water in which a detergent was dissolved, and ultrasonically cleaned. At this time, a product manufactured by Fischer Co. was used as the detergent, and as the distilled water, distilled water filtered twice using a filter manufactured by Millipore Co. was used. After the ITO was cleaned for 30 minutes, ultrasonic cleaning was repeated twice using distilled water for 10 minutes. After the cleaning with distilled water was completed, the substrate was ultrasonically cleaned with solvents of isopropyl alcohol, acetone, and methanol, dried, and then transferred to a plasma cleaner. In addition, the substrate was cleaned for 5 minutes using oxygen plasma and then transferred to a vacuum depositor.

On the ITO transparent electrode thus prepared, the following compound [HI-A] was thermally vacuum-deposited to a thickness of 600 Å to form a hole injection layer. Hexanitrile hexaazatriphenylene (HAT, 50 Å) the following compound [HT-A] (600 Å) were sequentially vacuum-deposited to form a hole transport layer.

Then, the following compounds [BH] and [BD] were vacuum-deposited at a ratio of 25:1 on the hole transport layer to a thickness of 200 Å to form a light emitting layer.

Compound 1 prepared in the previous Preparation Example 1 and the following compound [LiQ] (lithiumquinolate) were vacuum-deposited at a ratio of 1:1 on the light emitting layer to form an electron injection and transport layer with a thickness of 150 Å. Lithium fluoride (LiF) and aluminum were sequentially deposited to have a thickness of 10 Å and 1,000 Å, respectively, on the electron injection and transport layer, thereby forming a cathode.

In the above-mentioned process, the vapor deposition rate of the organic material was maintained at 0.4 to 0.9 Å/sec, the deposition rates of lithium fluoride and aluminum of the cathode were maintained at 0.3 Å/sec and at 2 Å/sec, respectively, and the degree of vacuum during the deposition was maintained at $1 \times 10^{-7}$ to $5 \times 10^{-8}$ torr, thereby manufacturing an organic light emitting device.

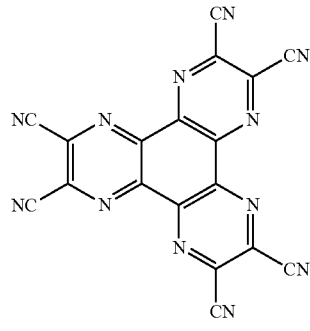

[HAT]

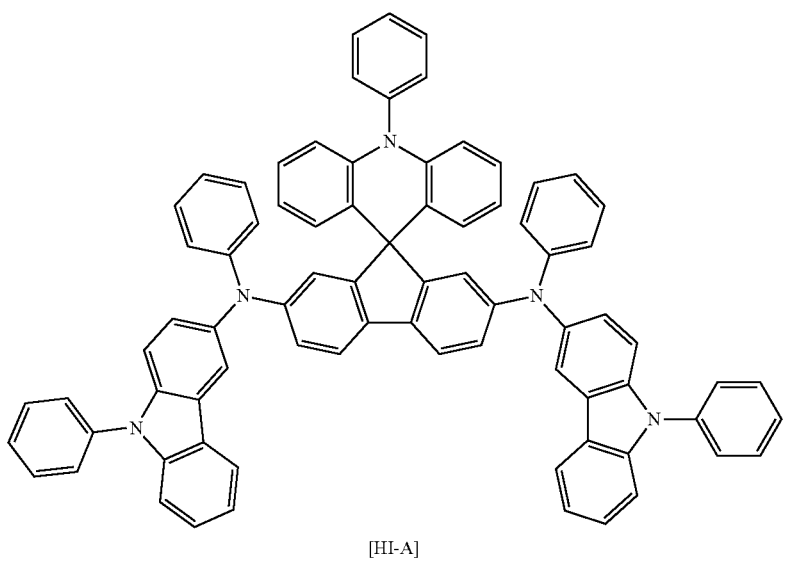

[HI-A]

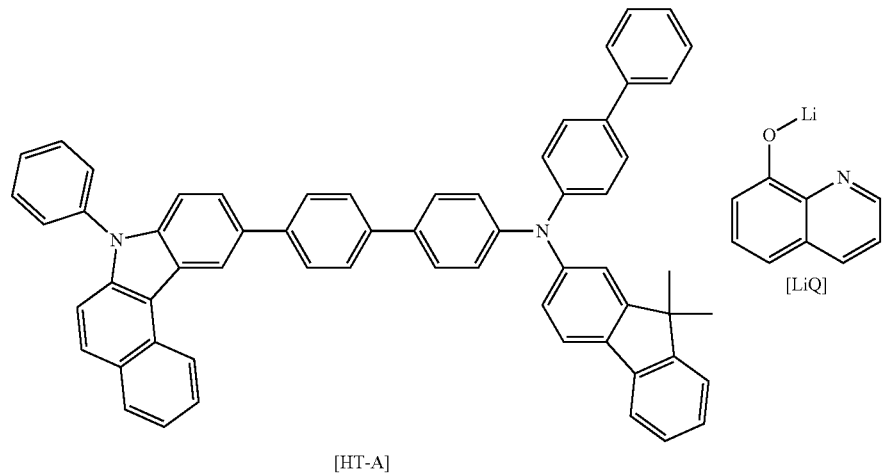

[HT-A]

[LiQ]

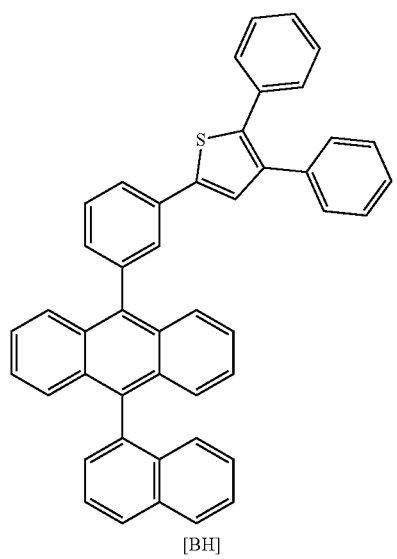

[BH]

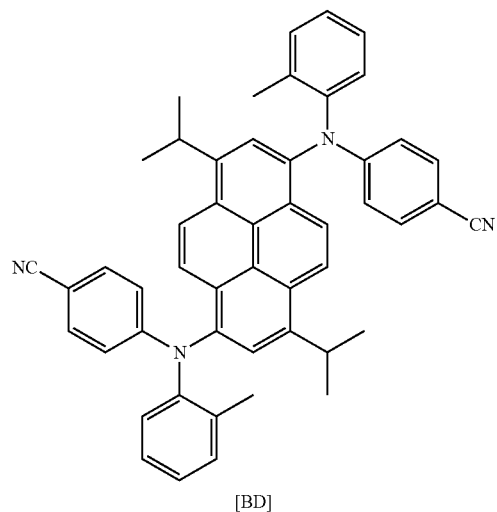

[BD]

Experimental Examples 2 to 16

An organic light emitting device was manufactured in the same manner as in Experimental Example 1, except that the compounds shown in Table 1 below were used instead of Compound 1 in Experimental Example 1.

Comparative Examples 1 to 6

An organic light emitting device was manufactured in the same manner as in Experimental Example 1, except that the compounds shown in Table 1 below were used instead of Compound 1 in Experimental Example 1. The compounds of ET-01 to ET-06 shown in Table 1 are as follows.

-continued

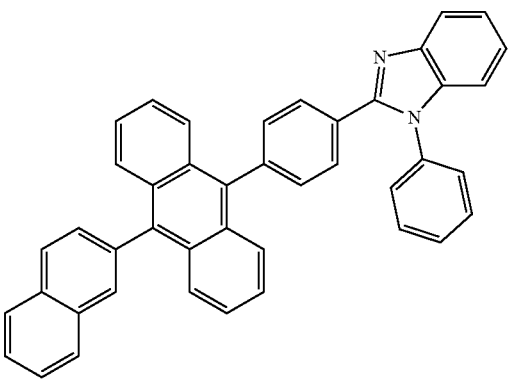

[ET-02]

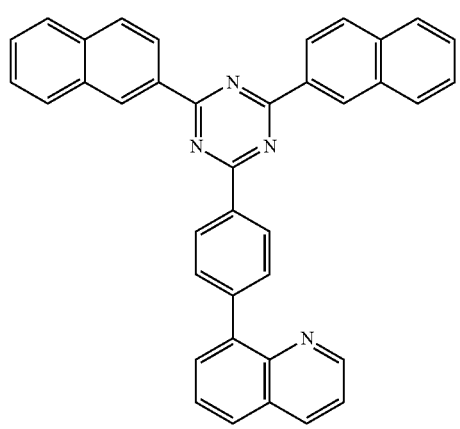

[ET-01]

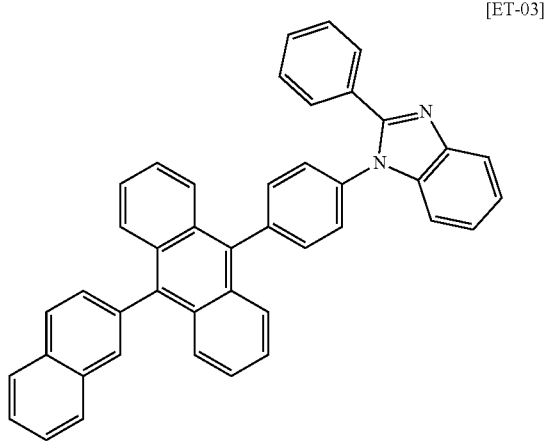

[ET-03]

-continued

[ET-04]

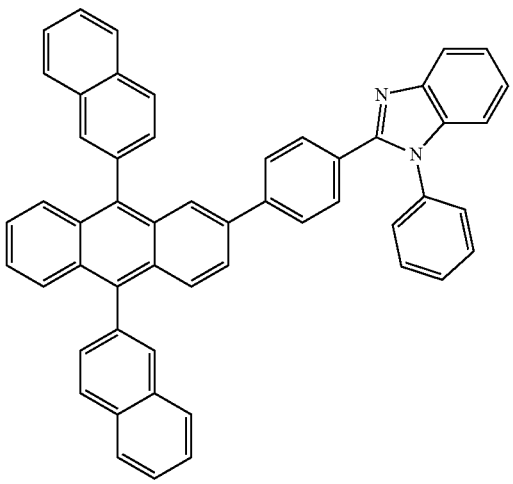

[ET-05]

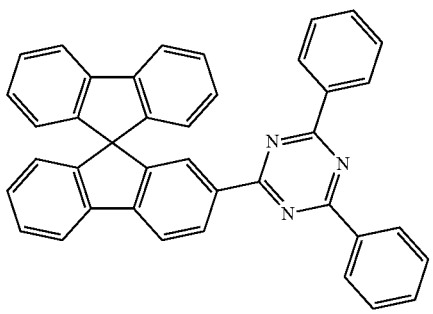

[ET-06]

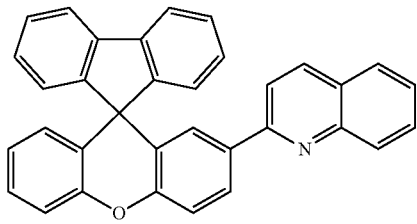

For the organic light emitting devices manufactured using the respective compounds as the hole transport layer in the Experimental Examples and Comparative Examples, the driving voltage and emission efficiency were measure at a current density of 10 mA/cm², and the time ($LT_{98}$) required for the luminance to be reduced to 98% of the initial luminance was measured at a current density of 20 mA/cm², and the results are shown in Table 1 below.

TABLE 1

| Category | Electron transport layer | Voltage (V) | Current efficiency (cd/A) | $LT_{98}$(hr) at 20 mA/cm² |
| --- | --- | --- | --- | --- |
| Experimental Example 1 | Compound 1 | 3.82 | 5.40 | 68 |
| Experimental Example 2 | Compound 2 | 3.80 | 5.42 | 62 |
| Experimental Example 3 | Compound 3 | 3.77 | 5.48 | 59 |
| Experimental Example 4 | Compound 4 | 3.75 | 5.55 | 65 |
| Experimental Example 5 | Compound 5 | 3.68 | 5.52 | 63 |
| Experimental Example 6 | Compound 6 | 3.71 | 5.49 | 59 |
| Experimental Example 7 | Compound 7 | 3.64 | 5.62 | 67 |
| Experimental Example 8 | Compound 8 | 3.82 | 5.60 | 70 |
| Experimental Example 9 | Compound 9 | 3.66 | 5.48 | 71 |
| Experimental Example 10 | Compound 10 | 3.59 | 5.43 | 66 |
| Experimental Example 11 | Compound 11 | 3.61 | 5.60 | 65 |

TABLE 1-continued

| Category | Electron transport layer | Voltage (V) | Current efficiency (cd/A) | $LT_{98}$(hr) at 20 mA/cm² |
| --- | --- | --- | --- | --- |
| Experimental Example 12 | Compound 12 | 3.37 | 5.45 | 77 |
| Experimental Example 13 | Compound 13 | 3.77 | 5.59 | 78 |
| Experimental Example 14 | Compound 14 | 3.58 | 5.48 | 81 |
| Experimental Example 15 | Compound 15 | 3.64 | 5.44 | 76 |
| Experimental Example 16 | Compound 16 | 3.70 | 5.63 | 65 |
| Comparative Example 1 | ET-01 | 4.60 | 4.51 | 30 |
| Comparative Example 2 | ET-02 | 4.62 | 4.44 | 25 |
| Comparative Example 3 | ET-03 | 4.55 | 4.49 | 26 |
| Comparative Example 4 | ET-04 | 4.68 | 4.43 | 21 |
| Comparative Example 5 | ET-05 | 4.71 | 4.55 | 22 |
| Comparative Example 6 | ET-06 | 4.59 | 4.37 | 19 |

As shown in Table 1, it was confirmed that when the compound of the present disclosure was used as a hole transport layer material, it exhibited excellent efficiency and lifetime compared to Comparative Examples. This result is considered to be due to increased chemical structural stability of the compound represented by Chemical Formula 1 by introducing the adamantane structure in the core.

DESCRIPTION OF REFERENCE NUMBERS

| 1: substrate | 2: anode |
| --- | --- |
| 3: light emitting layer | 4: cathode |
| 5: hole injection layer | 6: hole transport layer |
| 7: light emitting layer | 8: electron transport layer |

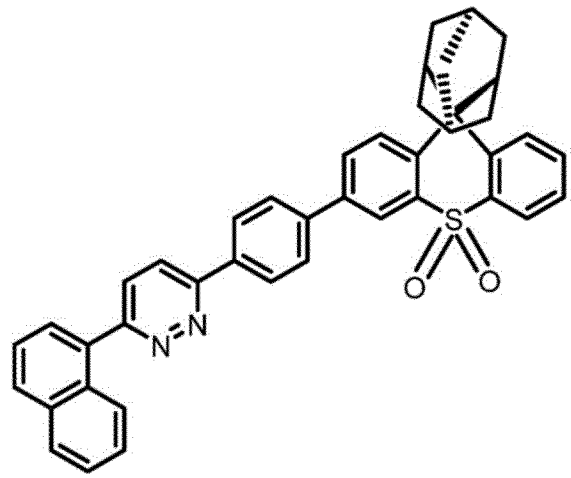

What is claimed is:

1. A compound represented by Chemical Formula 1:

[Chemical Formula 1]

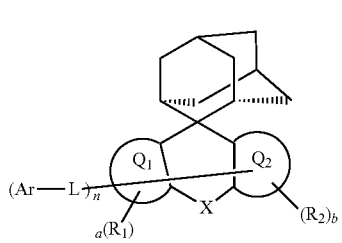

in Chemical Formula 1,
$Q_1$ and $Q_2$ are each independently a $C_{6-30}$ aromatic ring,
n is an integer of 1 to 3,
a and b are each independently an integer of 0 to 3,
X is a single bond; $CR_3R_4$; $SiR_5R_6$; $NR_7$; O; S; $SO_2$; or a substituent represented by Chemical Formula 2,

[Chemical Formula 2]

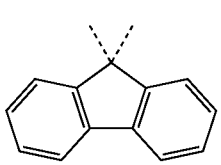

$R_1$ to $R_7$ are each independently hydrogen; deuterium; a substituted or unsubstituted $C_{1-60}$ alkyl; a substituted or unsubstituted $C_{1-60}$ alkoxy; a substituted or unsubstituted $C_{6-60}$ aryl; or a substituted or unsubstituted $C_{5-60}$ heteroaryl containing at least one heteroatom selected from the group consisting of N, O and S, or adjacent groups of $R_1$ to $R_7$ are bonded to each other to form a ring, L is a single bond; a substituted or unsubstituted $C_{6-60}$ arylene; or a substituted or unsubstituted $C_{2-60}$ heteroarylene containing at least one heteroatom selected from the group consisting of N, O and S, and Ar is an unsubstituted $C_{6-60}$ aryl; a $C_{6-60}$ aryl substituted with one or more substituents selected from the group consisting of deuterium, a cyano group, a nitro group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a heterocyclic group containing at least one of N, O and S atoms, or with a substituent in which two or more substituents of the above group of substituents of the $C_{6-60}$ aryl are connected to each other; a substituted or unsubstituted $C_{2-60}$ heteroaryl containing at least one heteroatom selected from the group consisting of N, O and S; or a di($C_{6-60}$ aryl) phosphine oxide group.

2. The compound of claim 1, wherein $Q_1$ and $Q_2$ are each independently a benzene or naphthalene ring.

3. The compound of claim 1, wherein X is a single bond; $C(CH_3)_2$; $C(phenyl)_2$; N(phenyl); O; S; $SO_2$; or a substituent represented by Chemical Formula 2:

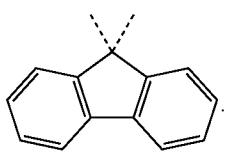

[Chemical Formula 2]

4. The compound of claim 1, wherein n is 1.
5. The compound of claim 1, wherein both a and b are 0.
6. The compound of claim 1, wherein L is a single bond; phenylene;
biphenyldiyl; naphthalenediyl; furandiyl; thiophenediyl; or pyridindiyl.

7. A compound represented by Chemical Formula 1:

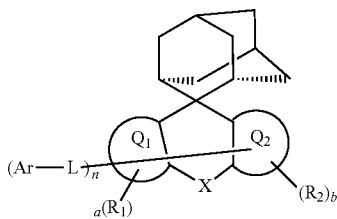

[Chemical Formula 1]

in Chemical Formula 1,
$Q_1$ and $Q_2$ are each independently a $C_{6-30}$ aromatic ring,
n is an integer of 1 to 3,
a and b are each independently an integer of 0 to 3,
X is a single bond; $CR_3R_4$; $SiR_5R_6$; $NR_7$; O; S; $SO_2$; or a substituent represented by Chemical Formula 2,

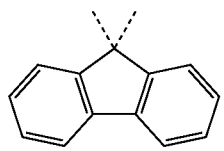

[Chemical Formula 2]

$R_1$ to $R_7$ are each independently hydrogen; deuterium; a substituted or unsubstituted $C_{1-60}$ alkyl; a substituted or unsubstituted $C_{1-60}$ alkoxy; a substituted or unsubstituted $C_{6-60}$ aryl; or a substituted or unsubstituted $C_{5-60}$ heteroaryl containing at least one heteroatom selected from the group consisting of N, O and S, or adjacent groups of $R_1$ to $R_7$ are bonded to each other to form a ring, L is a single bond; a substituted or unsubstituted $C_{6-60}$ arylene; or a substituted or unsubstituted $C_{2-60}$ heteroarylene containing at least one heteroatom selected from the group consisting of N, O and S, and Ar is a phenyl substituted with cyano; —P(O)(phenyl)$_2$; or any one selected from the group consisting of the following:

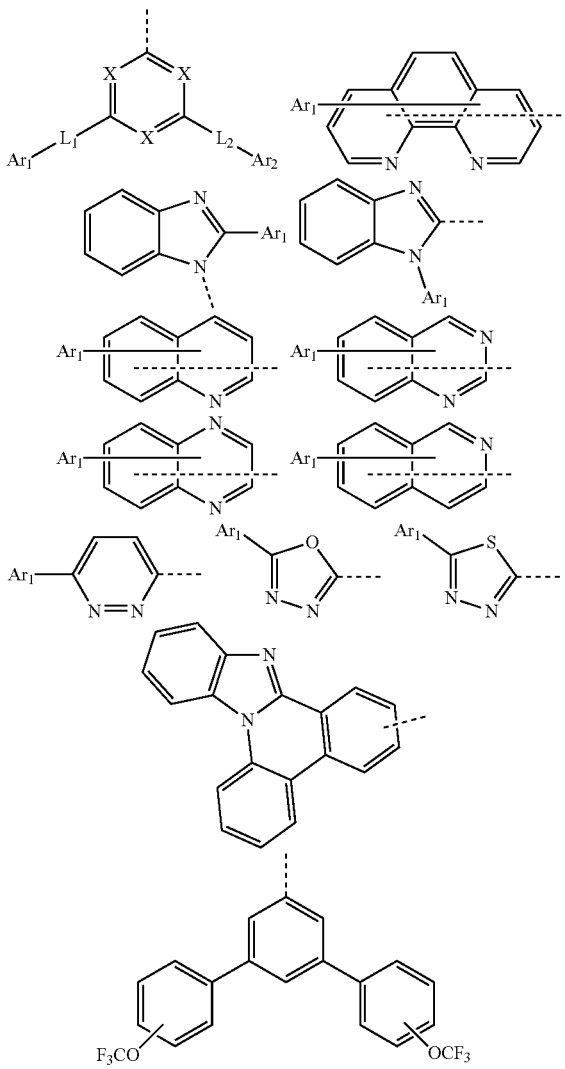

wherein,

L₁ and L₂ are each independently a single bond; a substituted or unsubstituted $C_{6-60}$ arylene; or a substituted or unsubstituted $C_{2-60}$ heteroarylene containing at least one heteroatom selected from the group consisting of N, O, and S, X is each independently N or C(R₈), provided that at least one of X is N, Ar₁ and Ar₂ are each independently hydrogen; a substituted or unsubstituted $C_{6-60}$ aryl; or a substituted or unsubstituted $C_{2-60}$ heteroaryl containing at least one heteroatom selected from the group consisting of N, O, and S, and R₈ is hydrogen; deuterium; a substituted or unsubstituted $C_{1-60}$ alkyl; a substituted or unsubstituted $C_{1-60}$ alkoxy; a substituted or unsubstituted $C_{6-60}$ aryl; a substituted or unsubstituted $C_{5-60}$ heteroaryl containing at least one heteroatom selected from the group consisting of N, O and S.

8. The compound of claim 7, wherein L₁ and L₂ are each independently a single bond; phenylene; biphenyldiyl; or naphthalenediyl.

9. The compound of claim 7, wherein Ar₁ and Ar₂ are each independently hydrogen; phenyl; phenyl substituted with cyano; biphenylene; terphenylene; naphthyl; phenanthrenyl; 9,10-dimethylphenanthrenyl; triphenylenyl; pyridinyl; dimethylfluorenyl; dibenzofuranyl; dibenzothiophenyl; carbazolyl; benzocarbazolyl; phenalenyl; quinolinyl; fluoranthenyl; phenoxazinyl; phenothiazinyl; 10-phenylphenazinyl; or 9,9-dimethylacridinyl.

10. The compound of claim 1, wherein Ar is any one selected from the group consisting of the following:

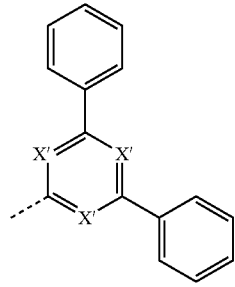

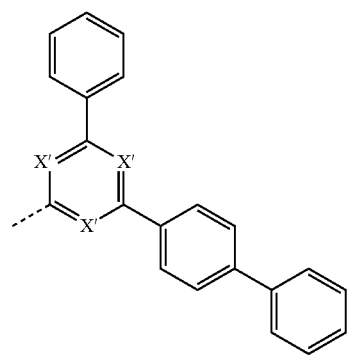

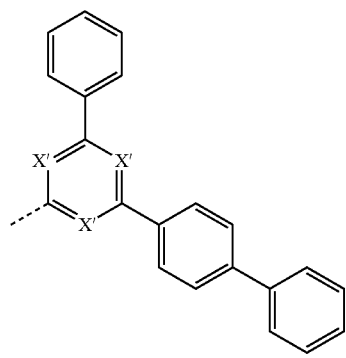

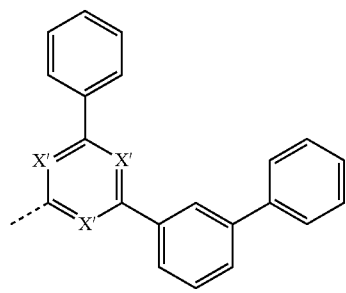

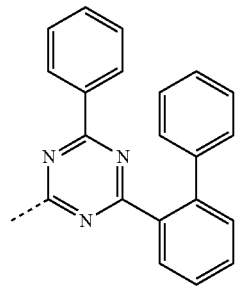

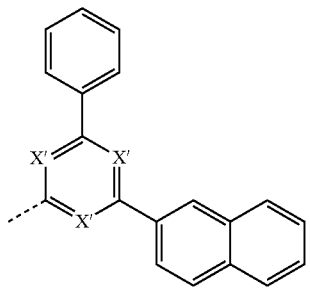

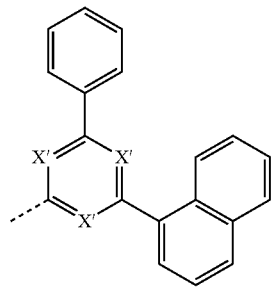

213
-continued
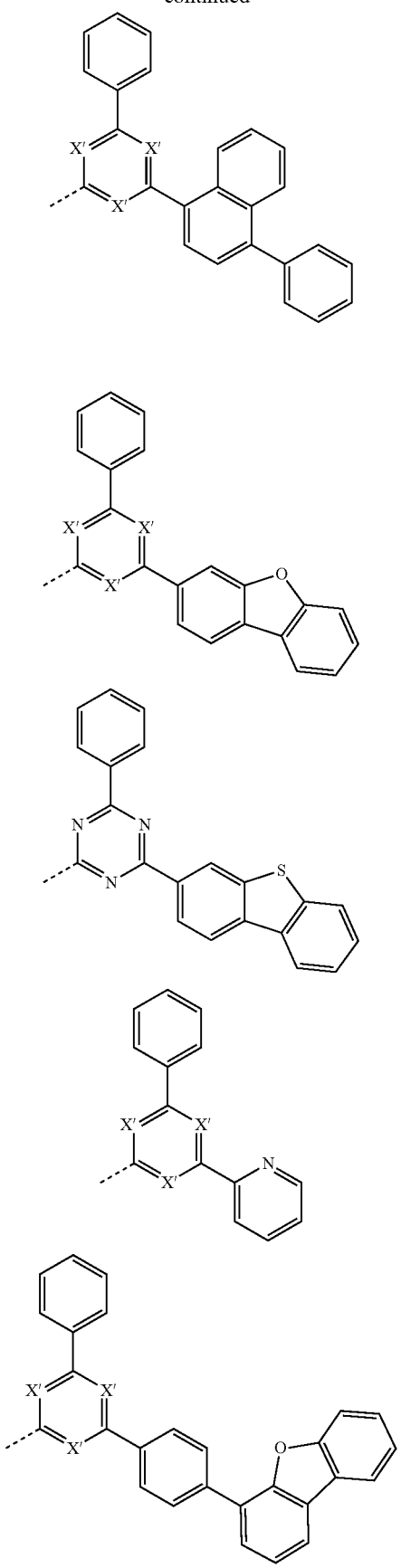
214
-continued
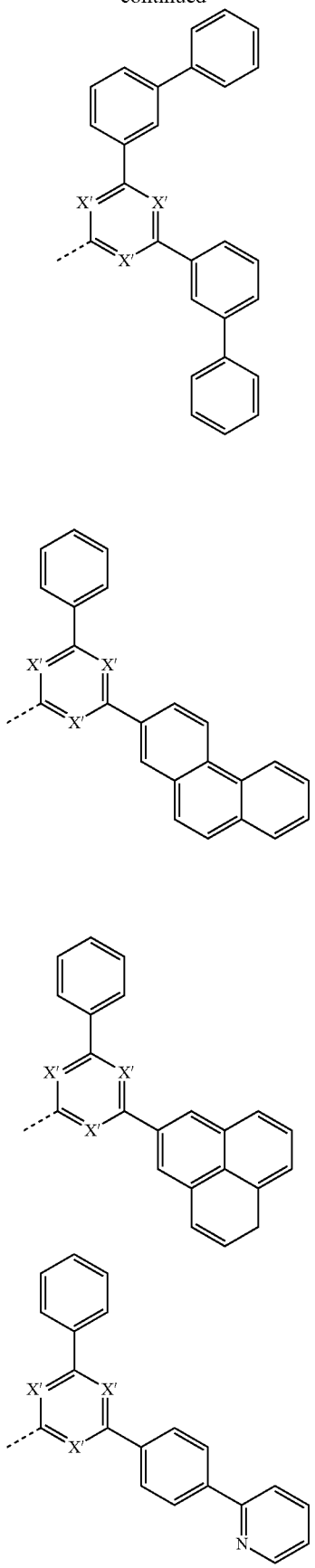

215
-continued
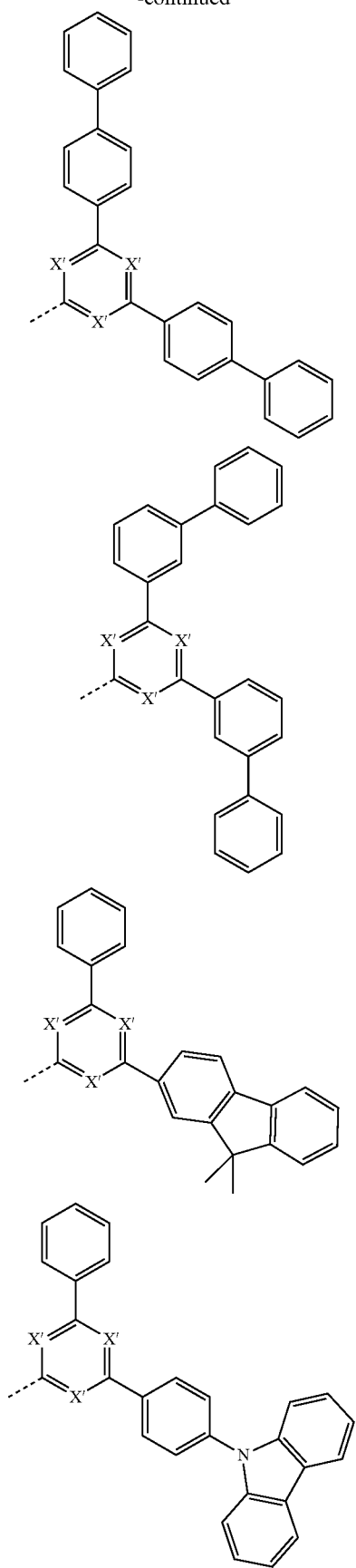
216
-continued
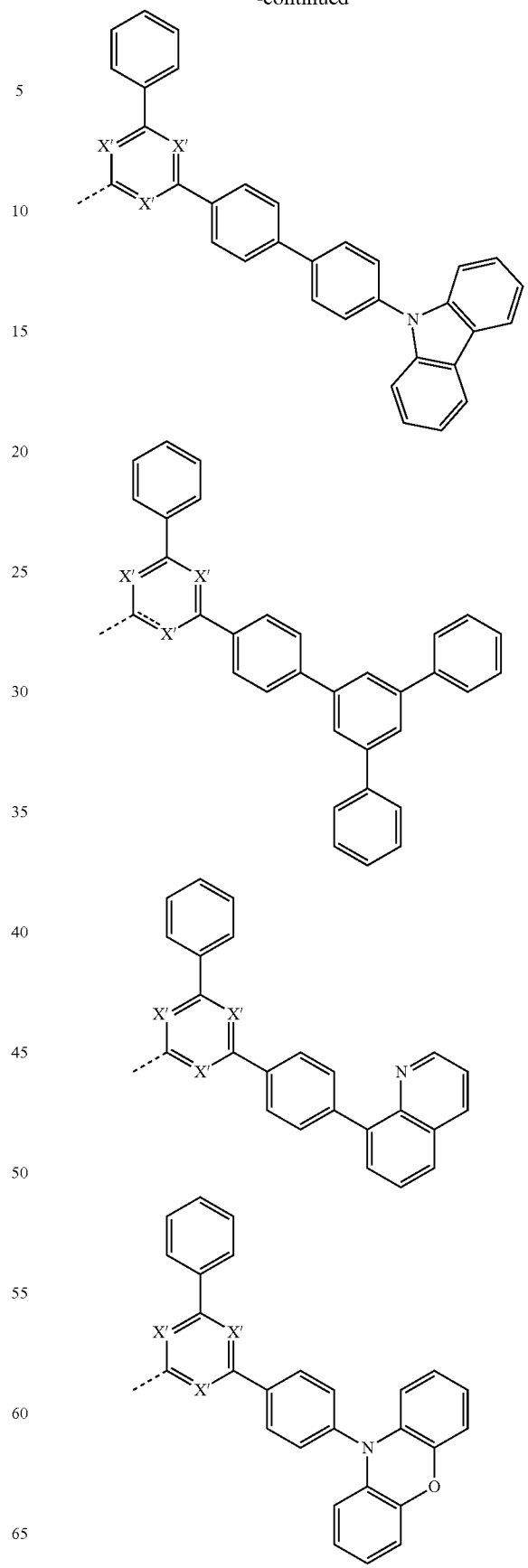

217
-continued
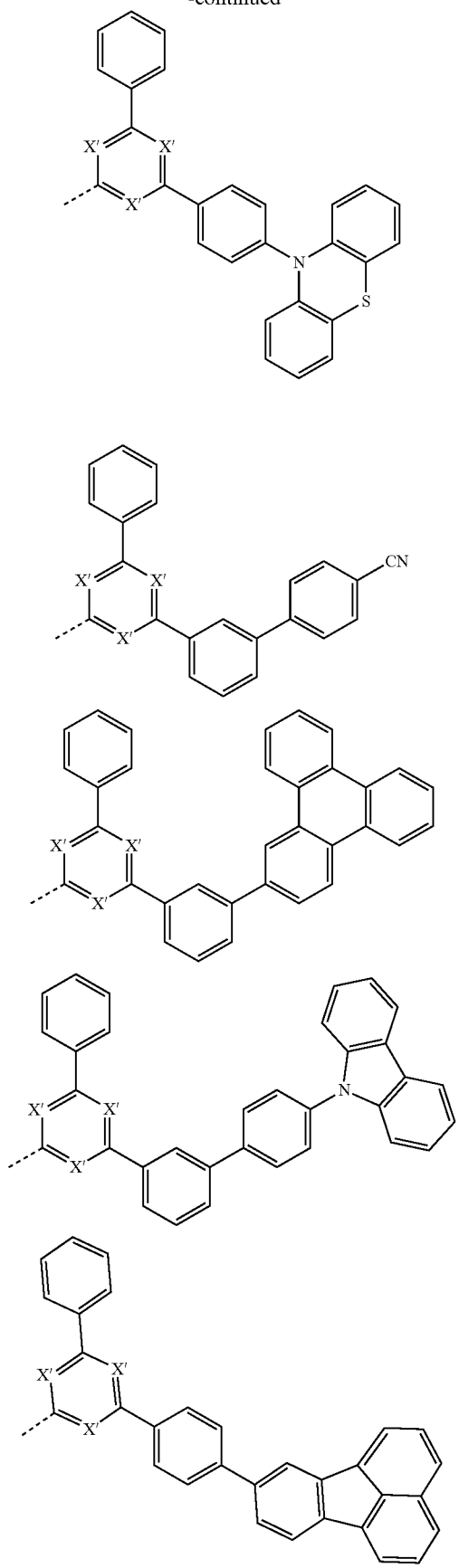
218
-continued
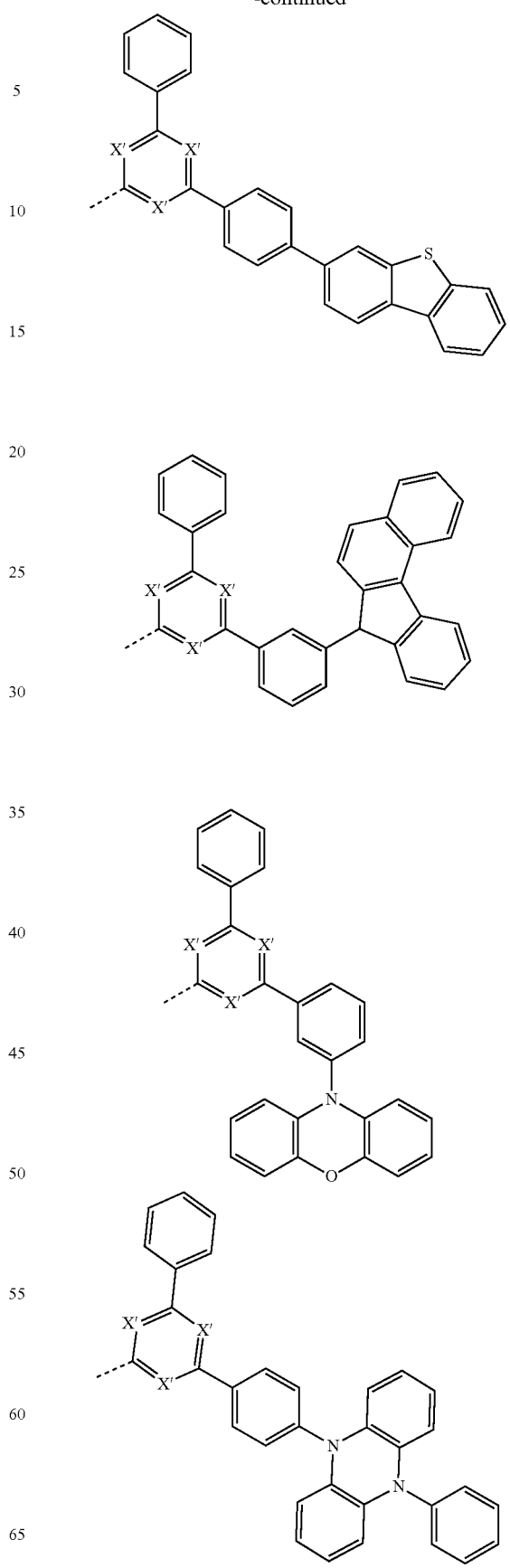

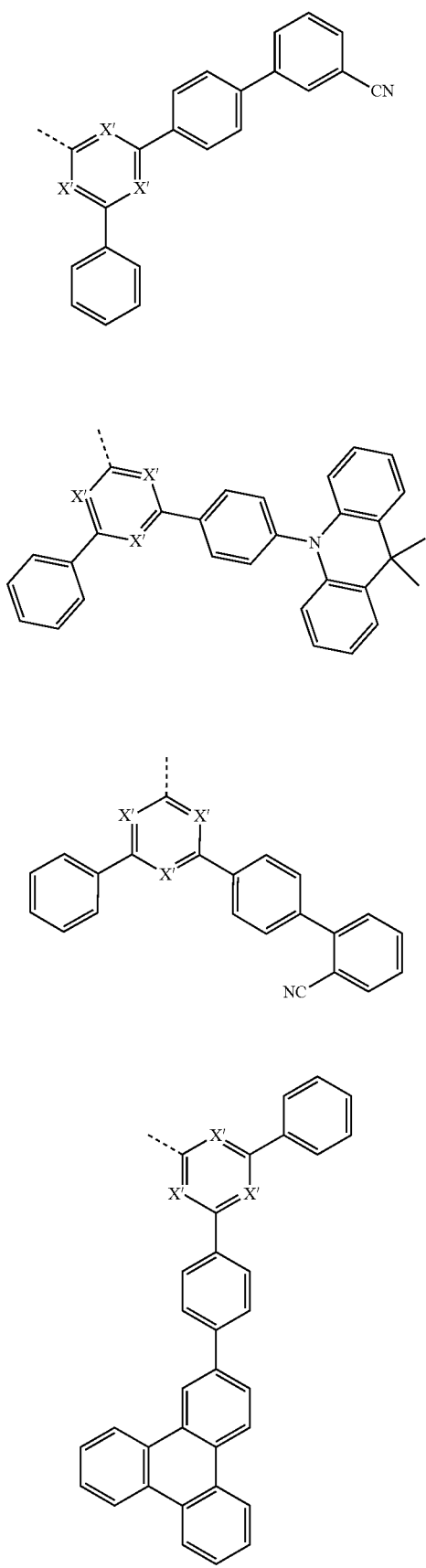
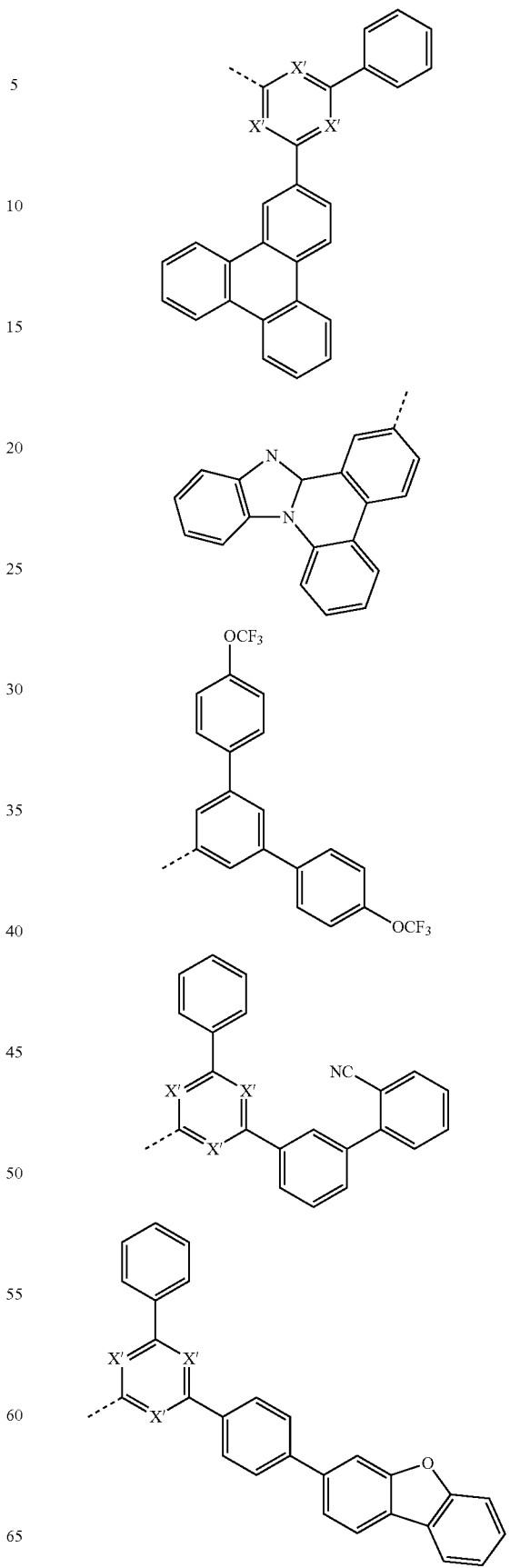

221
-continued
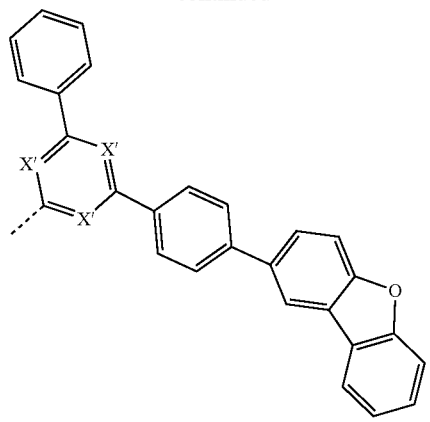
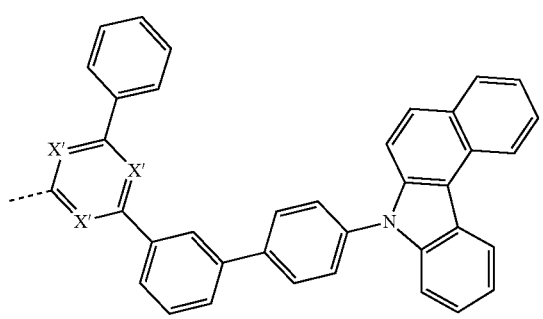
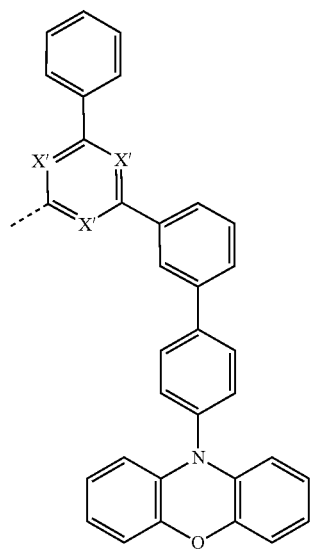
222
-continued
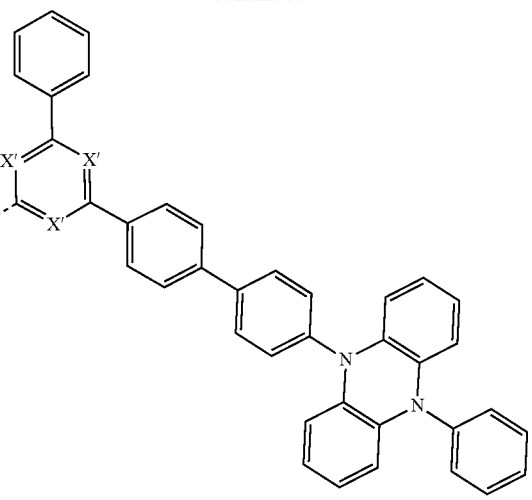
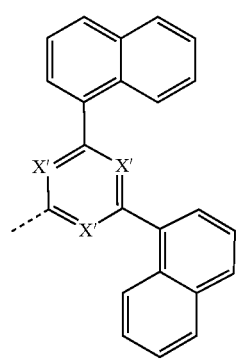
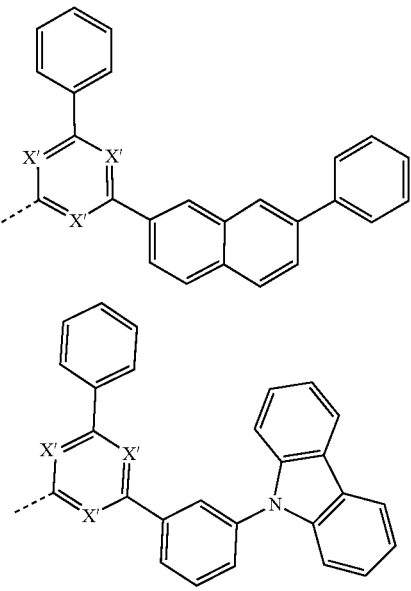

-continued
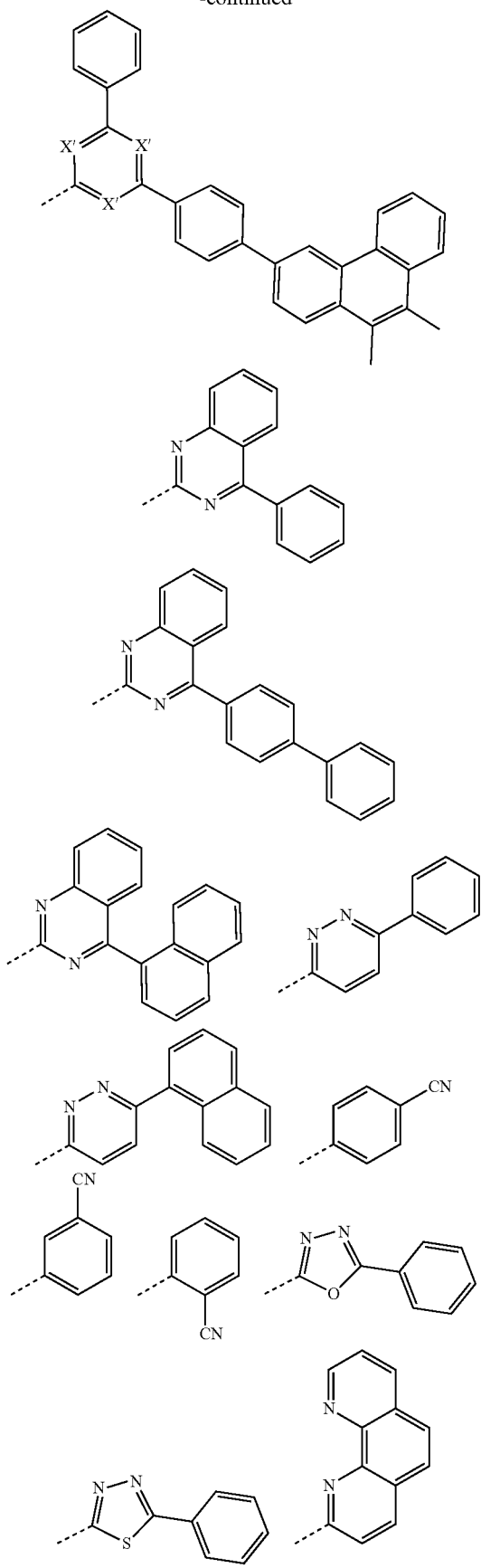
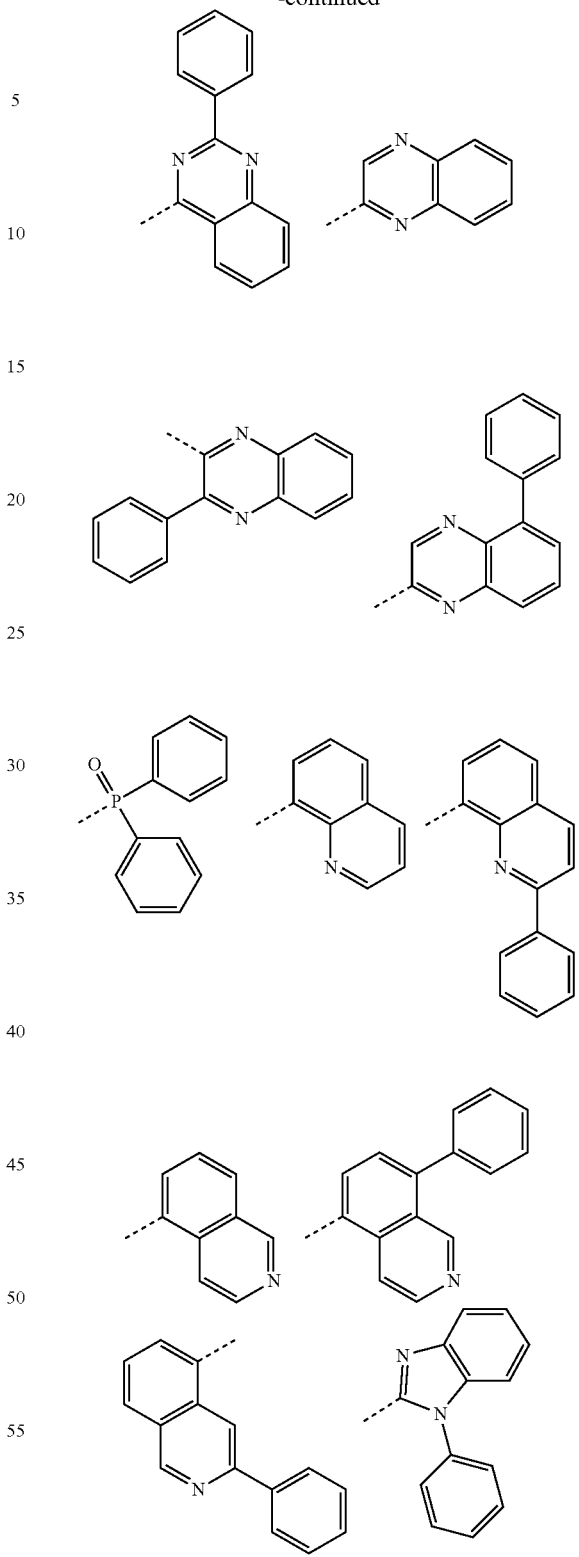
wherein,
X' is N or CH, with the proviso that at least one of X' within each of the groups is N.
11. Any one compound selected from the group consisting of the following:

225 226
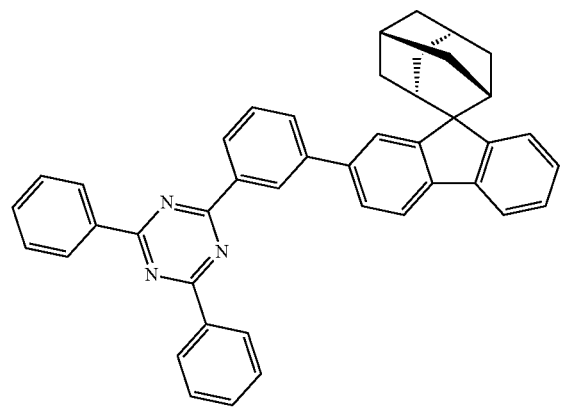
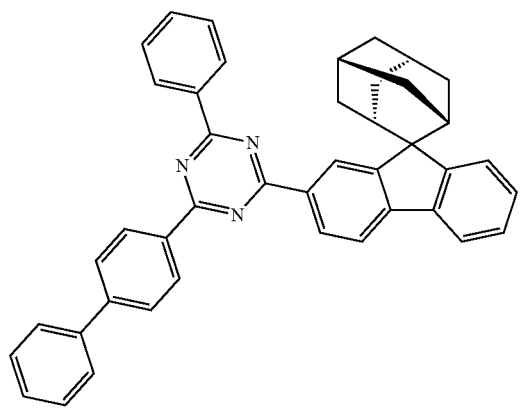
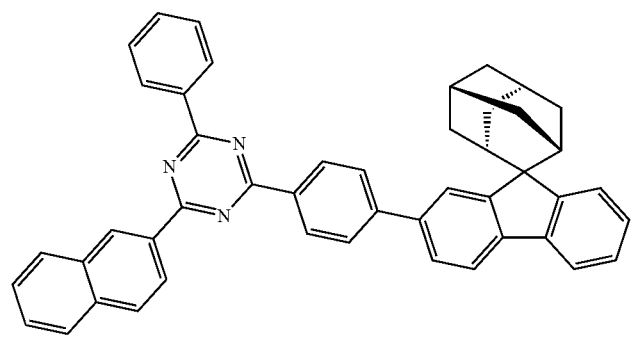
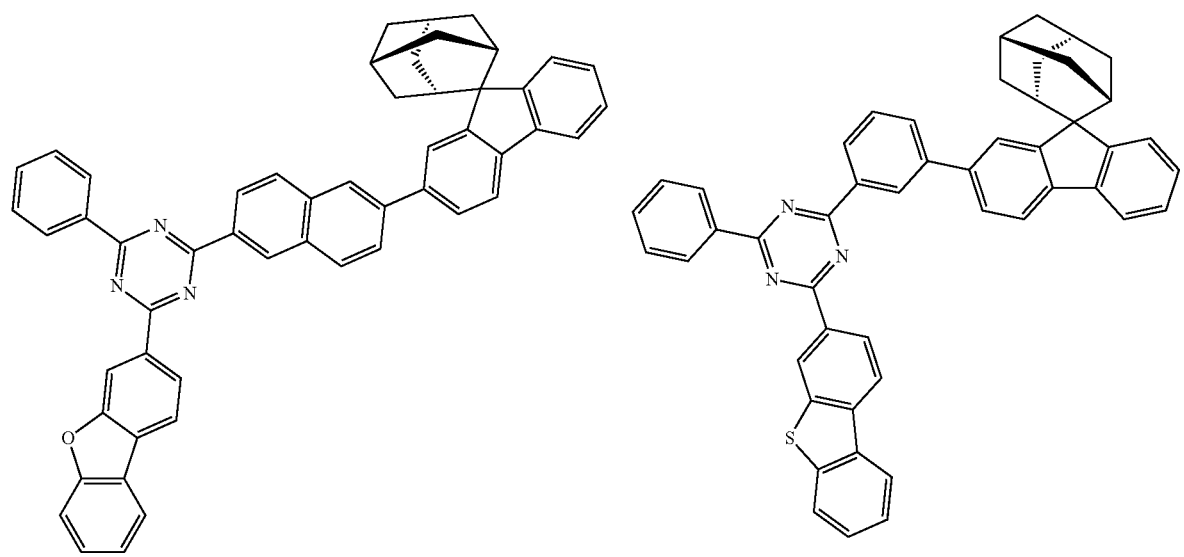

227
228
-continued
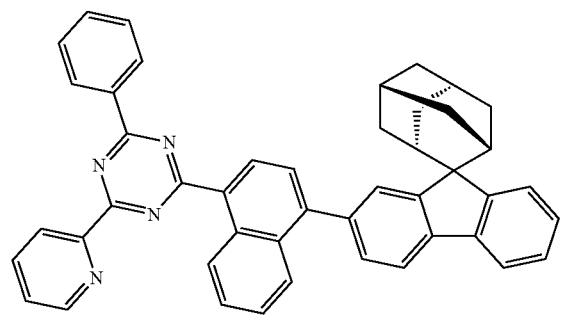
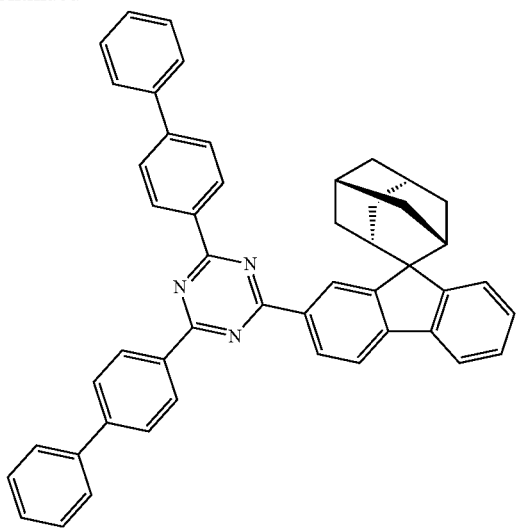
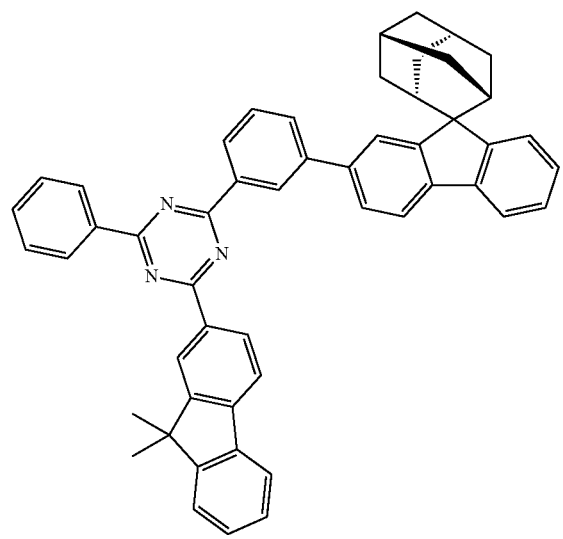
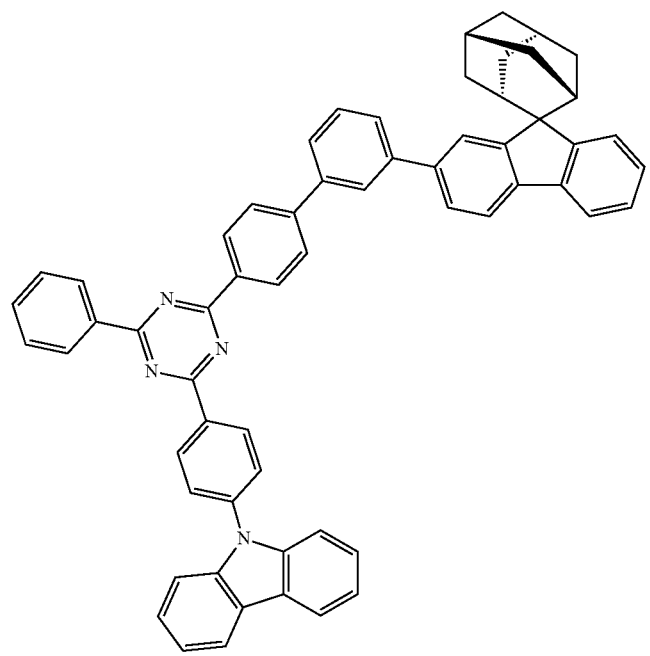

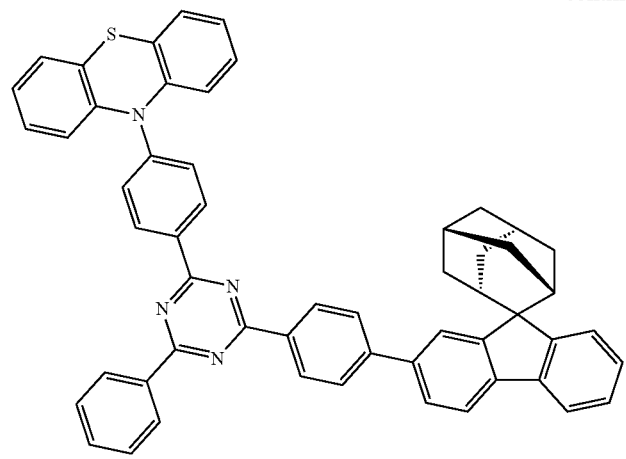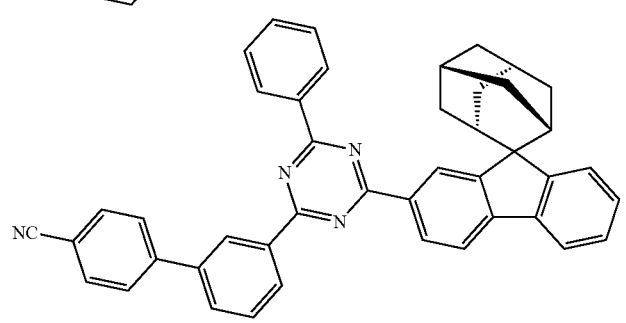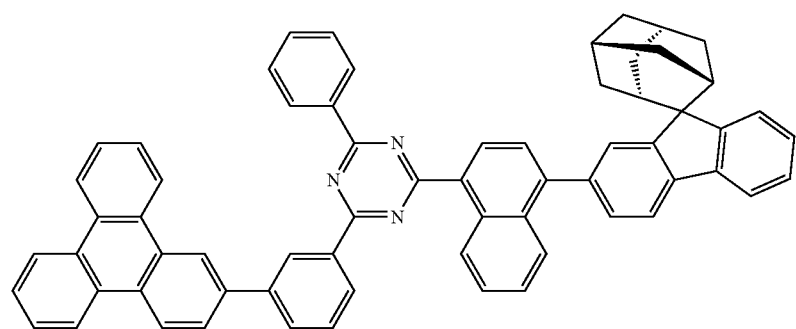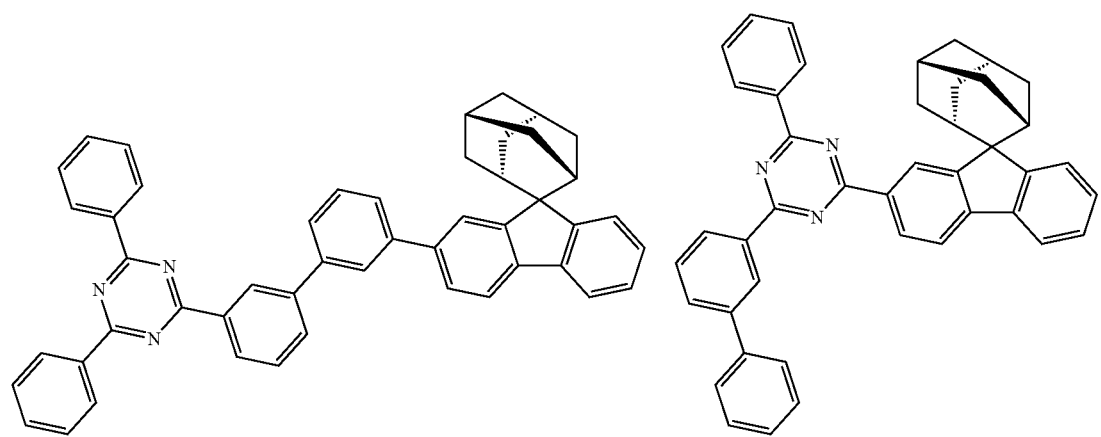

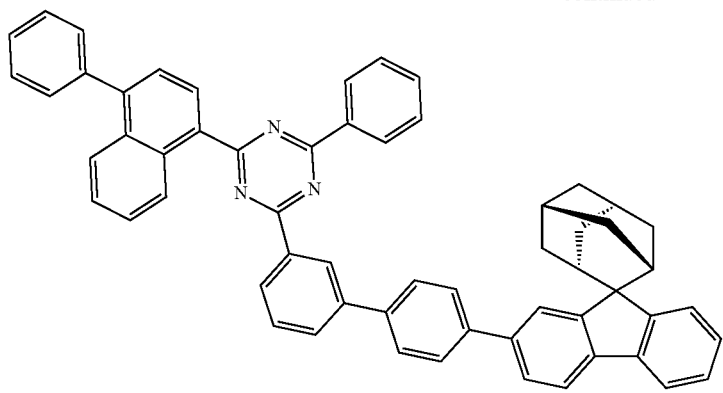
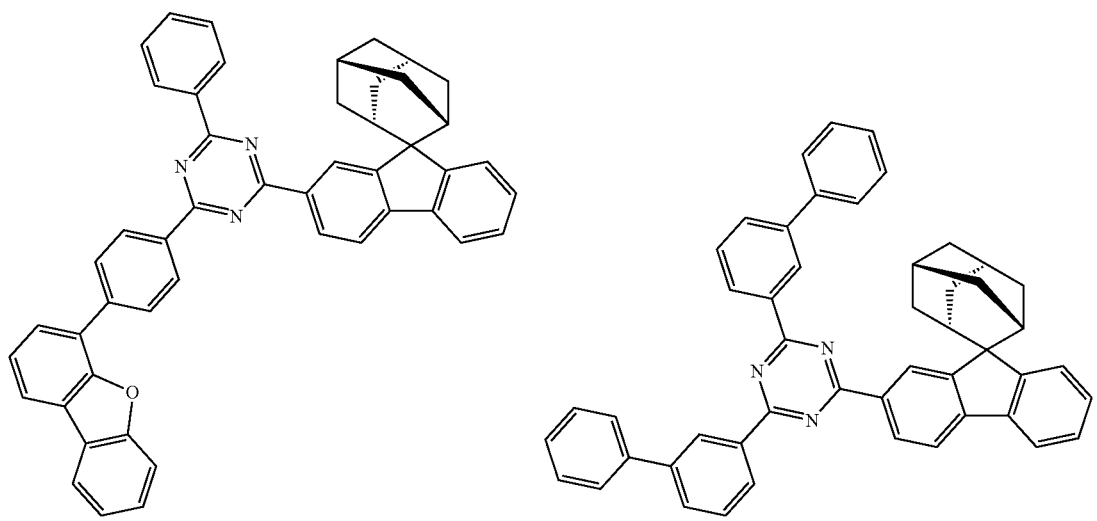
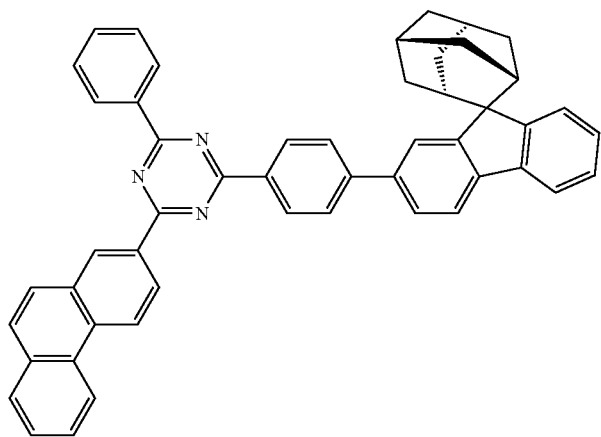

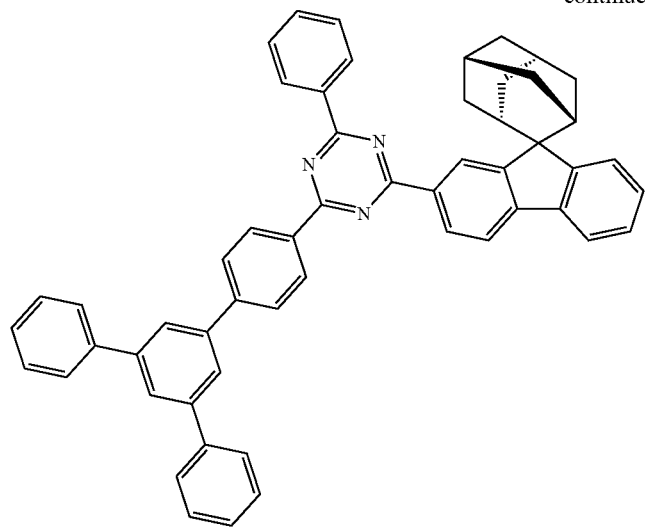
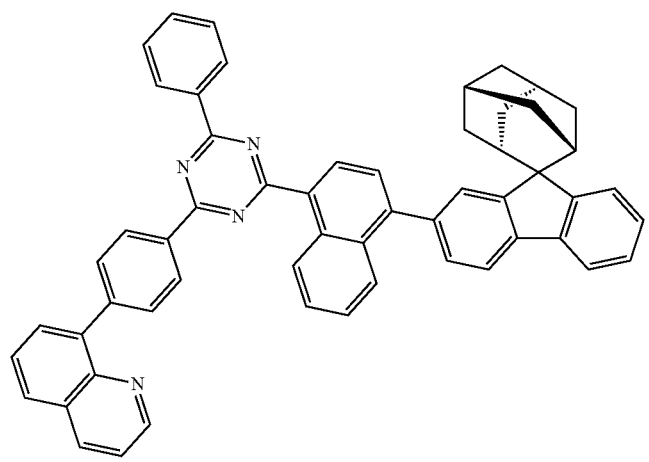
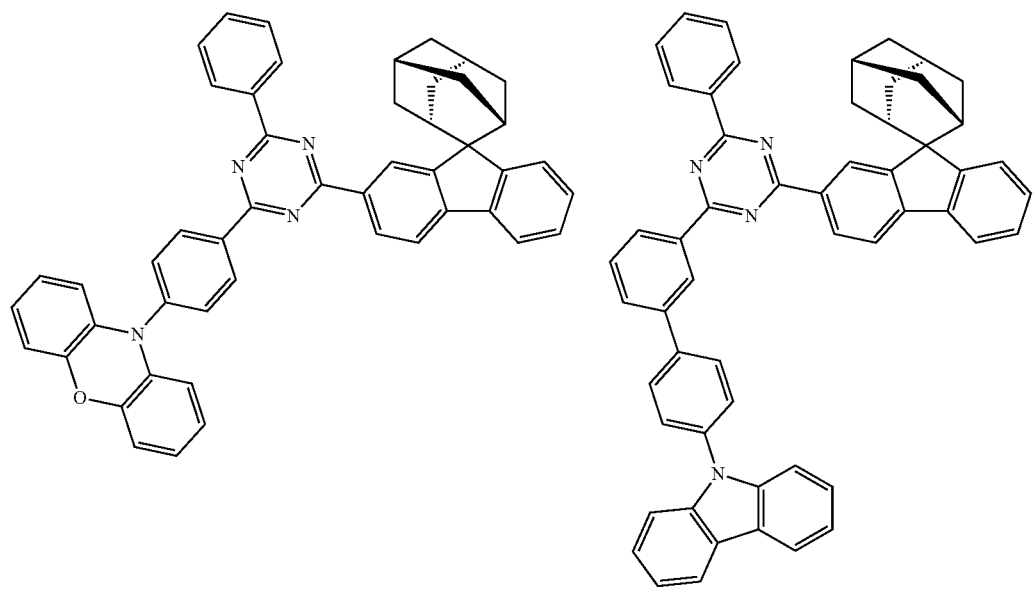

235
236
-continued
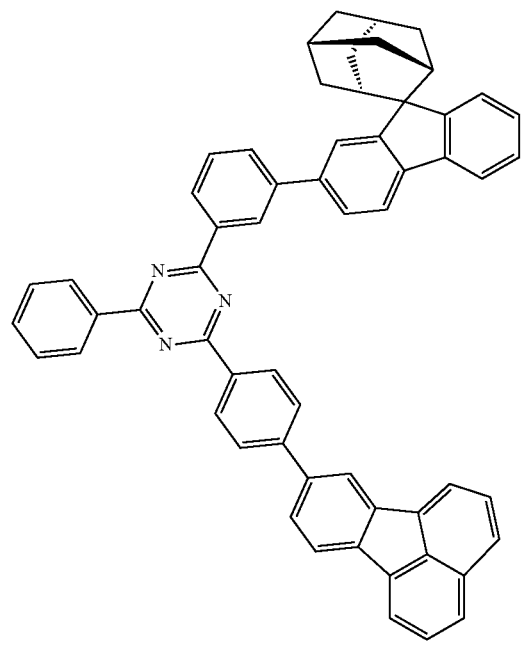
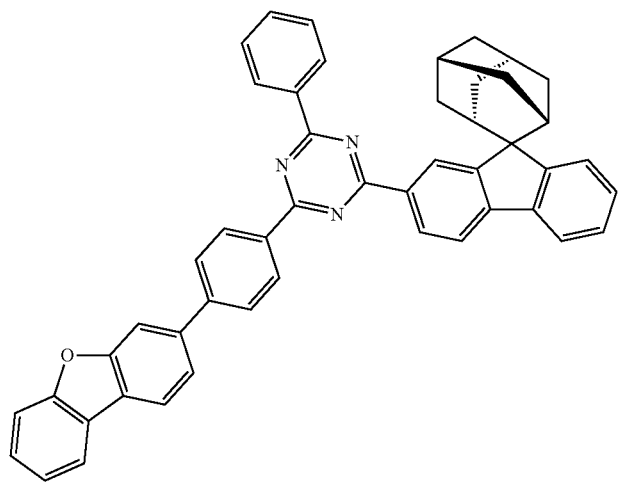
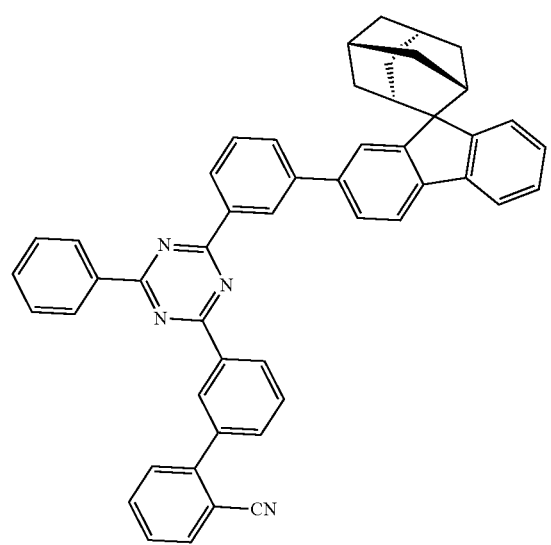

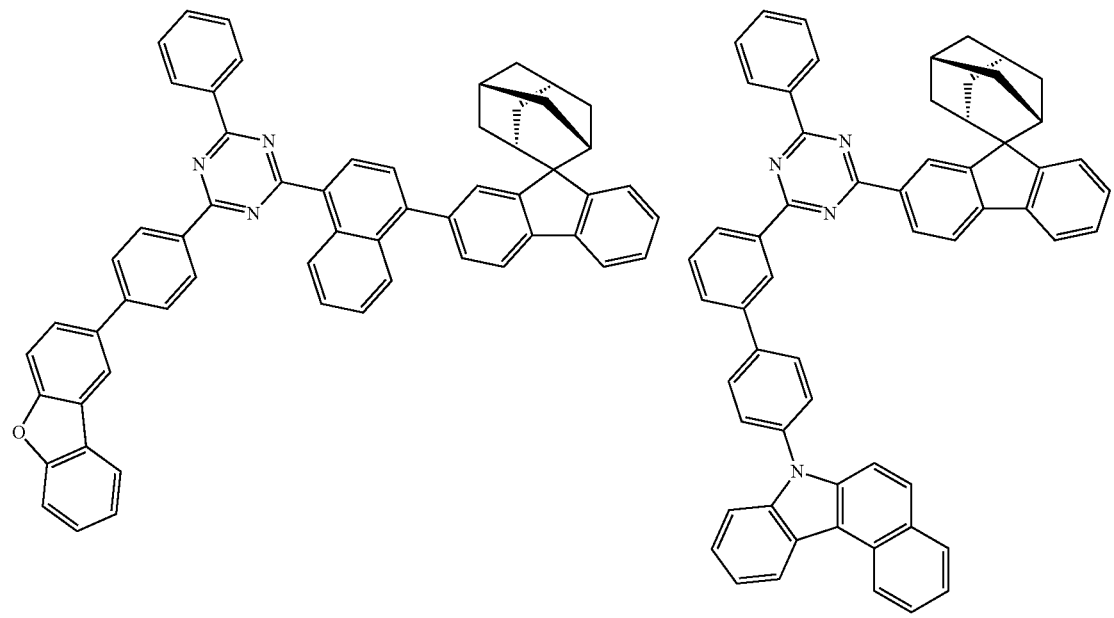
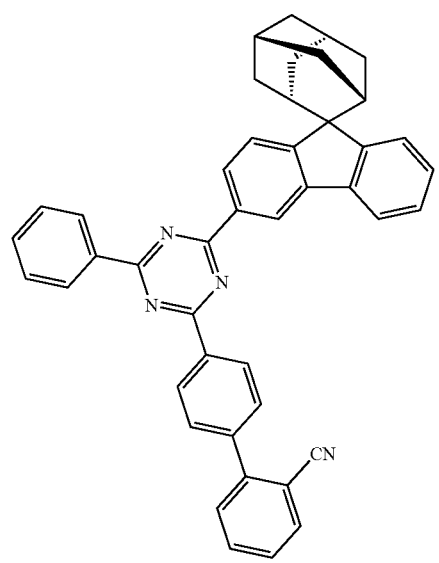

-continued
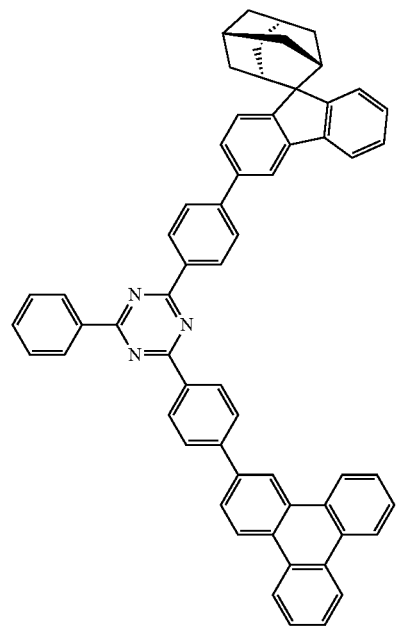
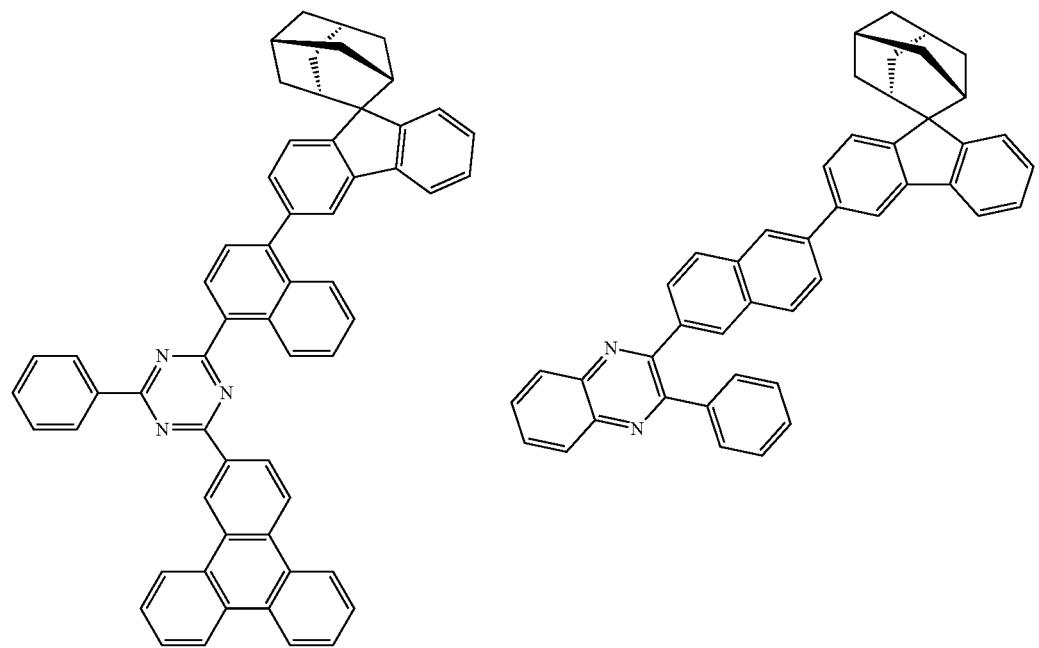

241 242
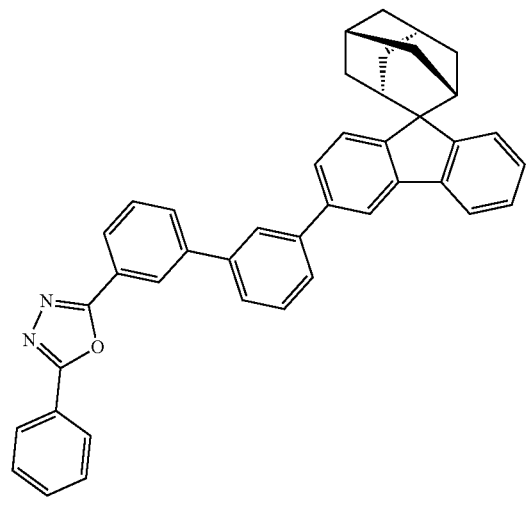
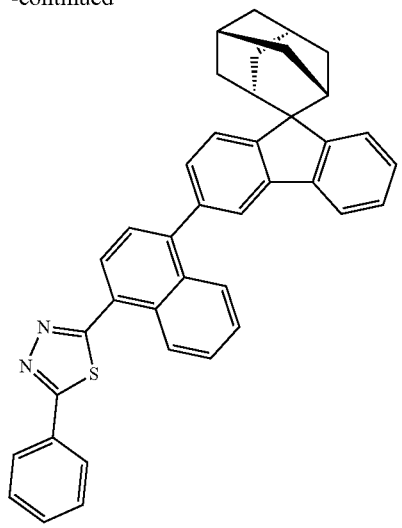
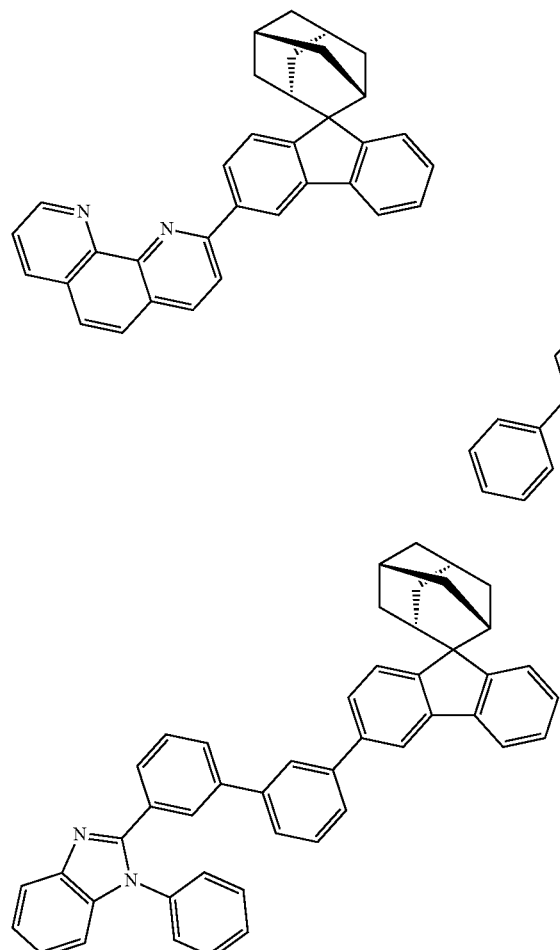
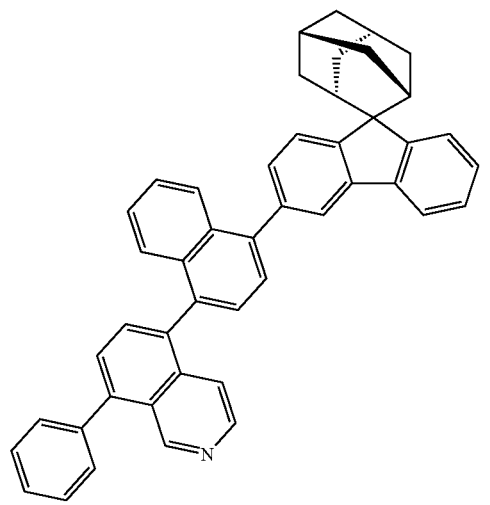
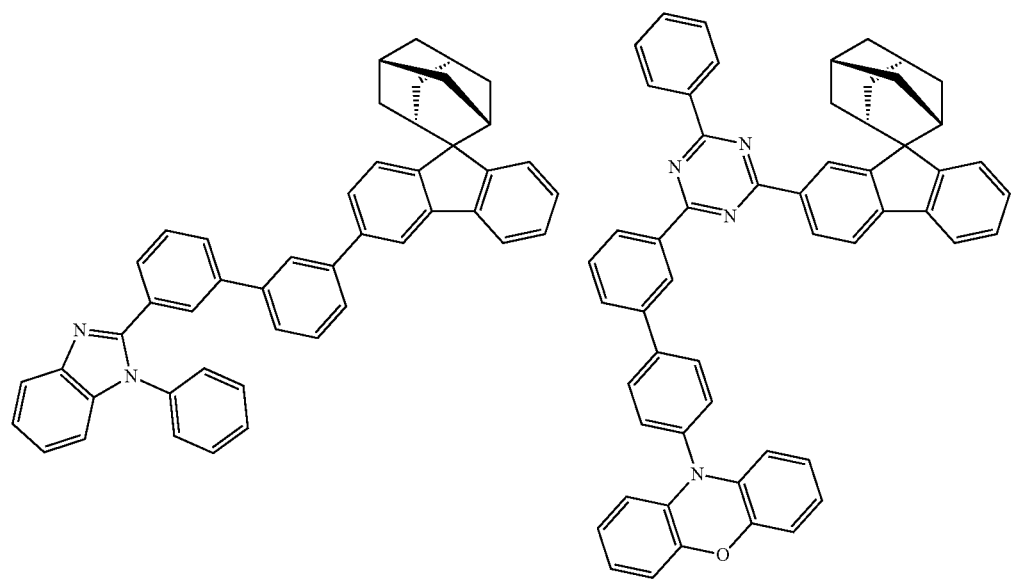

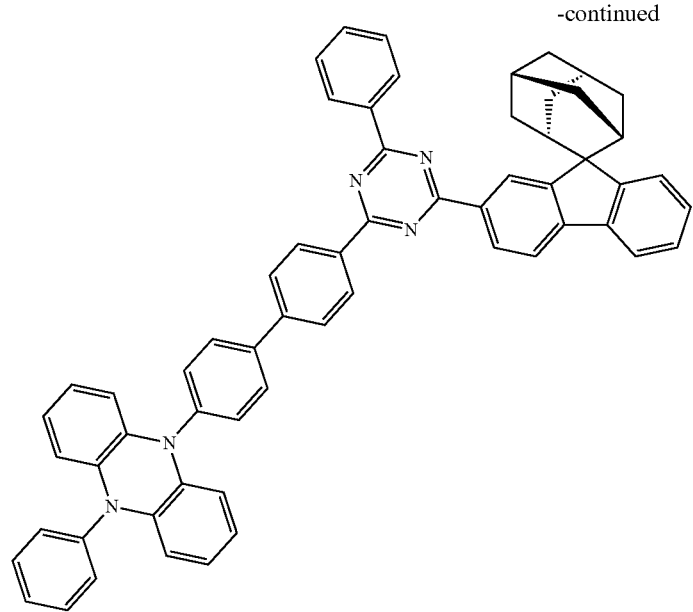
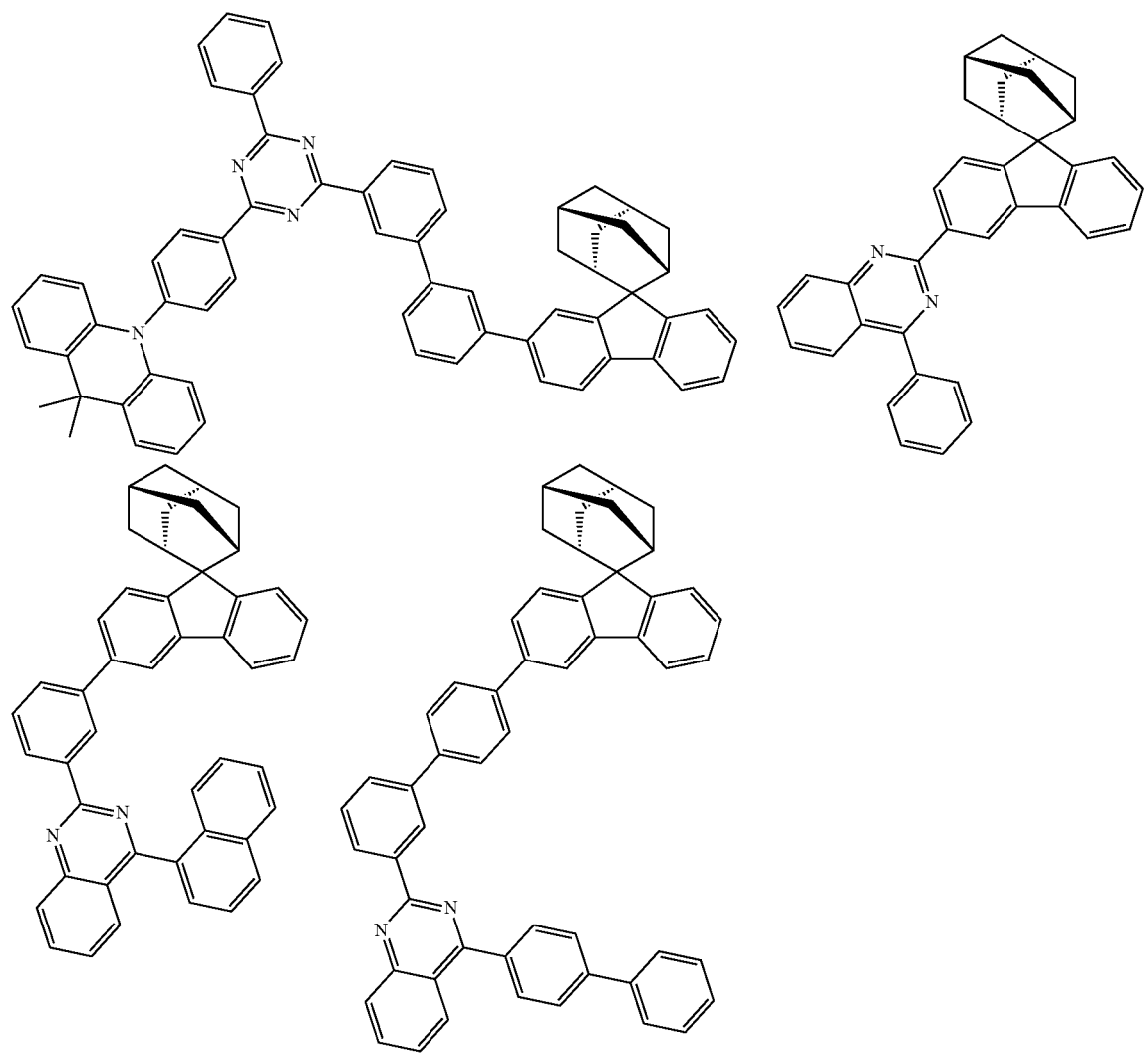

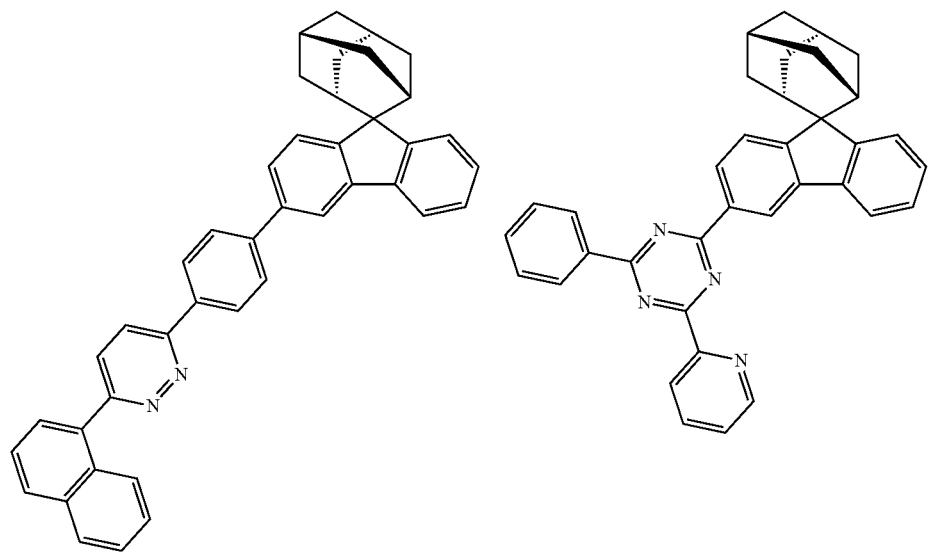
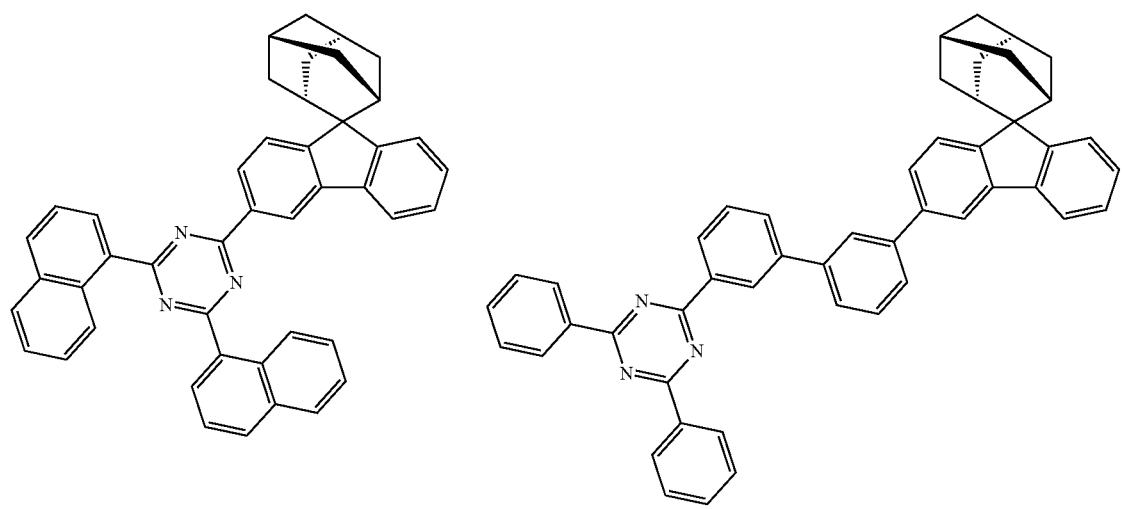
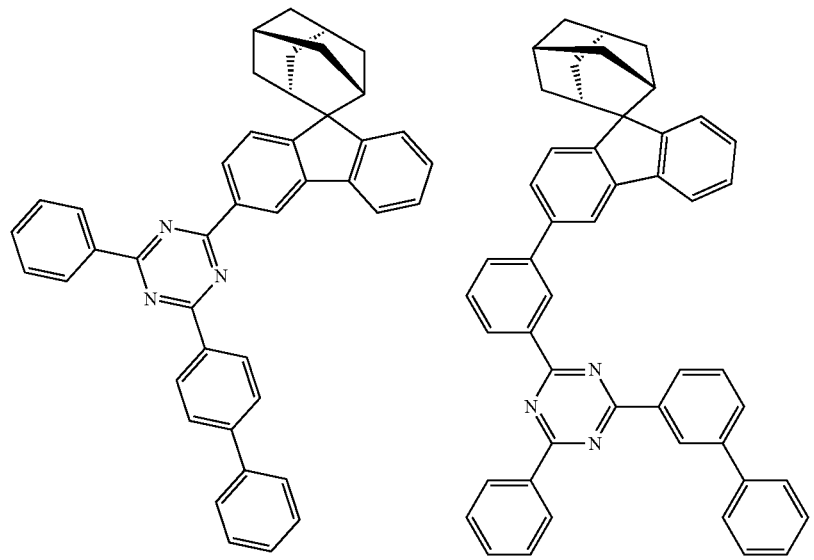

247
248
-continued
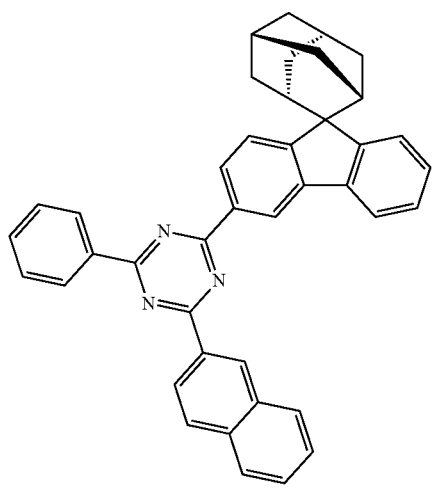
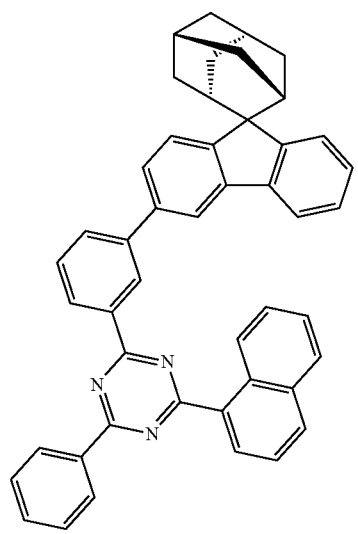
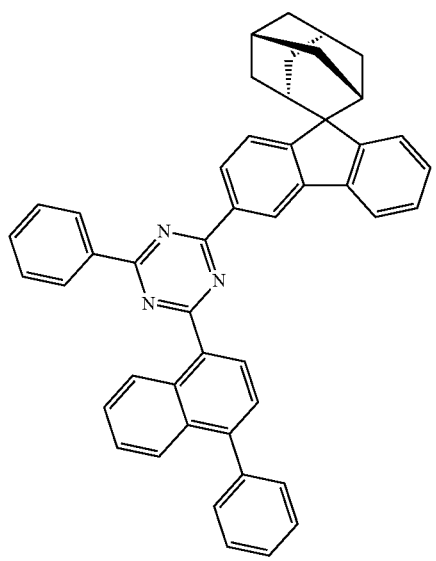
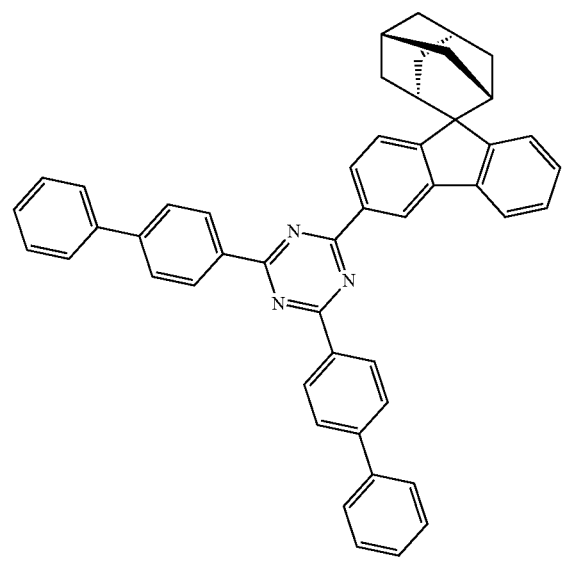
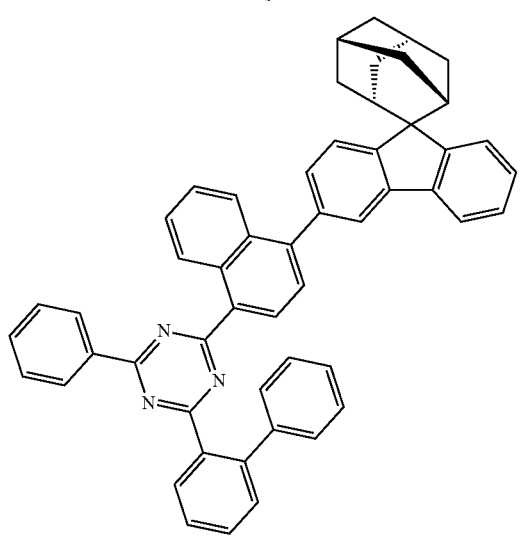
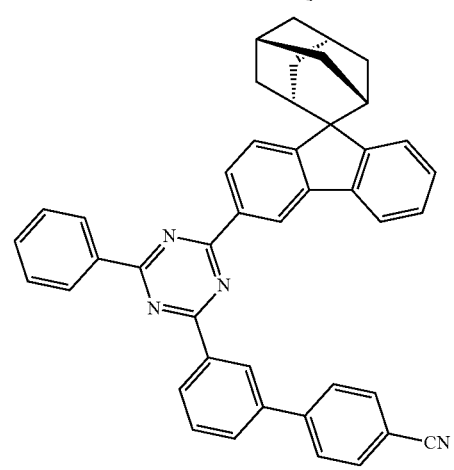

249  250
-continued
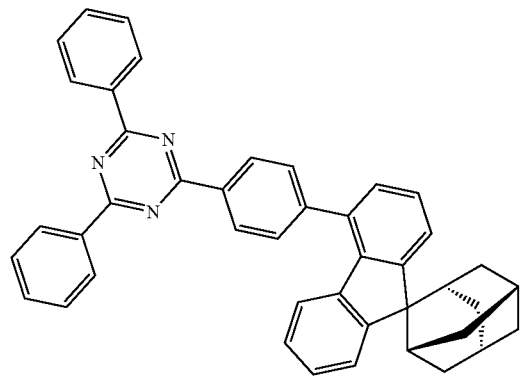
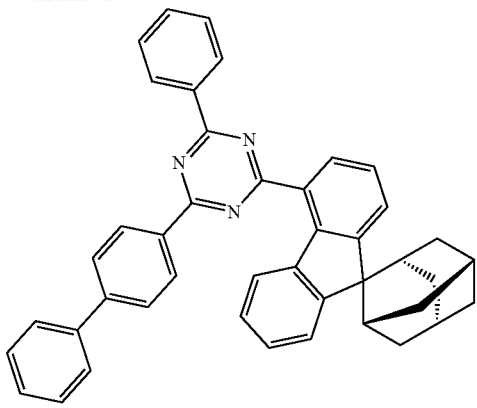
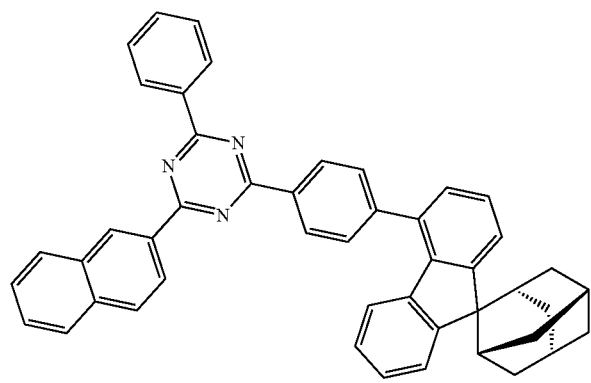
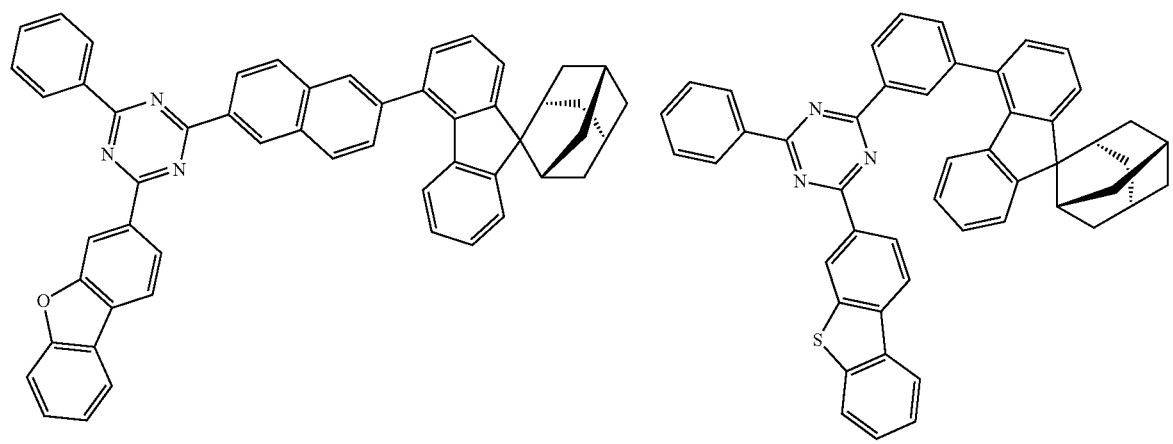

251
252
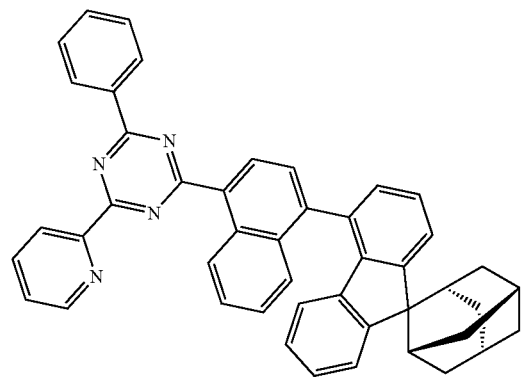
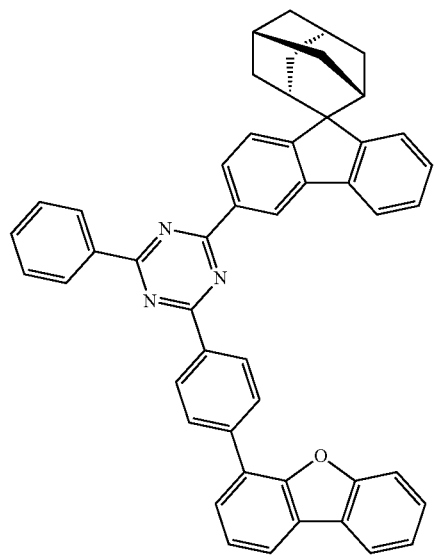
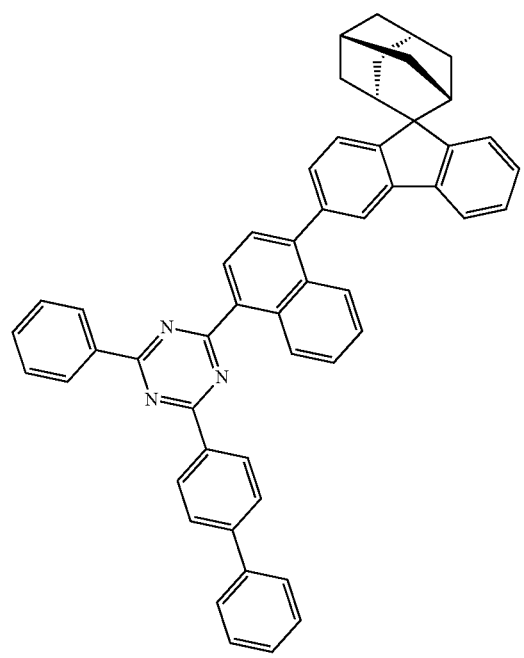
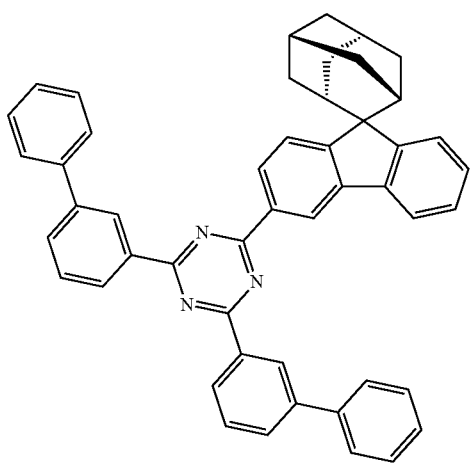

-continued
253                                    254
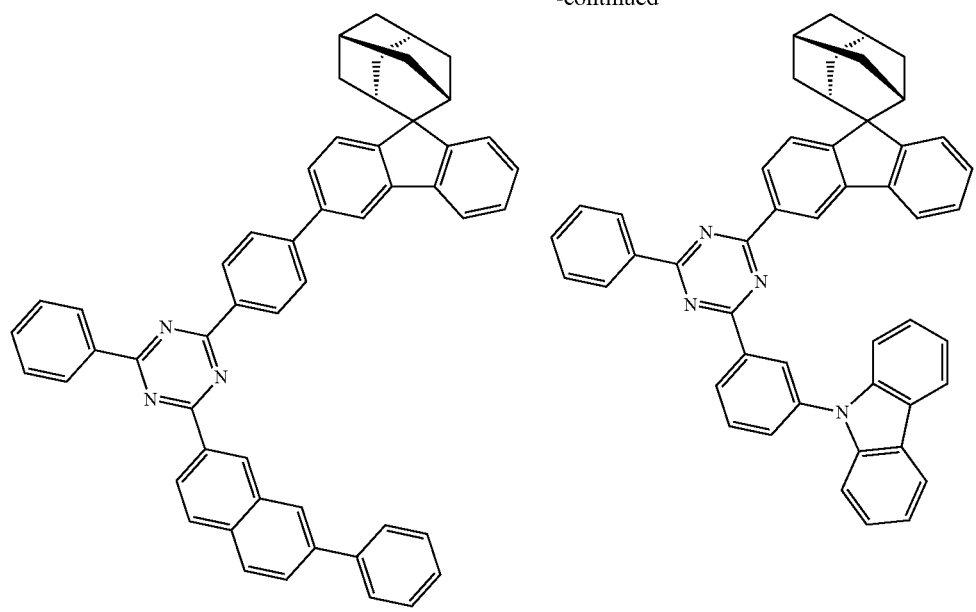
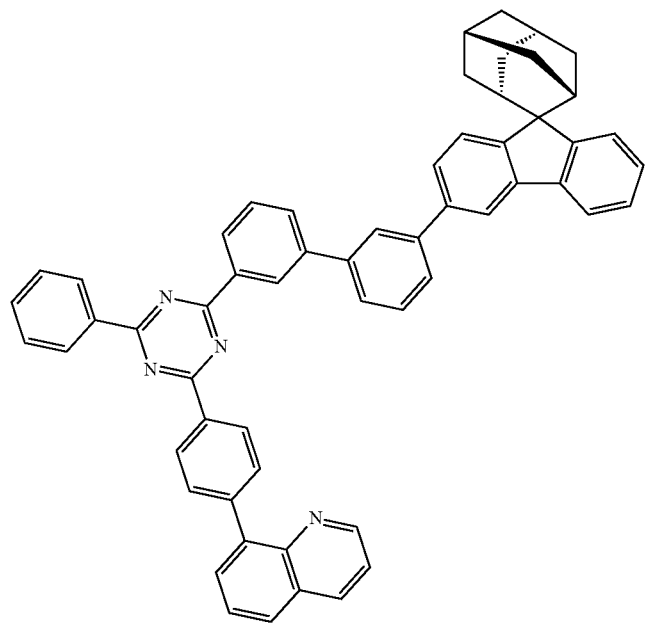
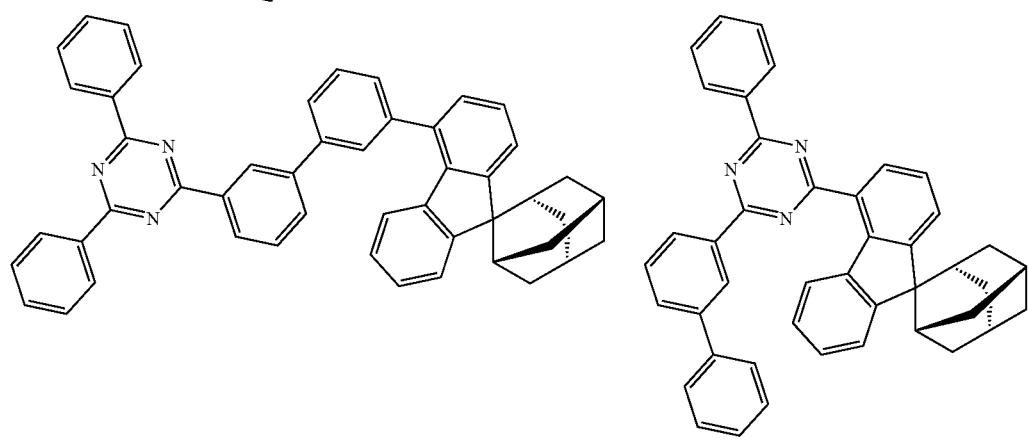

255
256
-continued
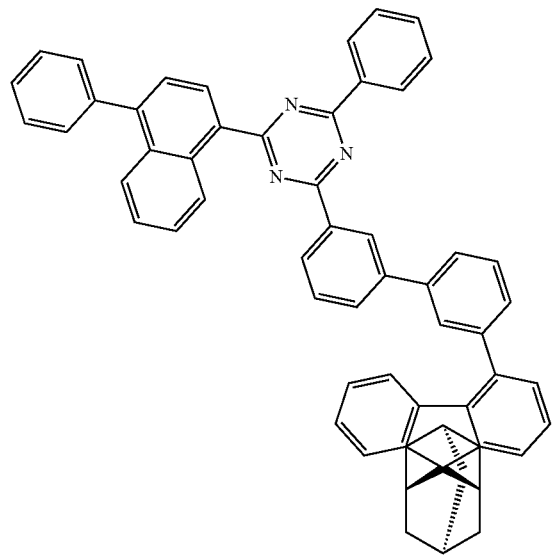
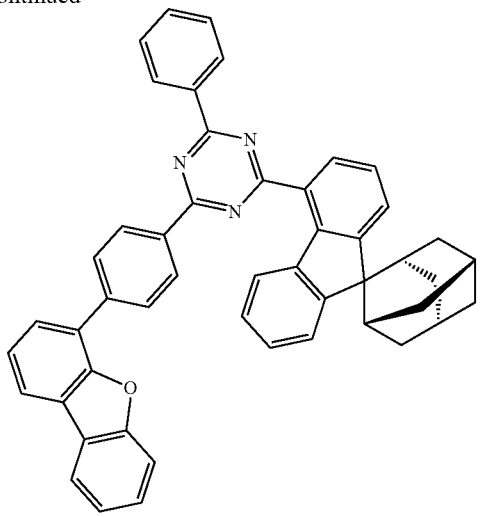
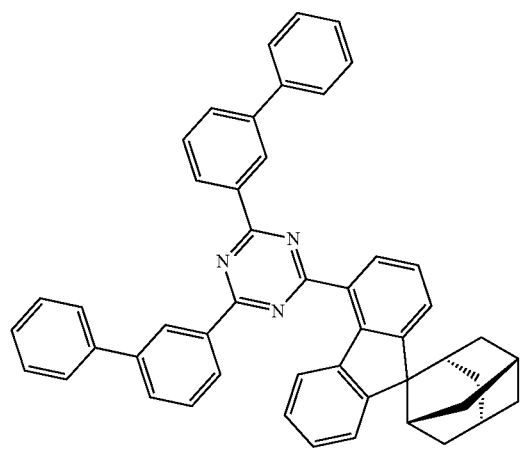
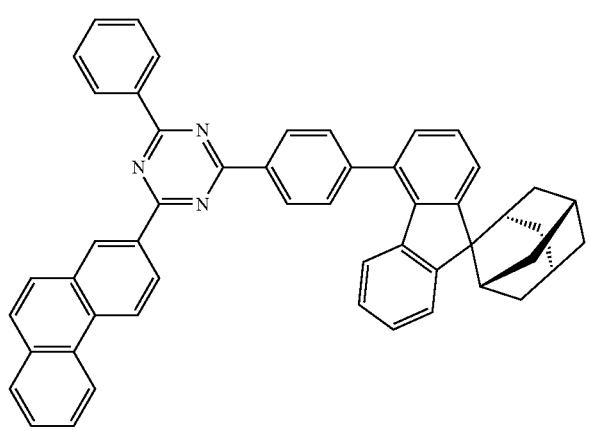
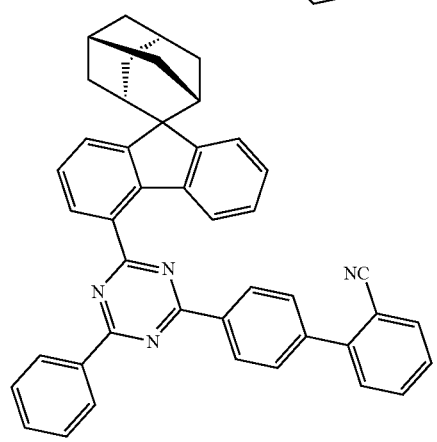
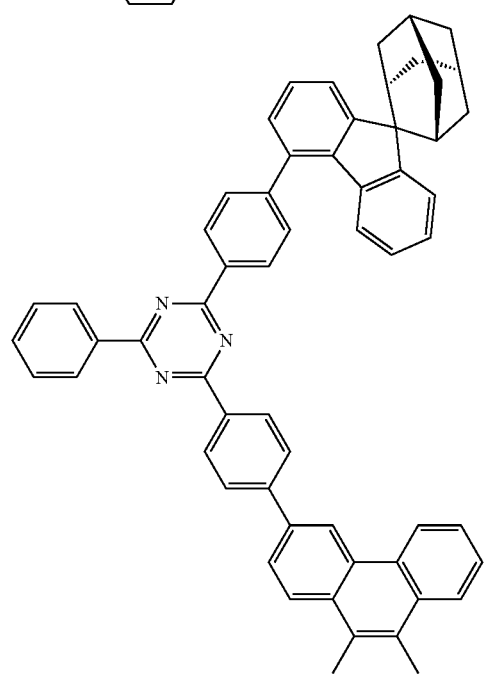

-continued
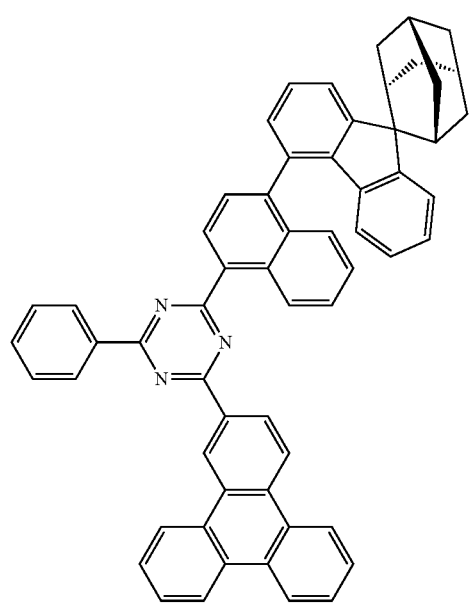 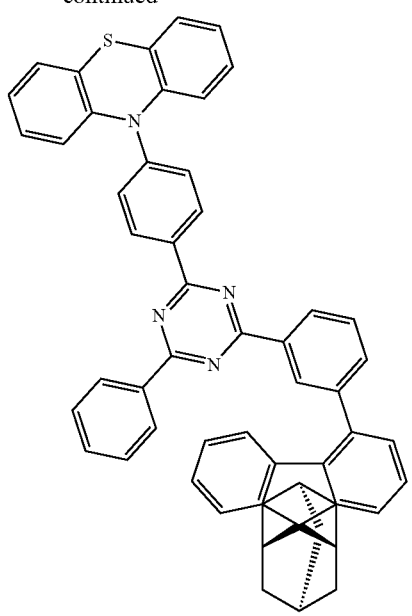
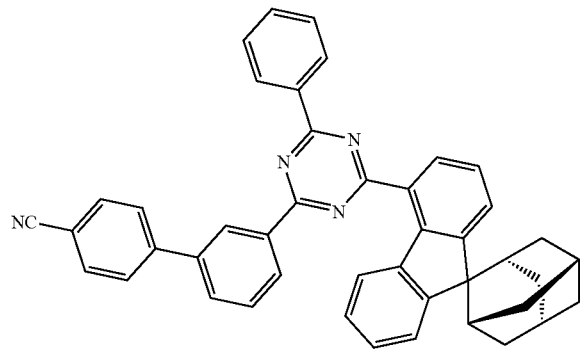
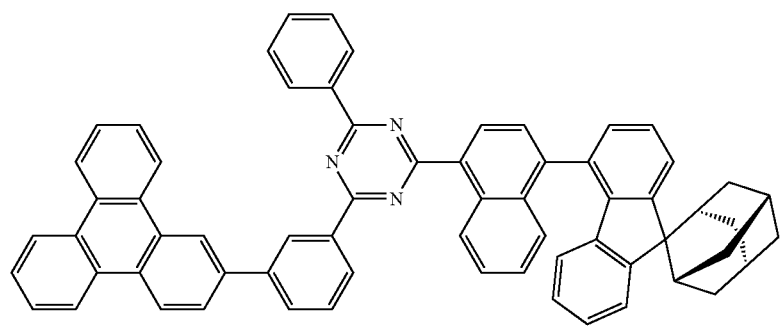

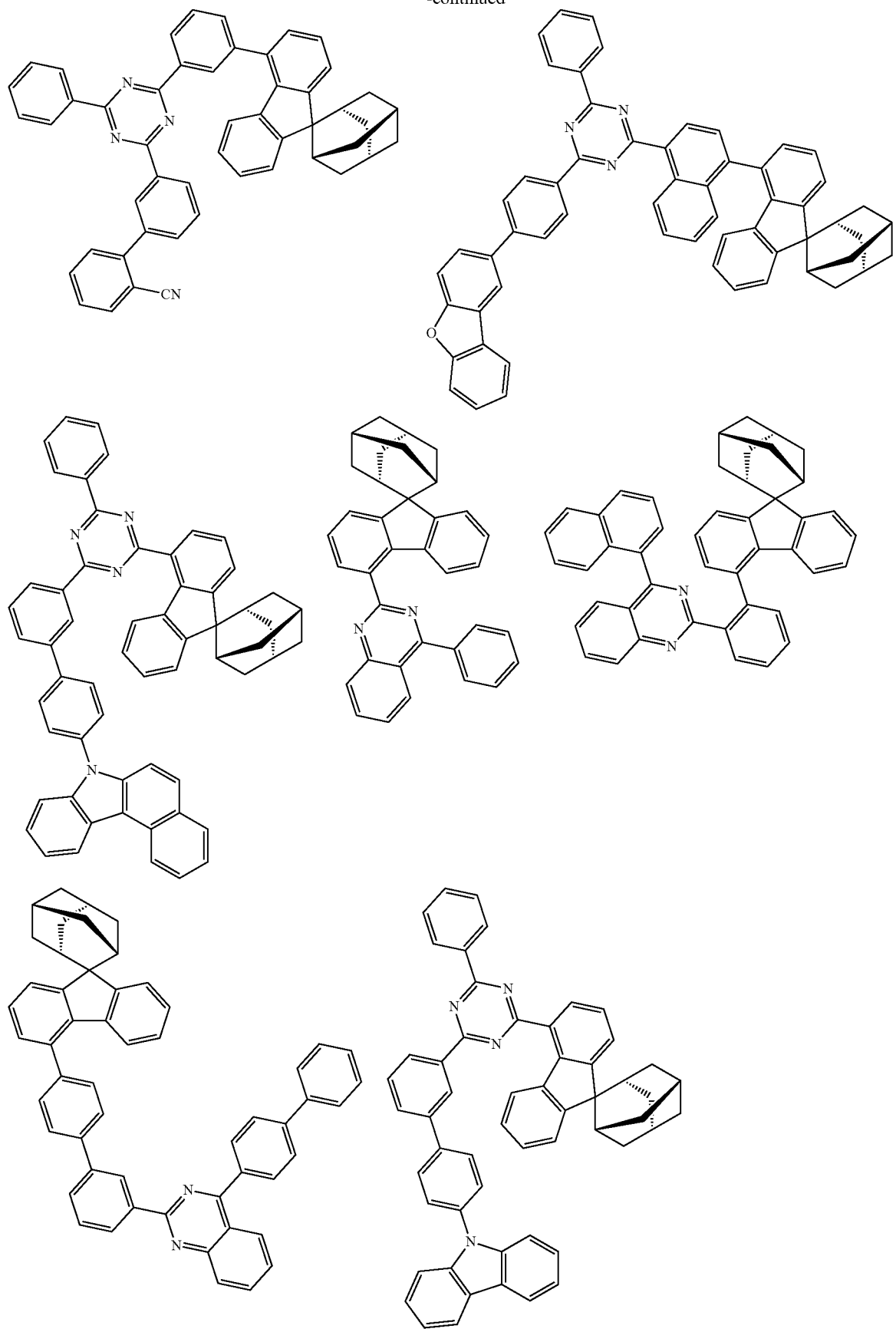

-continued
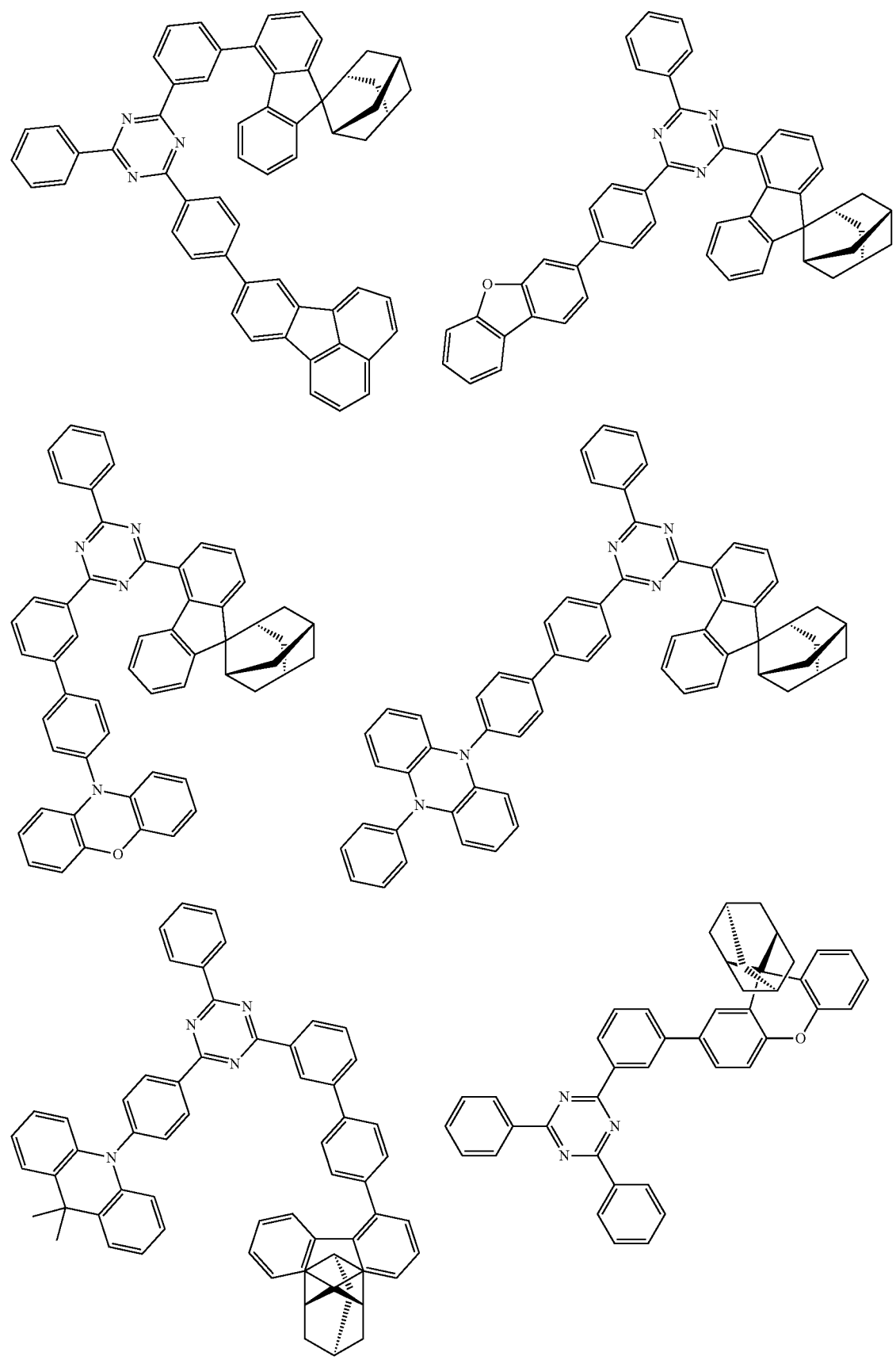

263 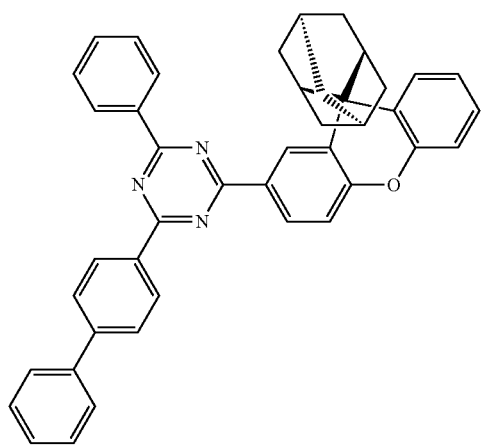
264 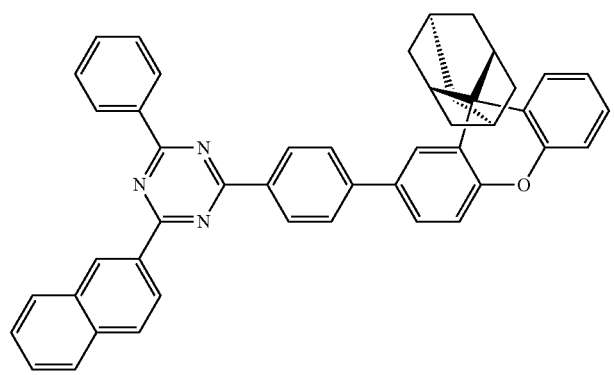
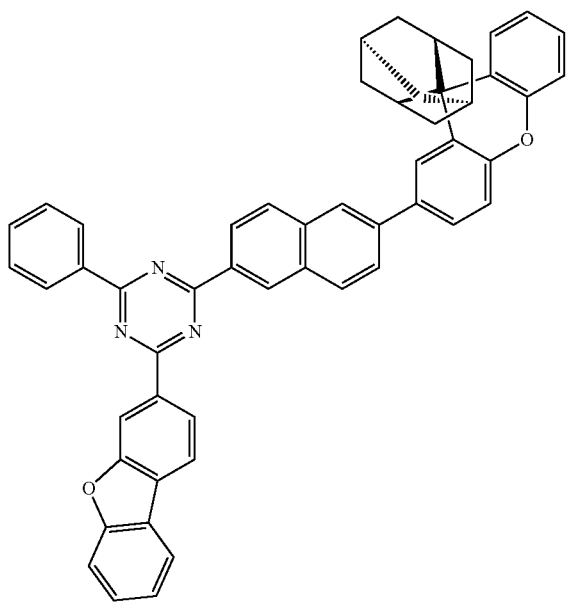
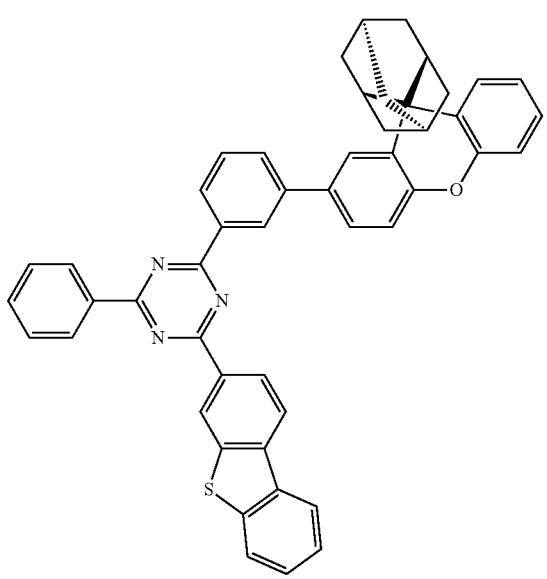
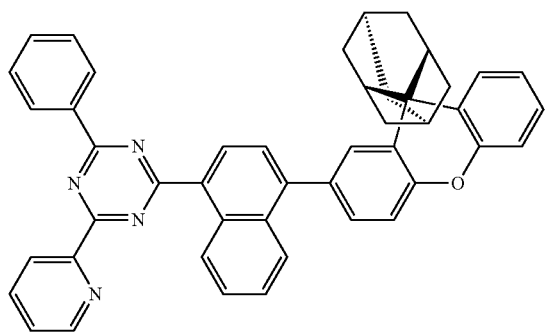
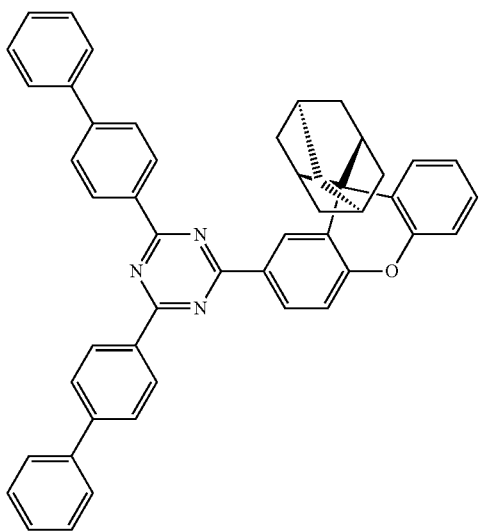

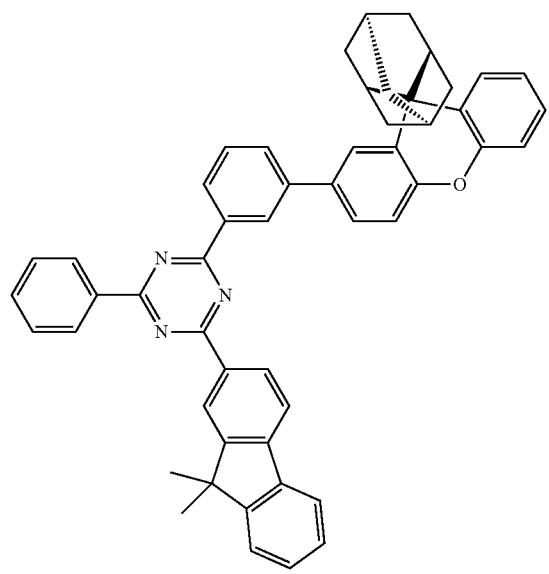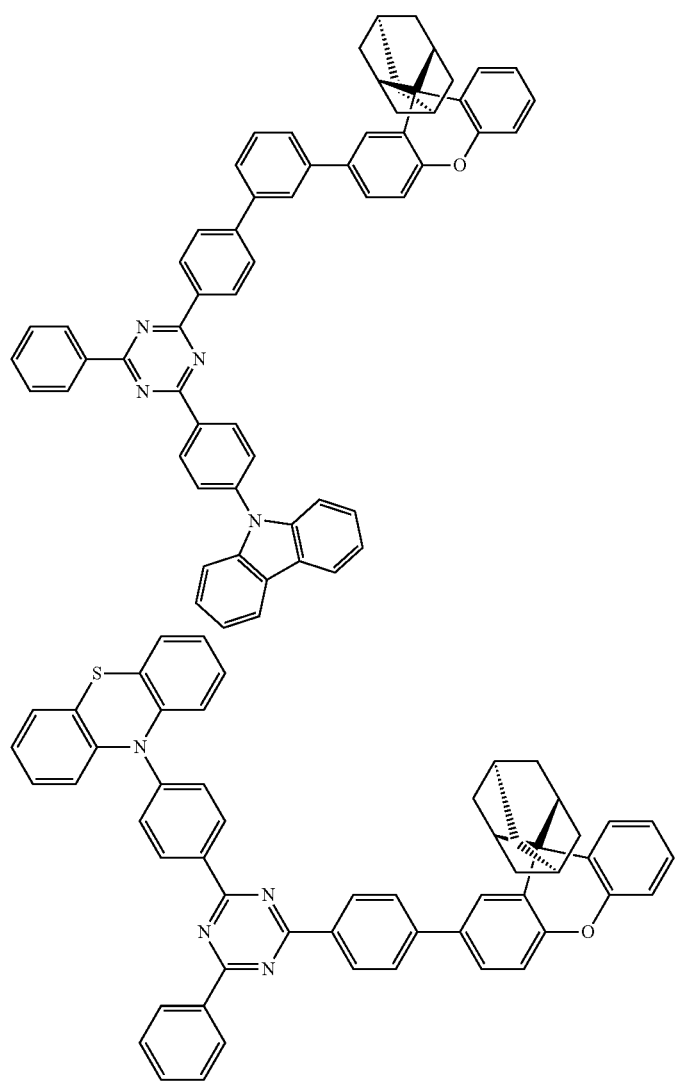

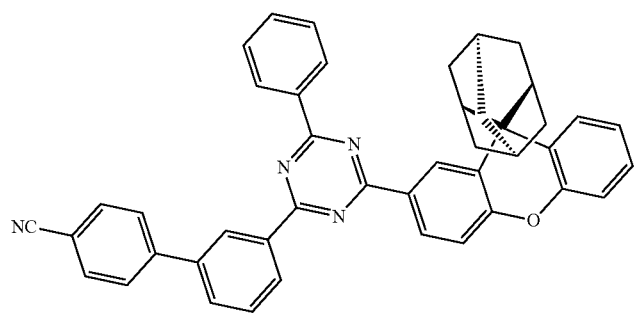
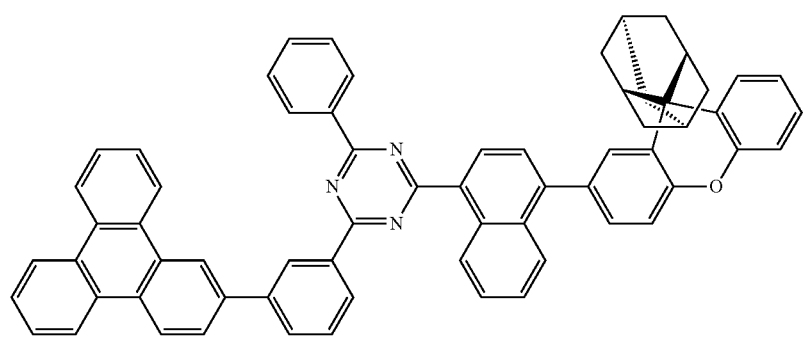
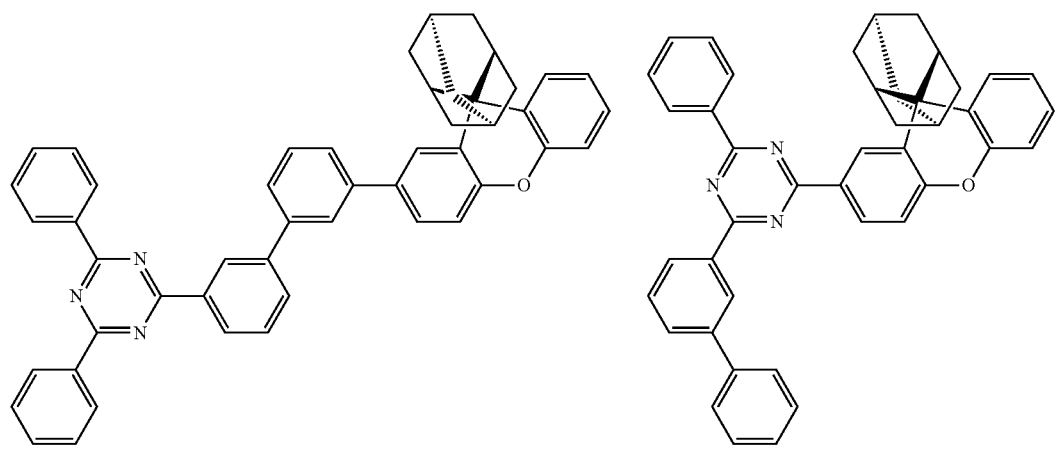
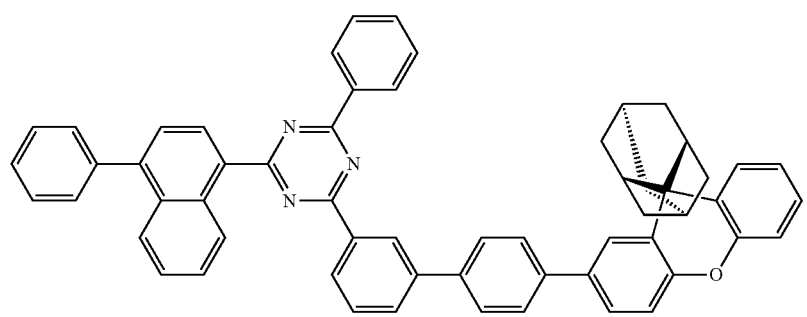

269
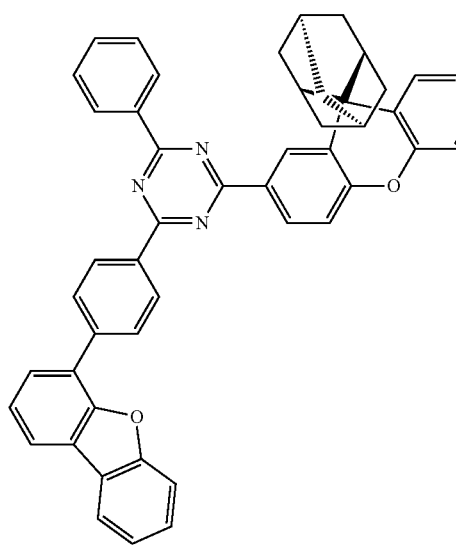
270
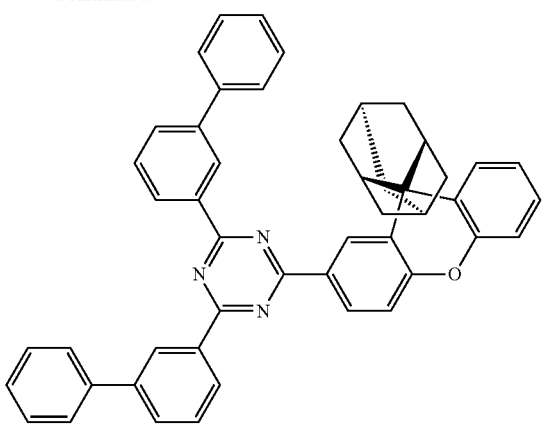
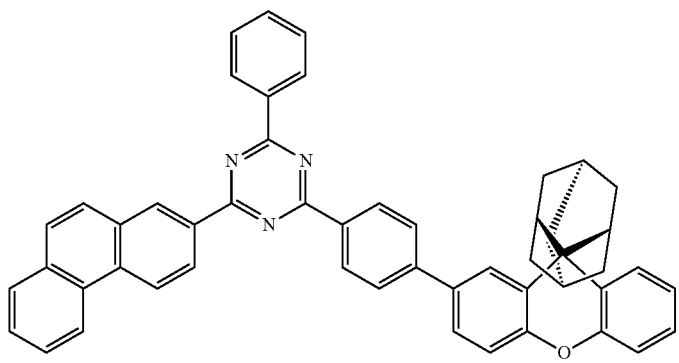
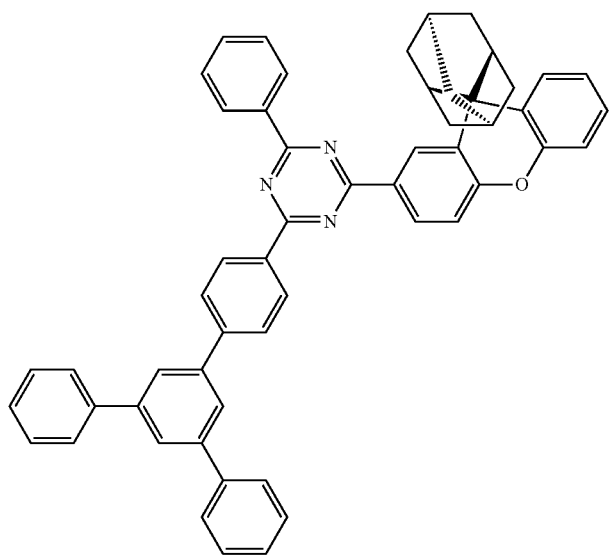

271
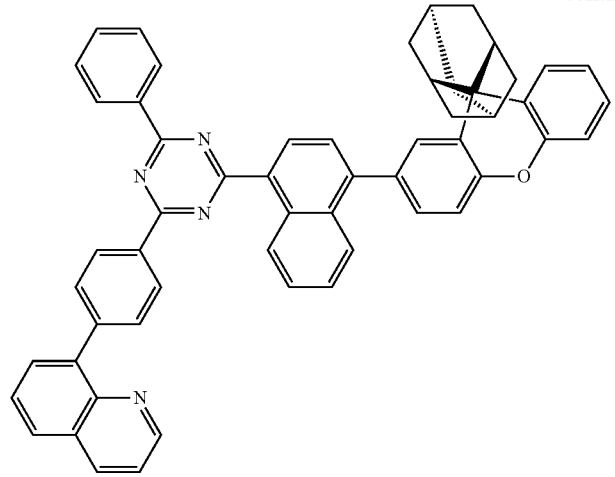
272
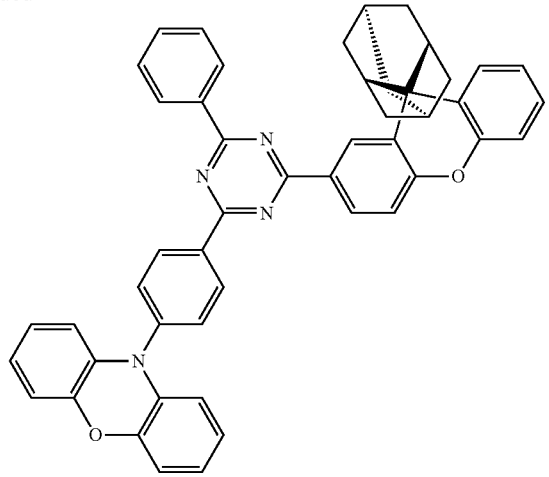
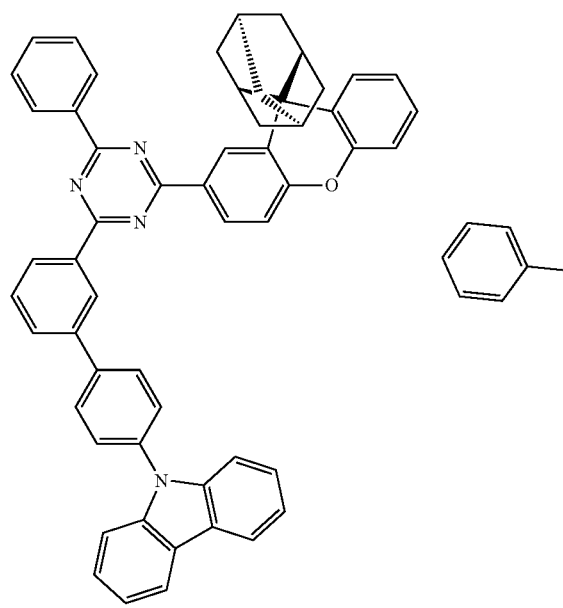
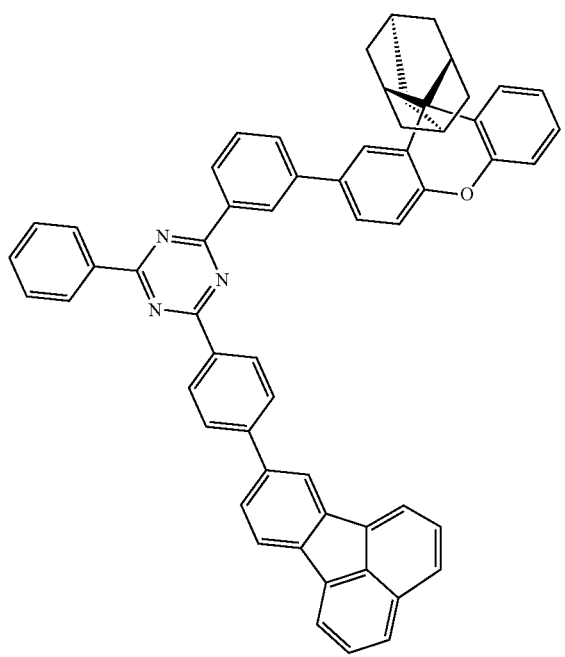
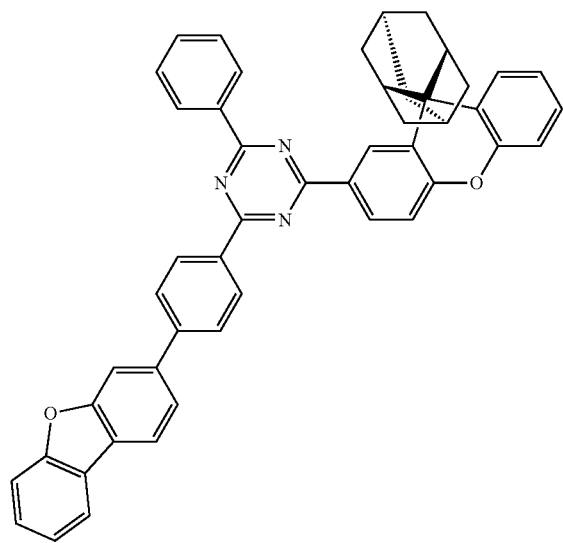
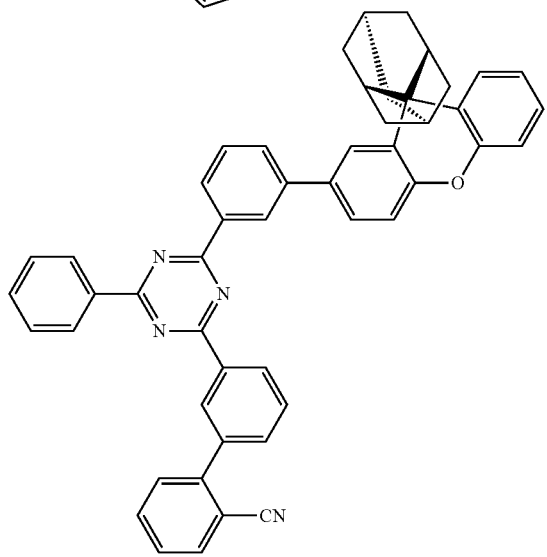

273
274
-continued
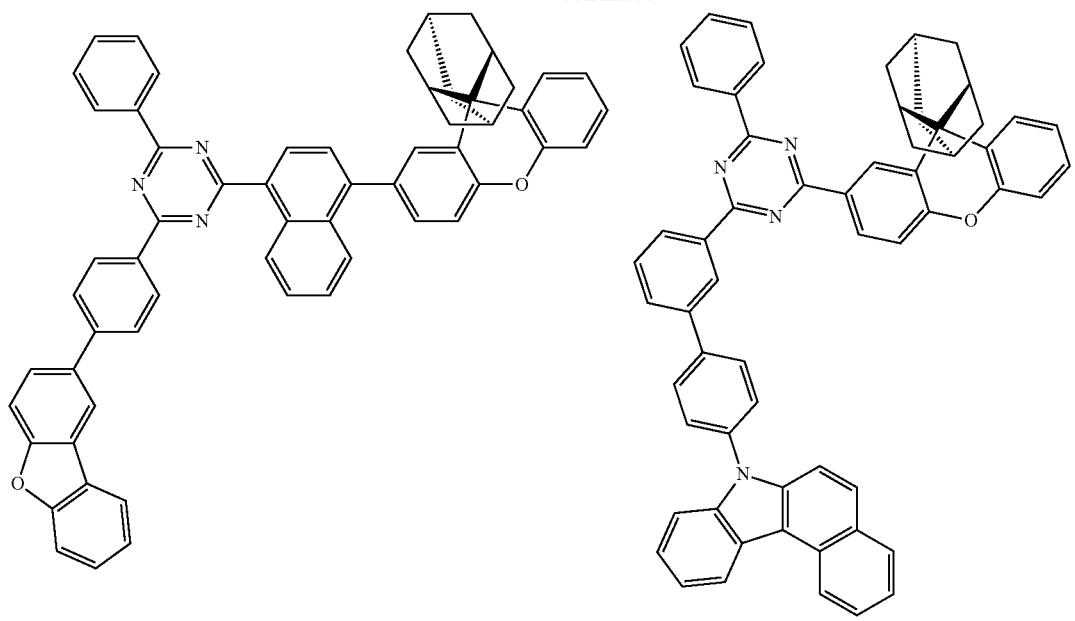
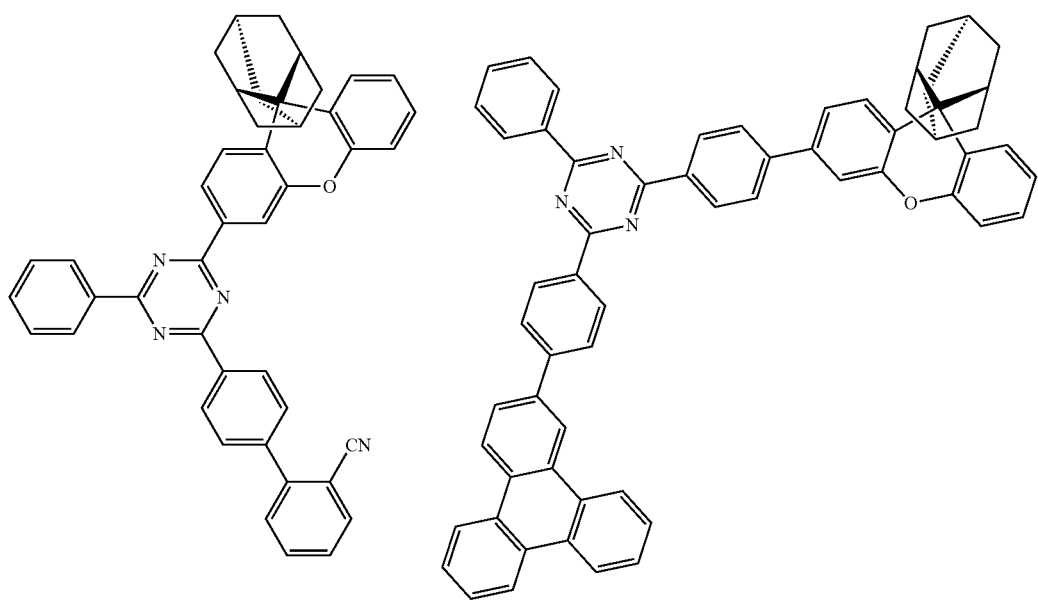

-continued
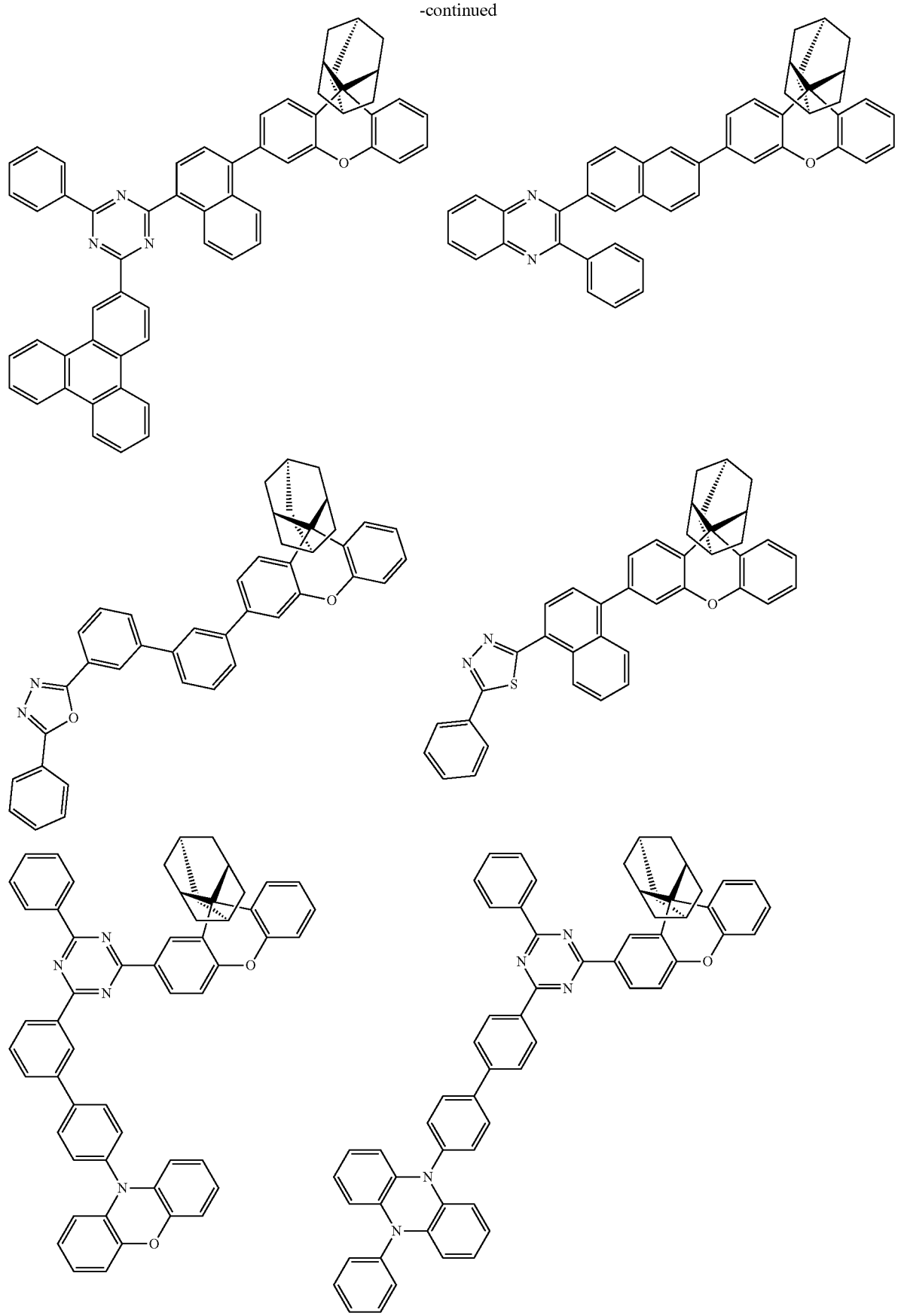

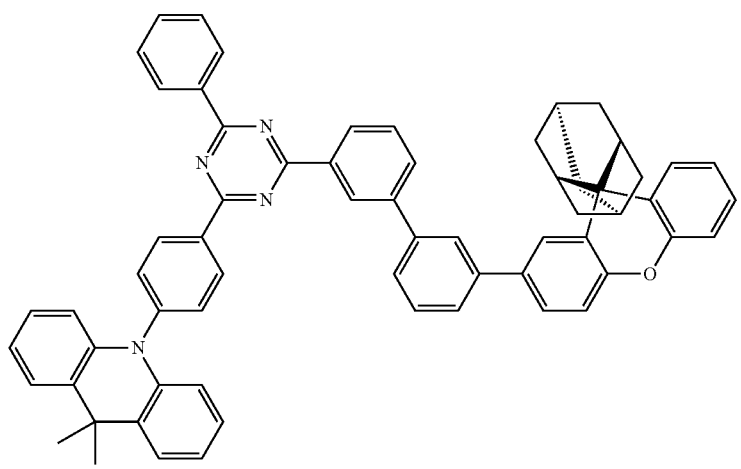
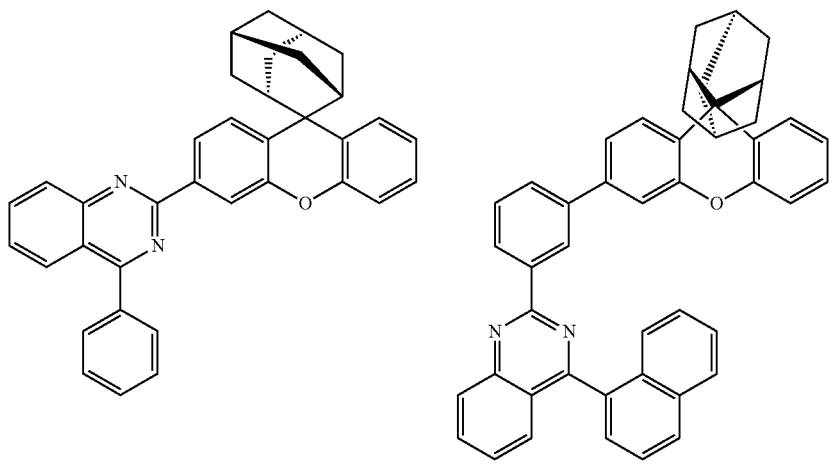
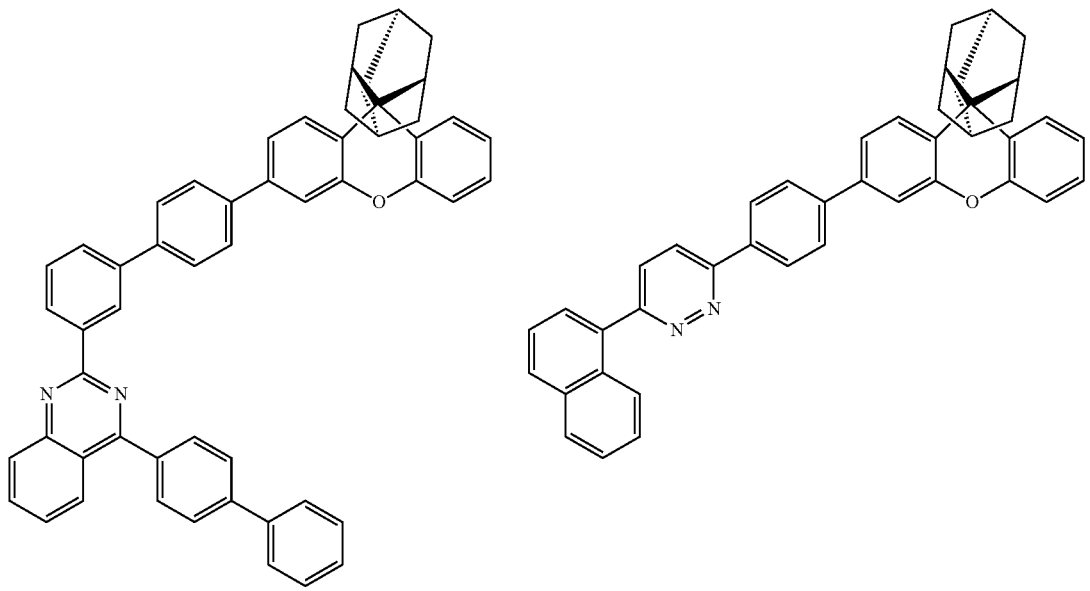

-continued
279
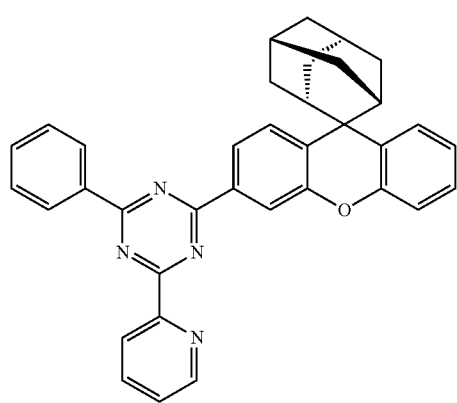
280
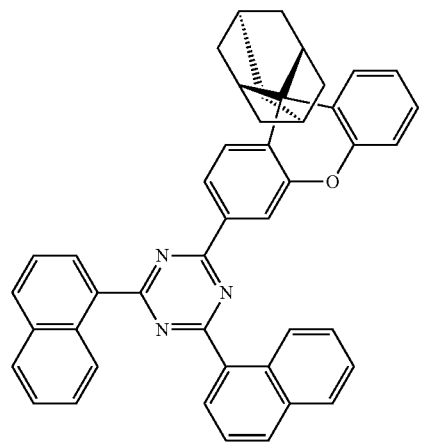
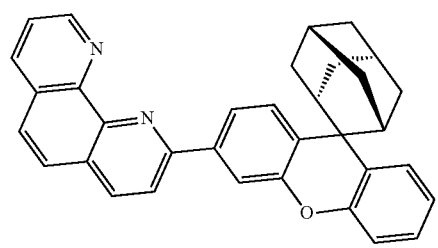
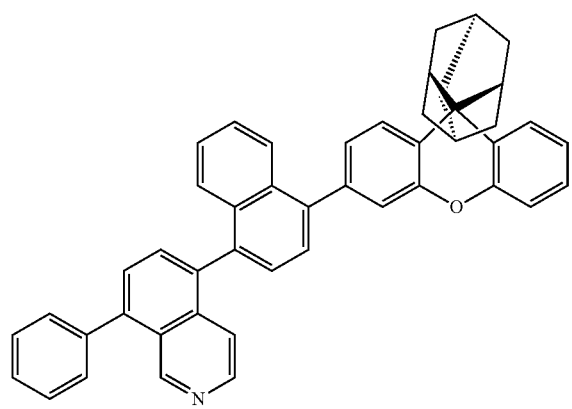
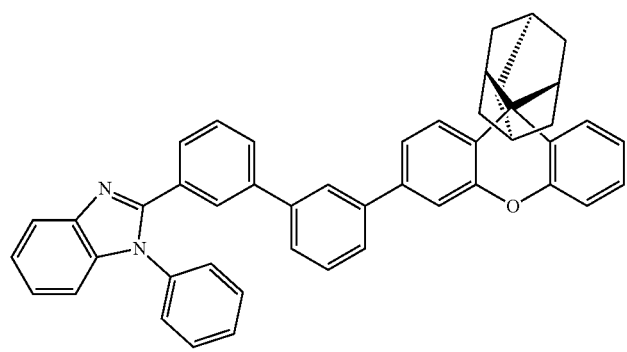
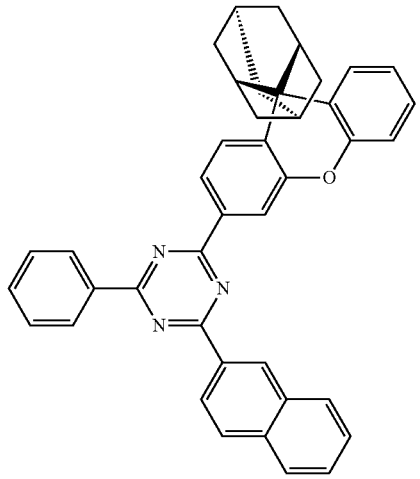

281
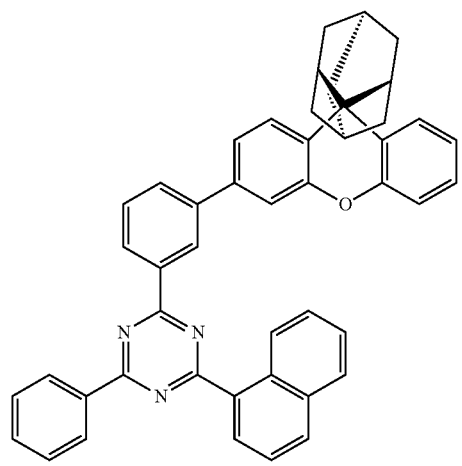
282
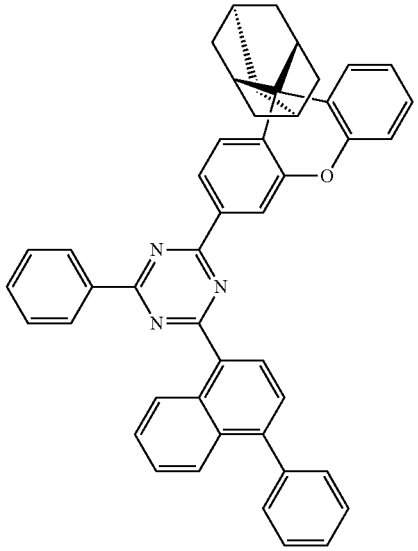
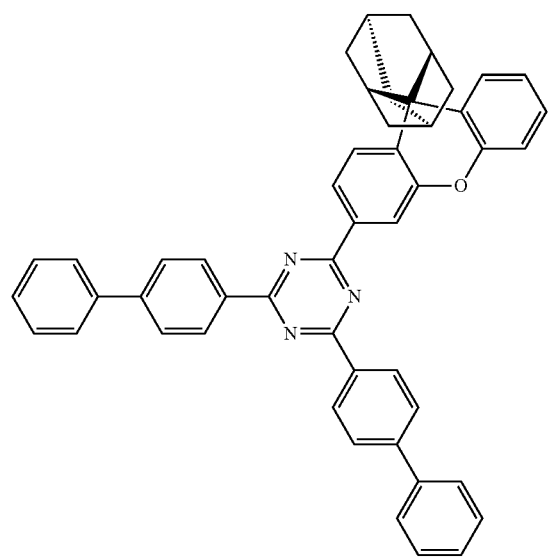
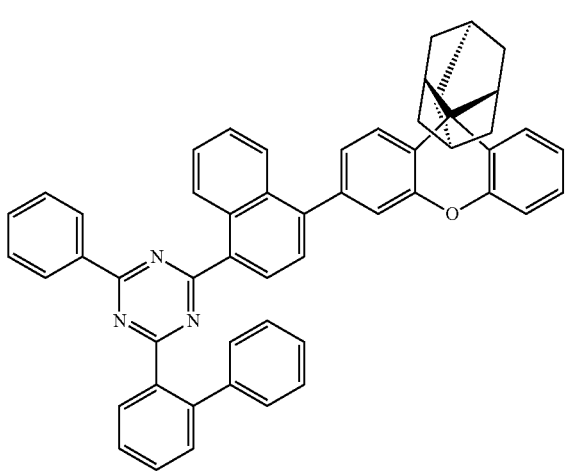
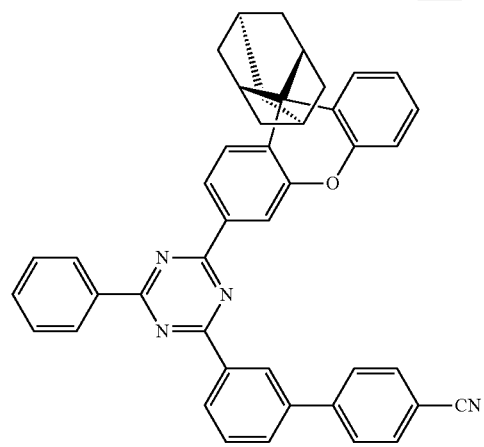
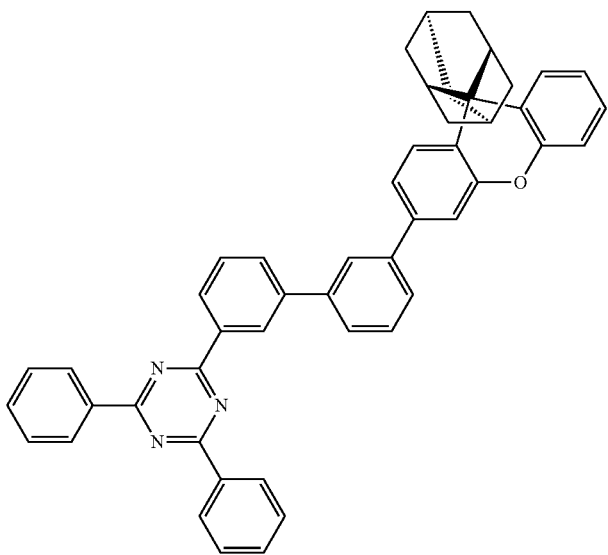

283
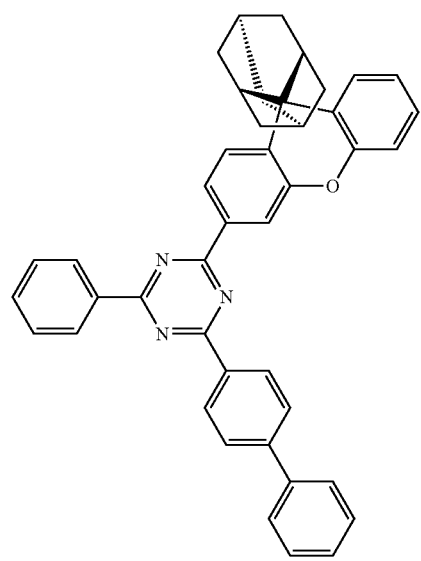
284
-continued
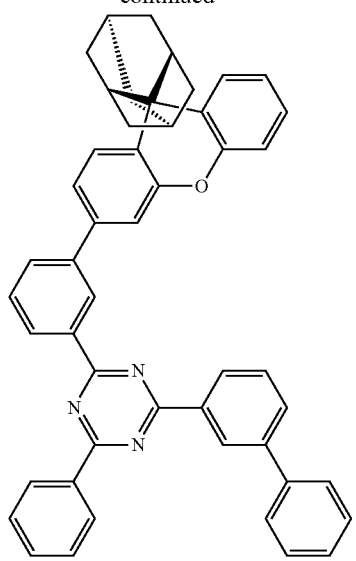
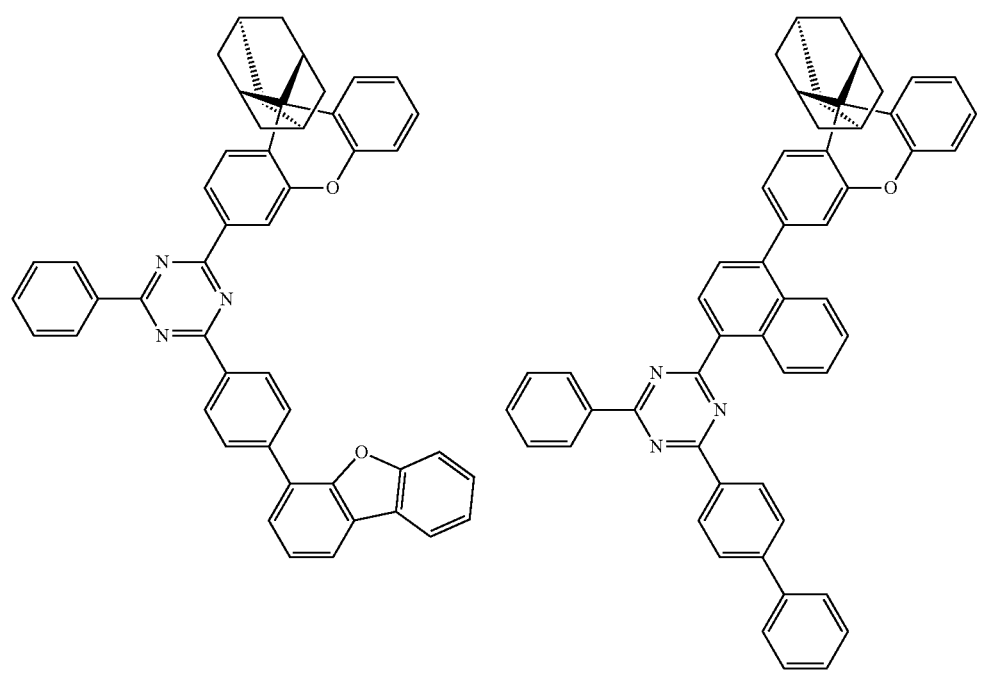

-continued
285 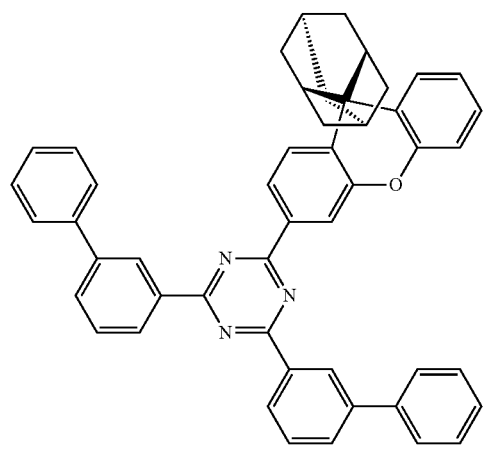
286 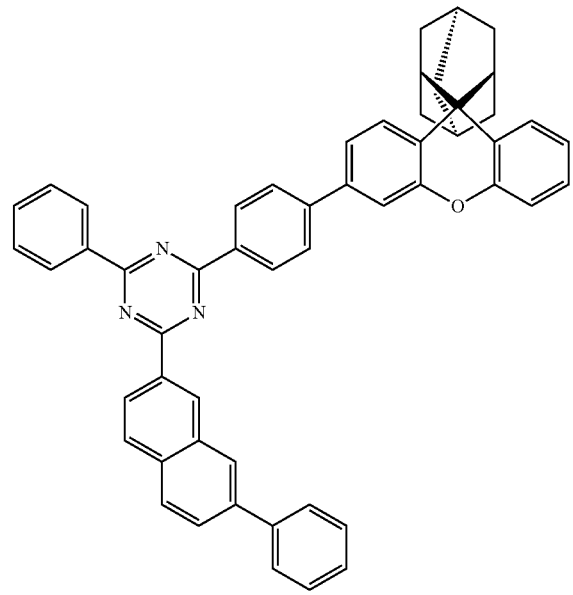
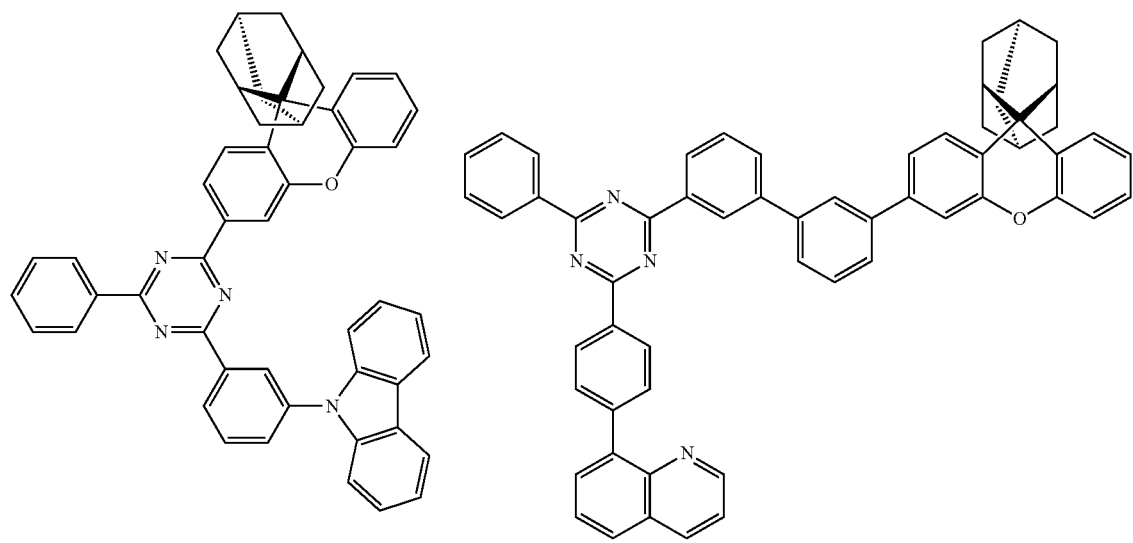
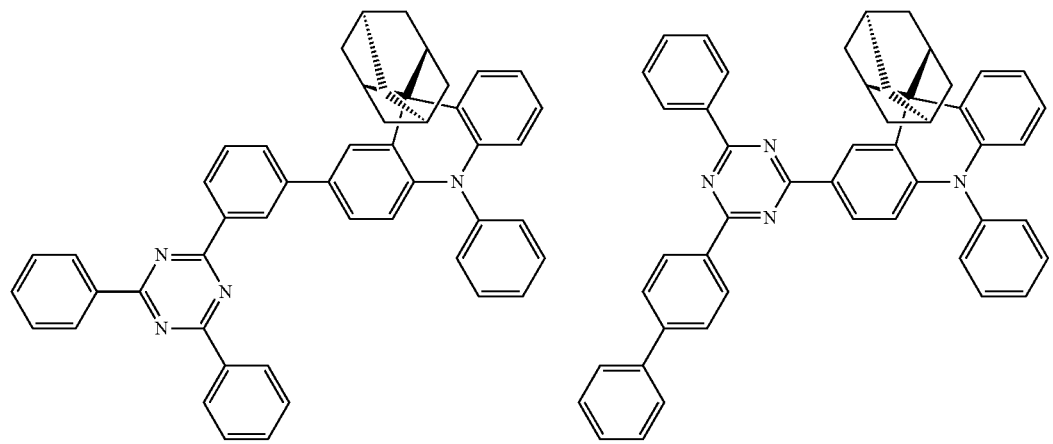

287
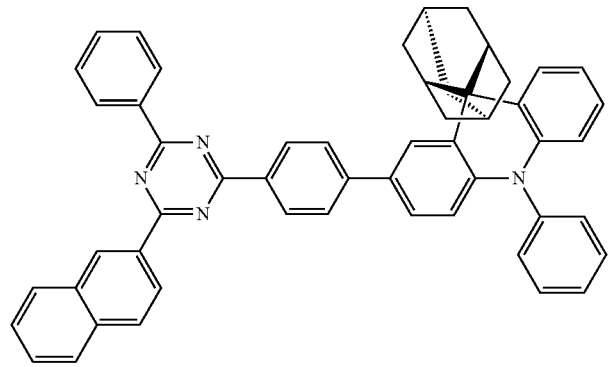
-continued
288
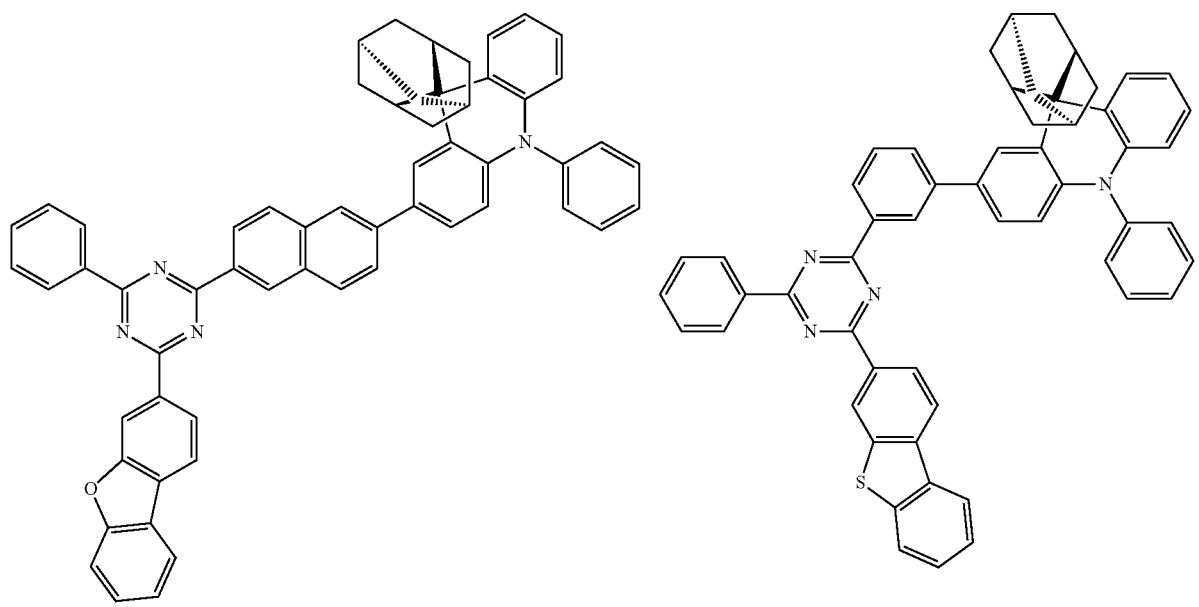
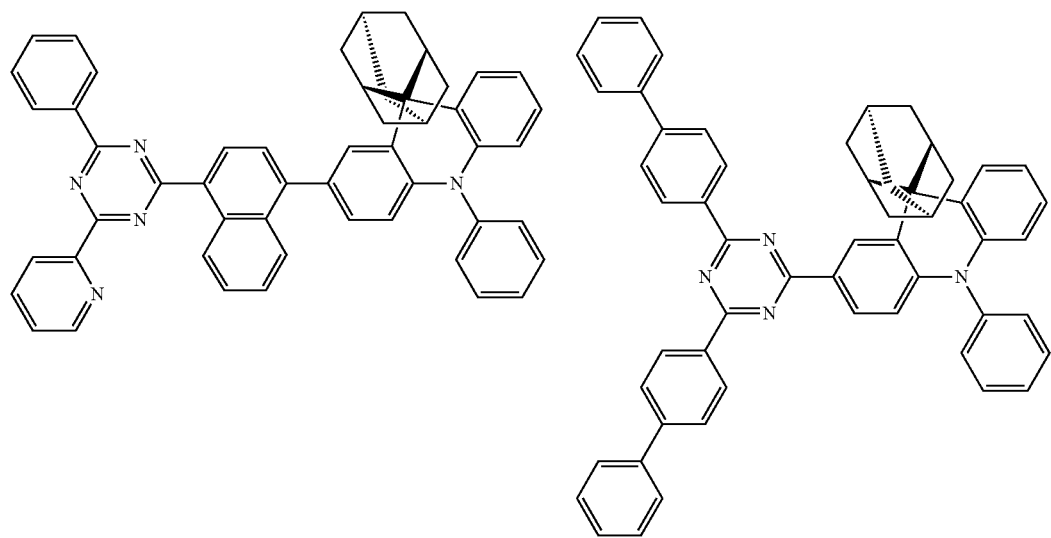

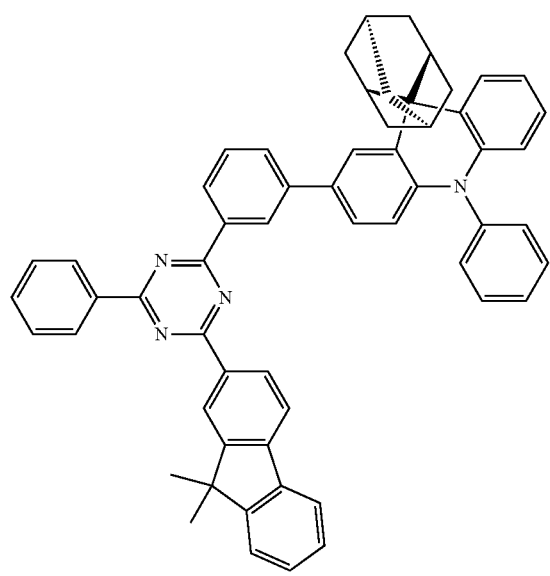
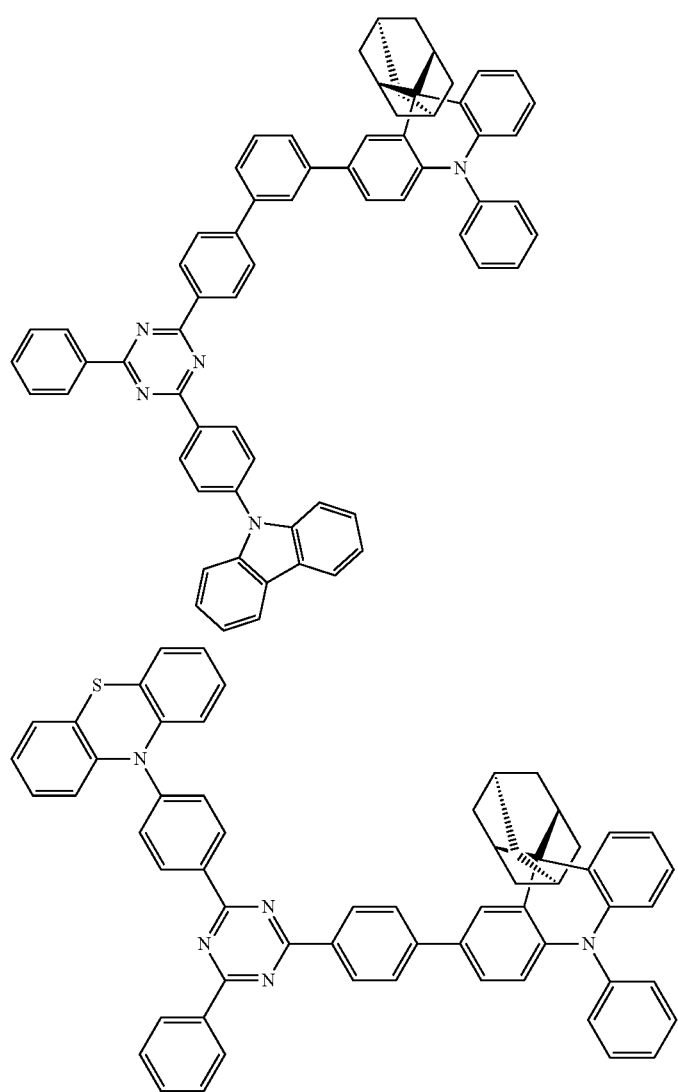

291
292
-continued
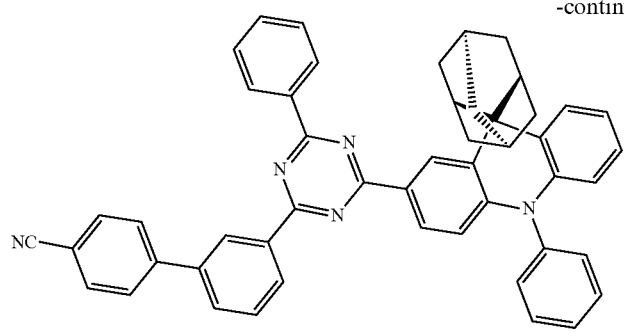
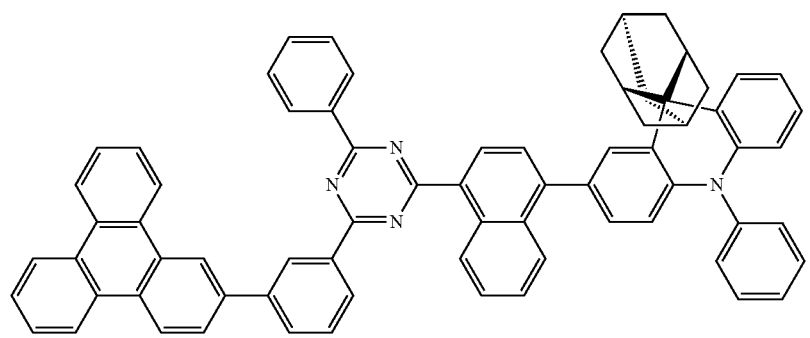
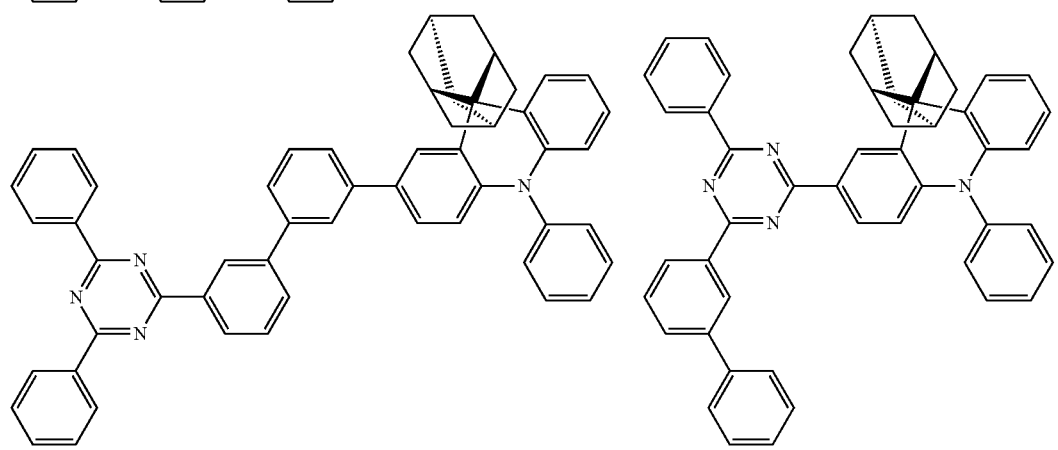
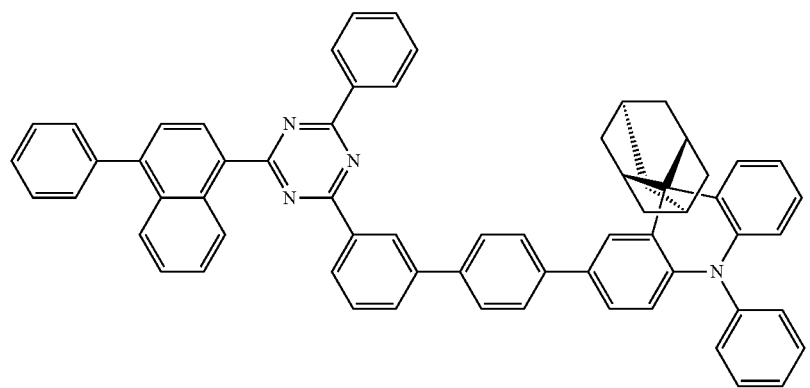

293
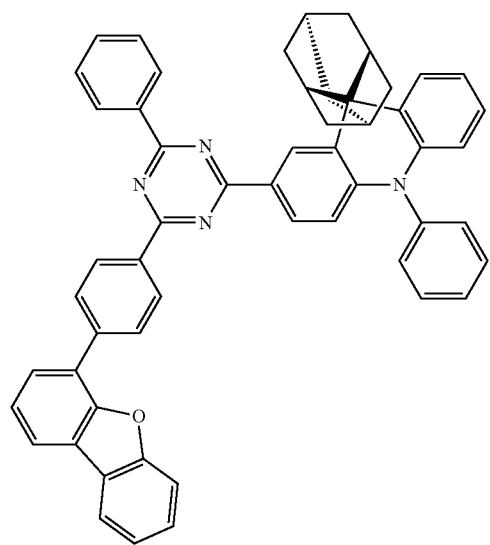
294
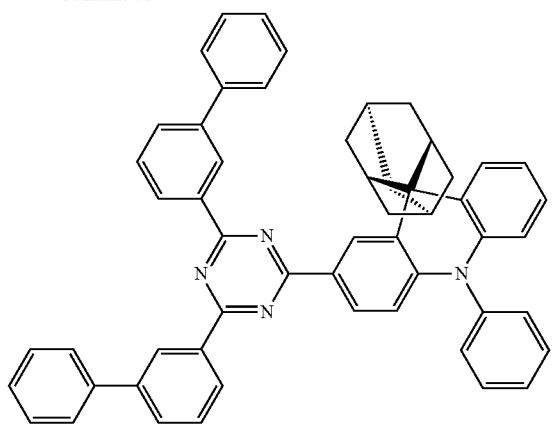
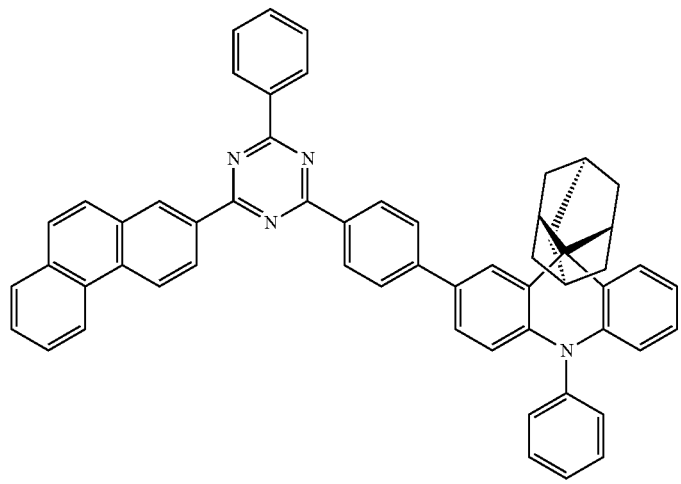
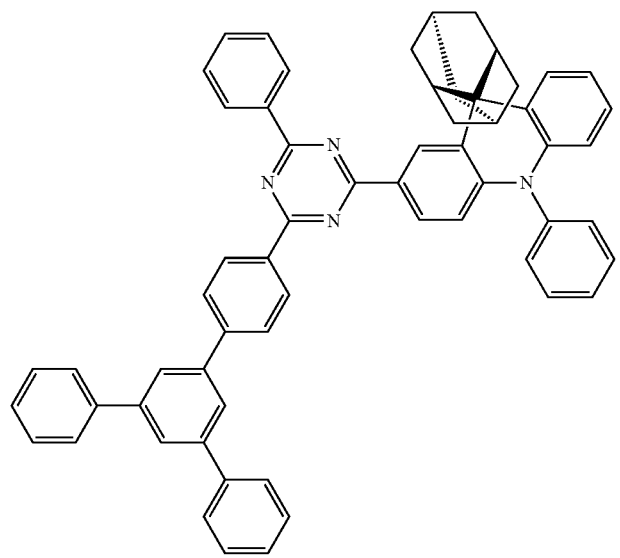

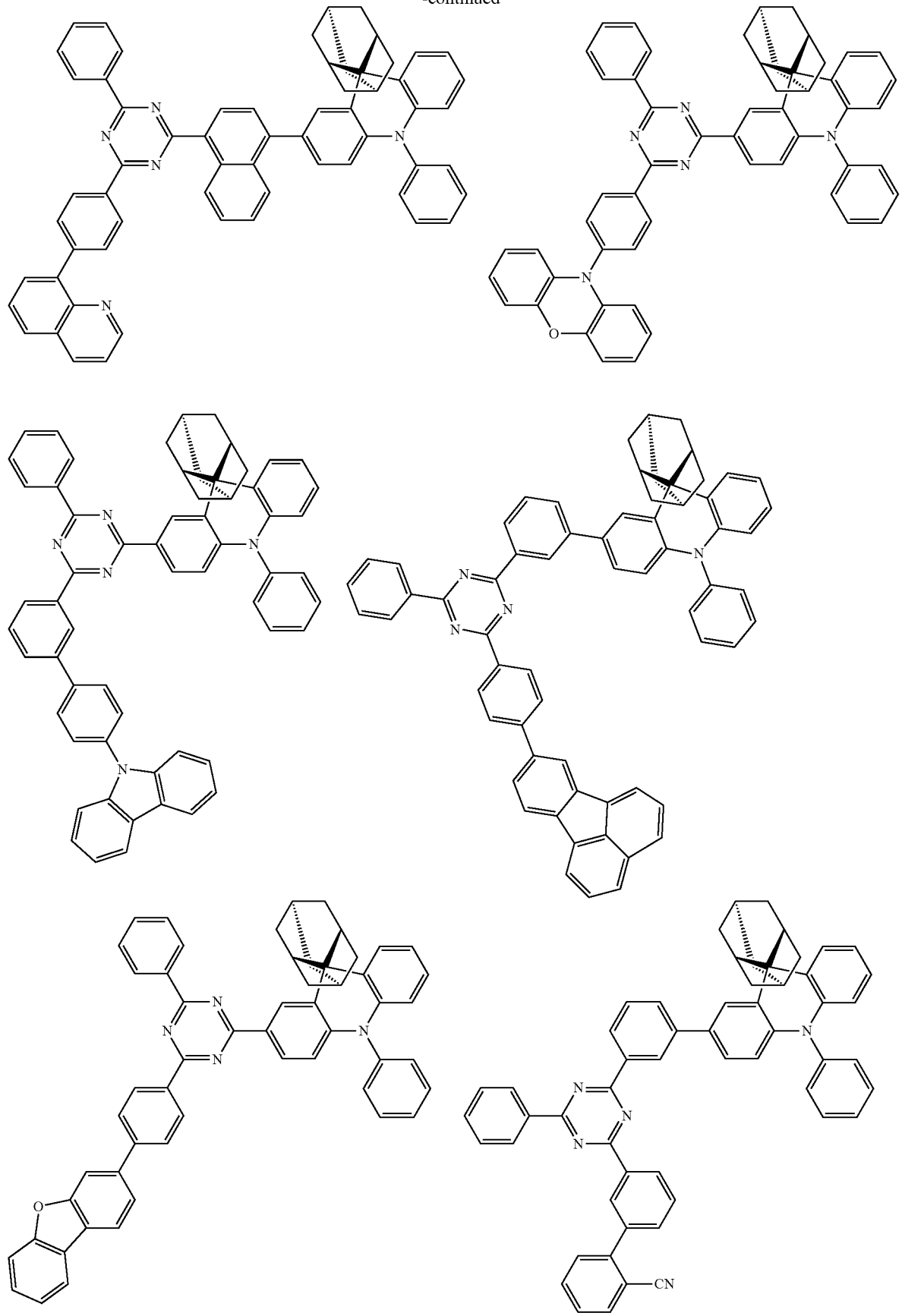

297 298
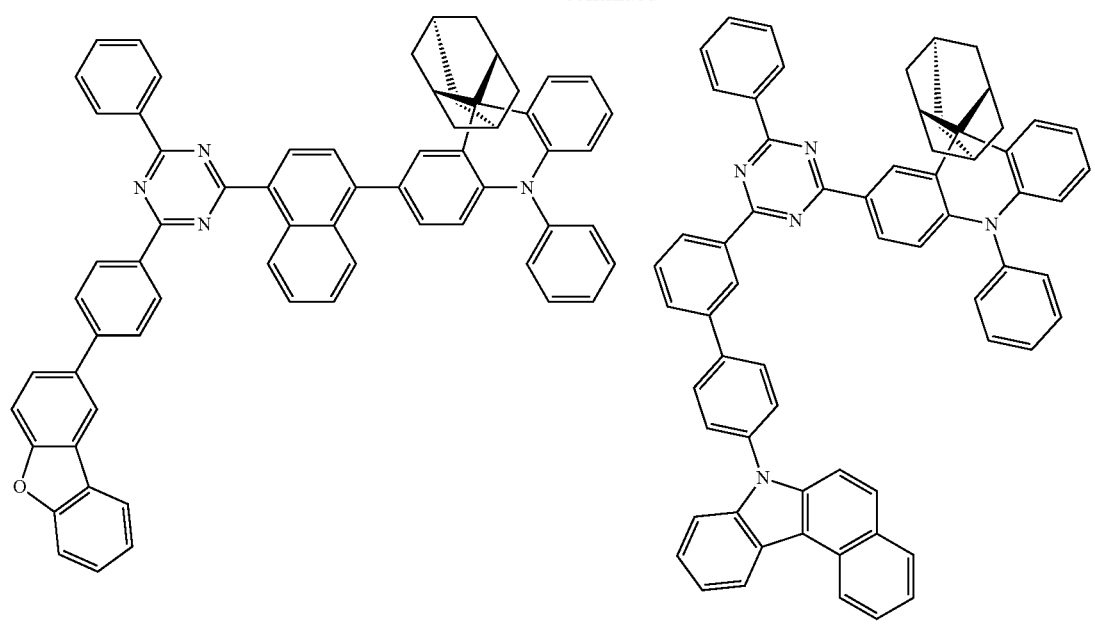
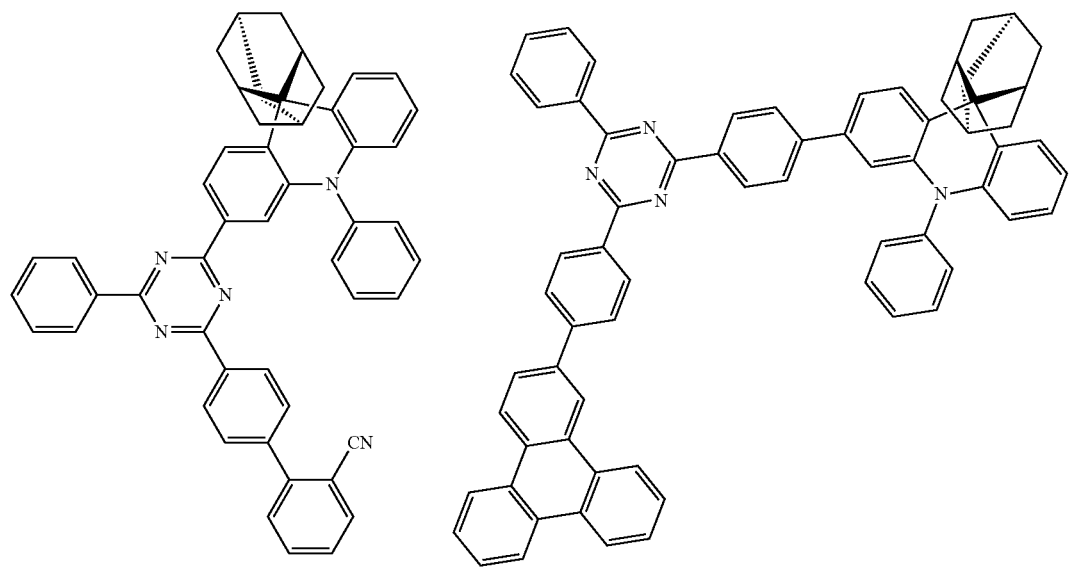

299 300
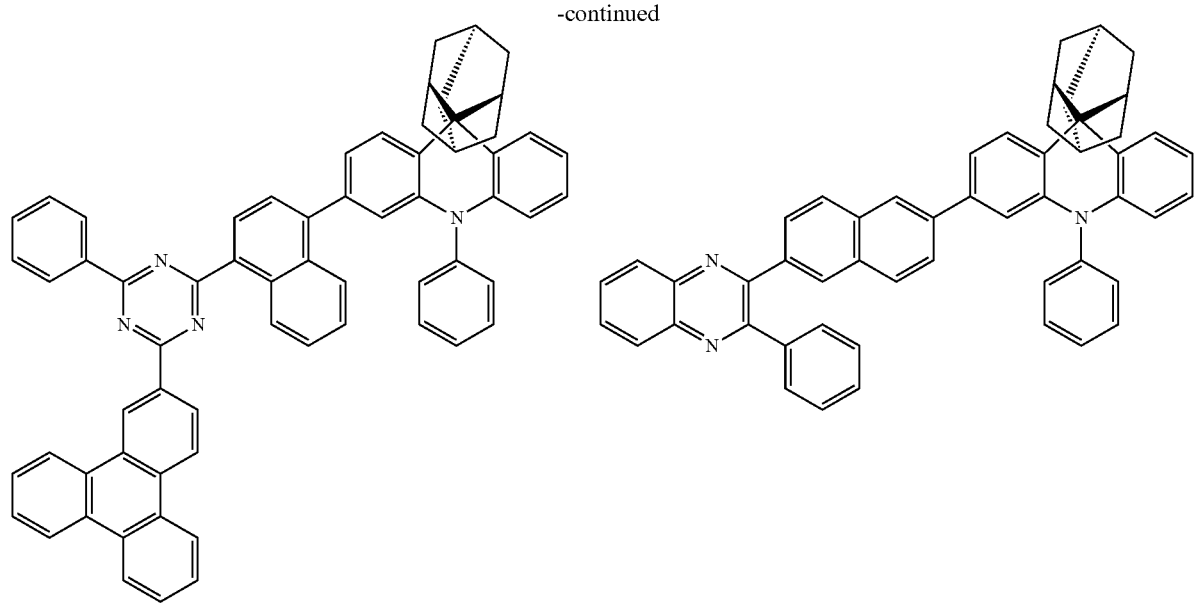
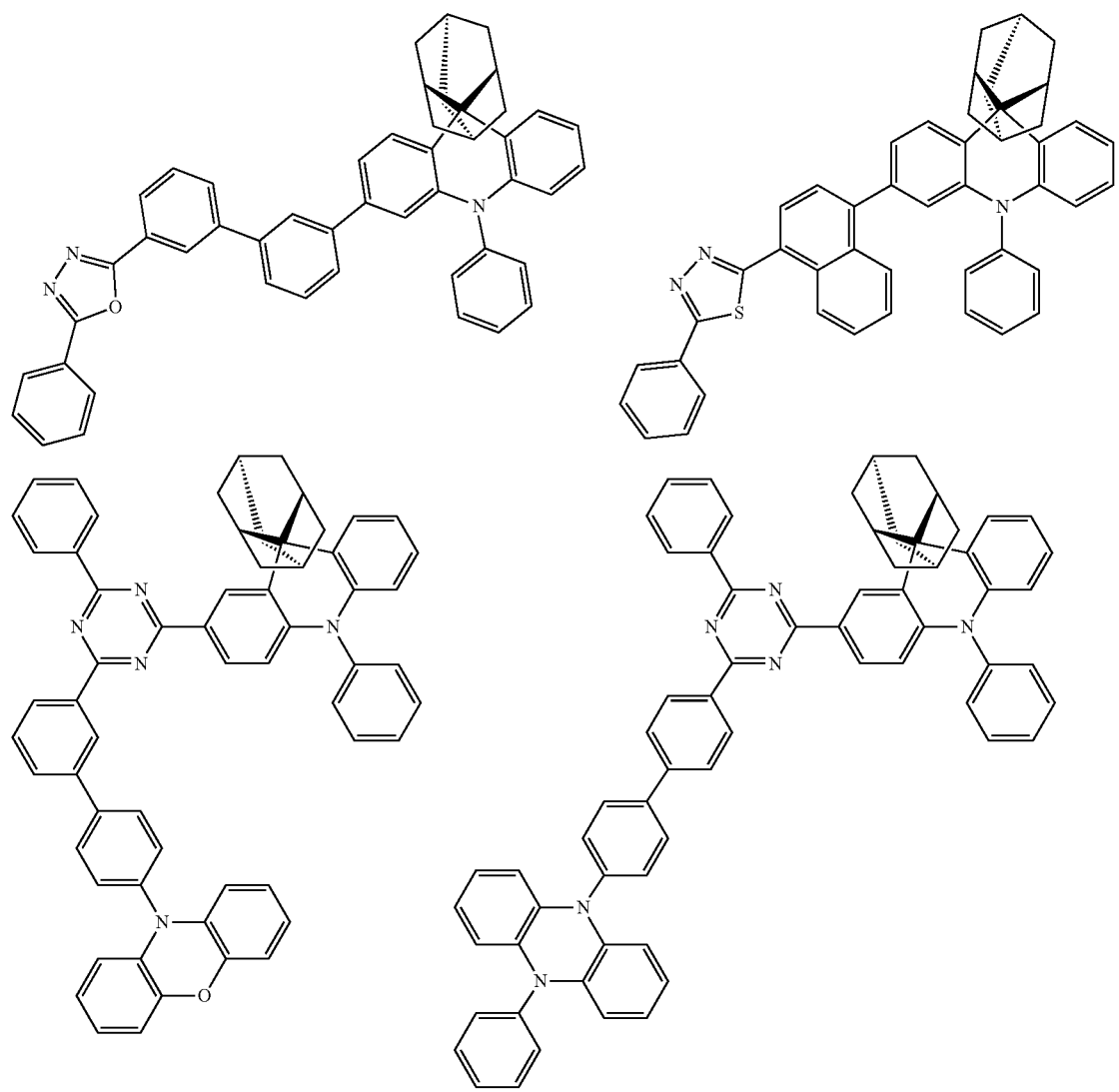

301
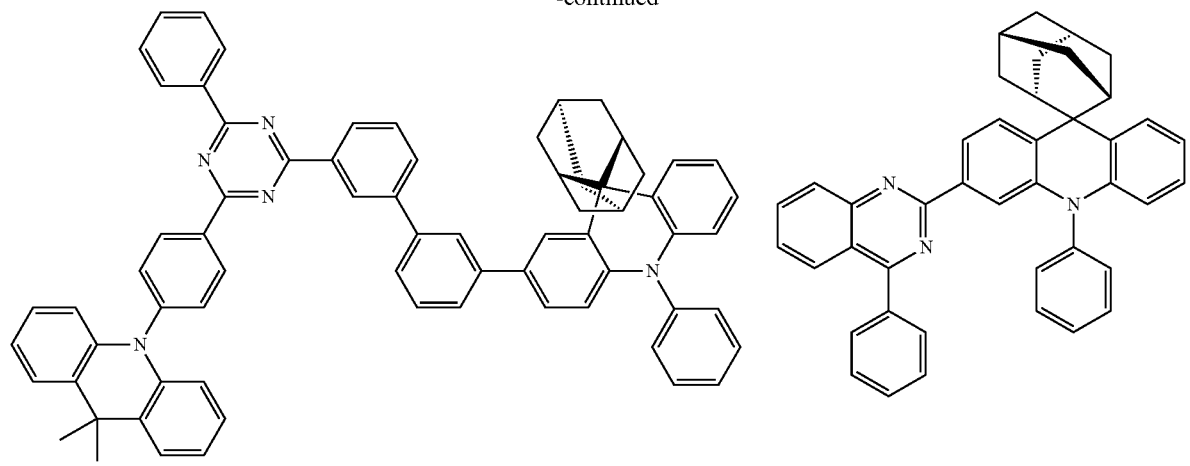
302
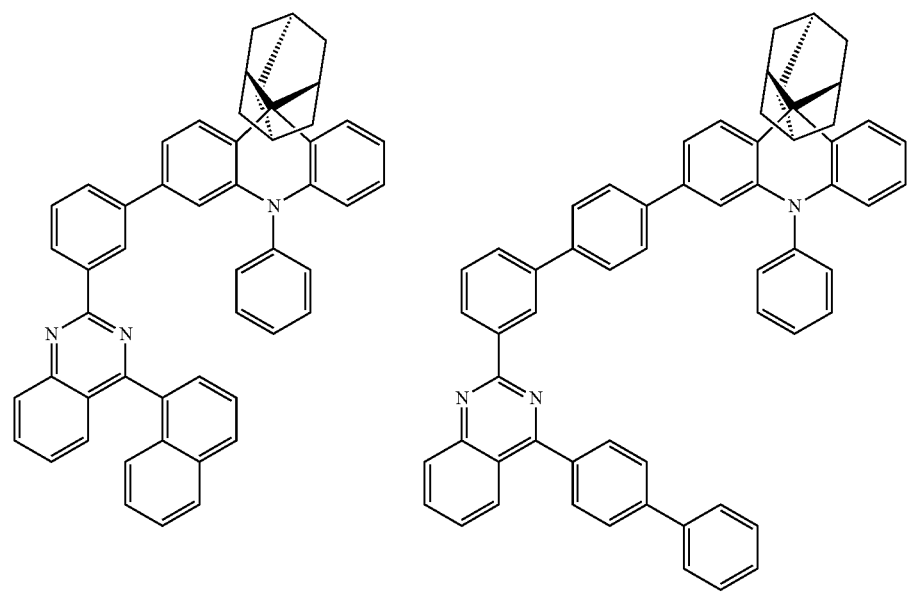
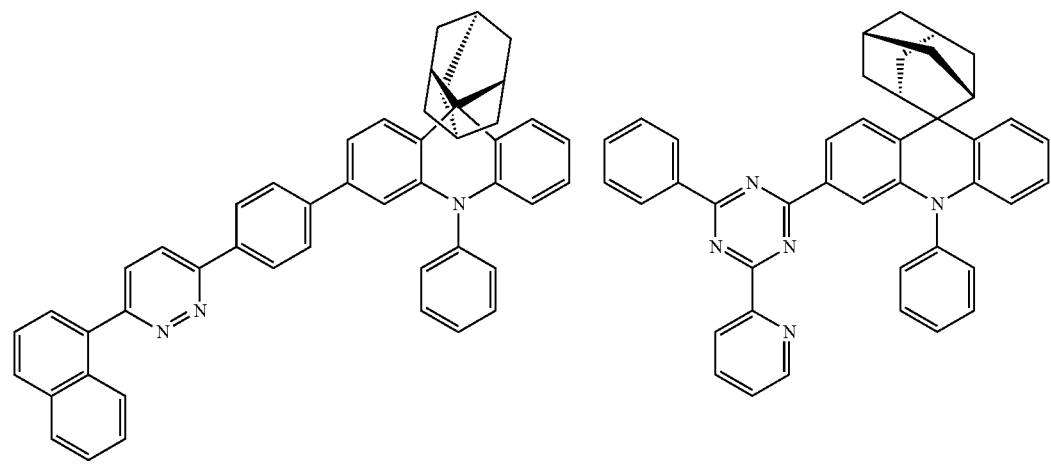

-continued
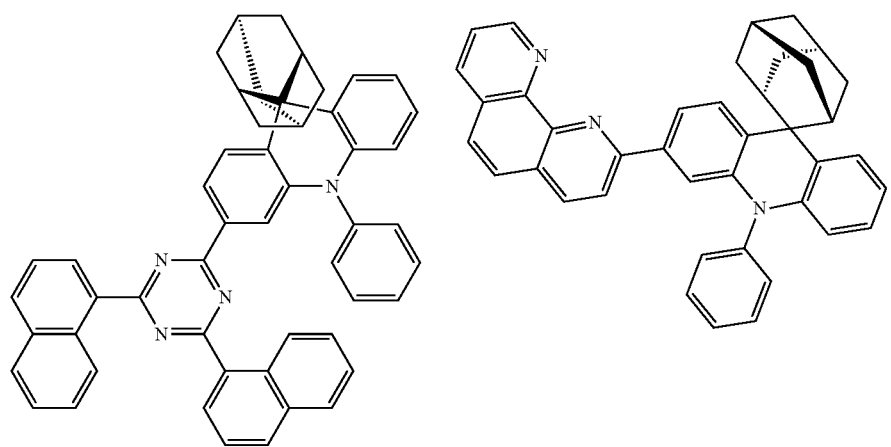
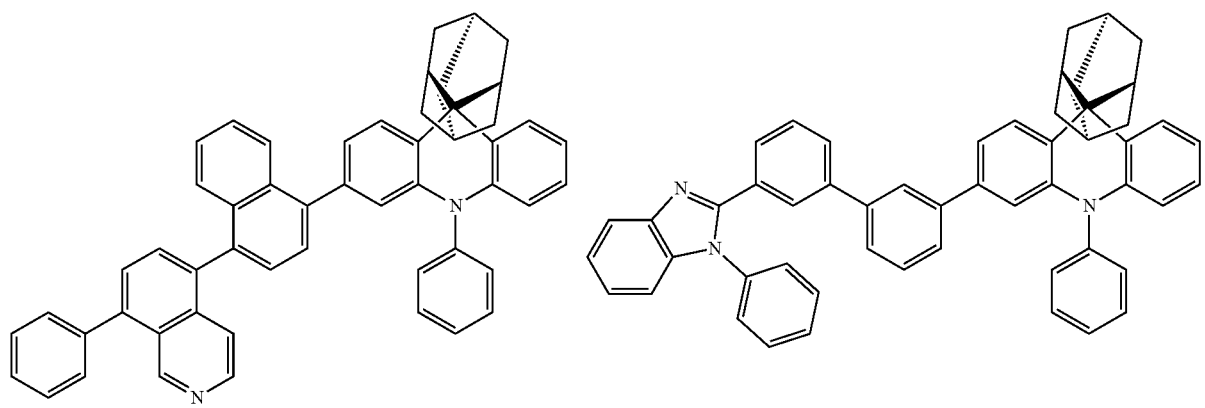
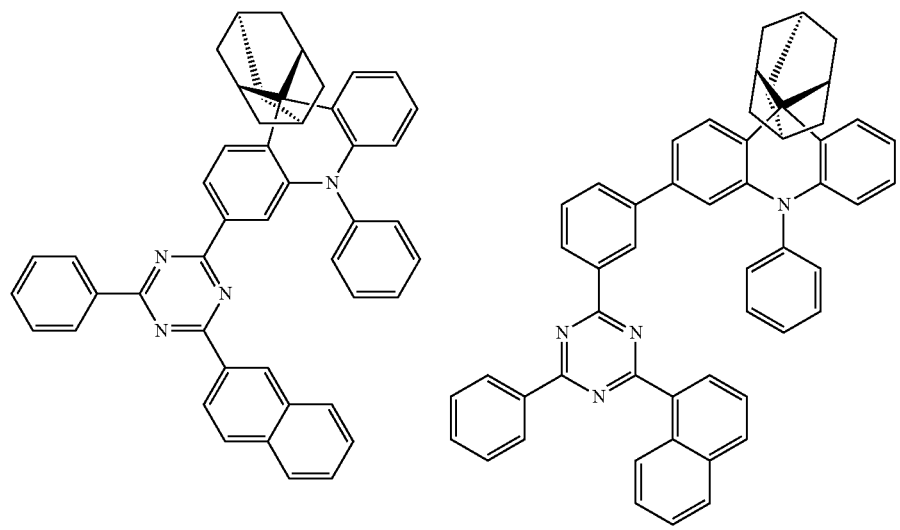

305 306
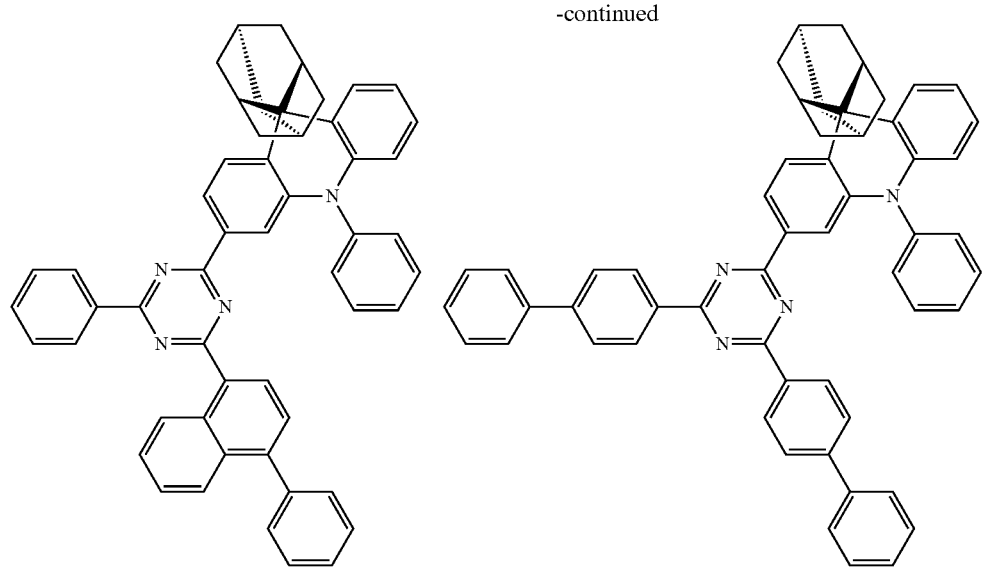
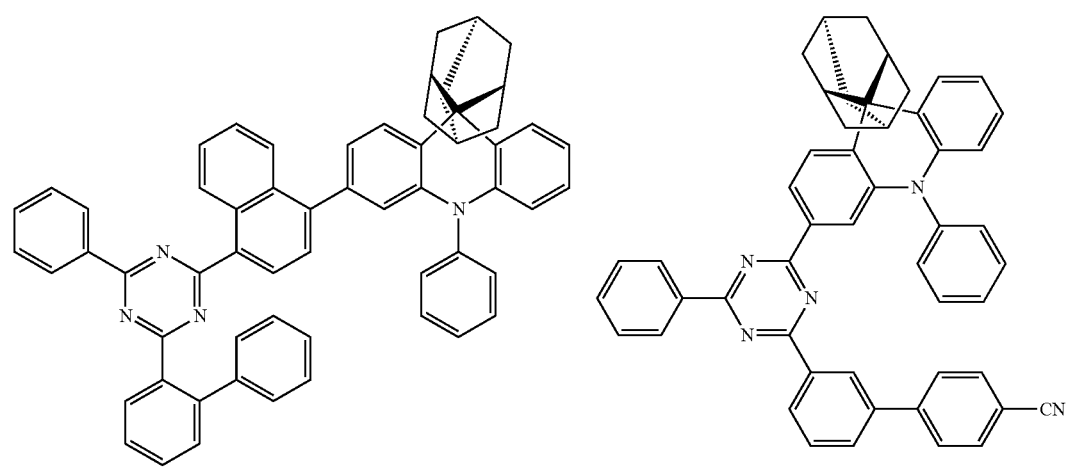
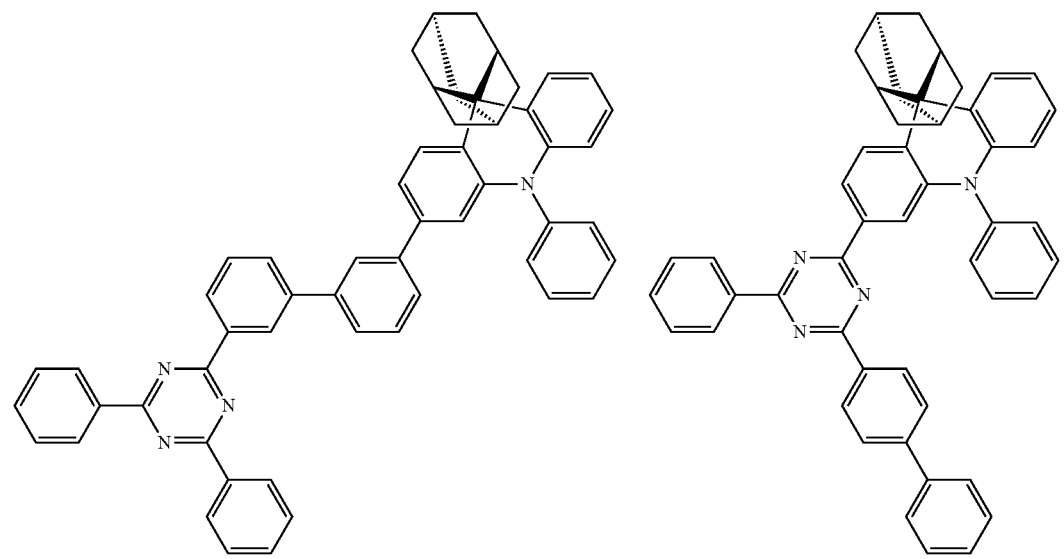

307
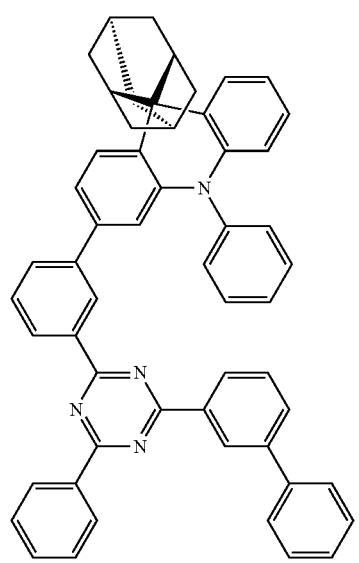
308
-continued
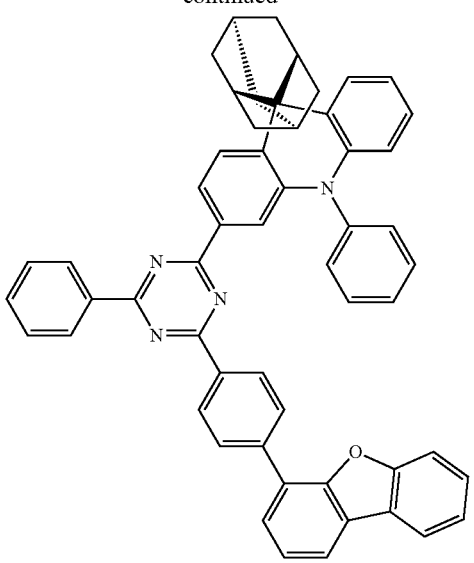
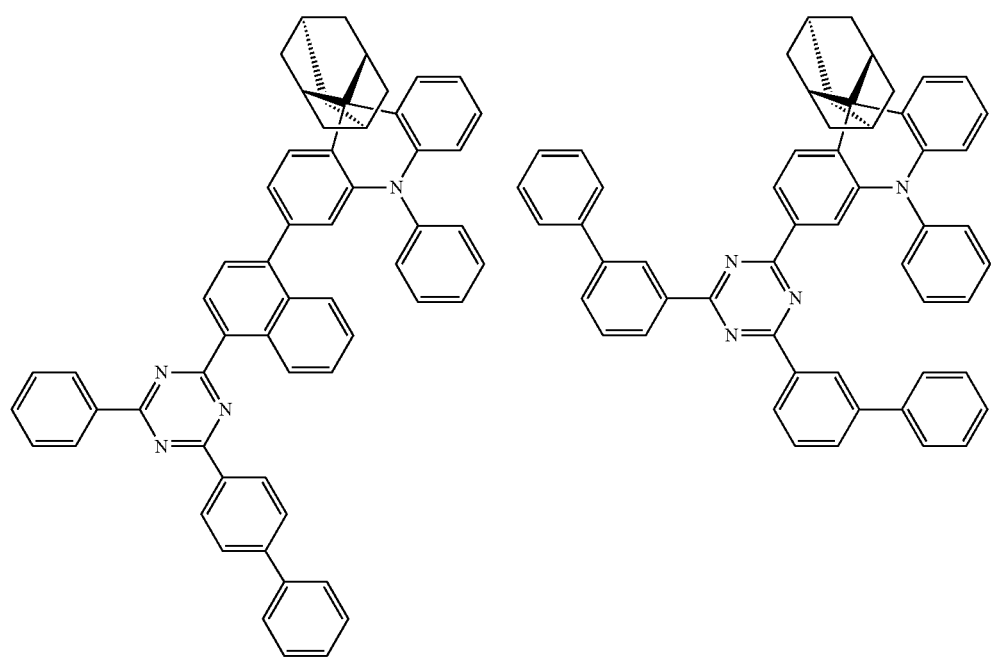

-continued
309
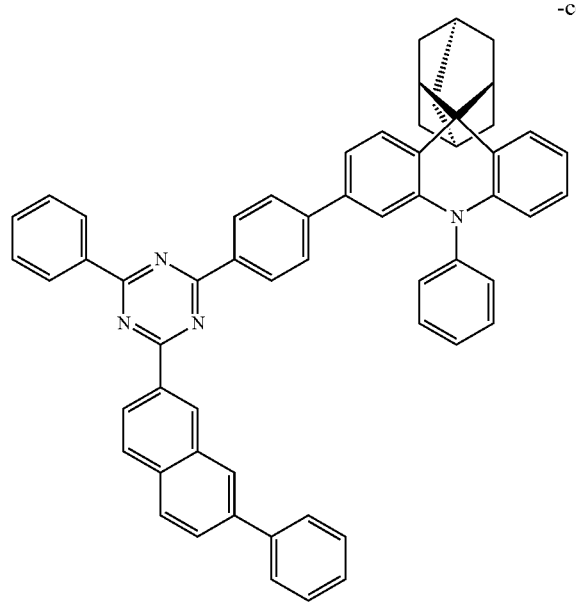
310
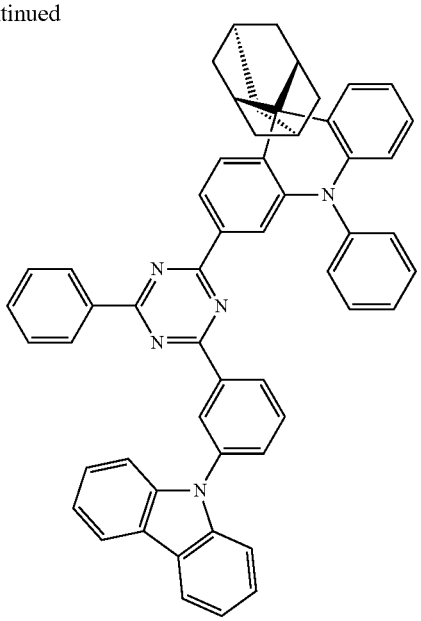
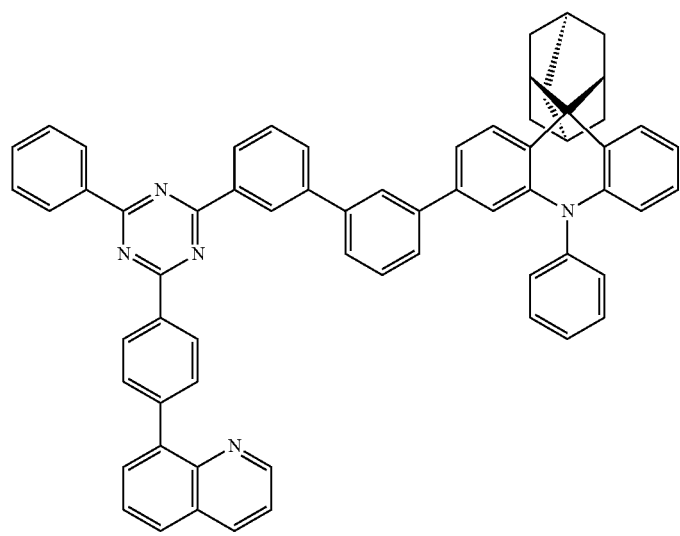
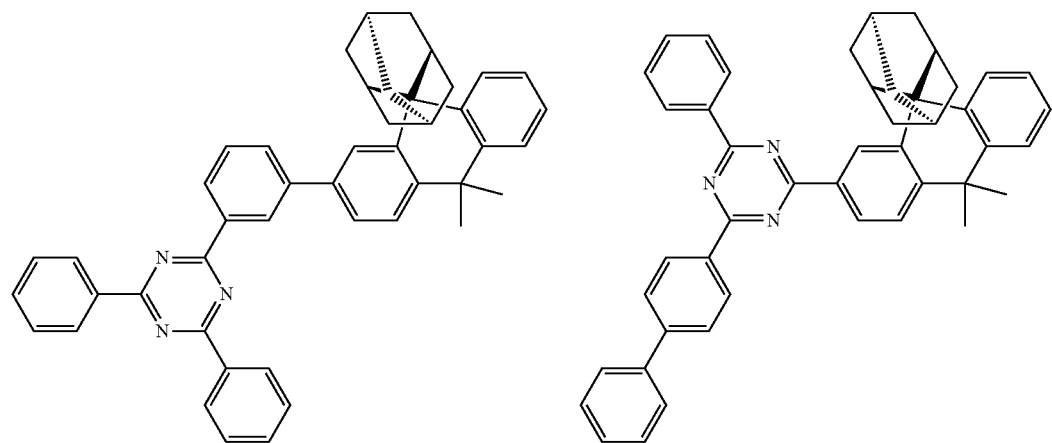

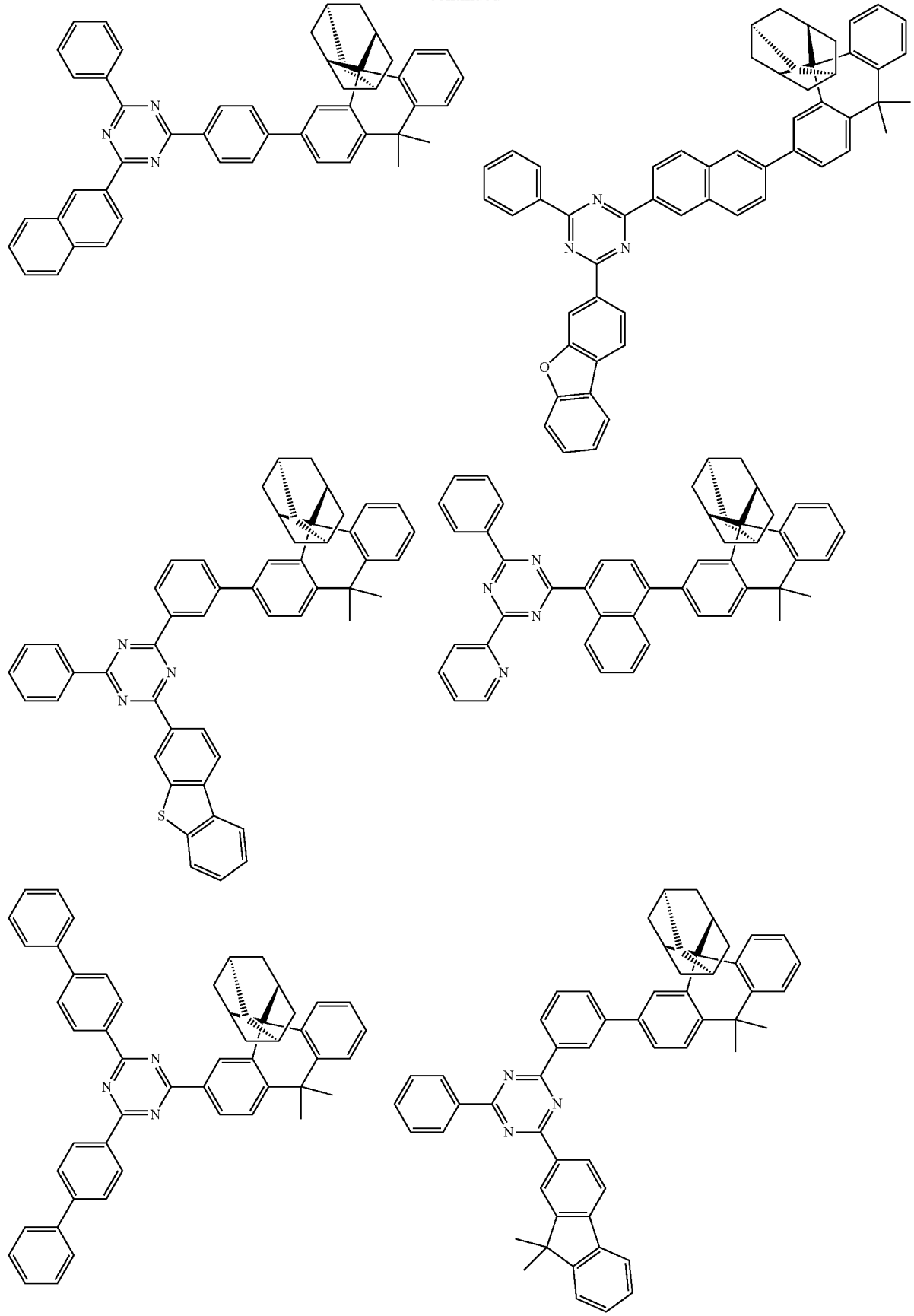

-continued
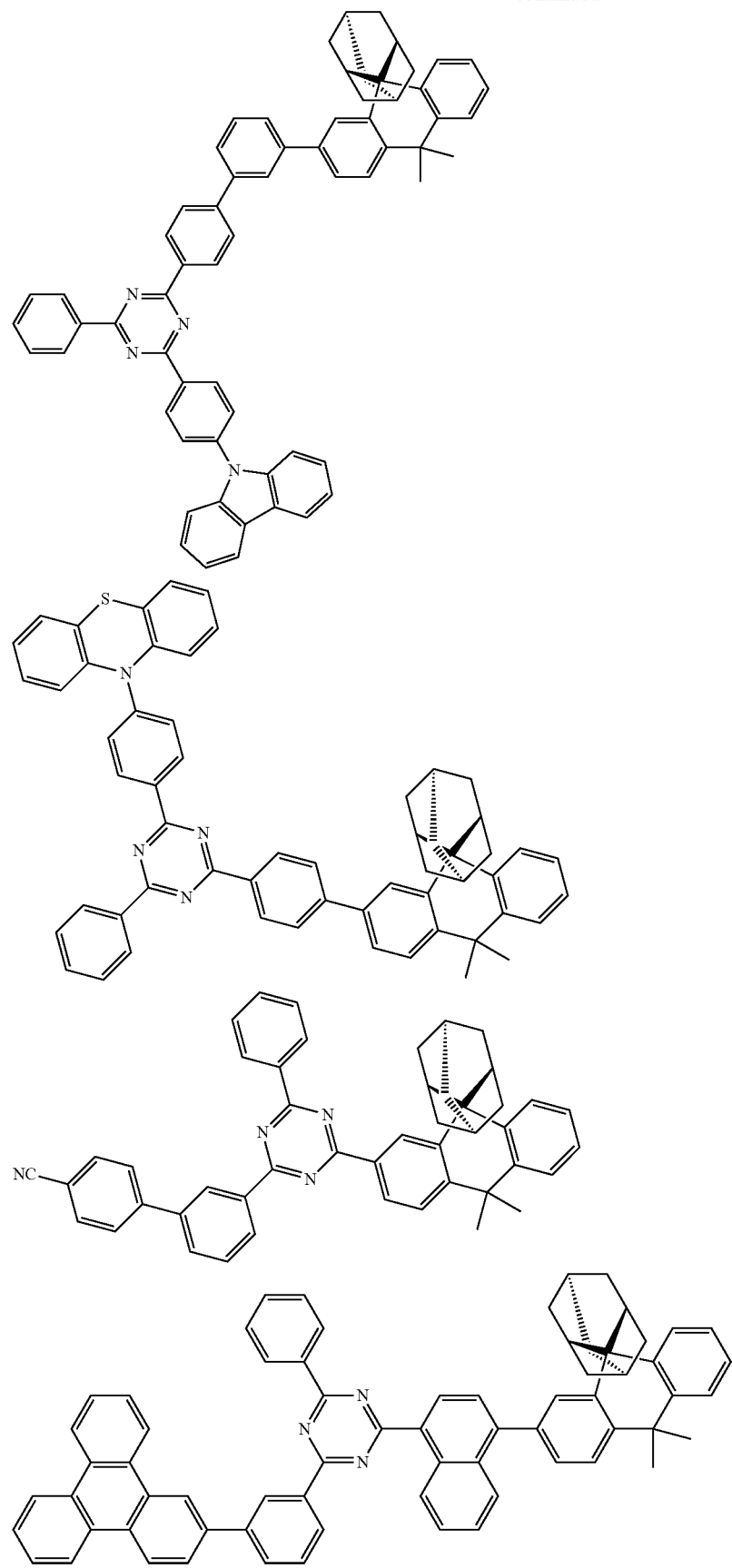

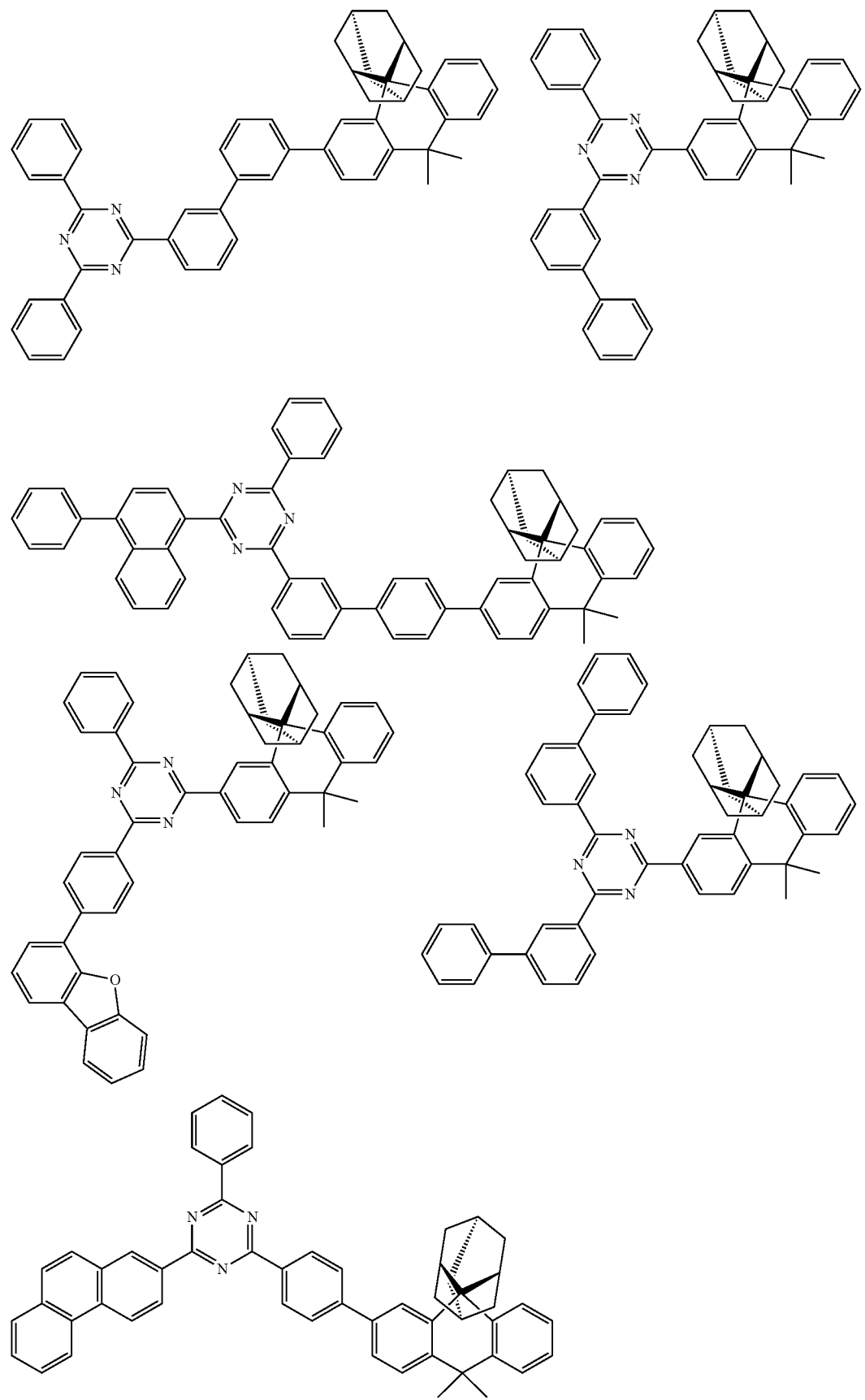

-continued
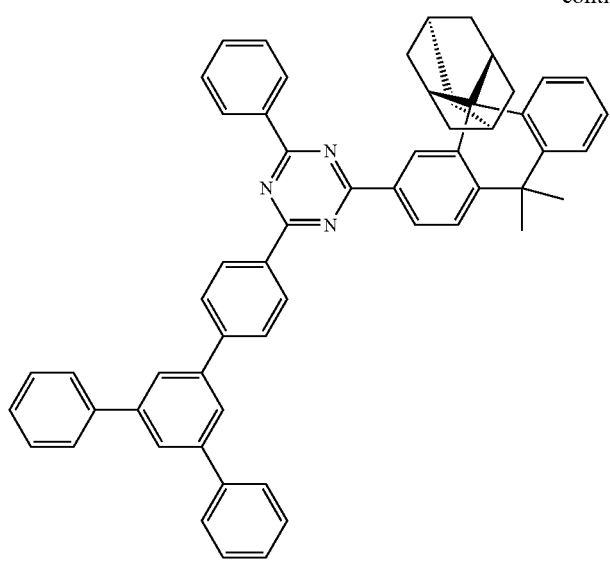
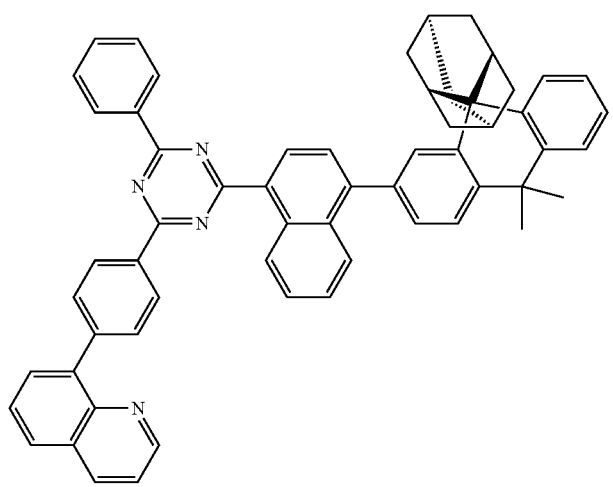
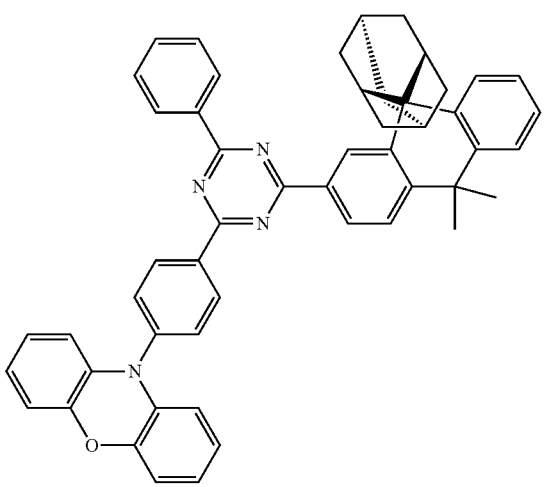
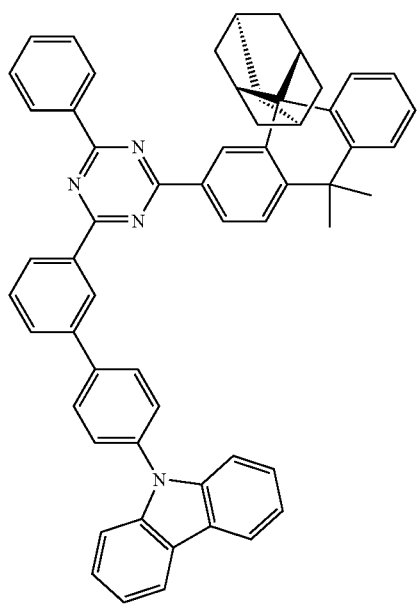
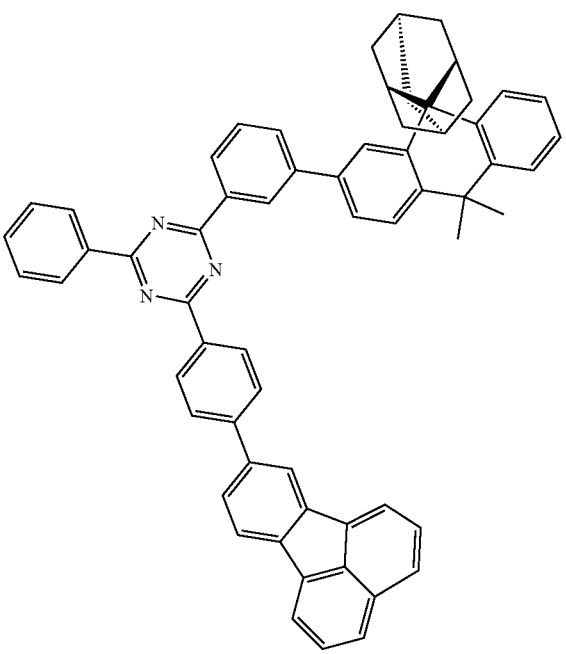

319
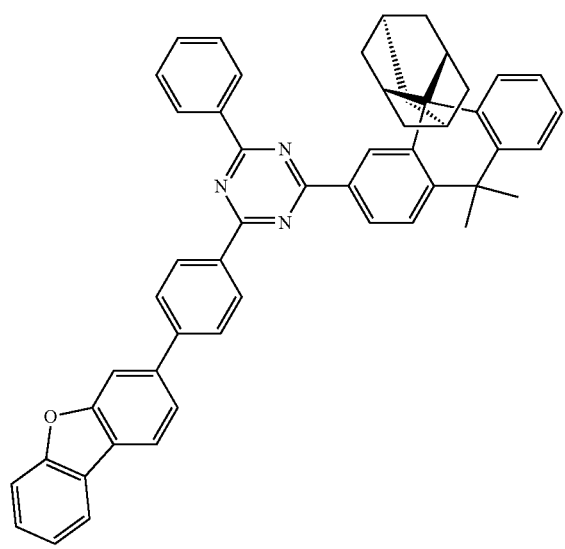
-continued
320
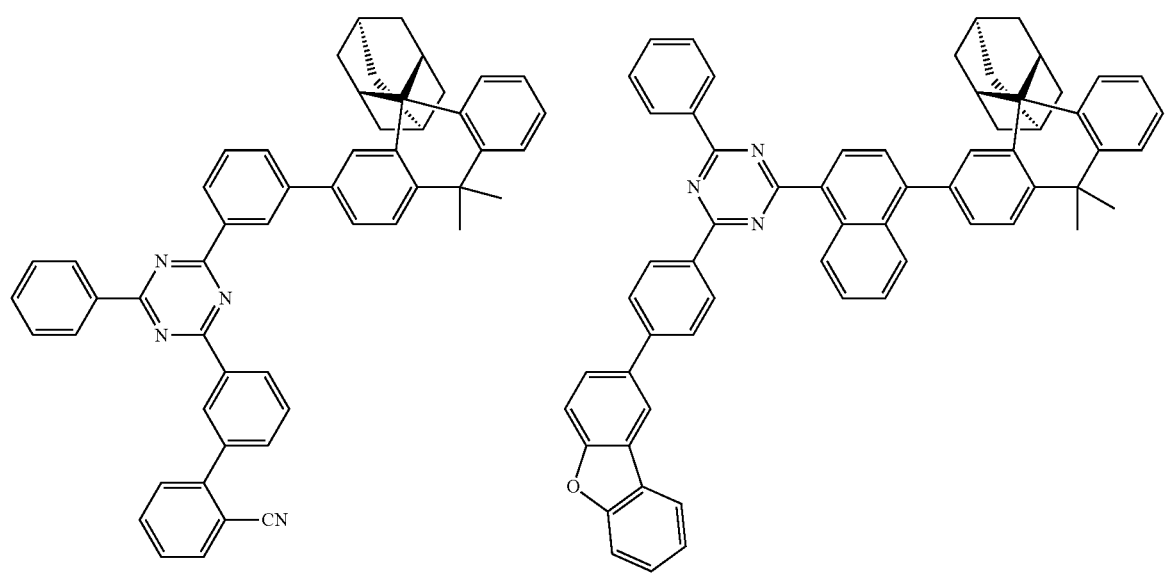

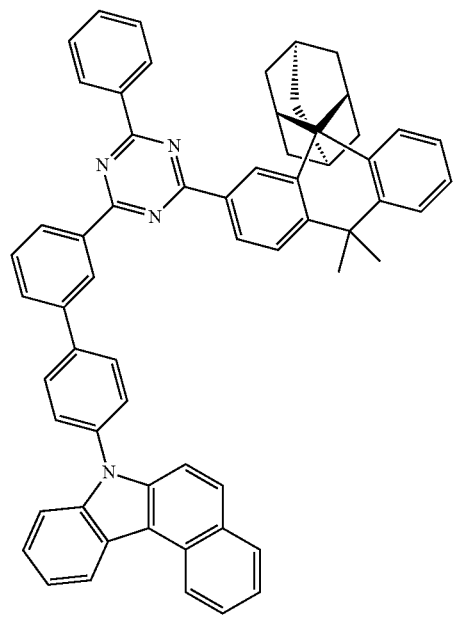
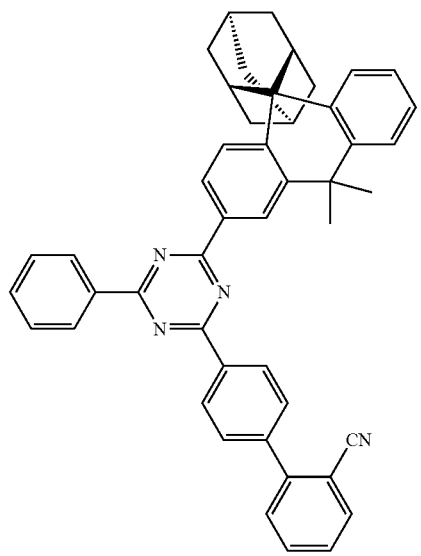
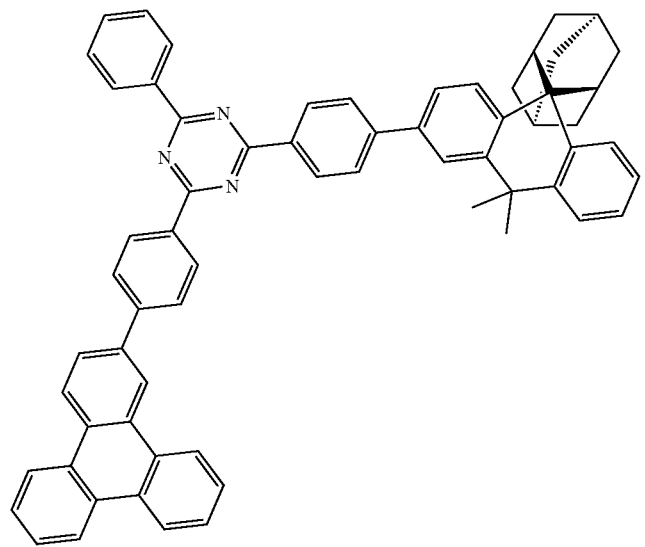

-continued
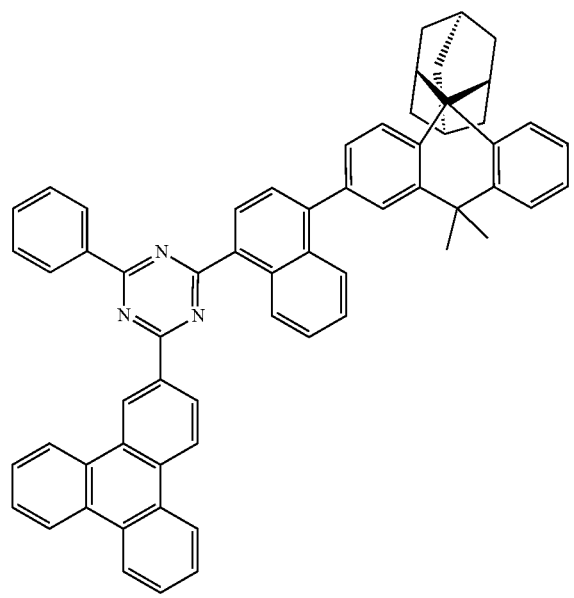
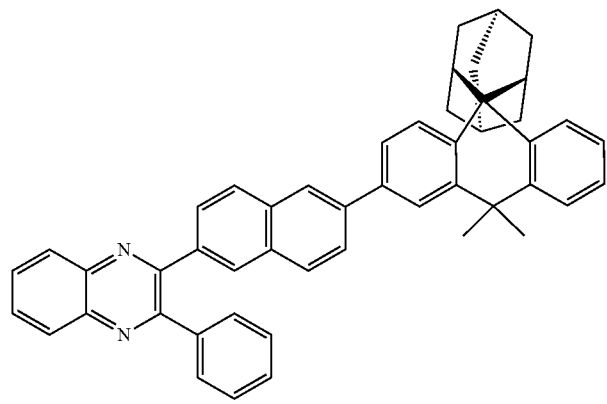
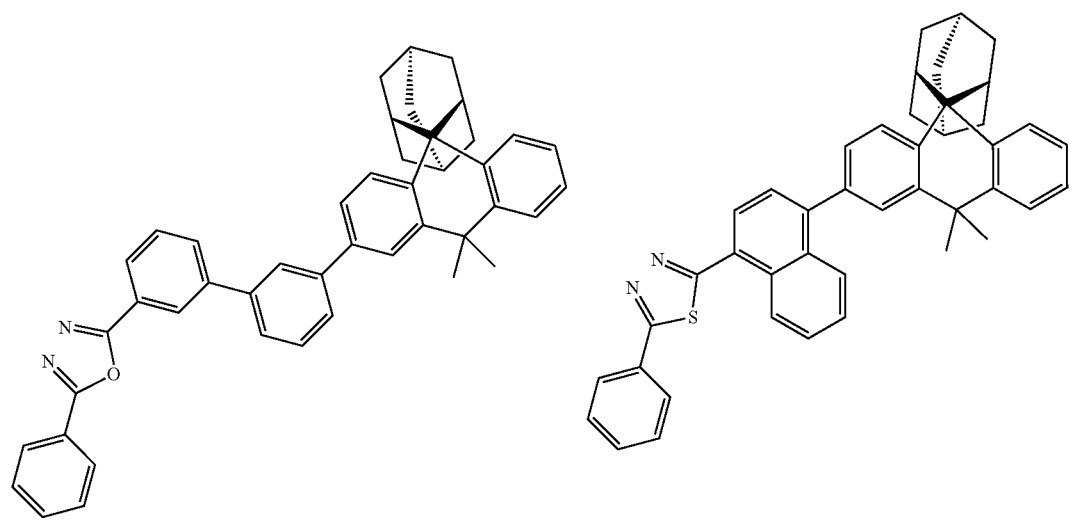

325
326
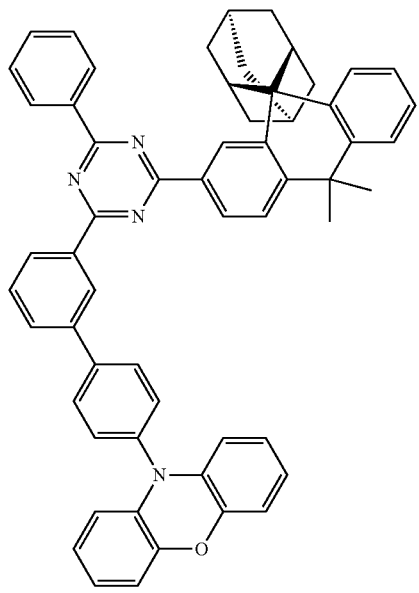
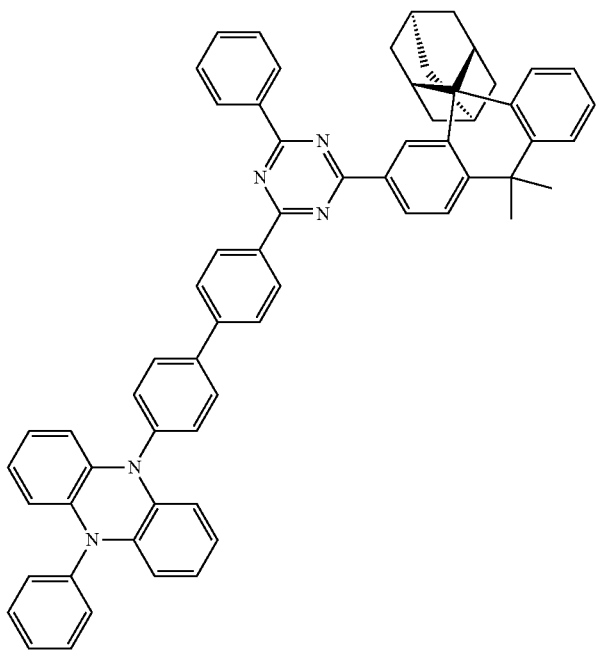
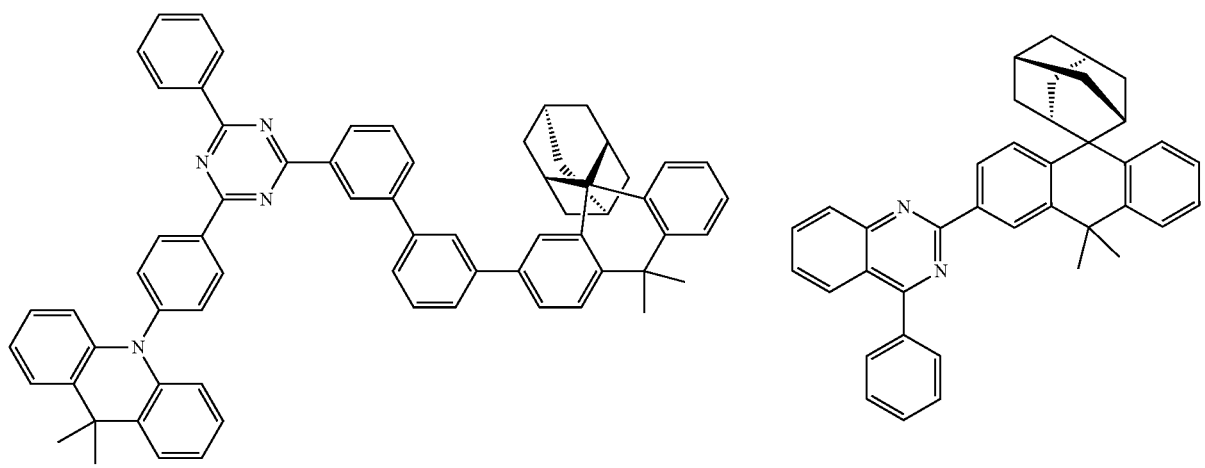
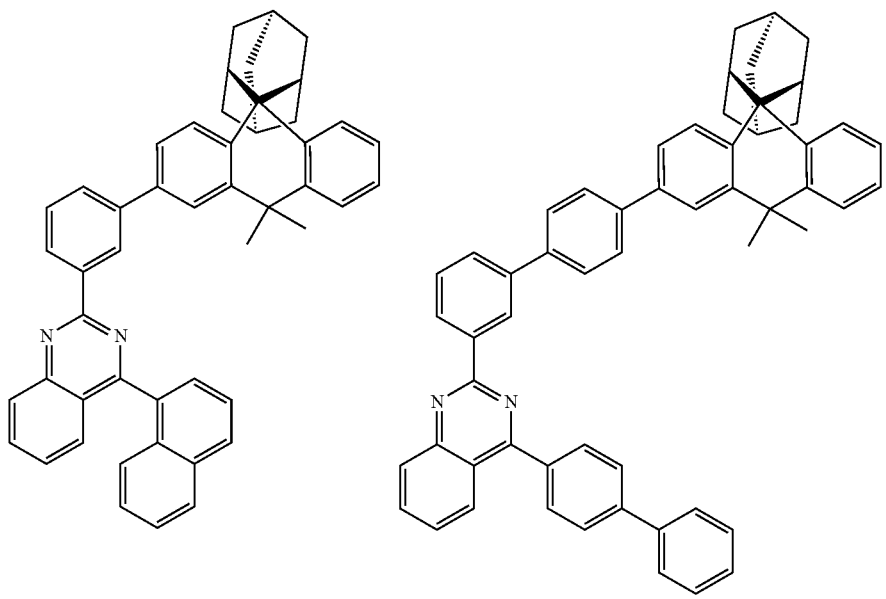

327
328
-continued
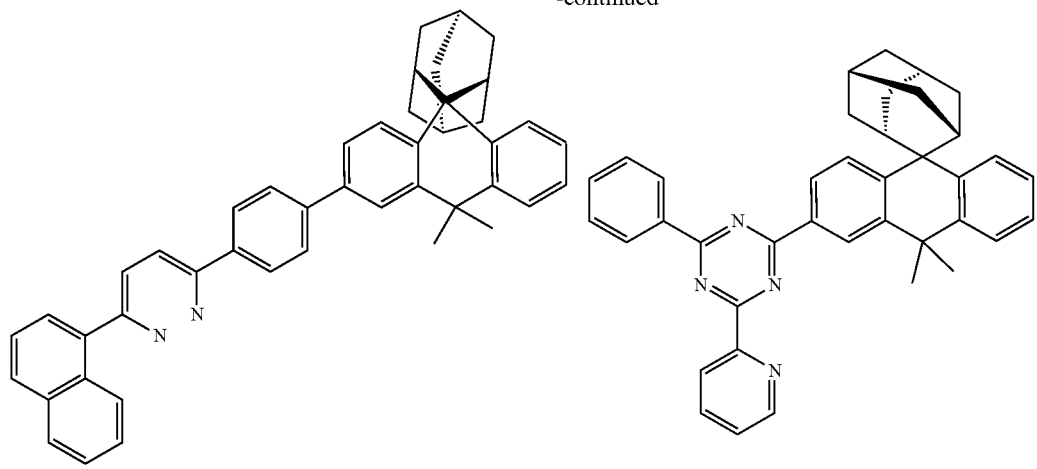
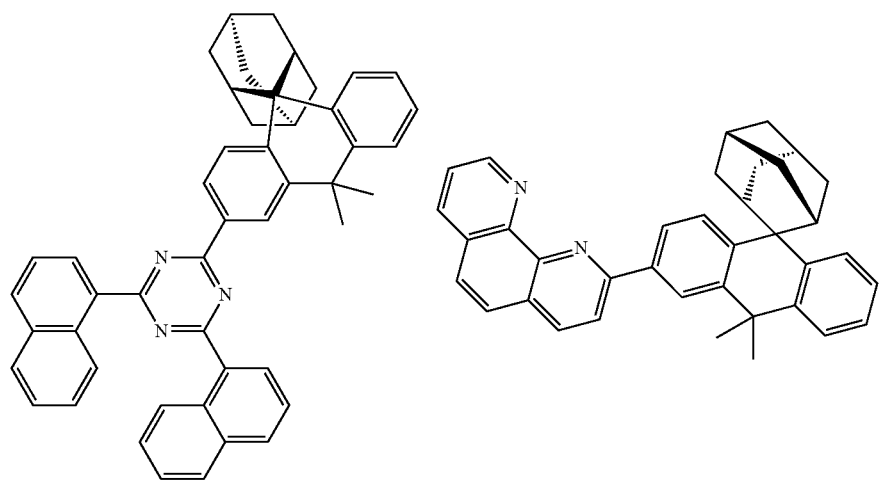
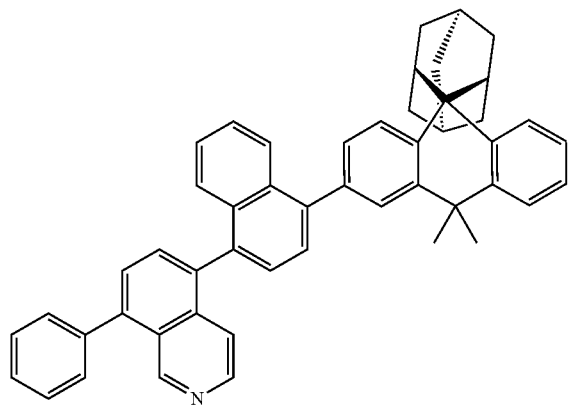

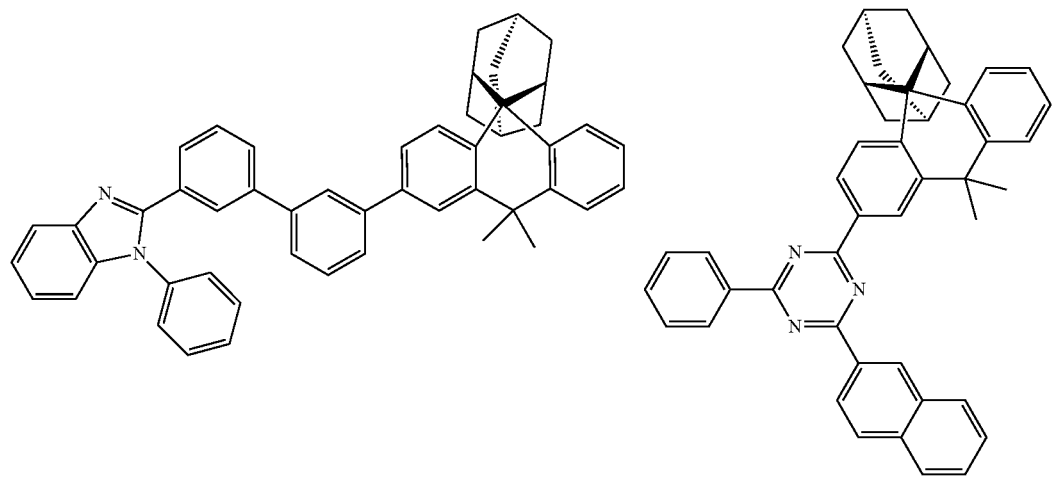
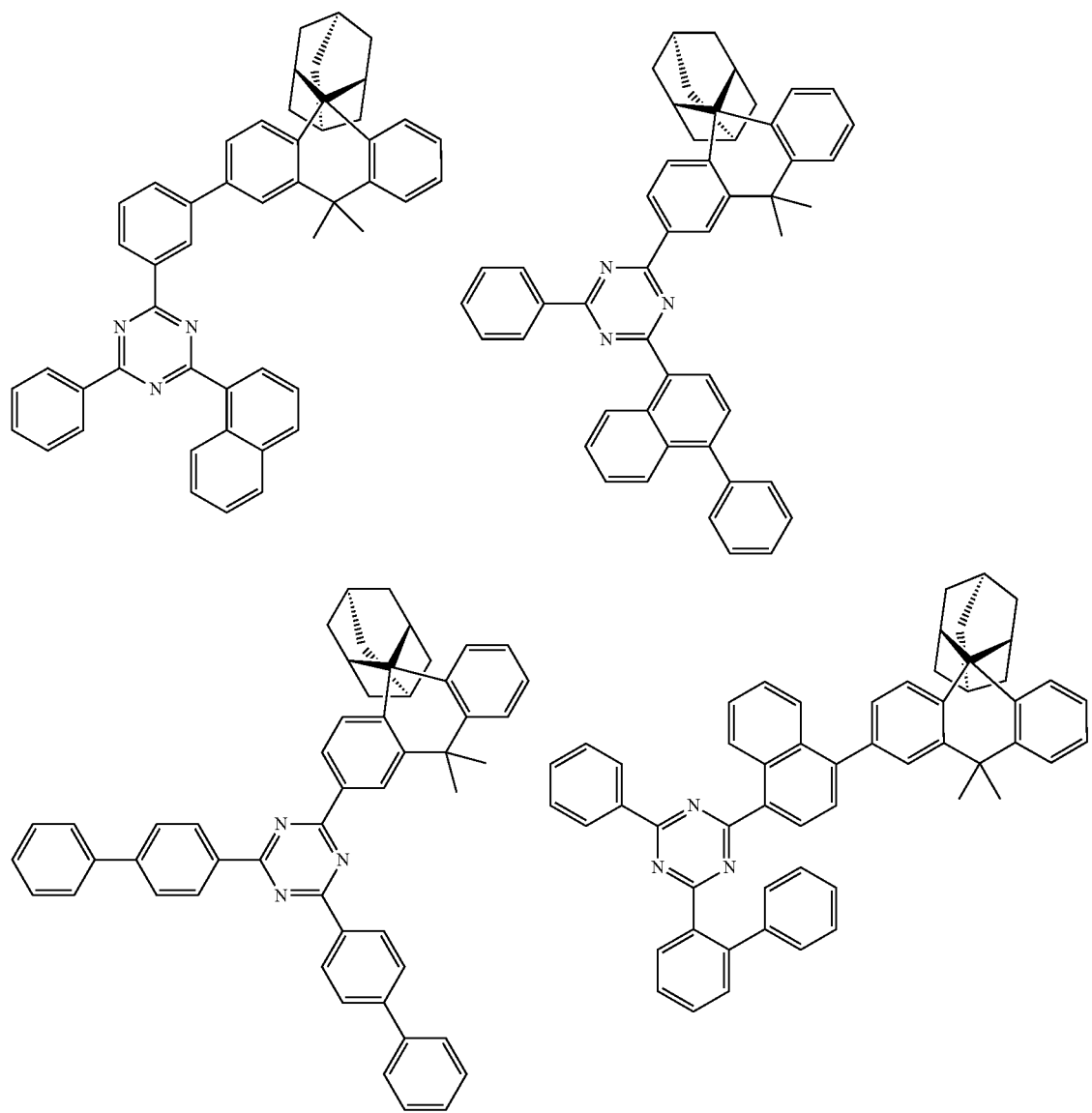

331 332
-continued
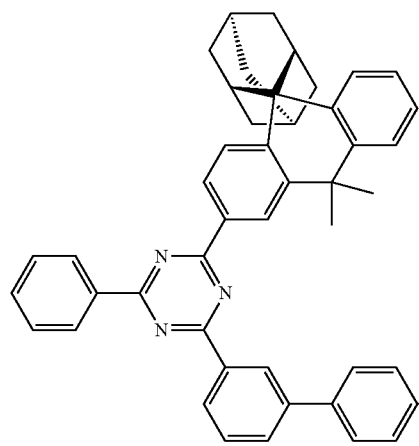
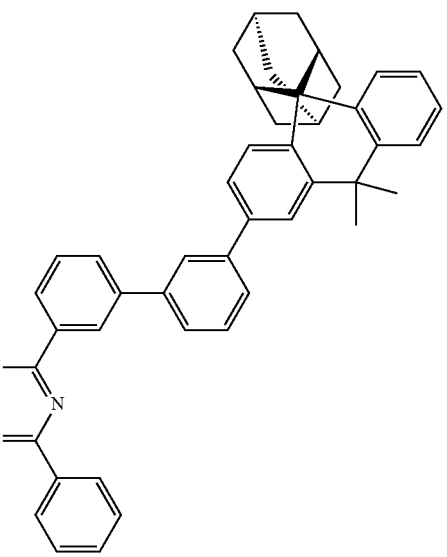
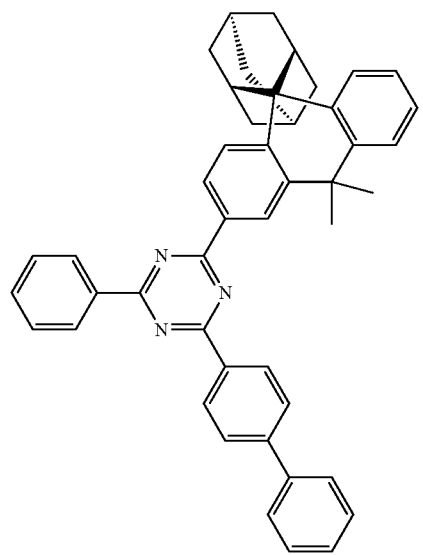
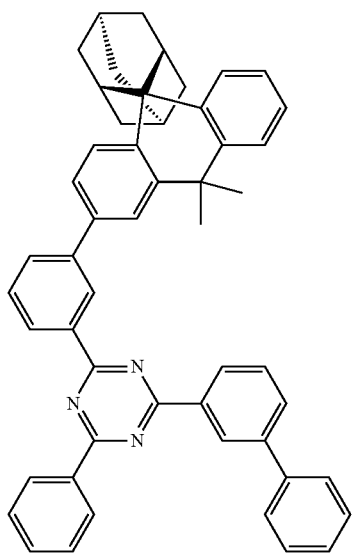

333 334
-continued
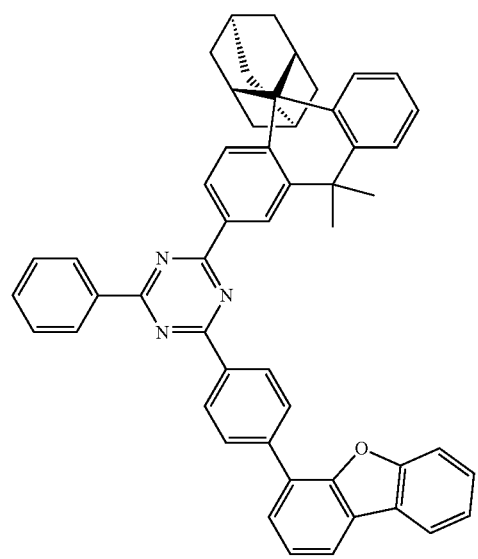
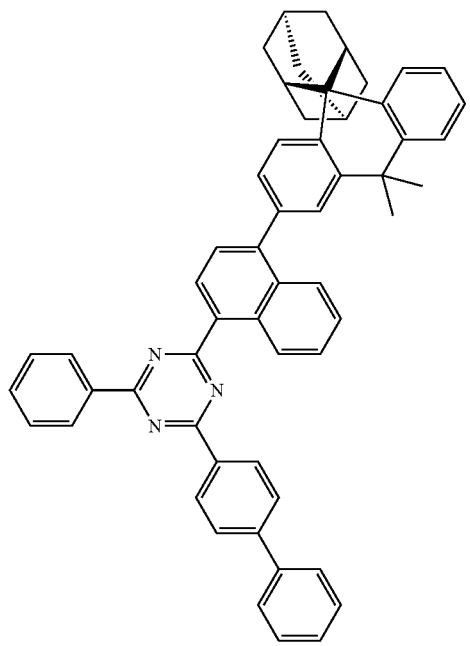
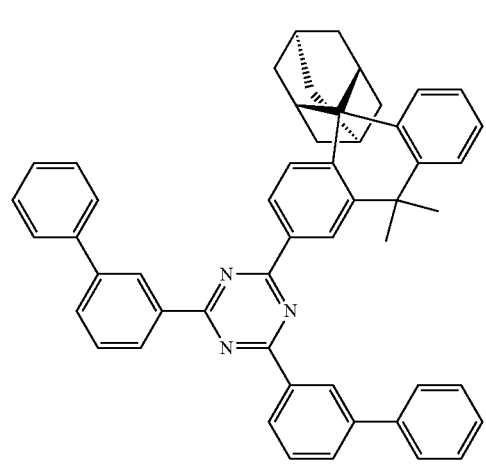
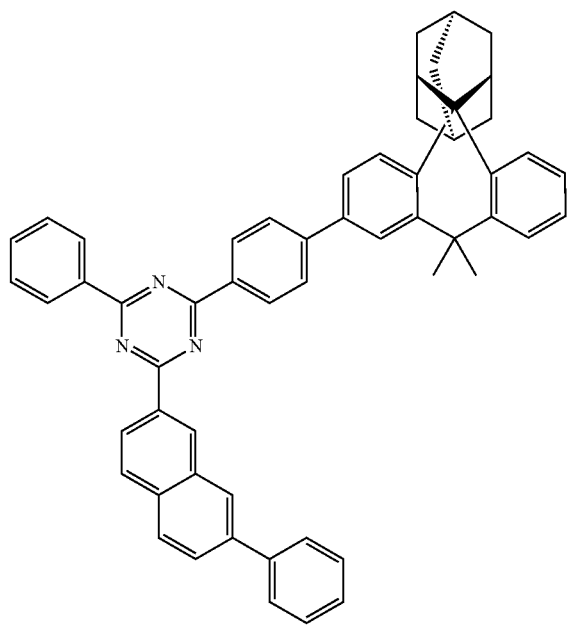

335 336
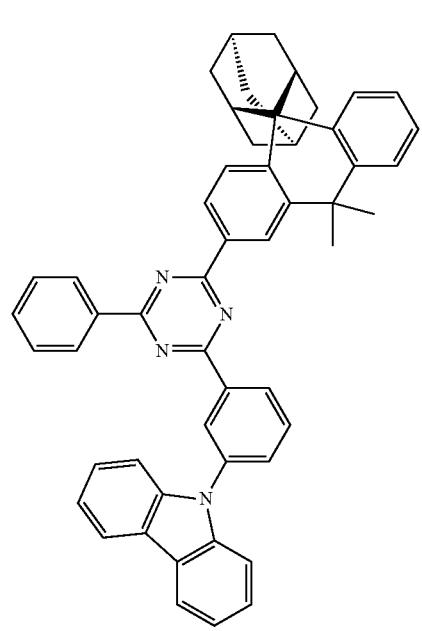 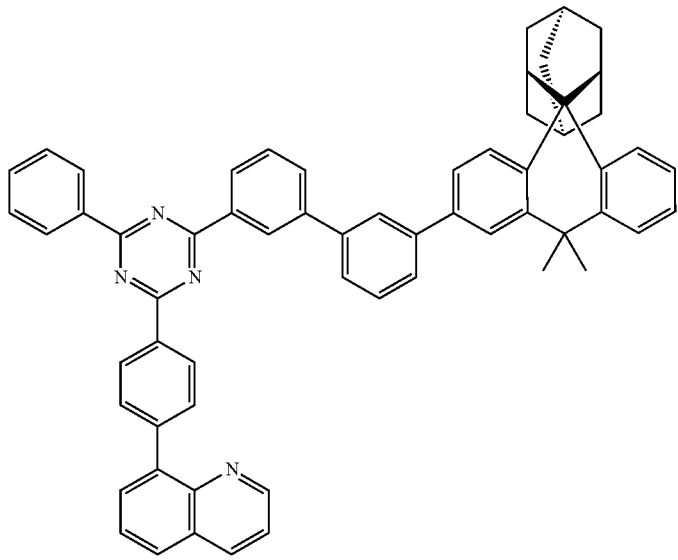
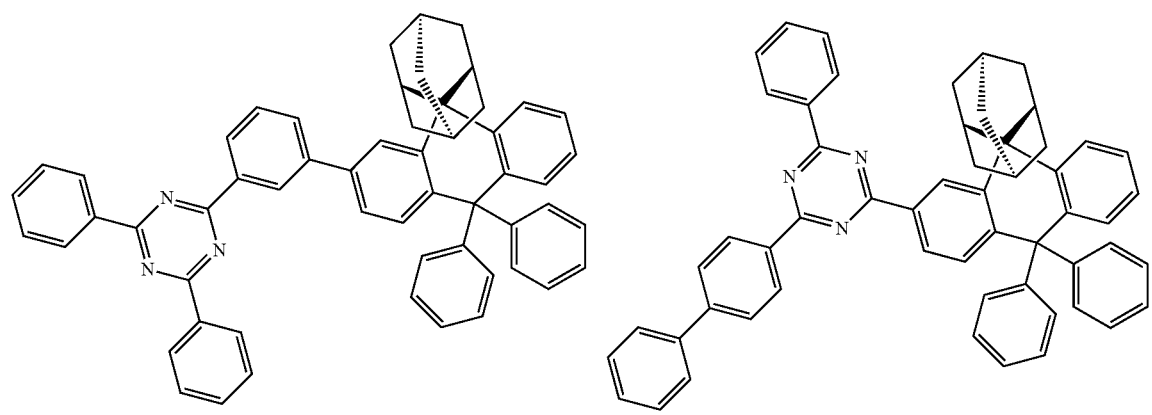
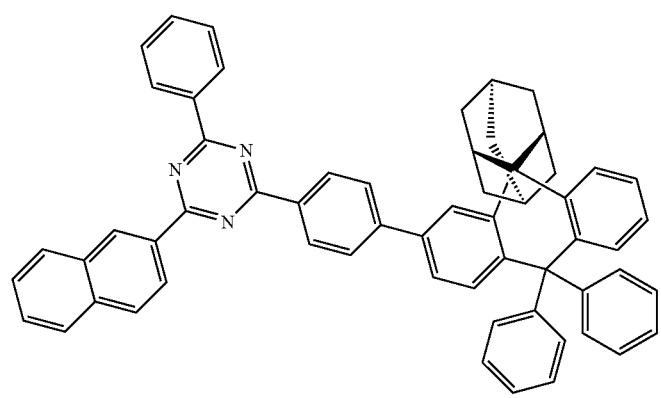

-continued
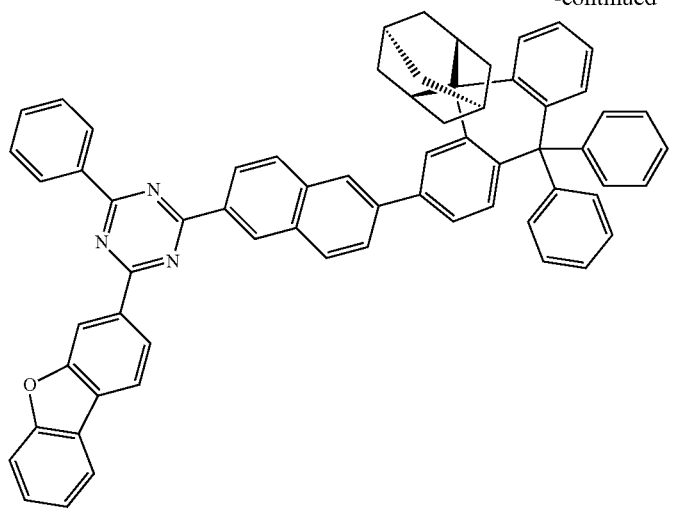
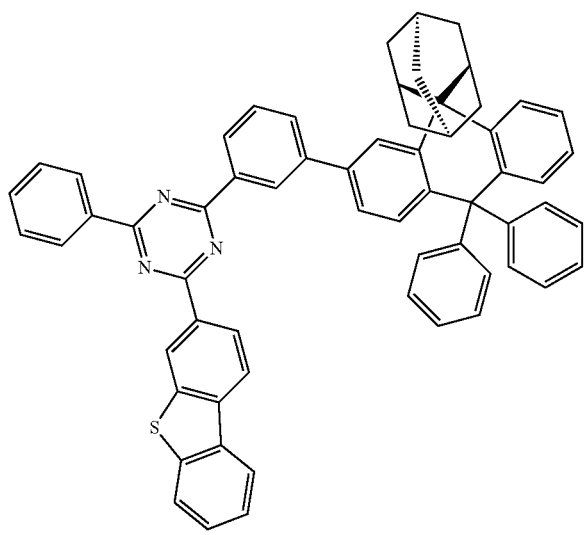
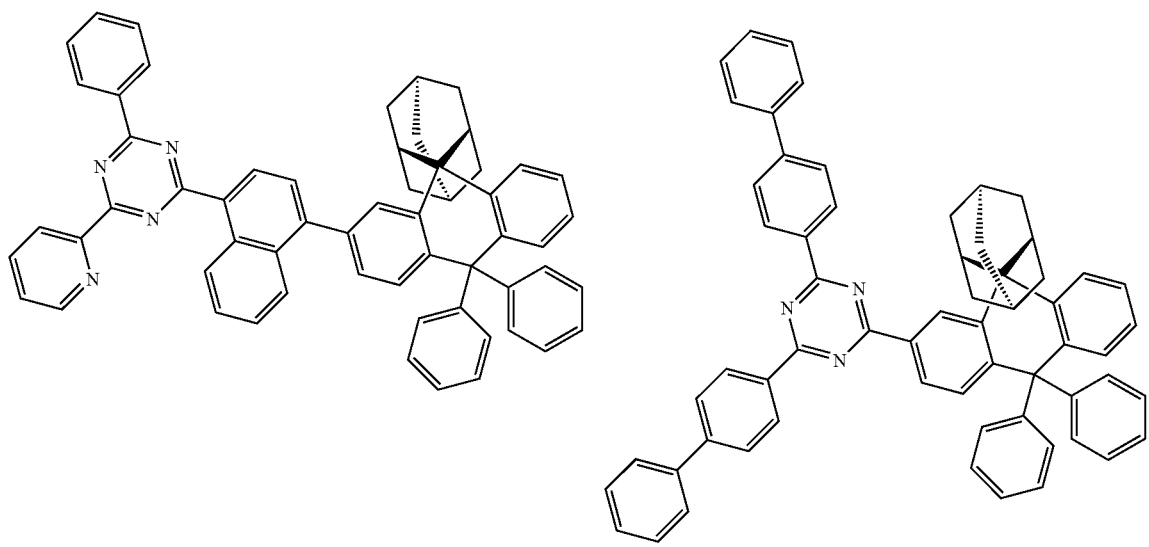

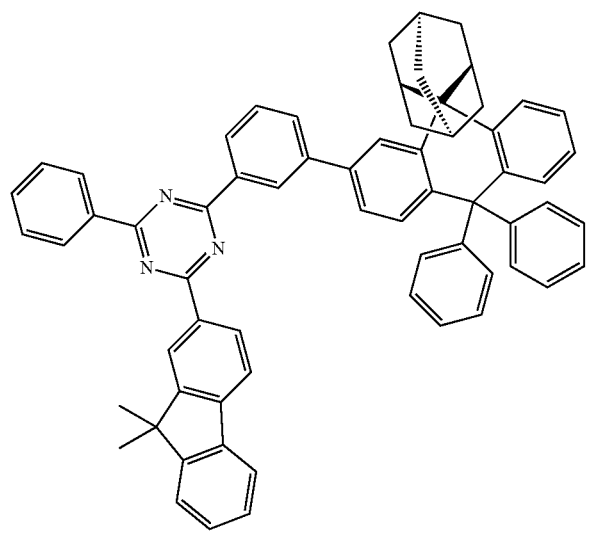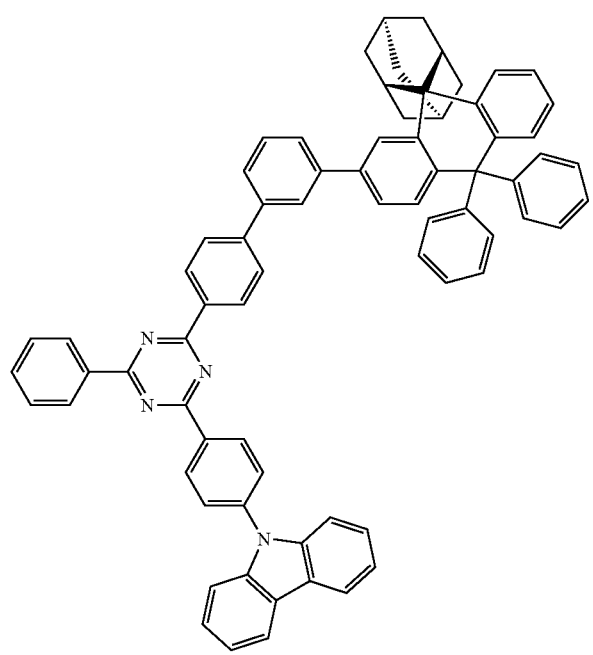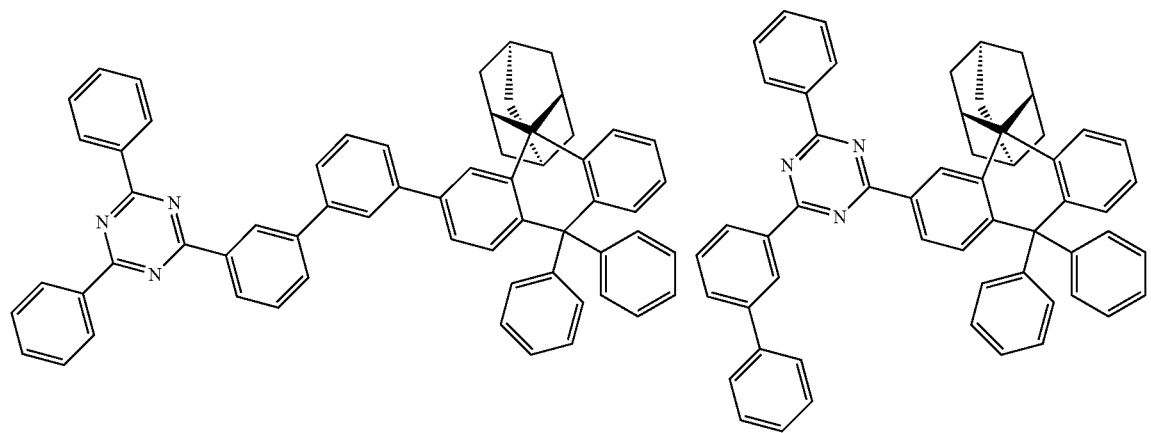

341
342
-continued
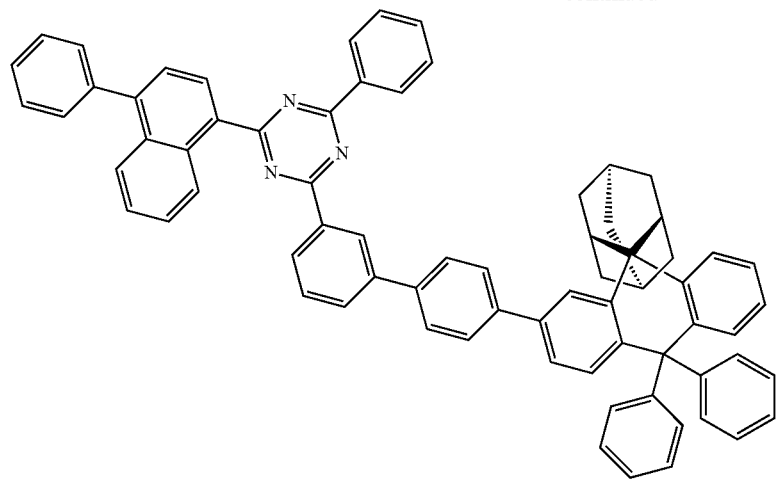
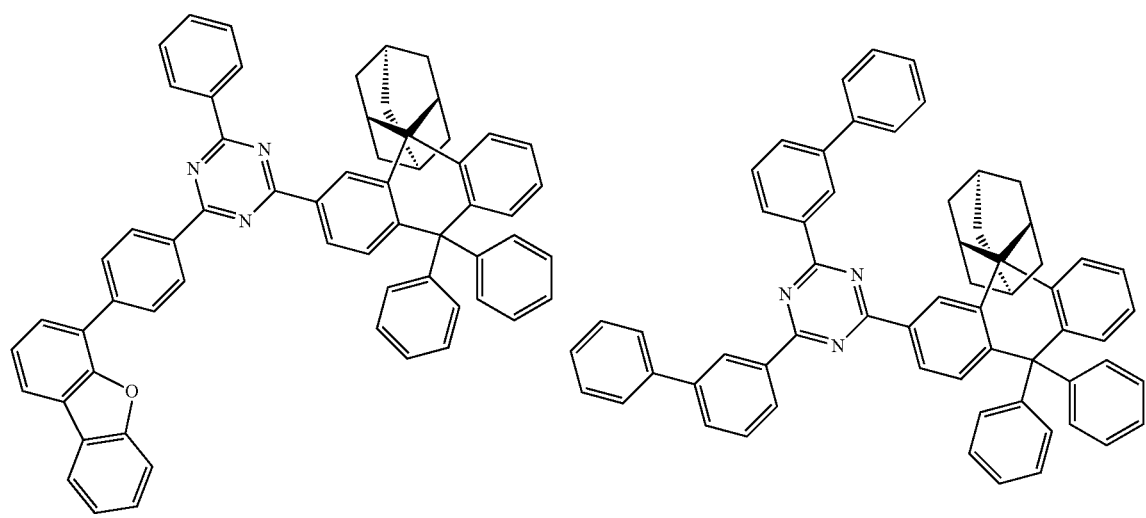
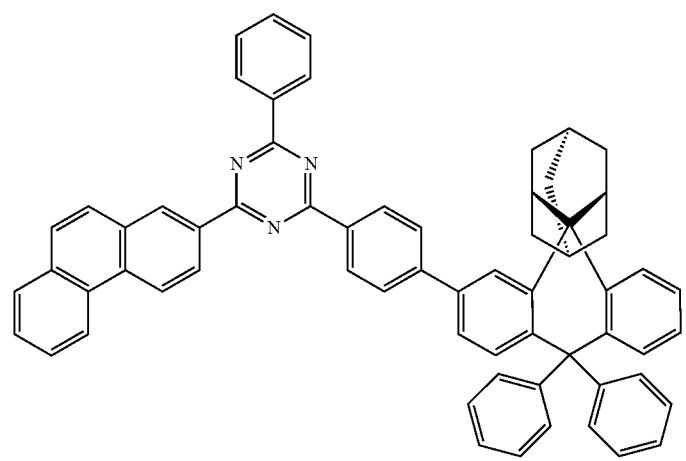

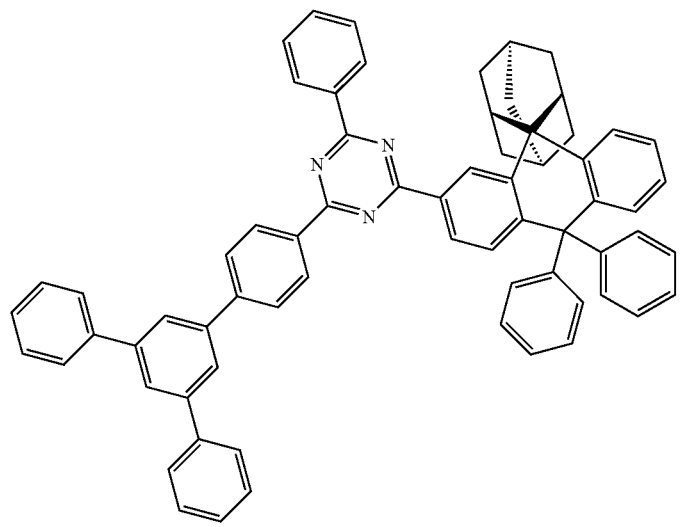
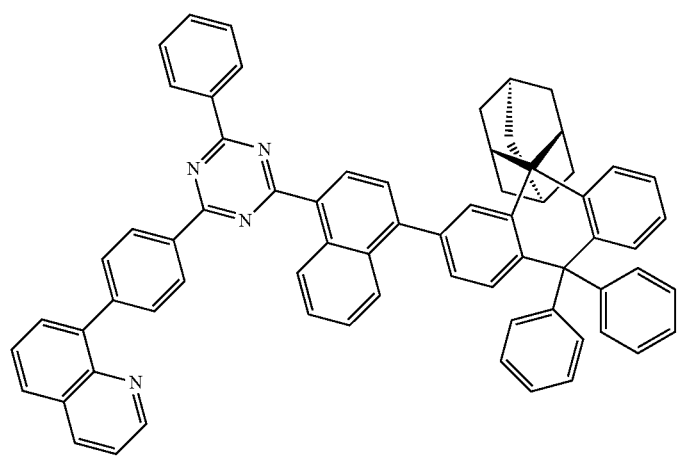
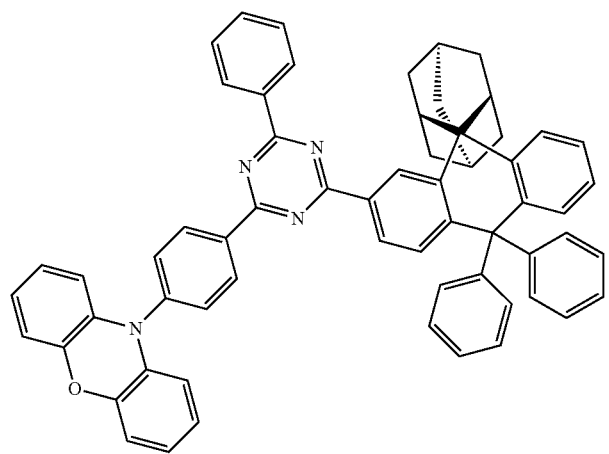

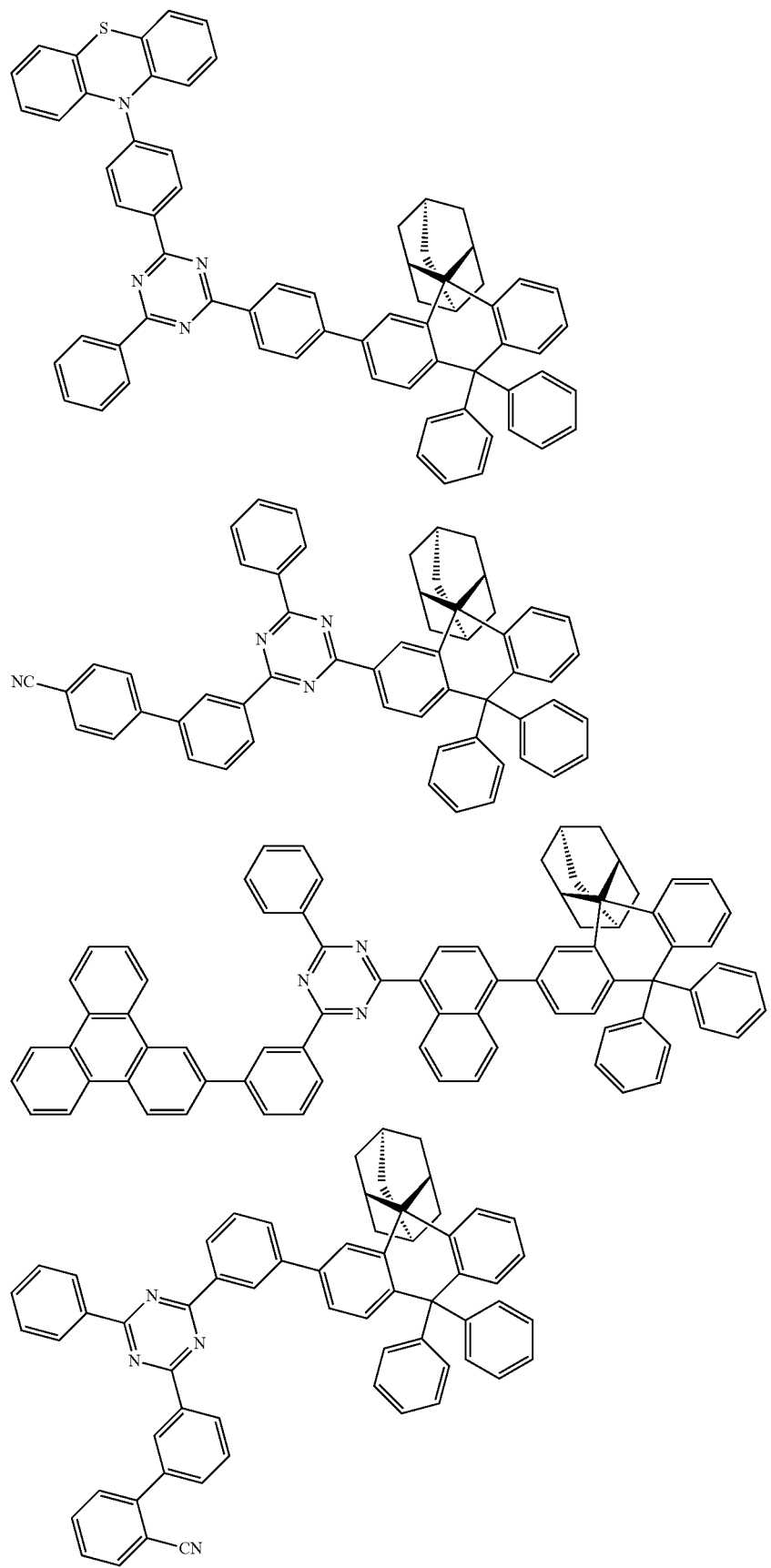

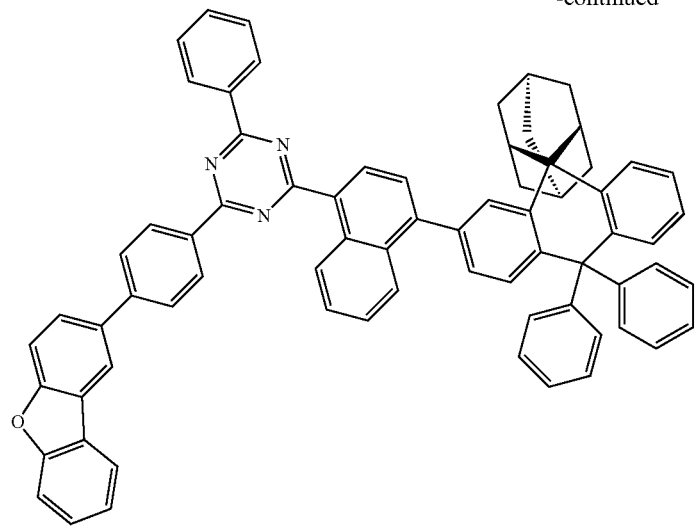
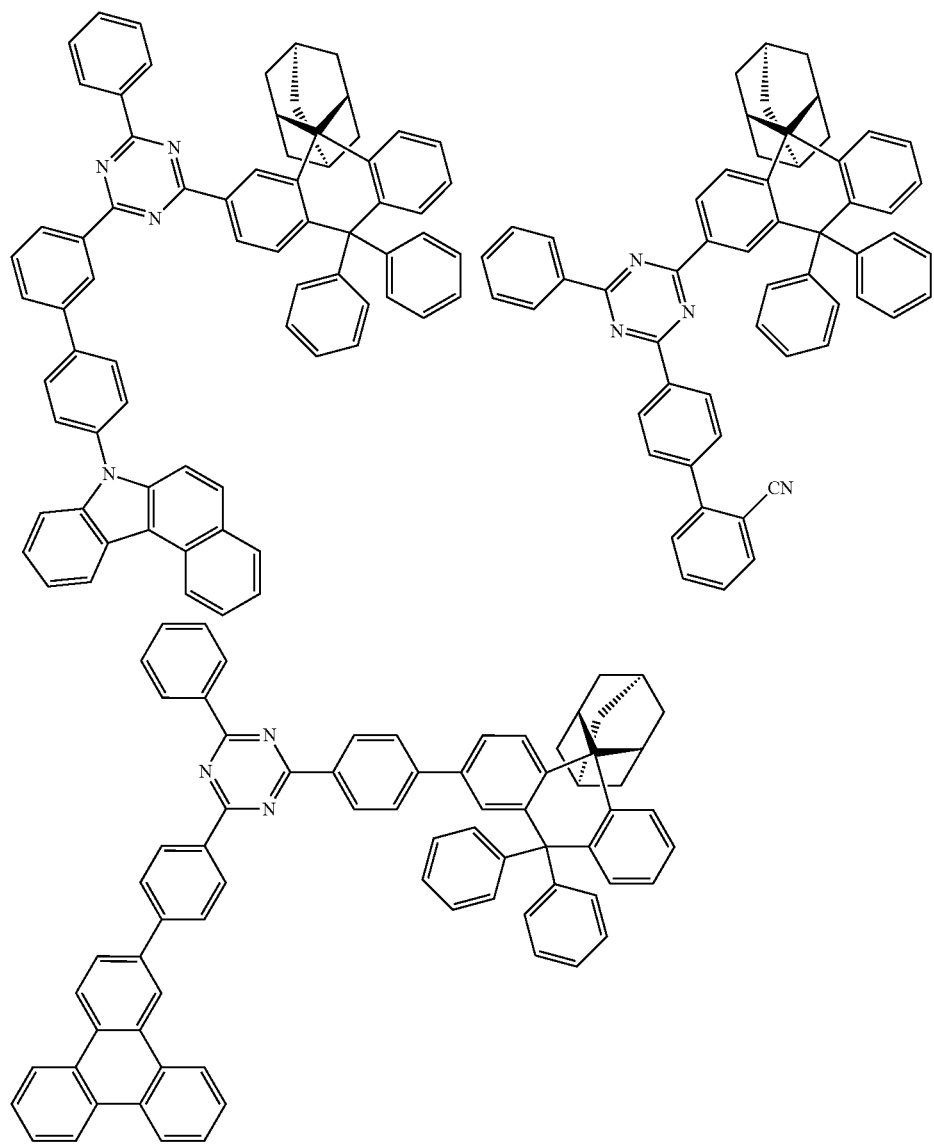

349 350
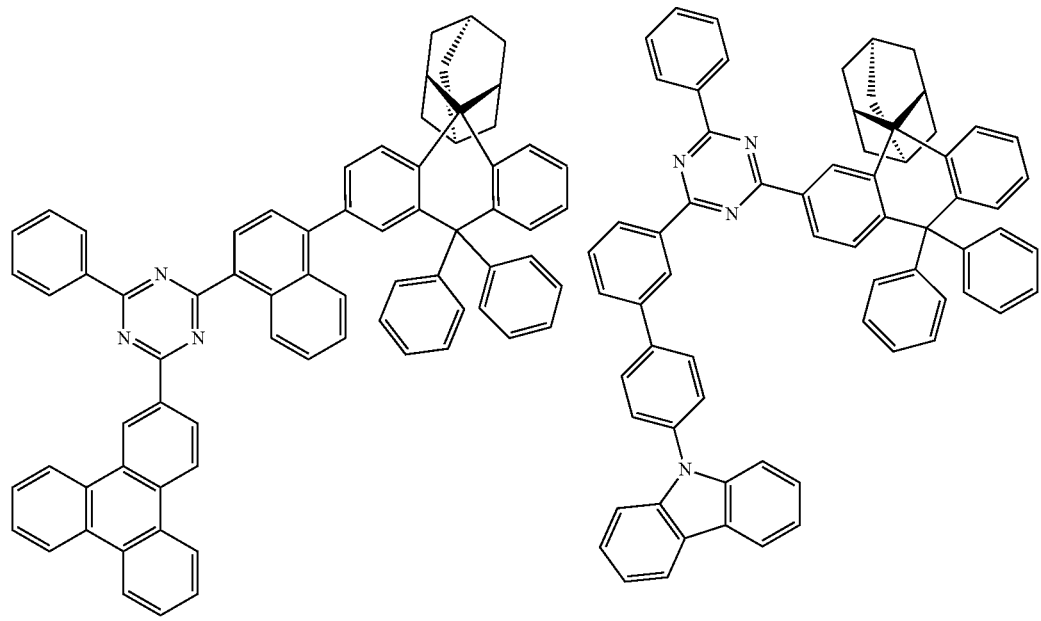
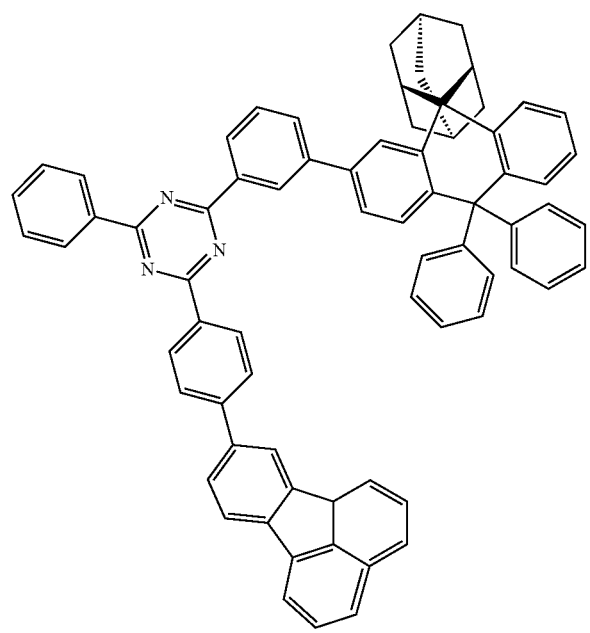

351 352
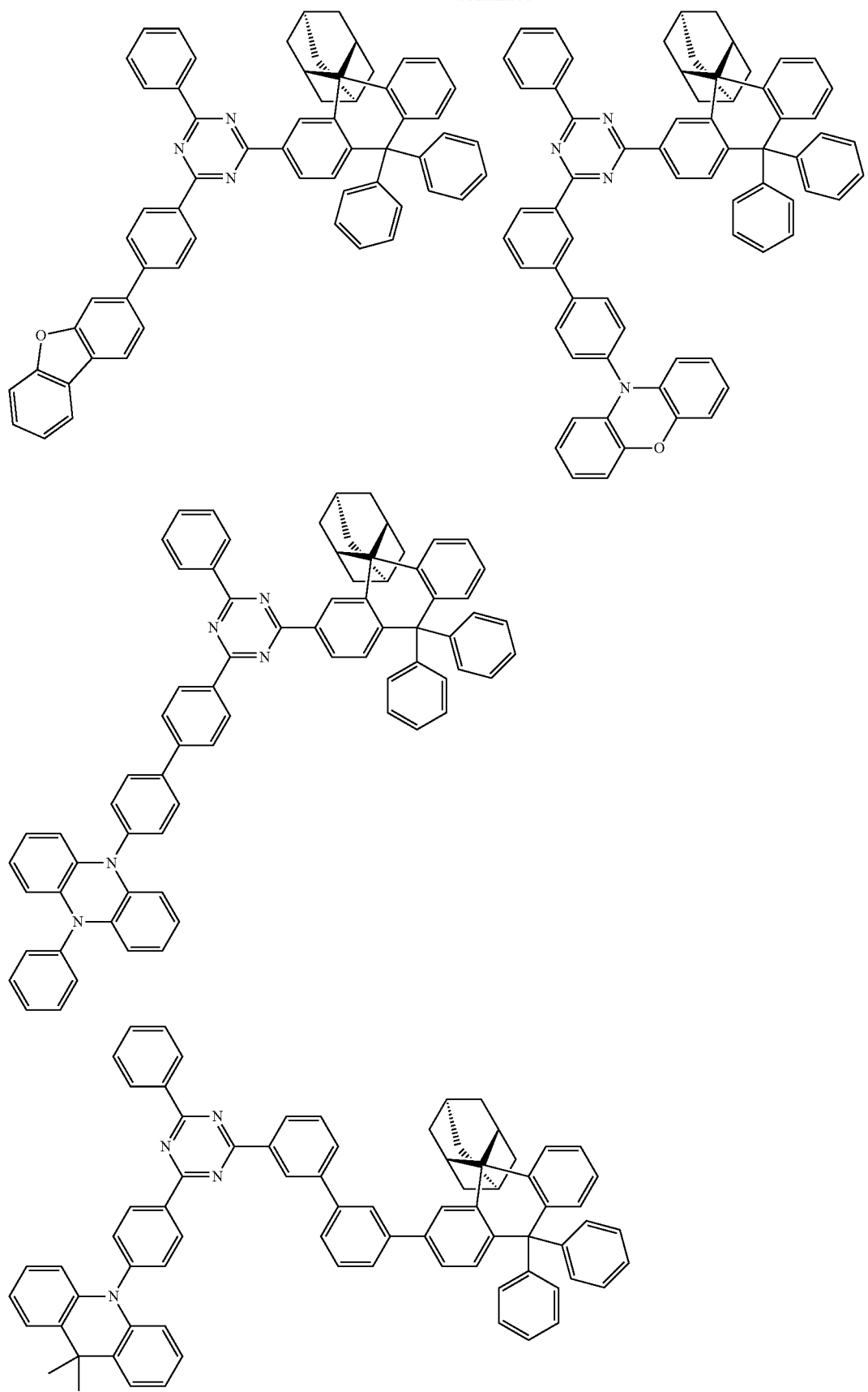

-continued
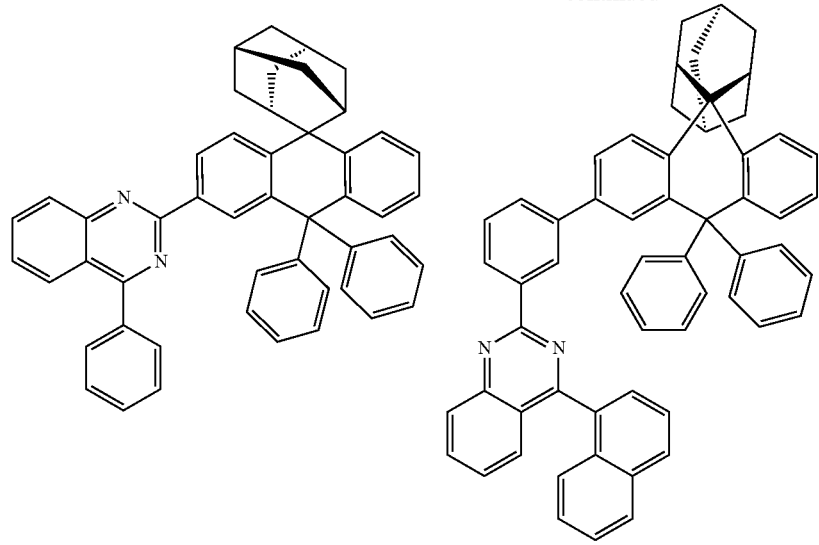
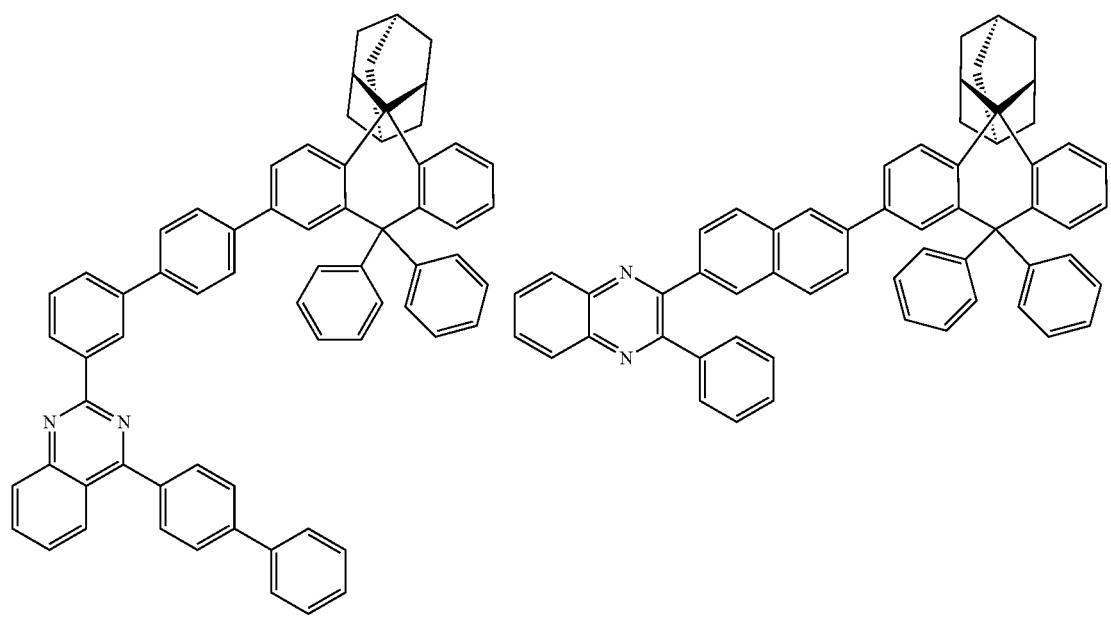
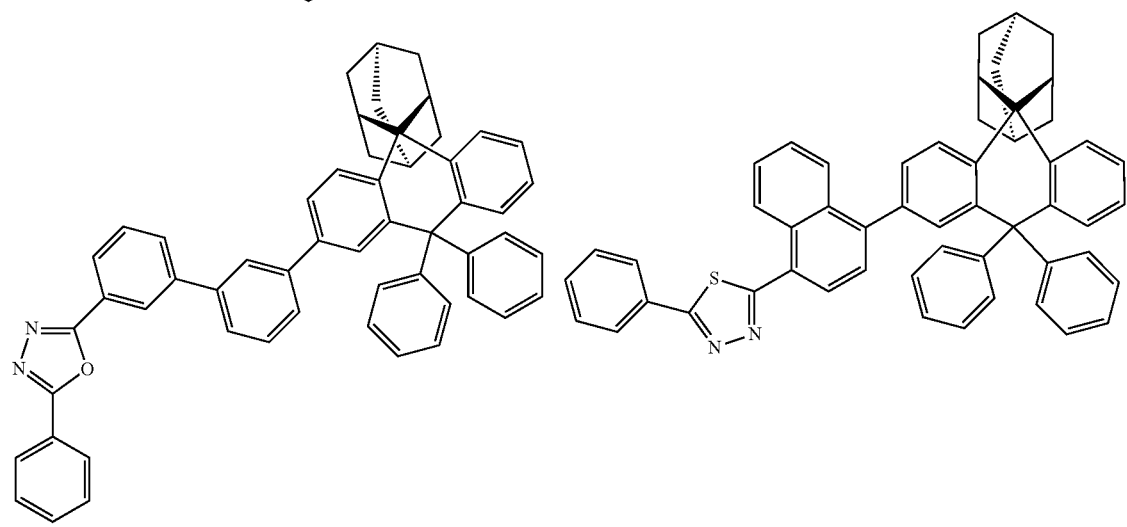

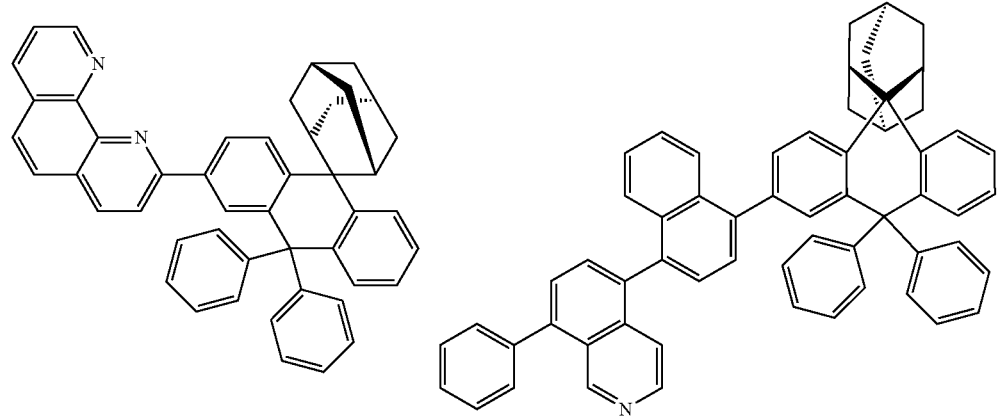
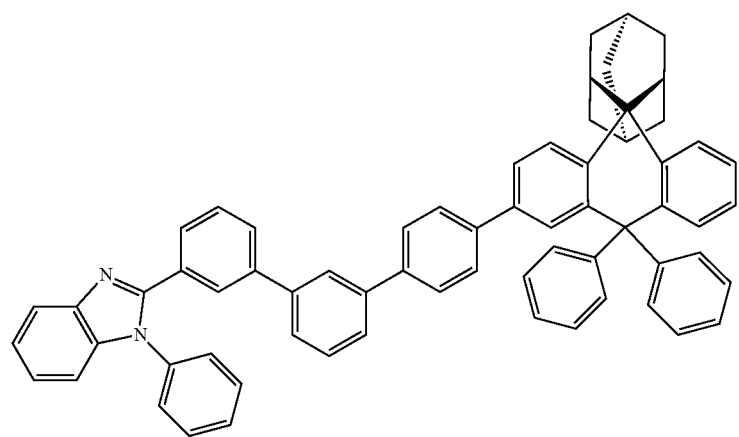
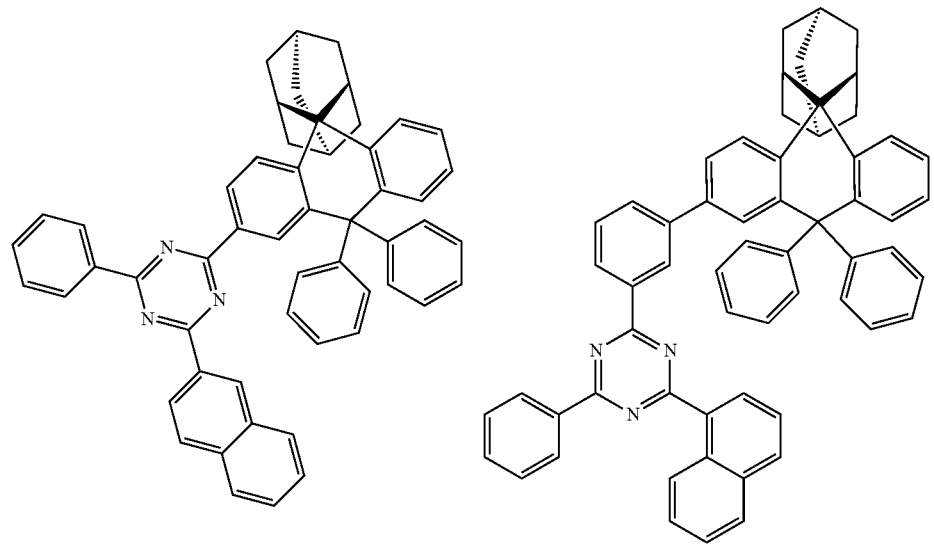

357 358
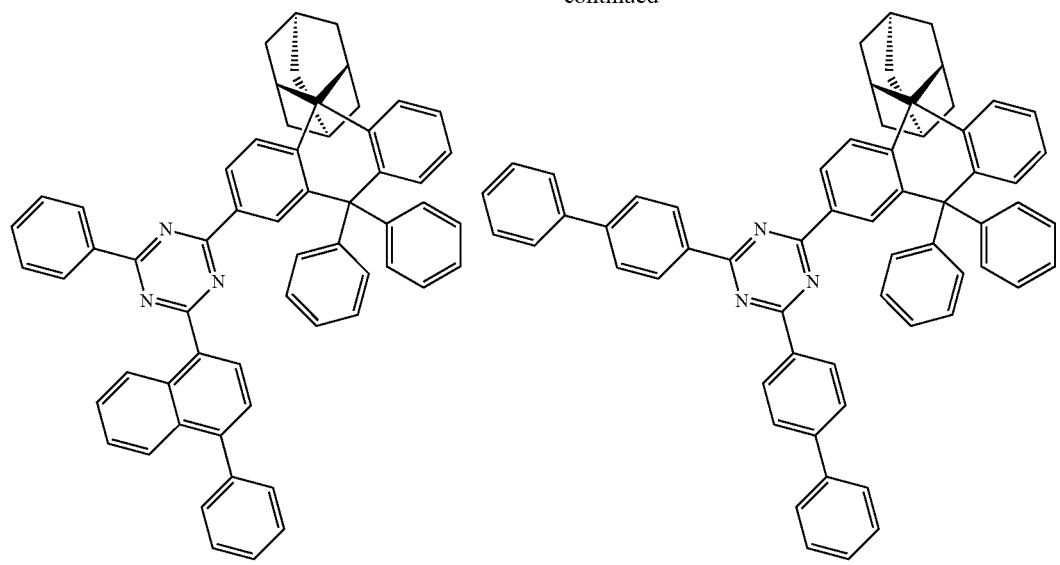
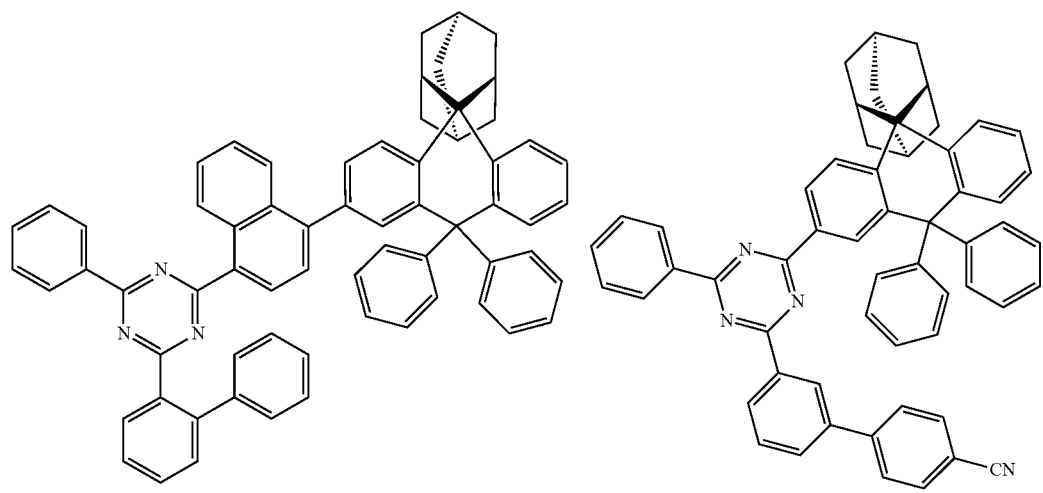
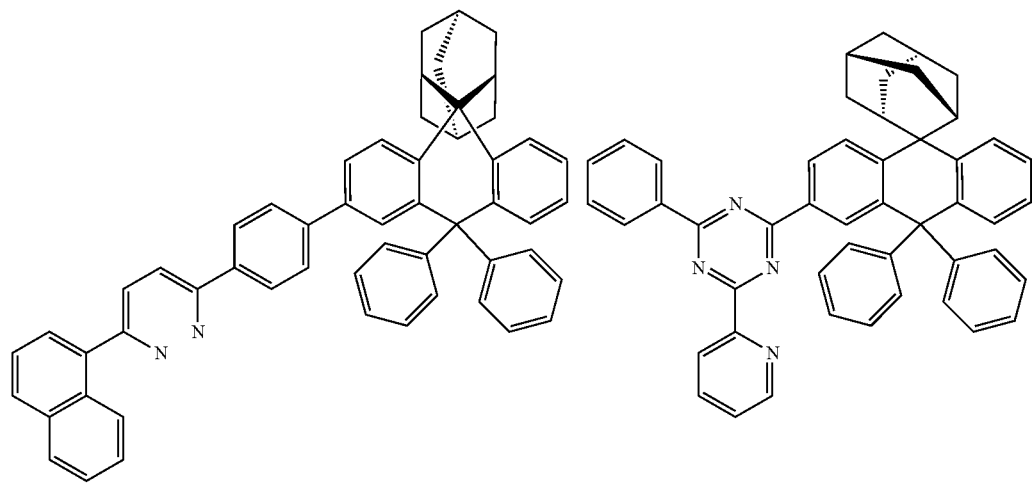

359        360
-continued
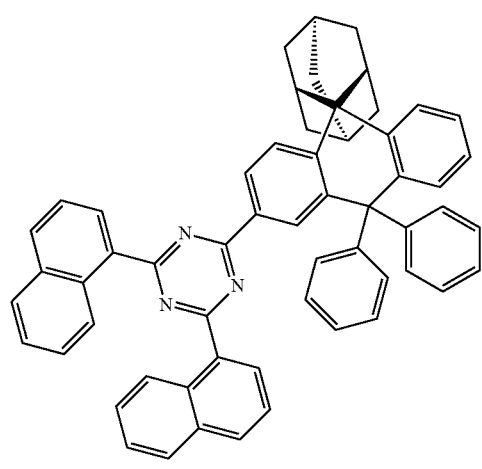
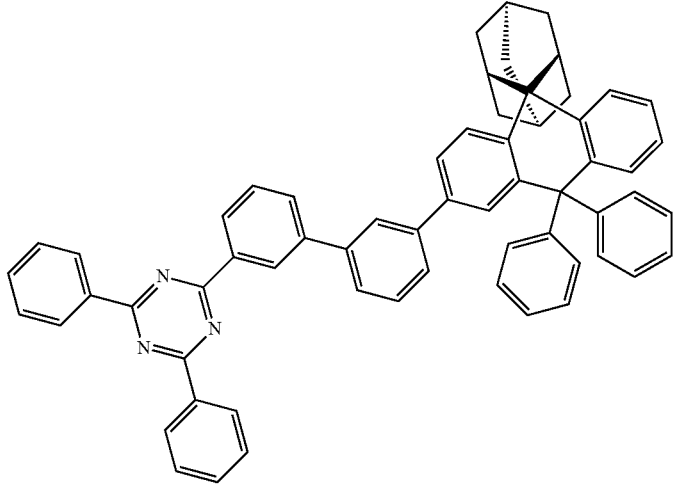
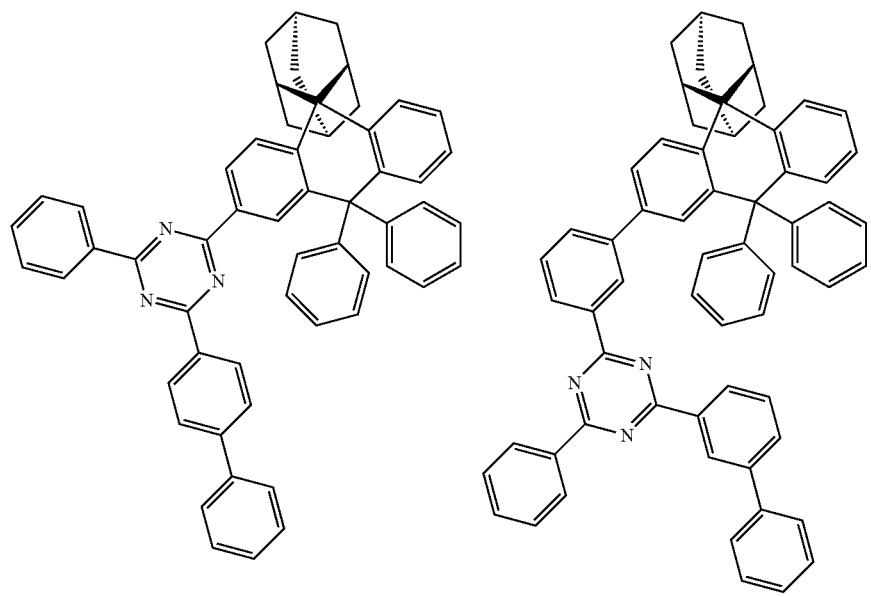
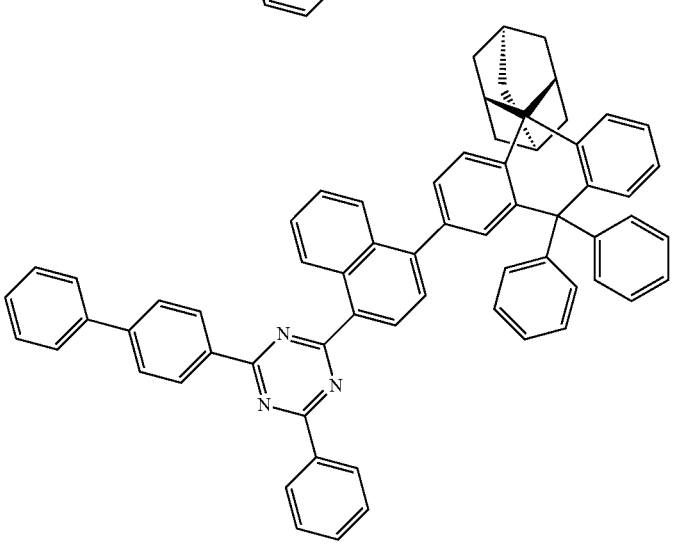

361 362
-continued
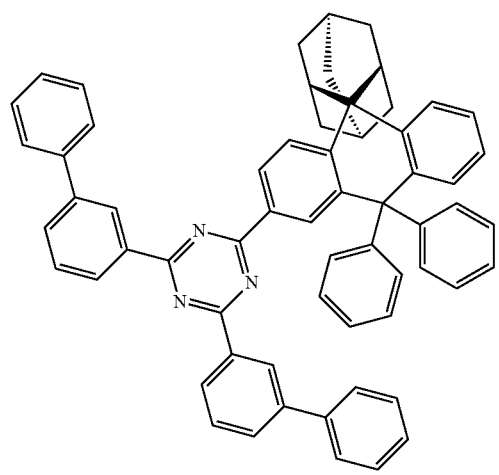
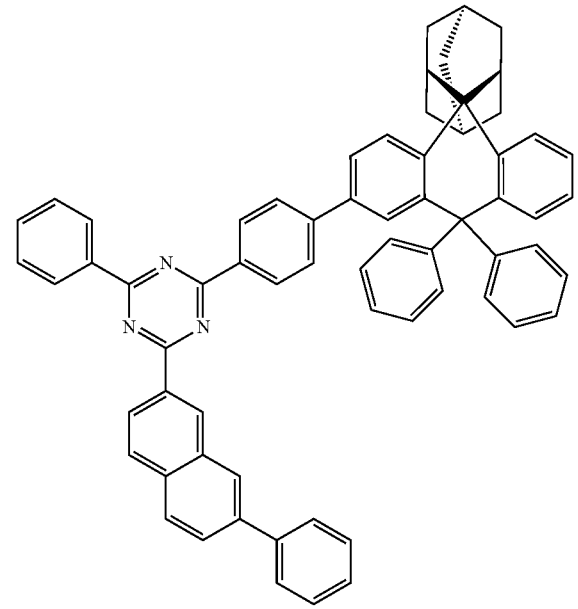
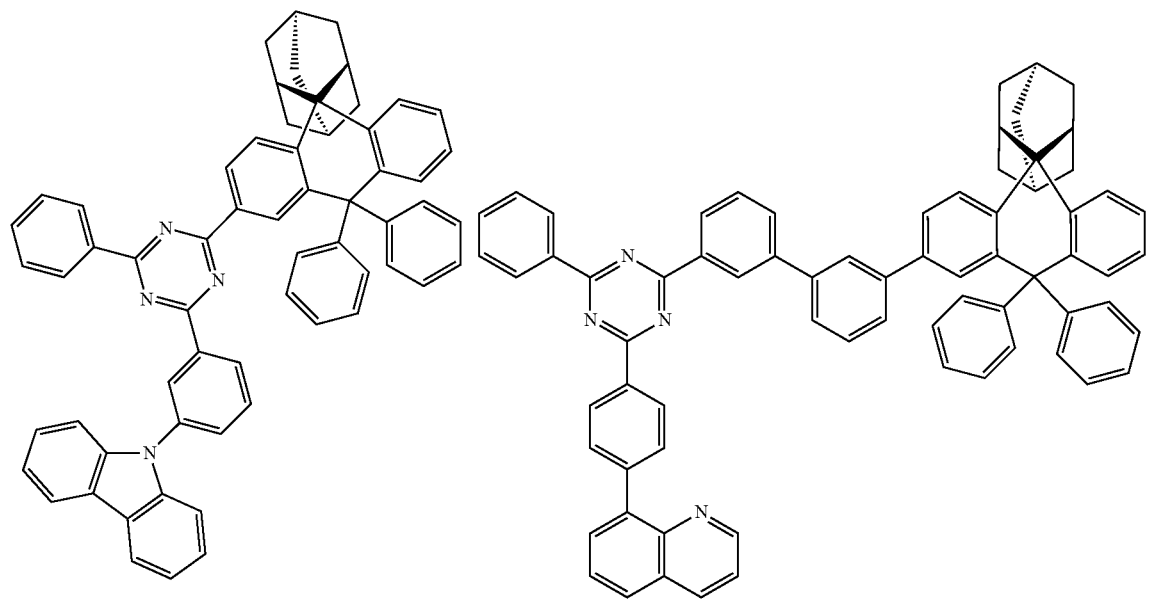
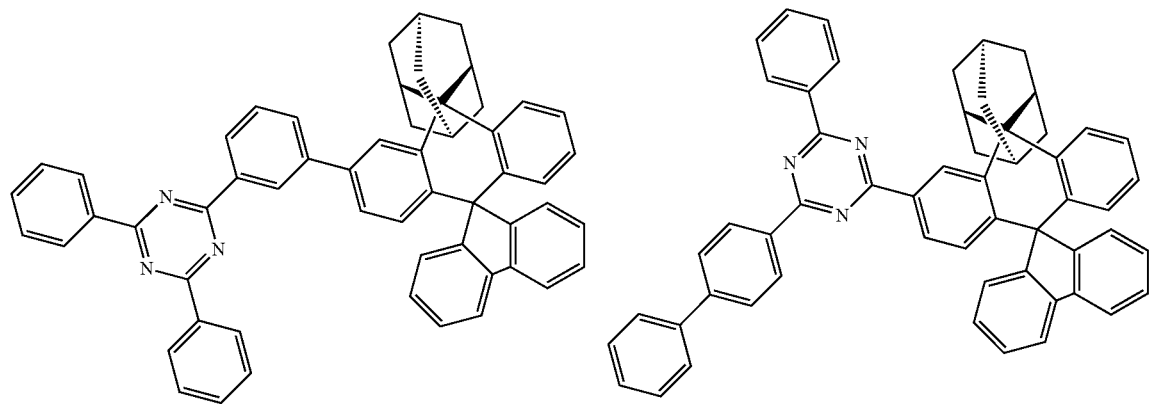

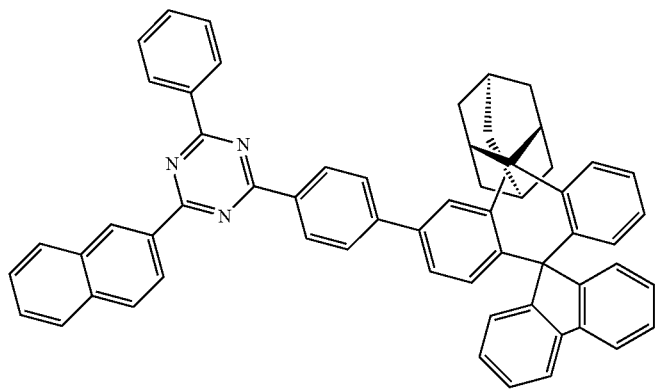
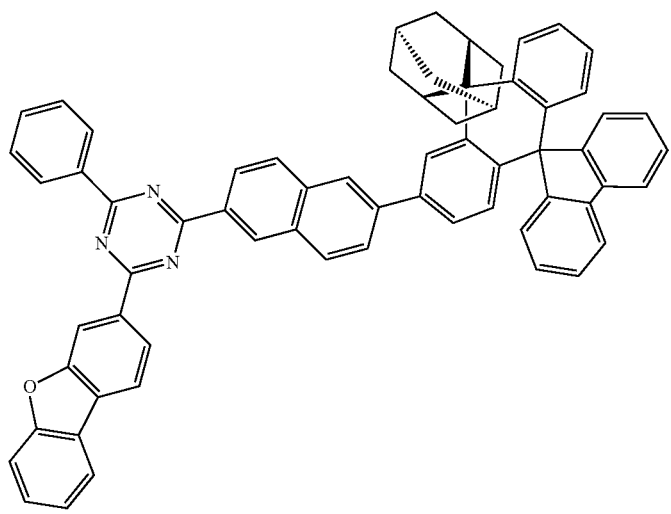
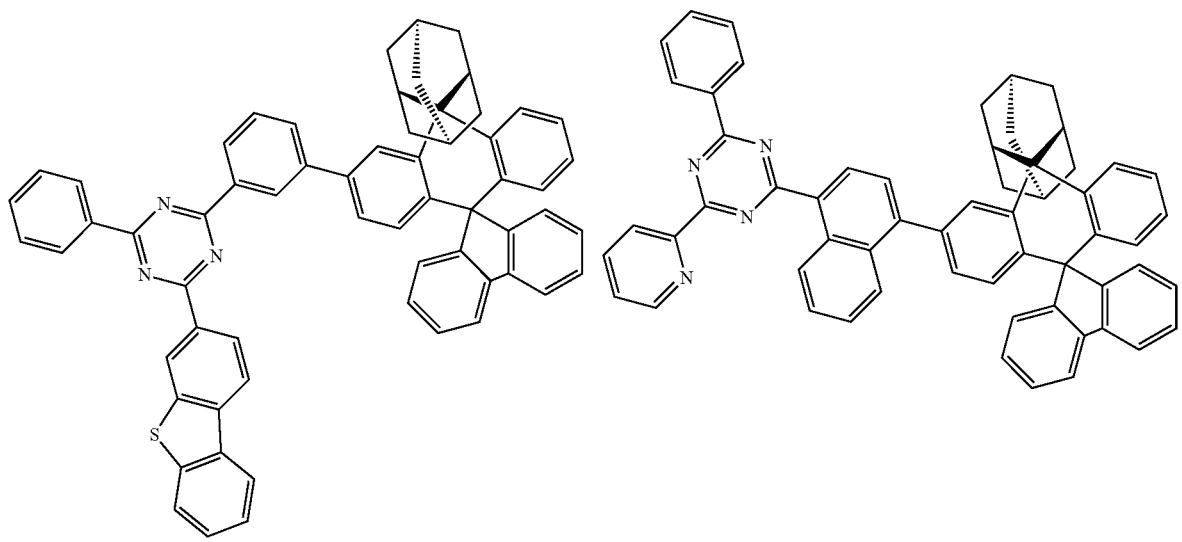

365 366
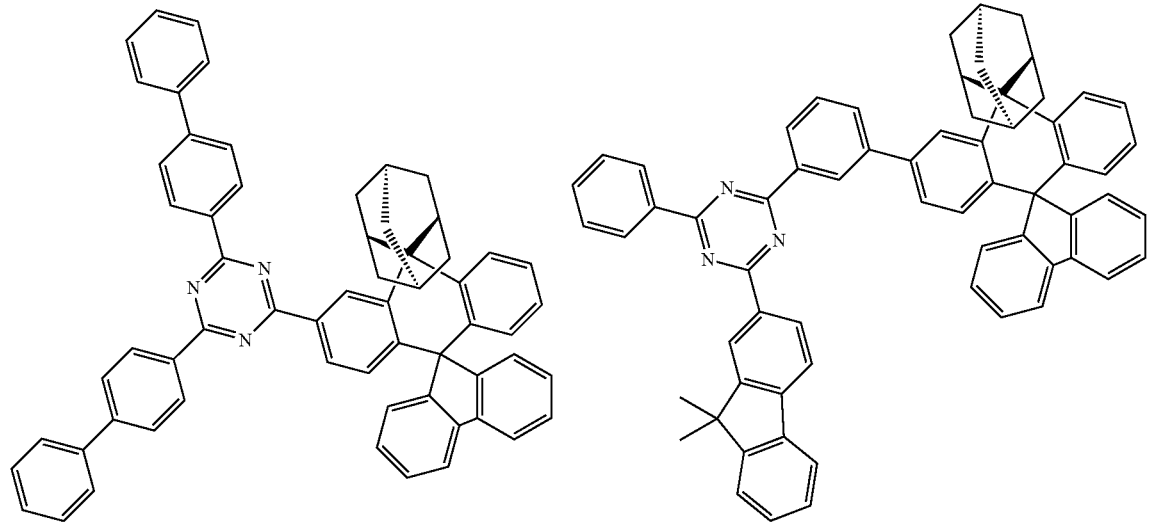
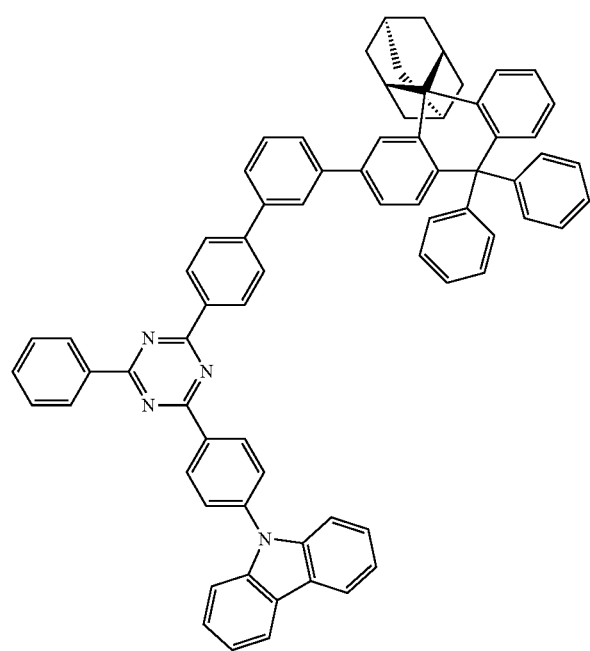
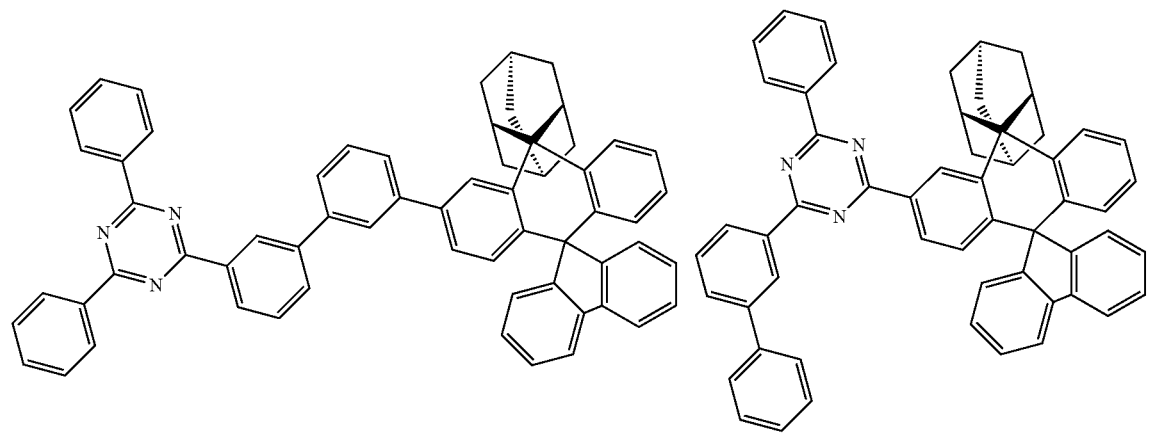

-continued
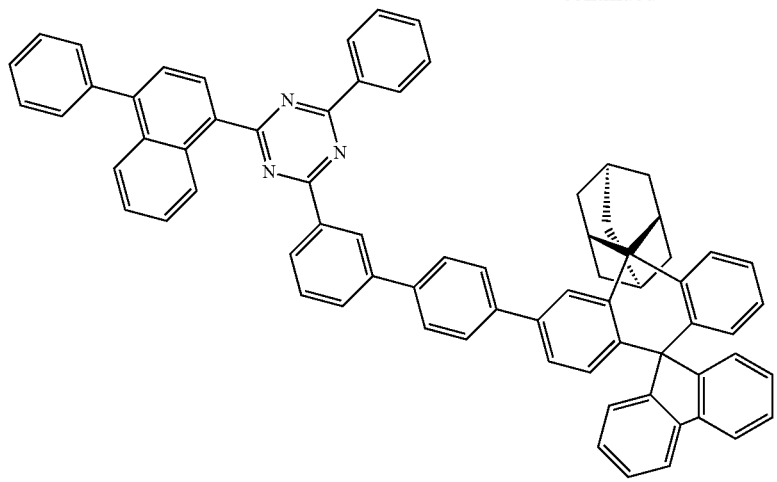
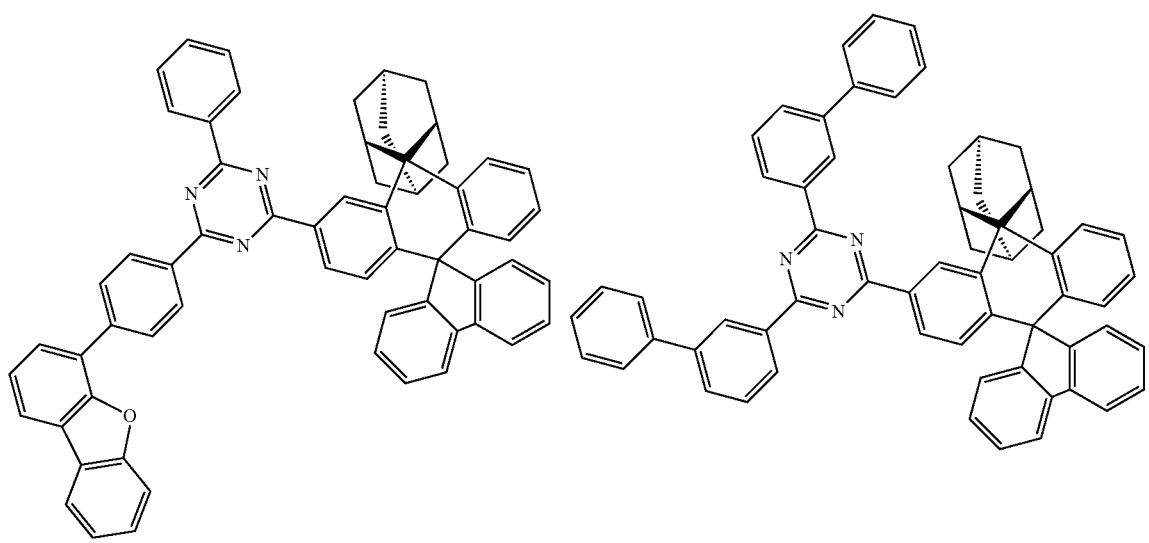
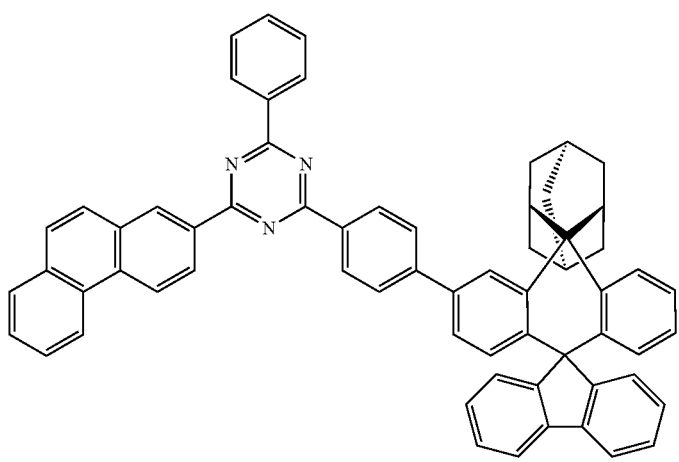

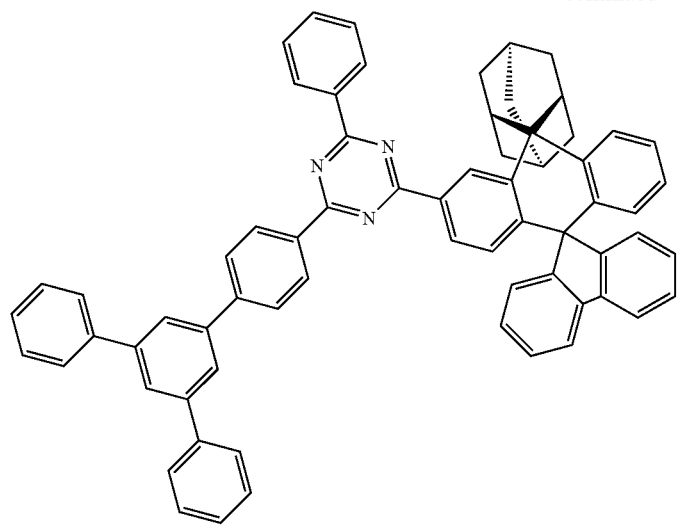
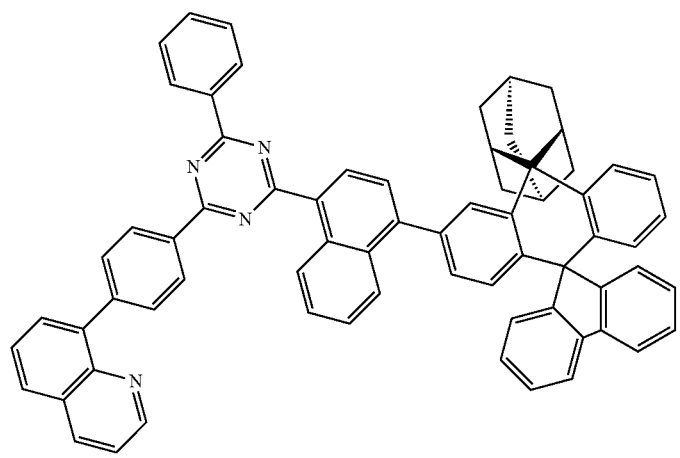
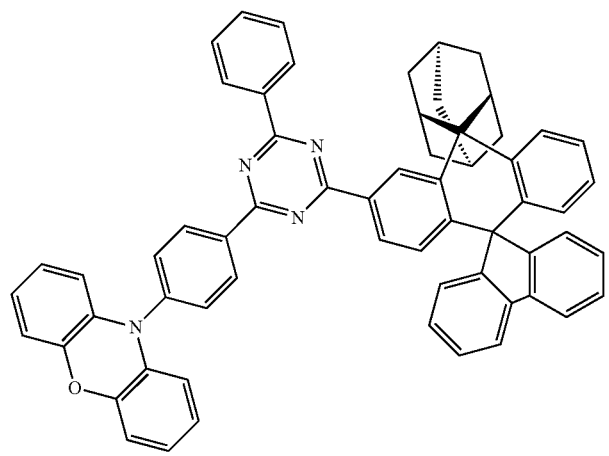

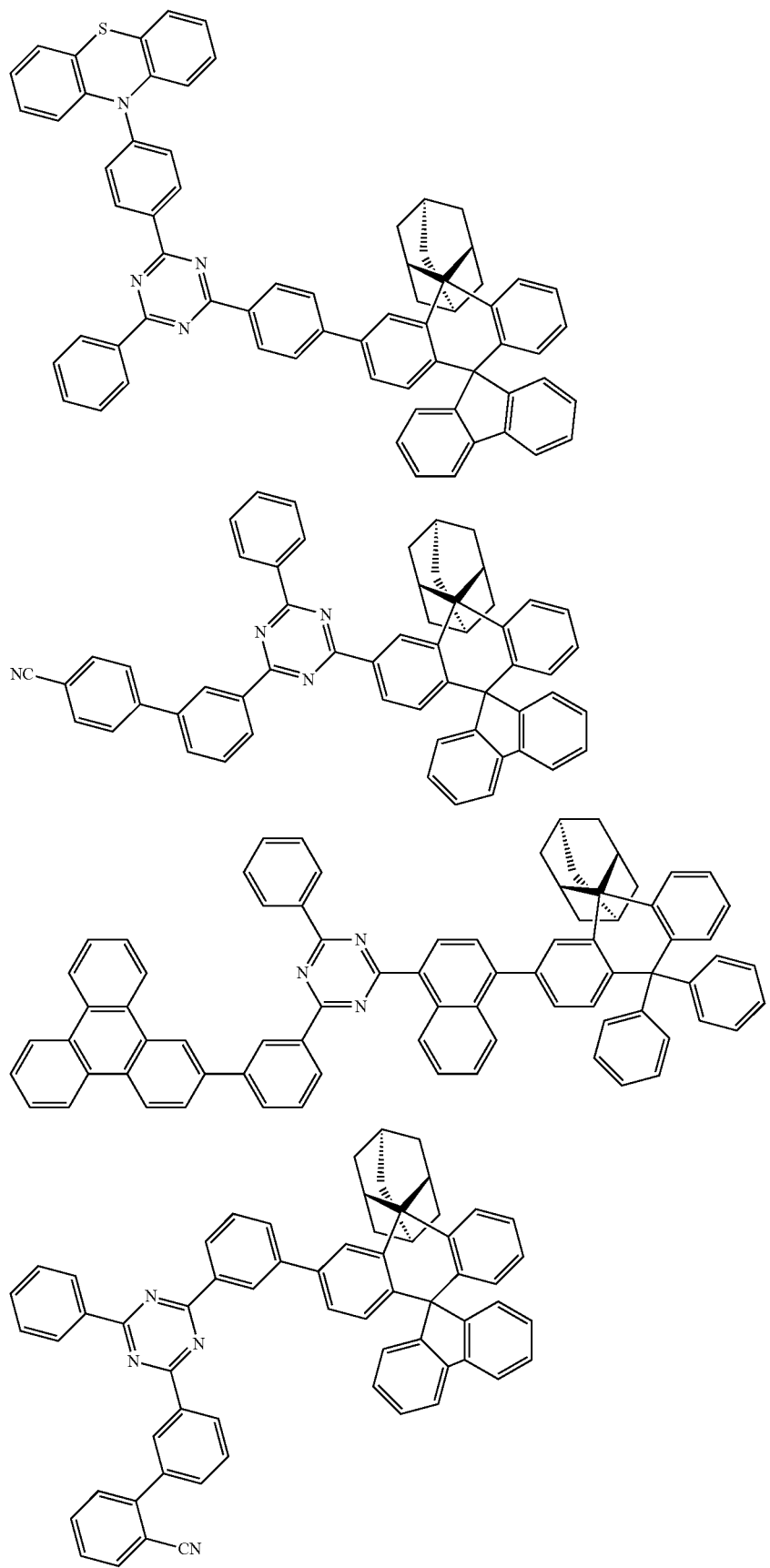

373 374
-continued
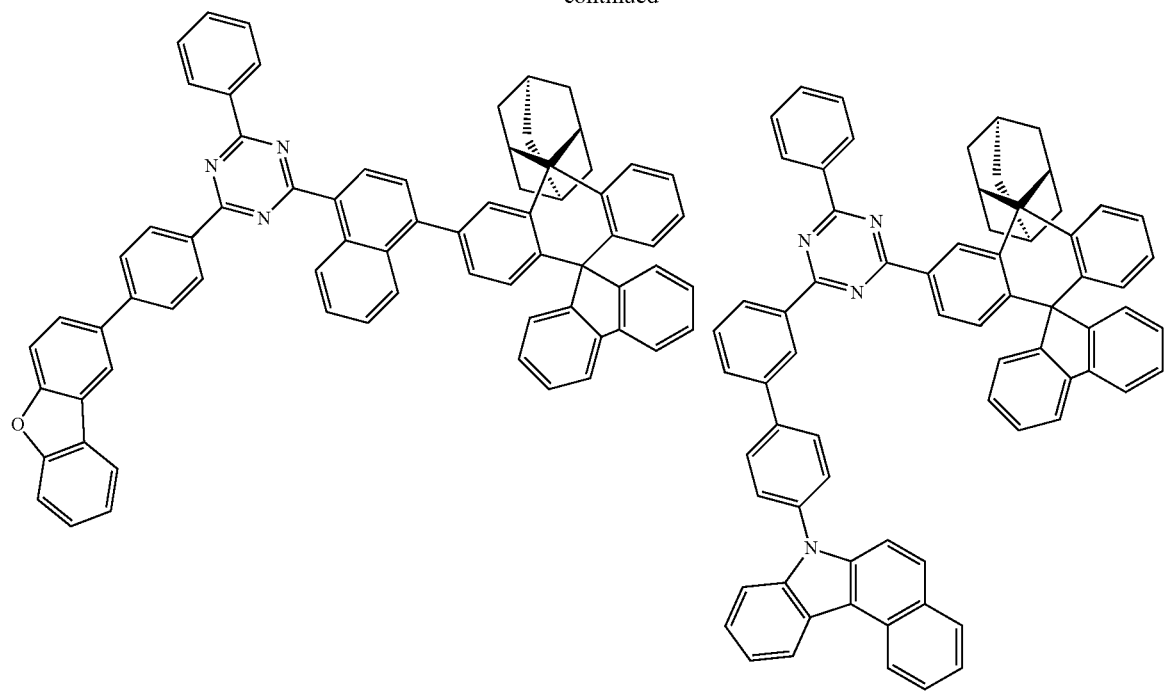
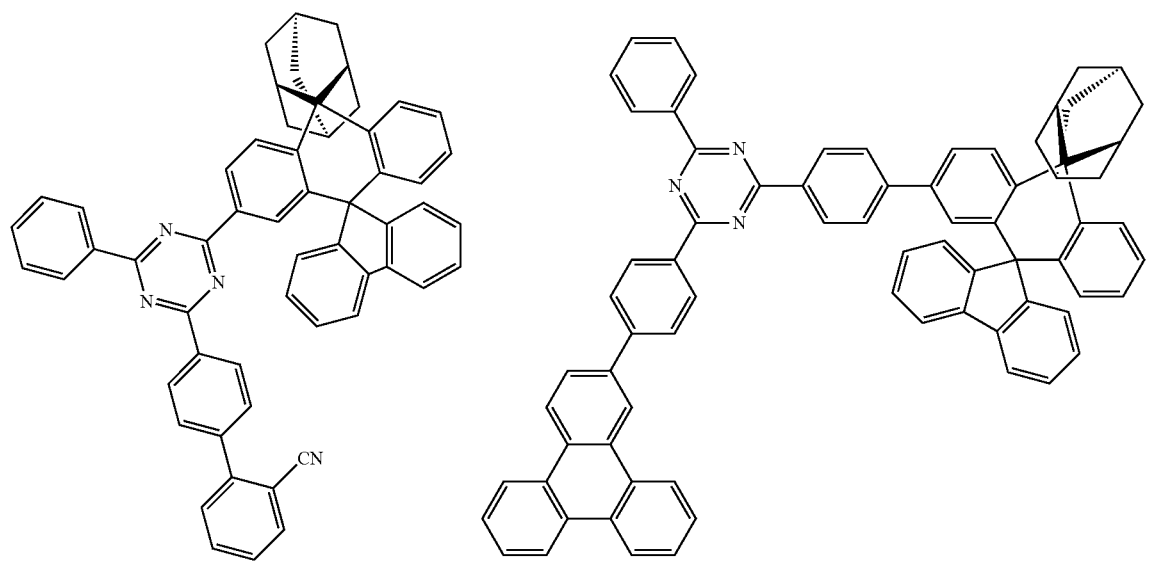

375 376
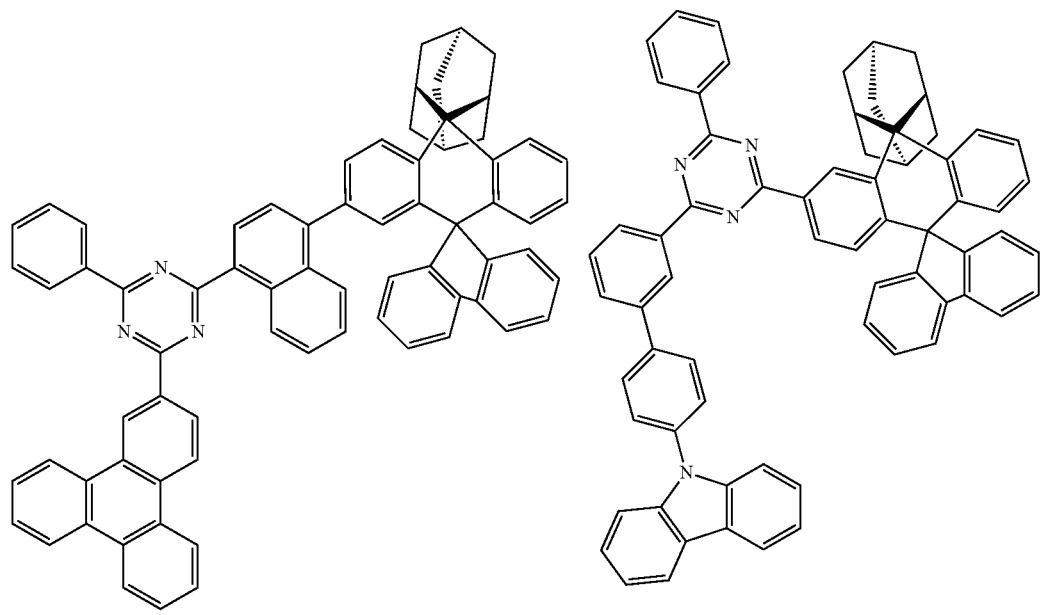

-continued
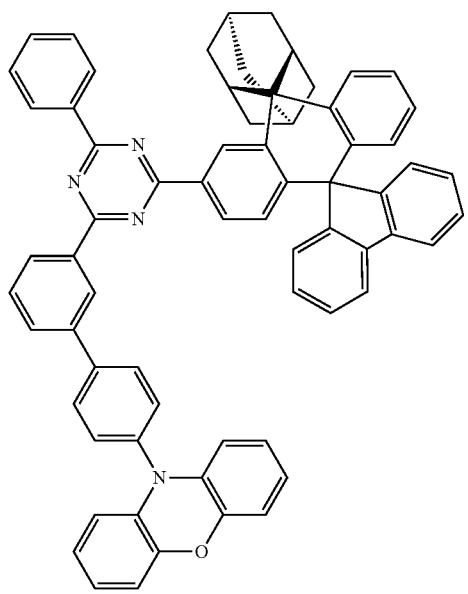
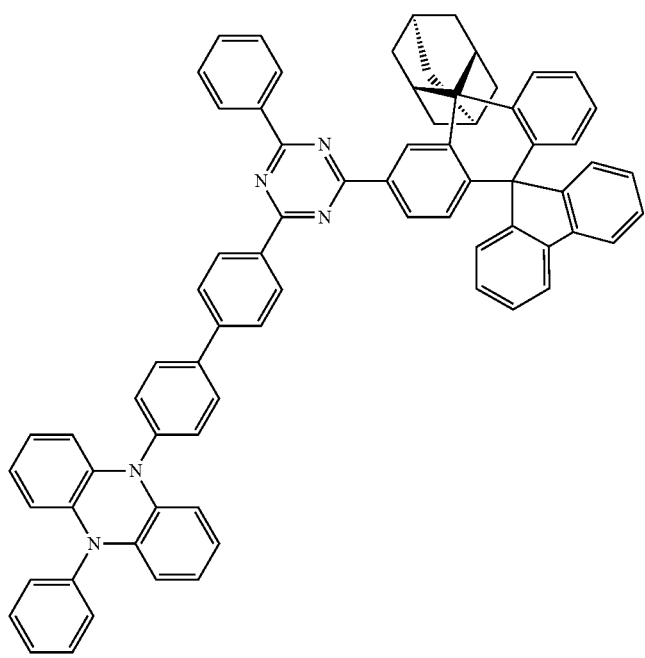
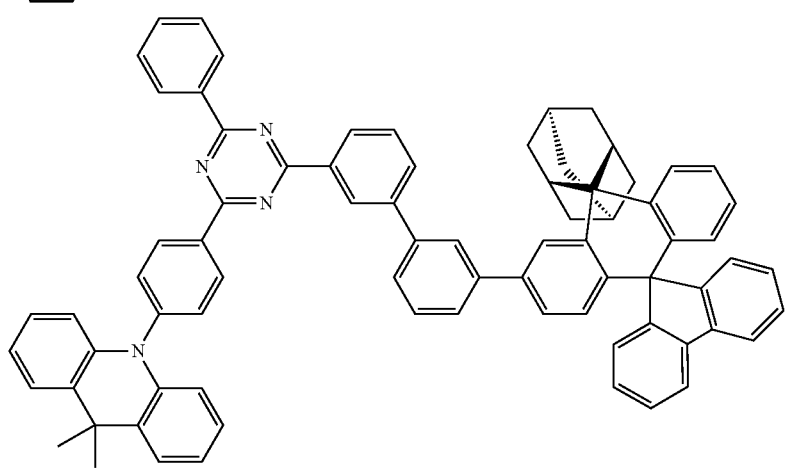

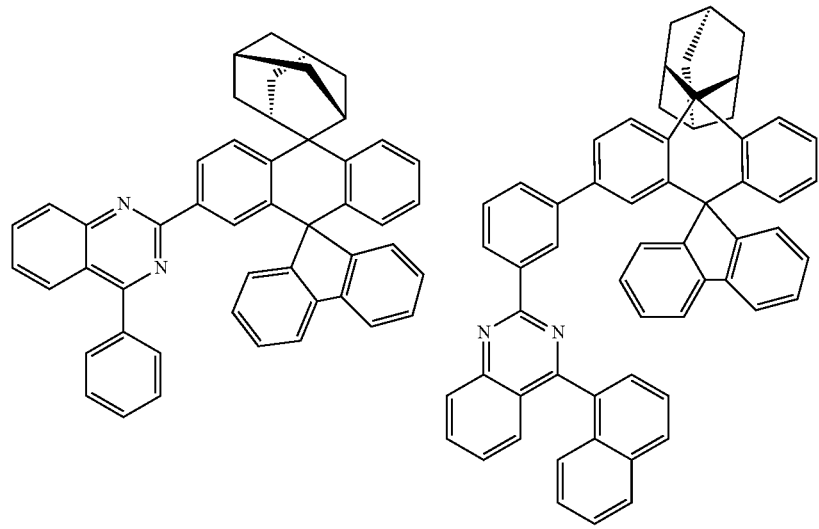
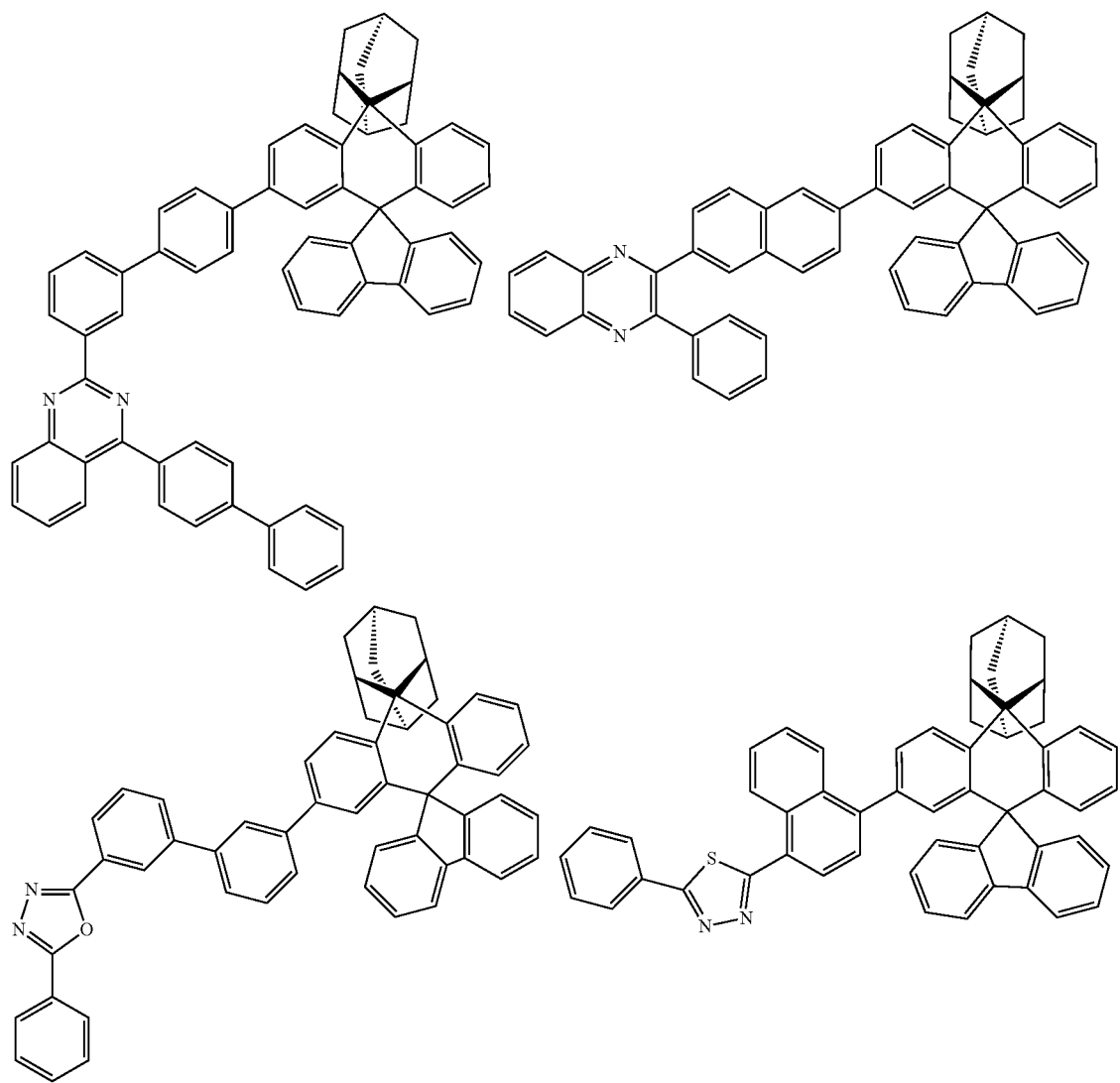

-continued
| 381 | 382 |
|---|---|
| 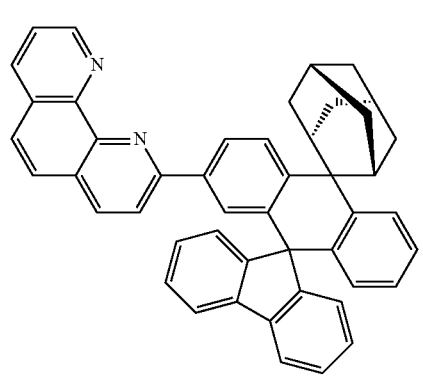 | 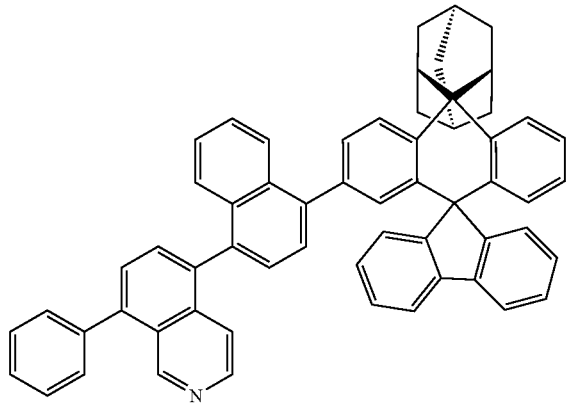 |
| 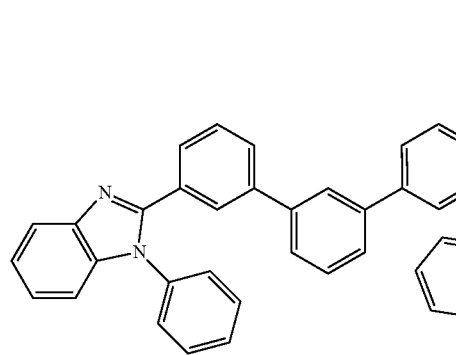 | 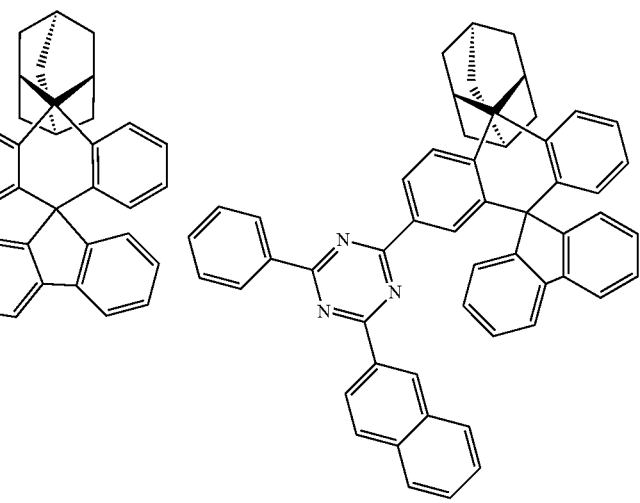 |
| 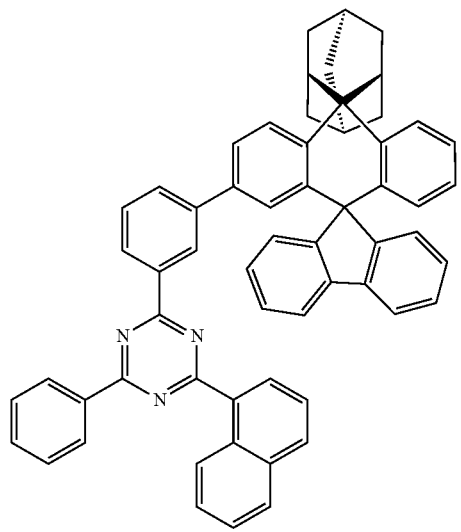 | 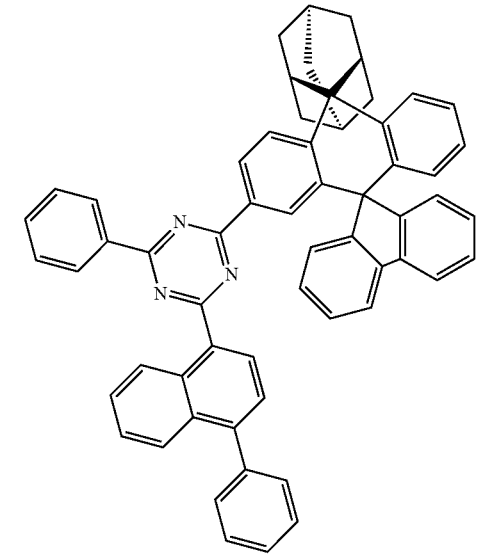 |

383 384
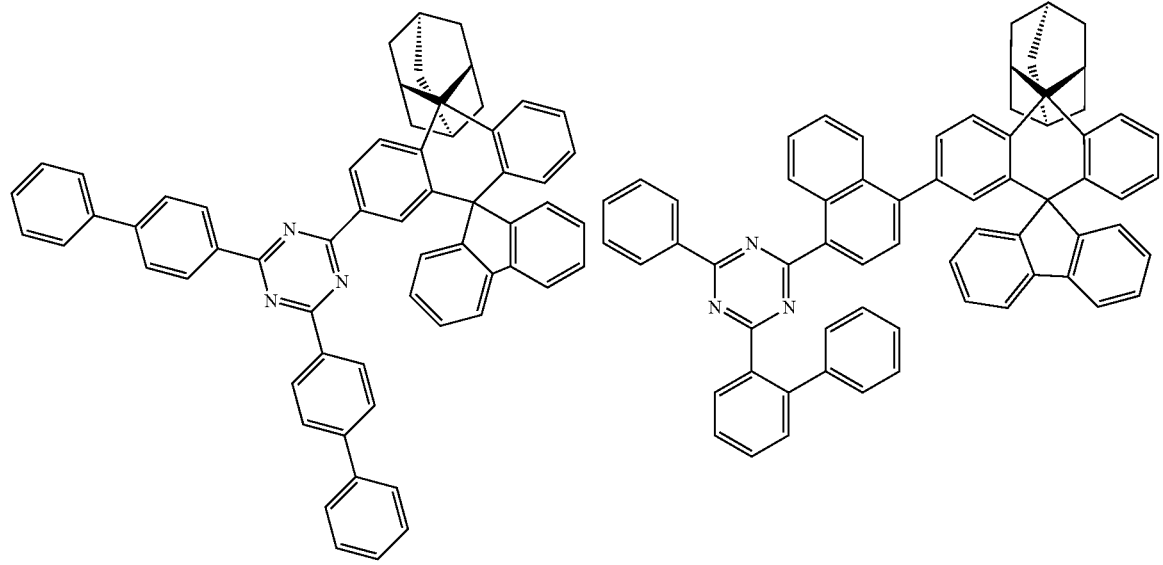
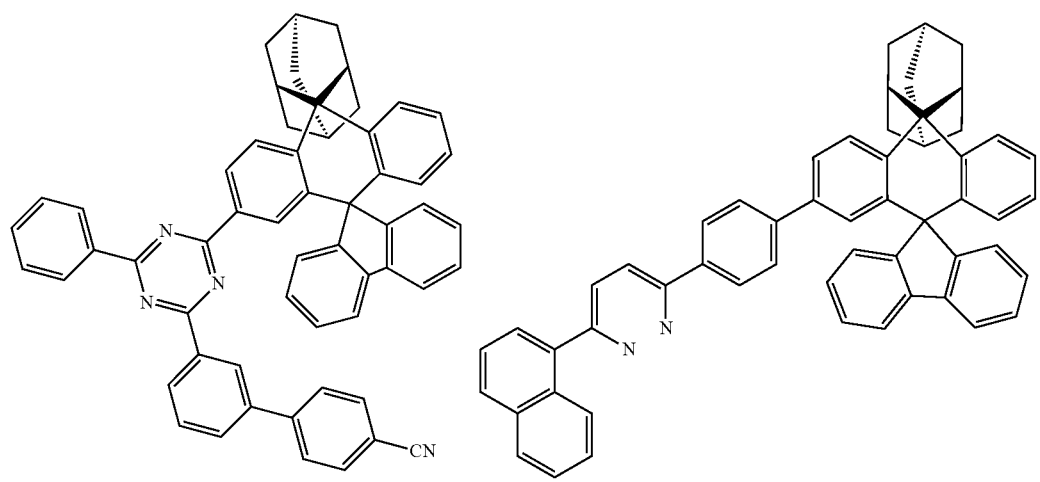
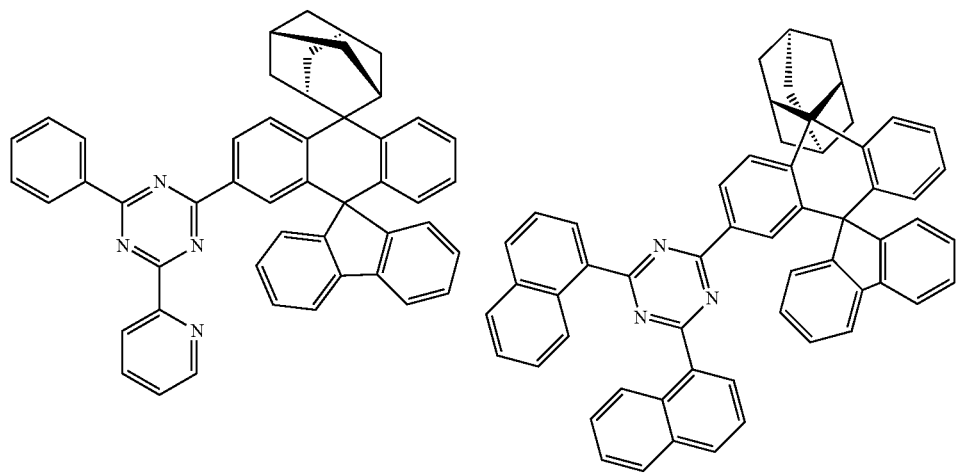

385 386
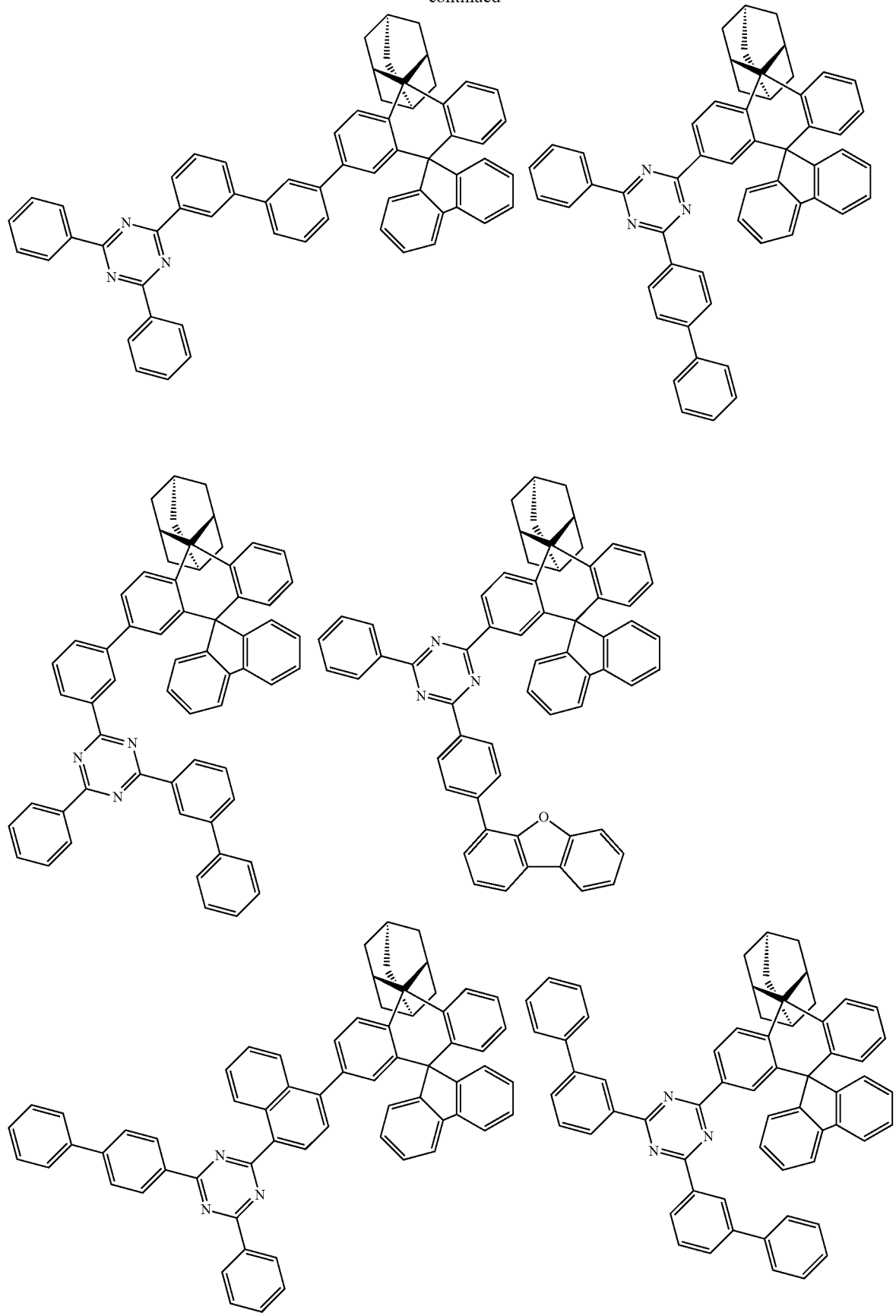

-continued
387 388
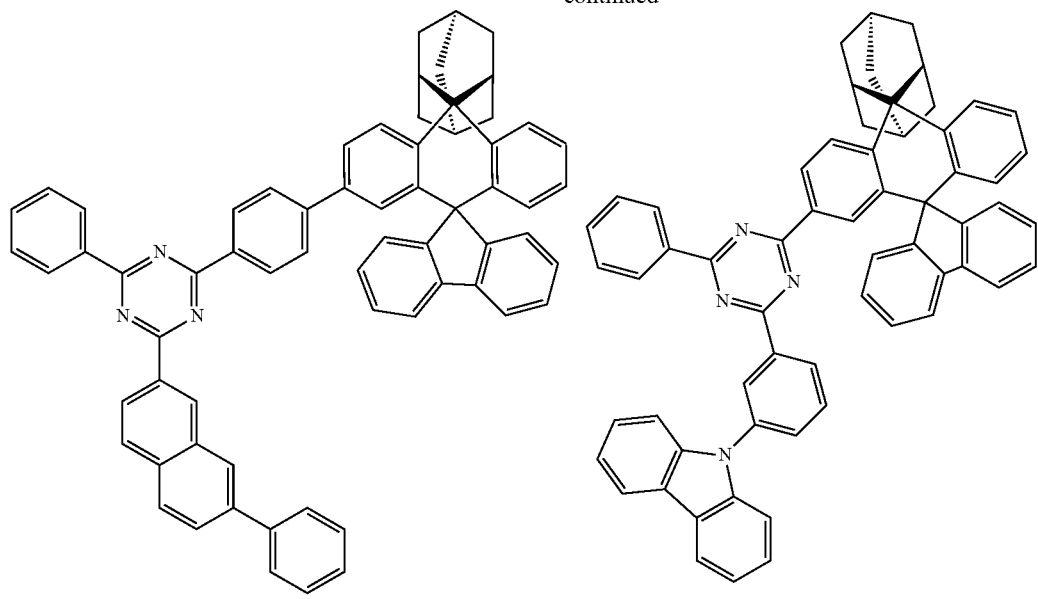
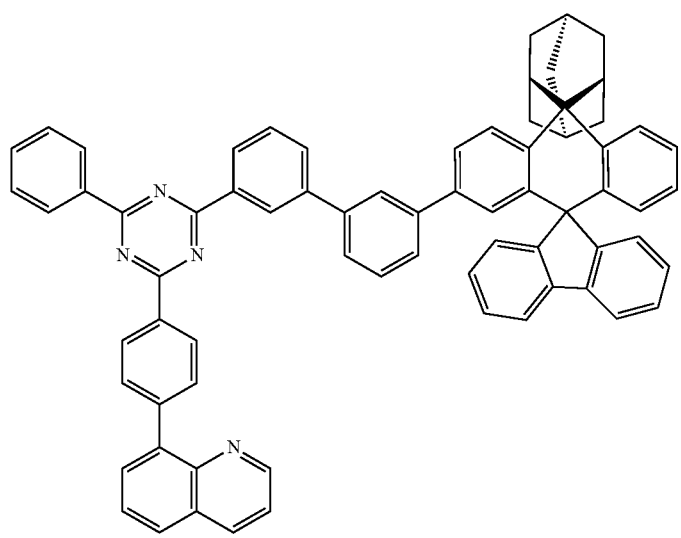
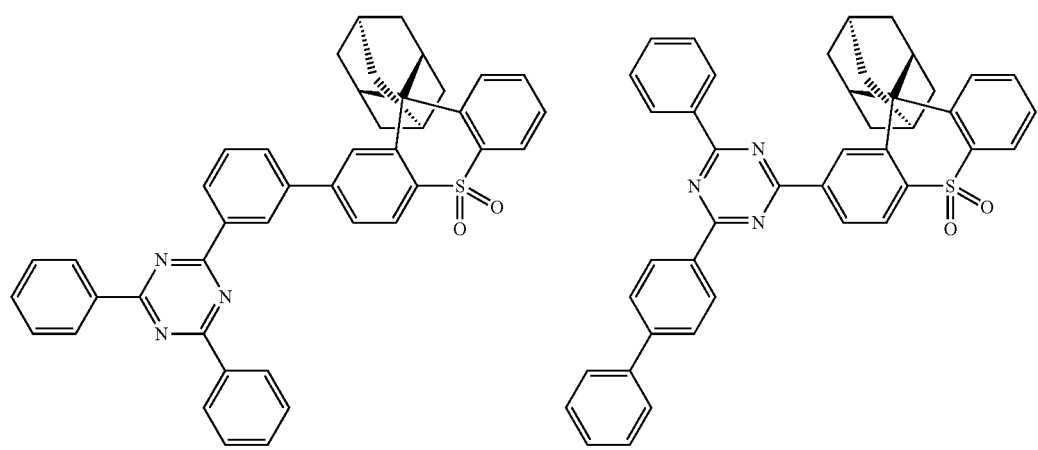

389 390
-continued
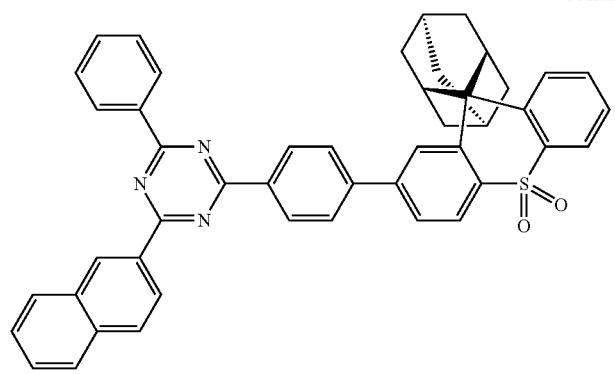
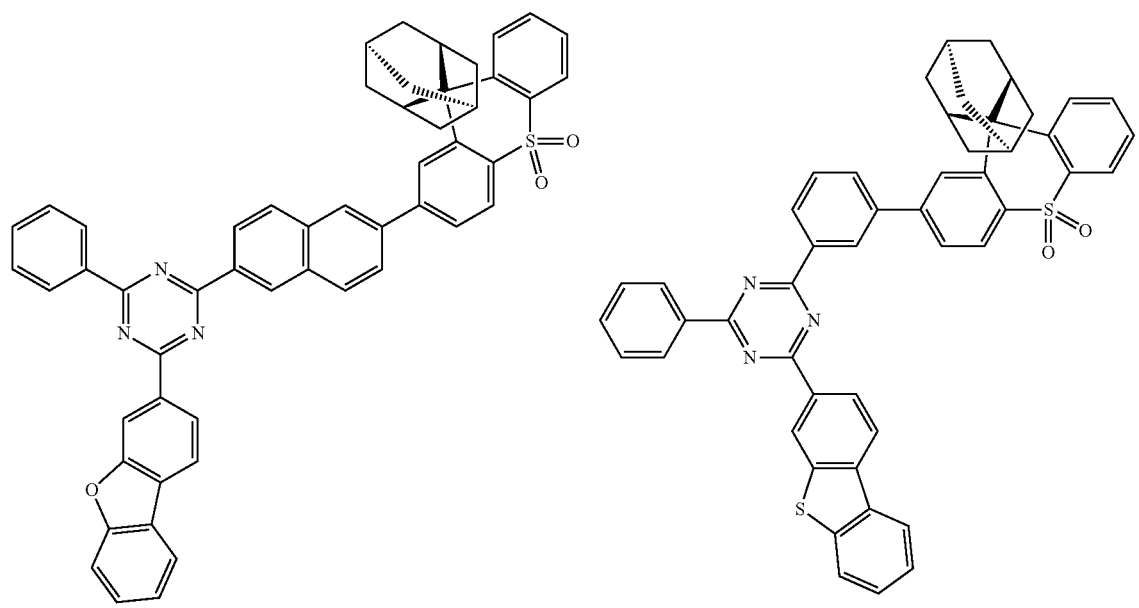
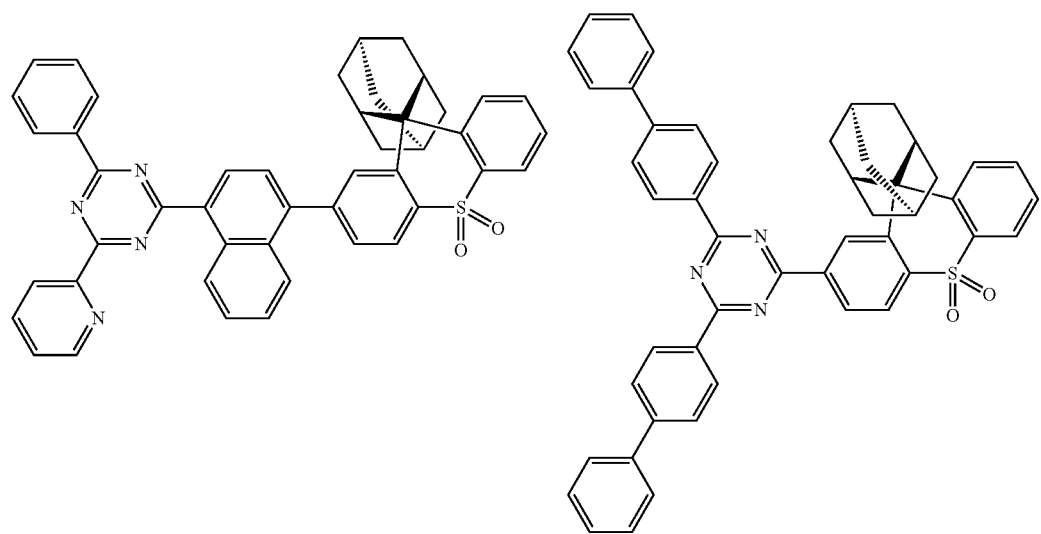

391
392
-continued
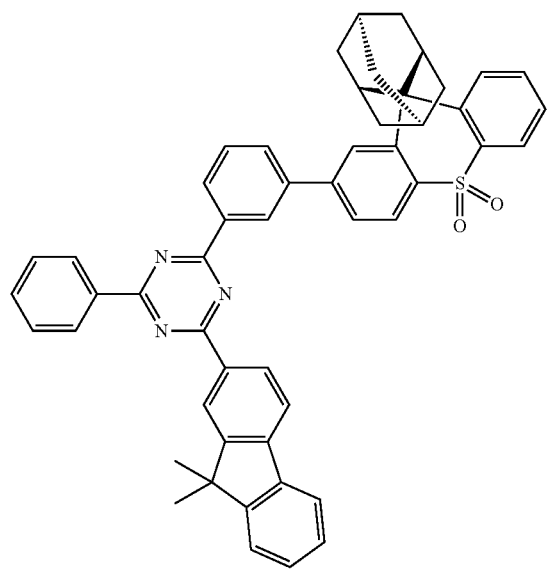
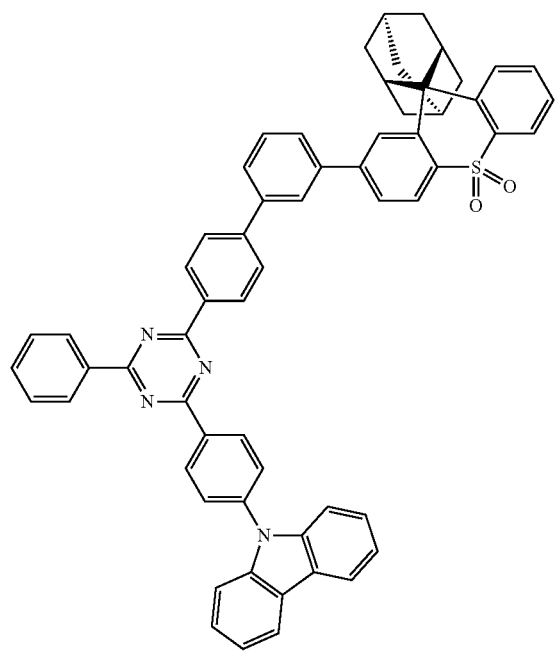
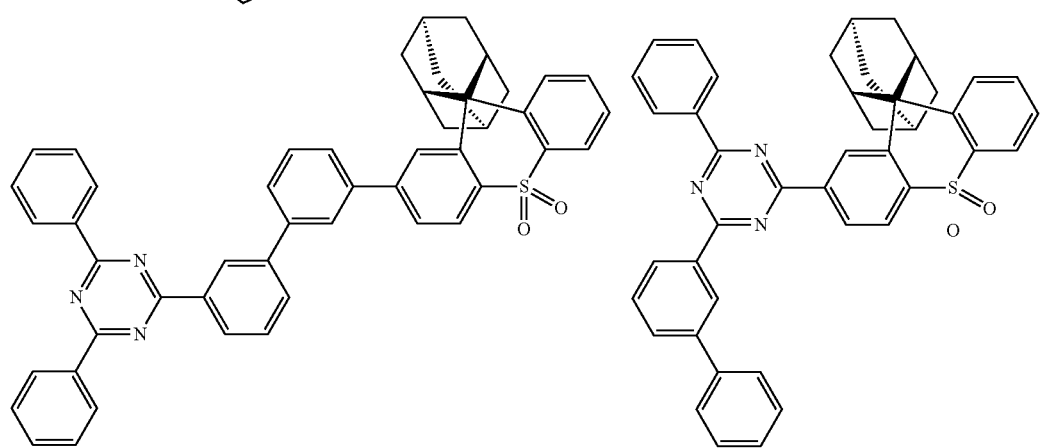

393
394
-continued
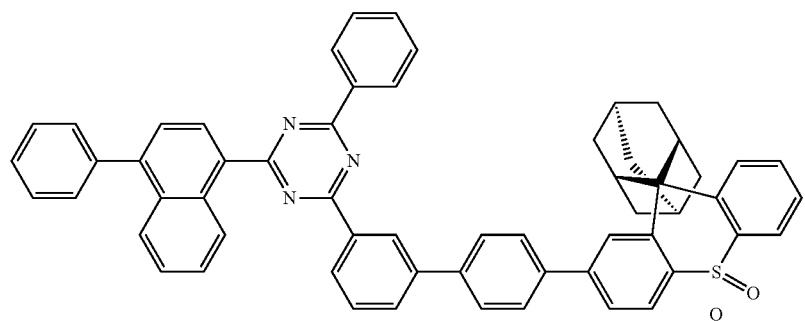
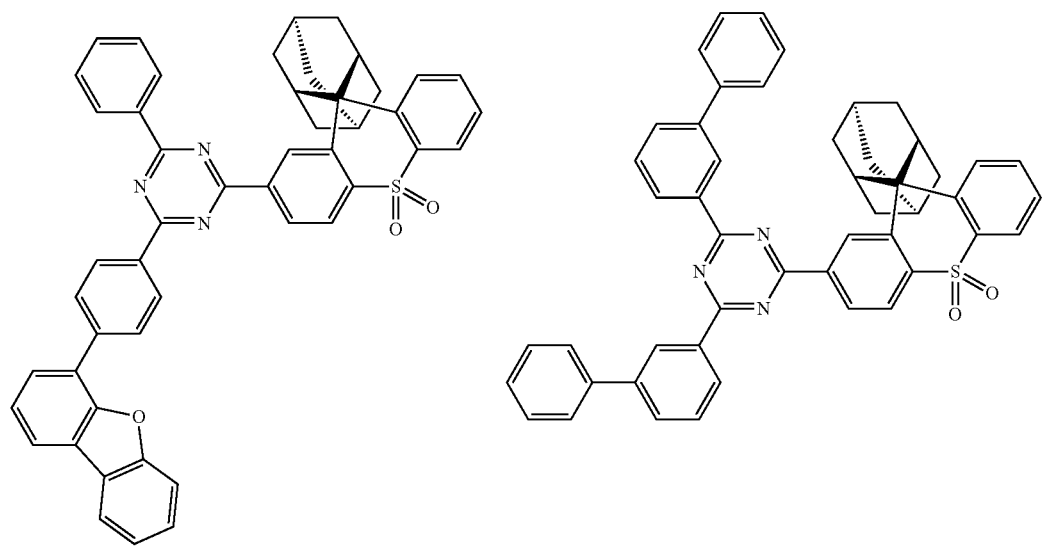
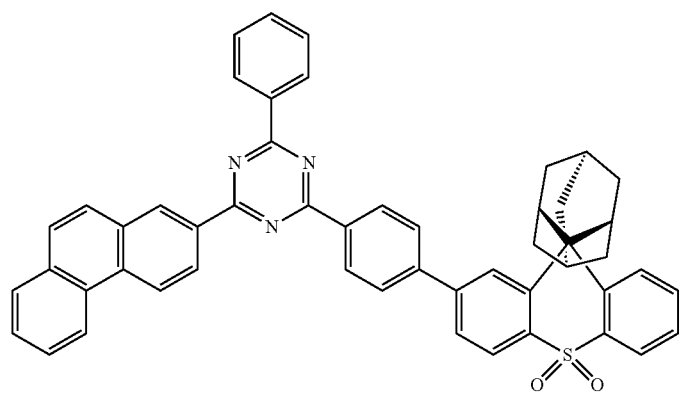

395
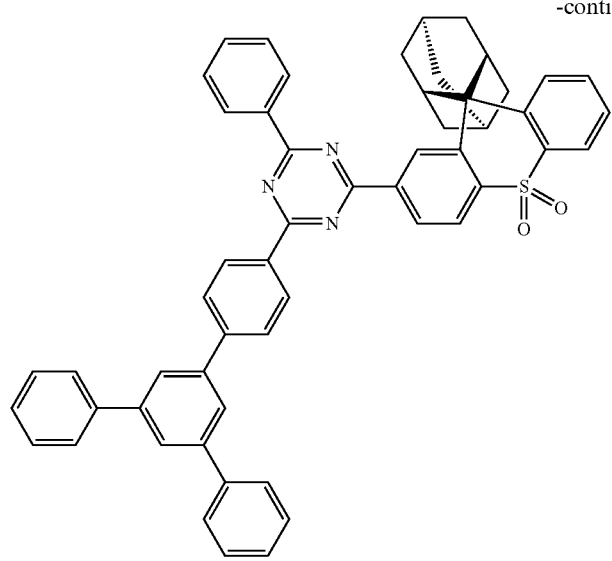
-continued
396
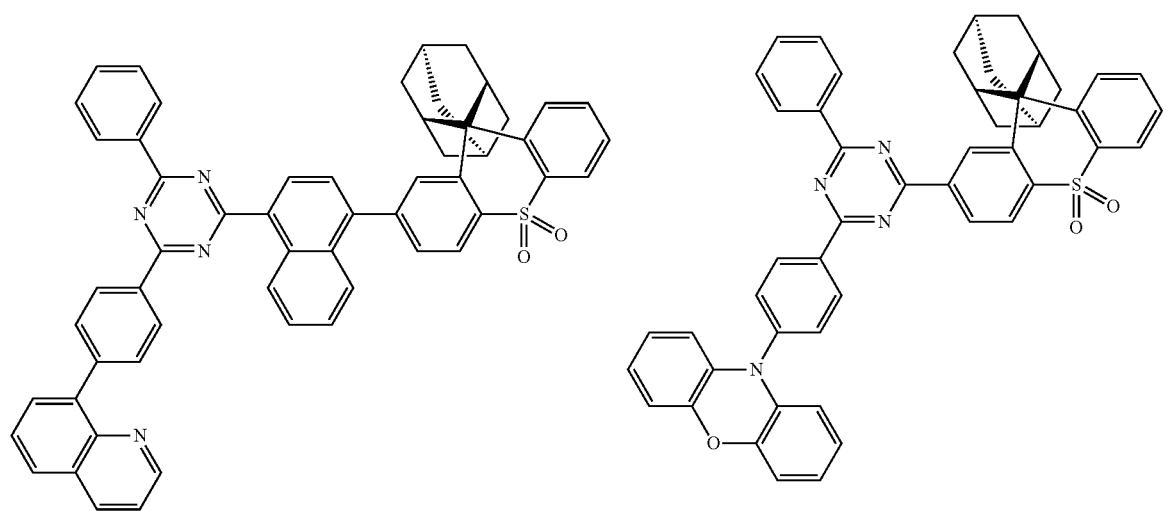
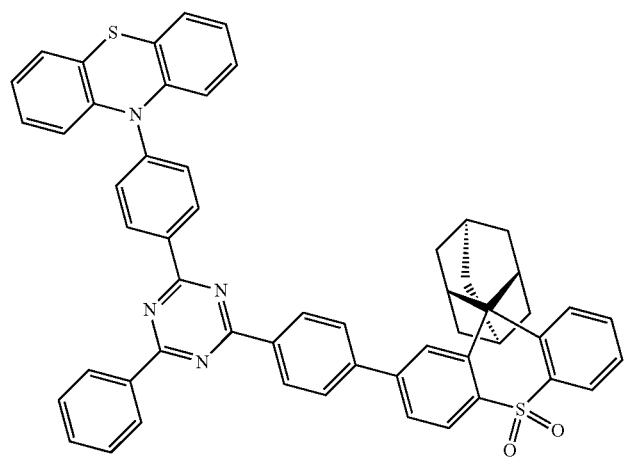

397 398
-continued
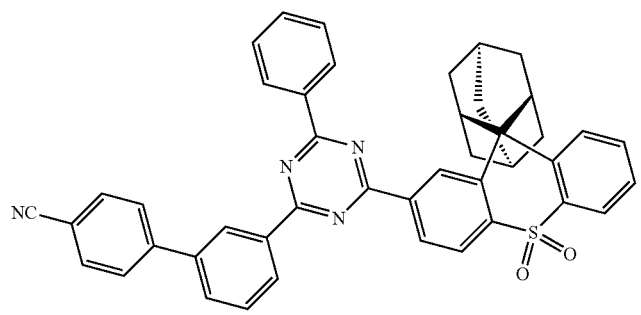
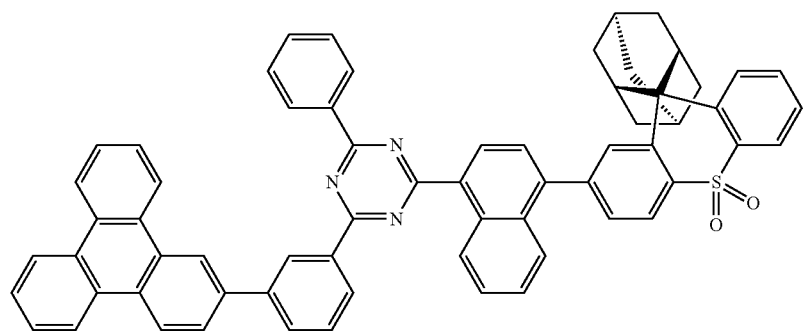
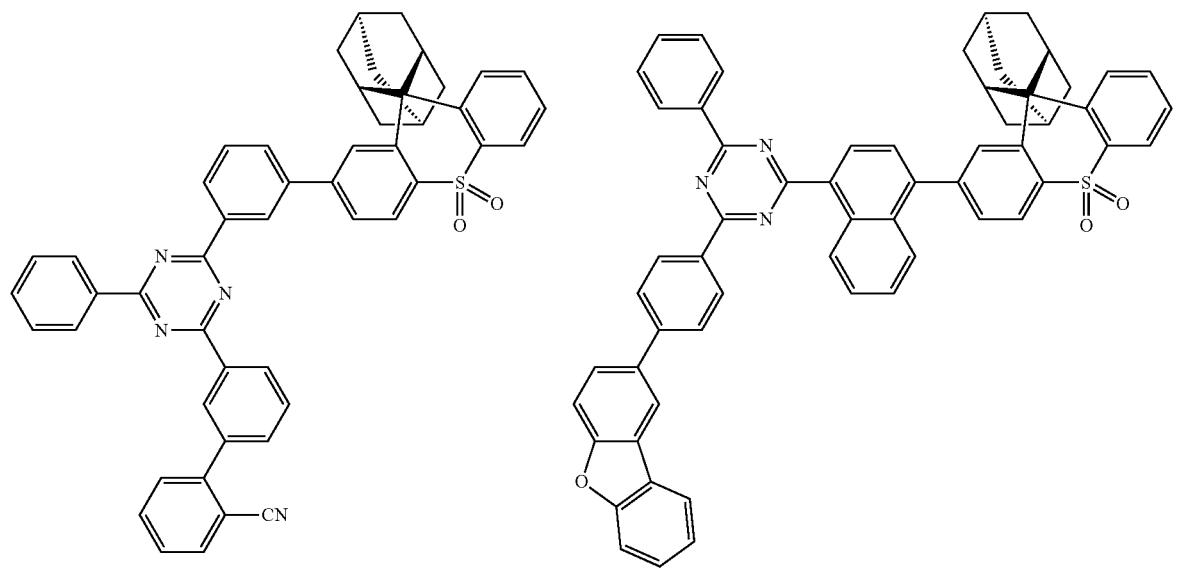

-continued
399    400
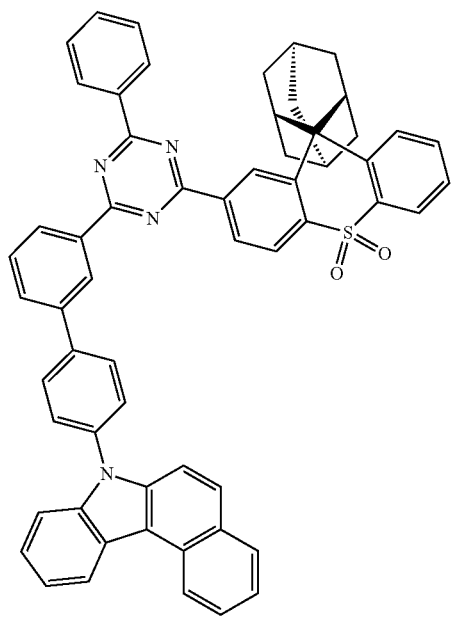 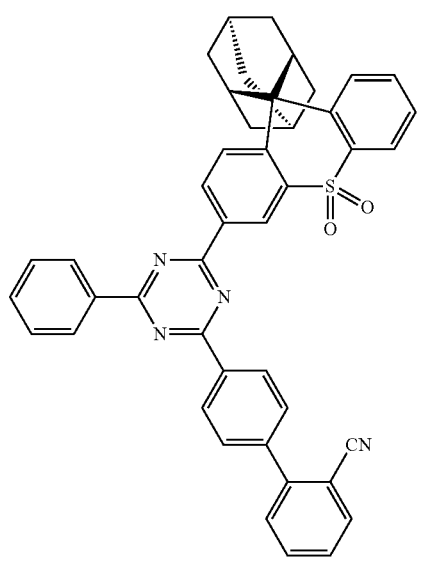
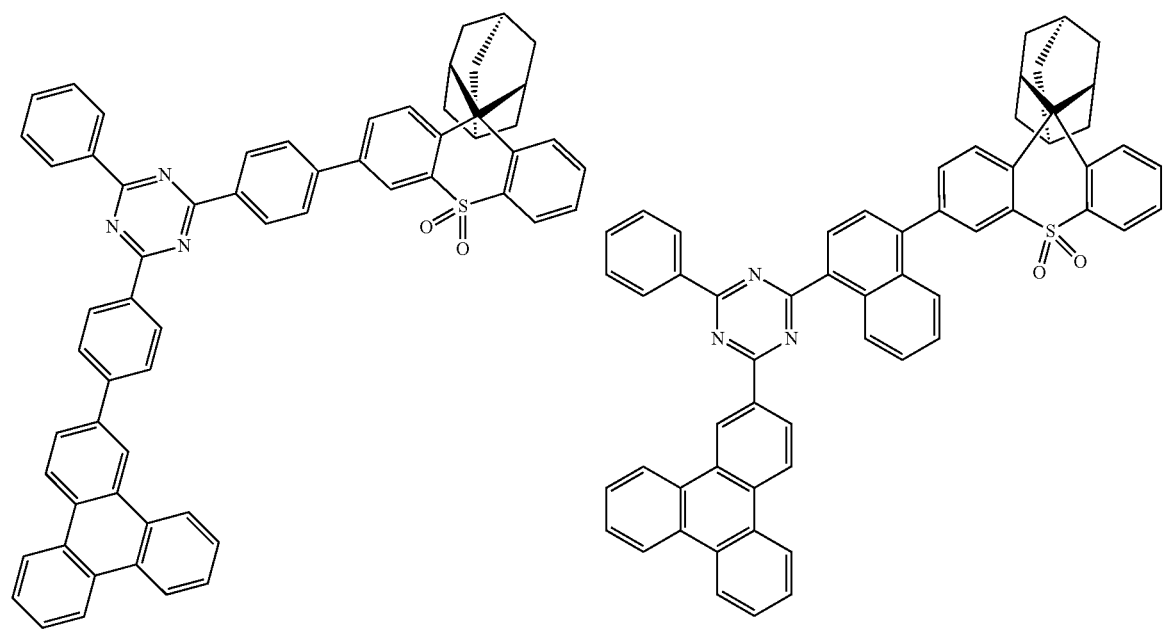

401 402
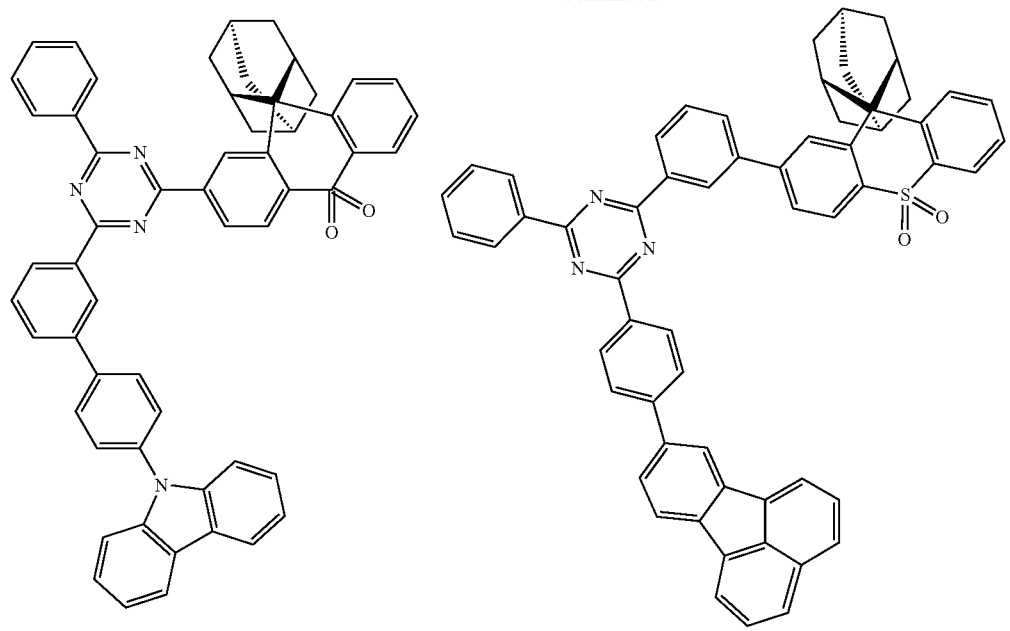
-continued
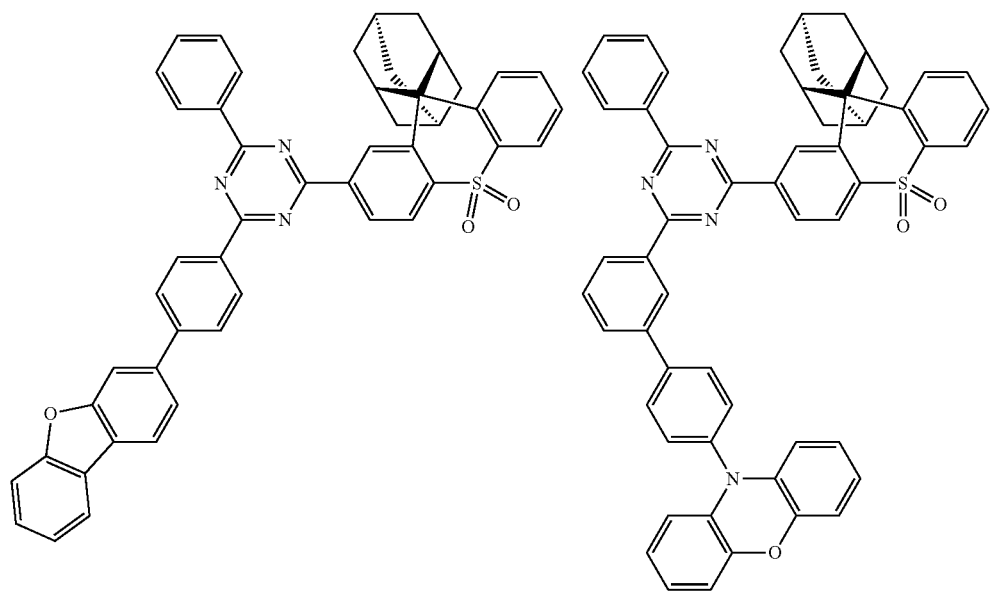

-continued
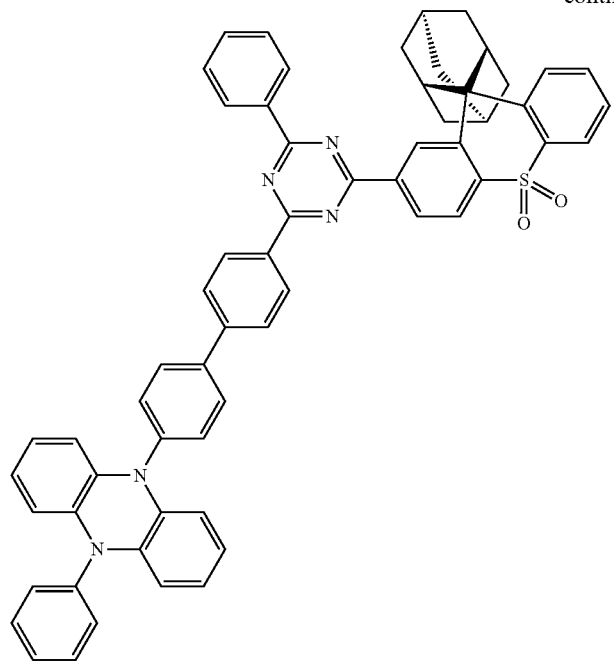
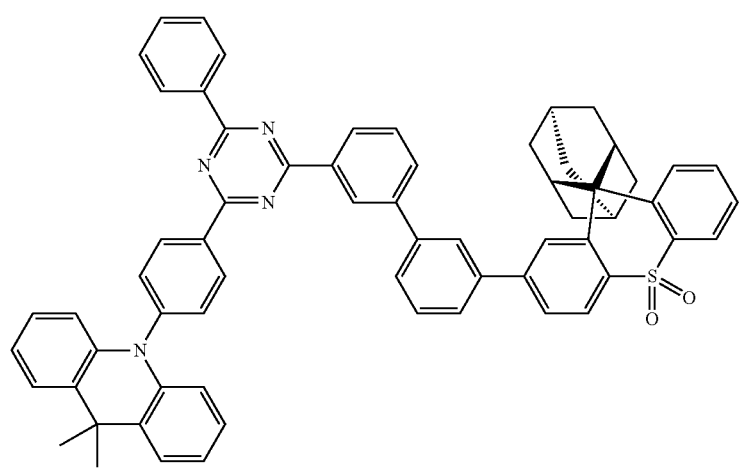
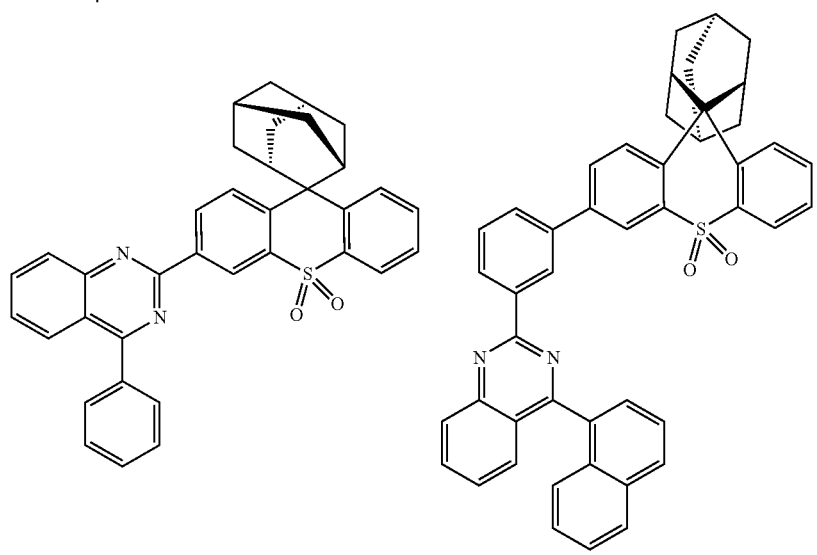

-continued
| 405 | 406 |
|---|---|
| 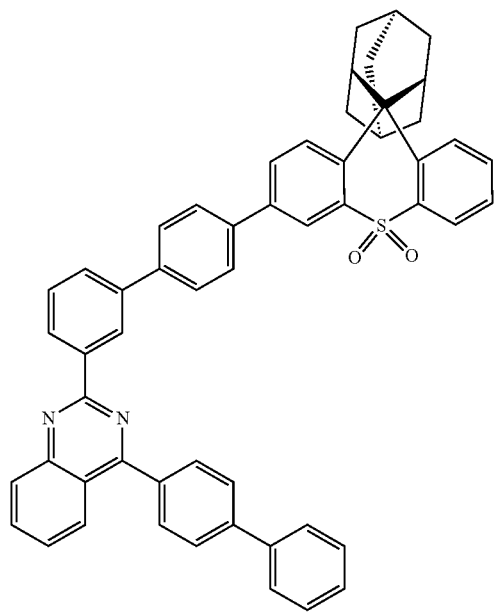 | 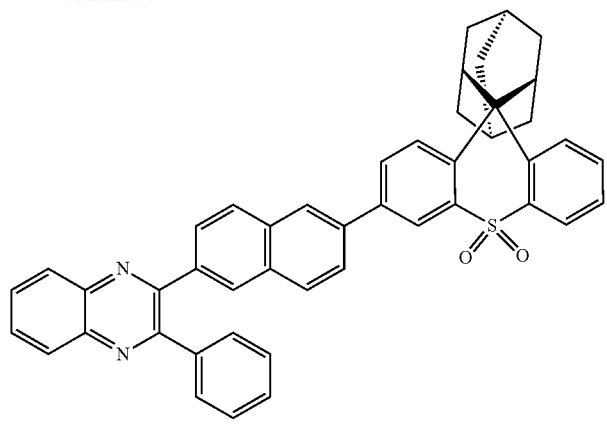 |
| 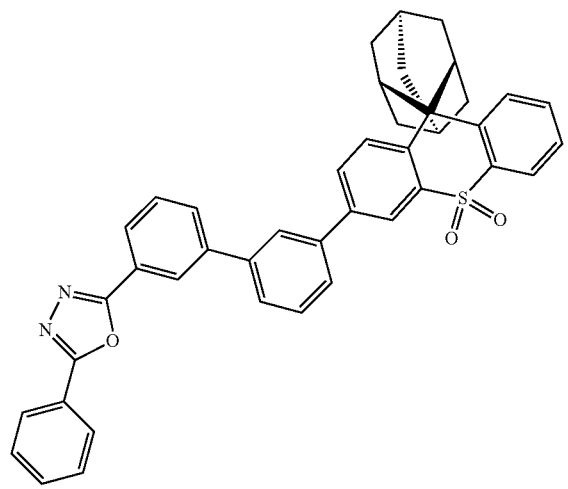 | 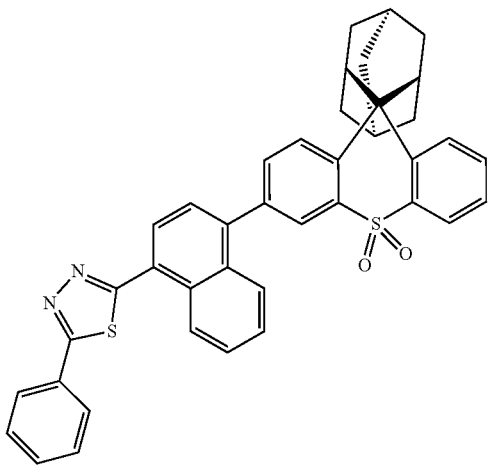 |
| 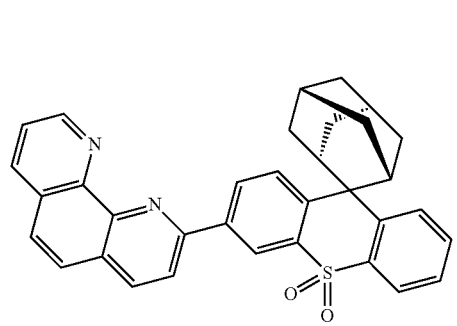 | 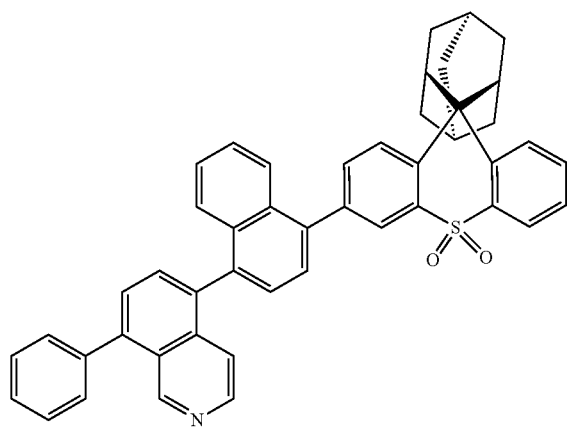 |

-continued
407
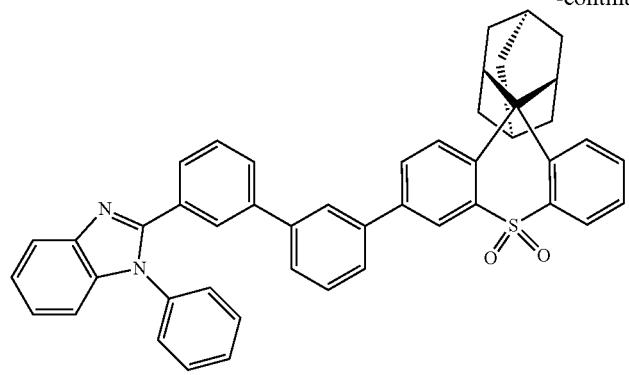
408
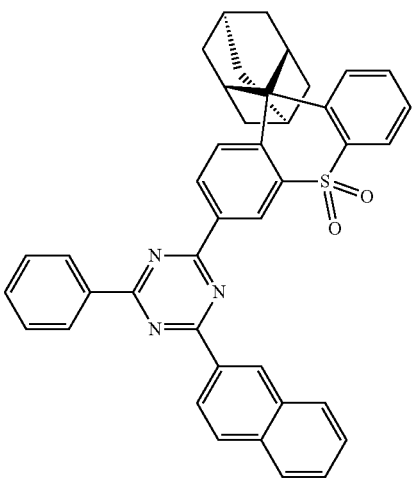
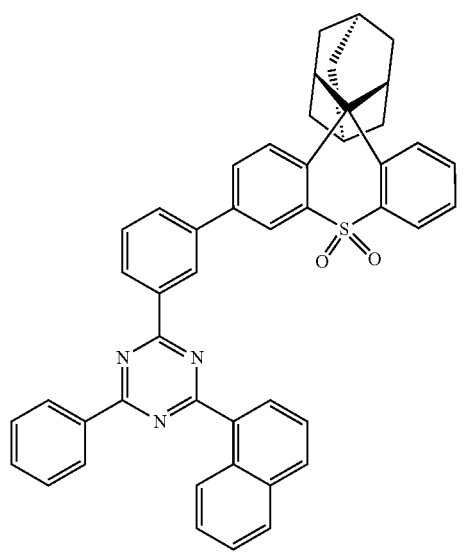
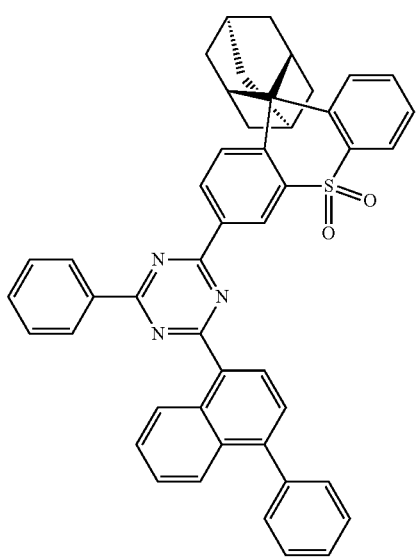
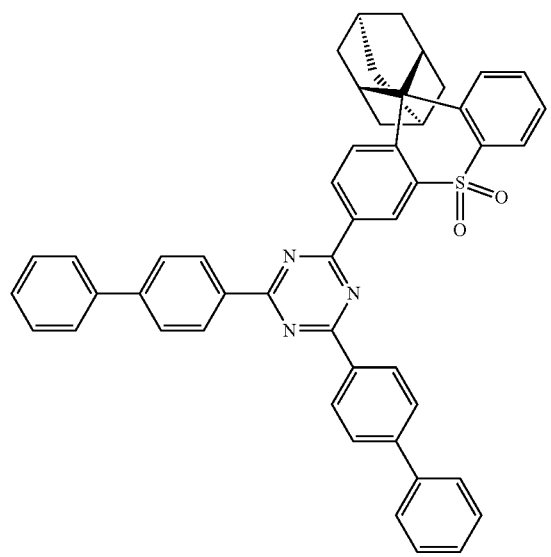
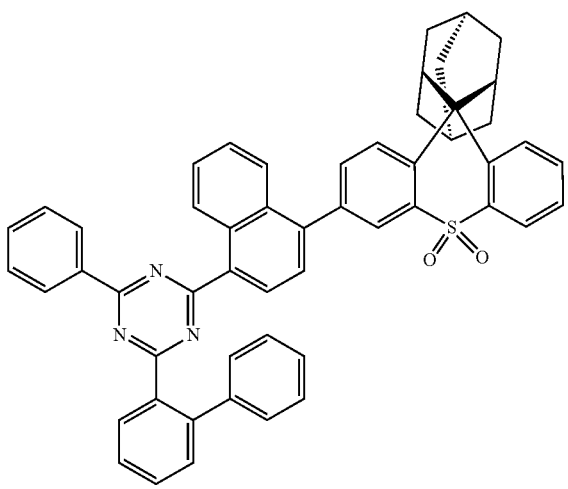

-continued
409 410
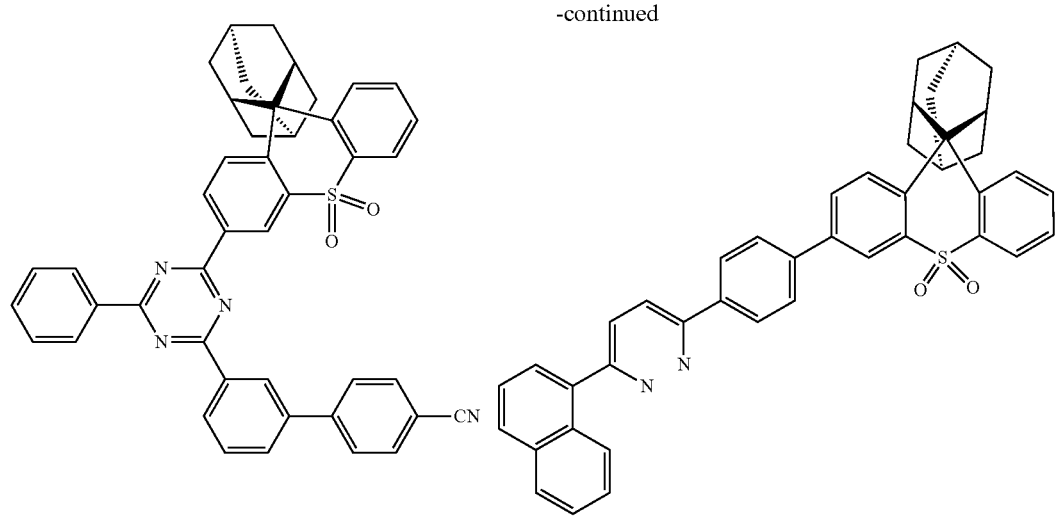
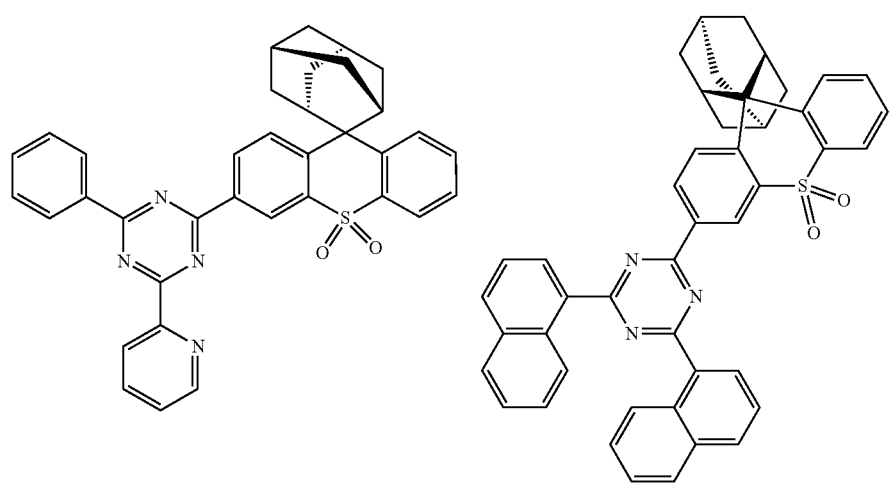
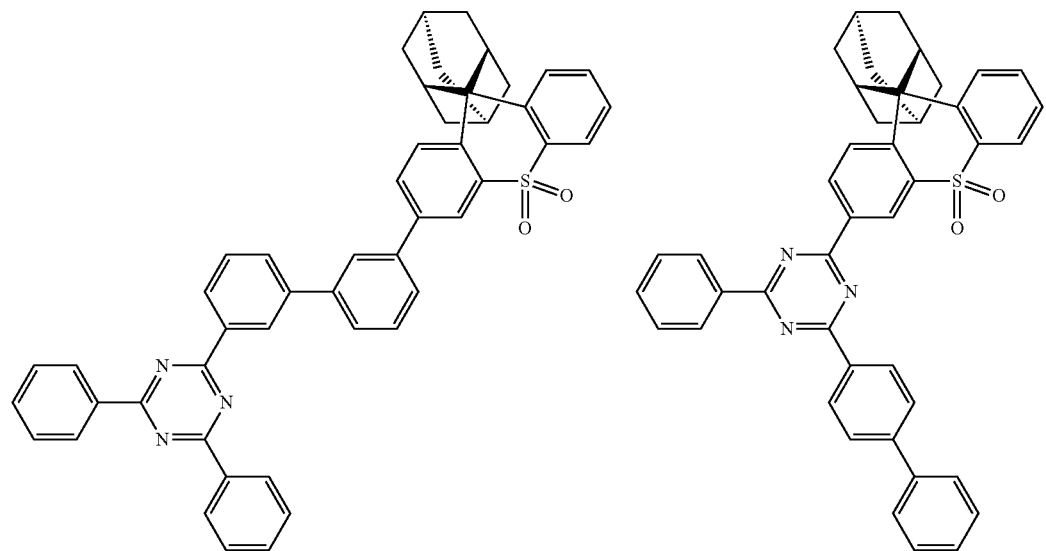

411 412
-continued
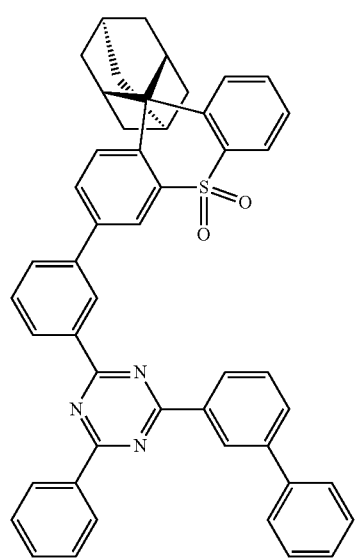
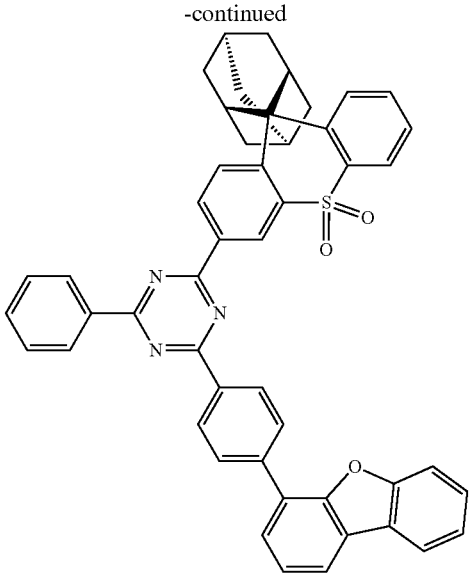
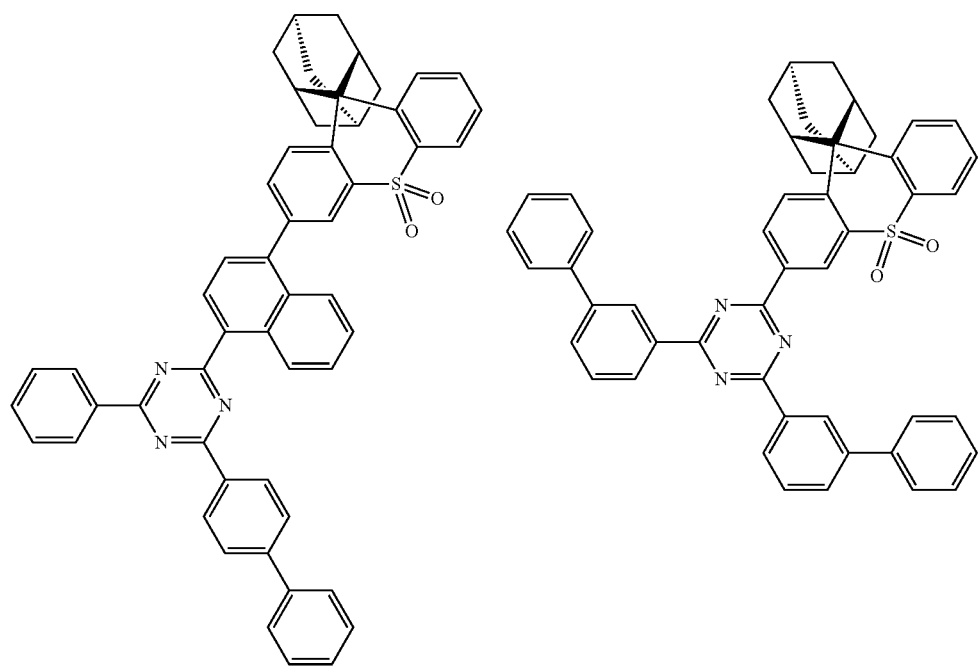

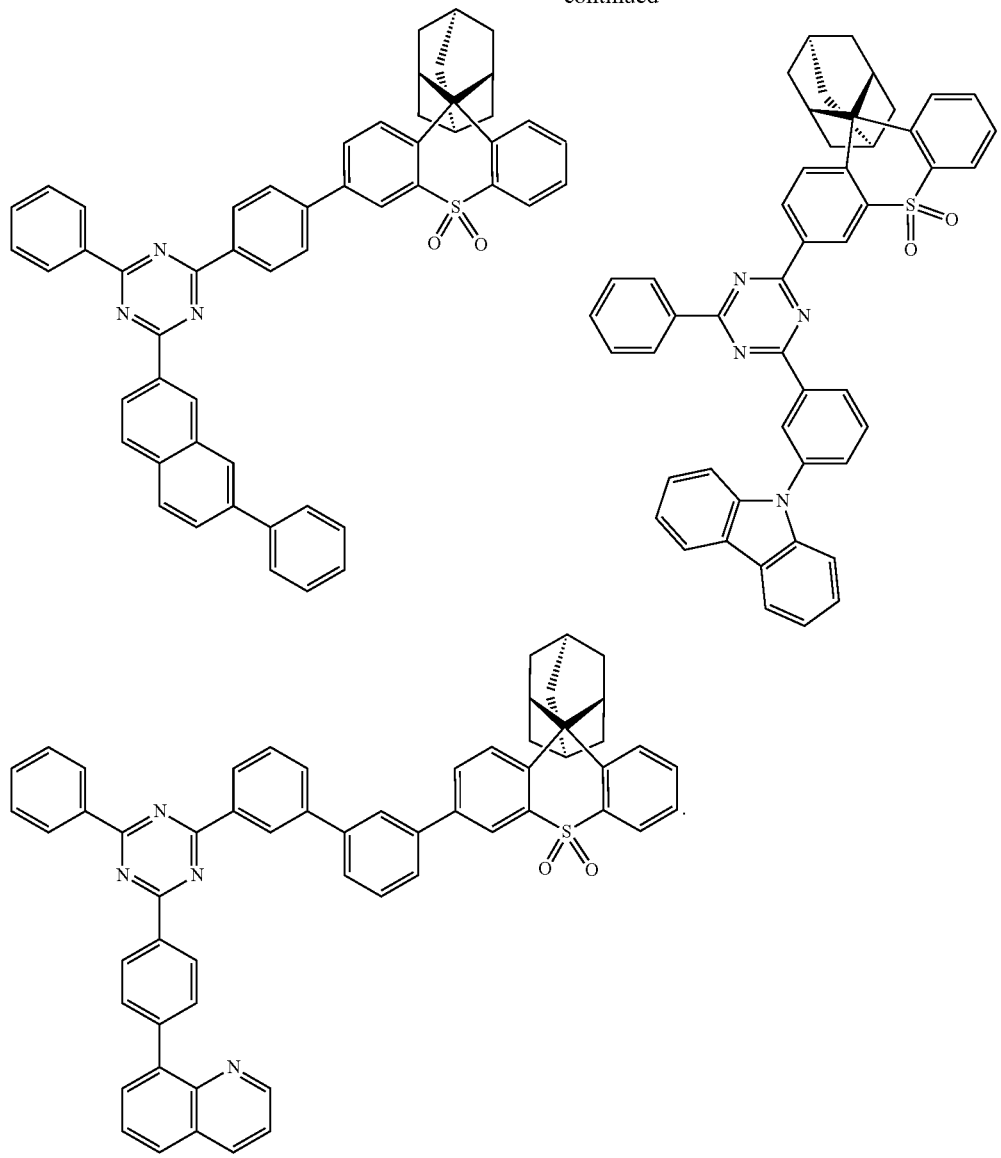

12. An organic light emitting device comprising: a first electrode; a second electrode that is provided to face the first electrode; and one or more organic material layers that are provided between the first electrode and the second electrode, wherein one or more layers of the organic material layers include a compound of claim 1.

13. An organic light emitting device comprising: a first electrode; a second electrode that is provided to face the first electrode; and one or more organic material layers that are provided between the first electrode and the second electrode, wherein one or more layers of the organic material layers include a compound of claim 7.

14. An organic light emitting device comprising: a first electrode; a second electrode that is provided to face the first electrode; and one or more organic material layers that are provided between the first electrode and the second electrode, wherein one or more layers of the organic material layers include a compound of claim 11.

* * * * *

UNITED STATES PATENT AND TRADEMARK OFFICE
CERTIFICATE OF CORRECTION

PATENT NO. : 11,997,925 B2  
APPLICATION NO. : 17/269190  
DATED : May 28, 2024  
INVENTOR(S) : Kim et al.

Page 1 of 4

It is certified that error appears in the above-identified patent and that said Letters Patent is hereby corrected as shown below:

In the Claims

In Claim 10, Column 212, Lines 1-15, the structure should be deleted.

In Claim 10, Column 218, Lines 20-30, the structure should be:

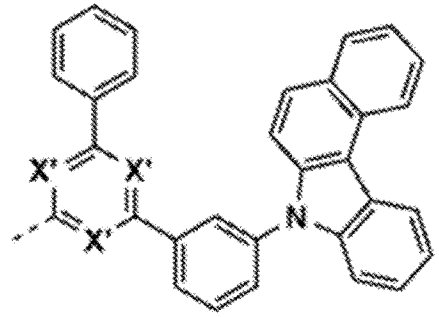

In Claim 11, Column 323, the structure of the compound should be:

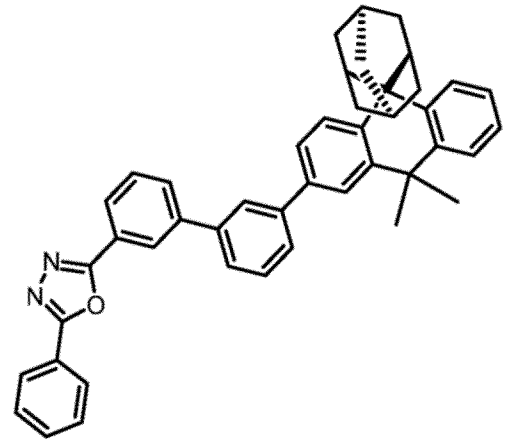

Signed and Sealed this  
Sixth Day of August, 2024

*Katherine Kelly Vidal*

Katherine Kelly Vidal  
*Director of the United States Patent and Trademark Office*

CERTIFICATE OF CORRECTION (continued)
U.S. Pat. No. 11,997,925 B2

Page 2 of 4

In Claim 11, Column 324, the structure of the compound should be:

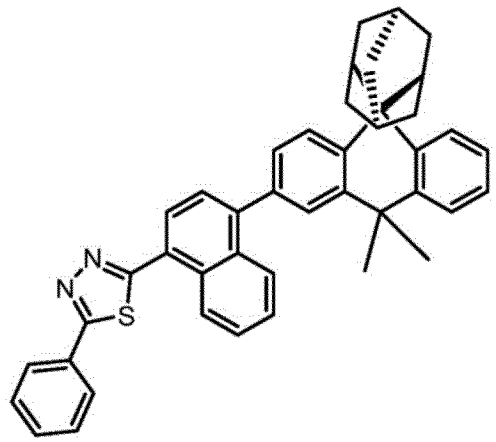

In Claim 11, Column 327, the structure of the first compound should be:

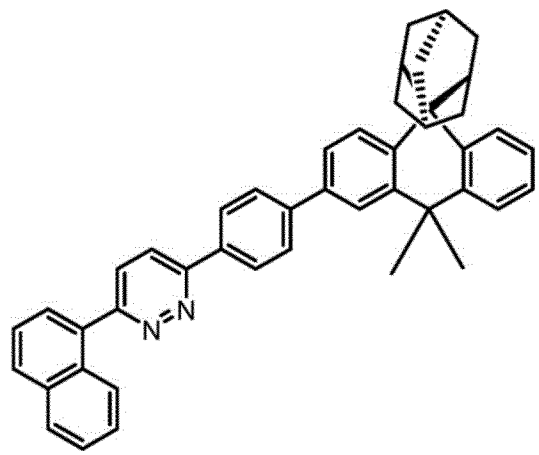

In Claim 11, Column 357, the structure of the last compound should be:

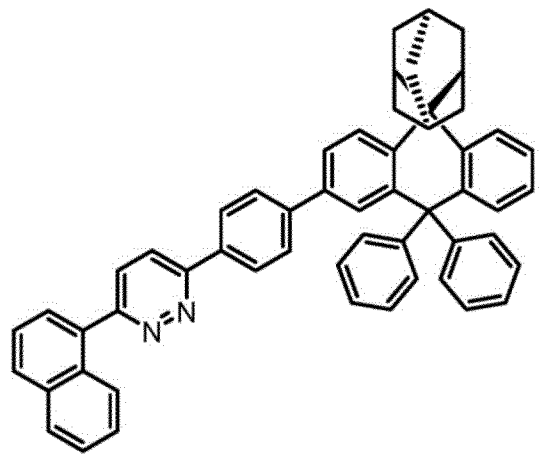

CERTIFICATE OF CORRECTION (continued)
U.S. Pat. No. 11,997,925 B2

Page 3 of 4

In Claim 11, Column 384, the structure of the second compound should be:

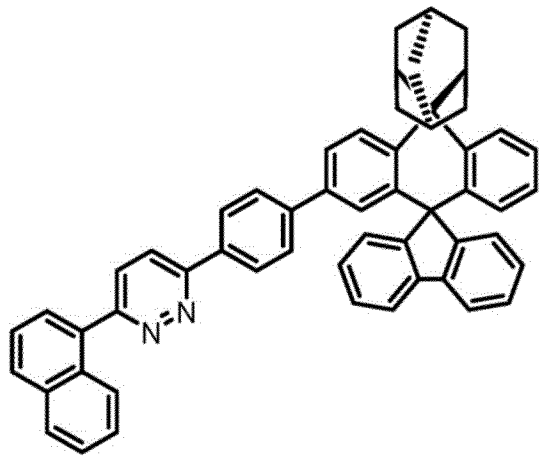

In Claim 11, Column 392, the structure of the compound should be:

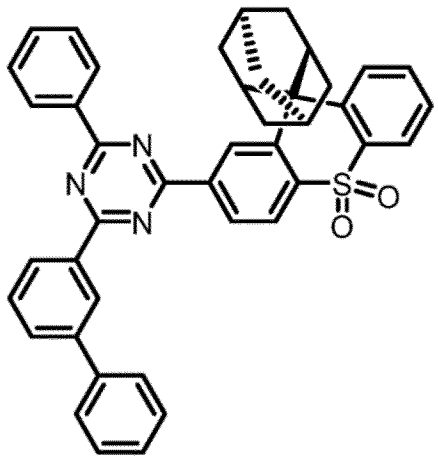

In Claim 11, Column 393, the structure of the first compound should be:

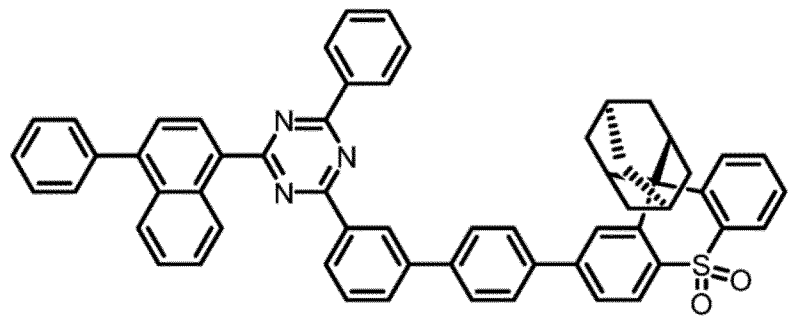

In Claim 11, Column 401, the first compound should be deleted.

CERTIFICATE OF CORRECTION (continued)
U.S. Pat. No. 11,997,925 B2

In Claim 11, Column 410, the structure of the first compound should be: